(12) United States Patent
Jin et al.

(10) Patent No.: US 11,034,671 B2
(45) Date of Patent: Jun. 15, 2021

(54) APOPTOSIS SIGNAL-REGULATING KINASE INHIBITORS AND USES THEREOF

(71) Applicant: SICHUAN HAISCO PHARMACEUTICAL CO., LTD., Sichuan (CN)

(72) Inventors: Bohan Jin, San Diego, CA (US); Qing Dong, San Diego, CA (US); Gene Hung, San Diego, CA (US)

(73) Assignee: SICHUAN HAISCO PHARMACEUTICAL CO., LTD., Sichuan (CN)

( * ) Notice: Subject to any disclaimer, the term of this patent is extended or adjusted under 35 U.S.C. 154(b) by 0 days.

(21) Appl. No.: 16/645,411

(22) PCT Filed: Sep. 7, 2018

(86) PCT No.: PCT/US2018/050013
§ 371 (c)(1),
(2) Date: Mar. 6, 2020

(87) PCT Pub. No.: WO2019/051265
PCT Pub. Date: Mar. 14, 2019

(65) Prior Publication Data
US 2020/0283404 A1      Sep. 10, 2020

Related U.S. Application Data

(60) Provisional application No. 62/555,961, filed on Sep. 8, 2017.

(51) Int. Cl.
C07D 401/14 (2006.01)
A61K 9/00 (2006.01)
C07D 401/04 (2006.01)

(52) U.S. Cl.
CPC .......... *C07D 401/14* (2013.01); *A61K 9/0014* (2013.01); *A61K 9/0019* (2013.01); *A61K 9/0043* (2013.01); *A61K 9/0048* (2013.01); *A61K 9/0053* (2013.01); *C07D 401/04* (2013.01)

(58) Field of Classification Search
None
See application file for complete search history.

(56) References Cited

U.S. PATENT DOCUMENTS

| 8,742,126 B2 | 6/2014 | Notte |
| 2011/0009410 A1 | 1/2011 | Corkey et al. |
| 2017/0174671 A1 | 6/2017 | Wu et al. |
| 2017/0204116 A1 | 7/2017 | Gray et al. |

FOREIGN PATENT DOCUMENTS

| WO | WO-2011008709 A1 | 1/2011 |
| WO | WO-2018148204 A1 | 8/2018 |
| WO | WO-2019051265 A1 | 3/2019 |

OTHER PUBLICATIONS

PCT/US2018/050013 International Search Report and Written Opinion dated Oct. 29, 2018.

*Primary Examiner* — Zinna Northington Davis
(74) *Attorney, Agent, or Firm* — Wilson Sonsini Goodrich & Rosati

(57) ABSTRACT

Described herein are ASK1 inhibitors and pharmaceutical compositions comprising said compounds. The subject compounds and compositions are useful for the treatment of blood disease, autoimmune disorders, pulmonary disorders, hypertension, inflammatory diseases, fibrotic diseases, diabetes, diabetic nephropathy, renal diseases, respiratory diseases, cardiovascular diseases, acute lung injuries, acute or chronic liver diseases, and neurodegenerative diseases.

16 Claims, No Drawings

APOPTOSIS SIGNAL-REGULATING KINASE INHIBITORS AND USES THEREOF

CROSS-REFERENCE

This application is a national stage entry of PCT/US2018/050013, filed on Sep. 7, 2018, and claims the benefit of U.S. Application Ser. No. 62/555,961, filed Sep. 8, 2017, which are hereby incorporated by reference in their entirety.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with apoptosis signal-regulating kinase 1 such as blood diseases, autoimmune disorders, pulmonary disorders, hypertension, inflammatory diseases, fibrotic diseases (such as idiosyncratic pulmonary fibrosis, chronic kidney disease/kidney fibrosis, irritable bowel disease, scleroderma, and liver fibrosis), diabetes, diabetic nephropathy, renal diseases, respiratory diseases, cardiovascular diseases, acute lung injuries, acute or chronic liver diseases, and neurodegenerative diseases.

BACKGROUND OF THE INVENTION

Apoptosis signal-regulating kinase 1 (ASK1) activation and signaling have been reported to play an important role in a broad range of diseases including neurodegenerative, cardiovascular, inflammatory, autoimmune, and metabolic disorders. In addition, ASK1 has been implicated in mediating organ damage following ischemia and reperfusion of the heart, brain, and kidney.

ASK1 has also been identified as an important signaling pathway in non-alcoholic steatohepatitis (NASH), a type of non-alcoholic fatty liver disease (NAFLD), chronic obstructive pulmonary disease (COPD), hypertension, multiple sclerosis, Alzheimer's disease, Parkinson's disease, platelet activation, sickle cell disease, kidney disease, and oxidative stress. Therefore, therapeutic agents that function as inhibitors of ASK1 have potential to remedy or improve the lives of patients suffering from such conditions.

BRIEF SUMMARY OF THE INVENTION

Disclosed herein is a compound of Formula (I), or a pharmaceutically acceptable salt, solvate, tautomer, or stereoisomer thereof:

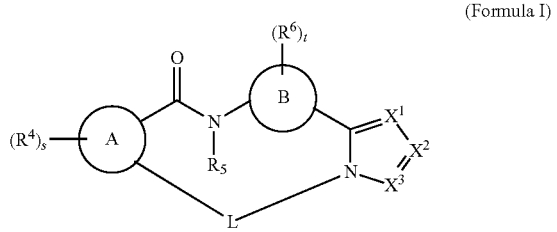

(Formula I)

wherein:
Ring A is aryl or heteroaryl;
Ring B is aryl or heteroaryl;
L is a saturated or unsaturated linear aliphatic chain having 4-10 carbon atoms optionally substituted with 1-6 $R^7$,
wherein 1, 2, or 3 carbon atoms are optionally replaced with —$NR^7$—, —O—, —S—, —S(=O)—, or —S(=O)$_2$—;
$X^1$ is N or $CR^1$;
$X^2$ is N or $CR^2$;
$X^3$ is N or $CR^3$;
each $R^1$, $R^2$, and $R^3$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
each $R^4$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
or two $R^4$ are taken together to form an optionally substituted cycloalkyl, optionally substituted heterocycloalkyl, optionally substituted aryl, or optionally substituted heteroaryl;
$R^5$ is hydrogen, —S(=O)$R^b$, —S(=O)$_2R^d$, —S(=O)$_2NR^cR^d$, —C(=O)$R^b$, —$OCO_2R^a$, —C(=O)$NR^cR^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
each $R^6$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
each $R^7$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
or two $R^7$ on the same carbon atom are taken together to form an oxo;
or two $R^7$ are taken together to form an optionally substituted cycloalkyl;

$R^a$ is hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^b$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^c$ and $R^d$ is independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^c$ and $R^d$, together with the nitrogen atom to which they are attached, form an optionally substituted heterocycloalkyl or optionally substituted heteroaryl;

s is 1-3; and t is 1-3.

Disclosed herein is a pharmaceutical composition comprising a therapeutically effective amount of a compound disclosed herein, and a pharmaceutically acceptable excipient.

Also disclosed herein is a method for treating a disease in a mammal comprising administering to the mammal a therapeutically effective amount of a compound or a pharmaceutical composition disclosed herein.

INCORPORATION BY REFERENCE

All publications, patents, and patent applications mentioned in this specification are herein incorporated by reference for the specific purposes identified herein.

DETAILED DESCRIPTION OF THE INVENTION

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Aliphatic chain" refers to a linear chemical moiety that is composed of only carbons and hydrogens. In some embodiments, the aliphatic chain is saturated. In some embodiments, the aliphatic chain is unsaturated. In some embodiments, the unsaturated aliphatic chain contains one unsaturation. In some embodiments, the unsaturated aliphatic chain contains more than one unsaturation. In some embodiments, the unsaturated aliphatic chain contains two unsaturations. In some embodiments, the unsaturated aliphatic chain contains one double bond. In some embodiments, the unsaturated aliphatic chain contains two double bonds.

"Alkyl" refers to an optionally substituted straight-chain, or optionally substituted branched-chain saturated hydrocarbon monoradical having from one to about ten carbon atoms, or from one to six carbon atoms, wherein a sp3-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein a sp2-hybridized carbon of the alkenyl residue is attached to the rest of the molecule by a single bond. The group may be in either the cis or trans conformation about the double bond (s), and should be understood to include both isomers. Examples include, but are not limited to ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from 1 to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl. Unless stated otherwise specifically in the specification, a Heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

Compounds

Described herein are compounds that are ASK1 inhibitors. These compounds, and compositions comprising these compounds, are useful for the treatment of blood diseases, autoimmune disorders, pulmonary disorders, hypertension, inflammatory diseases, fibrotic diseases (such as idiosyncratic pulmonary fibrosis, chronic kidney disease/kidney fibrosis, irritable bowel disease, scleroderma, and liver fibrosis), diabetes, diabetic nephropathy, renal diseases, respiratory diseases, cardiovascular diseases, acute lung injuries, acute or chronic liver diseases, and neurodegenerative diseases.

Disclosed herein is a compound of Formula (I), or a pharmaceutically acceptable salt, solvate, tautomer, or stereoisomer thereof:

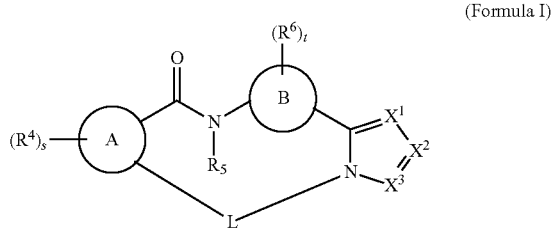

(Formula I)

wherein:

Ring A is aryl or heteroaryl;

Ring B is aryl or heteroaryl;

L is a saturated or unsaturated linear aliphatic chain having 4-10 carbon atoms optionally substituted with 1-6 $R^7$, wherein 1, 2, or 3 carbon atoms are optionally replaced with —$NR^7$—, —O—, —S—, —S(=O)—, or —S(=O)$_2$—;

$X^1$ is N or $CR^1$;

$X^2$ is N or $CR^2$;

$X^3$ is N or $CR^3$;

each $R^1$, $R^2$, and $R^3$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^4$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or two $R^4$ are taken together to form an optionally substituted cycloalkyl, optionally substituted heterocycloalkyl, optionally substituted aryl, or optionally substituted heteroaryl;

$R^5$ is hydrogen, —S(=O)$R^b$, —S(=O)$_2R^d$, —S(=O)$_2NR^cR^d$, —C(=O)$R^b$, —$OCO_2R^a$, —C(=O)$NR^cR^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^6$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^7$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or two $R^7$ on the same carbon atom are taken together to form an oxo;

or two $R^7$ are taken together to form an optionally substituted cycloalkyl;

$R^a$ is hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^b$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^c$ and $R^d$ is independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^c$ and $R^d$, together with the nitrogen atom to which they are attached, form an optionally substituted heterocycloalkyl or optionally substituted heteroaryl;

s is 1-3; and t is 1-3.

In some embodiments of a compound of Formula (I), Ring A is aryl. In some embodiments of a compound of Formula (I), Ring A is phenyl. In some embodiments of a compound of Formula (I), Ring A is heteroaryl. In some embodiments of a compound of Formula (I), Ring A is a 6-membered heteroaryl. In some embodiments of a compound of Formula (I), Ring A is pyridinyl, pyrimidinyl, pyrazinyl, or pyridazinyl. In some embodiments of a compound of Formula (I), Ring A is pyridinyl. In some embodiments of a compound of Formula (I), Ring A is a 5-membered heteroaryl. In some embodiments of a compound of Formula (I), Ring A is thienyl, furyl, pyrrolyl, thiazolyl, oxazolyl, isothiazolyl, isoxazolyl, imidazolyl, pyrazolyl, or triazolyl. In some embodiments of a compound of Formula (I), Ring A is phenyl or pyridyl. In some embodiments of a compound of Formula (I), Ring A is selected from

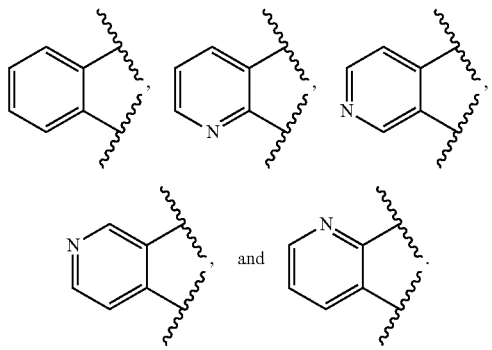

In some embodiments of a compound of Formula (I), Ring A is

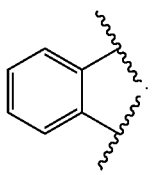 [SMILES: *c1ccccc1*]

In some embodiments of a compound of Formula (I), Ring B is aryl. In some embodiments of a compound of Formula (I), Ring B is phenyl. In some embodiments of a compound of Formula (I), Ring B is heteroaryl. In some embodiments of a compound of Formula (I), Ring B is a 6-membered heteroaryl. In some embodiments of a compound of Formula (I), Ring B is pyridinyl, pyrimidinyl, pyrazinyl, or pyridazinyl. In some embodiments of a compound of Formula (I), Ring B is pyridinyl. In some embodiments of a compound of Formula (I), Ring B is a 5-membered heteroaryl. In some embodiments of a compound of Formula (I), Ring B is thienyl, furyl, pyrrolyl, thiazolyl, oxazolyl, isothiazolyl, isoxazolyl, imidazolyl, pyrazolyl, or triazolyl. In some embodiments of a compound of Formula (I), Ring B is phenyl or pyridyl. In some embodiments of a compound of Formula (I), Ring B is selected from

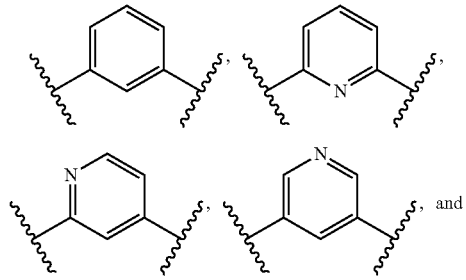

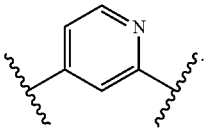

In some embodiments of a compound of Formula (I), Ring B is,

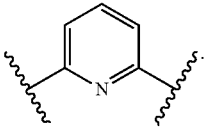 [SMILES: *c1cccc(*)n1]

In some embodiments the compound of Formula (I) is of Formula (Ia):

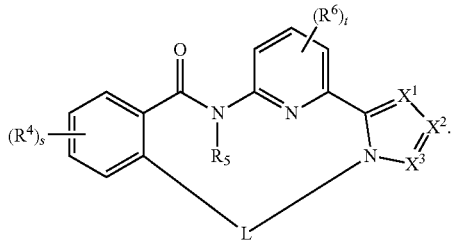

Formula (Ia)

In some embodiments of a compound of Formula (I) or (Ia), $X^1$ is N. In some embodiments of a compound of Formula (I) or (Ia), $X^1$ is $CR^1$.

In some embodiments of a compound of Formula (I) or (Ia), $R^1$ is hydrogen, halogen, —$OR^a$, —$NR^cR^d$, —$CO_2R^a$, —$C(=O)NR^cR^d$, optionally substituted $C_1$-$C_6$ alkyl, or optionally substituted $C_1$-$C_6$ heteroalkyl. In some embodiments of a compound of Formula (I) or (Ia), $R^1$ is hydrogen, halogen, or optionally substituted $C_1$-$C_6$ alkyl. In some embodiments of a compound of Formula (I) or (Ia), $R^1$ is hydrogen, halogen, $C_1$-$C_6$ alkyl, or $C_1$-$C_6$ haloalkyl. In some embodiments of a compound of Formula (I) or (Ia), $R^1$ is hydrogen or halogen. In some embodiments of a compound of Formula (I) or (Ia), $R^1$ is hydrogen.

In some embodiments of a compound of Formula (I) or (Ia), $X^2$ is N. In some embodiments of a compound of Formula (I) or (Ia), $X^2$ is $CR^2$.

In some embodiments of a compound of Formula (I) or (Ia), $R^2$ is hydrogen, halogen, —$OR^a$, —$NR^cR^d$, —$CO_2R^a$, —$C(=O)NR^cR^d$, optionally substituted $C_1$-$C_6$ alkyl, or optionally substituted $C_1$-$C_6$ heteroalkyl. In some embodiments of a compound of Formula (I) or (Ia), $R^2$ is hydrogen, halogen, or optionally substituted $C_1$-$C_6$ alkyl. In some embodiments of a compound of Formula (I) or (Ia), $R^2$ is hydrogen, halogen, $C_1$-$C_6$ alkyl, or $C_1$-$C_6$ haloalkyl. In some embodiments of a compound of Formula (I) or (Ia), $R^2$ is hydrogen or halogen. In some embodiments of a compound of Formula (I) or (Ia), $R^2$ is hydrogen.

In some embodiments of a compound of Formula (I) or (Ia), $X^3$ is N. In some embodiments of a compound of Formula (I) or (Ia), $X^3$ is $CR^3$.

In some embodiments the compound of Formula (I) or (Ia) is of Formula (Ia'):

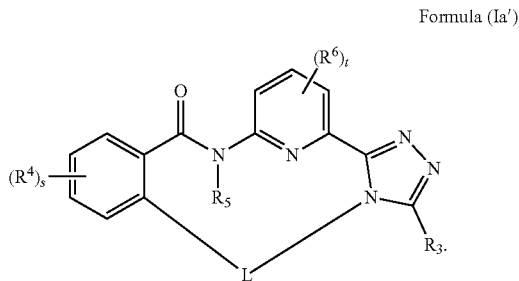

Formula (Ia')

In some embodiments of a compound of Formula (I), (Ia), or (Ia'), $R^3$ is hydrogen, halogen, —$OR^a$, —$NR^cR^d$, —$CO_2R^a$, —C(=O)$NR^cR^d$, optionally substituted $C_1$-$C_6$ alkyl, or optionally substituted $C_1$-$C_6$ heteroalkyl. In some embodiments of a compound of Formula (I), (Ia), or (Ia'), $R^3$ is hydrogen, halogen, or optionally substituted $C_1$-$C_6$ alkyl. In some embodiments of a compound of Formula (I), (Ia), or (Ia'), $R^3$ is halogen or optionally substituted $C_1$-$C_6$ alkyl. In some embodiments of a compound of Formula (I), (Ia), or (Ia'), $R^3$ is hydrogen, halogen, $C_1$-$C_6$ alkyl, or $C_1$-$C_6$ haloalkyl. In some embodiments of a compound of Formula (I), (Ia), or (Ia'), $R^3$ is halogen, $C_1$-$C_6$ alkyl, or $C_1$-$C_6$ haloalkyl. In some embodiments of a compound of Formula (I), (Ia), or (Ia'), $R^3$ is halogen or $C_1$-$C_6$ alkyl. In some embodiments of a compound of Formula (I), (Ia), or (Ia'), $R^3$ is hydrogen or halogen. In some embodiments of a compound of Formula (I), (Ia), or (Ia'), $R^3$ is hydrogen. In some embodiments of a compound of Formula (I), (Ia), or (Ia'), $R^3$ is not hydrogen.

In some embodiments the compound of Formula (I), (Ia), or (Ia') is of Formula (Ib):

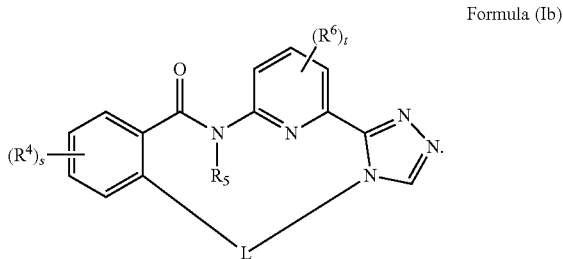

Formula (Ib)

In some embodiments of a compound of Formula (I), (Ia), (Ia'), or (Ib), each $R^4$ is independently hydrogen, halogen, —CN, —$OR^a$, —$NR^cR^d$, —$CO_2R^a$, —C(=O)$NR^cR^d$, optionally substituted $C_1$-$C_6$ alkyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), each $R^4$ is independently hydrogen, halogen, —CN, —$OR^a$, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), each $R^4$ is independently hydrogen, —$OR^a$, or optionally substituted heteroaryl. In some embodiments of a compound of Formula (I), (Ia), (Ia'), or (Ib), each $R^4$ is independently hydrogen or —$OR^a$. In some embodiments of a compound of Formula (I), (Ia), (Ia'), or (Ib), each $R^4$ is independently hydrogen or optionally substituted heteroaryl. In some embodiments of a compound of Formula (I), (Ia), (Ia'), or (Ib), each $R^4$ is independently hydrogen or optionally substituted 6-membered heteroaryl selected from pyridinyl, pyrimidinyl, pyrazinyl, and pyridazinyl. In some embodiments of a compound of Formula (I), (Ia), (Ia'), or (Ib), each $R^4$ is independently hydrogen or optionally substituted: pyridinyl, pyrimidinyl, pyrazinyl, or pyridazinyl. In some embodiments of a compound of Formula (I), (Ia), (Ia'), or (Ib), each $R^4$ is hydrogen. In some embodiments of a compound of Formula (I), (Ia), (Ia'), or (Ib), each $R^4$ is independently optionally substituted pyridinyl. In some embodiments of a compound of Formula (I), (Ia), (Ia'), or (Ib), each $R^4$ is independently optionally substituted 3-pyridinyl. In some embodiments of a compound of Formula (I), (Ia), (Ia'), or (Ib), each $R^4$ is independently substituted 3-pyridinyl.

In some embodiments the compound is of Formula (Ic):

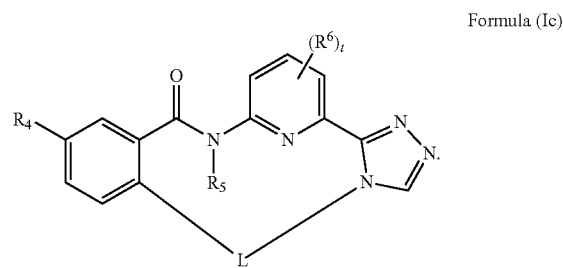

Formula (Ic)

In some embodiments of a compound of Formula (Ic), $R^4$ is halogen, —CN, —$OR^a$, —$NR^cR^d$, —$CO_2R^a$, —C(=O)$NR^cR^d$, optionally substituted $C_1$-$C_6$ alkyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (Ic), $R^4$ is halogen, —CN, —$OR^a$, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (Ic), $R^4$ is —$OR^a$ or optionally substituted heteroaryl. In some embodiments of a compound of Formula (Ic), $R^4$ is —$OR^a$. In some embodiments of a compound of Formula (Ic), $R^4$ is optionally substituted heteroaryl. In some embodiments of a compound of Formula (Ic), $R^4$ is substituted heteroaryl. In some embodiments of a compound of Formula (Ic), $R^4$ is optionally substituted 6-membered heteroaryl selected from pyridinyl, pyrimidinyl, pyrazinyl, and pyridazinyl. In some embodiments of a compound of Formula (Ic), $R^4$ is optionally substituted pyridinyl. In some embodiments of a compound of Formula (Ic), $R^4$ is optionally substituted 3-pyridinyl. In some embodiments of a compound of Formula (Ic), $R^4$ is substituted 3-pyridinyl.

In some embodiments of a compound of Formula (I), (Ia), (Ia'), (Ib), or (Ic), each optional substituent on $R^4$ is independently halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O)$NR^cR^d$, —$NR^aC$(=O)$R^b$, —$NR^aC$(=O)$OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), (Ib), or (Ic), each optional substituent on $R^4$ is independently halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), (Ib), or (Ic), each optional substituent on $R^4$ is independently halogen, optionally substituted $C_1$-$C_6$ alkyl, or optionally substituted cycloalkyl. In some embodiments of a compound of Formula (I), (Ia), (Ia'), (Ib), or (Ic), each optional substituent on $R^4$ is independently halogen, $C_1$-$C_6$ alkyl, $C_1$-$C_6$ haloalkyl, or cycloalkyl. In some embodiments of a compound of Formula (I), (Ia), (Ia'), (Ib), or (Ic), each optional substituent on $R^4$ is independently halogen, —OR$^a$, —NR$^c$R$^d$, $C_1$-$C_6$ alkyl, $C_1$-$C_6$ haloalkyl, optionally substituted cycloalkyl, or optionally substituted heterocycloalkyl.

In some embodiments of a compound of Formula (I), (Ia), (Ia'), or (Ib), two $R^4$ are taken together to form a cycloalkyl, heterocycloalkyl, aryl, or heteroaryl; each optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), two $R^4$ are taken together to form a cycloalkyl, heterocycloalkyl, aryl, or heteroaryl; each optionally substituted with halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), or (Ib), two $R^4$ are taken together to form a cycloalkyl, heterocycloalkyl, aryl, or heteroaryl; each optionally substituted with halogen, —CN, —OR$^a$, —NR$^c$R$^d$, optionally substituted $C_1$-$C_6$ alkyl, or optionally substituted cycloalkyl. In some embodiments of a compound of Formula (I), (Ia), (Ia'), or (Ib), two $R^4$ are taken together to form a cycloalkyl, heterocycloalkyl, aryl, or heteroaryl; each optionally substituted with halogen, —OR$^a$, $C_1$-$C_6$ alkyl, $C_1$-$C_6$ haloalkyl, or cycloalkyl. In some embodiments of a compound of Formula (I), (Ia), (Ia'), or (Ib), two $R^4$ are taken together to form a cycloalkyl, heterocycloalkyl, aryl, or heteroaryl; each optionally substituted with —OR$^a$, $C_1$-$C_6$ alkyl, or cycloalkyl.

In some embodiments of a compound of Formula (I), (Ia), (Ia'), or (Ib), two $R^4$ are taken together to form a cycloalkyl or heterocycloalkyl; each optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), two $R^4$ are taken together to form a cycloalkyl or heterocycloalkyl; each optionally substituted with halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), or (Ib), two $R^4$ are taken together to form a cycloalkyl or heterocycloalkyl; each optionally substituted with halogen, —CN, —OR$^a$, —NR$^c$R$^d$, optionally substituted $C_1$-$C_6$ alkyl, or optionally substituted cycloalkyl. In some embodiments of a compound of Formula (I), (Ia), (Ia'), or (Ib), two $R^4$ are taken together to form a cycloalkyl or heterocycloalkyl; each optionally substituted with halogen, —OR$^a$, $C_1$-$C_6$ alkyl, $C_1$-$C_6$ haloalkyl, or cycloalkyl. In some embodiments of a compound of Formula (I), (Ia), (Ia'), or (Ib), two $R^4$ are taken together to form a cycloalkyl or heterocycloalkyl; each optionally substituted with —OR$^a$, $C_1$-$C_6$ alkyl, or cycloalkyl.

In some embodiments of a compound of Formula (I), (Ia), (Ia'), or (Ib), two $R^4$ are taken together to form a heterocycloalkyl; each optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), two $R^4$ are taken together to form a heterocycloalkyl; each optionally substituted with halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), or (Ib), two $R^4$ are taken together to form a heterocycloalkyl; each optionally substituted with halogen, —CN, —OR$^a$, —NR$^c$R$^d$, optionally substituted $C_1$-$C_6$ alkyl, or optionally substituted cycloalkyl. In some embodiments of a compound of Formula (I), (Ia), (Ia'), or (Ib), two $R^4$ are taken together to form a heterocycloalkyl; each optionally substituted with halogen, —OR$^a$, $C_1$-$C_6$ alkyl, $C_1$-$C_6$ haloalkyl, or cycloalkyl. In some embodiments of a compound of Formula (I), (Ia), (Ia'), or (Ib), two $R^4$ are taken together to form a heterocycloalkyl; each optionally substituted with —OR$^a$, $C_1$-$C_6$ alkyl, or cycloalkyl.

In some embodiments of a compound of Formula (I), (Ia), (Ia'), or (Ib), two $R^4$ are taken together to form an aryl or heteroaryl; each optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), or (Ib), two $R^4$ are taken together to form an aryl or heteroaryl; each optionally substituted with halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), or (Ib), two R⁴ are taken together to form an aryl or heteroaryl; each optionally substituted with halogen, —CN, —OR$^a$, —NR$^c$R$^d$, optionally substituted C$_1$-C$_6$ alkyl, or optionally substituted cycloalkyl. In some embodiments of a compound of Formula (I), (Ia), (Ia'), or (Ib), two R⁴ are taken together to form an aryl or heteroaryl; each optionally substituted with halogen, —OR$^a$, C$_1$-C$_6$ alkyl, C$_1$-C$_6$ haloalkyl, or cycloalkyl. In some embodiments of a compound of Formula (I), (Ia), (Ia'), or (Ib), two R⁴ are taken together to form an aryl or heteroaryl; each optionally substituted with —OR$^a$, C$_1$-C$_6$ alkyl, or cycloalkyl.

In some embodiments of a compound of Formula (I), (Ia), (Ia'), (Ib), or (Ic), s is 1 and R⁴ is In some embodiments of a compound of Formula (I), (Ia), (Ia'), (Ib), or (Ic), s is 1 and R⁴ is In some embodiments of a compound of Formula (I), (Ia), (Ia'), or (Ib), s is 1 or 2. In some embodiments of a compound of Formula (I), (Ia), (Ia'), or (Ib), s is 3. In some embodiments of a compound of Formula (I), (Ia), (Ia'), or (Ib), s is 2. In some embodiments of a compound of Formula (I), (Ia), (Ia'), or (Ib), s is 1.

In some embodiments of a compound of Formula (I), (Ia), (Ia'), (Ib), or (Ic), each R⁶ is independently hydrogen, halogen, —CN, —OR$^a$, —NR$^c$R$^d$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), (Ib), or (Ic), each R⁶ is independently hydrogen, halogen, —CN, —OR$^a$, —NR$^c$R$^d$, —CO$_2$R$^a$, —C(=O)NR$^c$R$^d$, optionally substituted C$_1$-C$_6$ alkyl, or optionally substituted C$_1$-C$_6$ heteroalkyl. In some embodiments of a compound of Formula (I), (Ia), (Ia'), (Ib), or (Ic), each R⁶ is independently hydrogen, halogen, —CN, —OR$^a$, or optionally substituted C$_1$-C$_6$ alkyl. In some embodiments of a compound of Formula (I), (Ia), (Ia'), (Ib), or (Ic), each R⁶ is independently hydrogen, halogen, optionally substituted C$_1$-C$_6$ alkyl, or optionally substituted C$_1$-C$_6$ heteroalkyl. In some embodiments of a compound of Formula (I), (Ia), (Ia'), (Ib), or (Ic), each R⁶ is independently hydrogen, halogen, or optionally substituted C$_1$-C$_6$ alkyl. In some embodiments of a compound of Formula (I), (Ia), (Ia'), (Ib), or (Ic), each R⁶ is independently hydrogen, halogen, C$_1$-C$_6$ alkyl, or C$_1$-C$_6$ haloalkyl. In some embodiments of a compound of Formula (I), (Ia), (Ia'), (Ib), or (Ic), each R⁶ is independently hydrogen or halogen. In some embodiments of a compound of Formula (I), (Ia), (Ia'), (Ib), or (Ic), each R⁶ is hydrogen.

In some embodiments of a compound of Formula (I), (Ia), (Ia'), (Ib), or (Ic), each optional substituent on R⁶ is independently halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C (=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), (Ib), or (Ic), each optional substituent on R$^6$ is independently halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), (Ib), or (Ic), each optional substituent on R$^6$ is independently halogen, optionally substituted $C_1$-$C_6$ alkyl, or optionally substituted cycloalkyl. In some embodiments of a compound of Formula (I), (Ia), (Ia'), (Ib), or (Ic), each optional substituent on R$^6$ is independently halogen, $C_1$-$C_6$ alkyl, $C_1$-$C_6$ haloalkyl, or cycloalkyl.

In some embodiments of a compound of Formula (I), (Ia), (Ia'), (Ib), or (Ic), t is 1 or 2. In some embodiments of a compound of Formula (I), (Ia), (Ia'), (Ib), or (Ic), t is 3. In some embodiments of a compound of Formula (I), (Ia), (Ia'), (Ib), or (Ic), t is 2. In some embodiments of a compound of Formula (I), (Ia), (Ia'), (Ib), or (Ic), t is 1.

In some embodiments of a compound of Formula (I), (Ia), (Ia'), (Ib), or (Ic), R$^5$ is hydrogen or optionally substituted $C_1$-$C_6$ alkyl. In some embodiments of a compound of Formula (I), (Ia), (Ia'), (Ib), or (Ic), R$^5$ is hydrogen, $C_1$-$C_6$ alkyl, or $C_1$-$C_6$ haloalkyl. In some embodiments of a compound of Formula (I), (Ia), (Ia'), (Ib), or (Ic), R$^5$ is hydrogen or $C_1$-$C_6$ alkyl. In some embodiments of a compound of Formula (I), (Ia), (Ia'), (Ib), or (Ic), R$^5$ is hydrogen.

Linker L

In some embodiments of a compound of Formula (I), (Ia), (Ia'), (Ib), or (Ic), L is a saturated or unsaturated linear aliphatic chain having 4-10 carbon atoms optionally substituted with 1-4 R$^7$, wherein 1, 2, or 3 carbon atoms are optionally replaced with —NR$^7$—, —O—, —S—, —S(=O)—, or —S(=O)$_2$—.

In some embodiments of a compound of Formula (I), (Ia), (Ia'), (Ib), or (Ic), L is a saturated or unsaturated linear aliphatic chain having 4-10 carbon atoms optionally substituted with 1-4 R$^7$, wherein 1 or 2 carbon atoms are optionally replaced with —NR$^7$—, —O—, —S—, —S(=O)—, or —S(=O)$_2$—.

In some embodiments of a compound of Formula (I), (Ia), (Ia'), (Ib), or (Ic), L is a saturated or unsaturated linear aliphatic chain having 4-10 carbon atoms optionally substituted with 1-4 R$^7$, wherein 1 or 2 carbon atoms are optionally replaced with —NR$^7$— or —O—.

In some embodiments of a compound of Formula (I), (Ia), (Ia'), (Ib), or (Ic), L is a saturated or unsaturated linear aliphatic chain having 4-10 carbon atoms optionally substituted with 1-4 R$^7$, wherein 1 carbon atom is optionally replaced with —NR$^7$— or —O—.

In some embodiments of a compound of Formula (I), (Ia), (Ia'), (Ib), or (Ic), L is a saturated or unsaturated linear aliphatic chain having 4-10 carbon atoms optionally substituted with 1-4 R$^7$, wherein 1 carbon atom is optionally replaced with —O—.

In some embodiments of a compound of Formula (I), (Ia), (Ia'), (Ib), or (Ic), L is a saturated or unsaturated linear aliphatic chain having 4-10 carbon atoms optionally substituted with 1 or 2 R$^7$, wherein 1, 2, or 3 carbon atoms are optionally replaced with —NR$^7$—, —O—, —S—, —S(=O)—, or —S(=O)$_2$—.

In some embodiments of a compound of Formula (I), (Ia), (Ia'), (Ib), or (Ic), L is a saturated or unsaturated linear aliphatic chain having 4-10 carbon atoms optionally substituted with 1 or 2 R$^7$, wherein 1 or 2 carbon atoms are optionally replaced with —NR$^7$—, —O—, —S—, —S(=O)—, or —S(=O)$_2$—.

In some embodiments of a compound of Formula (I), (Ia), (Ia'), (Ib), or (Ic), L is a saturated or unsaturated linear aliphatic chain having 4-10 carbon atoms optionally substituted with 1 or 2 R$^7$, wherein 1 or 2 carbon atoms are optionally replaced with —NR$^7$— or —O—.

In some embodiments of a compound of Formula (I), (Ia), (Ia'), (Ib), or (Ic), L is a saturated or unsaturated linear aliphatic chain having 4-10 carbon atoms optionally substituted with 1 or 2 R$^7$, wherein 1 carbon atom is optionally replaced with —NR$^7$— or —O—.

In some embodiments of a compound of Formula (I), (Ia), (Ia'), (Ib), or (Ic), L is a saturated or unsaturated linear aliphatic chain having 4-10 carbon atoms optionally substituted with 1 or 2 R$^7$, wherein 1 carbon atom is optionally replaced with —O—.

In some embodiments of a compound of Formula (I), (Ia), (Ia'), (Ib), or (Ic), L is a saturated linear aliphatic chain having 4-10 carbon atoms optionally substituted with 1 or 2 R$^7$.

In some embodiments of a compound of Formula (I), (Ia), (Ia'), (Ib), or (Ic), L is a saturated linear aliphatic chain having 4-8 carbon atoms optionally substituted with 1 or 2 R$^7$. In some embodiments of a compound of Formula (I), (Ia), (Ia'), (Ib), or (Ic), L is a saturated linear aliphatic chain having 5-7 carbon atoms optionally substituted with 1 or 2 R$^7$.

In some embodiments of a compound of Formula (I), (Ia), (Ia'), (Ib), or (Ic), L is a saturated linear aliphatic chain having 4-10 carbon atoms optionally substituted with 1 or 2 R$^7$, wherein 1 carbon atom is replaced with NR$^7$, O, or S.

In some embodiments of a compound of Formula (I), (Ia), (Ia'), (Ib), or (Ic), L is a saturated linear aliphatic chain having 4-8 carbon atoms optionally substituted with 1 or 2 R$^7$, wherein 1 carbon atom is replaced with NR$^7$, O, or S.

In some embodiments of a compound of Formula (I), (Ia), (Ia'), (Ib), or (Ic), L is a saturated linear aliphatic chain having 5-7 carbon atoms optionally substituted with 1 or 2 R$^7$, wherein 1 carbon atom is replaced with NR$^7$, O, or S.

In some embodiments of a compound of Formula (I), (Ia), (Ia'), (Ib), or (Ic), L is a saturated linear aliphatic chain having 4-10 carbon atoms optionally substituted with 1 or 2 R$^7$, wherein 1 carbon atom is replaced with NR$^7$ or O.

In some embodiments of a compound of Formula (I), (Ia), (Ia'), (Ib), or (Ic), L is a saturated linear aliphatic chain having 4-8 carbon atoms optionally substituted with 1 or 2 R$^7$, wherein 1 carbon atom is replaced with NR$^7$ or O.

In some embodiments of a compound of Formula (I), (Ia), (Ia'), (Ib), or (Ic), L is a saturated linear aliphatic chain having 5-7 carbon atoms optionally substituted with 1 or 2 R$^7$, wherein 1 carbon atom is replaced with NR$^7$ or O.

In some embodiments of a compound of Formula (I), (Ia), (Ia'), (Ib), or (Ic), L is a saturated linear aliphatic chain having 4-10 carbon atoms optionally substituted with 1 or 2 R$^7$, wherein 1 carbon atom is replaced with O.

In some embodiments of a compound of Formula (I), (Ia), (Ia'), (Ib), or (Ic), L is a saturated linear aliphatic chain having 4-8 carbon atoms optionally substituted with 1 or 2 R$^7$, wherein 1 carbon atom is replaced with O.

In some embodiments of a compound of Formula (I), (Ia), (Ia'), (Ib), or (Ic), L is a saturated linear aliphatic chain having 5-7 carbon atoms optionally substituted with 1 or 2 $R^7$, wherein 1 carbon atom is replaced with O.

In some embodiments of a compound of Formula (I), (Ia), (Ia'), (Ib), or (Ic), L is an unsaturated linear aliphatic chain having 4-10 carbon atoms optionally substituted with 1 or 2 $R^7$.

In some embodiments of a compound of Formula (I), (Ia), (Ia'), (Ib), or (Ic), L is an unsaturated linear aliphatic chain having 4-8 carbon atoms optionally substituted with 1 or 2 $R^7$.

In some embodiments of a compound of Formula (I), (Ia), (Ia'), (Ib), or (Ic), L is an unsaturated linear aliphatic chain having 5-7 carbon atoms optionally substituted with 1 or 2 $R^7$.

In some embodiments of a compound of Formula (I), (Ia), (Ia'), (Ib), or (Ic), L is an unsaturated linear aliphatic chain having 4-10 carbon atoms optionally substituted with 1 or 2 $R^7$, wherein 1 carbon atom is replaced with $NR^7$, O, or S.

In some embodiments of a compound of Formula (I), (Ia), (Ia'), (Ib), or (Ic), L is an unsaturated linear aliphatic chain having 4-8 carbon atoms optionally substituted with 1 or 2 $R^7$, wherein 1 carbon atom is replaced with $NR^7$, O, or S.

In some embodiments of a compound of Formula (I), (Ia), (Ia'), (Ib), or (Ic), L is an unsaturated linear aliphatic chain having 5-7 carbon atoms optionally substituted with 1 or 2 $R^7$, wherein 1 carbon atom is replaced with $NR^7$, O, or S.

In some embodiments of a compound of Formula (I), (Ia), (Ia'), (Ib), or (Ic), L is an unsaturated linear aliphatic chain having 4-10 carbon atoms optionally substituted with 1 or 2 $R^7$, wherein 1 carbon atom is replaced with $NR^7$ or O.

In some embodiments of a compound of Formula (I), (Ia), (Ia'), (Ib), or (Ic), L is an unsaturated linear aliphatic chain having 4-8 carbon atoms optionally substituted with 1 or 2 $R^7$, wherein 1 carbon atom is replaced with $NR^7$ or O.

In some embodiments of a compound of Formula (I), (Ia), (Ia'), (Ib), or (Ic), L is an unsaturated linear aliphatic chain having 5-7 carbon atoms optionally substituted with 1 or 2 $R^7$, wherein 1 carbon atom is replaced with $NR^7$ or O.

In some embodiments of a compound of Formula (I), (Ia), (Ia'), (Ib), or (Ic), L is an unsaturated linear aliphatic chain having 4-10 carbon atoms optionally substituted with 1 or 2 $R^7$, wherein 1 carbon atom is replaced with O.

In some embodiments of a compound of Formula (I), (Ia), (Ia'), (Ib), or (Ic), L is an unsaturated linear aliphatic chain having 4-8 carbon atoms optionally substituted with 1 or 2 $R^7$, wherein 1 carbon atom is replaced with O.

In some embodiments of a compound of Formula (I), (Ia), (Ia'), (Ib), or (Ic), L is an unsaturated linear aliphatic chain having 5-7 carbon atoms optionally substituted with 1 or 2 $R^7$, wherein 1 carbon atom is replaced with O.

In some embodiments of a compound of Formula (I), (Ia), (Ia'), (Ib), or (Ic), L is an unsaturated linear aliphatic chain comprising one double bond. In some embodiments of a compound of Formula (I), (Ia), (Ia'), (Ib), or (Ic), L is an unsaturated linear aliphatic chain comprising two double bonds. In some embodiments of a compound of Formula (I), (Ia), (Ia'), (Ib), or (Ic), L is an unsaturated linear aliphatic chain comprising one triple bond. In some embodiments of a compound of Formula (I), (Ia), (Ia'), (Ib), or (Ic), L is an unsaturated linear aliphatic chain comprising two triple bonds. In some embodiments of a compound of Formula (I), (Ia), (Ia'), (Ib), or (Ic), L is an unsaturated linear aliphatic chain comprising one double bond and one triple bond.

In some embodiments of a compound of Formula (I), (Ia), (Ia'), (Ib), or (Ic), each $R^7$ is independently hydrogen, halogen, —CN, —$OR^a$, —$NR^cR^d$, —$CO_2R^a$, —C(=O)$NR^cR^d$, optionally substituted $C_1$-$C_6$ alkyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), (Ib), or (Ic), each $R^7$ is independently hydrogen, halogen, —CN, —$OR^a$, optionally substituted $C_1$-$C_6$ alkyl, optionally substituted cycloalkyl, or optionally substituted heterocycloalkyl. In some embodiments of a compound of Formula (I), (Ia), (Ia'), (Ib), or (Ic), each $R^7$ is independently hydrogen, halogen, or optionally substituted $C_1$-$C_6$ alkyl. In some embodiments of a compound of Formula (I), (Ia), (Ia'), (Ib), or (Ic), each $R^7$ is independently hydrogen, halogen, $C_1$-$C_6$ alkyl, or $C_1$-$C_6$ haloalkyl. In some embodiments of a compound of Formula (I), (Ia), (Ia'), (Ib), or (Ic), each $R^7$ is independently hydrogen or halogen. In some embodiments of a compound of Formula (I), (Ia), (Ia'), (Ib), or (Ic), each $R^7$ is hydrogen. In some embodiments of a compound of Formula (I), (Ia), (Ia'), (Ib), or (Ic), two $R^7$ on the same carbon atom are taken together to form an oxo. In some embodiments of a compound of Formula (I), (Ia), (Ia'), (Ib), or (Ic), two $R^7$ are taken together to form an optionally substituted cycloalkyl. In some embodiments of a compound of Formula (I), (Ia), (Ia'), (Ib), or (Ic), two $R^7$ are taken together to form a cycloalkyl. In some embodiments, the cycloalkyl is cyclopropyl, cyclobutyl, cyclopentyl, or cyclobutyl. In some embodiments of a compound of Formula (I), (Ia), (Ia'), (Ib), or (Ic), the two $R^7$ are on the same carbon. In some embodiments of a compound of Formula (I), (Ia), (Ia'), (Ib), or (Ic), the two $R^7$ are on adjacent carbons. In some embodiments of a compound of Formula (I), (Ia), (Ia'), (Ib), or (Ic), the two $R^7$ are on adjacent carbons +1. In some embodiments of a compound of Formula (I), (Ia), (Ia'), (Ib), or (Ic), the two $R^7$ are on adjacent carbons +2.

In some embodiments of a compound of Formula (I), (Ia), (Ia'), (Ib), or (Ic), L is selected from:

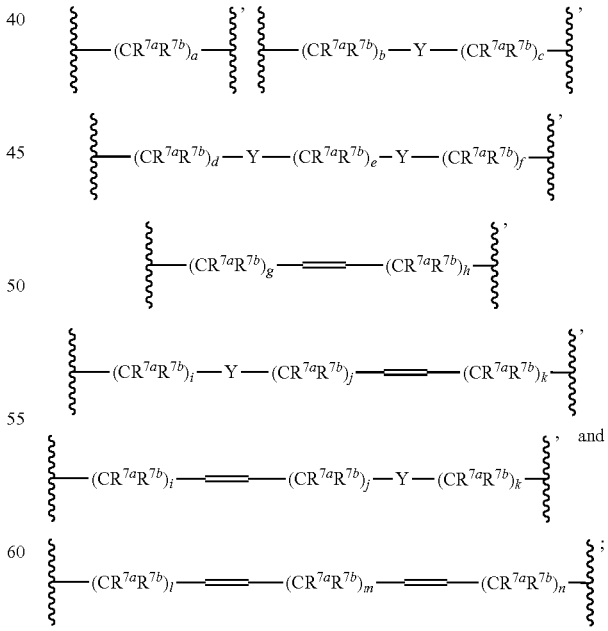

wherein:
each $R^{7a}$ and $R^{7b}$ is independently hydrogen, halogen, —CN, —$OR^a$, —$SR^a$, —S(=O)$R^b$, —$NO_2$, —$NR^cR^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl;

or R$^{7a}$ and R$^{7b}$ on the same carbon atom are taken together to form an oxo;

or two R$^{7a}$ are taken together to form an optionally substituted cycloalkyl;

each Y is independently —NR$^{7c}$—, —O—, —S—, —S(=O)—, or —S(=O)$_2$—;

each R$^{7c}$ is independently hydrogen, —S(=O)R$^b$, —S(=O)$_2$R$^d$, —S(=O)$_2$NR$^c$R$^d$, —C(=O)R$^b$, —CO$_2$R$^a$, —C(=O)NR$^c$R$^d$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl;

a is 4-10;
b is 0-9 and c is 0-9; provided that 3≤b+c≤9;
d is 0-8; e is 2-8; and f is 0-8; provided that 2≤d+e+f≤8;
g is 0-8 and h is 0-8; provided that 2≤g+h≤8;
i is 0-7; j is 0-7; and k is 0-7; provided that 1≤i+j+k≤7;
l is 0-6; m is 0-6; and n is 0-6; provided that 0≤l+m+n≤6.

In some embodiments of a compound of Formula (I), (Ia), (Ia'), (Ib), or (Ic), L is selected from:

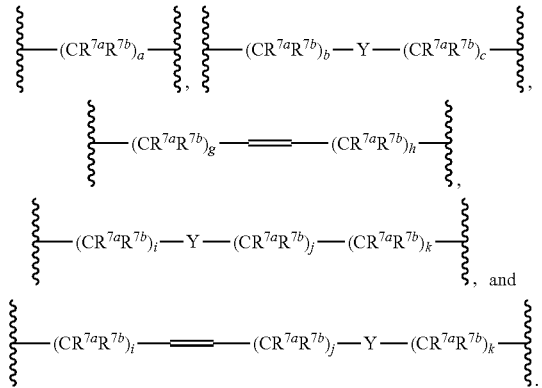

In some embodiments of a compound of Formula (I), (Ia), (Ia'), (Ib), or (Ic), L is

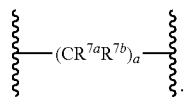

In some embodiments of a compound of Formula (I), (Ia), (Ia'), (Ib), or (Ic), L is

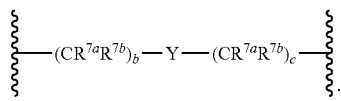

In some embodiments of a compound of Formula (I), (Ia), (Ia'), (Ib), or (Ic), L is

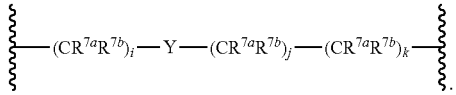

In some embodiments of a compound of Formula (I), (Ia), (Ia'), (Ib), or (Ic), Y is —NR$^{7c}$—, —O—, or —S—. In some embodiments of a compound of Formula (I), (Ia), (Ia'), (Ib), or (Ic), each Y is independently —NR$^{7c}$— or —O—. In some embodiments of a compound of Formula (I), (Ia), (Ia'), (Ib), or (Ic), Y is —O—.

In some embodiments of a compound of Formula (I), (Ia), (Ia'), (Ib), or (Ic), a is 4-8. In some embodiments of a compound of Formula (I), (Ia), (Ia'), (Ib), or (Ic), a is 5-7. In some embodiments of a compound of Formula (I), (Ia), (Ia'), (Ib), or (Ic), a is 4. In some embodiments of a compound of Formula (I), (Ia), (Ia'), (Ib), or (Ic), a is 5. In some embodiments of a compound of Formula (I), (Ia), (Ia'), (Ib), or (Ic), a is 6. In some embodiments of a compound of Formula (I), (Ia), (Ia'), (Ib), or (Ic), a is 7. In some embodiments of a compound of Formula (I), (Ia), (Ia'), (Ib), or (Ic), a is 8. In some embodiments of a compound of Formula (I), (Ia), (Ia'), (Ib), or (Ic), a is 9. In some embodiments of a compound of Formula (I), (Ia), (Ia'), (Ib), or (Ic), a is 10.

In some embodiments of a compound of Formula (I), (Ia), (Ia'), (Ib), or (Ic), b is 0-5. In some embodiments of a compound of Formula (I), (Ia), (Ia'), (Ib), or (Ic), b is 0-4. In some embodiments of a compound of Formula (I), (Ia), (Ia'), (Ib), or (Ic), b is 0-3. In some embodiments of a compound of Formula (I), (Ia), (Ia'), (Ib), or (Ic), b is 0-2. In some embodiments of a compound of Formula (I), (Ia), (Ia'), (Ib), or (Ic), b is 5-9. In some embodiments of a compound of Formula (I), (Ia), (Ia'), (Ib), or (Ic), b is 5-8. In some embodiments of a compound of Formula (I), (Ia), (Ia'), (Ib), or (Ic), b is 5-7. In some embodiments of a compound of Formula (I), (Ia), (Ia'), (Ib), or (Ic), b is 0. In some embodiments of a compound of Formula (I), (Ia), (Ia'), (Ib), or (Ic), b is 1. In some embodiments of a compound of Formula (I), (Ia), (Ia'), (Ib), or (Ic), b is 2. In some embodiments of a compound of Formula (I), (Ia), (Ia'), (Ib), or (Ic), b is 3. In some embodiments of a compound of Formula (I), (Ia), (Ia'), (Ib), or (Ic), b is 4. In some embodiments of a compound of Formula (I), (Ia), (Ia'), (Ib), or (Ic), b is 5. In some embodiments of a compound of Formula (I), (Ia), (Ia'), (Ib), or (Ic), b is 6. In some embodiments of a compound of Formula (I), (Ia), (Ia'), (Ib), or (Ic), b is 7. In some embodiments of a compound of Formula (I), (Ia), (Ia'), (Ib), or (Ic), b is 8. In some embodiments of a compound of Formula (I), (Ia), (Ia'), (Ib), or (Ic), b is 9.

In some embodiments of a compound of Formula (I), (Ia), (Ia'), (Ib), or (Ic), c is 4-9. In some embodiments of a compound of Formula (I), (Ia), (Ia'), (Ib), or (Ic), c is 4-8. In some embodiments of a compound of Formula (I), (Ia), (Ia'), (Ib), or (Ic), c is 4-7. In some embodiments of a compound of Formula (I), (Ia), (Ia'), (Ib), or (Ic), c is 0-4. In some embodiments of a compound of Formula (I), (Ia), (Ia'), (Ib), or (Ic), c is 0-3. In some embodiments of a compound of Formula (I), (Ia), (Ia'), (Ib), or (Ic), c is 0-2. In some embodiments of a compound of Formula (I), (Ia), (Ia'), (Ib), or (Ic), c is 0. In some embodiments of a compound of Formula (I), (Ia), (Ia'), (Ib), or (Ic), c is 1. In some embodiments of a compound of Formula (I), (Ia), (Ia'), (Ib), or (Ic), c is 2. In some embodiments of a compound of Formula (I), (Ia), (Ia'), (Ib), or (Ic), c is 3. In some embodiments of a compound of Formula (I), (Ia), (Ia'), (Ib), or (Ic), c is 4. In some embodiments of a compound of Formula (I), (Ia), (Ia'), (Ib), or (Ic), c is 5. In some embodiments of a compound of Formula (I), (Ia), (Ia'), (Ib), or (Ic), c is 6. In some embodiments of a compound of Formula (I), (Ia), (Ia'), (Ib), or (Ic), c is 7. In some embodiments of a compound of Formula (I), (Ia), (Ia'), (Ib), or (Ic), c is 8. In some embodiments of a compound of Formula (I), (Ia), (Ia'), (Ib), or (Ic), c is 9.

In some embodiments of a compound of Formula (I), (Ia), (Ia'), (Ib), or (Ic), d is 0-5. In some embodiments of a compound of Formula (I), (Ia), (Ia'), (Ib), or (Ic), d is 0-4. In some embodiments of a compound of Formula (I), (Ia), (Ia'), (Ib), or (Ic), d is 0-3. In some embodiments of a compound of Formula (I), (Ia), (Ia'), (Ib), or (Ic), d is 0-2. In some embodiments of a compound of Formula (I), (Ia), (Ia'), (Ib), or (Ic), d is 5-8. In some embodiments of a compound of Formula (I), (Ia), (Ia'), (Ib), or (Ic), d is 5-7. In some embodiments of a compound of Formula (I), (Ia), (Ia'), (Ib), or (Ic), d is 0. In some embodiments of a compound of Formula (I), (Ia), (Ia'), (Ib), or (Ic), d is 1. In some embodiments of a compound of Formula (I), (Ia), (Ia'), (Ib), or (Ic), d is 2. In some embodiments of a compound of Formula (I), (Ia), (Ia'), (Ib), or (Ic), d is 3. In some embodiments of a compound of Formula (I), (Ia), (Ia'), (Ib), or (Ic), d is 4. In some embodiments of a compound of Formula (I), (Ia), (Ia'), (Ib), or (Ic), d is 5. In some embodiments of a compound of Formula (I), (Ia), (Ia'), (Ib), or (Ic), d is 6. In some embodiments of a compound of Formula (I), (Ia), (Ia'), (Ib), or (Ic), d is 7. In some embodiments of a compound of Formula (I), (Ia), (Ia'), (Ib), or (Ic), d is 8.

In some embodiments of a compound of Formula (I), (Ia), (Ia'), (Ib), or (Ic), e is 2-5. In some embodiments of a compound of Formula (I), (Ia), (Ia'), (Ib), or (Ic), e is 2-4. In some embodiments of a compound of Formula (I), (Ia), (Ia'), (Ib), or (Ic), e is 2 or 3. In some embodiments of a compound of Formula (I), (Ia), (Ia'), (Ib), or (Ic), e is 5-8. In some embodiments of a compound of Formula (I), (Ia), (Ia'), (Ib), or (Ic), e is 5-7. In some embodiments of a compound of Formula (I), (Ia), (Ia'), (Ib), or (Ic), e is 5 or 6. In some embodiments of a compound of Formula (I), (Ia), (Ia'), (Ib), or (Ic), e is 2. In some embodiments of a compound of Formula (I), (Ia), (Ia'), (Ib), or (Ic), e is 3. In some embodiments of a compound of Formula (I), (Ia), (Ia'), (Ib), or (Ic), e is 4. In some embodiments of a compound of Formula (I), (Ia), (Ia'), (Ib), or (Ic), e is 5. In some embodiments of a compound of Formula (I), (Ia), (Ia'), (Ib), or (Ic), e is 6. In some embodiments of a compound of Formula (I), (Ia), (Ia'), (Ib), or (Ic), e is 7. In some embodiments of a compound of Formula (I), (Ia), (Ia'), (Ib), or (Ic), e is 8.

In some embodiments of a compound of Formula (I), (Ia), (Ia'), (Ib), or (Ic), f is 0-5. In some embodiments of a compound of Formula (I), (Ia), (Ia'), (Ib), or (Ic), f is 0-4. In some embodiments of a compound of Formula (I), (Ia), (Ia'), (Ib), or (Ic), f is 0-3. In some embodiments of a compound of Formula (I), (Ia), (Ia'), (Ib), or (Ic), f is 0-2. In some embodiments of a compound of Formula (I), (Ia), (Ia'), (Ib), or (Ic), f is 5-8. In some embodiments of a compound of Formula (I), (Ia), (Ia'), (Ib), or (Ic), f is 5-7. In some embodiments of a compound of Formula (I), (Ia), (Ia'), (Ib), or (Ic), f is 0. In some embodiments of a compound of Formula (I), (Ia), (Ia'), (Ib), or (Ic), f is 1. In some embodiments of a compound of Formula (I), (Ia), (Ia'), (Ib), or (Ic), f is 2. In some embodiments of a compound of Formula (I), (Ia), (Ia'), (Ib), or (Ic), f is 3. In some embodiments of a compound of Formula (I), (Ia), (Ia'), (Ib), or (Ic), f is 4. In some embodiments of a compound of Formula (I), (Ia), (Ia'), (Ib), or (Ic), f is 5. In some embodiments of a compound of Formula (I), (Ia), (Ia'), (Ib), or (Ic), f is 6. In some embodiments of a compound of Formula (I), (Ia), (Ia'), (Ib), or (Ic), f is 7. In some embodiments of a compound of Formula (I), (Ia), (Ia'), (Ib), or (Ic), f is 8.

In some embodiments of a compound of Formula (I), (Ia), (Ia'), (Ib), or (Ic), g is 0-5. In some embodiments of a compound of Formula (I), (Ia), (Ia'), (Ib), or (Ic), g is 0-4. In some embodiments of a compound of Formula (I), (Ia), (Ia'), (Ib), or (Ic), g is 0-3. In some embodiments of a compound of Formula (I), (Ia), (Ia'), (Ib), or (Ic), g is 0-2. In some embodiments of a compound of Formula (I), (Ia), (Ia'), (Ib), or (Ic), g is 5-8. In some embodiments of a compound of Formula (I), (Ia), (Ia'), (Ib), or (Ic), g is 5-7. In some embodiments of a compound of Formula (I), (Ia), (Ia'), (Ib), or (Ic), g is 0. In some embodiments of a compound of Formula (I), (Ia), (Ia'), (Ib), or (Ic), g is 1. In some embodiments of a compound of Formula (I), (Ia), (Ia'), (Ib), or (Ic), g is 2. In some embodiments of a compound of Formula (I), (Ia), (Ia'), (Ib), or (Ic), g is 3. In some embodiments of a compound of Formula (I), (Ia), (Ia'), (Ib), or (Ic), g is 4. In some embodiments of a compound of Formula (I), (Ia), (Ia'), (Ib), or (Ic), g is 5. In some embodiments of a compound of Formula (I), (Ia), (Ia'), (Ib), or (Ic), g is 6. In some embodiments of a compound of Formula (I), (Ia), (Ia'), (Ib), or (Ic), g is 7. In some embodiments of a compound of Formula (I), (Ia), (Ia'), (Ib), or (Ic), g is 8.

In some embodiments of a compound of Formula (I), (Ia), (Ia'), (Ib), or (Ic), h is 0-5. In some embodiments of a compound of Formula (I), (Ia), (Ia'), (Ib), or (Ic), h is 0-4. In some embodiments of a compound of Formula (I), (Ia), (Ia'), (Ib), or (Ic), h is 0-3. In some embodiments of a compound of Formula (I), (Ia), (Ia'), (Ib), or (Ic), h is 0-2. In some embodiments of a compound of Formula (I), (Ia), (Ia'), (Ib), or (Ic), h is 5-8. In some embodiments of a compound of Formula (I), (Ia), (Ia'), (Ib), or (Ic), h is 5-7. In some embodiments of a compound of Formula (I), (Ia), (Ia'), (Ib), or (Ic), h is 0. In some embodiments of a compound of Formula (I), (Ia), (Ia'), (Ib), or (Ic), h is 1. In some embodiments of a compound of Formula (I), (Ia), (Ia'), (Ib), or (Ic), h is 2. In some embodiments of a compound of Formula (I), (Ia), (Ia'), (Ib), or (Ic), h is 3. In some embodiments of a compound of Formula (I), (Ia), (Ia'), (Ib), or (Ic), h is 4. In some embodiments of a compound of Formula (I), (Ia), (Ia'), (Ib), or (Ic), h is 5. In some embodiments of a compound of Formula (I), (Ia), (Ia'), (Ib), or (Ic), h is 6. In some embodiments of a compound of Formula (I), (Ia), (Ia'), (Ib), or (Ic), h is 7. In some embodiments of a compound of Formula (I), (Ia), (Ia'), (Ib), or (Ic), h is 8.

In some embodiments of a compound of Formula (I), (Ia), (Ia'), (Ib), or (Ic), i is 0-5. In some embodiments of a compound of Formula (I), (Ia), (Ia'), (Ib), or (Ic), i is 0-4. In some embodiments of a compound of Formula (I), (Ia), (Ia'), (Ib), or (Ic), i is 0-3. In some embodiments of a compound of Formula (I), (Ia), (Ia'), (Ib), or (Ic), i is 0-2. In some embodiments of a compound of Formula (I), (Ia), (Ia'), (Ib), or (Ic), i is 5-7. In some embodiments of a compound of Formula (I), (Ia), (Ia'), (Ib), or (Ic), i is 0. In some embodiments of a compound of Formula (I), (Ia), (Ia'), (Ib), or (Ic), i is 1. In some embodiments of a compound of Formula (I), (Ia), (Ia'), (Ib), or (Ic), i is 2. In some embodiments of a compound of Formula (I), (Ia), (Ia'), (Ib), or (Ic), i is 3. In some embodiments of a compound of Formula (I), (Ia), (Ia'), (Ib), or (Ic), i is 4. In some embodiments of a compound of Formula (I), (Ia), (Ia'), (Ib), or (Ic), i is 5. In some embodiments of a compound of Formula (I), (Ia), (Ia'), (Ib), or (Ic), i is 6. In some embodiments of a compound of Formula (I), (Ia), (Ia'), (Ib), or (Ic), i is 7.

In some embodiments of a compound of Formula (I), (Ia), (Ia'), (Ib), or (Ic), j is 0-5. In some embodiments of a compound of Formula (I), (Ia), (Ia'), (Ib), or (Ic), j is 0-4. In some embodiments of a compound of Formula (I), (Ia), (Ia'), (Ib), or (Ic), j is 0-3. In some embodiments of a compound of Formula (I), (Ia), (Ia'), (Ib), or (Ic), j is 0-2. In some embodiments of a compound of Formula (I), (Ia), (Ia'), (Ib), or (Ic), j is 5-7. In some embodiments of a compound of Formula (I), (Ia), (Ia'), (Ib), or (Ic), j is 0. In some embodiments of a compound of Formula (I), (Ia), (Ia'), (Ib), or (Ic), j is 1. In some embodiments of a compound of Formula (I), (Ia), (Ia'), (Ib), or (Ic), j is 2. In some embodiments of a compound of Formula (I), (Ia), (Ia'), (Ib), or (Ic), j is 3. In some embodiments of a compound of Formula (I), (Ia), (Ia'), (Ib), or (Ic), j is 4. In some embodiments of a compound of Formula (I), (Ia), (Ia'), (Ib), or (Ic), j is 5. In some embodiments of a compound of Formula (I), (Ia), (Ia'), (Ib), or (Ic), j is 6. In some embodiments of a compound of Formula (I), (Ia), (Ia'), (Ib), or (Ic), j is 7.

In some embodiments of a compound of Formula (I), (Ia), (Ia'), (Ib), or (Ic), k is 0-5. In some embodiments of a compound of Formula (I), (Ia), (Ia'), (Ib), or (Ic), k is 0-4. In some embodiments of a compound of Formula (I), (Ia), (Ia'), (Ib), or (Ic), k is 0-3. In some embodiments of a compound of Formula (I), (Ia), (Ia'), (Ib), or (Ic), k is 0-2. In some embodiments of a compound of Formula (I), (Ia), (Ia'), (Ib), or (Ic), k is 5-7. In some embodiments of a compound of Formula (I), (Ia), (Ia'), (Ib), or (Ic), k is 0. In some embodiments of a compound of Formula (I), (Ia), (Ia'), (Ib), or (Ic), k is 1. In some embodiments of a compound of Formula (I), (Ia), (Ia'), (Ib), or (Ic), k is 2. In some embodiments of a compound of Formula (I), (Ia), (Ia'), (Ib), or (Ic), k is 3. In some embodiments of a compound of Formula (I), (Ia), (Ia'), (Ib), or (Ic), k is 4. In some embodiments of a compound of Formula (I), (Ia), (Ia'), (Ib), or (Ic), k is 5. In some embodiments of a compound of Formula (I), (Ia), (Ia'), (Ib), or (Ic), k is 6. In some embodiments of a compound of Formula (I), (Ia), (Ia'), (Ib), or (Ic), k is 7.

In some embodiments of a compound of Formula (I), (Ia), (Ia'), (Ib), or (Ic), l is 0-5. In some embodiments of a compound of Formula (I), (Ia), (Ia'), (Ib), or (Ic), l is 0-4. In some embodiments of a compound of Formula (I), (Ia), (Ia'), (Ib), or (Ic), l is 0-3. In some embodiments of a compound of Formula (I), (Ia), (Ia'), (Ib), or (Ic), l is 0-2. In some embodiments of a compound of Formula (I), (Ia), (Ia'), (Ib), or (Ic), l is 5-6. In some embodiments of a compound of Formula (I), (Ia), (Ia'), (Ib), or (Ic), l is 0. In some embodiments of a compound of Formula (I), (Ia), (Ia'), (Ib), or (Ic), l is 1. In some embodiments of a compound of Formula (I), (Ia), (Ia'), (Ib), or (Ic), l is 2. In some embodiments of a compound of Formula (I), (Ia), (Ia'), (Ib), or (Ic), l is 3. In some embodiments of a compound of Formula (I), (Ia), (Ia'), (Ib), or (Ic), l is 4. In some embodiments of a compound of Formula (I), (Ia), (Ia'), (Ib), or (Ic), l is 5. In some embodiments of a compound of Formula (I), (Ia), (Ia'), (Ib), or (Ic), l is 6.

In some embodiments of a compound of Formula (I), (Ia), (Ia'), (Ib), or (Ic), m is 0-5. In some embodiments of a compound of Formula (I), (Ia), (Ia'), (Ib), or (Ic), m is 0-4. In some embodiments of a compound of Formula (I), (Ia), (Ia'), (Ib), or (Ic), m is 0-3. In some embodiments of a compound of Formula (I), (Ia), (Ia'), (Ib), or (Ic), m is 0-2. In some embodiments of a compound of Formula (I), (Ia), (Ia'), (Ib), or (Ic), m is 5-6. In some embodiments of a compound of Formula (I), (Ia), (Ia'), (Ib), or (Ic), m is 0. In some embodiments of a compound of Formula (I), (Ia), (Ia'), (Ib), or (Ic), m is 1. In some embodiments of a compound of Formula (I), (Ia), (Ia'), (Ib), or (Ic), m is 2. In some embodiments of a compound of Formula (I), (Ia), (Ia'), (Ib), or (Ic), m is 3. In some embodiments of a compound of Formula (I), (Ia), (Ia'), (Ib), or (Ic), m is 4. In some embodiments of a compound of Formula (I), (Ia), (Ia'), (Ib), or (Ic), m is 5. In some embodiments of a compound of Formula (I), (Ia), (Ia'), (Ib), or (Ic), m is 6.

In some embodiments of a compound of Formula (I), (Ia), (Ia'), (Ib), or (Ic), n is 0-5. In some embodiments of a compound of Formula (I), (Ia), (Ia'), (Ib), or (Ic), n is 0-4. In some embodiments of a compound of Formula (I), (Ia), (Ia'), (Ib), or (Ic), n is 0-3. In some embodiments of a compound of Formula (I), (Ia), (Ia'), (Ib), or (Ic), n is 0-2. In some embodiments of a compound of Formula (I), (Ia), (Ia'), (Ib), or (Ic), n is 5-6. In some embodiments of a compound of Formula (I), (Ia), (Ia'), (Ib), or (Ic), n is 0. In some embodiments of a compound of Formula (I), (Ia), (Ia'), (Ib), or (Ic), n is 1. In some embodiments of a compound of Formula (I), (Ia), (Ia'), (Ib), or (Ic), n is 2. In some embodiments of a compound of Formula (I), (Ia), (Ia'), (Ib), or (Ic), n is 3. In some embodiments of a compound of Formula (I), (Ia), (Ia'), (Ib), or (Ic), n is 4. In some embodiments of a compound of Formula (I), (Ia), (Ia'), (Ib), or (Ic), n is 5. In some embodiments of a compound of Formula (I), (Ia), (Ia'), (Ib), or (Ic), n is 6.

In some embodiments of a compound of Formula (I), (Ia), (Ia'), (Ib), or (Ic), each $R^{7a}$ and $R^{7b}$ is independently hydrogen, halogen, —CN, —$OR^a$, —$NR^cR^d$, —$CO_2R^a$, —C(=O)$NR^cR^d$, optionally substituted $C_1$-$C_6$ alkyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (I), (Ia), (Ia'), (Ib), or (Ic), each $R^{7a}$ and $R^{7b}$ is independently hydrogen, halogen, —CN, —$OR^a$, —$NR^cR^d$, —$CO_2R^a$, —C(=O)$NR^cR^d$, optionally substituted $C_1$-$C_6$ alkyl, or optionally substituted $C_1$-$C_6$ heteroalkyl. In some embodiments of a compound of Formula (I), (Ia), (Ia'), (Ib), or (Ic), each $R^{7a}$ and $R^{7b}$ is independently hydrogen, halogen, —CN, —$OR^a$, —$NR^cR^d$, optionally substituted $C_1$-$C_6$ alkyl, or optionally substituted $C_1$-$C_6$ heteroalkyl. In some embodiments of a compound of Formula (I), (Ia), (Ia'), (Ib), or (Ic), each $R^{7a}$ and $R^{7b}$ is independently hydrogen, halogen, or optionally substituted $C_1$-$C_6$ alkyl. In some embodiments of a compound of Formula (I), (Ia), (Ia'), (Ib), or (Ic), each $R^{7a}$ and $R^{7b}$ is independently hydrogen, halogen, $C_1$-$C_6$ alkyl, or $C_1$-$C_6$ haloalkyl. In some embodiments of a compound of Formula (I), (Ia), (Ia'), (Ib), or (Ic), each $R^{7a}$ and $R^{7b}$ is independently hydrogen or halogen. In some embodiments of a compound of Formula (I), (Ia), (Ia'), (Ib), or (Ic), each $R^{7a}$ and $R^{7b}$ is hydrogen. In some embodiments of a compound of Formula (I), (Ia), (Ia'), (Ib), or (Ic), $R^{7a}$ and $R^{7b}$ on the same carbon atom are taken together to form an oxo. In some embodiments of a compound of Formula (I), (Ia), (Ia'), (Ib), or (Ic), two $R^{7a}$ are taken together to form a cycloalkyl. In some embodiments, the cycloalkyl is cyclopropyl, cyclobutyl, cyclopentyl, or cyclobutyl. In some embodiments of a compound of Formula (I), (Ia), (Ia'), (Ib), or (Ic), the two $R^{7a}$ are on the same carbon. In some embodiments of a compound of Formula (I), (Ia), (Ia'), (Ib), or (Ic), the two $R^{7a}$ are on adjacent carbons. In some embodiments of a compound of Formula (I), (Ia), (Ib), or (Ic), the two $R^{7a}$ are on adjacent carbons +1. In some embodiments of a compound of Formula (I), (Ia), (Ia'), (Ib), or (Ic), the two $R^{7a}$ are on adjacent carbons +2.

In some embodiments of a compound of Formula (I), (Ia), (Ia'), (Ib), or (Ic), each $R^{7c}$ is independently hydrogen or optionally substituted $C_1$-$C_6$ alkyl. In some embodiments of a compound of Formula (I), (Ia), (Ia'), (Ib), or (Ic), each $R^{7c}$ is independently hydrogen, $C_1$-$C_6$ alkyl, or $C_1$-$C_6$ haloalkyl. In some embodiments of a compound of Formula (I), (Ia), (Ia'), (Ib), or (Ic), each $R^{7c}$ is independently hydrogen or $C_1$-$C_6$ alkyl. In some embodiments of a compound of Formula (I), (Ia), (Ia'), (Ib), or (Ic), each $R^{7c}$ is hydrogen.

In some embodiments of a compound of Formula (I), (Ia), (Ia'), (Ib), or (Ic), L is selected from:

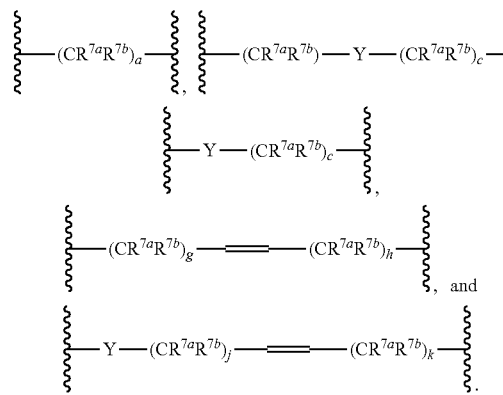

In some embodiments of a compound of Formula (I), (Ia), (Ia'), (Ib), or (Ic), L is

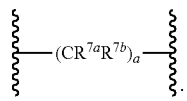

In some embodiments of a compound of Formula (I), (Ia), (Ia'), (Ib), or (Ic), L is

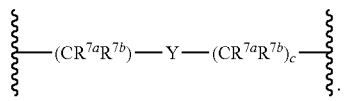

In some embodiments of a compound of Formula (I), (Ia), (Ia'), (Ib), or (Ic), L is

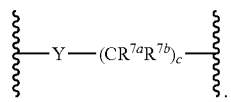

In some embodiments of a compound of Formula (I), (Ia), (Ia'), (Ib), or (Ic), L is

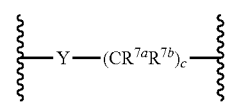

and 2 $R^{7a}$ are taken together to form a cycloalkyl. In some embodiments of a compound of Formula (I), (Ia), (Ia'), (Ib), or (Ic), L is

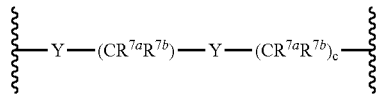

and 2 $R^{7a}$ are taken together to form a cycloalkyl.

In some embodiments of a compound of Formula (I), (Ia), (Ia'), (Ib), or (Ic), L is selected from:

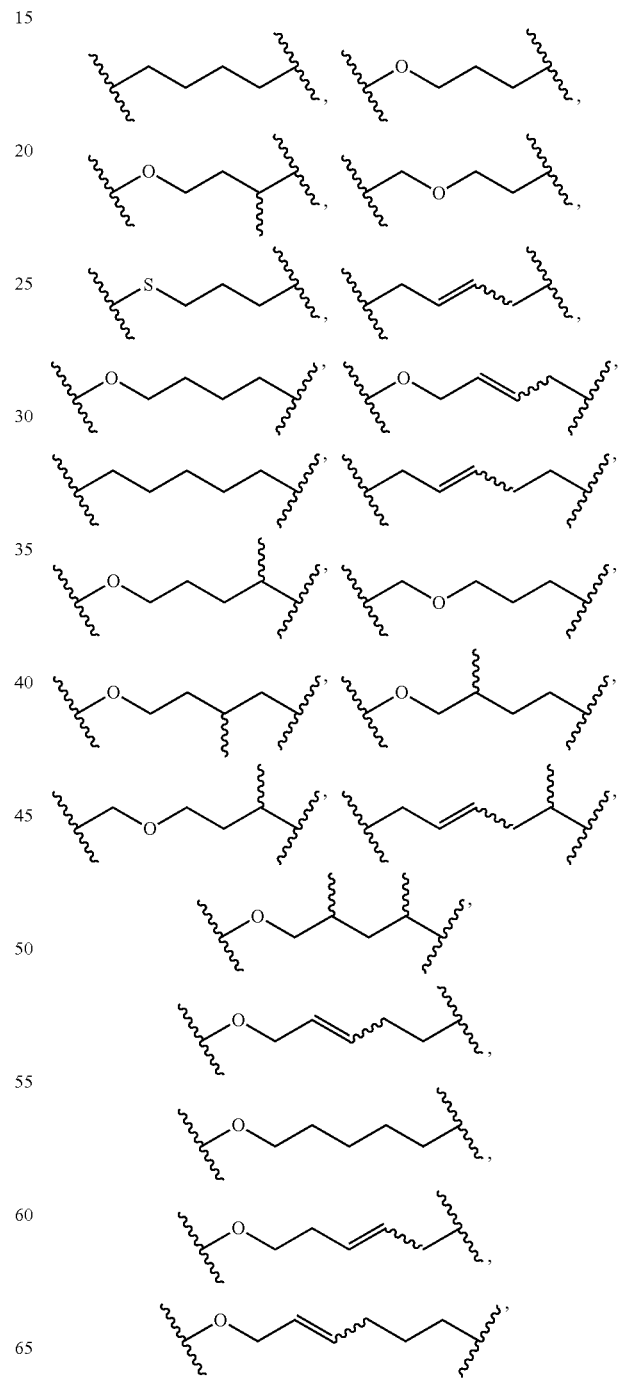

-continued

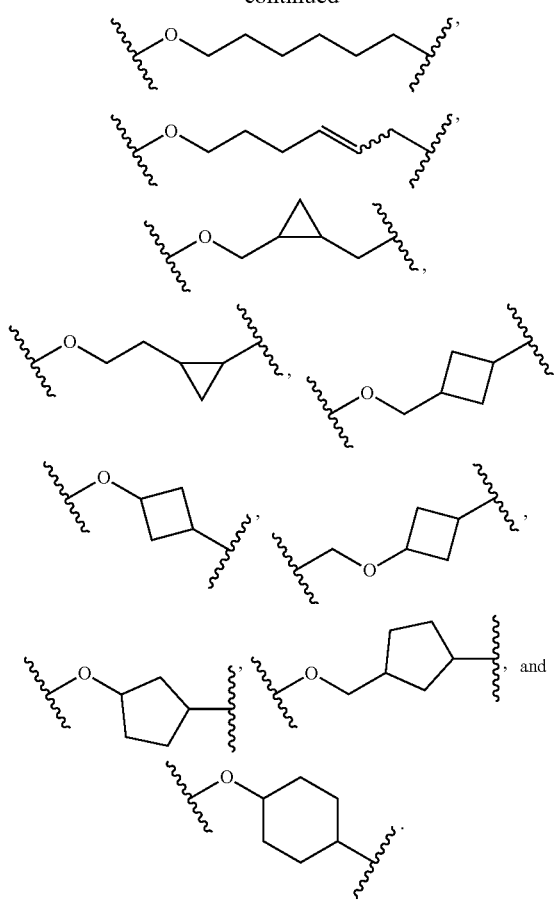

In some embodiments of a compound of Formula (I), (Ia), (Ia'), (Ib), or (Ic), L is selected from:

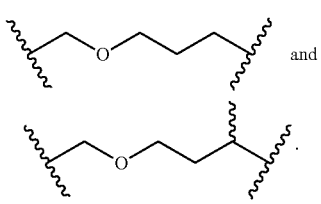 and

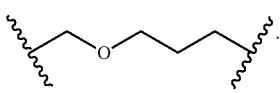 [SMILES: *CCCOC*]

In some embodiments of a compound of Formula (I), (Ia), (Ia'), (Ib), or (Ic), L is

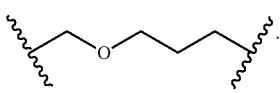 [SMILES: *CCCOC*]

In some embodiments of a compound of Formula (I), (Ia), (Ia'), (Ib), or (Ic), L is

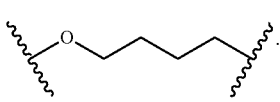 [SMILES: *CCCCO*]

In some embodiments of a compound of Formula (I), (Ia), (Ia'), (Ib), or (Ic), L is

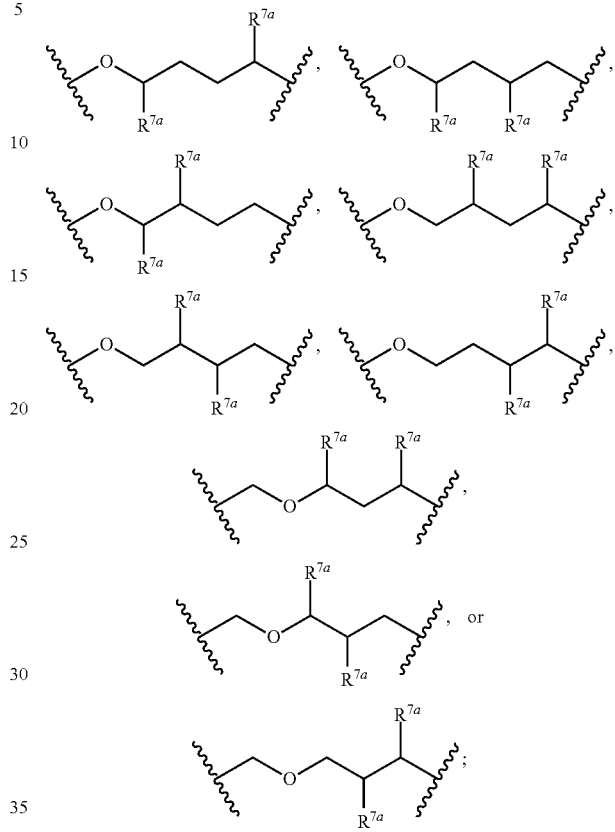

and 2 $R^{7a}$ are taken together to form a cycloalkyl selected from cyclopropyl, cyclobutyl, cyclopentyl and cyclohexyl.

In some embodiments of a compound of Formula (I), (Ia), (Ia'), (Ib), or (Ic), L is selected from:

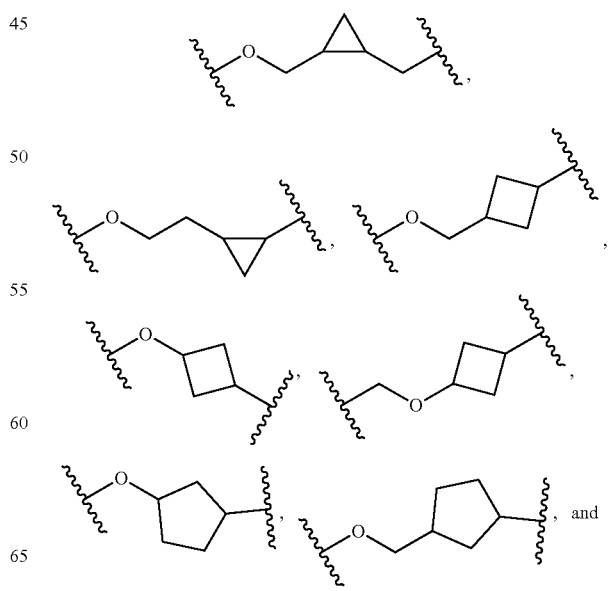

-continued

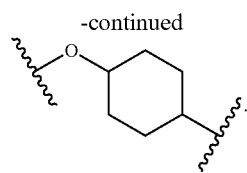

In some embodiments of a compound of Formula (I), (Ia), (Ia'), (Ib), or (Ic), $R^a$ is hydrogen, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), (Ib), or (Ic), $R^a$ is hydrogen or optionally substituted $C_1$-$C_6$ alkyl. In some embodiments of a compound of Formula (I), (Ia), (Ia'), (Ib), or (Ic), $R^a$ is hydrogen, $C_1$-$C_6$ alkyl, or $C_1$-$C_6$ haloalkyl. In some embodiments of a compound of Formula (I), (Ia), (Ia'), (Ib), or (Ic), $R^a$ is hydrogen or $C_1$-$C_6$ alkyl. In some embodiments of a compound of Formula (I), (Ia), (Ia'), (Ib), or (Ic), $R^a$ is hydrogen. In some embodiments of a compound of Formula (I), (Ia), (Ia'), (Ib), or (Ic), $R^a$ is $C_1$-$C_6$ alkyl. In some embodiments of a compound of Formula (I), (Ia), (Ia'), (Ib), or (Ic), $R^a$ is heterocycloalkyl.

In some embodiments of a compound of Formula (I), (Ia), (Ia'), (Ib), or (Ic), $R^b$ is optionally substituted $C_1$-$C_6$ alkyl or optionally substituted $C_1$-$C_6$ heteroalkyl. In some embodiments of a compound of Formula (I), (Ia), (Ia'), (Ib), or (Ic), $R^b$ is optionally substituted $C_1$-$C_6$ alkyl. In some embodiments of a compound of Formula (I), (Ia), (Ia'), (Ib), or (Ic), $R^b$ is $C_1$-$C_6$ alkyl or $C_1$-$C_6$ haloalkyl. In some embodiments of a compound of Formula (I), (Ia), (Ia'), (Ib), or (Ic), $R^b$ is $C_1$-$C_6$ alkyl.

In some embodiments of a compound of Formula (I), (Ia), (Ia'), (Ib), or (Ic), each $R^c$ and $R^d$ is independently hydrogen, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (I), (Ia), (Ia'), (Ib), or (Ic), each $R^c$ and $R^d$ is independently hydrogen or optionally substituted $C_1$-$C_6$ alkyl. In some embodiments of a compound of Formula (I), (Ia), (Ia'), (Ib), or (Ic), each and $R^d$ is independently hydrogen, $C_1$-$C_6$ alkyl, or $C_1$-$C_6$ haloalkyl. In some embodiments of a compound of Formula (I), (Ia), (Ia'), (Ib), or (Ic), each $R^c$ and $R^d$ is independently hydrogen or $C_1$-$C_6$ alkyl. In some embodiments of a compound of Formula (I), (Ia), (Ia'), (Ib), or (Ic), each $R^c$ and $R^d$ is hydrogen.

In some embodiments of a compound of Formula (I), (Ia), (Ia'), (Ib), or (Ic), $R^c$ and $R^d$, together with the nitrogen atom to which they are attached, form an optionally substituted heterocycloalkyl or optionally substituted heteroaryl. In some embodiments of a compound of Formula (I), (Ia), (Ia'), (Ib), or (Ic), $R^c$ and $R^d$, together with the nitrogen atom to which they are attached, form an optionally substituted heterocycloalkyl.

In some embodiments is a compound of Formula (I), (Ia), (Ia'), (Ib), or (Ic), or a pharmaceutically acceptable salt, solvate, or stereoisomer thereof, having a structure selected from:

| Ex. | Structure |
| --- | --- |
| 1 | 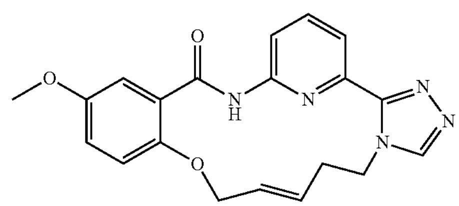 [SMILES: COc1ccc2c(c1)C(=O)Nc1cccc(n1)-c1nncn1CC/C=C/CO2] |
| 2 | 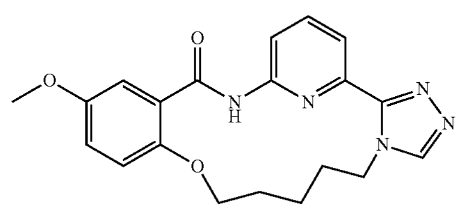 [SMILES: COc1ccc2c(c1)C(=O)Nc1cccc(n1)-c1nncn1CCCCCO2] |
| 3 | 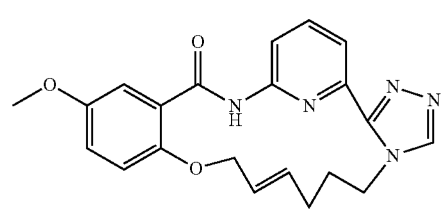 [SMILES: COc1ccc2c(c1)C(=O)Nc1cccc(n1)-c1nncn1CCC/C=C/CO2] |
| 4 | 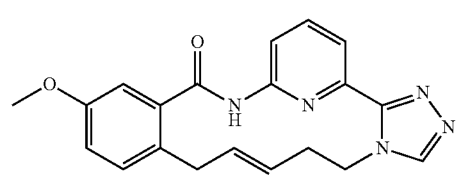 [SMILES: COc1ccc2c(c1)C(=O)Nc1cccc(n1)-c1nncn1CC/C=C/C2] |

| Ex. | Structure |
|---|---|
| 5 | 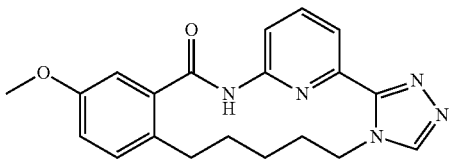 [SMILES: COc1ccc2c(c1)C(=O)Nc1cccc(n1)-c1nncn1CCCCC2] |
| 6 | 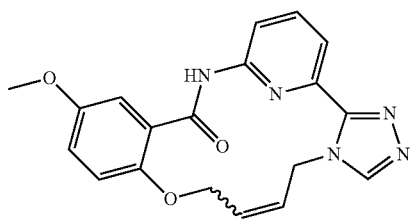 [SMILES: COc1ccc2c(c1)C(=O)Nc1cccc(n1)-c1nncn1CC=CCO2] |
| 7 | 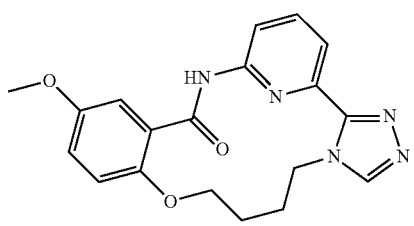 [SMILES: COc1ccc2c(c1)C(=O)Nc1cccc(n1)-c1nncn1CCCCO2] |
| 8 | 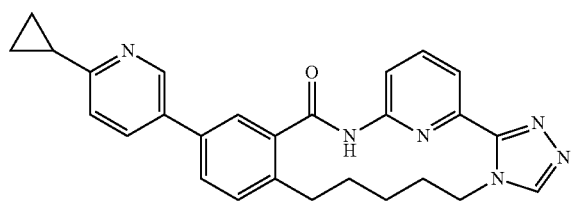 [SMILES: O=C1Nc2cccc(n2)-c2nncn2CCCCCc2ccc(-c3ccc(C4CC4)nc3)cc21] |
| 9 | 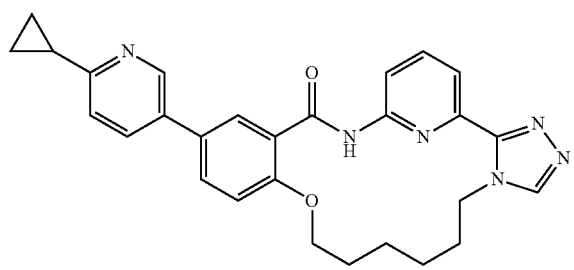 [SMILES: O=C1Nc2cccc(n2)-c2nncn2CCCCCCOc2ccc(-c3ccc(C4CC4)nc3)cc21] |
| 10 | 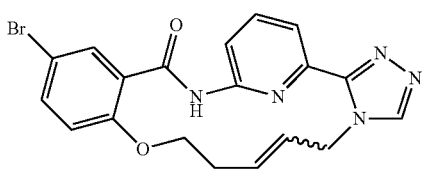 [SMILES: O=C1Nc2cccc(n2)-c2nncn2CC=CCCOc2ccc(Br)cc21] |
| 11 | 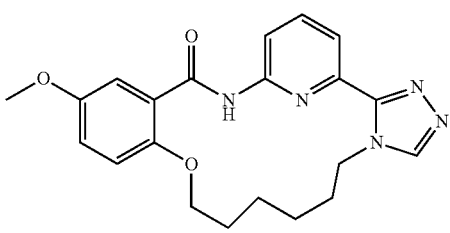 [SMILES: COc1ccc2c(c1)C(=O)Nc1cccc(n1)-c1nncn1CCCCCCO2] |

-continued
| Ex. | Structure |
|---|---|
| 12 | 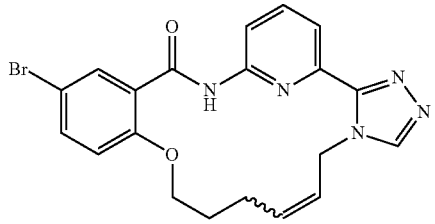 [SMILES: O=C1Nc2cccc(n2)-c2nncn2CC=CCCCOc2ccc(Br)cc21] |
| 13 | 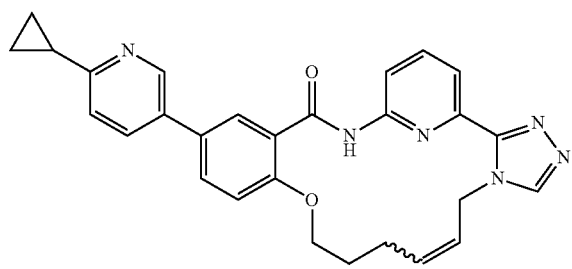 [SMILES: O=C1Nc2cccc(n2)-c2nncn2CC=CCCCOc2ccc(-c3ccc(C4CC4)nc3)cc21] |
| 14 | 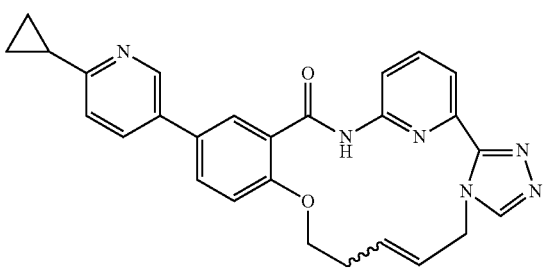 [SMILES: O=C1Nc2cccc(n2)-c2nncn2CC=CCCOc2ccc(-c3ccc(C4CC4)nc3)cc21] |
| 15 | 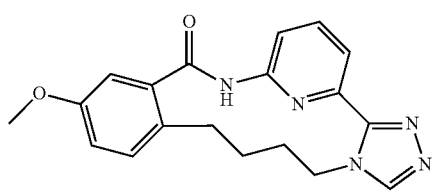 [SMILES: COc1ccc2c(c1)C(=O)Nc1cccc(n1)-c1nncn1CCCC2] |
| 16 | 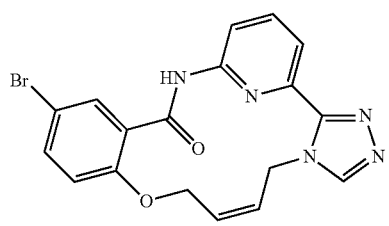 [SMILES: O=C1Nc2cccc(n2)-c2nncn2C/C=C\COc2ccc(Br)cc21] |
| 17 | 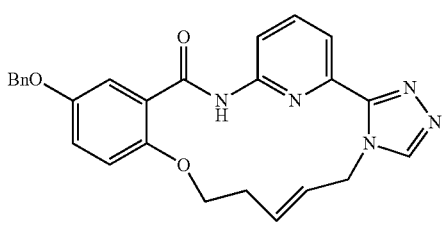 [SMILES: O=C1Nc2cccc(n2)-c2nncn2C/C=C/CCOc2ccc(OCc3ccccc3)cc21] |

| Ex. | Structure |
|---|---|
| 18 | 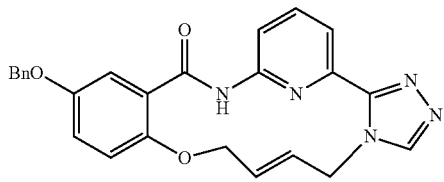 [SMILES: O=C1Nc2cccc(n2)-c2nncn2C/C=C/COc2ccc(OCc3ccccc3)cc21] |
| 19 | 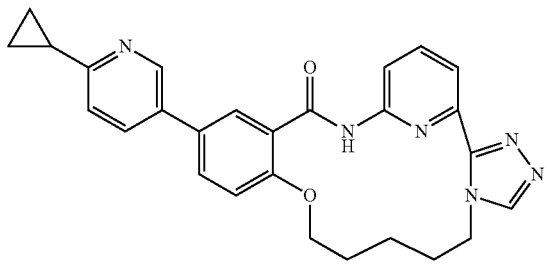 [SMILES: O=C1Nc2cccc(n2)-c2nncn2CCCCCOc2ccc(-c3ccc(C4CC4)nc3)cc21] |
| 20 | 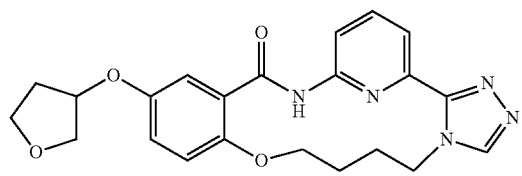 [SMILES: O=C1Nc2cccc(n2)-c2nncn2CCCCOc2ccc(OC3CCOC3)cc21] |
| 21 | 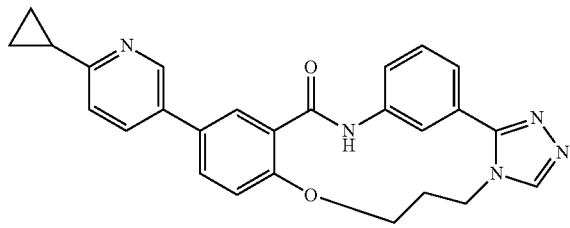 [SMILES: O=C1Nc2cccc(c2)-c2nncn2CCCOc2ccc(-c3ccc(C4CC4)nc3)cc21] |
| 22 | 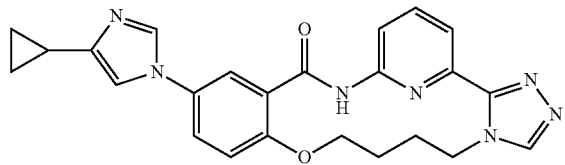 [SMILES: O=C1Nc2cccc(n2)-c2nncn2CCCCOc2ccc(-n3cnc(C4CC4)c3)cc21] |
| 23 | 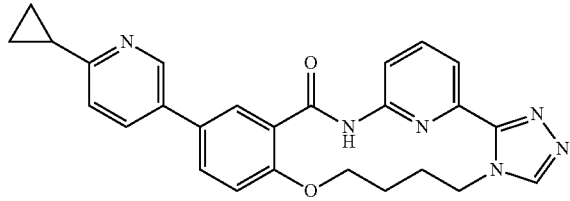 [SMILES: O=C1Nc2cccc(n2)-c2nncn2CCCCOc2ccc(-c3ccc(C4CC4)nc3)cc21] |
| 24 | 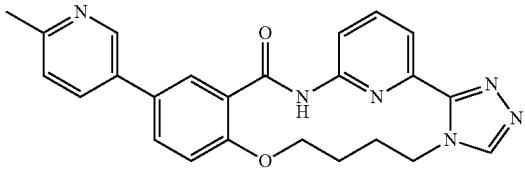 [SMILES: Cc1ccc(-c2ccc3c(c2)C(=O)Nc2cccc(n2)-c2nncn2CCCCO3)cn1] |

| Ex. | Structure |
|---|---|
| 25 | 4,5-difluoro-2-(4-(4H-1,2,4-triazol-4-yl)butoxy)-N-(6-(4H-1,2,4-triazol-3-yl)pyridin-2-yl)benzamide |
| 28 | 5-bromo-4-fluoro-2-(4-(4H-1,2,4-triazol-4-yl)butoxy)-N-(6-(4H-1,2,4-triazol-3-yl)pyridin-2-yl)benzamide |
| 29 | 4,5-dimethoxy-2-(4-(4H-1,2,4-triazol-4-yl)butoxy)-N-(6-(4H-1,2,4-triazol-3-yl)pyridin-2-yl)benzamide |
| 30 | 2,2-dimethyl-5-(4-(4H-1,2,4-triazol-4-yl)butoxy)-N-(6-(4H-1,2,4-triazol-3-yl)pyridin-2-yl)-2,3-dihydrobenzofuran-6-carboxamide |
| 31 | 5-cyano-2-(4-(4H-1,2,4-triazol-4-yl)butoxy)-N-(6-(4H-1,2,4-triazol-3-yl)pyridin-2-yl)benzamide |
| 32 | 2-(4-(4H-1,2,4-triazol-4-yl)butoxy)-5-(trifluoromethyl)-N-(6-(4H-1,2,4-triazol-3-yl)pyridin-2-yl)benzamide |
| 33 | 5-bromo-2-(3-(4H-1,2,4-triazol-4-yl)propoxy)-N-(6-(4H-1,2,4-triazol-3-yl)pyridin-2-yl)benzamide |
| 35 | 5-fluoro-2-(4-(4H-1,2,4-triazol-4-yl)butoxy)-N-(6-(4H-1,2,4-triazol-3-yl)pyridin-2-yl)benzamide |

| Ex. | Structure |
|---|---|
| 37 | 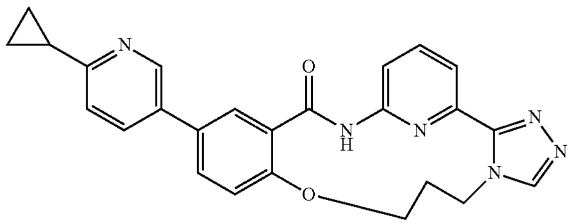 [SMILES: O=C1Nc2cccc(n2)-c2nncn2CCCOc2ccc(-c3ccc(C4CC4)nc3)cc21] |
| 38 | 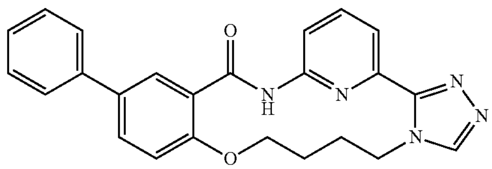 [SMILES: O=C1Nc2cccc(n2)-c2nncn2CCCCOc2ccc(-c3ccccc3)cc21] |
| 39 | 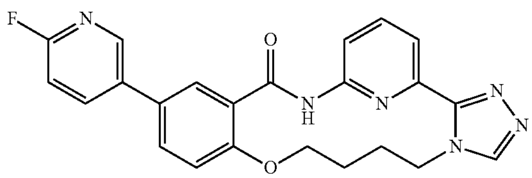 [SMILES: O=C1Nc2cccc(n2)-c2nncn2CCCCOc2ccc(-c3ccc(F)nc3)cc21] |
| 40 | 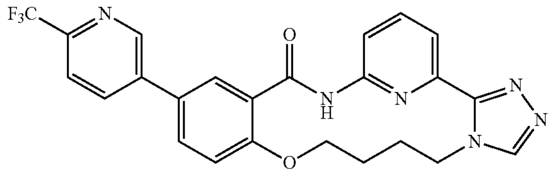 [SMILES: O=C1Nc2cccc(n2)-c2nncn2CCCCOc2ccc(-c3ccc(C(F)(F)F)nc3)cc21] |
| 41 | 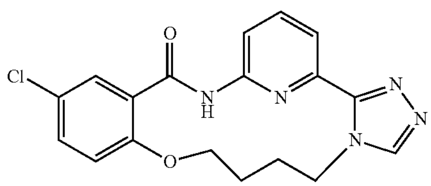 [SMILES: O=C1Nc2cccc(n2)-c2nncn2CCCCOc2ccc(Cl)cc21] |
| 42 | 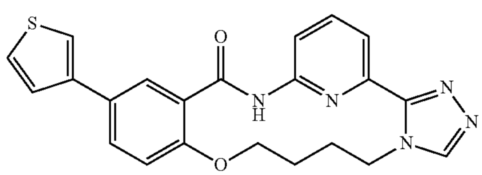 [SMILES: O=C1Nc2cccc(n2)-c2nncn2CCCCOc2ccc(-c3ccsc3)cc21] |
| 43 | 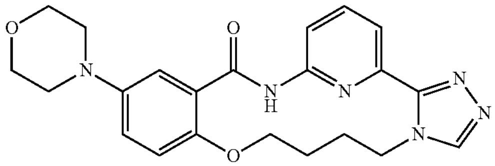 [SMILES: O=C1Nc2cccc(n2)-c2nncn2CCCCOc2ccc(N3CCOCC3)cc21] |
| 44 | 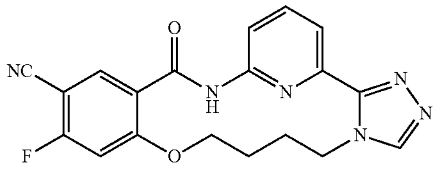 [SMILES: N#Cc1cc2c(cc1F)OCCCCn1cnnc1-c1cccc(n1)NC2=O] |

-continued
| Ex. | Structure |
|---|---|
| 45 | 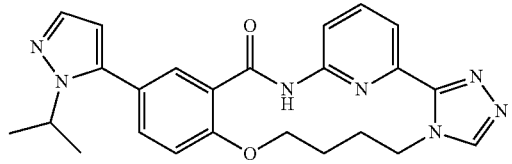 |
| 46 | 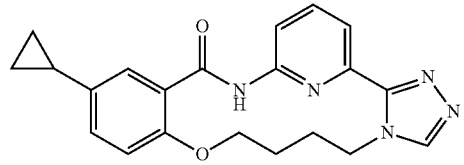 [SMILES: O=C1Nc2cccc(n2)-c2nncn2CCCCOc2ccc(C3CC3)cc21] |
| 47 | 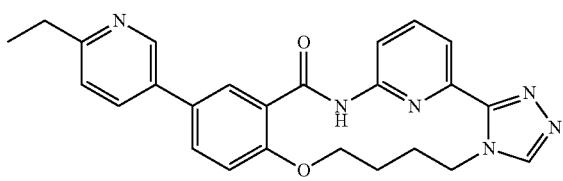 [SMILES: CCc1ccc(-c2ccc3c(c2)C(=O)Nc2cccc(n2)-c2nncn2CCCCO3)cn1] |
| 48 | 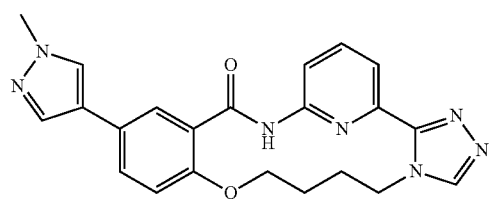 [SMILES: Cn1cc(-c2ccc3c(c2)C(=O)Nc2cccc(n2)-c2nncn2CCCCO3)cn1] |
| 50 | 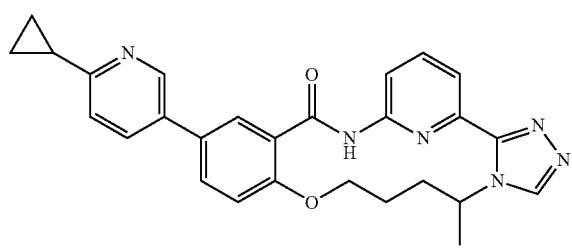 [SMILES: CC1CCCOc2ccc(-c3ccc(C4CC4)nc3)cc2C(=O)Nc2cccc(n2)-c2nncn21] |
| 51 | 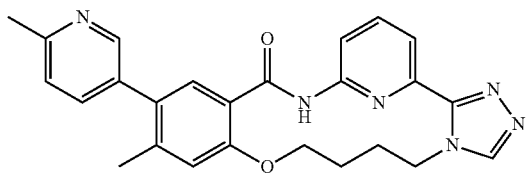 [SMILES: Cc1ccc(-c2cc3c(cc2C)OCCCCn2cnnc2-c2cccc(n2)NC3=O)cn1] |
| 52 | 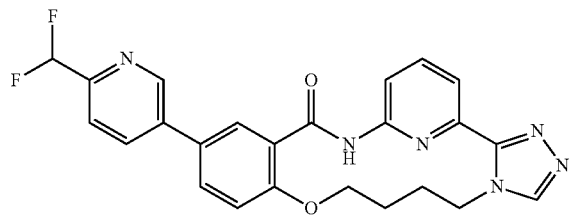 [SMILES: O=C1Nc2cccc(n2)-c2nncn2CCCCOc2ccc(-c3ccc(C(F)F)nc3)cc21] |

| Ex. | Structure |
|---|---|
| 53 | 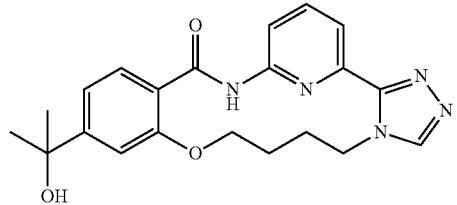 [SMILES: CC(C)(O)c1ccc2c(c1)OCCCCn1cnnc1-c1cccc(n1)NC2=O] |
| 54 | 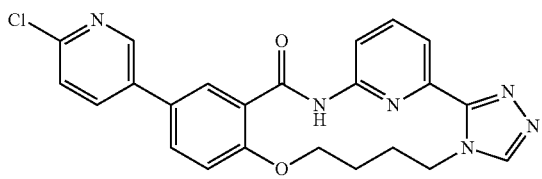 [SMILES: O=C1Nc2cccc(n2)-c2nncn2CCCCOc2ccc(-c3ccc(Cl)nc3)cc21] |
| 55 | 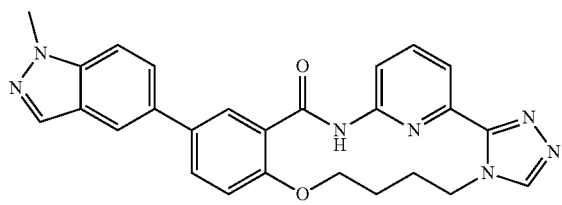 [SMILES: Cn1ncc2cc(-c3ccc4c(c3)C(=O)Nc3cccc(n3)-c3nncn3CCCCO4)ccc21] |
| 56 | 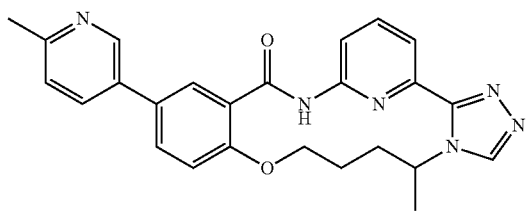 [SMILES: Cc1ccc(-c2ccc3c(c2)C(=O)Nc2cccc(n2)-c2nncn2C(C)CCCO3)cn1] |
| 57 | 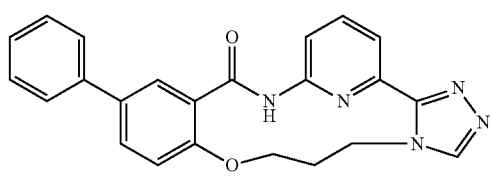 [SMILES: O=C1Nc2cccc(n2)-c2nncn2CCCOc2ccc(-c3ccccc3)cc21] |
| 58 | 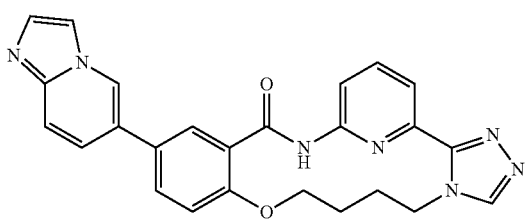 [SMILES: O=C1Nc2cccc(n2)-c2nncn2CCCCOc2ccc(-c3ccc4nccn4c3)cc21] |
| 59 | 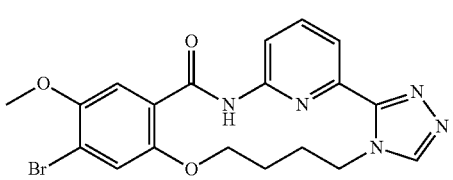 [SMILES: COc1cc2c(cc1Br)OCCCCn1cnnc1-c1cccc(n1)NC2=O] |

-continued
| Ex. | Structure |
|---|---|
| 60 | 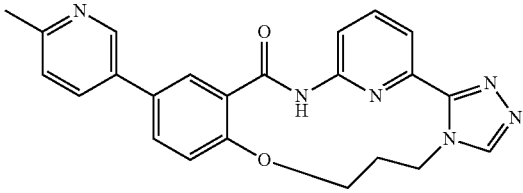 [SMILES: Cc1ccc(-c2ccc3c(c2)C(=O)Nc2cccc(n2)-c2nncn2CCCO3)cn1] |
| 61 | 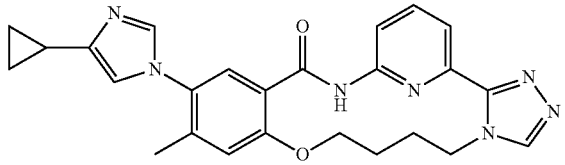 [SMILES: Cc1cc2c(cc1-n1cnc(C3CC3)c1)C(=O)Nc1cccc(n1)-c1nncn1CCCCO2] |
| 62 | 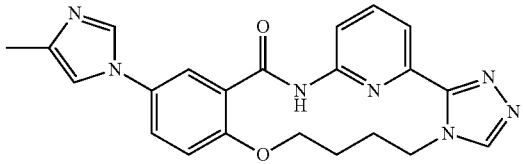 [SMILES: Cc1cn(-c2ccc3c(c2)C(=O)Nc2cccc(n2)-c2nncn2CCCCO3)cn1] |
| 63 | 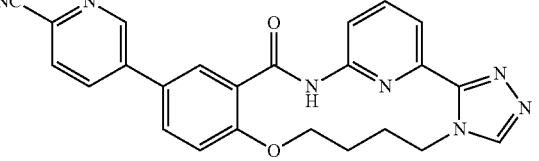 |
| 64 | 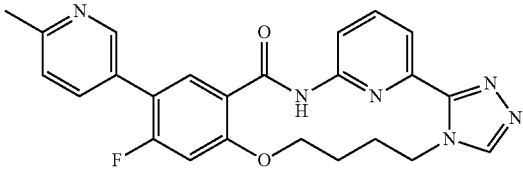 |
| 65 | 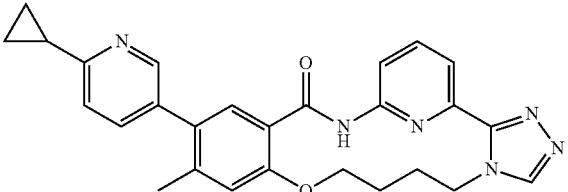 |
| 66 | 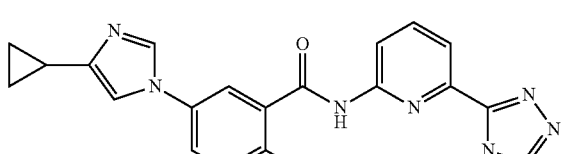 |
| 67 | 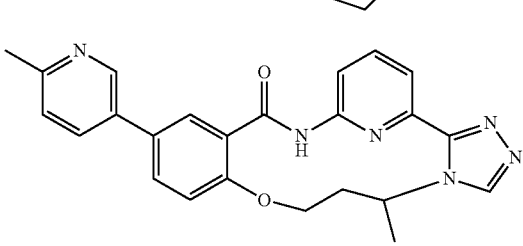 |

| Ex. | Structure |
|---|---|
| 68 | 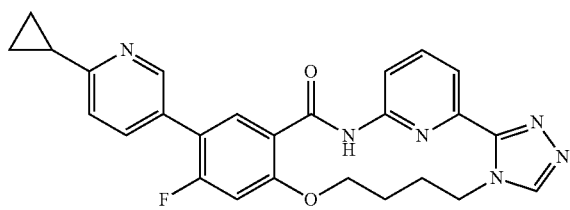 [SMILES: O=C1Nc2cccc(n2)-c2nncn2CCCCOc2cc(F)c(-c3ccc(C4CC4)nc3)cc21] |
| 69 | 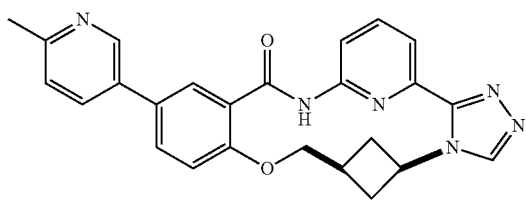 |
| 70 | 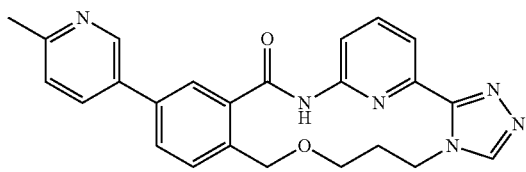 [SMILES: Cc1ccc(-c2ccc3c(c2)C(=O)Nc2cccc(n2)-c2nncn2CCCOC3)cn1] |
| 71 | 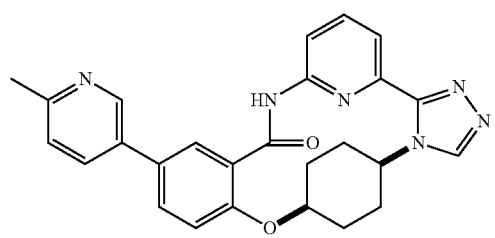 |
| 72 | 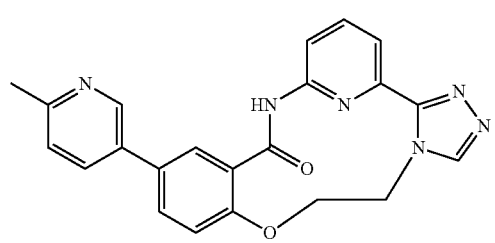 [SMILES: Cc1ccc(-c2ccc3c(c2)C(=O)Nc2cccc(n2)-c2nncn2CCO3)cn1] |
| 73 | 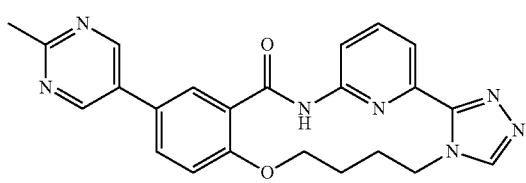 [SMILES: Cc1ncc(-c2ccc3c(c2)C(=O)Nc2cccc(n2)-c2nncn2CCCCO3)cn1] |
| 74 | 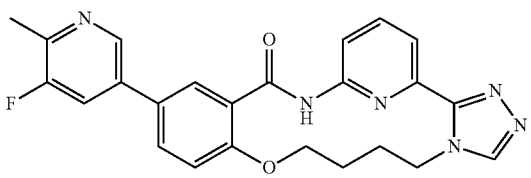 [SMILES: Cc1ncc(-c2ccc3c(c2)C(=O)Nc2cccc(n2)-c2nncn2CCCCO3)cc1F] |

-continued
| Ex. | Structure |
|---|---|
| 75 | 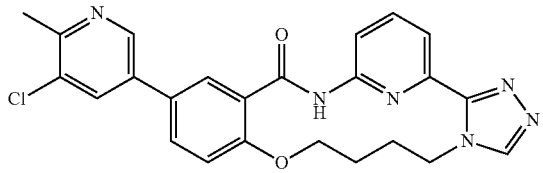 |
| 77 | 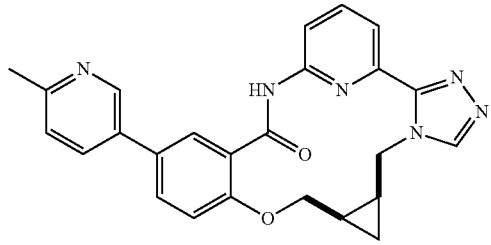 |
| 78 | 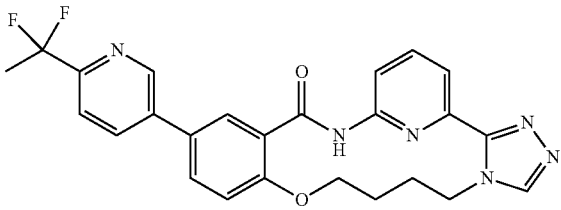 [SMILES: CC(F)(F)c1ccc(-c2ccc3c(c2)C(=O)Nc2cccc(n2)-c2nncn2CCCCO3)cn1] |
| 79 | 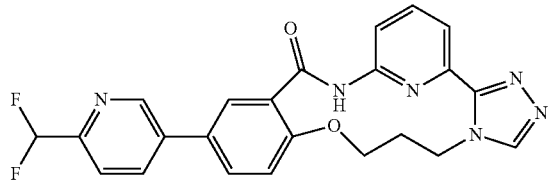 [SMILES: O=C1Nc2cccc(n2)-c2nncn2CCCOc2ccc(-c3ccc(C(F)F)nc3)cc21] |
| 80 | 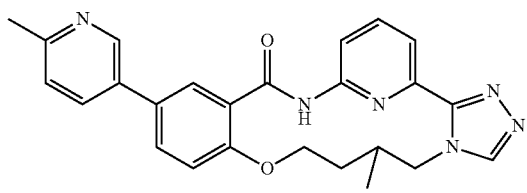 [SMILES: Cc1ccc(-c2ccc3c(c2)C(=O)Nc2cccc(n2)-c2nncn2CC(C)CCO3)cn1] |
| 81 | 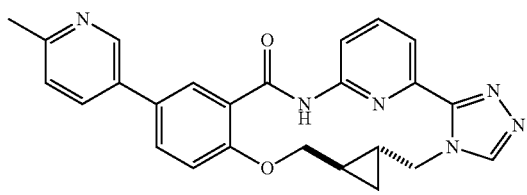 |
| 82 | 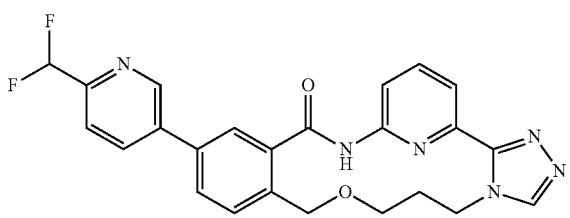 [SMILES: O=C1Nc2cccc(n2)-c2nncn2CCCOCc2ccc(-c3ccc(C(F)F)nc3)cc21] |

-continued

| Ex. | Structure |
|---|---|
| 83 | 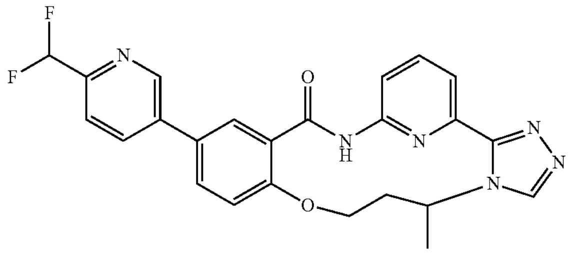 [SMILES: CC1CCOc2ccc(-c3ccc(C(F)F)nc3)cc2C(=O)Nc2cccc(n2)-c2nncn21] |
| 84 | 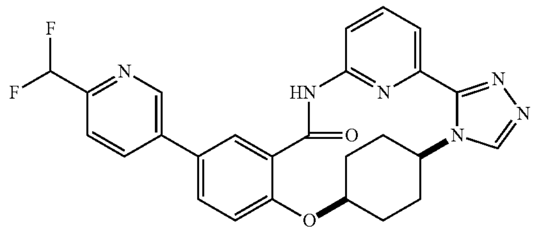 |
| 86 | 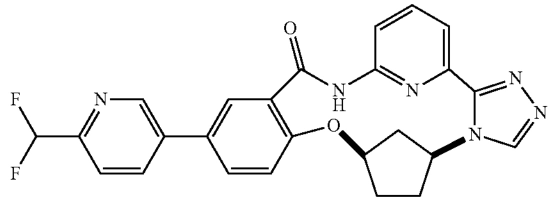 |
| 87 | 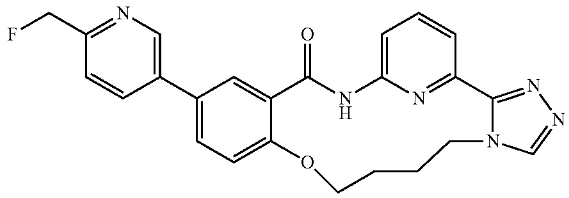 [SMILES: O=C1Nc2cccc(n2)-c2nncn2CCCCOc2ccc(-c3ccc(CF)nc3)cc21] |
| 88 | 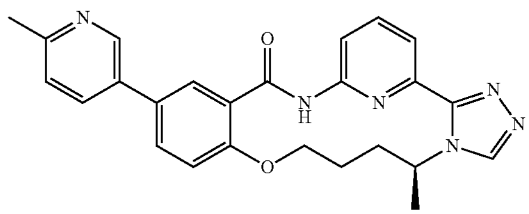 [SMILES: Cc1ccc(-c2ccc3c(c2)C(=O)Nc2cccc(n2)-c2nncn2[C@@H](C)CCCO3)cn1] |
| 89 | 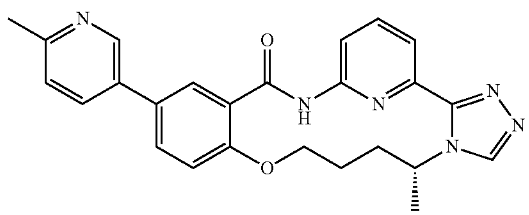 |
| 90 | 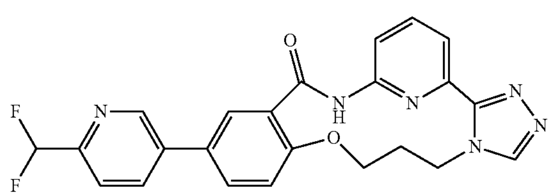 [SMILES: O=C1Nc2cccc(n2)-c2nncn2CCCOc2ccc(-c3ccc(C(F)F)nc3)cc21] |

-continued

| Ex. | Structure |
|---|---|
| 91 | 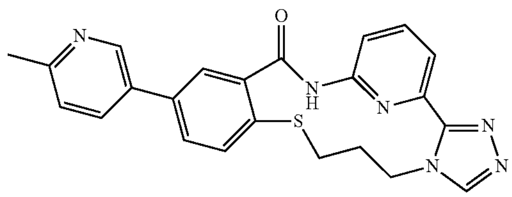 [SMILES: Cc1ccc(-c2ccc3c(c2)C(=O)Nc2cccc(n2)-c2nncn2CCCS3)cn1] |
| 93 | 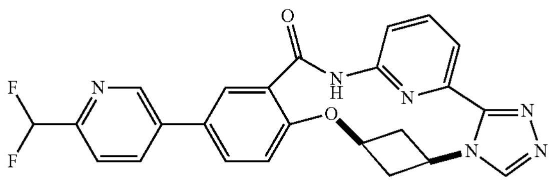 |
| 94 | 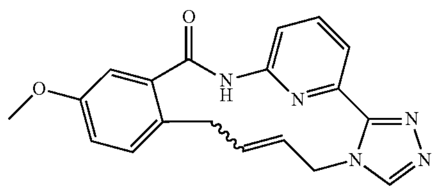 [SMILES: COc1ccc2c(c1)C(=O)Nc1cccc(n1)-c1nncn1CC=CC2] |
| 95 | 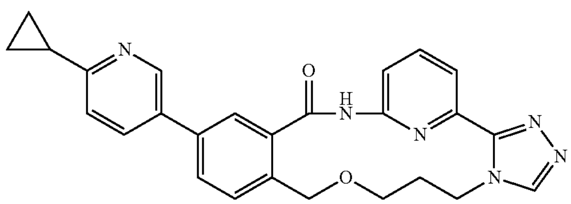 [SMILES: O=C1Nc2cccc(n2)-c2nncn2CCCOCc2ccc(-c3ccc(C4CC4)nc3)cc21] |
| 96 | 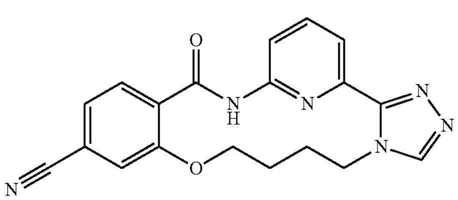 [SMILES: N#Cc1ccc2c(c1)OCCCCn1cnnc1-c1cccc(n1)NC2=O] |
| 97 | 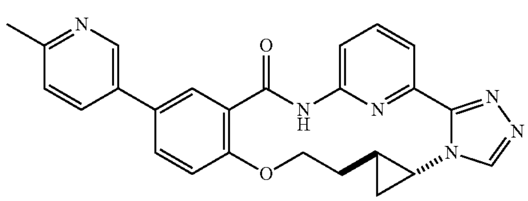 |
| 98 | 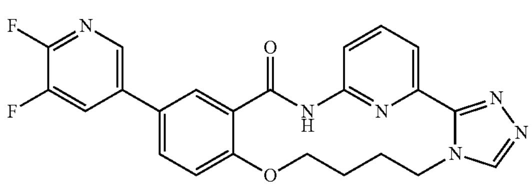 [SMILES: O=C1Nc2cccc(n2)-c2nncn2CCCCOc2ccc(-c3cnc(F)c(F)c3)cc21] |
| 99 | 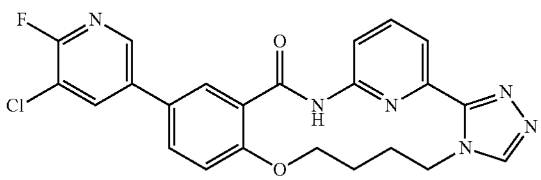 [SMILES: O=C1Nc2cccc(n2)-c2nncn2CCCCOc2ccc(-c3cnc(F)c(Cl)c3)cc21] |

-continued
| Ex. | Structure |
|---|---|
| 100 | 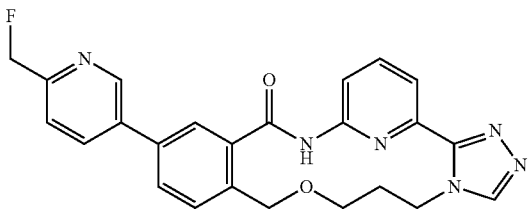 [SMILES: O=C1Nc2cccc(n2)-c2nncn2CCCOCc2ccc(-c3ccc(CF)nc3)cc21] |
| 101 | 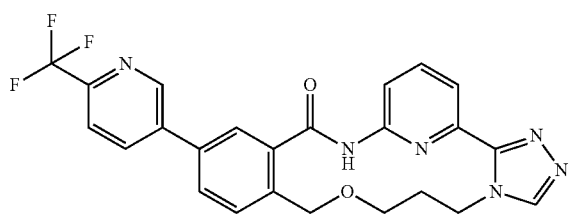 [SMILES: O=C1Nc2cccc(n2)-c2nncn2CCCOCc2ccc(-c3ccc(C(F)(F)F)nc3)cc21] |
| 102 | 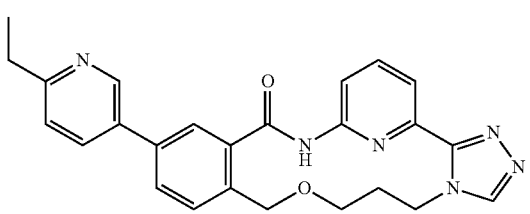 [SMILES: CCc1ccc(-c2ccc3c(c2)C(=O)Nc2cccc(n2)-c2nncn2CCCOC3)cn1] |
| 103 | 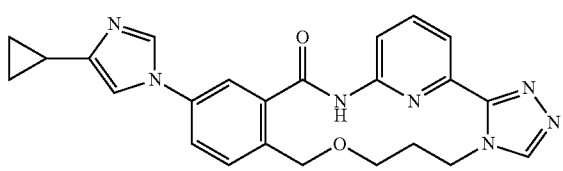 [SMILES: O=C1Nc2cccc(n2)-c2nncn2CCCOCc2ccc(-n3cnc(C4CC4)c3)cc21] |
| 104 | 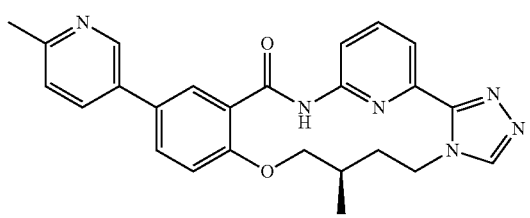 [SMILES: Cc1ccc(-c2ccc3c(c2)C(=O)Nc2cccc(n2)-c2nncn2CC[C@@H](C)CO3)cn1] |
| 105 | 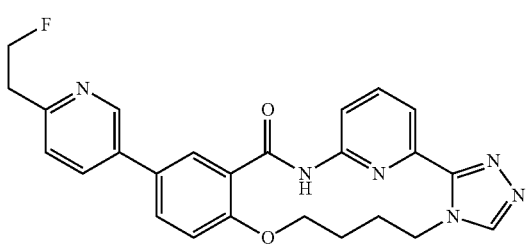 [SMILES: O=C1Nc2cccc(n2)-c2nncn2CCCCOc2ccc(-c3ccc(CCF)nc3)cc21] |
| 106 | 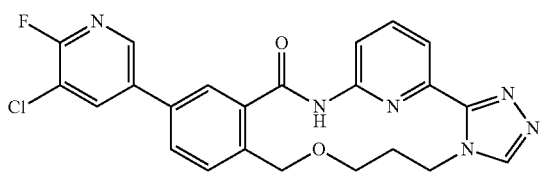 [SMILES: O=C1Nc2cccc(n2)-c2nncn2CCCOCc2ccc(-c3cnc(F)c(Cl)c3)cc21] |

-continued
| Ex. | Structure |
|---|---|
| 107 | 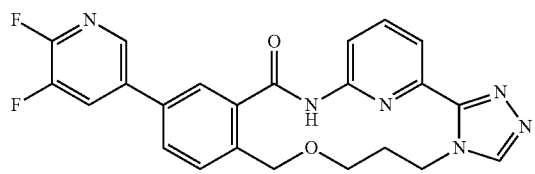 [SMILES: O=C1Nc2cccc(n2)-c2nncn2CCCOCc2ccc(-c3cnc(F)c(F)c3)cc21] |
| 108 | 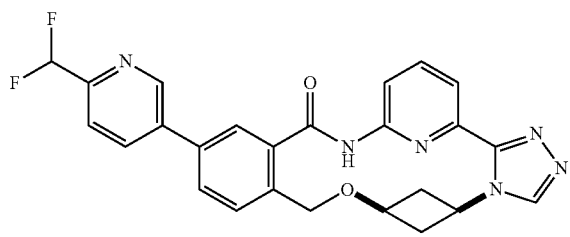 |
| 109 | 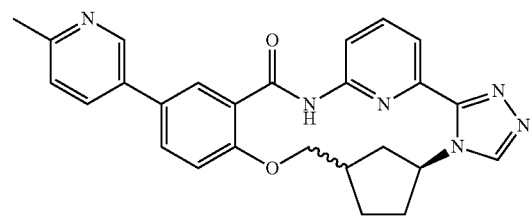 [SMILES: Cc1ccc(-c2ccc3c(c2)C(=O)Nc2cccc(n2)-c2nncn2[C@H]2CCC(CO3)C2)cn1] |
| 110 | 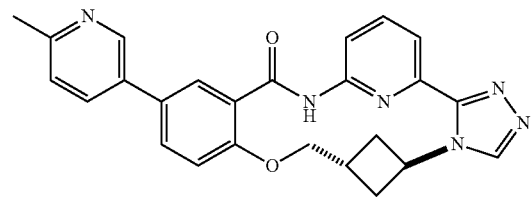 |
| 111 | 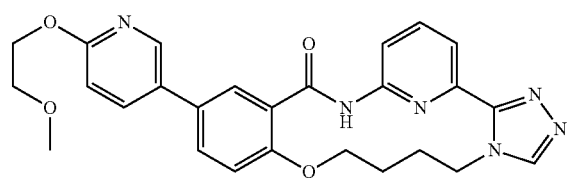 [SMILES: COCCOc1ccc(-c2ccc3c(c2)C(=O)Nc2cccc(n2)-c2nncn2CCCCO3)cn1] |
| 112 | 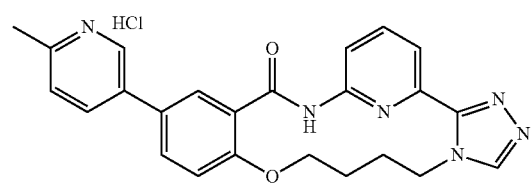 [SMILES: Cl ; Cc1ccc(-c2ccc3c(c2)C(=O)Nc2cccc(n2)-c2nncn2CCCCO3)cn1] |
| 113 | 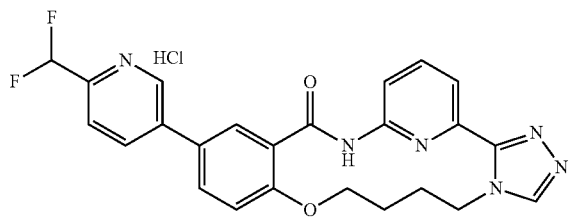 [SMILES: O=C1Nc2cccc(n2)-c2nncn2CCCCOc2ccc(-c3ccc(C(F)F)nc3)cc21 ; Cl] |

-continued
| Ex. | Structure |
|---|---|
| 114 | 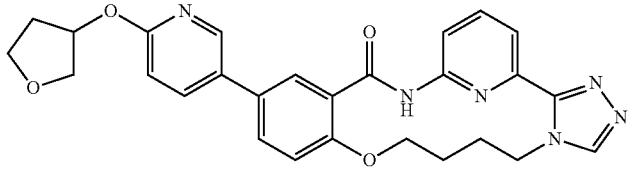 [SMILES: O=C1Nc2cccc(n2)-c2nncn2CCCCOc2ccc(-c3ccc(OC4CCOC4)nc3)cc21] |
| 115 | 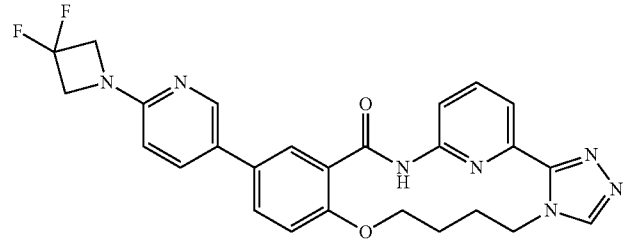 [SMILES: O=C1Nc2cccc(n2)-c2nncn2CCCCOc2ccc(-c3ccc(N4CC(F)(F)C4)nc3)cc21] |
| 116 | 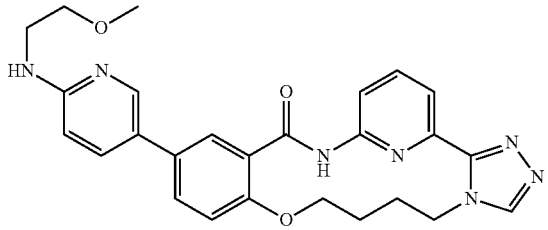 [SMILES: COCCNc1ccc(-c2ccc3c(c2)C(=O)Nc2cccc(n2)-c2nncn2CCCCO3)cn1] |
| 117 | 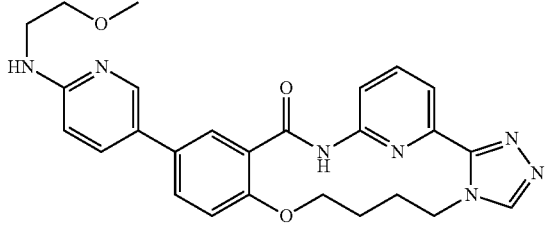 [SMILES: COCCNc1ccc(-c2ccc3c(c2)C(=O)Nc2cccc(n2)-c2nncn2CCCCO3)cn1] |
| 118 | 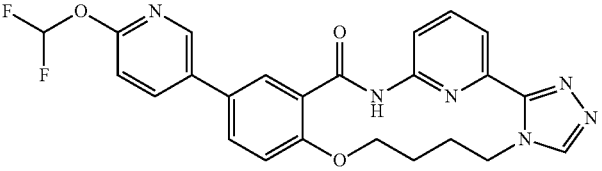 [SMILES: O=C1Nc2cccc(n2)-c2nncn2CCCCOc2ccc(-c3ccc(OC(F)F)nc3)cc21] |
| 119 | 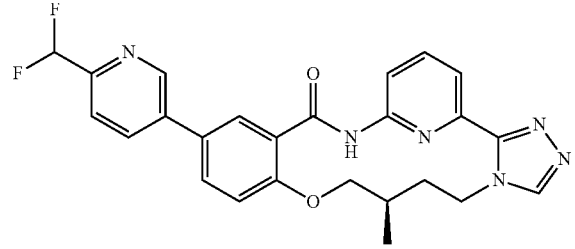 [SMILES: C[C@@H]1CCn2cnnc2-c2cccc(n2)NC(=O)c2cc(-c3ccc(C(F)F)nc3)ccc2OC1] |
| 120 | 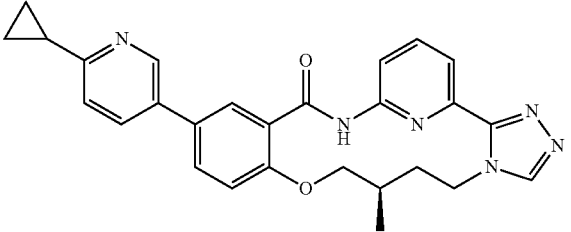 [SMILES: C[C@@H]1CCn2cnnc2-c2cccc(n2)NC(=O)c2cc(-c3ccc(C4CC4)nc3)ccc2OC1] |

| Ex. | Structure |
|---|---|
| 121 | 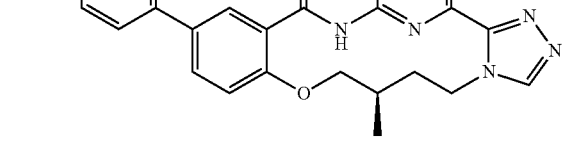 |
| 122 | 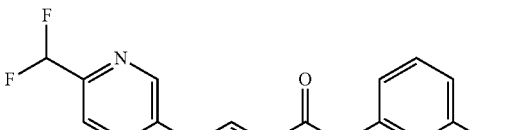 |
| 123 | 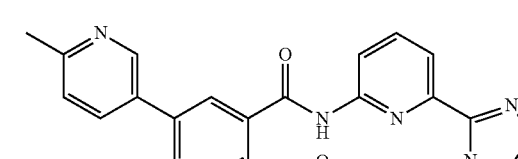 |
| 124 | 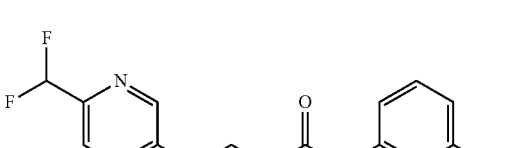 |
| 125 | 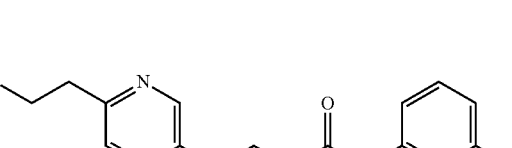 |
| 126 | 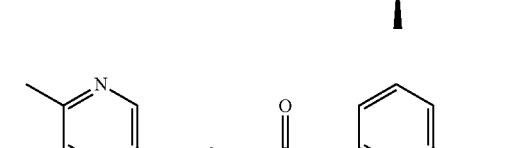 |

-continued
| Ex. | Structure |
|---|---|
| 127 | 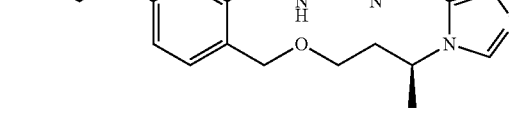 |
| 128 | 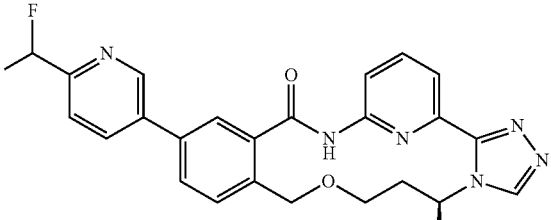 |
| 129 | 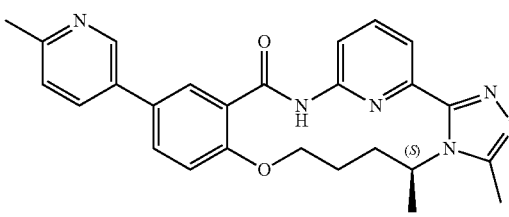 |
| 130 | 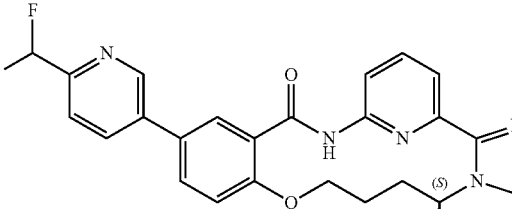 |
| 131 | 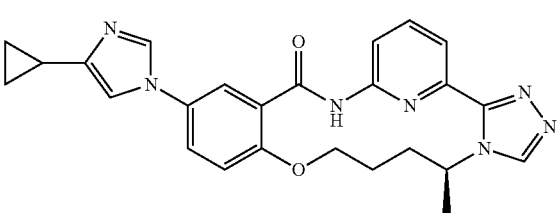 [SMILES: C[C@H]1CCCOc2ccc(-n3cnc(C4CC4)c3)cc2C(=O)Nc2cccc(n2)-c2nncn21] |
| 132 | 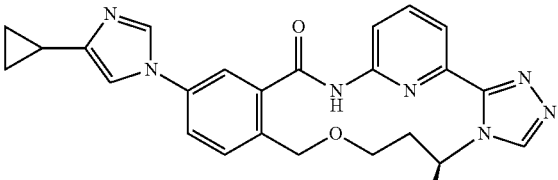 |

| Ex. | Structure |
|---|---|
| 133 | 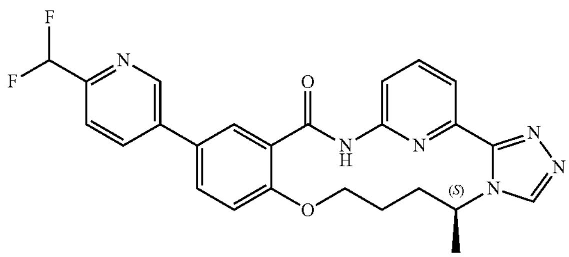 |
| 134 | 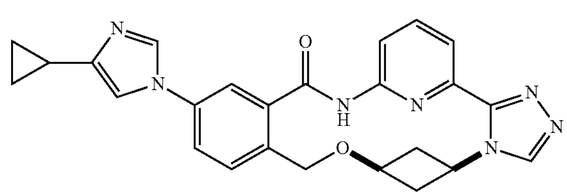 |
| 135 | 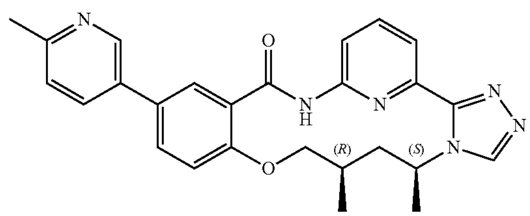 |
| 136 | 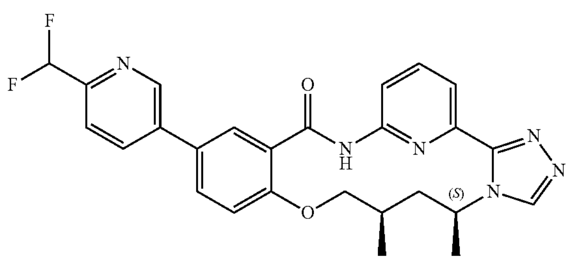 |
| 137 | 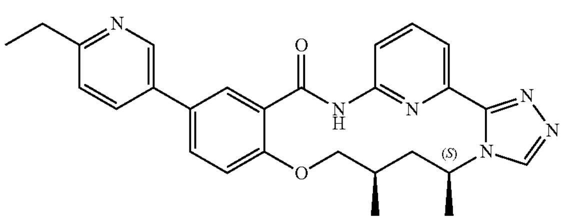 |
| 138 | 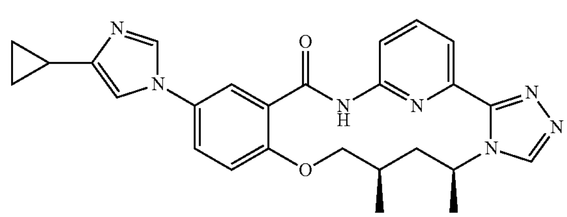 [SMILES: C[C@H]1COc2ccc(-n3cnc(C4CC4)c3)cc2C(=O)Nc2cccc(n2)-c2nncn2[C@@H](C)C1] |
| 139 | 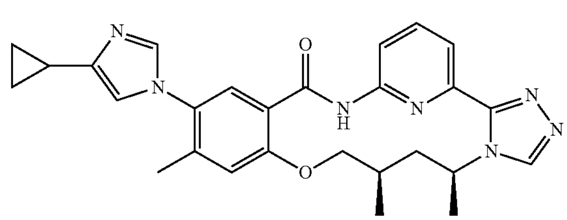 [SMILES: Cc1cc2c(cc1-n1cnc(C3CC3)c1)C(=O)Nc1cccc(n1)-c1nncn1[C@@H](C)C[C@@H](C)CO2] |

-continued
| Ex. | Structure |
|---|---|
| 140 | 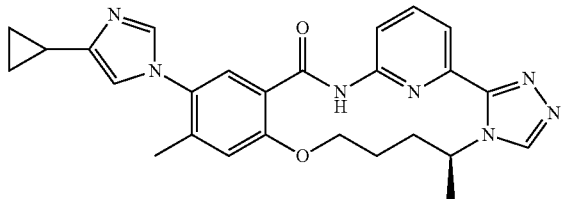 [SMILES: Cc1cc2c(cc1-n1cnc(C3CC3)c1)C(=O)Nc1cccc(n1)-c1nncn1[C@@H](C)CCCO2] |
| 141 | 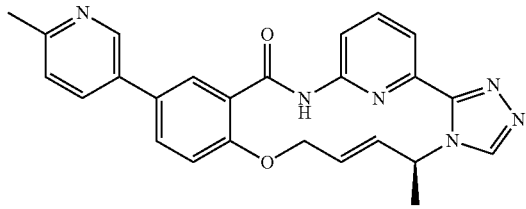 [SMILES: Cc1ccc(-c2ccc3c(c2)C(=O)Nc2cccc(n2)-c2nncn2[C@@H](C)/C=C/CO3)cn1] |
In some embodiments is a compound of Formula (I), (Ia), (Ia'), (Ib), or (Ic), or a pharmaceutically acceptable salt, solvate, or stereoisomer thereof, having a structure selected from:
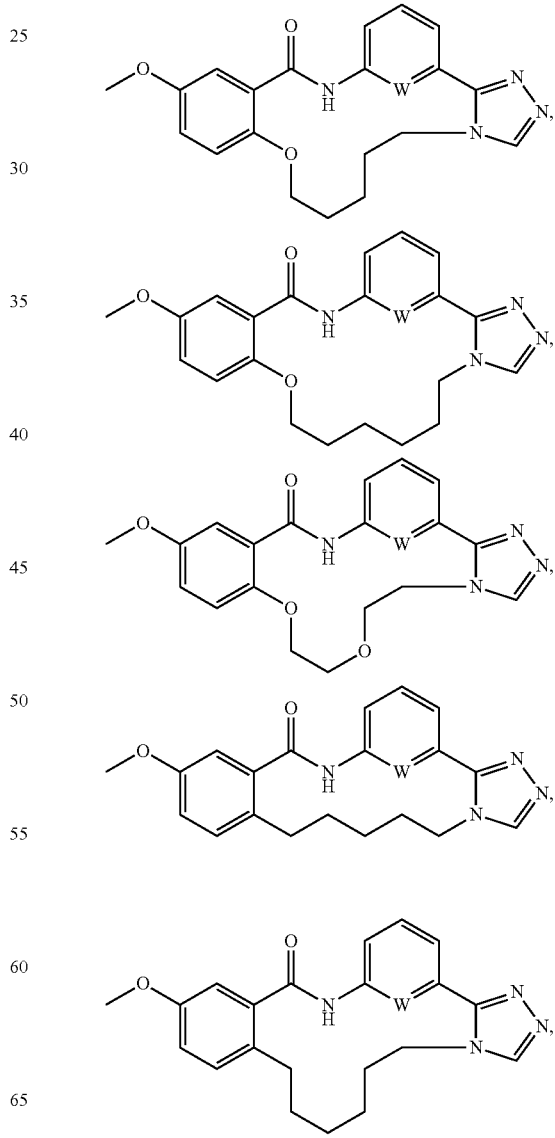

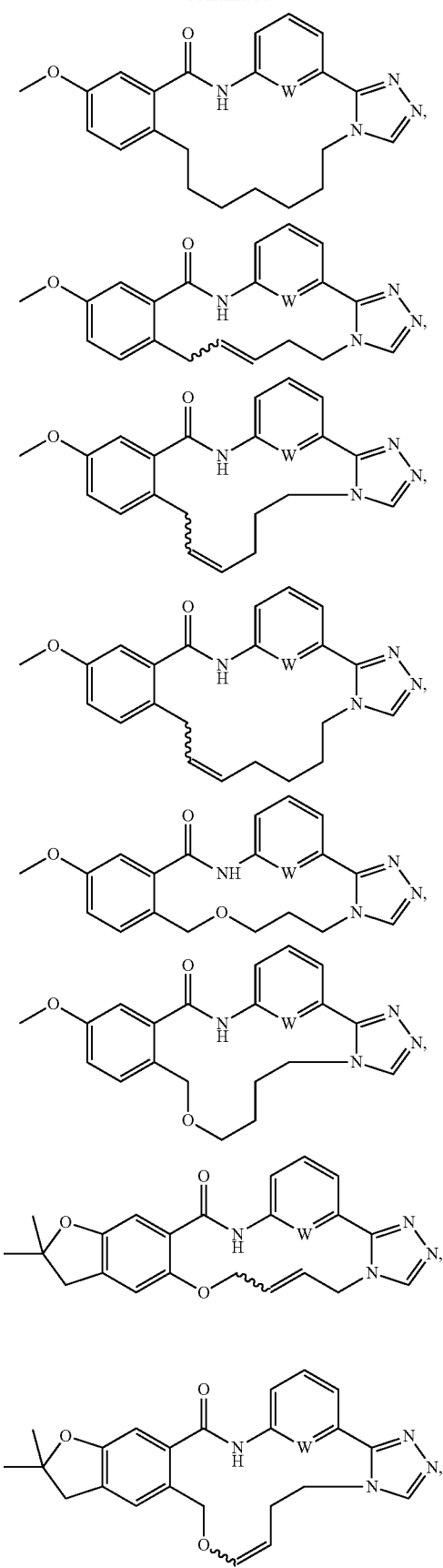
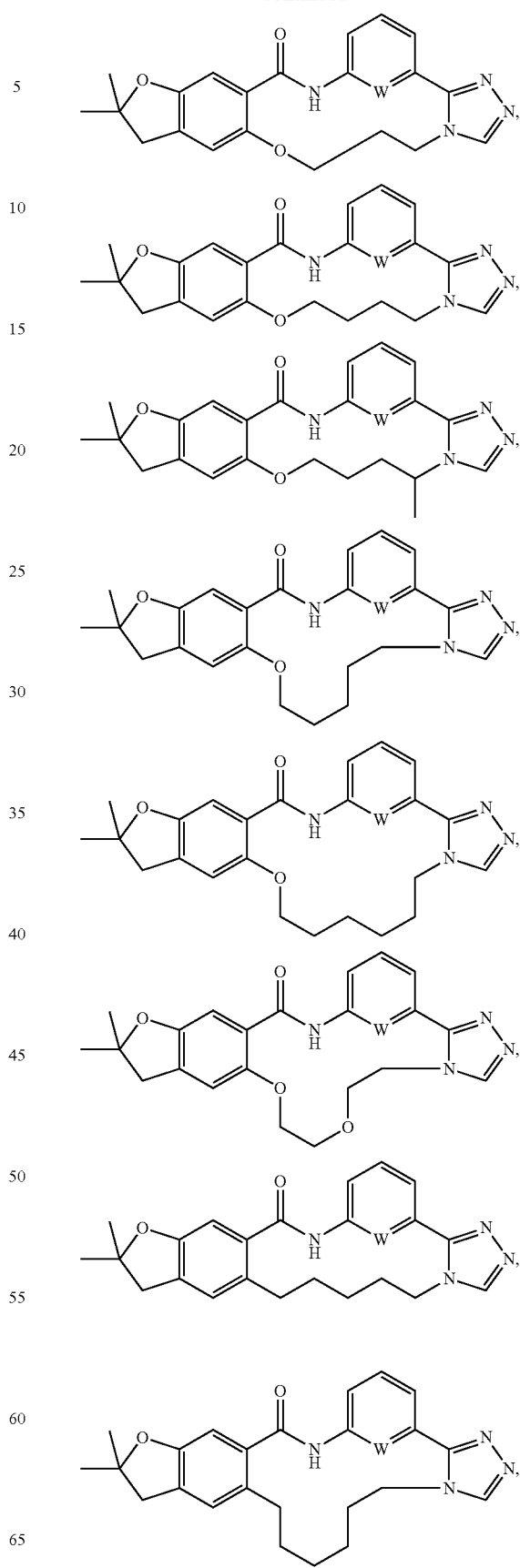

-continued
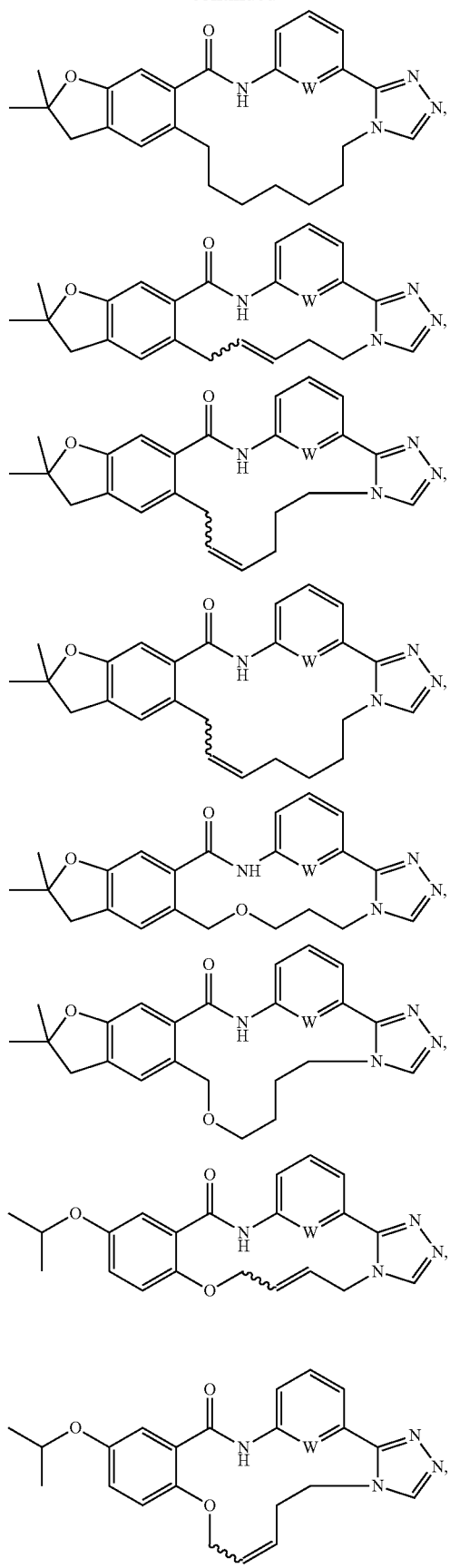
-continued
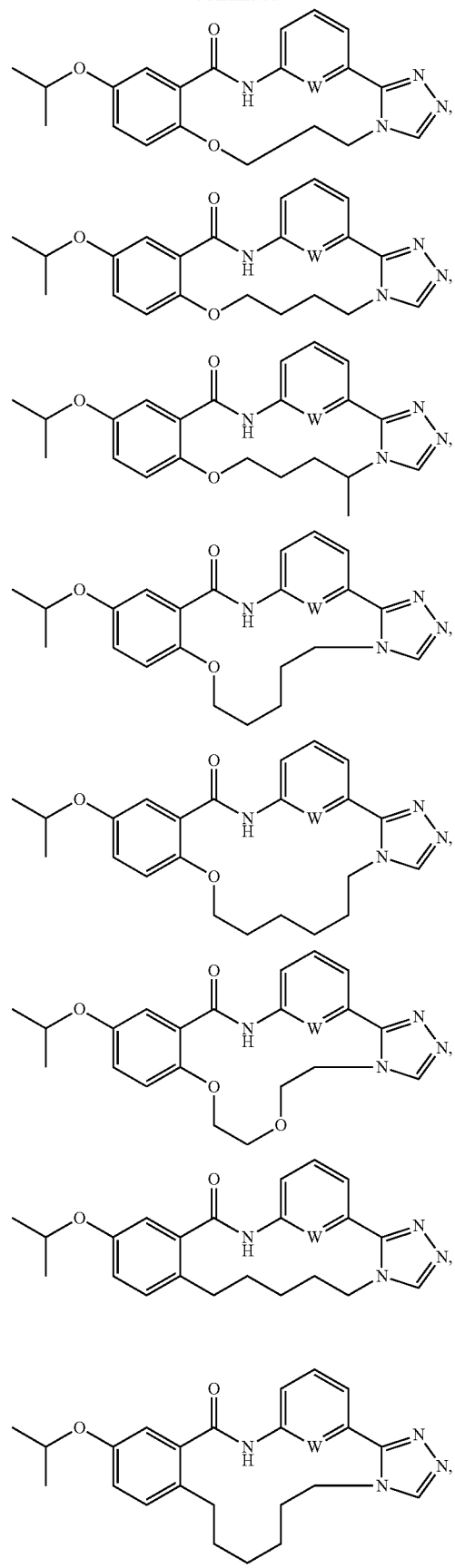

77
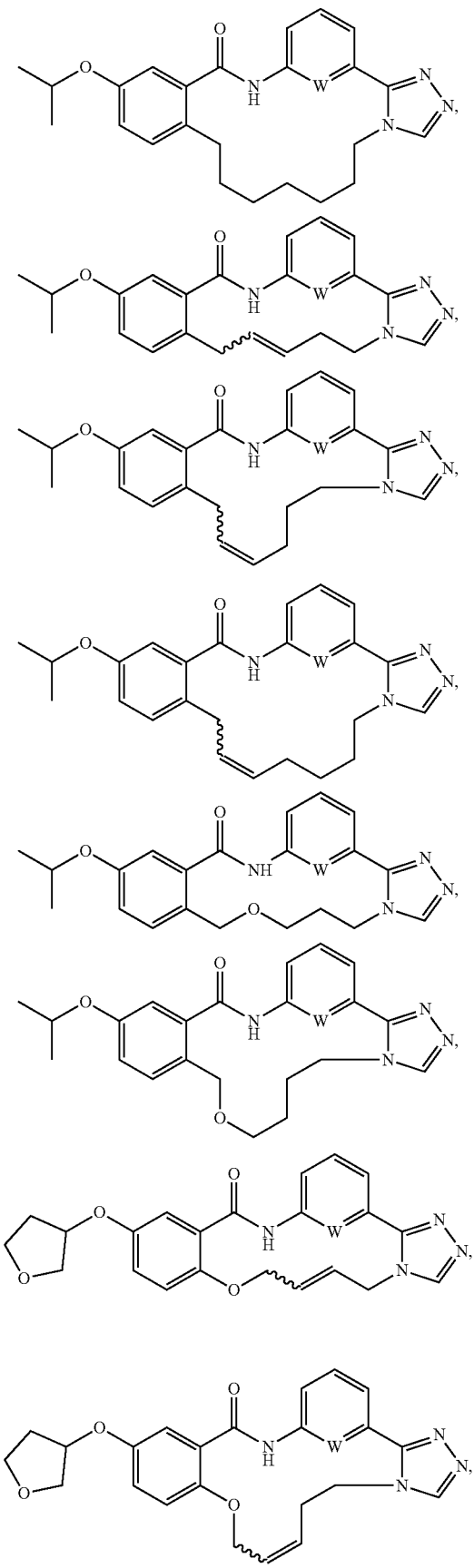
78
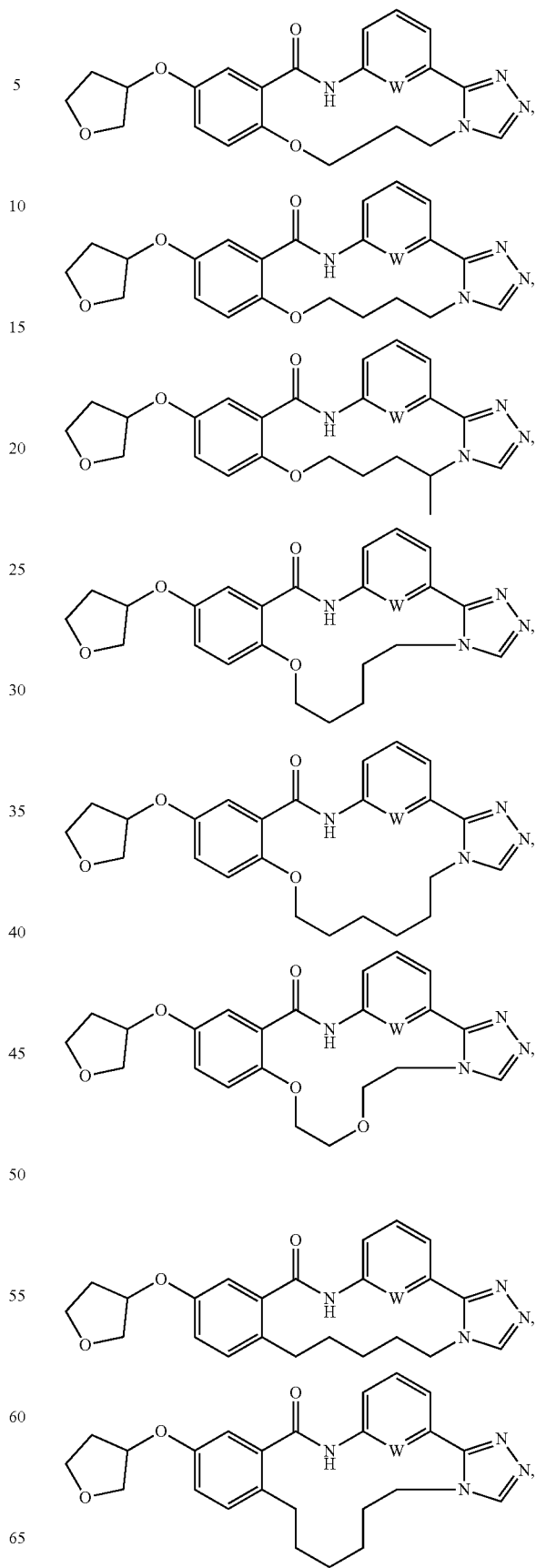

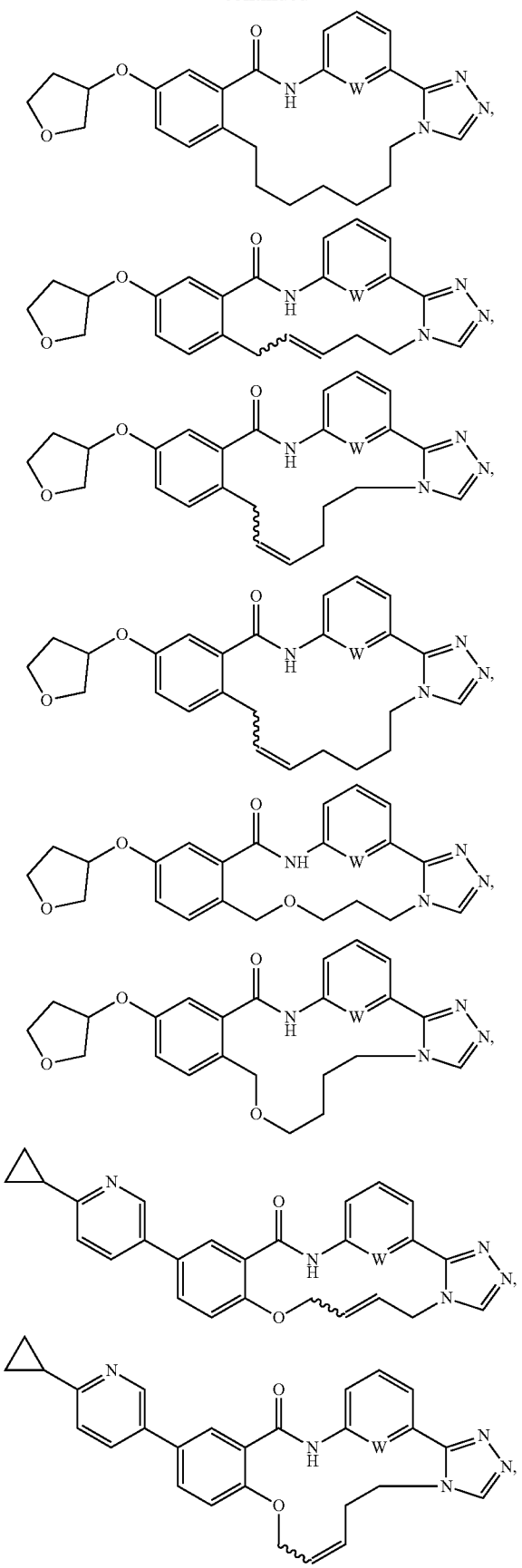
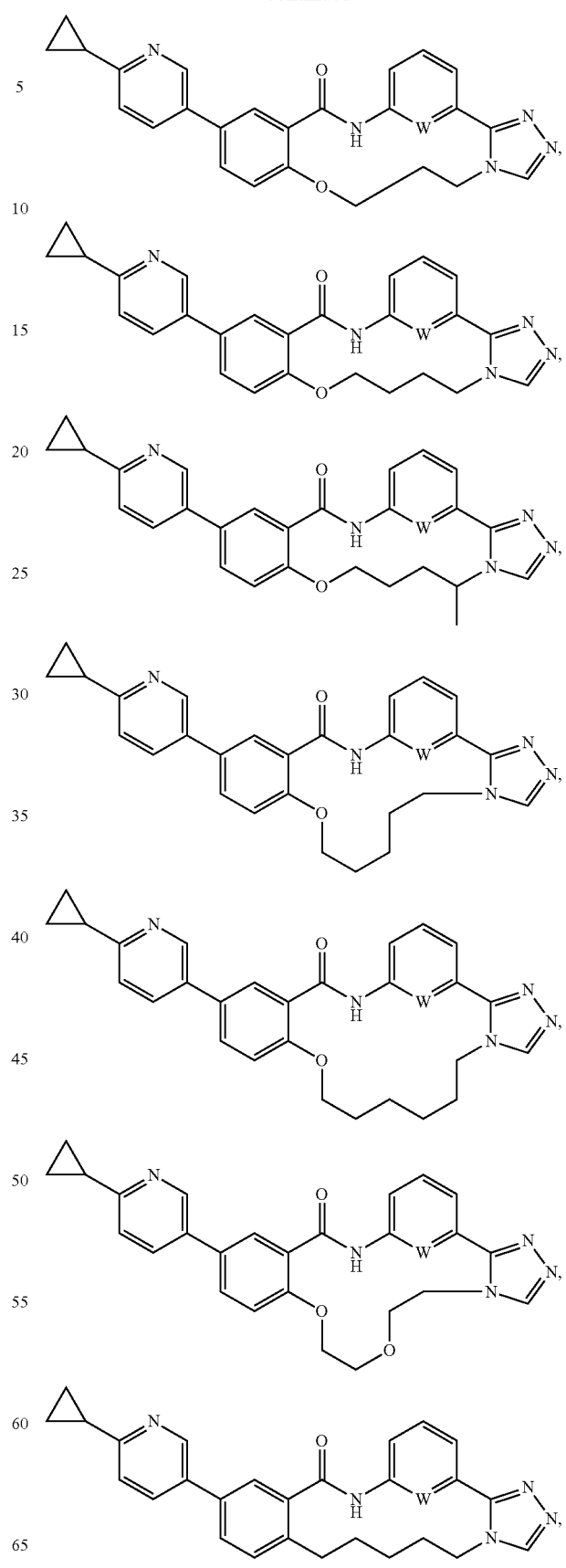

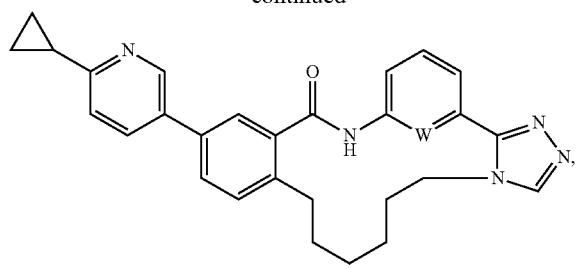
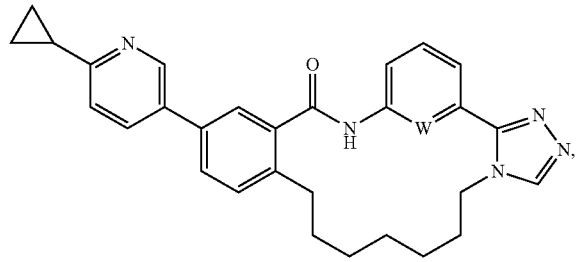
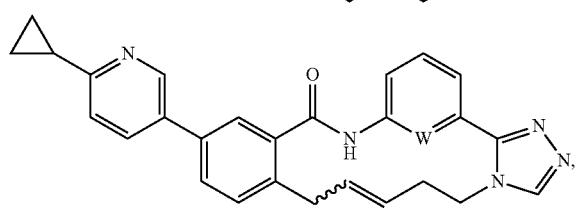
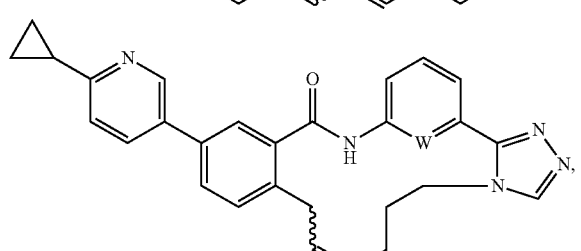
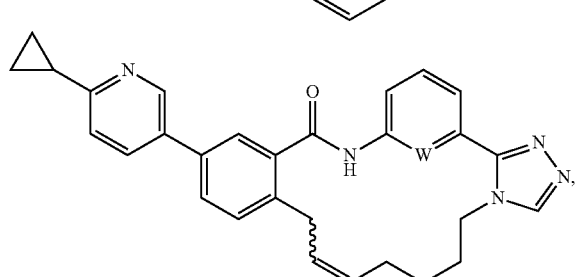
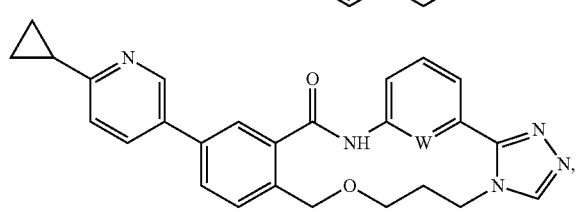
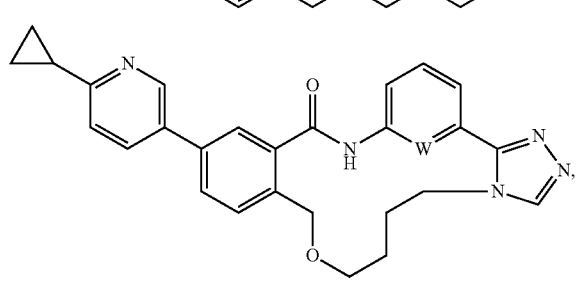
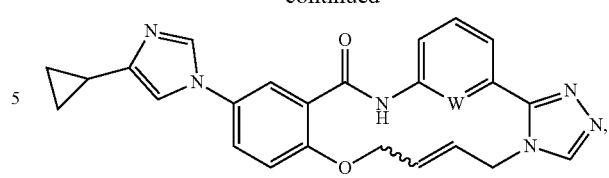
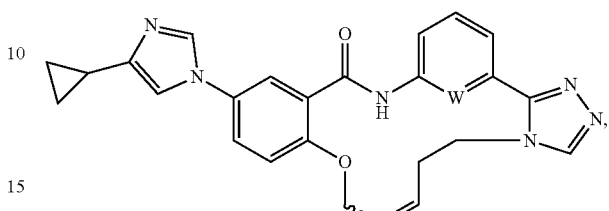
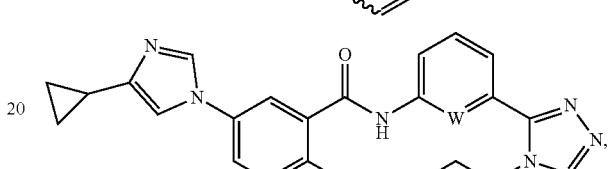

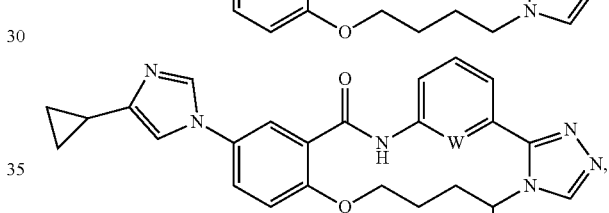
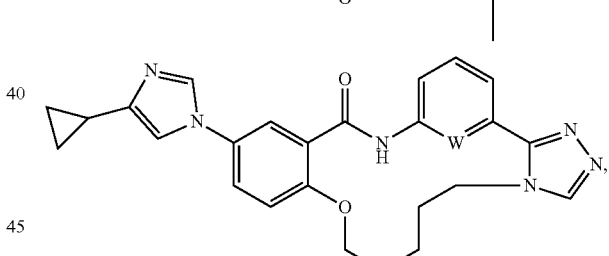
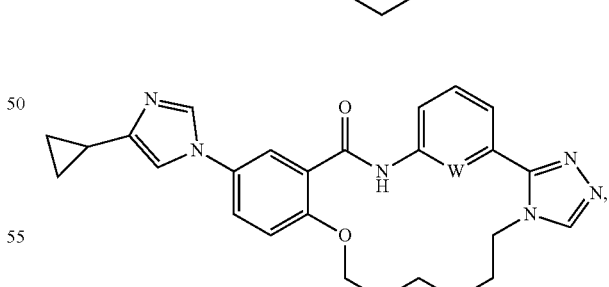
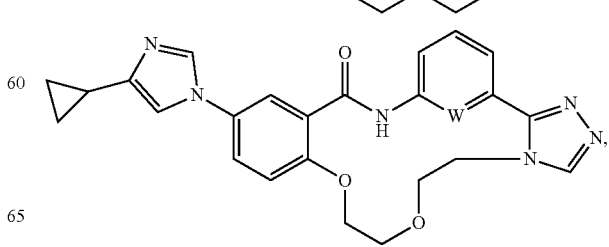

-continued

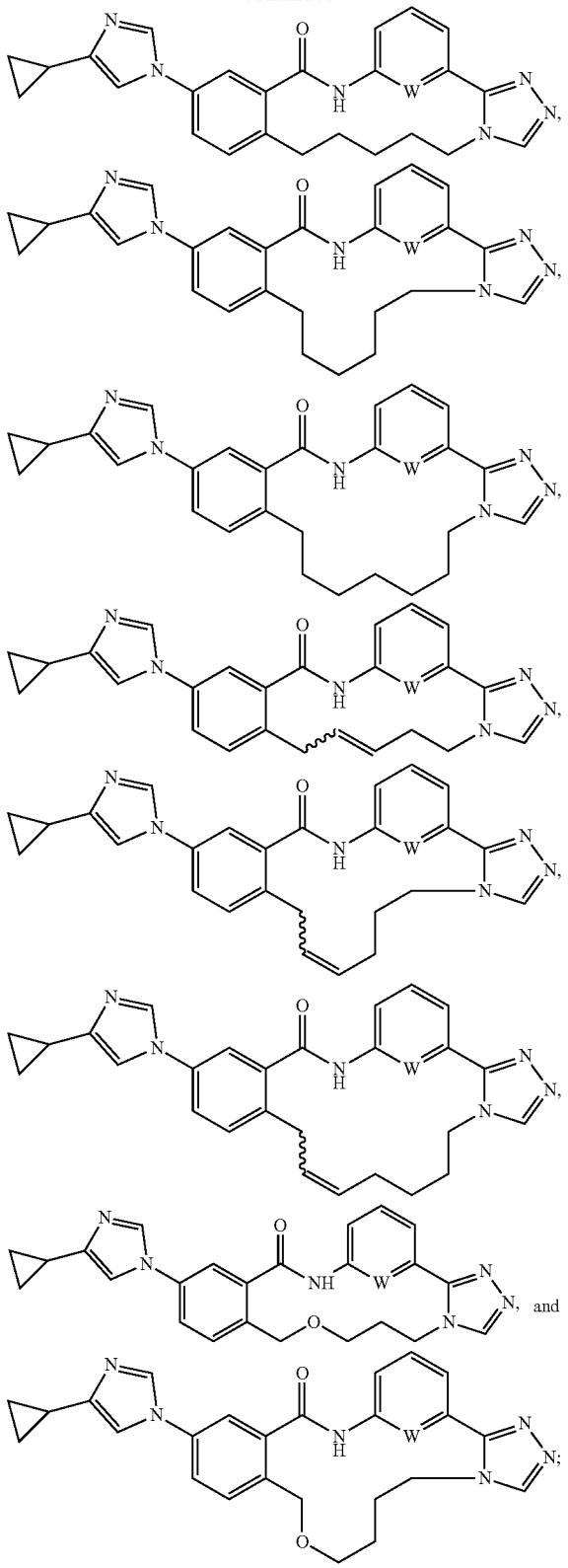

wherein W is CH or N.

Also disclosed herein is a compound of Formula (II), or a pharmaceutically acceptable salt, solvate, tautomer, or stereoisomer thereof:

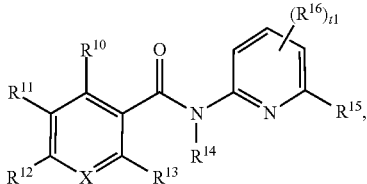

(Formula II)

wherein:

X is N or $CR^X$;

$R^{13}$ and $R^{14}$ are taken together with the atoms to which they are attached to form an optionally substituted heterocycloalkyl or an optionally substituted heteroaryl;

$R^{10}$ and $R^X$ are independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —$S(=O)_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^{11}$ and $R^{12}$ are taken together with the atoms to which they are attached to form an optionally substituted cycloalkyl, optionally substituted heterocycloalkyl, optionally substituted aryl, or optionally substituted heteroaryl;

$R^{15}$ is optionally substituted heterocycloalkyl or optionally substituted heteroaryl;

each $R^{16}$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —$S(=O)_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)$ $NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^a$ is hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^b$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^c$ and $R^d$ is independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^c$ and $R^d$, together with the nitrogen atom to which they are attached, form an optionally substituted heterocycloalkyl or optionally substituted heteroaryl; and t1 is 1-3.

In some embodiments of a compound of Formula (II), $R^{13}$ and $R^{14}$ are taken together with the atom to which they are attached to form an optionally substituted 5- or 6-membered heterocycloalkyl.

In some embodiments of a compound of Formula (II), $R^{13}$ and $R^{14}$ are taken together with the atom to which they are attached to form a 5- or 6-membered heterocycloalkyl, each optionally substituted with oxo, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl.

In some embodiments of a compound of Formula (II), $R^{13}$ and $R^{14}$ are taken together with the atom to which they are attached to form a 5-membered heterocycloalkyl, each optionally substituted with oxo, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), $R^{13}$ and $R^{14}$ are taken together with the atom to which they are attached to form a 5-membered heterocycloalkyl optionally substituted with oxo, halogen, —CN, —OR$^a$, —NR$^c$R$^d$, —CO$_2$R$^a$, optionally substituted $C_1$-$C_6$ alkyl, or optionally substituted $C_1$-$C_6$ heteroalkyl. In some embodiments of a compound of Formula (II), $R^{13}$ and $R^{14}$ are taken together with the atom to which they are attached to form a 5-membered heterocycloalkyl optionally substituted with oxo, halogen, —OR$^a$, or optionally substituted $C_1$-$C_6$ alkyl. In some embodiments of a compound of Formula (II), $R^{13}$ and $R^{14}$ are taken together with the atom to which they are attached to form a 5-membered heterocycloalkyl optionally substituted with oxo. In some embodiments of a compound of Formula (II), $R^{13}$ and $R^{14}$ are taken together with the atom to which they are attached to form a 5-membered heterocycloalkyl.

In some embodiments of a compound of Formula (II), $R^{13}$ and $R^{14}$ are taken together with the atom to which they are attached to form a 6-membered heterocycloalkyl, each optionally substituted with oxo, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), $R^{13}$ and $R^{14}$ are taken together with the atom to which they are attached to form a 6-membered heterocycloalkyl optionally substituted with oxo, halogen, —CN, —OR$^a$, —NR$^c$R$^d$, —CO$_2$R$^a$, optionally substituted $C_1$-$C_6$ alkyl, or optionally substituted $C_1$-$C_6$ heteroalkyl. In some embodiments of a compound of Formula (II), $R^{13}$ and $R^{14}$ are taken together with the atom to which they are attached to form a 6-membered heterocycloalkyl optionally substituted with oxo, halogen, —OR$^a$, or optionally substituted $C_1$-$C_6$ alkyl. In some embodiments of a compound of Formula (II), $R^{13}$ and $R^{14}$ are taken together with the atom to which they are attached to form a 6-membered heterocycloalkyl optionally substituted with oxo. In some embodiments of a compound of Formula (II), $R^{13}$ and $R^{14}$ are taken together with the atom to which they are attached to form a 6-membered heterocycloalkyl.

In some embodiments of a compound of Formula (II), $R^{13}$ and $R^{14}$ are taken together with the atom to which they are attached to form an optionally substituted 6-membered heteroaryl. In some embodiments of a compound of Formula (II), $R^{13}$ and $R^{14}$ are taken together with the atom to which they are attached to form a 6-membered heteroaryl optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), $R^{13}$ and $R^{14}$ are taken together with the atom to which they are attached to form a 6-membered heteroaryl optionally substituted with halogen, —CN, —OR$^a$, —NR$^c$R$^d$, —CO$_2$R$^a$, optionally substituted $C_1$-$C_6$ alkyl, or optionally substituted $C_1$-$C_6$ heteroalkyl. In some embodiments of a compound of Formula (II), $R^{13}$ and $R^{14}$ are taken together with the atom to which they are attached to form a 6-membered heteroaryl optionally substituted with halogen, —OR$^a$, or optionally substituted $C_1$-$C_6$ alkyl. In some embodiments of a compound of Formula (II), $R^{13}$ and $R^{14}$ are taken together with the atom to which they are attached to form a 6-membered heteroaryl optionally substituted with halogen. In some embodiments of a compound of Formula (II), $R^{13}$ and $R^{14}$ are taken together with the atom to which they are attached to form a 6-membered heteroaryl.

In some embodiments the compound of Formula (II) is of Formula (IIa):

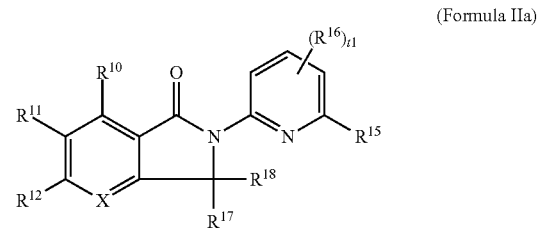

(Formula IIa)

wherein
$R^{17}$ and $R^{18}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^{17}$ and $R^{18}$ are taken together with the atom to which they are attached to form an oxo.

In some embodiments the compound of Formula (II) is of Formula (IIb):

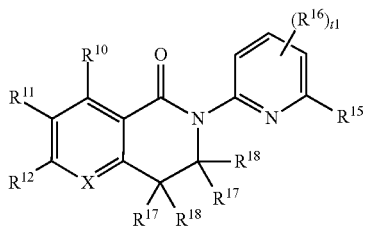

(Formula IIb)

wherein each $R^{17}$ and $R^{18}$ are independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O)$NR^cR^d$, —$NR^aC$(=O)$R^b$, —$NR^aC$(=O)$OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^{17}$ and $R^{18}$ on the same carbon are taken together with the atom to which they are attached to form an oxo.

In some embodiments of a compound of Formula (IIa) and (IIb), each $R^{17}$ and $R^{18}$ are independently hydrogen, halogen, —CN, —$OR^a$, —$NR^cR^d$, —$CO_2R^a$, —C(=O)$NR^cR^d$, optionally substituted $C_1$-$C_6$ alkyl, or optionally substituted $C_1$-$C_6$ heteroalkyl. In some embodiments of a compound of Formula (IIa) and (IIb), each $R^{17}$ and $R^{18}$ are independently hydrogen, halogen, —$OR^a$, or optionally substituted $C_1$-$C_6$ alkyl. In some embodiments of a compound of Formula (IIa) and (IIb), each $R^{17}$ and $R^{18}$ are independently hydrogen, halogen, —$OR^a$, or $C_1$-$C_6$ alkyl. In some embodiments of a compound of Formula (IIa) and (IIb), $R^{17}$ and $R^{18}$ are hydrogen. In some embodiments of a compound of Formula (IIa) and (IIb), $R^{17}$ and $R^{18}$ on the same carbon are taken together with the atom to which they are attached to form an oxo.

In some embodiments the compound of Formula (II) is of Formula (IIc):

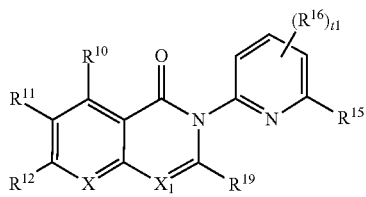

(Formula IIc)

wherein $X_1$ is N or $CR^{19}$; and each $R^{19}$ is independently hydrogen, halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O)$NR^cR^d$, —$NR^aC$(=O)$R^b$, —$NR^aC$(=O)$OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl.

In some embodiments of a compound of Formula (IIc), $X_1$ is N. In some embodiments of a compound of Formula (IIc), $X_1$ is $CR^{19}$.

In some embodiments of a compound of Formula (IIc), each $R^{19}$ is independently hydrogen, halogen, —CN, —$OR^a$, —$NR^cR^d$, —$CO_2R^a$, —C(=O)$NR^cR^d$, optionally substituted $C_1$-$C_6$ alkyl, optionally substituted $C_1$-$C_6$ heteroalkyl. In some embodiments of a compound of Formula (IIc), each $R^{19}$ is independently hydrogen, halogen, —$OR^a$, or optionally substituted $C_1$-$C_6$ alkyl. In some embodiments of a compound of Formula (IIc), each $R^{19}$ is independently hydrogen or optionally substituted $C_1$-$C_6$ alkyl. In some embodiments of a compound of Formula (IIc), each $R^{19}$ is independently hydrogen or $C_1$-$C_6$ alkyl. In some embodiments of a compound of Formula (IIc), each $R^{19}$ are hydrogen.

In some embodiments of a compound of Formula (II), (IIa), (IIb), (IIc), $R^{15}$ is an optionally substituted heteroaryl.

In some embodiments of a compound of Formula (II), (IIa), (IIb), (IIc), $R^{15}$ is an optionally substituted 5-membered heteroaryl selected from imidazole, pyrazole, pyrrole, triazole, tetrazole, thiophene, furan, thiazole, isothiazole, oxazole, and isoxazole. In some embodiments of a compound of Formula (II), (IIa), (IIb), (IIc), $R^{15}$ is optionally substituted 5-membered heteroaryl selected from triazole, tetrazole, and isoxazole. In some embodiments of a compound of Formula (II), (IIa), (IIb), (IIc), $R^{15}$ is an optionally substituted triazole. In some embodiments of a compound of Formula (II), (IIa), (IIb), (IIc), $R^{15}$ is an optionally substituted tetrazole. In some embodiments of a compound of Formula (II), (IIa), (IIb), (IIc), $R^{15}$ is an optionally substituted pyrazole.

In some embodiments of a compound of Formula (II), (IIa), (IIb), (IIc), $R^{15}$ is an optionally substituted 6-membered heteroaryl selected from pyridine, pyrimidine, pyrazine, and pyridazine. In some embodiments of a compound of Formula (II), (IIa), (IIb), (IIc), $R^{15}$ is optionally substituted pyridine.

In some embodiments of a compound of Formula (II), (IIa), (IIb), (IIc), $R^{15}$ is optionally substituted with halogen, —CN, —$OR^a$, —$SR^a$, —S(=O)$R^b$, —$NO_2$, —$NR^cR^d$, —S(=O)$_2R^d$, —$NR^aS$(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC$(=O)$NR^cR^d$, —$NR^aC$(=O)$R^b$, —$NR^aC$(=O)$OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), (IIa), (IIb), (IIc), $R^{15}$ is optionally substituted with halogen, —CN, —$OR^a$, —$NR^cR^d$, optionally substituted $C_1$-$C_6$ alkyl, optionally substituted cycloalkyl, or optionally substituted heterocycloalkyl.

In some embodiments of a compound of Formula (II), (IIa), (IIb), (IIc), $R^{15}$ is optionally substituted with halogen, —CN, —OH, —$NH_2$, $C_1$-$C_6$ alkyl, $C_1$-$C_6$ haloalkyl, $C_1$-$C_6$ hydroxyalkyl, or cycloalkyl. In some embodiments of a compound of Formula (II), (IIa), (IIb), (IIc), $R^{15}$ is optionally substituted with $C_1$-$C_6$ alkyl.

In some embodiments of a compound of Formula (II), (IIa), (IIb), (IIc), X is N. In some embodiments of a compound of Formula (II), (IIa), (IIb), (IIc), X is $CR^X$ and $R^X$ is hydrogen, halogen, or optionally substituted $C_1$-$C_6$ alkyl. In some embodiments of a compound of Formula (II), (IIa), (IIb), (IIc), X is $CR^X$ and $R^X$ is hydrogen, halogen, or $C_1$-$C_6$ alkyl. In some embodiments of a compound of Formula (II), (IIa), (IIb), (IIc), $R^X$ is hydrogen.

In some embodiments of a compound of Formula (II), (IIa), (IIb), (IIc), $R^{10}$ is hydrogen, halogen, —CN, —$OR^a$, —$NR^cR^d$, —$CO_2R^a$, —$C(=O)NR^cR^d$, optionally substituted $C_1$-$C_6$ alkyl, optionally substituted $C_1$-$C_6$ heteroalkyl, optionally substituted cycloalkyl. In some embodiments of a compound of Formula (II), (IIa), (IIb), (IIc), $R^{10}$ is hydrogen, halogen, —$OR^a$, or optionally substituted $C_1$-$C_6$ alkyl. In some embodiments of a compound of Formula (II), (IIa), (IIb), (IIc), $R^{10}$ is hydrogen, halogen, or optionally substituted $C_1$-$C_6$ alkyl. In some embodiments of a compound of Formula (II), (IIa), (IIb), (IIc), $R^{10}$ is hydrogen, halogen, or $C_1$-$C_6$ alkyl. In some embodiments of a compound of Formula (II), (IIa), (IIb), (IIc), $R^{10}$ is hydrogen.

In some embodiments of a compound of Formula (II), (IIa), (IIb), (IIc), $R^{16}$ is hydrogen, halogen, —CN, —$OR^a$, —$NR^cR^d$, —$CO_2R^a$, —$C(=O)NR^cR^d$, optionally substituted $C_1$-$C_6$ alkyl, optionally substituted $C_1$-$C_6$ heteroalkyl, optionally substituted cycloalkyl. In some embodiments of a compound of Formula (II), (IIa), (IIb), (IIc), $R^{16}$ is hydrogen, halogen, —$OR^a$, or optionally substituted $C_1$-$C_6$ alkyl. In some embodiments of a compound of Formula (II), (IIa), (IIb), (IIc), $R^{16}$ is hydrogen, halogen, or optionally substituted $C_1$-$C_6$ alkyl. In some embodiments of a compound of Formula (II), (IIa), (IIb), (IIc), $R^{16}$ is hydrogen, halogen, or $C_1$-$C_6$ alkyl. In some embodiments of a compound of Formula (II), (IIa), (IIb), (IIc), $R^{16}$ is hydrogen.

In some embodiments of a compound of Formula (II), (IIa), (IIb), (IIc), t1 is 1 or 2. In some embodiments of a compound of Formula (II), (IIa), (IIb), (IIc), t1 is 1. In some embodiments of a compound of Formula (II), (IIa), (IIb), (IIc), t1 is 2. In some embodiments of a compound of Formula (II), (IIa), (IIb), (IIc), t1 is 3.

In some embodiments of a compound of Formula (II), (IIa), (IIb), (IIc), $R^{11}$ and $R^{12}$ are taken together with the atoms to which they are attached to form an optionally substituted 5-membered heterocycloalkyl. In some embodiments of a compound of Formula (II), (IIa), (IIb), (IIc), $R^{11}$ and $R^{12}$ are taken together with the atoms to which they are attached to form an optionally substituted 6-membered heterocycloalkyl. In some embodiments of a compound of Formula (II), (IIa), (IIb), (IIc), $R^{11}$ and $R^{12}$ are taken together with the atoms to which they are attached to form an optionally substituted bicyclic heterocycloalkyl.

In some embodiments of a compound of Formula (II), (IIa), (IIb), (IIc), the optional substituent on the ring formed when $R^{11}$ and $R^{12}$ are taken together with the atoms to which they are attached is halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), (IIa), (IIb), (IIc), the optional substituent on the ring formed when $R^{11}$ and $R^{12}$ are taken together with the atoms to which they are attached is halogen, —CN, —$OR^a$, —$NR^cR^d$, —$CO_2R^a$, —$C(=O)NR^cR^d$, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (II), (IIa), (IIb), (IIc), the optional substituent on the ring formed when $R^{11}$ and $R^{12}$ are taken together with the atoms to which they are attached is halogen, —$OR^a$, optionally substituted $C_1$-$C_6$ alkyl, or optionally substituted cycloalkyl. In some embodiments of a compound of Formula (II), (IIa), (IIb), (IIc), the optional substituent on the ring formed when $R^{11}$ and $R^{12}$ are taken together with the atoms to which they are attached is halogen, optionally substituted $C_1$-$C_6$ alkyl, or optionally substituted cycloalkyl. In some embodiments of a compound of Formula (II), (IIa), (IIb), (IIc), the optional substituent on the ring formed when $R^{11}$ and $R^{12}$ are taken together with the atoms to which they are attached is halogen, $C_1$-$C_6$ alkyl, or cycloalkyl.

In some embodiments of a compound of Formula (II), (IIa), (IIb), (IIc),

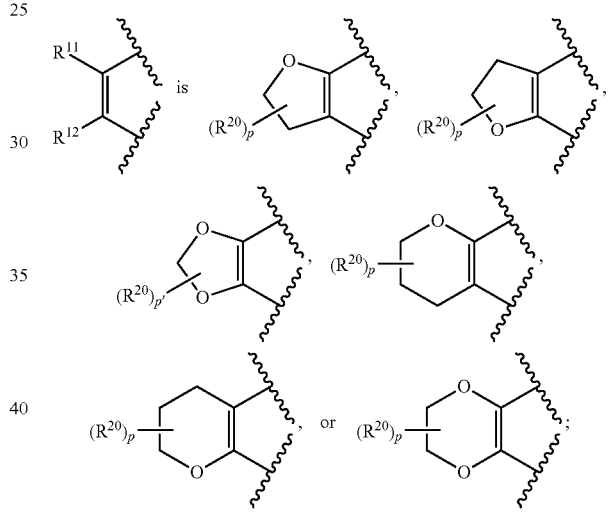

wherein
each $R^{20}$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
or two $R^{20}$ on the same carbon atom are taken together to form an oxo;
or two $R^{20}$ on the same carbon atom are taken together to form an optionally substituted cycloalkyl or optionally substituted heterocycloalkyl;
or two $R^{20}$ on the different carbon atom are taken together to form an optionally substituted cycloalkyl or optionally substituted heterocycloalkyl; p is 1-4, and p' is 1 or 2.

In some embodiments of a compound of Formula (II), (IIa), (IIb), (IIc),

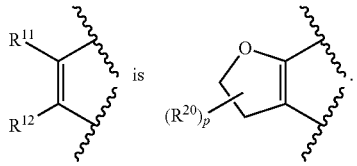

In some embodiments of a compound of Formula (II), (IIa), (IIb), (IIc),

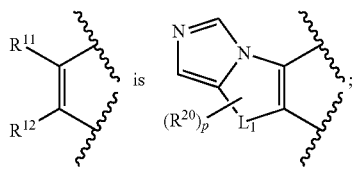

wherein $L_1$ is $C_1$-$C_4$ alkylene or $C_1$-$C_4$ heteroalkylene;

each $R^{20}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or two $R^{20}$ on the same carbon atom are taken together to form an oxo;

or two $R^{20}$ on the same carbon atom are taken together to form an optionally substituted cycloalkyl or optionally substituted heterocycloalkyl;

or two $R^{20}$ on the different carbon atom are taken together to form an optionally substituted cycloalkyl or optionally substituted heterocycloalkyl; and p is 1-4.

In some embodiments of a compound of Formula (II), (IIa), (IIb), (IIc),

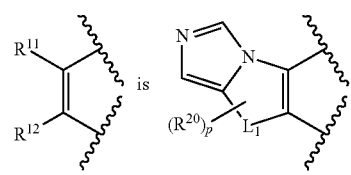

and $L_1$ is $C_1$-$C_4$ alkylene. In some embodiments of a compound of Formula (II), (IIa), (IIb), (IIc),

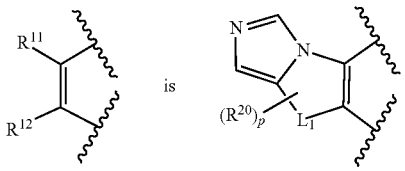

and $L_1$ is $C_1$-$C_2$ alkylene. In some embodiments of a compound of Formula (II), (IIa), (IIb), (IIc),

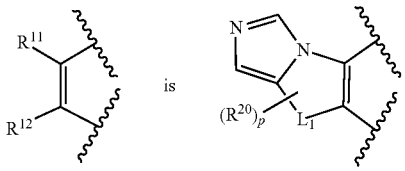

and $L_1$ is $C_1$-$C_4$ heteroalkylene. In some embodiments of a compound of Formula (II), (IIa), (IIb), (IIc),

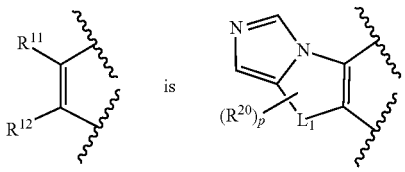

and $L_1$ is $C_1$-$C_2$ heteroalkylene.

In some embodiments of a compound of Formula (II), (IIa), (IIb), (IIc),

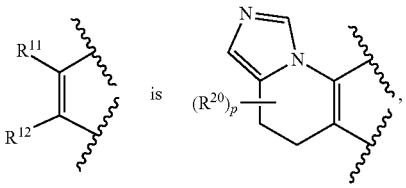

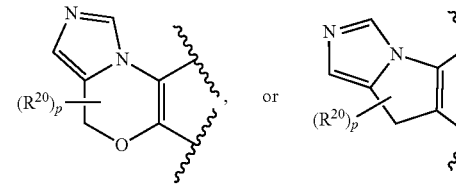

In some embodiments of a compound of Formula (II), (IIa), (IIb), (IIc), each $R^{20}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl. In some embodiments of a compound of Formula (II), (IIa), (IIb), (IIc), each $R^{20}$ is independently hydrogen, halogen, —CN, —OR$^a$, —NR$^c$R$^d$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl, or optionally substituted heterocycloalkyl. In some embodiments of a compound of Formula (II), (IIa), (IIb), (IIc), each R$^{20}$ is independently hydrogen, halogen, —OR$^a$, optionally substituted C$_1$-C$_6$ alkyl, or optionally substituted cycloalkyl. In some embodiments of a compound of Formula (II), (IIa), (IIb), (IIc), each R$^{20}$ is independently hydrogen, halogen, —OR$^a$, C$_1$-C$_6$ alkyl, or cycloalkyl. In some embodiments of a compound of Formula (II), (IIa), (IIb), (IIc), each R$^{20}$ is independently hydrogen, —OR$^a$, optionally substituted C$_1$-C$_6$ alkyl, or optionally substituted cycloalkyl. In some embodiments of a compound of Formula (II), (IIa), (IIb), (IIc), each R$^{20}$ is independently hydrogen, —OH, optionally substituted C$_1$-C$_6$ alkyl, or optionally substituted cycloalkyl. In some embodiments of a compound of Formula (II), (IIa), (IIb), (IIc), each R$^{20}$ is independently hydrogen, —OH, C$_1$-C$_6$ alkyl, or cycloalkyl. In some embodiments of a compound of Formula (II), (IIa), (IIb), (IIc), two R$^{20}$ on the same carbon atom are taken together to form an optionally substituted cycloalkyl selected from cyclopropyl, cyclobutyl, cyclopentyl, or cyclohexyl. In some embodiments of a compound of Formula (II), (IIa), (IIb), (IIc), two R$^{20}$ on the same carbon atom are taken together to form an optionally substituted cycloalkyl selected from cyclopropyl or cyclobutyl. In some embodiments of a compound of Formula (II), (IIa), (IIb), (IIc), the optional substituent on the cycloalkyl formed by two R$^{20}$ on the same carbon atom is halogen or C$_1$-C$_6$ alkyl.

In some embodiments of a compound of Formula (II), (IIa), (IIb), (IIc), p is 1 or 2. In some embodiments of a compound of Formula (II), (IIa), (IIb), (IIc), p is 1. In some embodiments of a compound of Formula (II), (IIa), (IIb), (IIc), p is 2. In some embodiments of a compound of Formula (II), (IIa), (IIb), (IIc), p is 3. In some embodiments of a compound of Formula (II), (IIa), (IIb), (IIc), p is 4. In some embodiments of a compound of Formula (II), (IIa), (IIb), (IIc), p' is 1. In some embodiments of a compound of Formula (II), (IIa), (IIb), (IIc), p' is 2.

In some embodiments of a compound of Formula (II), (IIa), (IIb), (IIc), each R$^{20}$ is independently hydrogen, halogen, —OR$^a$, optionally substituted C$_1$-C$_6$ alkyl, or optionally substituted cycloalkyl; or two R$^{20}$ on the same carbon atom are taken together to form an optionally substituted cycloalkyl; and p is 1-3.

In some embodiments of a compound of Formula (II), (IIa), (IIb), or (IIc), R$^a$ is hydrogen, optionally substituted C$_1$-C$_6$ alkyl, optionally substituted C$_1$-C$_6$ heteroalkyl, optionally substituted cycloalkyl, or optionally substituted heterocycloalkyl. In some embodiments of a compound of Formula (II), (IIa), (IIb), or (IIc), R$^a$ is hydrogen or optionally substituted C$_1$-C$_6$ alkyl. In some embodiments of a compound of Formula (II), (IIa), (IIb), or (IIc), R$^a$ is hydrogen, C$_1$-C$_6$ alkyl, or C$_1$-C$_6$ haloalkyl. In some embodiments of a compound of Formula (II), (IIa), (IIb), or (IIc), R$^a$ is hydrogen or C$_1$-C$_6$ alkyl. In some embodiments of a compound of Formula (II), (IIa), (IIb), or (IIc), R$^a$ is hydrogen. In some embodiments of a compound of Formula (II), (IIa), (IIb), or (ITC), R$^a$ is C$_1$-C$_6$ alkyl. In some embodiments of a compound of Formula (II), (IIa), (IIb), or (IIc), R$^a$ is heterocycloalkyl.

In some embodiments of a compound of Formula (II), (IIa), (IIb), or (IIc), R$^b$ is optionally substituted C$_1$-C$_6$ alkyl or optionally substituted C$_1$-C$_6$ heteroalkyl. In some embodiments of a compound of Formula (II), (IIa), (IIb), or (IIc), R$^b$ is optionally substituted C$_1$-C$_6$ alkyl. In some embodiments of a compound of Formula (II), (IIa), (IIb), or (IIc), R$^b$ is C$_1$-C$_6$ alkyl or C$_1$-C$_6$ haloalkyl. In some embodiments of a compound of Formula (II), (IIa), (IIb), or (IIc), R$^b$ is C$_1$-C$_6$ alkyl.

In some embodiments of a compound of Formula (II), (IIa), (IIb), or (IIc), each R$^c$ and R$^d$ is independently hydrogen, optionally substituted C$_1$-C$_6$ alkyl, optionally substituted C$_1$-C$_6$ heteroalkyl, optionally substituted cycloalkyl, or optionally substituted heterocycloalkyl. In some embodiments of a compound of Formula (II), (IIa), (IIb), or (IIc), each R$^c$ and R$^d$ is independently hydrogen or optionally substituted C$_1$-C$_6$ alkyl. In some embodiments of a compound of Formula (II), (IIa), (IIb), or (IIc), each and R$^d$ is independently hydrogen, C$_1$-C$_6$ alkyl, or C$_1$-C$_6$ haloalkyl. In some embodiments of a compound of Formula (II), (IIa), (IIb), or (IIc), each R$^c$ and R$^d$ is independently hydrogen or C$_1$-C$_6$ alkyl. In some embodiments of a compound of Formula (II), (IIa), (IIb), or (IIc), each R$^c$ and R$^d$ is hydrogen.

In some embodiments of a compound of Formula (II), (IIa), (IIb), or (IIc), R$^c$ and R$^d$, together with the nitrogen atom to which they are attached, form an optionally substituted heterocycloalkyl or optionally substituted heteroaryl. In some embodiments of a compound of Formula (II), (IIa), (IIb), or (IIc), R$^c$ and R$^d$, together with the nitrogen atom to which they are attached, form an optionally substituted heterocycloalkyl.

In some embodiments is a compound of Formula (II), (IIa), (IIb), or (IIc), or a pharmaceutically acceptable salt, solvate, or stereoisomer thereof, having a structure selected from:

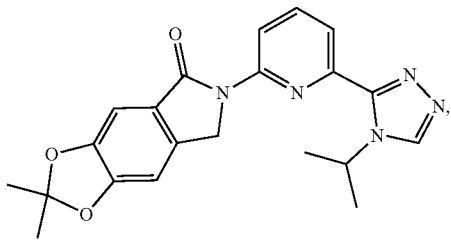

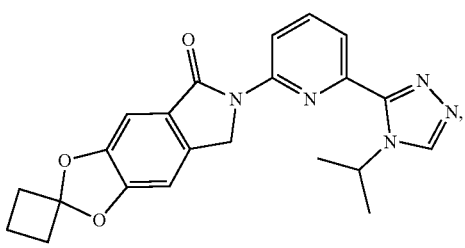

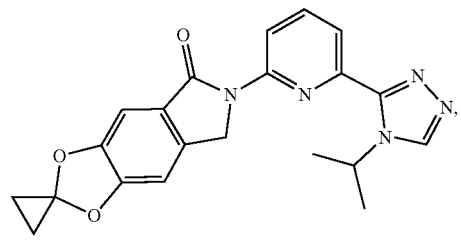

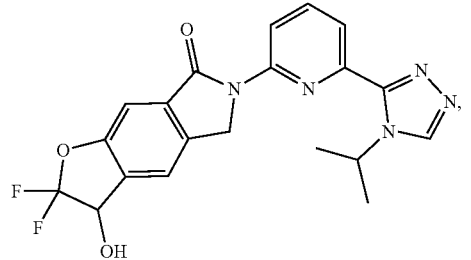
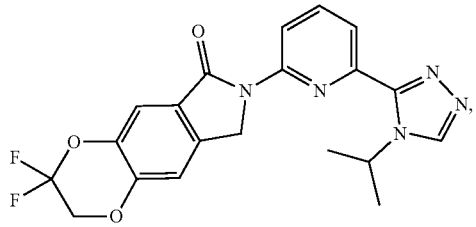
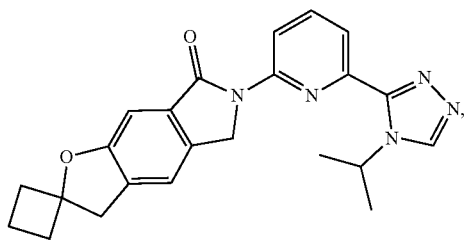
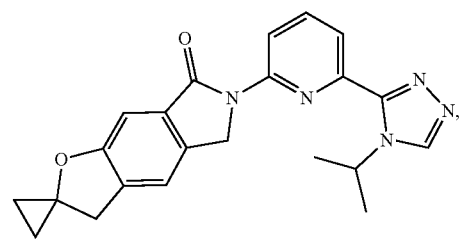
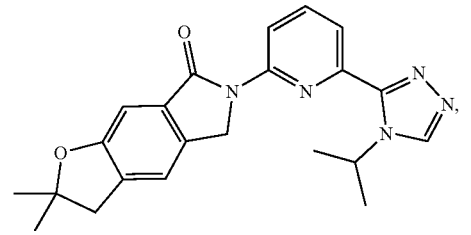
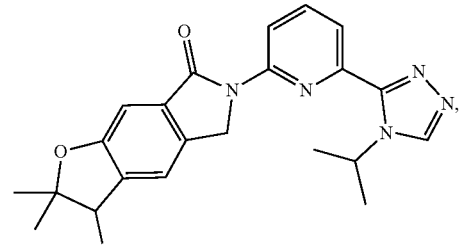
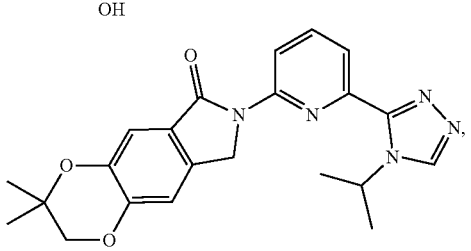
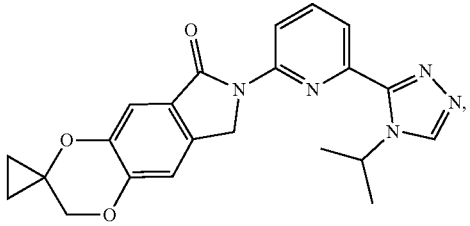
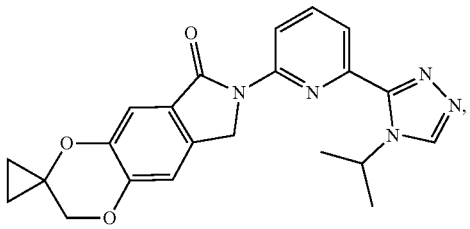
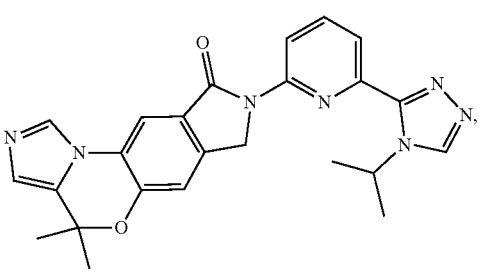
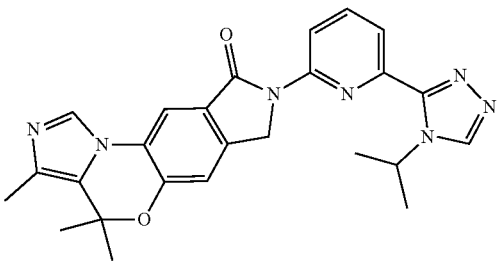
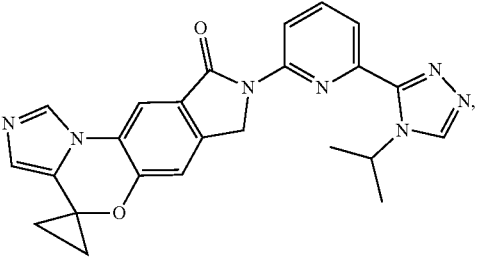
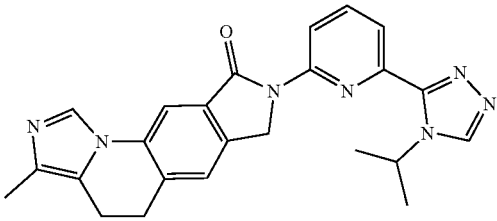
Also disclosed herein is a compound of Formula (III), or a pharmaceutically acceptable salt, solvate, tautomer, or stereoisomer thereof:

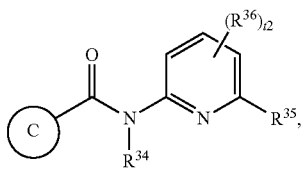

(Formula III)

wherein:
Ring C is an optionally substituted tricyclic ring;
$R^{34}$ is hydrogen, —S(=O)$R^b$, —S(=O)$_2R^d$, —S(=O)$_2$NR$^c$R$^d$, —C(=O)R$^b$, —OCO$_2$R$^a$, —C(=O)NR$^c$R$^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
$R^{35}$ is optionally substituted heterocycloalkyl or optionally substituted heteroaryl;
each $R^{36}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
$R^a$ is hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
$R^b$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
each $R^c$ and $R^d$ is independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
or $R^c$ and $R^d$, together with the nitrogen atom to which they are attached, form an optionally substituted heterocycloalkyl or optionally substituted heteroaryl; and
t2 is 1-3.

In some embodiments the compound of Formula (III) is of Formula (IIIa):

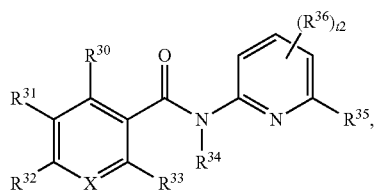

(Formula IIIa)

wherein:
$X_1$ is N or CR$^{X1}$;
$R^{30}$, $R^{32}$, $R^{33}$, and $R^{X1}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
provided that:
$R^{31}$ and $R^{32}$ are taken together with the atoms to which they are attached to form an optionally substituted bicyclic ring;
or $R^{30}$ and $R^{31}$ are taken together with the atoms to which they are attached to form an optionally substituted bicyclic ring.

In some embodiments of a compound of Formula (IIIa), $X_1$ is N. In some embodiments of a compound of Formula (IIIa), $X_1$ is CR$^{X1}$ and R$^{X1}$ is hydrogen, halogen, or optionally substituted $C_1$-$C_6$ alkyl. In some embodiments of a compound of Formula (IIIa), $X_1$ is CR$^{X1}$ and R$^{X1}$ is hydrogen, halogen, or $C_1$-$C_6$ alkyl. In some embodiments is a compound of Formula (IIIa), $X_1$ is CR$^{X1}$; and CR$^{X1}$ is hydrogen.

In some embodiments of a compound of Formula (IIIa), $R^{33}$ is hydrogen, halogen, —CN, —OR$^a$, —NR$^c$R$^d$, —CO$_2$R$^a$, —C(=O)NR$^c$R$^d$, optionally substituted $C_1$-$C_6$ alkyl, optionally substituted $C_1$-$C_6$ heteroalkyl, optionally substituted cycloalkyl. In some embodiments of a compound of Formula (IIIa), $R^{33}$ is hydrogen, halogen, —OR$^a$, or optionally substituted $C_1$-$C_6$ alkyl. In some embodiments of a compound of Formula (IIIa), $R^{33}$ is hydrogen, halogen, or optionally substituted $C_1$-$C_6$ alkyl. In some embodiments of a compound of Formula (IIIa), $R^{33}$ is hydrogen, halogen, or $C_1$-$C_6$ alkyl. In some embodiments of a compound of Formula (IIIa), $R^{33}$ is hydrogen. In some embodiments is a compound of Formula (IIIa), $R^{33}$ is hydrogen or halogen. In some embodiments is a compound of Formula (IIIa), $R^{33}$ is halogen.

In some embodiments the compound of Formula (III) is of Formula (IIIb):

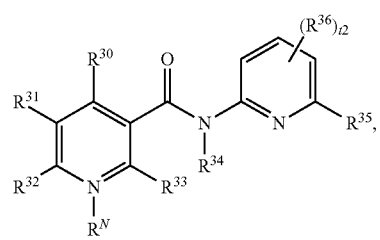

(Formula IIIb)

wherein:
$R^N$ is hydrogen, —S(=O)R$^b$, —S(=O)$_2$R$^d$, —S(=O)$_2$NR$^c$R$^d$, —C(=O)R$^b$, —OCO$_2$R$^a$, —C(=O)NR$^c$R$^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl; and $R^{30}$, $R^{32}$, and $R^{33}$ are independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl;

provided that:

$R^{31}$ and $R^{32}$ are taken together with the atoms to which they are attached to form an optionally substituted bicyclic ring;

or $R^{30}$ and $R^{31}$ are taken together with the atoms to which they are attached to form an optionally substituted bicyclic ring.

In some embodiments is a compound of Formula (IIIb), $R^N$ is hydrogen, optionally substituted C$_1$-C$_6$ alkyl, optionally substituted C$_1$-C$_6$ heteroalkyl, or optionally substituted cycloalkyl. In some embodiments is a compound of Formula (IIIb), $R^N$ is hydrogen or optionally substituted C$_1$-C$_6$ alkyl. In some embodiments is a compound of Formula (IIIb), $R^N$ is hydrogen or C$_1$-C$_6$ alkyl. In some embodiments is a compound of Formula (IIIb), $R^N$ is C$_1$-C$_6$ alkyl. In some embodiments is a compound of Formula (IIIb), $R^N$ is hydrogen.

In some embodiments of a compound of Formula (III), (IIIa), or (IIIb), $R^{35}$ is an optionally substituted heteroaryl.

In some embodiments of a compound of Formula (III), (IIIa), or (IIIb), $R^{35}$ is an optionally substituted 5-membered heteroaryl selected from imidazole, pyrazole, pyrrole, triazole, tetrazole, thiophene, furan, thiazole, isothiazole, oxazole, and isoxazole. In some embodiments of a compound of Formula (III), (IIIa), or (IIIb), $R^{35}$ is optionally substituted 5-membered heteroaryl selected from triazole, tetrazole, and isoxazole. In some embodiments of a compound of Formula (III), (IIIa), or (IIIb), $R^{35}$ is an optionally substituted triazole. In some embodiments of a compound of Formula (III), (IIIa), or (IIIb), $R^{35}$ is an optionally substituted tetrazole. In some embodiments of a compound of Formula (III), (IIIa), or (IIIb), $R^{35}$ is an optionally substituted pyrazole.

In some embodiments of a compound of Formula (III), (IIIa), or (IIIb), $R^{35}$ is an optionally substituted 6-membered heteroaryl selected from pyridine, pyrimidine, pyrazine, and pyridazine. In some embodiments of a compound of Formula (III), (IIIa), or (IIIb), $R^{35}$ is optionally substituted pyridine.

In some embodiments of a compound of Formula (III), (IIIa), or (IIIb), $R^{35}$ is optionally substituted with halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl. In some embodiments of a compound of Formula (III), (IIIa), or (IIIb), $R^{35}$ is optionally substituted with halogen, —CN, —OR$^a$, —NR$^c$R$^d$, optionally substituted C$_1$-C$_6$ alkyl, optionally substituted cycloalkyl, or optionally substituted heterocycloalkyl. In some embodiments of a compound of Formula (III), (IIIa), or (IIIb), $R^{35}$ is optionally substituted with halogen, —CN, —OH, —NH$_2$, C$_1$-C$_6$ alkyl, C$_1$-C$_6$ haloalkyl, C$_1$-C$_6$ hydroxyalkyl, or cycloalkyl. In some embodiments of a compound of Formula (III), (IIIa), or (IIIb), $R^{35}$ is optionally substituted with C$_1$-C$_6$ alkyl.

In some embodiments of a compound of Formula (III), (IIIa), or (IIIb), $R^{36}$ is hydrogen, halogen, —CN, —OR$^a$, —NR$^c$R$^d$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl. In some embodiments of a compound of Formula (III), (IIIa), or (IIIb), $R^{36}$ is hydrogen, halogen, —OR$^a$, or optionally substituted C$_1$-C$_6$ alkyl. In some embodiments of a compound of Formula (III), (IIIa), or (IIIb), $R^{36}$ is hydrogen, halogen, or optionally substituted C$_1$-C$_6$ alkyl. In some embodiments of a compound of Formula (III), (IIIa), or (IIIb), $R^{36}$ is hydrogen, halogen, or C$_1$-C$_6$ alkyl. In some embodiments of a compound of Formula (III), (IIIa), or (IIIb), $R^{36}$ is hydrogen.

In some embodiments of a compound of Formula (III), (IIIa), or (IIIb), t2 is 1 or 2. In some embodiments of a compound of Formula (III), (IIIa), or (IIIb), t2 is 1. In some embodiments of a compound of Formula (III), (IIIa), or (IIIb), t2 is 2. In some embodiments of a compound of Formula (III), (IIIa), or (IIIb), t2 is 3.

In some embodiments is a compound of Formula (III), (IIIa), or (IIIb), $R^{34}$ is hydrogen, optionally substituted C$_1$-C$_6$ alkyl, optionally substituted C$_1$-C$_6$ heteroalkyl, or optionally substituted cycloalkyl. In some embodiments is a compound of Formula (III), (IIIa), or (IIIb), $R^{34}$ is hydrogen or optionally substituted C$_1$-C$_6$ alkyl. In some embodiments is a compound of Formula (IIIb), $R^{34}$ is hydrogen or C$_1$-C$_6$ alkyl. In some embodiments is a compound of Formula (III), (IIIa), or (IIIb), $R^{34}$ is C$_1$-C$_6$ alkyl. In some embodiments is a compound of Formula (III), (IIIa), or (IIIb), $R^{34}$ is hydrogen.

In some embodiments of a compound of Formula (IIIa) or (IIIb), $R^{30}$ is hydrogen, halogen, —CN, —OR$^a$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl. In some embodiments of a compound of Formula (IIIa) or (IIIb), $R^{30}$ is hydrogen, halogen, —OR$^a$, or optionally substituted C$_1$-C$_6$ alkyl. In some embodiments of a compound of Formula (IIIa) or (IIIb), $R^{30}$ is hydrogen, halogen, or optionally substituted C$_1$-C$_6$ alkyl. In some embodiments of a compound of Formula (IIIa) or (IIIb), $R^{30}$ is hydrogen, halogen, or C$_1$-C$_6$ alkyl. In some embodiments of a compound of Formula (IIIa) or (IIIb), $R^{30}$ is hydrogen.

In some embodiments of a compound of Formula (IIIa) or (IIIb), $R^{32}$ is hydrogen, halogen, —CN, —OR$^a$, —NR$^c$R$^d$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl. In some embodiments of a compound of Formula (IIIa) or (IIIb), $R^{32}$ is hydrogen, halogen, —OR$^a$, or optionally substituted C$_1$-C$_6$ alkyl. In some embodiments of a compound of Formula (IIIa) or (IIIb), $R^{32}$ is hydrogen, halogen, or optionally substituted C$_1$-C$_6$ alkyl. In some embodiments of a compound of Formula (IIIa) or (IIIb), $R^{32}$ is hydrogen, halogen, or C$_1$-C$_6$ alkyl. In some embodiments of a compound of Formula (IIIa) or (IIIb), $R^{32}$ is hydrogen.

In some embodiments of a compound of Formula (IIIa) or (IIIb),

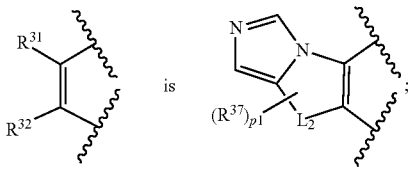

wherein:
L₂ is $C_1$-$C_4$ alkylene or $C_1$-$C_4$ heteroalkylene;
each $R^{37}$ is independently hydrogen, halogen, —CN, —OR$^a$, —SR$^a$, —S(=O)R$^b$, —NO₂, —NR$^c$R$^d$, —S(=O)₂R$^d$, —NR$^a$S(=O)₂R$^d$, —S(=O)₂NR$^c$R$^d$, —C(=O)R$^b$, —OC(=O)R$^b$, —CO₂R$^a$, —OCO₂R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;
or two $R^{37}$ on the same carbon atom are taken together to form an oxo;
or two $R^{37}$ on the same carbon atom are taken together to form an optionally substituted cycloalkyl or optionally substituted heterocycloalkyl;
or two $R^{37}$ on the different carbon atom are taken together to form an optionally substituted cycloalkyl or optionally substituted heterocycloalkyl; and
p1 is 1-4.

In some embodiments of a compound of Formula (IIIa) or (IIIb),

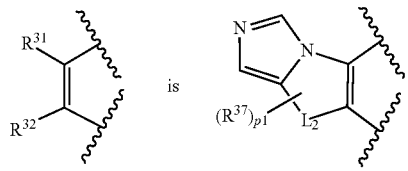

and L₂ is $C_1$-$C_4$ alkylene. In some embodiments of a compound of Formula (IIIa) or (IIIb),

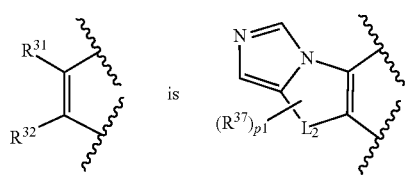

and L₂ is $C_1$-$C_2$ alkylene. In some embodiments of a compound of Formula (IIIa) or (IIIb),

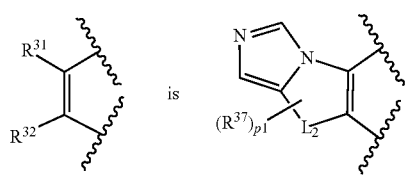

and L₂ is $C_1$-$C_4$ heteroalkylene. In some embodiments of a compound of Formula (IIIa) or (IIIb),

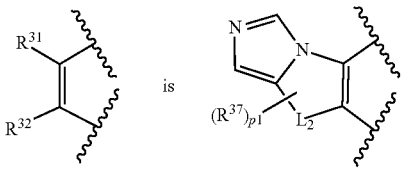

and L₂ is $C_1$-$C_2$ heteroalkylene.

In some embodiments of a compound of Formula (IIIa) or (IIIb),

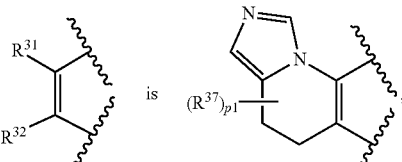

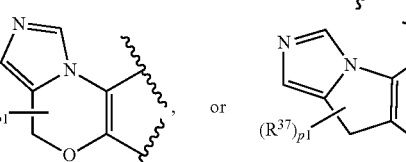

In some embodiments of a compound of Formula (IIIa) or (IIIb),

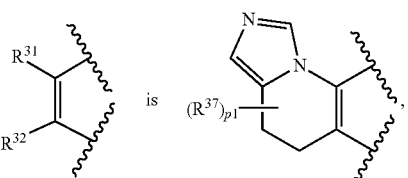

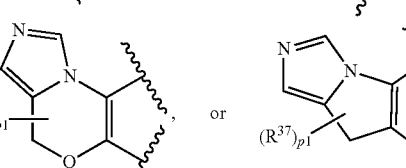

In some embodiments of a compound of Formula (IIIa) or (IIIb),

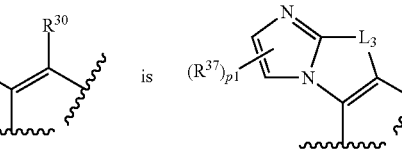

wherein:
L₃ is $C_1$-$C_4$ alkylene or $C_1$-$C_4$ heteroalkylene;
each $R^{37}$ is independently hydrogen, halogen, —CN, —OR$^a$, —SR$^a$, —S(=O)R$^b$, —NO₂, —NR$^c$R$^d$, —S(=O)₂R$^d$, —NR$^a$S(=O)₂R$^d$, —S(=O)₂NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl;

or two R$^{37}$ on the same carbon atom are taken together to form an oxo;

or two R$^{37}$ on the same carbon atom are taken together to form an optionally substituted cycloalkyl or optionally substituted heterocycloalkyl;

or two R$^{37}$ on the different carbon atom are taken together to form an optionally substituted cycloalkyl or optionally substituted heterocycloalkyl; and p1 is 1-4.

In some embodiments of a compound of Formula (IIIa) or (IIIb),

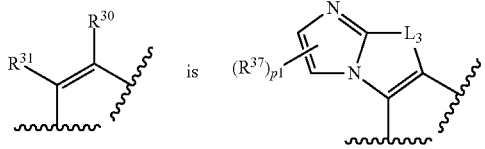

and L$_3$ is C$_1$-C$_4$ alkylene. In some embodiments of a compound of Formula (IIIa) or (IIIb),

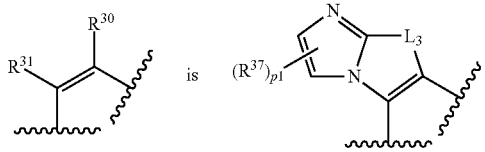

and L$_3$ is C$_1$-C$_2$ alkylene. In some embodiments of a compound of Formula (IIIa) or (IIIb),

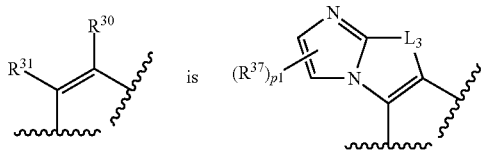

and L$_3$ is C$_1$-C$_4$ heteroalkylene. In some embodiments of a compound of Formula (IIIa) or (IIIb),

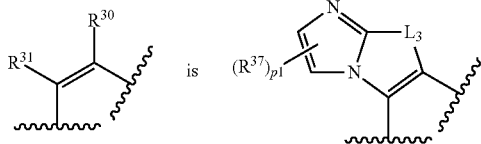

and L$_3$ is C$_1$-C$_2$ heteroalkylene.

In some embodiments of a compound of Formula (IIIa) or (IIIb),

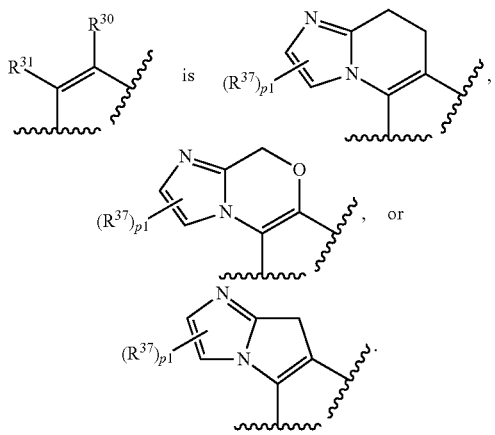

In some embodiments of a compound of Formula (IIIa) or (IIIb), each R$^{37}$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ heteroalkyl, optionally substituted cycloalkyl, optionally substituted heterocycloalkyl, optionally substituted aryl, or optionally substituted heteroaryl. In some embodiments of a compound of Formula (IIIa) or (IIIb), each R$^{37}$ is independently hydrogen, halogen, —CN, —OR$^a$, —NR$^c$R$^d$, —CO$_2$R$^a$, —C(=O)NR$^c$R$^d$, optionally substituted C$_1$-C$_6$ alkyl, optionally substituted C$_1$-C$_6$ heteroalkyl, optionally substituted cycloalkyl, or optionally substituted heterocycloalkyl. In some embodiments of a compound of Formula (IIIa) or (IIIb), each R$^{37}$ is independently hydrogen, halogen, —OR$^a$, optionally substituted C$_1$-C$_6$ alkyl, or optionally substituted cycloalkyl. In some embodiments of a compound of Formula (IIIa) or (IIIb), each R$^{37}$ is independently hydrogen, halogen, —OR$^a$, C$_1$-C$_6$ alkyl, or cycloalkyl. In some embodiments of a compound of Formula (IIIa) or (IIIb), each R$^{37}$ is independently hydrogen, —OR$^a$, optionally substituted C$_1$-C$_6$ alkyl, or optionally substituted cycloalkyl. In some embodiments of a compound of Formula (IIIa) or (IIIb), each R$^{37}$ is independently hydrogen, —OH, optionally substituted C$_1$-C$_6$ alkyl, or optionally substituted cycloalkyl. In some embodiments of a compound of Formula (IIIa) or (IIIb), each R$^{37}$ is independently hydrogen, —OH, C$_1$-C$_6$ alkyl, or cycloalkyl. In some embodiments of a compound of Formula (IIIa) or (IIIb), two R$^{37}$ on the same carbon atom are taken together to form an optionally substituted cycloalkyl selected from cyclopropyl, cyclobutyl, cyclopentyl, or cyclohexyl. In some embodiments of a compound of Formula (IIIa) or (IIIb), two R$^{37}$ on the same carbon atom are taken together to form an optionally substituted cycloalkyl selected from cyclopropyl or cyclobutyl. In some embodiments of a compound of Formula (IIIa) or (IIIb), the optional substituent on the cycloalkyl formed by two R$^{37}$ on the same carbon atom is halogen or C$_1$-C$_6$ alkyl.

In some embodiments of a compound of Formula (IIIa) or (IIIb), p1 is 1 or 2. In some embodiments of a compound of Formula (IIIa) or (IIIb), p is 1. In some embodiments of a compound of Formula (IIIa) or (IIIb), p1 is 2. In some embodiments of a compound of Formula (IIIa) or (IIIb), p1 is 3. In some embodiments of a compound of Formula (IIIa) or (IIIb), p1 is 4.

In some embodiments of a compound of Formula (IIIa) or (IIIb), each $R^{37}$ is independently hydrogen, halogen, —$OR^a$, optionally substituted $C_1$-$C_6$ alkyl, or optionally substituted cycloalkyl; or two $R^{37}$ on the same carbon atom are taken together to form an optionally substituted cycloalkyl; and p1 is 1-3.

In some embodiments of a compound of Formula (III), (IIIa), or (IIIb), $R^a$ is hydrogen, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (III), (IIIa), or (IIIb), $R^a$ is hydrogen or optionally substituted $C_1$-$C_6$ alkyl. In some embodiments of a compound of Formula (III), (IIIa), or (IIIb), $R^a$ is hydrogen, $C_1$-$C_6$ alkyl, or $C_1$-$C_6$ haloalkyl. In some embodiments of a compound of Formula (III), (IIIa), or (IIIb), $R^a$ is hydrogen or $C_1$-$C_6$ alkyl. In some embodiments of a compound of Formula (III), (IIIa), or (IIIb), $R^a$ is hydrogen. In some embodiments of a compound of Formula (III), (IIIa), or (IIIb), $R^a$ is $C_1$-$C_6$ alkyl. In some embodiments of a compound of Formula (III), (IIIa), or (IIIb), $R^a$ is heterocycloalkyl.

In some embodiments of a compound of Formula (III), (IIIa), or (IIIb), $R^b$ is optionally substituted $C_1$-$C_6$ alkyl or optionally substituted $C_1$-$C_6$ heteroalkyl. In some embodiments of a compound of Formula (III), (IIIa), or (IIIb), $R^b$ is optionally substituted $C_1$-$C_6$ alkyl. In some embodiments of a compound of Formula (III), (IIIa), or (IIIb), $R^b$ is $C_1$-$C_6$ alkyl or $C_1$-$C_6$ haloalkyl. In some embodiments of a compound of Formula (III), (IIIa), or (IIIb), $R^b$ is $C_1$-$C_6$ alkyl.

In some embodiments of a compound of Formula (III), (IIIa), or (IIIb), each $R^c$ and $R^d$ is independently hydrogen, optionally substituted $C_1$-$C_6$ alkyl, optionally substituted $C_1$-$C_6$ heteroalkyl, optionally substituted cycloalkyl, or optionally substituted heterocycloalkyl. In some embodiments of a compound of Formula (III), (IIIa), or (IIIb), each $R^c$ and $R^d$ is independently hydrogen or optionally substituted $C_1$-$C_6$ alkyl. In some embodiments of a compound of Formula (III), (IIIa), or (IIIb), each $R^c$ and $R^d$ is independently hydrogen, $C_1$-$C_6$ alkyl, or $C_1$-$C_6$ haloalkyl. In some embodiments of a compound of Formula (III), (IIIa), or (IIIb), each $R^c$ and $R^d$ is independently hydrogen or $C_1$-$C_6$ alkyl. In some embodiments of a compound of Formula (III), (IIIa), or (IIIb), each $R^c$ and $R^d$ is hydrogen.

In some embodiments of a compound of Formula (III), (IIIa), or (IIIb), $R^c$ and $R^d$, together with the nitrogen atom to which they are attached, form an optionally substituted heterocycloalkyl or optionally substituted heteroaryl. In some embodiments of a compound of Formula (III), (IIIa), or (IIIb), and $R^d$, together with the nitrogen atom to which they are attached, form an optionally substituted heterocycloalkyl.

In some embodiments is a compound of Formula (III), (IIIa), or (IIIb), or a pharmaceutically acceptable salt, solvate, or stereoisomer thereof, having a structure selected from:

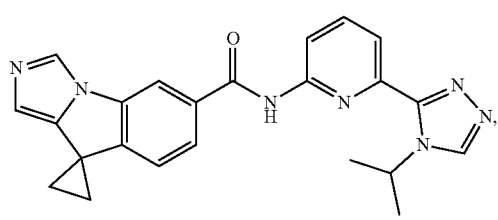

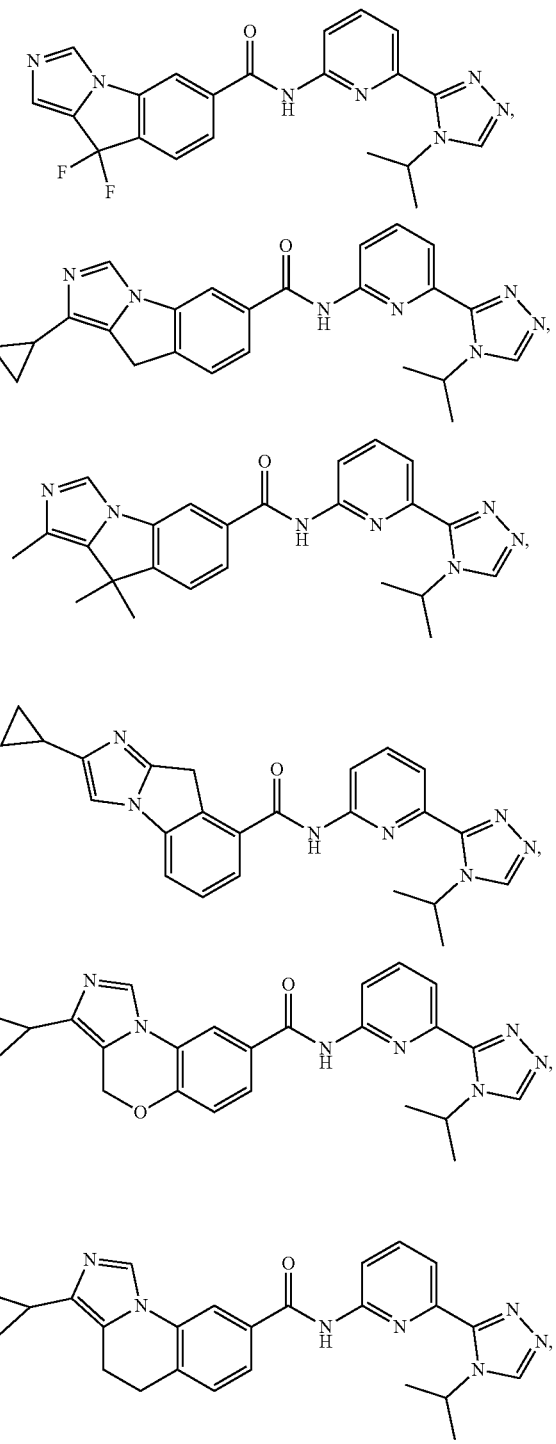

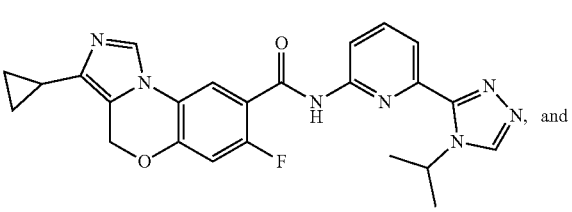

-continued

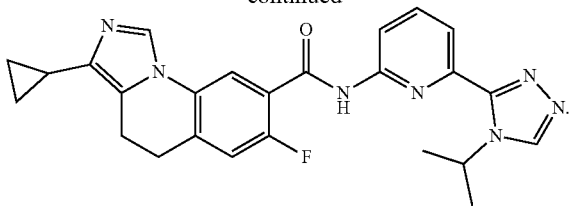

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$ isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts, and the like. Illustrative examples of bases include sodium hydroxide, potassium hydroxide, choline hydroxide, sodium carbonate, $N^+$ ($C_{1-4}$ alkyl)$_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising a compound described herein, or a pharmaceutically acceptable salt, solvate, tautomer, or stereoisomer thereof, and a pharmaceutically acceptable excipient.

In certain embodiments, the compound provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal and epidural and intranasal administration. Parenteral administration includes intramuscular, intravenous, intraarterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involve the administration of about 0.1 µg to about 50 mg of at least one compound of the invention per kg body weight of the subject. For a 70 kg patient, dosages of from about 10 µg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

The compounds disclosed herein, or a pharmaceutically acceptable salt, solvate, tautomer, or stereoisomer thereof, are useful as inhibitors of ASK1 and, therefore, useful in the treatment of diseases or disorders in which it is believed ASK1 activity plays a role.

Disclosed herein are methods of treating an ASK1 associated disease or disorder in a subject in need thereof comprising the step of administering to the subject an effective amount of a compound disclosed herein, or a pharmaceutically acceptable salt, solvate, or stereoisomer thereof.

In one aspect, described herein is a method for treating a disease in a mammal comprising administering to the mammal a therapeutically effective amount of a compound described herein, or a pharmaceutically acceptable salt, solvate, tautomer, or stereoisomer thereof. In one embodiment, the disease is selected from the group consisting of a blood disease, an autoimmune disorder, a pulmonary disorder, hypertension, an inflammatory disease, a fibrotic disease (such as idiosyncratic pulmonary fibrosis, chronic kidney disease/kidney fibrosis, irritable bowel disease, scleroderma, and liver fibrosis), diabetes, diabetic nephropathy, a renal disease, a respiratory disease, a cardiovascular disease, acute lung injury, acute or chronic liver disease, and a neurodegenerative disease. In one embodiment, the liver disease is selected from the group consisting of fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), porphyria, acetaminophen hepatotoxicity, Reye's syndrome, sarcoidosis, tyrosinemia, Wilson disease, Gilbert's syndrome, cirrhosis, and primary sclerosing cholangitis. In one embodiment, the liver disease is non-alcoholic steatohepatitis (NASH). In one embodiment, the liver disease is acute liver injury. In one embodiment, the liver disease is hepatic steatosis. In another embodiment, the pulmonary disorder is selected from the group consisting of chronic obstructive pulmonary disease (COPD), idiopathic pulmonary fibrosis (IPF), asthma, bronchitis, emphysema, lung cancer, pneumonia, cystic fibrosis, pulmonary embolism, pulmonary arterial hypertension, pulmonary edema, and pulmonary hemorrhage. In another embodiment, the autoimmune disorder is selected from the group consisting of alopecia areata, autoimmune hemolytic anemia, autoimmune hepatitis, dermatomyositis, diabetes (type 1), idiopathic arthritis, glomerulonephritis, Graves' disease, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, thyroiditis, uveitis, vitiligo, and granulomatosis with polyangiitis (Wegener's). In another embodiment, the inflammatory disease is selected from the group consisting of Alzheimer's, ankylosing spondylitis, arthritis (osteoarthritis, rheumatoid arthritis (RA), psoriatic arthritis), atherosclerosis, arteriosclerosis, cholestasis, Crohn's disease, colitis, dermatitis, diverticulitis, fibromyalgia, irritable bowel syndrome (IBS), systemic lupus erythematous (SLE), nephritis, Parkinson's disease, cardiac inflammation, and ulcerative colitis. In another embodiment, the renal disease is selected from the group consisting of Alport syndrome, renal fibrosis, kidney disease, diabetic nephropathy, fabry disease, diabetic kidney disease, diabetic nephropathy, renal inflammation, renal fibrosis focal segmental glomerulosclerosis, glomerulonephritis, IgA nephropathy (Berger's disease), kidney stones, minimal change disease, nephrotic syndrome, and polycystic kidney disease (PKD). In another embodiment, the neurodegenerative disease is selected from the group consisting of Alzheimer's disease, dementia, multiple sclerosis, optical neuritis, amyotrophic lateral sclerosis, Friedreich's ataxia, amyotrophic lateral sclerosis (ALS), Huntington's disease, Lewy body disease, Parkinson's disease, and spinal muscular atrophy. In another embodiment, the neurodegenerative disease is multiple sclerosis. In another embodiment, the neurodegenerative disease is amyotrophic lateral sclerosis. In another embodiment, the neurodegenerative disease is Alzheimer's disease. In another embodiment, the neurodegenerative disease is Parkinson's disease. In another embodiment, the cardiovascular disease is selected from the group consisting of endothelial dysfunction, metabolic syndrome, atherosclerosis, coronary artery disease, heart failure, peripheral artery disease, cardiac inflammation, cardiac fibrosis, cerebrovascular disease, and coronary syndrome. In another embodiment, the blood disease is sickle cell disease.

In one aspect, described herein is a method for reducing neuronal cell death following ischemic injury in a mammal comprising administering to the mammal a therapeutically effective amount of a compound described herein, or a pharmaceutically acceptable salt, solvate, tautomer, or stereoisomer thereof.

In another aspect, described herein is a method for modulating platelets in a mammal comprising administering to the mammal a therapeutically effective amount of a compound described herein, or a pharmaceutically acceptable salt, solvate, tautomer, or stereoisomer thereof. In one embodiment, the compound modulates platelet activation, platelet granule secretion, thromboxane A2 generation, or thrombosis modulation.

In another aspect, described herein is a method for modulating the level of a reactive oxidative species in a mammal comprising administering to the mammal a therapeutically effective amount of a compound described herein, or a pharmaceutically acceptable salt, solvate, tautomer, or stereoisomer thereof. In one embodiment, the reactive oxidative species is a reactive oxygen species. In another embodiment, the reactive oxidative species contains a radical on the oxygen atom.

In one embodiment, the disease is a cancer. In one embodiment, the disease is Sickle cell disease. In one embodiment, the disease is renal fibrosis. In one embodiment, the disease is a kidney disease. In one embodiment, the disease is a function of oxidative stress. In one embodiment, the disease is liver ischemia.

Combination Therapy

In certain instances, the compound described herein, or a pharmaceutically acceptable salt, solvate, tautomer, or stereoisomer thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, tautomer, or stereoisomer thereof, is co-administered with a second therapeutic agent, wherein the compound described herein, or a pharmaceutically acceptable salt, solvate, tautomer, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, tautomer, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, tautomer, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt, solvate, tautomer, or stereoisomer thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound of described herein, or a pharmaceutically acceptable salt, solvate, tautomer, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

EXAMPLES

Example 1: General Procedure for Synthesis of Compound Example 1

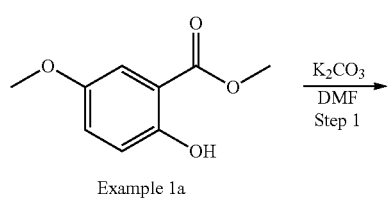

Example 1a

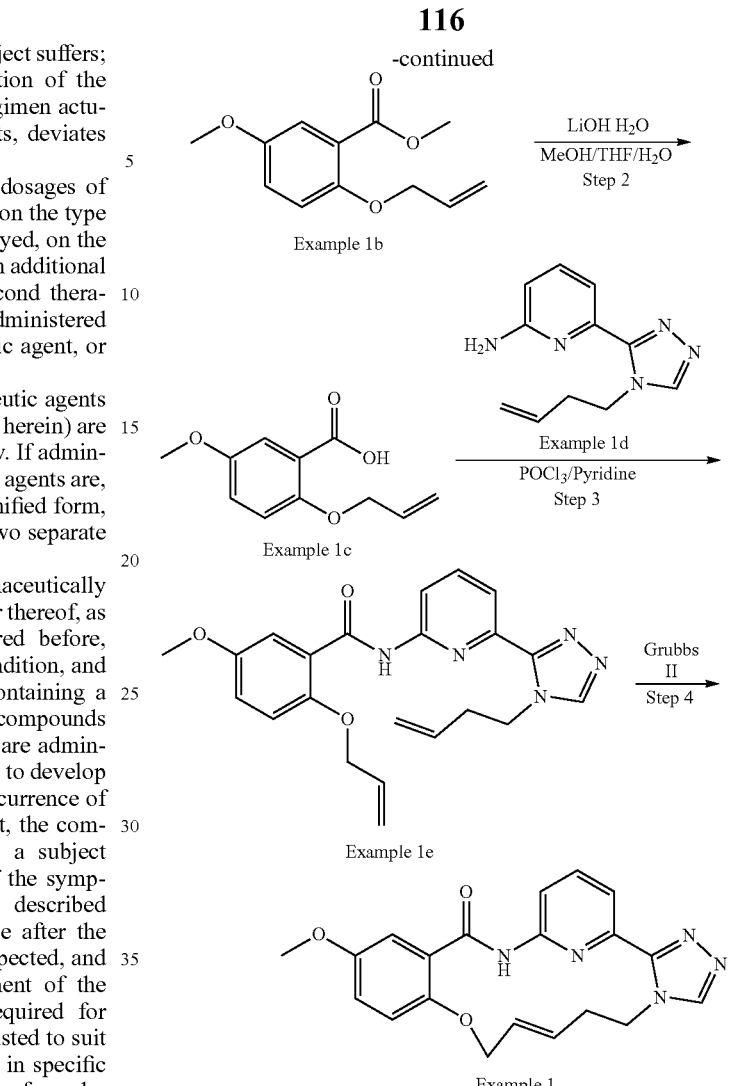

Step 1: Example 1b

To a solution of Example 1a (1 g, 5.5 mmol) and allyl bromide (811 mg, 6.6 mmol) in DMF (5 mL) was added K$_2$CO$_3$ (910 mg, 6.6 mmol). The mixture was stirred at r.t. overnight. After stirred for 20 h, the mixture was washed with H$_2$O (10 mL), extracted with EtOAc (10 mL*2). The combined organic phase was washed with brine, dried over Na$_2$SO$_4$, filtrated and the filtrate was concentrated under reduced pressure to obtain the desired product (Example 1b, 1.2 g, yield 98%) as a yellow oil. LCMS [M+1]$^+$=223.0.

Step 2: Example 1c

A mixture of Example 1b (600 mg, 2.7 mmol) and LiO.H$_2$O (125 mg, 3.0 mmol) in THF (9 mL), MeOH (3 mL) and H$_2$O (3 mL) was stirred at room temperature overnight. The resulting mixture was washed with EtOAc (10 mL), then adjusted with aqueous HCl solution to a pH of 2. After extraction with EtOAc (10 mL*2), combined organic layer was dried over anhydrous magnesium sulfate and concentrated under reduced pressure to give desired product (Example 1C, 500 mg, yield 89%) as a yellow solid. LCMS [M+1]$^+$=209.0. $^1$H NMR (400 MHz, DMSO-d$_6$) δ 7.15 (dd, J=2.3, 1.3 Hz, 1H), 7.08-6.98 (m, 2H), 5.99 (m1H), 5.41 (dd, J=17.2, 1.9 Hz, 1H), 5.20 (dd, J=10.6, 1.8 Hz, 1H), 4.53 (dt, J=4.9, 1.7 Hz, 2H), 3.70 (s, 3H).

Step 3: Example 1e

A mixture of Example 1c (339 mg, 1.6 mmol) and Example 1d (350 mg, 1.6 mmol) in pyridine (5 mL) was stirred at 0° C. for 10 min, then POCl$_3$ (1.2 g, 8.1 mmol) was slowly dropped into the reaction. The reaction was stirred at 0° C. for 10 min. The resulting mixture was quenched with water (10 mL). After extraction with DCM (10 mL*2), combined organic layer was dried over anhydrous magnesium sulfate and concentrated under reduced pressure. The residue was purified by doing silica gel chromatography (100% EtOAc) to give the desired product (Example 1d, 150 mg, yield 23%) as a white solid. LCMS [M+1]$^+$=406.0.

Step 4: Example 1

Under an atmosphere of N$_2$, a mixture of Example 1e (110 mg, 0.27 mmol) and Grubbs II (17 mg, 0.1 mmol) in toluene (30 mL) was refluxed overnight. The resulting mixture was concentrated under reduced pressure. The residue was purified by silica gel chromatography (100% EtOAc) to give Example 1 (9 mg, yield 9%) as a white solid. LCMS [M+1]$^+$=378.0. $^1$H NMR (400 MHz, DMSO-d$_6$) δ 11.17 (s, 1H), 9.29 (s, 1H), 8.74 (s, 1H), 8.34 (d, J=8.3 Hz, 1H), 8.02 (t, J=8.0 Hz, 1H), 7.91 (m, 1H), 7.59 (d, J=3.2 Hz, 1H), 7.25 (d, J=8.9 Hz, 1H), 6.42 (m, 1H), 6.09-5.97 (m, 1H), 4.70 (d, J=6.3 Hz, 2H), 4.52 (t, J=6.4 Hz, 2H), 3.77 (s, 3H), 2.65 (m, 2H).

Example 2: General Procedure for Synthesis of Compound Example 2

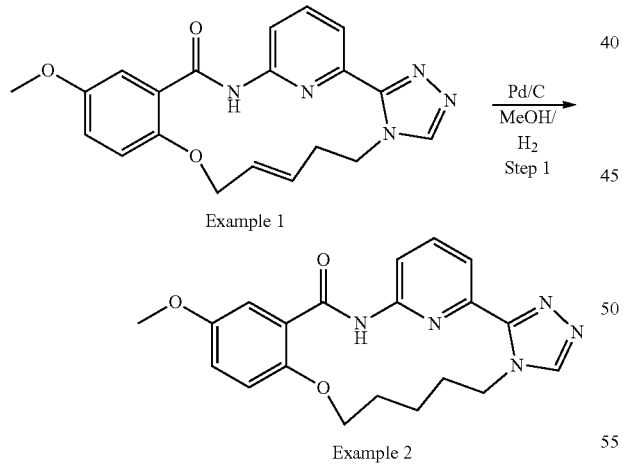

Step 1: Example 2

Under an atmosphere of H$_2$, a mixture of Example 1 (100 mg, 0.27 mmol) and Pd/C (10 mg) in MeOH (15 mL) was stirred at r.t. for 20 min. The resulting mixture was concentrated under reduced pressure to obtain crude product. The residue was purified by Prep-HPLC to give Example 2 (10 mg, yield 10%) as a white solid. LCMS [M+1]$^+$=380.0. $^1$H NMR (400 MHz, DMSO-d$_6$) δ 10.79 (s, 1H), 8.65 (s, 1H), 8.37 (d, J=8.4 Hz, 1H), 8.05 (d, J=8.0 Hz, 1H), 7.95 (d, J=7.2 Hz, 1H), 7.64 (s, 1H), 7.19 (s, 2H), 4.34-4.07 (m, 4H), 3.77 (s, 3H), 2.08-1.97 (m, 2H), 1.95-1.86 (m, 2H), 1.85-1.73 (m, 2H).

Example 3: General Procedure for Synthesis of Compound Example 3

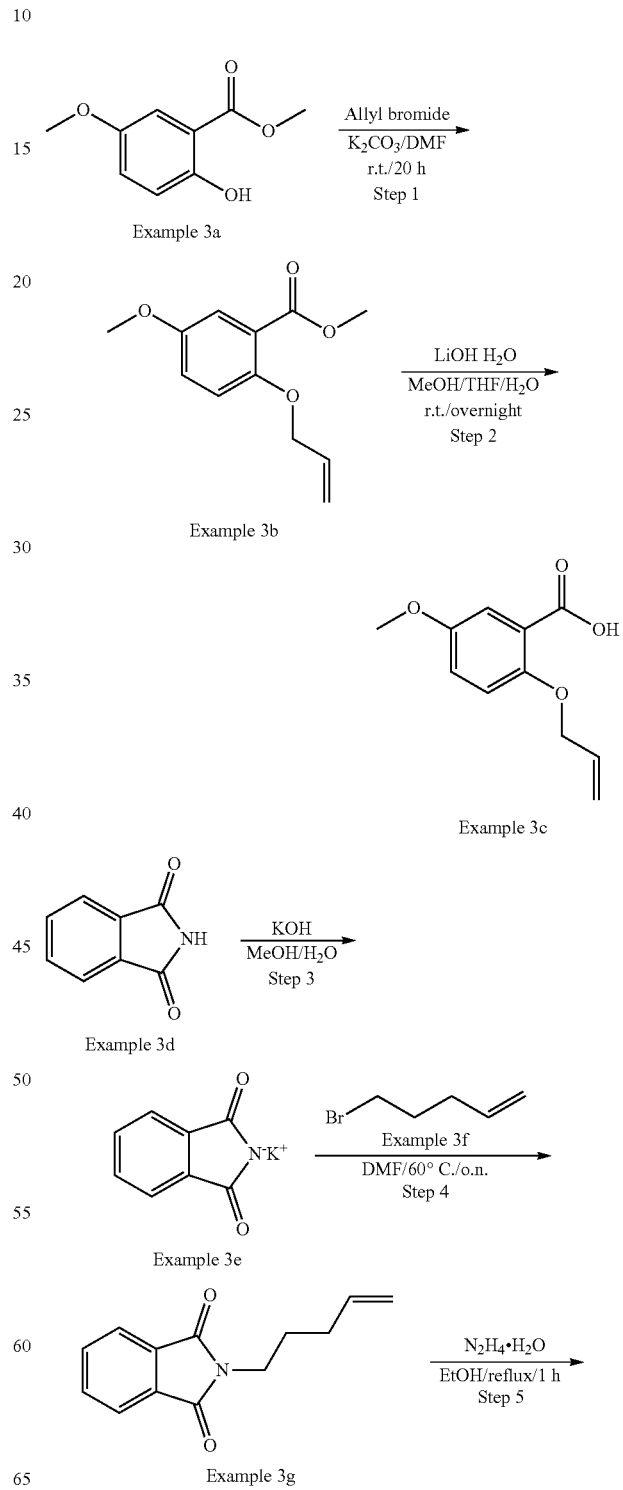

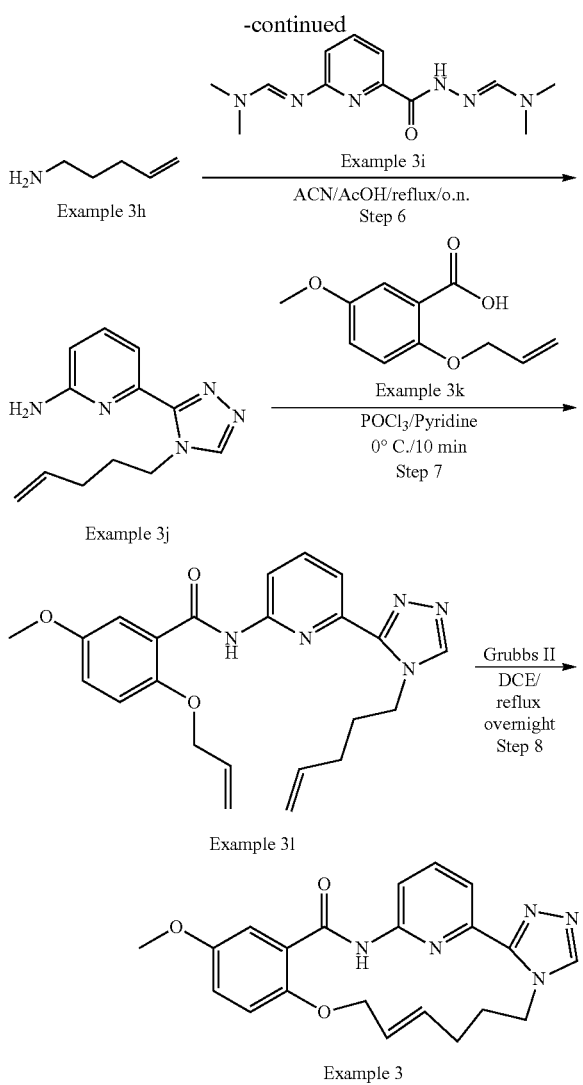

1H), 7.08-6.98 (m, 2H), 5.99 (m, 1H), 5.41 (dd, J=17.2, 1.9 Hz, 1H), 5.20 (dd, J=10.6, 1.8 Hz, 1H), 4.53 (dt, J=4.9, 1.7 Hz, 2H), 3.70 (s, 3H).

Step 3: Example 3e

Example 3d (20.0 g, 136 mmol) in MeOH (400 mL) was heated to slightly boiling. Then, the supernatant was poured into a solution of KOH (7.6 g, 136 mmol) in water (7.5 mL)/MeOH (23 mL). The solution was rapid cooling to r.t., and the precipitate was collected by filtration. The filter cake was washed with MeOH (20 mL) twice, dried under Vacuum to obtain the desired product Example 3e (14.4 g, yield 57%) as a white solid.

Step 4: Example 3g

Under an atmosphere of $N_2$, a mixture of Example 3e (18 g, 97.2 mmol) and Example 3f (12 g, 88.5 mmol) in DMF (180 mL) was heated to 60° C. overnight. The resulting mixture was cooled to r.t. and added to a solution of brine/water (v/v=3/1). After extraction with $Et_2O$ (30 mL*2), the combined organic layer was dried over anhydrous magnesium sulfate and concentrated under reduced pressure to give desired product Example 3g (19 g, yield 99%) as yellow oil. LCMS $[M+1]^+$=216.0.

Step 5: Example 3h

To a solution of Example 3g (12.1 g, 56 mmol) in dry EtOH (300 mL) at 50° C. was added $N_2H_4.H_2O$ (6.2 g, 124 mmol). Then the solution was refluxed for 1 h. The mixture was quenched with concentrated HCl (20 mL) and stirred for 10 min. The white solid was filtered off and washed with EtOH (30 mL*2). The filtrate was concentrated under reduced pressure and remaining aqueous solution was adjusted to basic by 30% NaOH. After extraction with $Et_2O$ (30 mL*2), the combined organic layer was dried over anhydrous magnesium sulfate and concentrated under reduced pressure to give the desired product Example 3h (6 g, yield 88%) as yellow oil.

Step 6: Example 3j

A solution of Example 3h (2.5 g, 23.5 mmol) and Example 3i (4.1 g, 15.6 mmol) in MeCN (24 mL) and AcOH (6 mL) was refluxed overnight. The resulting solution was washed with 30% NaOH (15 mL*2). After extraction with $Et_2O$ (30 mL*2), the combined organic layer was dried over anhydrous magnesium sulfate and concentrated under reduced pressure. The residue was purified by silica gel chromatography (100% EtOAc) to give the desired product Example 3j (2.3 g, yield 64%) as a yellow solid. LCMS $[M+1]^+$=230.1.

Step 7: Example 3l

A mixture of Example 3k (416 mg, 2.0 mmol) and Example 3j (458 mg, 2.0 mmol) in pyridine (10 mL) was stirred at 0° C. for 10 min, then $POCl_3$ (1.5 g, 10 mmol) was added into the reaction dropwise. The reaction mixture was stirred at 0° C. for 10 min. The resulting mixture was quenched with water (15 mL). After extraction with DCM (10 mL*2), the combined organic layer was dried over anhydrous magnesium sulfate and concentrated under reduced pressure. The residue was purified by silica gel Step 1: Example 3b To a solution of Example 3a (10.0 g, 55 mmol) and allyl bromide (8.1 g, 66 mmol) in DMF (30 mL) was added $K_2CO_3$ (9.1 g, 66 mmol). After stirred at r.t. for 20 h, there action mixture was diluted with $H_2O$ (100 mL), and extracted with EtOAc (50 mL*2). The combined organic phase was washed with brine, dried over $Na_2SO_4$, filtrated and the filtrate was concentrated under reduced pressure to give the desired product Example 3b (12.0 g, yield 98%) as yellow oil. LCMS $[M+1]^+$=223.0

Step 2: Example 3c

A mixture of Example 3b (14.4 g, 65 mmol) and $LiO.H_2O$ (4.1 g, 97 mmol) in THF/MeOH/$H_2O$ (40 mL/15 mL/15 mL) was stirred at room temperature overnight. The resulting mixture was washed with EtOAc (30 mL), and then adjusted with aqueous HCl solution to a pH of 2. After extraction with EtOAc (50 mL*2), the combined organic layer was dried over anhydrous magnesium sulfate and concentrated under reduced pressure to give the desired product Example 3c (13.0 g, yield 96%) as a yellow solid. LCMS $[M+1]^+$=209.0.
$^1$H NMR (400 MHz, DMSO-$d_6$) δ 7.15 (dd, J=2.3, 1.3 Hz, chromatography (100% EtOAc) to give the desired product Example 3l (170 mg, yield 20%) as a white solid.

LCMS [M+1]$^+$=420.0.

Step 8: Example 3

Under an atmosphere of N$_2$, a mixture of Example 3l (43 mg, 0.1 mmol) and Grubbs II (13 mg, 0.02 mmol) in DCE (10 mL) was refluxed overnight. The resulting mixture was concentrated under reduced pressure. The residue was purified by silica gel chromatography (100% EtOAc) to give the desired product Example 3 (3 mg, yield 9%) as a white solid. LCMS [M+1]$^+$=392.0. $^1$H NMR (400 MHz, Chloroform-d) δ 10.73 (s, 1H), 8.57 (d, J=8.4 Hz, 1H), 8.26 (s, 1H), 8.17 (d, J=7.7 Hz, 1H), 7.97-7.80 (m, 2H), 7.12-6.91 (m, 2H), 6.27-6.05 (m, 1H), 6.02-5.83 (m, 1H), 4.77-4.62 (m, 2H), 4.61 (d, J=5.0 Hz, 2H), 3.86 (s, 3H), 2.34 (m, 2H), 1.99 (m, 2H).

Example 4: General Procedure for Synthesis of Compound Example 4

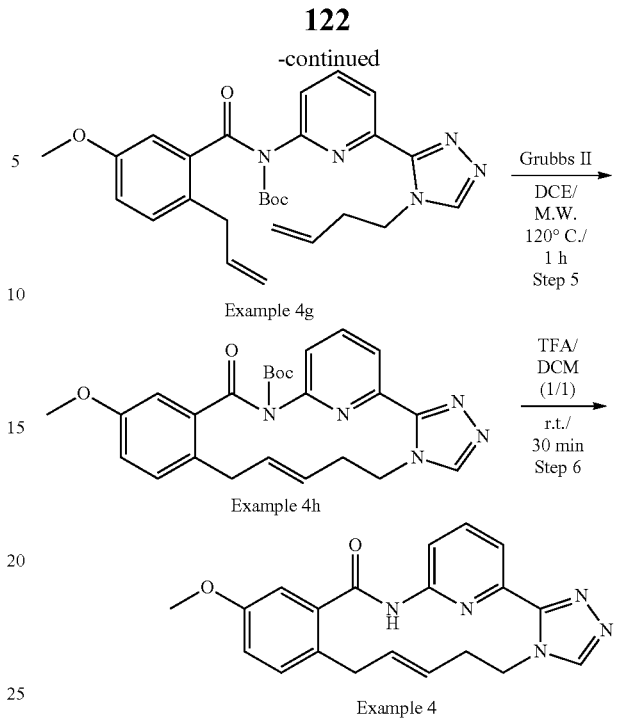

Step 1: Example 4c

To a slurry of Example 4a (5.0 g, 20.4 mmol), Example 4b (8.1 g, 24.5 mmol), LiCl (1.7 g, 40.8 mmol) in DMF (100 mL) was added Pd(PPh$_3$)$_2$Cl$_2$ (2.14 g, 3.0 mmol), which was degassed with N$_2$ for 3 times and heated at 100° C. overnight. The mixture was concentrated under reduced pressure and the residue was extracted with EtOAc (100 mL*3). The combined organic layer was dried over anhydrous magnesium sulfate and concentrated under reduced pressure. The residue was purified by silica gel chromatography (Petroleum Ether/EtOAc=1/0~1/1) to give the desired product Example 4c (1.6 g, yield 38%) as colorless oil. LCMS [M+1]$^+$=207.0

Step 2: Example 4d

To a mixture of Example 4c (1.6 g, 7.77 mmol) in MeOH/THF/H$_2$O (10 mL/10 mL/10 mL) was added LiO.H$_2$O (932 mg, 23.31 mmol). The mixture was stirred at r.t. overnight. After that, the mixture was adjusted to pH 7.0 and extracted with EtOAc (100 mL*3). The combined organic layer was dried over anhydrous magnesium sulfate and concentrated under reduced pressure. The residue was purified by silica gel chromatography (Petroleum Ether/EtOAc=1/0~1/1) to give the desired product Example 4d (1.6 g, yield 38%) as yellow oil. LCMS [M+1]$^+$=193.0

Step 3: Example 4f

To a mixture of Example 4d (500 mg, 2.60 mmol) and Example 4e (840 mg, 3.91 mmol) in pyridine (10 mL) at 0° C. was added POCl$_3$ (1.99 g, 13.00 mmol) dropwise. The mixture was stirred at 0° C. for 1 h. To the mixture was added water (50 mL), which was then extracted with EtOAc (50 mL*3). The combined organic layer was dried over anhydrous magnesium sulfate and concentrated under reduced pressure. The residue was purified by silica gel chromatography (Petroleum Ether/EtOAc=1/0~0/1) to give the desired product Example 4f (500 mg, yield 49%) as yellow oil. LCMS [M+1]⁺=390.0

Step 4: Example 4g

To a mixture of Example 4f (300 mg, 0.77 mmol) and DMAP (47 mg, 0.39 mmol) in ACN (10 mL) was added Boc$_2$O (840 mg, 3.85 mmol). The mixture was stirred at r.t. overnight. To the mixture was added water (50 mL), which was then extracted with EtOAc (30 mL*3). The combined organic layer was dried over anhydrous magnesium sulfate and concentrated under reduced pressure. The residue was purified by silica gel chromatography (Petroleum Ether/EtOAc=1/0~0/1) to give the desired product Example 4g (300 mg, yield 80%) as a yellow solid. LCMS [M+1]⁺=490.0

Step 5: Example 4h

A mixture of Example 4g (100 mg, 0.20 mmol) and Grubbs II (25.6 mg, 0.04 mmol) in DCE (10 mL) was degassed with N$_2$ for 3 times. The mixture was stirred at 120° C. for 1 h under microwave. The mixture was concentrated under reduced pressure and the residue was purified by Prep-TLC (DCM/MeOH=1/1) to give the desired product Example 4h (50 mg, yield 53%) as a white solid. LCMS [M+1]⁺=462.0

Step 6: Example 4

A mixture of Example 4h (50 mg, 0.11 mmol) in TFA/DCM (5 mL, v/v=1/1) was stirred at r.t. for 30 min. Then the mixture was concentrated under reduced pressure and the residue was purified by Prep-HPLC to give the desired product Example 4 (3.0 mg, yield 8%) as a white solid. LCMS [M+1]⁺=362.0

$^1$H NMR (400 MHz, DMSO-d$_6$) δ 10.64 (s, 1H), 8.65 (s, 1H), 8.04-7.98 (m, 2H), 7.35 (d, J=8.5 Hz, 1H), 7.25 (dd, J=6.2, 2.5 Hz, 1H), 7.00 (dd, J=8.4, 2.7 Hz, 1H), 6.95 (d, J=2.7 Hz, 1H), 5.51 (dd, J=12.3, 5.1 Hz, 1H), 5.31 (dd, J=12.6, 5.9 Hz, 1H), 4.40 (d, J=8.7 Hz, 2H), 3.77 (s, 3H), 3.49 (d, J=6.8 Hz, 2H), 2.65 (m, 2H).

Example 5: General Procedure for Synthesis of Compound Example 5

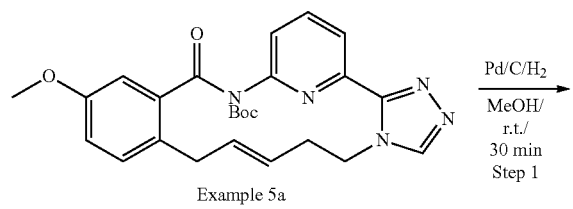

Example 5a

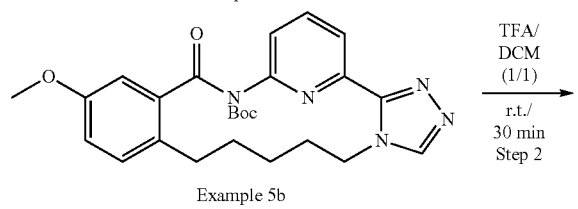

Example 5b

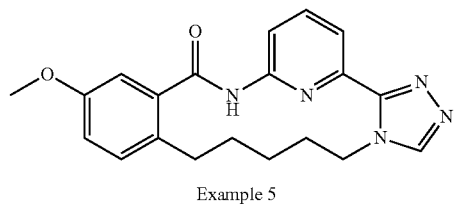

Example 5

Step 1: Example 5a

A slurry of Example 5a (30 mg, 0.07 mmol) and Pd/C (10 mg, 5%) in MeOH (5 mL) was degassed with H$_2$ for 3 times. The mixture was stirred at r.t. for 30 min. The mixture was filtered and concentrated under reduced pressure to give a crude product Example 5b (30 mg, crude yield 100%) as a white solid, which was used for the next step directly without further purification. LCMS [M+1]⁺=464.0

Step 2: Example 5

A mixture of Example 5b (30 mg, 0.07 mmol) in TFA/DCM (2 mL, v/v=1/1) was stirred at r.t. for 30 min. The mixture was concentrated under reduced pressure and the residue was purified by Prep-HPLC to give the desired product Example 5 (2.0 mg, yield 9% over two steps) as a white solid. LCMS [M+1]⁺=364.0. $^1$H NMR (400 MHz, DMSO-d$_6$) δ 10.34 (s, 1H), 8.63 (s, 1H), 8.06-7.98 (m, 2H), 7.54-7.49 (m, 1H), 7.26 (d, J=8.4 Hz, 1H), 6.97 (d, J=7.5 Hz, 2H), 4.56-4.48 (m, 2H), 3.75 (s, 3H), 2.63-2.55 (m, 2H), 1.86-1.70 (m, 4H), 1.53 (s, 2H).

Example 6: General Procedure for Synthesis of Compound Example 6

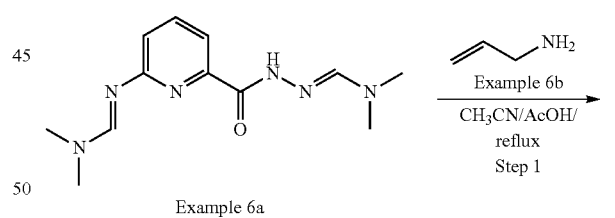

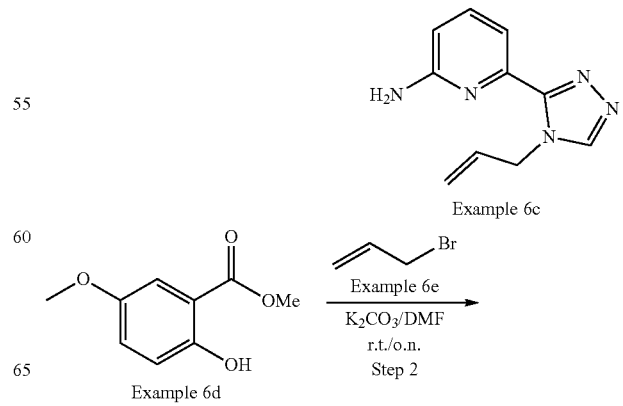

-continued

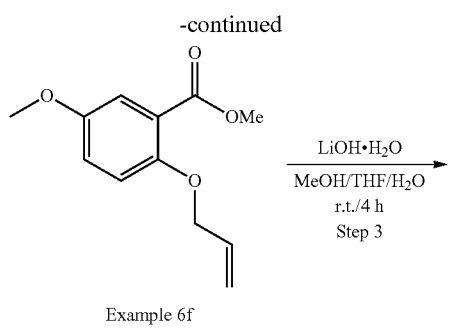

Example 6f

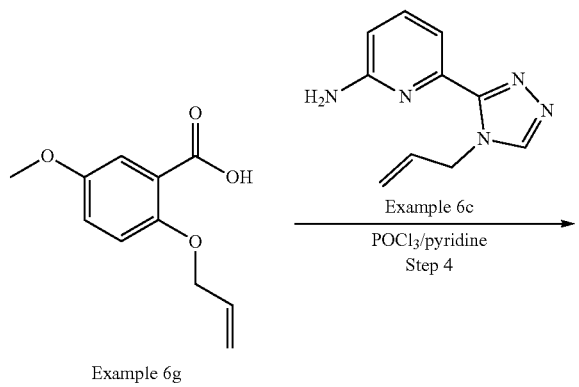

Example 6g

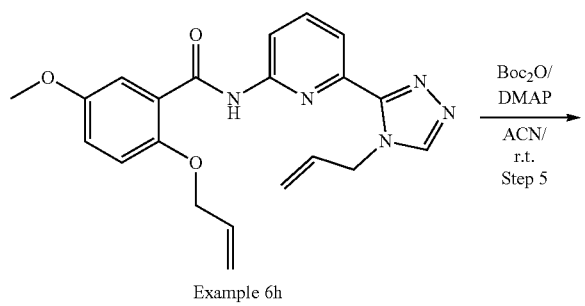

Example 6h

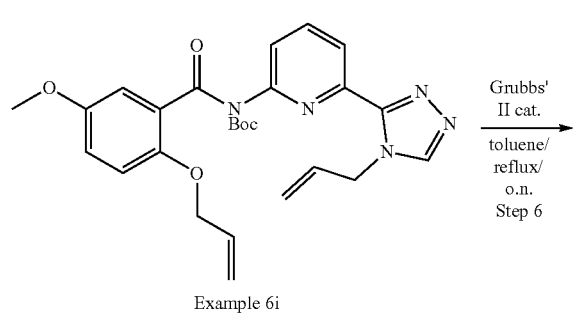

Example 6i

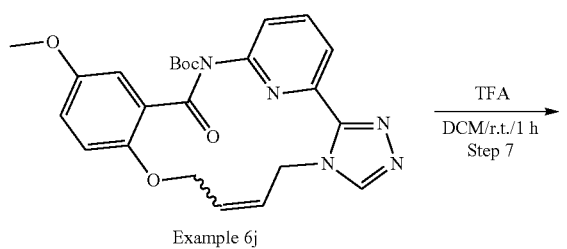

Example 6j

-continued

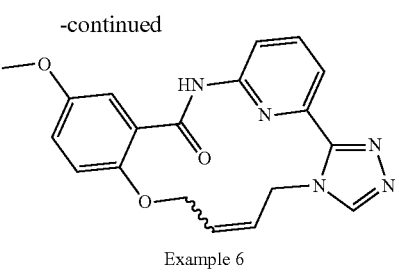

Example 6

Step 1: Example 6c

To a solution of Example 6a (45.0 g, 172 mmol) in acetonitrile/AcOH (400 mL/100 mL) was added Example 6b (14.3 g, 258 mmol) slowly at r.t. The resulting mixture was heated at 95° C. for overnight. The reaction mixture was concentrated and the residue was dissolved in ice water (250 mL), which was neutralized with sat. $Na_2CO_3$ (aq.) to pH=8. The aqueous solution was extracted with iPrOH/DCM (v/v=3/1, 200 mL*4). The combined organic layer was dried over sodium sulfate, filtered and concentrated. The residue was purified by silica gel chromatography (MeOH/DCM=20/1) to give the desired product Example 6c (22.4 g, yield 65%) in total as a white solid. LCMS $[M+1]^+$=202.0

Step 2: Example 6f

To a solution of Example 6d (12.0 g, 65.9 mmol) in DMF (35 mL) were added $K_2CO_3$ (10.9 g, 79.1 mmol), followed by Example 6e (9.6 g, 79.1 mmol) dropwise. at r.t. The brown solution was stirred at r.t. for overnight. EtOAc (200 mL) was added into the reaction mixture, which was filtered. The filtrate was extracted with water (400 mL*2). The organic layers were combined, dried over sodium sulfate, filtered and concentrated to afford the crude product Example 6f (12.0 g, crude yield 82%) as brown oil, which was used in the next step without further purification. LCMS $[M+1]^+$=222.9

Step 3: Example 6g

To a solution of Example 6f (12.0 g, 54.0 mmol) in MeOH/THF (20 mL/45 mL) at r.t. was added a solution of $LiO.H_2O$ (3.4 g, 81.1 mmol) in $H_2O$ (20 mL), which was stirred for 4 h. The mixture was neutralized with 2N HCl (aq.) and then extracted with DCM. The combined organic layer was dried over $Na_2SO_4$, filtered and concentrated. The residue was purified by silica gel chromatography (Petroleum ether/EtOAc=4/1) to afford the desired product Example 6g (9.5 g, yield 85%) as pale-green oil. LCMS $[M+1]^+$=209.0

Step 4: Example 6h

To a solution of Example 6g (2.58 g, 12.4 mmol) and Example 6c (2.50 g, 12.4 mmol) in pyridine (30 mL) at 0° C. was slowly added $POCl_3$ (5.8 mL, 62.0 mmol). After 15 min, yellow solid was precipitated out, which was filtered and washed with water. The cake was slurried in MeCN/MTBE to give the desired product Example 6h (1.65 g, yield 35%) as an off-white solid. LCMS $[M+1]^+$=392.0

Step 5: Example 6i

To a suspension of Example 6h (1.65 g, 4.22 mmol) in ACN (25 mL) were added DMAP (0.26 g, 2.11 mmol) and Boc₂O (3.67 g, 16.80 mmol) at r.t. The white suspension turned into a pale green solution. After being stirred at r.t. for 1 h, the reaction mixture was partitioned between EtOAc and water. The combined organic layer was saturated with brine, dried over sodium sulfate, filtered and concentrated. The residue was purified by silica gel chromatography (pure EtOAc) to give the desired product Example 6i (2.00 g, yield 97%) as a white solid. LCMS [M+1]⁺=492.1

Step 6: Example 6j

To a solution of Example 6i (450 mg, 0.92 mmol) in DCE (56 mL) was added Grubbs' II catalyst (115 mg, 0.18 mmol). The resulting mixture was degassed with N2 and heated under 90° C. for 4 h. The mixture was cooled to r.t., filtered and concentrated. The residue was purified by Prep-TLC to give the desired product Example 6j (100 mg, yield 24%) as red oil. LCMS [M+1]⁺=464.0

Step 7: Example 6

To a solution of Example 6j (50 mg, 0.11 mmol) in DCM/TFA (1 mL/0.5 mL) was stirred at r.t. for 1 h. The reaction mixture was concentrated and the residue was purified by Prep-HPLC to give the desired product Example 6 (8 mg, yield 20%) as a yellow solid. LCMS [M+1]⁺=364.0. ¹H NMR (400 MHz, DMSO-d₆) δ 10.84 (s, 1H), 8.74 (s, 1H), 8.01 (t, J=7.9 Hz, 1H), 7.83 (t, J=7.3 Hz, 2H), 7.44 (d, J=8.9 Hz, 1H), 7.33 (d, J=3.3 Hz, 1H), 7.15 (dd, J=8.9, 3.3 Hz, 1H), 5.87-5.79 (m, 1H), 5.59 (dt, J=11.5, 6.0 Hz, 1H), 5.25 (d, J=6.0 Hz, 2H), 4.87 (d, J=7.5 Hz, 2H), 3.78 (s, 3H).

Example 7: General Procedure for Synthesis of Compound Example 7

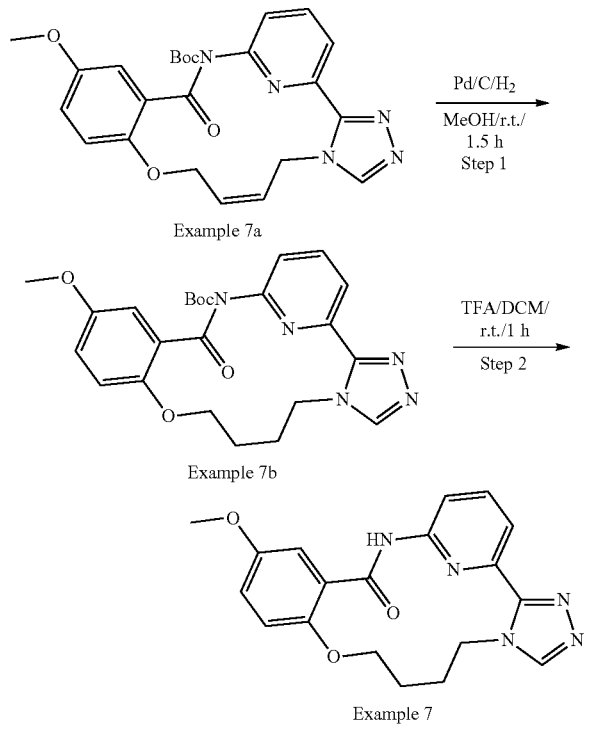

Step 1: Example 7b

To a solution of Example 7a (50 mg, 0.11 mmol) in MeOH (2 mL) was added 5% Pd/C (10 mg). The mixture was stirred at r.t. for 1.5 h under 1 atm hydrogen atmosphere. The mixture was filtered and the filtrate was concentrated to give Example 7b (60 mg, crude) as yellow oil. LCMS [M+1]⁺=466.0

Step 2: Example 7

A solution of Example 7b (60 mg, 0.13 mmol) in DCM/TFA (1 mL/0.5 mL) was stirred at r.t. for 1 h. The reaction mixture was concentrated and the residue was purified by Prep-HPLC to give the desired product Example 7 (16 mg, yield 34%) as a yellow solid. LCMS [M+1]⁺=366.0. ¹H NMR (400 MHz, DMSO-d₆) δ 11.43 (s, 1H), 8.66 (s, 1H), 8.04 (t, J=7.9 Hz, 1H), 7.87 (d, J=8.1 Hz, 1H), 7.83 (d, J=7.6 Hz, 1H), 7.50 (d, J=3.2 Hz, 1H), 7.24 (d, J=9.1 Hz, 1H), 7.16 (dd, J=9.0, 3.2 Hz, 1H), 4.29-4.19 (m, 4H), 3.77 (s, 3H), 2.45-2.36 (m, 2H), 1.98-1.89 (m, 2H).

Example 8: General Procedure for Synthesis of Compound Example 8

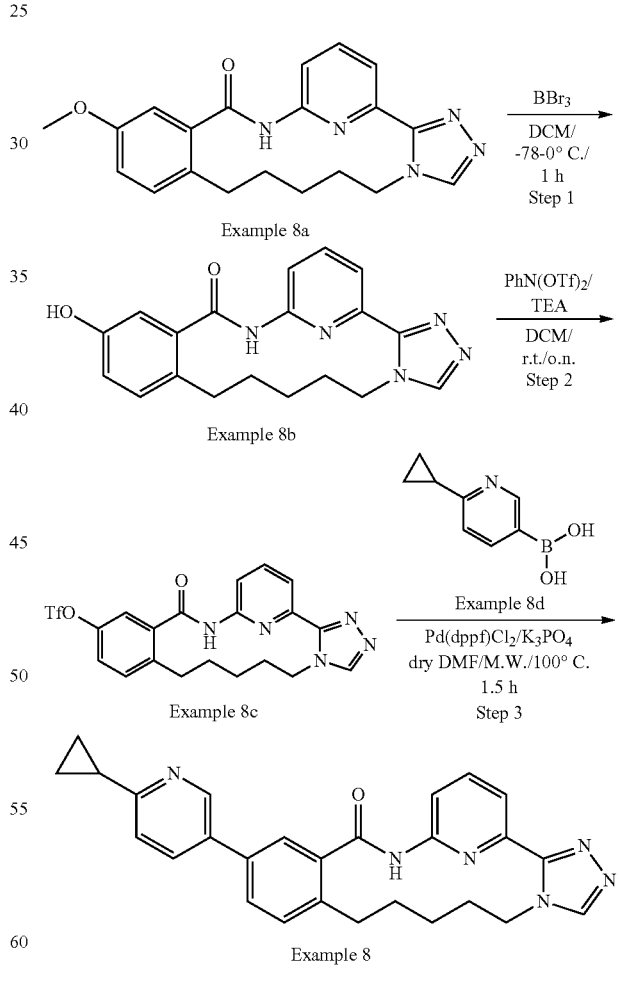

Step 1: Example 8b

A slurry of Example 8a (100 mg, crude) in DCM (5 mL) at −78° C., was added BBr₃ (108 mg, 0.44 mmol). The mixture was warmed to 0° C. and stirred for 1 h. The mixture was adjusted pH to 7.0 and extracted with EtOAc (30 mL*3). The combined organic layer was dried over anhydrous magnesium sulfate and concentrated under reduced pressure to give the desired product (Example 8b, 100 mg, crude) as a white solid. The crude product was used for next step directly. LCMS [M+1]⁺=350.0

Step 2: Example 8c

A mixture of Example 8b (100 mg, crude), TEA (87.87 mg, 0.87 mmol) in DCM (15 mL), was added PhN(OTf)₂ (153.5 mg, 0.43 mmol). The mixture was stirred at r.t. for overnight. The mixture was concentrated under reduced pressure to give a residue. The residue was purified by pre-TLC (DCM/MeOH=10/1) to give the desired product (Example 8c, 60 mg, two step yield 57.8%) as a white solid. LCMS [M+1]⁺=481.9

Step 3: Example 8

A mixture of Example 8c (60 mg, 0.12 mmol), Example 8d (39.12 mg, 0.18 mmol), K₃PO₄ (76.32 mg, 0.36 mmol) in DMF (2 mL), was added Pd(dppf)Cl₂ (10 mg). The mixture was degassed with N₂ for 3 times. Then the mixture was heated at 100° C. for 1.5 h under microwave. After then, the mixture was purified by Prep-HPLC to give product (Example 8, 1.3 mg, yield 2.3%) as a white solid. LCMS [M+1]⁺=451.0. ¹H NMR (400 MHz, CDCl₃) δ 8.69 (d, J=2.0 Hz, 1H), 8.28 (d, J=7.7 Hz, 1H), 8.19 (s, 1H), 8.11 (s, 1H), 8.06 (d, J=8.0 Hz, 1H), 7.96 (t, J=7.9 Hz, 1H), 7.90 (d, J=1.8 Hz, 1H), 7.78 (dd, J=8.1, 2.4 Hz, 1H), 7.66 (dd, J=8.0, 2.0 Hz, 1H), 7.44 (d, J=8.1 Hz, 1H), 7.21 (d, J=8.0 Hz, 1H), 4.63-4.53 (m, 2H), 2.96-2.84 (m, 2H), 2.14-1.92 (m, 5H), 1.85-1.75 (m, 2H), 1.09-1.03 (m, 4H).

Example 9: General Procedure for Synthesis of Compound Example 9

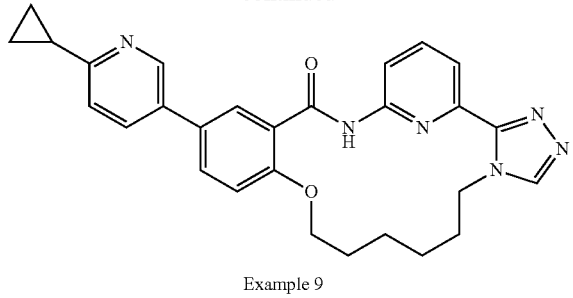

Example 9

Step 1: Example 9c

A mixture of Example 9a (0.14 g, 0.31 mmol), Example 9b (52 mg, 0.31 mmol), Pd(dppf)Cl₂ (24 mg, 0.03 mmol) and Cs₂CO₃ (0.3 g, 0.9 mmol) in Dioxane/H₂O (3 mL/0.3 mL), was exchange N₂ for 3 times. After stirred at 85° C. for 16 h at N₂, the mixture was concentrated under reduced pressure, the residue was purified by Pre-TLC (DCM/MeOH=10/1) to give desired product (Example 9c, 63 mg, yield 41.2%) as a yellow solid.

LCMS [M+1]⁺=479.0

Step 2: Example 9

A mixture of Example 9c (63 mg, 0.13 mmol), 5% Pd/C (10 mg) in EtOAc (3 mL), was exchange H₂ for 3 times. After the mixture was stirred at room temperature for 16 h. Then the solid was filtered off, and the filtrate was concentrated under reduced pressure. The residue was purified by Pre-TLC (DCM/MeOH=10/1) to give Example 9 (23 mg, yield 36.5%) as a yellow solid. LCMS [M+1]⁺=481.1. ¹H NMR (400 MHz, DMSO-d₆) δ 10.77 (s, 1H), 8.69 (d, J=1.9 Hz, 1H), 8.48 (d, J=8.3 Hz, 1H), 8.32 (d, J=2.4 Hz, 1H), 8.11-8.02 (m, 2H), 7.92 (d, J=10.3 Hz, 2H), 7.85 (d, J=7.5 Hz, 1H), 7.36 (d, J=7.8 Hz, 2H), 4.69 (t, J=7.1 Hz, 2H), 4.31 (sbr, 2H), 2.16-2.09 (m, 1H), 2.06-1.97 (m, 2H), 1.90 (sbr, 4H), 1.54-1.44 (m, 2H), 0.99-0.89 (m, 4H).

Example 10: General Procedure for Synthesis of Compound Example 10

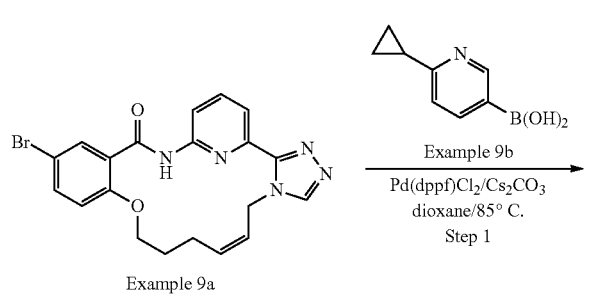

Example 9a

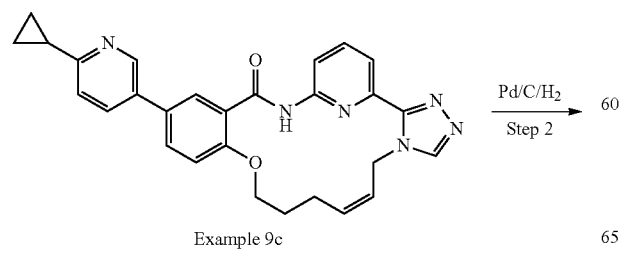

Example 9c

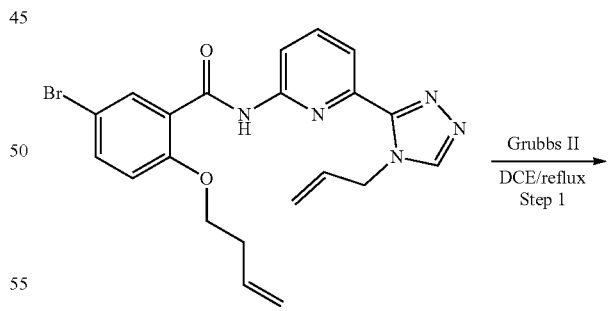

Example 10a

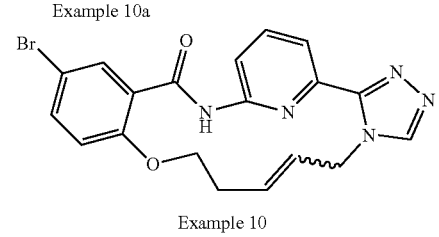

Example 10

Step 1: Example 10

Under an atmosphere of N$_2$, a mixture of Example 10a (1.6 g, 3.5 mmol) and Grubbs II (cas: 246047-72-3, 594 mg, 0.7 mmol) in DCE (300 mL) was refluxed overnight. The resulting mixture was concentrated under reduced pressure to obtain crude product. The residue was purified by doing silica gel chromatography (100% EtOAc) to give Example 10 (240 mg, yield: 16%) as a white solid. LCMS [M+1]$^+$=427.0 (Mixture of Z and E). $^1$H NMR (400 MHz, Chloroform-d) δ 10.65 (d, 1H), 8.54-8.28 (m, 2H), 8.22 (d, J=8.6 Hz, 1H), 8.13 (dd, J=34.7, 7.7 Hz, 1H), 7.88 (td, J=8.0, 3.7 Hz, 1H), 7.60 (dt, J=8.8, 3.1 Hz, 1H), 6.92 (dd, J=8.8, 7.1 Hz, 1H), 6.02-5.68 (m, 1H), 5.60 (d, J=3.5 Hz, 1H), 5.25 (s, 1H), 5.02 (d, J=4.2 Hz, 1H), 4.30 (dt, J=28.9, 5.3 Hz, 2H), 2.78 (s, 2H).

Example 11: General Procedure for Synthesis of Compound Example 11

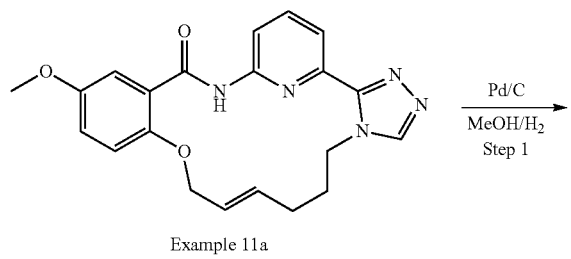

Example 11a

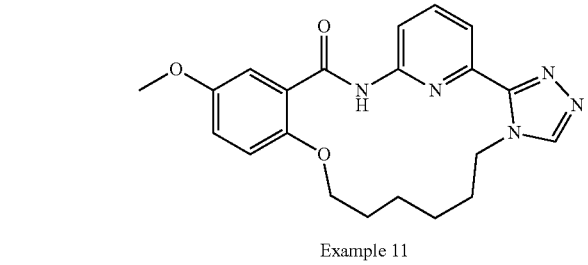

Example 11

Step 1: Example 11

Under an atmosphere of H$_2$, a mixture of Example 11a (100 mg, 0.26 mmol) and 5% Pd/C (10 mg) in MeOH (6 mL) was stirred at r.t. for 20 min. The resulting mixture was concentrated under reduced pressure. The residue was purified by Prep-HPLC to give Example 11 (3.2 mg, yield 3%) as a yellow solid. LCMS [M+1]$^+$=394.0. $^1$H NMR (400 MHz, Chloroform-d) δ 10.81 (s, 1H), 8.58 (d, J=8.3 Hz, 1H), 8.29 (s, 1H), 8.03 (d, J=7.6 Hz, 1H), 7.89 (t, J=6.5 Hz, 2H), 7.10-6.93 (m, 2H), 4.60 (m, 2H), 4.19 (d, J=4.7 Hz, 2H), 3.86 (s, 3H), 2.11-1.88 (m, 6H), 1.25 (s, 2H).

Example 12: General Procedure for Synthesis of Compound Example 12

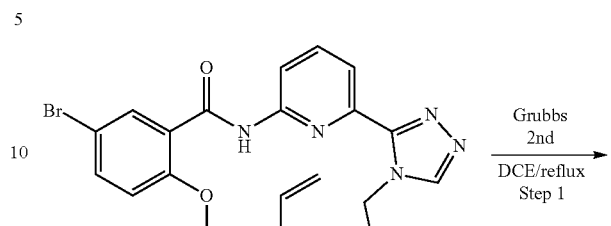

Example 12a

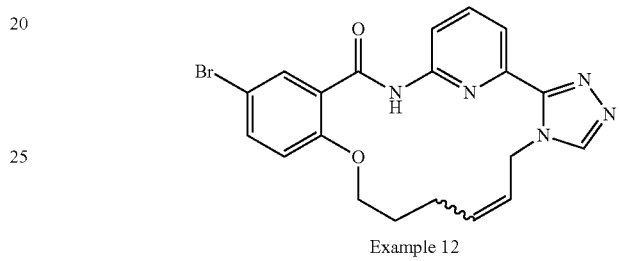

Example 12

Step 1: Example 12

A mixture of Example 12a (0.75 g, 1.6 mmol), Grubbs 2$^{nd}$ (cas: 246047-72-3, 272 mg, 0.32 mmol), in DCE (150 mL), was exchange N$_2$ for 3 times. After stirred at 85° C. for 16 h at N$_2$, the mixture was concentrated under reduced pressure, the residue was purified by silica gel chromatography (DCM/MeOH=30/1) to give desired product Example 12 (220 mg, yield 31.2%) as a yellow solid. LCMS [M+1]$^+$=439.9

$^1$H NMR (400 MHz, Chloroform-d) δ 10.49 (s, 1H), 8.54 (dd, J=8.4, 0.9 Hz, 1H), 8.46 (d, J=2.4 Hz, 1H), 8.35 (s, 1H), 8.15 (dd, J=7.8, 0.9 Hz, 1H), 7.90 (t, J=8.0 Hz, 1H), 7.61 (dd, J=8.8, 2.4 Hz, 1H), 6.93 (d, J=8.8 Hz, 1H), 5.90-5.71 (m, 2H), 5.47 (d, J=6.6 Hz, 2H), 4.26 (t, J=4.8 Hz, 2H) 2.79-2.62 (m, 2H), 2.08-2.01 (m, 2H).

Example 13: General Procedure for Synthesis of Compound Example 13

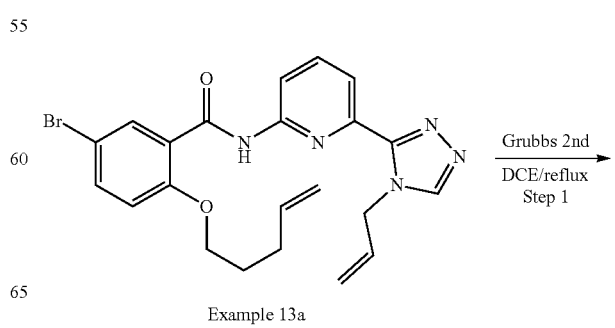

Example 13a

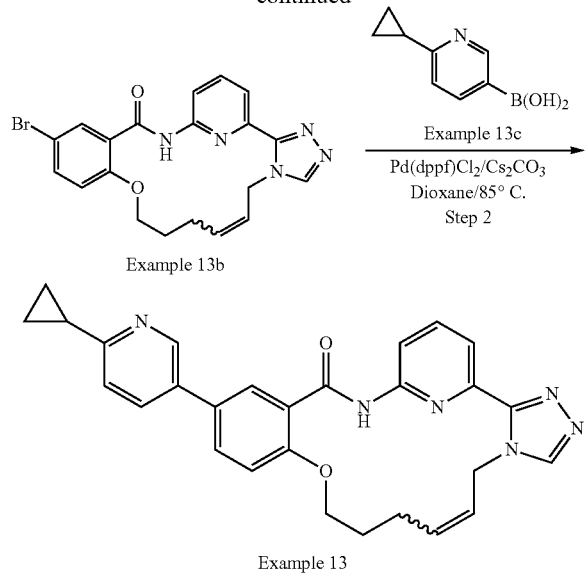

Step 1: Example 13b

A mixture of Example 13a (0.75 g, 1.6 mmol), Grubbs $2^{nd}$ (cas: 246047-72-3, 272 mg, 0.32 mmol), in DCE (150 mL), was exchange $N_2$ for 3 times. After stirred at 85° C. for 16 h at $N_2$, the mixture was concentrated under reduced pressure, the residue was purified by doing silica gel chromatography (DCM/MeOH=50/1) to give desired product (Example 13b, 220 mg, yield 31.2%) as a yellow solid. LCMS $[M+1]^+$=439.9

Step 2: Example 13

A mixture of Example 13b (0.13 g, 0.3 mmol), Example 13c (48 mg, 0.3 mmol), Pd(dppf)Cl$_2$ (22 mg, 0.03 mmol) and Cs$_2$CO$_3$ (0.3 g, 0.9 mmol) in Dioxane/H$_2$O (3 mL/0.3 mL), was exchange $N_2$ for 3 times. After stirred at 85° C. for 16 h at $N_2$, the mixture was concentrated under reduced pressure, the residue was purified by Pre-TLC (DCM/MeOH=10/1) to give desired product (Example 13, 40 mg, yield 30.6%) as a yellow solid. LCMS $[M+1]^+$=479.0. $^1$H NMR (400 MHz, DMSO-d$_6$) δ 10.72 (s, 1H), 8.70 (s, 1H), 8.49 (d, J=8.3 Hz, 1H), 8.39-8.25 (m, 1H), 8.04 (t, J=9.1 Hz, 1H), 7.95-7.84 (m, 2H), 7.72-7.46 (m, 2H), 7.37 (d, J=8.3 Hz, 2H), 5.89-5.73 (m, 2H), 5.61 (d, J=6.8 Hz, 2H), 4.37-4.27 (m, 2H), 2.68-2.62 (m, 2H), 1.98-1.84 (m, 3H), 1.02-0.89 (m, 4H).

Example 14: General Procedure for Synthesis of Compound Example 14

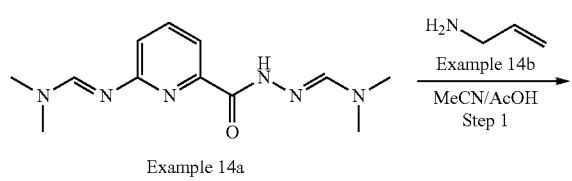

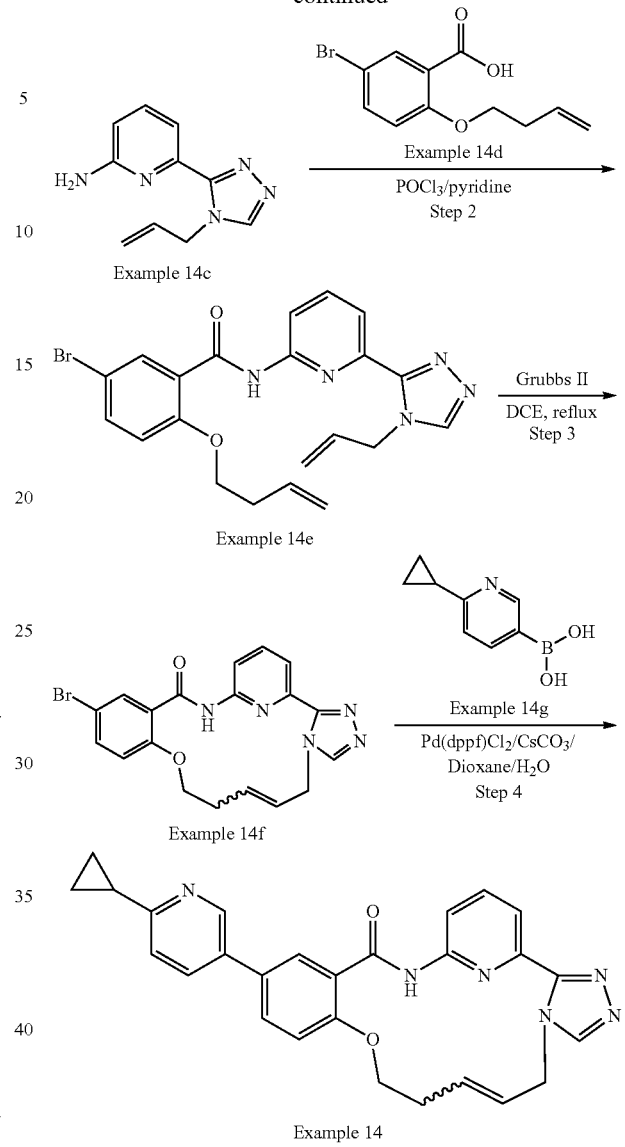

Step 1: Example 14c

To a solution of Example 14a (15 g, 57.2 mmol) in MeCN (80 mL) and AcOH (20 mL), was added Example 14b (4.9 g, 85.9 mmol). The resulting mixture was heated to reflux overnight. The solution was washed with 30% NaOH (50 mL). After extraction with EtOAc (50 mL*2), combined organic layer was dried over anhydrous magnesium sulfate and concentrated under reduced pressure. The residue was purified by silica gel chromatography (100% EtOAc) to give the desired product (Example 14c, 10.6 g, yield 92%) as a yellow solid. LCMS $[M+1]^+$=202.0.

Step 2: Example 14e

A mixture of Example 14c (1.4 g, 7 mmol) and Example 14d (1.9 g, 7 mmol) in pyridine (30 mL) was stirred at 0° C. for 10 min, then POCl$_3$ (5.4 g, 35 mmol) was slowly dropped into the reaction. The reaction was stirred at 0° C. for 10 min. The resulting mixture was quenched with water (20 mL). After extraction with DCM (20 mL*2), combined organic layer was dried over anhydrous magnesium sulfate and concentrated under reduced pressure. The residue was purified by silica gel chromatography (100% EtOAc) to give the desired product (Example 14e, 1.6 g, yield 50%) as a white solid.

LCMS [M+1]+=454.9.

Step 3: Example 14f

Under an atmosphere of $N_2$, a mixture of Example 14e (1.6 g, 3.5 mmol) and Grubbs II (cas 246047-72-3, 169 mg, 0.2 mmol) in DCE (300 mL) was refluxed overnight. The resulting mixture was concentrated under reduced pressure to obtain crude product. The residue was purified by doing silica gel chromatography (100% EtOAc) to give the desired product (Example 14f, 240 mg, yield 16%) as a yellow solid. LCMS [M+1]+=426.9.

Step 4: Example 14

A mixture of Example 14f (120 mg, 0.3 mmol), Example 14g (46 mg, 0.3 mmol), Pd(dppf)Cl$_2$ (22 mg, 0.03 mmol) and Cs$_2$CO$_3$ (0.3 g, 0.9 mmol) in Dioxane/H$_2$O (12 mL/1 mL), was exchange N$_2$ for 3 times. After stirred at 85° C. for 16 h at N$_2$, the mixture was concentrated under reduced pressure, the residue was purified by Pre-TLC (DCM/MeOH=10/1) to give desired product (Example 14, 12 mg, yield 9%) as a white solid. LCMS [M+1]+=465.0. $^1$H NMR (400 MHz, Chloroform-d) δ 10.81 (s, 0.55H), 10.50 (s), 8.68 (s, 1H), 8.55 (s, 1H), 8.51 (d, J=8.0 Hz), 8.43 (d, J=8.0 Hz, 0.55), 8.22-8.07 (m, 2H), 7.93-7.82 (m, 1H), 7.78 (d, J=7.6 Hz, 1H), 7.70 (d, J=8.4 Hz, 1H), 7.23-7.04 (m, 2H), 6.03-5.70 (m, 1H), 5.64-5.54 (m, 1H), 4.36 (dt, J=27.0, 5.4 Hz, 2H), 3.48 (s, 2H), 2.95-2.64 (m, 2H), 2.08 (m, 1H), 1.25 (m, 2H), 1.04 (m, 2H).

Example 15: General Procedure for Synthesis of Compound Example 15

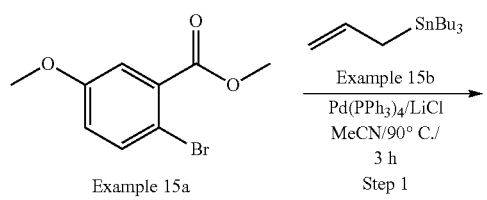

Example 15a

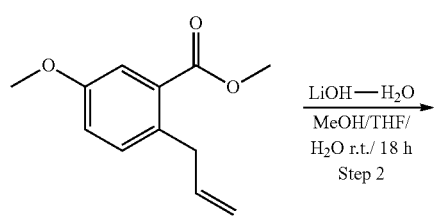

Example 15c

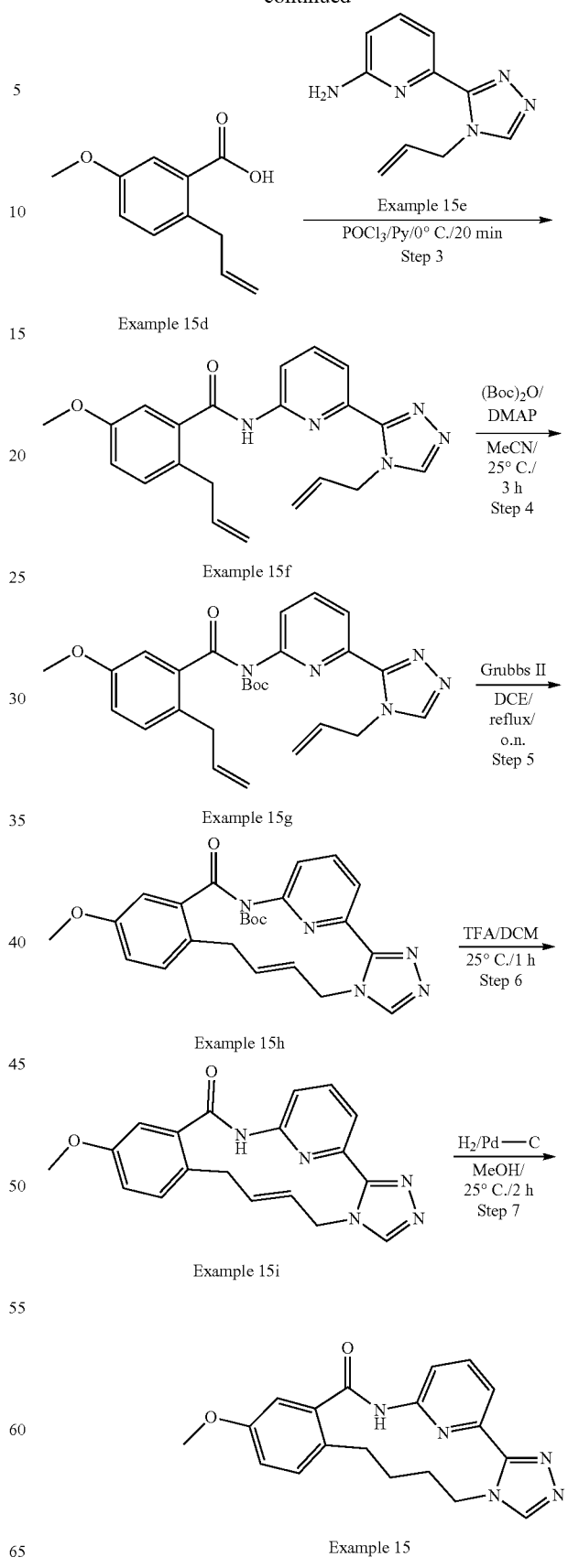

Step 1: Example 15c

To a solution of Example 15a (3.0 g, 12.24 mmol) and 15b (4.5 g, 13.47 mmol) in MeCN (30 mL) were added Pd(PPh$_3$)$_4$ (674 mg, 1.22 mmol) and LiCl (1.0 g, 24.48 mmol). The mixture was stirred at 90° C. for 3 h. H$_2$O (50 mL) and KF (3.0 g) were added into the mixture and the mixture was stirred at r.t. for 1 h. The mixture was extracted with EtOAc (30 mL*3). The combined organic phase was washed with brine, dried over Na$_2$SO$_4$, filtrated and the filtrate was concentrated under reduced pressure. The residue was purified by silica gel chromatography (Petroleum Ether/EtOAc=100/1 to 10/1) to give the desired product Example 15c (2.2 g, yield 87%) as yellow oil. LCMS [M+1]$^+$=207.0

Step 2: Example 15d

A mixture of Example 15c (2.2 g, 10.68 mmol) and LiO.H$_2$O (1.8 g, 42.72 mmol) in THF/MeOH/H$_2$O (40 mL/15 mL/15 mL) was stirred at room temperature overnight. The resulting mixture was washed with EtOAc (30 mL), and the pH was then adjusted with aqueous HCl solution to 2. After extraction with EtOAc (50 mL*2), the combined organic layer was dried over anhydrous magnesium sulfate and concentrated under reduced pressure to give the desired product Example 15d (2.1 g, crude yield 100%) as yellow oil. LCMS [M+1]$^+$=193.0

Step 3: Example 15f

A mixture of Example 15d (2.10 g, 10.93 mmol) and Example 15e (2.42 g, 12.03 mmol) in pyridine (20 mL) was stirred at 0° C. for 10 min. Then POCl$_3$ (5.01 g, 32.79 mmol) was slowly dropped into the reaction. The reaction was stirred at 0° C. for 10 min. The resulting mixture was quenched with water (150 mL). After extraction with DCM (30 mL*4), the combined organic layer was dried over anhydrous magnesium sulfate and concentrated under reduced pressure. The residue was purified by silica gel chromatography (100% EtOAc) to give the desired product Example 15f (2.50 g, yield 61%) as yellow oil.
LCMS [M+1]$^+$=376.0

Step 4: Example 15g

To a mixture of Example 15f (1.50 g, 3.99 mmol) and DMAP (244 mg, 1.99 mmol) in MeCN (20 mL) was added (Boc)$_2$O (3.45 g, 15.96 mmol), and the mixture was stirred at 25° C. for 3 h. The mixture was concentrated under reduced pressure. The residue was purified by silica gel chromatography (100% EtOAc) to give the desired product Example 15g (1.45 g, yield 76%) as yellow oil.

Step 5: Example 15h

Under an atmosphere of N$_2$, a mixture of Example 15g (1.45 g, 3.05 mmol) and Grubbs II (382 mg, 0.61 mmol) in DCE (150 mL) was refluxed overnight. The resulting mixture was concentrated under reduced pressure. The residue was purified by silica gel chromatography (100% EtOAc) to give the desired product Example 15h (200 mg, crude yield 14%) as yellow oil. LCMS [M+1]$^+$=448.0

Step 6: Example 15i

To a mixture of Example 15Oh (200 mg, crude) in DCM (5 mL) was added TFA (1 mL), which was stirred at 25° C.

for 1 h. The mixture was concentrated under reduced pressure and the residue was purified by prep-TLC (100% EtOAc) to give the crude product Example 15l (100 mg, crude) as yellow oil.

Step 7: Example 15

To a mixture of Example 15i (100 mg, crude) in MeOH (8 mL) was added Pd/C (20 mg, 5%), and the mixture was stirred at 25° C. for 2 h under H$_2$. The mixture was filtered and concentrated under reduced pressure and the residue was purified by prep-TLC (100% EtOAc) to give the desired product Example 15 (2.2 mg, yield 2%) as a white solid. LCMS [M+1]$^+$=350.0. $^1$H NMR (400 MHz, Chloroform-d) δ 8.59 (s, 1H), 8.17 (d, J=7.8 Hz, 1H), 8.06 (s, 1H), 7.83 (t, J=7.9 Hz, 1H), 7.19 (dd, J=24.7, 8.2 Hz, 2H), 6.80 (dd, J=8.6, 2.8 Hz, 1H), 6.65 (d, J=2.7 Hz, 1H), 3.61 (m, 5H), 3.03 (m, 2H), 1.96 (m, 2H), 1.85 (m, 2H).

Example 16: General Procedure for Synthesis of Compound Example 16

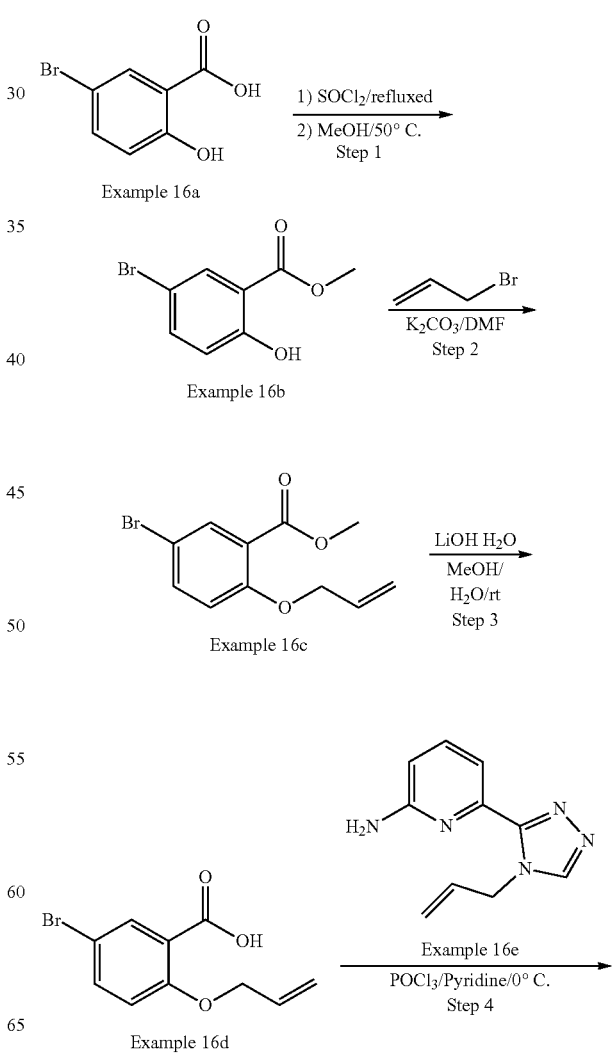

-continued

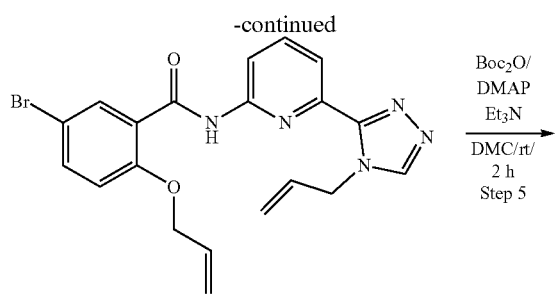

Example 16f

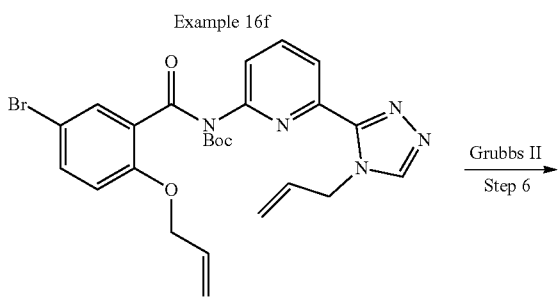

Example 16g

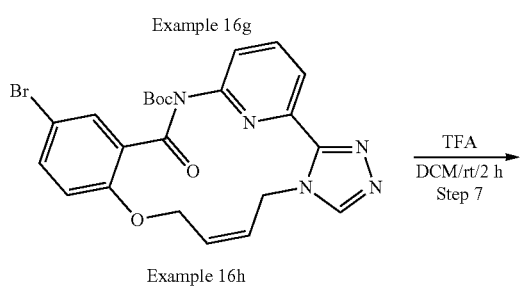

Example 16h

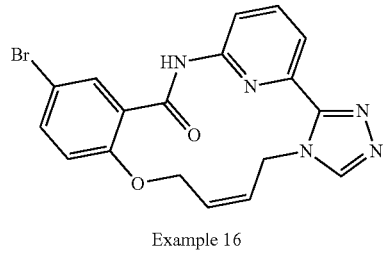

Example 16

Step 1: Example 16b

To a solution of Example 16a (10 g, 46 mmol) in 50 mL of MeOH was added SOCl$_2$ (13.7 g, 115 mmol). The mixture was heated at 80° C. for 4 h. The resulting mixture was concentrated under reduced pressure to obtain crude product. 40 mL of MeOH was added and stirred at 50° C. for 16 h. The resulting mixture was concentrated under reduced pressure. The mixture was washed with NaHCO$_3$ (50 mL), extracted with EA (15 mL*3). The combined organic phase was washed with brine, dried over Na$_2$SO$_4$, filtrated and the filtrate was concentrated under reduced pressure to give crude product (Example 16b, 10 g, yield 92%) as a white solid.

Step 2: Example 16c

To a solution of Example 16b (10 g, 43.3 mmol) and allyl bromide (10.5 g, 86.6 mmol) in DMF (100 mL) was added K$_2$CO$_3$ (7.2 mg, 52 mmol) and stirred at rt for 16 h. The resulting mixture was washed with H$_2$O (200 mL), extracted with EtOAc (50 mL*3). The combined organic phase was washed with brine, dried over Na$_2$SO$_4$, filtrated and the filtrate was concentrated under reduced pressure to obtain the desired product (Example 16c, 11.2 g, yield 96%) as a white solid. LCMS [M+1]$^+$=272.9.

Step 3: Example 16d

A mixture of Example 16c (11.2 g, 41.3 mmol) and LiO.H$_2$O (8.3 g, 207 mmol) in MeOH (100 mL) and H$_2$O (50 mL) was stirred at room temperature for 3 h. The resulting mixture was washed with EtOAc (50 mL), then adjusted with aqueous HCl solution to a pH of 2, After extraction with EtOAc (50 mL*3), combined organic layer was dried over anhydrous magnesium sulfate and concentrated under reduced pressure to give desired product (Example 16d, 9.9 g, yield 93%) as a white solid. LCMS [M+1]$^+$=258.9.

Step 4: Example 16f

A mixture of Example 16d (4 g, 15.6 mmol) and Example 16e (3.1 g, 15.6 mmol) in pyridine (40 mL) was stirred at 0° C. for 10 min, then POCl$_3$ (7.1 g, 46.7 mmol) was slowly dropped into the reaction. The reaction was stirred at 0° C. for 30 min. The resulting mixture was quenched with water (40 mL). After extraction with DCM (20 mL*3), combined organic layer was dried over anhydrous magnesium sulfate and concentrated under reduced pressure to give crude product. The residue was purified by silica gel chromatography (Petroleum ether/EtOAc=20/1~0/1) to give the desired product (Example 16f, 5.4 g, yield 78%) as an orange solid. LCMS [M+1]$^+$=441.9.

Step 5: Example 16g

To a solution of Example 16f (3.8 g, 8.6 mmol), DMAP (527 mg, 4.3 mmol), Et$_3$N (1.3 g, 13 mmol), Boc$_2$O (5.6 g, 26 mmol) in DCM (50 mL) was stirred at rt for 2 h. The resulting mixture was concentrated under reduced pressure. The residue was purified by silica gel chromatography to give product (crude). The mixture was washed with NH$_4$Cl (30 mL), extracted with EtOAc (15 mL*3). The combined organic phase was washed with brine, dried over Na$_2$SO$_4$, filtrated and the filtrate was concentrated under reduced pressure to obtain the desired product (Example 16g, 2.8 g, yield 60%) as a white solid. LCMS [M+1]$^+$=540.9.

Step 6: Example 16h

Under an atmosphere of N$_2$, a mixture of Example 16g (800 mg, 1.5 mmol) and Grubbs II (cas: 246047-72-3, 255 mg, 0.3 mmol) in DCE (250 mL) was refluxed for 18 h. The resulting mixture was concentrated under reduced pressure. The residue was purified by silica gel chromatography (DCM/MeOH=20/1), followed by Prep-HPLC to give Example 16h (120 mg, yield 15%) as a yellow solid. LCMS [M+1]$^+$=513.9.

Step 6: Example 16

To a solution of Example 16h (100 mg, 0.2 mmol), TFA (0.5 mL) in DCM (2 mL) was stirred at rt for 2 h. The resulting mixture was concentrated under reduced pressure, then adjusted with NaHCO$_3$ to a pH of 7. Collected by filtration, washed with H$_2$O and dried in vacuum to give Example 16 (80 mg, yield 99%) as a white solid. LCMS

[M+1]⁺=411.9. ¹H NMR (400 MHz, DMSO-d₆) δ 10.58 (s, 1H), 8.71 (s, 1H), 7.99 (t, J=7.9 Hz, 1H), 7.87-7.80 (m, 2H), 7.78 (d, J=8.0 Hz, 1H), 7.73 (dd, J=8.8, 2.6 Hz, 1H), 7.47 (d, J=8.8 Hz, 1H), 5.81-5.69 (m, 1H), 5.50 (dt, J=11.0, 5.7 Hz, 1H), 5.37 (d, J=5.0 Hz, 2H), 4.92 (d, J=7.8 Hz, 2H).

Example 17: General Procedure for Synthesis of Compound Example 17

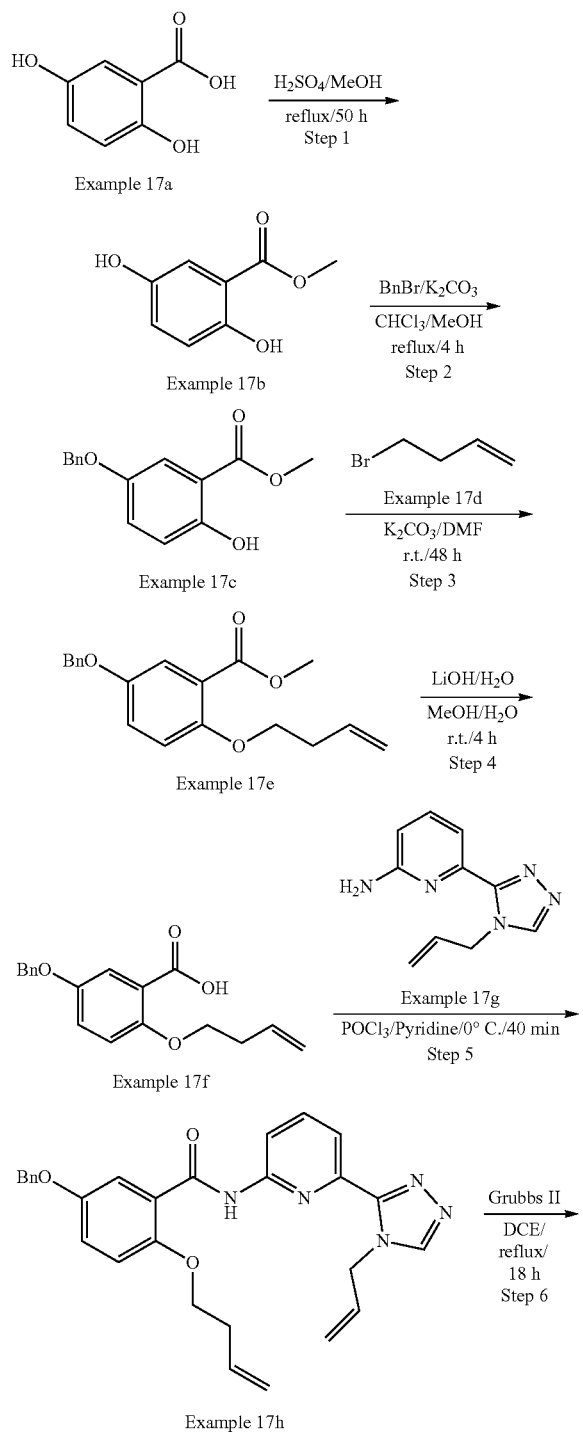

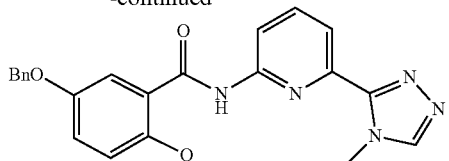

Example 17

Step 1: Example 17b

To a solution of Example 17a (20.0 g, 130 mmol) in MeOH (200 mL) was added H₂SO₄ (8.5 mL). The mixture was heated at reflux for 50 h. The resulting mixture was concentrated under reduced pressure. The residue was washed with sat. NaHCO₃ (50 mL*2), and then extracted with EtOAc (50 mL*3). The combined organic phase was washed with brine, dried over Na₂SO₄, filtrated and the filtrate was concentrated under reduced pressure to give the crude product Example 17b (20.5 g, yield 94%) as a white solid.

Step 2: Example 17c

To a mixture of Example 17b (19.3 g, 115 mmol) and K₂CO₃ (63.5 g, 460 mmol) in MeOH (325 mL) and CHCl₃ (650 mL) at reflux was added BnBr (13.7 mL, 115 mmol). The reaction mixture was stirred at reflux for 4 h. The resulting mixture was filtered and the residue was washed with DCM. The filtrate was concentrated under reduced pressure. The residue was purified by silica gel chromatography (Petroleum Ether/EtOAc=20/1) to give the desired product Example 17c (16.0 g, yield 52%) as a white solid. LCMS [M+1]⁺=259.0

Step 3: Example 17e

To a mixture of Example 17c (15.0 g, 58 mmol) and Example 17d (15.7 g, 116 mmol) in DMF (150 mL) was added K₂CO₃ (9.6 g, 69 mmol), which was stirred at r.t. for 48 h. The resulting mixture was washed with H₂O (200 mL), and then extracted with EtOAc (50 mL*3). The combined organic phase was washed with brine, dried over Na₂SO₄, filtrated and the filtrate was concentrated under reduced pressure. The residue was purified by silica gel chromatography (Petroleum Ether/EtOAc=20/1) to recover Example 17c (12.0 g) and obtain the crude product Example 17e (4.5 g, crude yield 25%) as a white solid.

Step 4: Example 17f

A mixture of Example 17e (4.5 g, 14.4 mmol) and LiO.H₂O (2.9 g, 72.0 mmol) in MeOH (50 mL) and H₂O (25 mL) was stirred at room temperature for 4 h. The resulting mixture was washed with EtOAc (50 mL), and then adjusted pH to 2 with aqueous HCl solution. After extraction with EtOAc (20 mL*3), the combined organic layer was dried over anhydrous magnesium sulfate and concentrated under reduced pressure to give the desired product Example 17f (4.1 g, yield 97%) as a white solid. LCMS [M+1]⁺=299.0

Step 5: Example 17h

A mixture of Example 17f (4.1 g, 13.9 mmol) and Example 17g (2.8 g, 13.9 mmol) in pyridine (40 mL) was stirred at 0° C. for 10 min. Then POCl₃ (6.4 g, 41.7 mmol) was slowly dropped into the reaction. The reaction was stirred at 0° C. for 30 min. The resulting mixture was quenched with water (40 mL). After extraction with DCM (20 mL*3), the combined organic layer was dried over anhydrous magnesium sulfate and concentrated under reduced pressure. The residue was purified by silica gel chromatography (Petroleum Ether/EtOAc=1/1) to give the desired product Example 17h (3.1 g, yield 46%) as an orange solid. LCMS [M+1]⁺=482.0

Step 6: Example 17

Under an atmosphere of N₂, a mixture of Example 17h (1.2 g, 2.5 mmol) and Grubbs II (240 mg, 0.5 mmol) in DCE (300 mL) was refluxed for 18 h. The resulting mixture was concentrated under reduced pressure and the residue was purified by silica gel chromatography (DCM/MeOH=20/1) to give the desired product Example 17 (200 mg, yield 18%) as a white solid. LCMS [M+1]⁺=454.0. ¹H NMR (400 MHz, DMSO-d₆) δ 10.94 (s, 1H), 8.69 (d, J=9.3 Hz, 1H), 8.36-8.25 (m, 1H), 7.93 (dd, J=36.3, 6.3 Hz, 2H), 7.72 (dd, J=5.7, 3.1 Hz, 1H), 7.45 (d, J=7.5 Hz, 2H), 7.38 (t, J=7.4 Hz, 2H), 7.32 (d, J=7.1 Hz, 1H), 7.26-7.16 (m, 2H), 5.81-5.72 (m, 1H), 5.57-5.42 (m, 2H), 5.22 (s, 1H), 5.12 (s, 2H), 4.98 (s, 1H), 4.34-4.24 (m, 2H), 2.67 (d, J=23.2 Hz, 2H).

Example 18: General Procedure for Synthesis of Compound Example 18

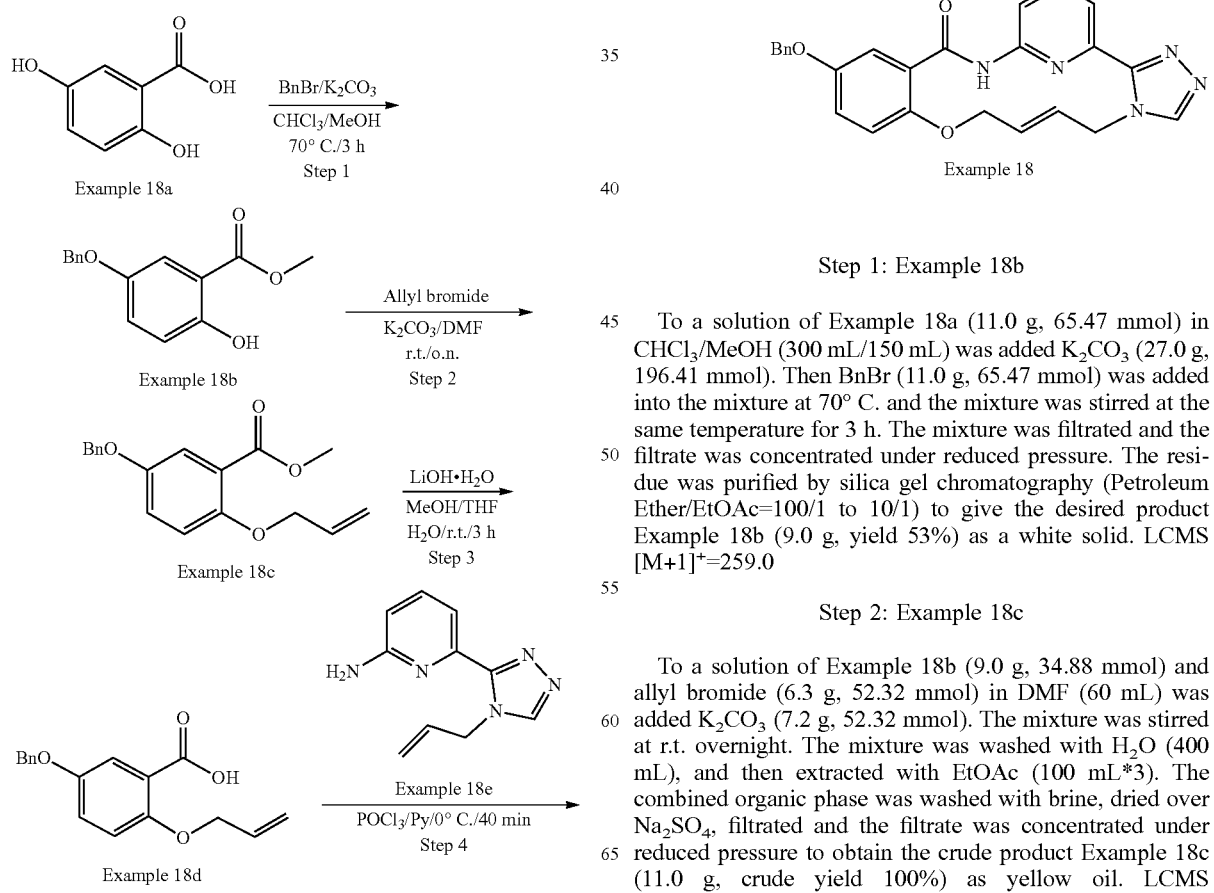

Step 1: Example 18b

To a solution of Example 18a (11.0 g, 65.47 mmol) in CHCl₃/MeOH (300 mL/150 mL) was added K₂CO₃ (27.0 g, 196.41 mmol). Then BnBr (11.0 g, 65.47 mmol) was added into the mixture at 70° C. and the mixture was stirred at the same temperature for 3 h. The mixture was filtrated and the filtrate was concentrated under reduced pressure. The residue was purified by silica gel chromatography (Petroleum Ether/EtOAc=100/1 to 10/1) to give the desired product Example 18b (9.0 g, yield 53%) as a white solid. LCMS [M+1]⁺=259.0

Step 2: Example 18c

To a solution of Example 18b (9.0 g, 34.88 mmol) and allyl bromide (6.3 g, 52.32 mmol) in DMF (60 mL) was added K₂CO₃ (7.2 g, 52.32 mmol). The mixture was stirred at r.t. overnight. The mixture was washed with H₂O (400 mL), and then extracted with EtOAc (100 mL*3). The combined organic phase was washed with brine, dried over Na₂SO₄, filtrated and the filtrate was concentrated under reduced pressure to obtain the crude product Example 18c (11.0 g, crude yield 100%) as yellow oil. LCMS [M+1]⁺=299.0

Step 3: Example 18d

A mixture of Example 18c (11.0 g, 36.91 mmol) and LiO.H$_2$O (5.9 g, 147.6 mmol) in THF/MeOH/H$_2$O (80 mL/80 mL/30 mL) was stirred at room temperature for 3 h. The pH of the mixture was adjusted to 2 with aqueous HCl solution. The suspension was filtered to give the crude product Example 18d (10.5 g, crude yield 100%) as a white solid. LCMS [M+1]$^+$=285.0

Step 4: Example 18f

A mixture of Example 18d (5.68 g, 20 mmol) and Example 18e (4.20 g, 22 mmol) in pyridine (40 mL) was stirred at 0° C. for 10 min, then POCl$_3$ (9.18 g, 60 mmol) was slowly dropped into the reaction. The reaction was stirred at 0° C. for 30 min. The resulting mixture was quenched with water (250 mL). Brown solid was formed. The suspension was filtered to give the desired product Example 18f (4.80 g, yield 51%) as a white solid. LCMS [M+1]$^+$=468.0

Step 5: Example 18g

To a mixture of Example 18f (4.80 g, 10.27 mmol) and DMAP (626 mg, 5.14 mmol) in MeCN (80 mL) was added (Boc)$_2$O (4.48 g, 20.54 mmol) and the mixture was stirred at 25° C. for 3 h. The mixture was concentrated under reduced pressure and the residue was purified by silica gel chromatography (100% EtOAc) to give the desired product Example 18g (2.81 g, yield 50%) as a yellow gum.

Step 6: Example 18h

Under an atmosphere of N$_2$, a mixture of Example 18g (2810 mg, 4.955 mmol) and Grubbs II (622 mg, 0.91 mmol) in DCE (500 mL) was refluxed overnight. The resulting mixture was concentrated under reduced pressure and the residue was purified by silica gel chromatography (100% EtOAc) to give the desired product Example 18h (500 mg, crude,) as yellow oil. LCMS [M+1]$^+$=540.0

Step 7: Example 18

To a mixture of Example 18h (100 mg, crude) in DCM (5 mL) was added TFA (1 mL), and the mixture was stirred at 25° C. for 1 h. The mixture was concentrated under reduced pressure and the residue was purified by prep-TLC (100% EtOAc) to give the Example 18 (4.1 mg, yield 5%) as a white solid. LCMS [M+1]$^+$=440.0. $^1$H NMR (400 MHz, Chloroform-d) δ 11.31 (s, 1H), 8.30 (s, 1H), 8.11-7.72 (m, 4H), 7.57-7.26 (m, 5H), 7.24-7.10 (m, 2H), 6.07 (m, 1H), 5.85 (m, 1H), 5.12 (m, 2H), 5.07 (s, 2H), 4.71 (d, J=7.4 Hz, 2H).

Example 19: General Procedure for Synthesis of Compound Example 19

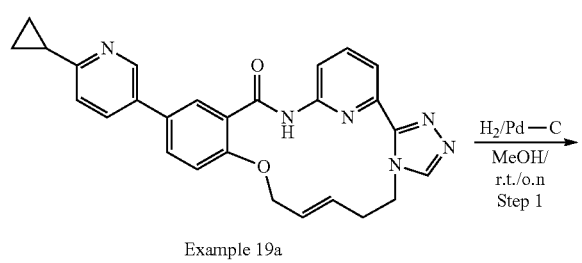

Example 19a

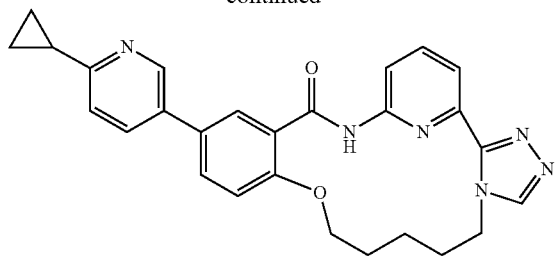

Example 19

Step 1: Example 19

Under an atmosphere of H$_2$, a mixture of Example 19a (50 mg, 0.11 mmol) and Pd/C (5 mg, 5%) in MeOH (5 mL) was stirred at r.t. overnight. The resulting mixture was filtered, and the filtrate was concentrated under reduced pressure. The residue was purified by Prep-HPLC to give the desired product Example 19 (1.8 mg, yield 4%) as a white solid. LCMS [M+1]$^+$=467.0. $^1$H NMR (400 MHz, Chloroform-d) δ 10.70 (s, 1H), 8.73 (s, 1H), 8.64-8.48 (m, 2H), 8.30-8.11 (m, 2H), 7.93 (t, J=8.1 Hz, 2H), 7.73 (d, J=8.6 Hz, 1H), 7.13 (d, J=8.5 Hz, 2H), 4.47-4.07 (m, 4H), 2.22 (m, 2H), 2.12-1.94 (m, 3H), 1.16 (m, 4H), 0.88 (m, 2H).

Example 20: General Procedure for Synthesis of Compound Example 20

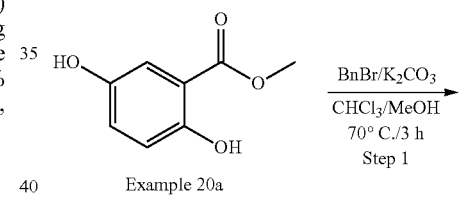

Example 20a

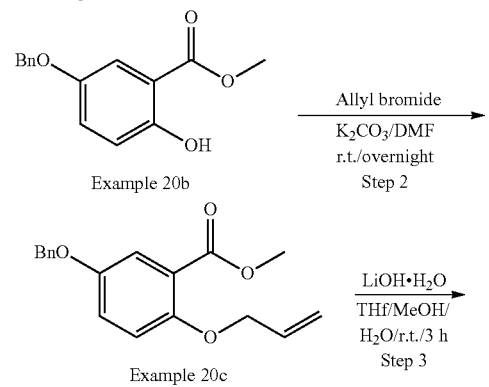

Example 20b

Example 20c

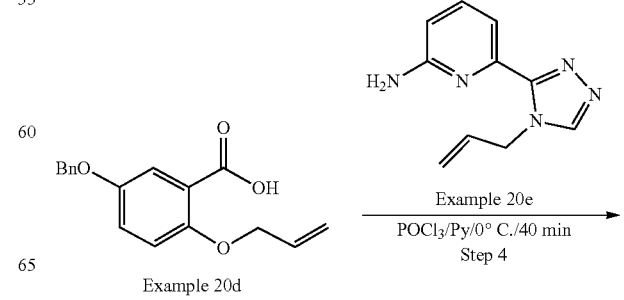

Example 20d

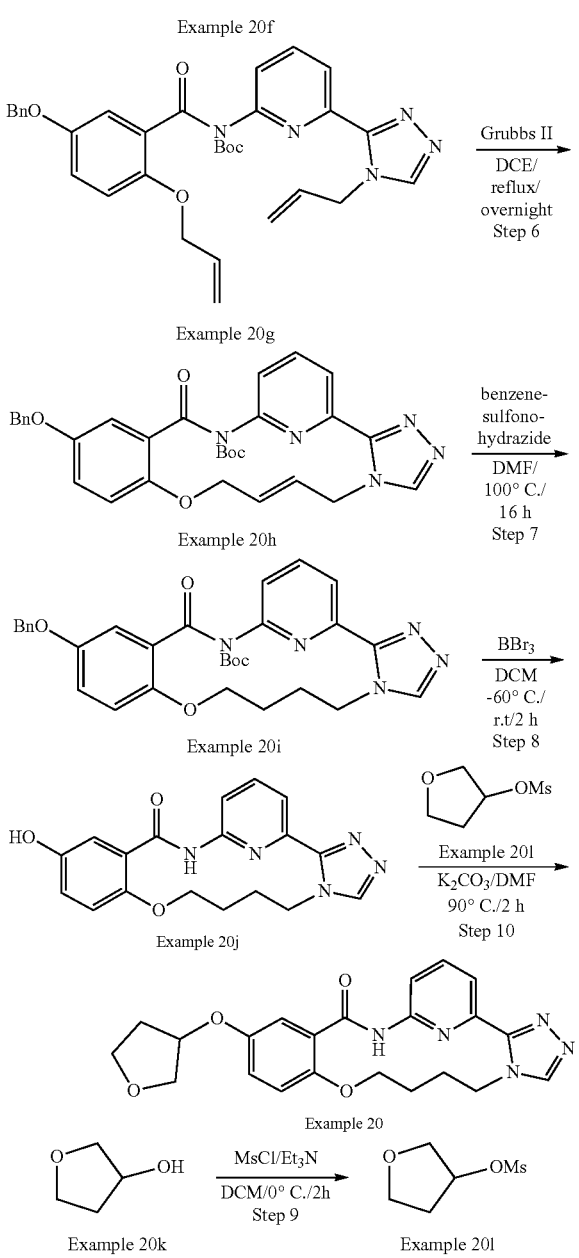

70° C. for 3 h. The mixture was filtered and the filtrate was concentrated under reduced pressure. The residue was purified by silica gel chromatography (Petroleum Ether/EtOAc=100/1 to 10/1) to give desired product Example 20b (9.0 g, yield 53%) as a white solid. LCMS [M+1]$^+$=259.0

Step 2: Example 20c

To a solution of Example 20b (9.0 g, 34.88 mmol) and allyl bromide (6.3 g, 52.32 mmol) in DMF (60 mL) was added $K_2CO_3$ (7.2 g, 52.32 mmol). The mixture was stirred at r.t. overnight. The mixture was washed with $H_2O$ (400 mL), and extracted with EtOAc (100 mL*3). The combined organic phase was washed with brine, dried over $Na_2SO_4$, filtrated and the filtrate was concentrated under reduced pressure to obtain the crude product Example 20c (11.0 g, crude yield 100%) as yellow oil. LCMS [M+1]$^+$=299.0

Step 3: Example 20d

A mixture of Example 20c (11.0 g, 36.91 mmol) and $LiO.H_2O$ (5.9 g, 147.6 mmol) in THF (80 mL), MeOH (80 mL) and $H_2O$ (30 mL) was stirred at room temperature for 3 h. White solid was separated out. The pH of the mixture was adjusted to 2 with aqueous HCl solution. The suspension was filtered to give the desired product Example 20d (10.5 g, yield 100%) as a white solid. LCMS [M+1]$^+$=285.0

Step 4: Example 20f

A mixture of Example 20d (5.68 mg, 20 mmol) and Example 20e (4.20 g, 22 mmol) in pyridine (40 mL) was stirred at 0° C. for 10 min, then $POCl_3$ (9180 mg, 60 mmol) was added dropwise into the reaction. The reaction was stirred at 0° C. for 30 min. The resulting mixture was quenched with water (250 mL). Brown solid was separated out. The suspension was filtered to give the desired product Example 20f (4.8 g, yield 51%) as a white solid. LCMS [M+1]$^+$=468.0

Step 5: Example 20g

A mixture of Example 20f (4.80 g, 10.27 mmol) and DMAP (626 mg, 5.14 mmol) in MeCN (80 mL) was added $(Boc)_2O$ (4.48 g, 20.54 mmol) and the mixture was stirred at 25° C. for 3 h. The mixture was concentrated under reduced pressure to give crude product. The residue was purified by silica gel chromatography (100% EtOAc) to give the desired product Example 20g (2.81 g, yield 50%) as a yellow gum.

Step 6: Example 20h

Under an atmosphere of $N_2$, a mixture of Example 20g (2.81 g, 4.96 mmol) and Grubbs II (622 mg, 0.91 mmol) in DCE (500 mL) was refluxed overnight. The resulting mixture was concentrated under reduced pressure to obtain crude product. The residue was purified by silica gel chromatography (100% EtOAc) to give the desired product Example 20h (500 mg, crude yield 18%) as yellow oil. LCMS [M+1]$^+$=540.0

Step 7: Example 20i

To a mixture of Example 20h (500 mg, crude) in DMF (15 mL) was added benzenesulfonohydrazide (478 mg, 2.78 mmol), which was stirred at 100° C. for 16 h. The mixture Step 1: Example 20b To a solution of Example 20a (11.0 g, 65.47 mmol) in $CHCl_3$/MeOH (300 mL/150 mL) was added $K_2CO_3$ (27 g, 196.41 mmol). Then BnBr (11.0 g, 65.47 mmol) was added into the above mixture at 70° C., which was then stirred at was washed with H$_2$O (100 mL), and extracted with EtOAc (30 mL*4). The combined organic phase was washed with brine, dried over Na$_2$SO$_4$, filtrated and the filtrate was concentrated under reduced pressure. The residue was purified by prep-TLC (100% EtOAc) to give the crude product Example 20i (300 mg, crude yield 60%) as yellow oil. LCMS [M+1]$^+$=542.0

Step 8: Example 20j

To a solution of Example 20i (300 mg, crude) in DCM (15 mL) was added BBr$_3$ (2.027 mmol) at −60° C., which was gradually warmed up to r.t. for 2 h. MeOH (50 mL) was slowly added into the mixture. The mixture was concentrated under reduced pressure and the residue was re-purified by silica gel chromatography (DCM/MeOH=10/1) to afford the desired product Example 20j (100 mg, yield 33%) as yellow oil. LCMS [M+1]$^+$=352.0

Step 9: Example 20l

To a solution of Example 20k (500 mg, 4.90 mmol) in DCM (15 mL) were added Et$_3$N (980 mg, 9.80 mmol) and MsCl (670 mg, 5.88 mmol) at 0° C. The mixture was stirred at 0° C. for 2 h. Water (50 mL) was added into the mixture, which was extracted with DCM (15 mL*3). The combined organic layer was concentrated under reduced pressure to afford the crude product Example 20l (950 mg, crude yield 100%) as yellow oil, which was used in the next step without further purification.

Step 10: Example 20

To a solution of Example 20j (50 mg, 0.14 mmol) in DMF (4 mL) were added Example 20l (140 mg, 0.85 mmol) and K$_2$CO$_3$ (117 mg, 0.85 mmol). The mixture was stirred at 90° C. for 2 h. Water (50 mL) was added into the mixture, which was extracted with DCM (15 mL*3). The combined organic layer was concentrated under reduced pressure and the residue was purified by prep-TLC (DCM/MeOH=20/1) to afford the desired product Example 20 (3 mg, yield 6%) as a white solid. LCMS [M+1]$^+$=422.0. $^1$H NMR (400 MHz, DMSO-d$_6$) δ 11.41 (s, 1H), 8.67 (s, 1H), 8.04 (t, J=7.9 Hz, 1H), 7.86 (dd, J=16.3, 7.9 Hz, 2H), 7.48 (d, J=3.2 Hz, 1H), 7.25 (d, J=9.1 Hz, 1H), 7.17 (dd, J=9.0, 3.2 Hz, 1H), 4.40-4.09 (m, 4H), 3.95-3.61 (m, 5H), 2.20 (dd, J=13.6, 6.1 Hz, 2H), 2.07-1.79 (m, 4H).

Example 21: General Procedure for Synthesis of Compound Example 21

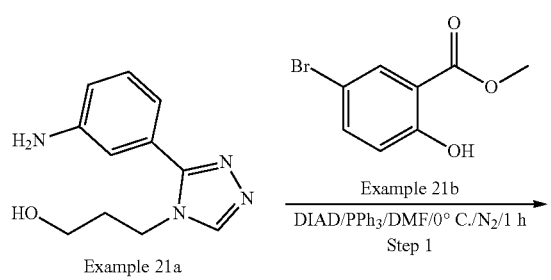

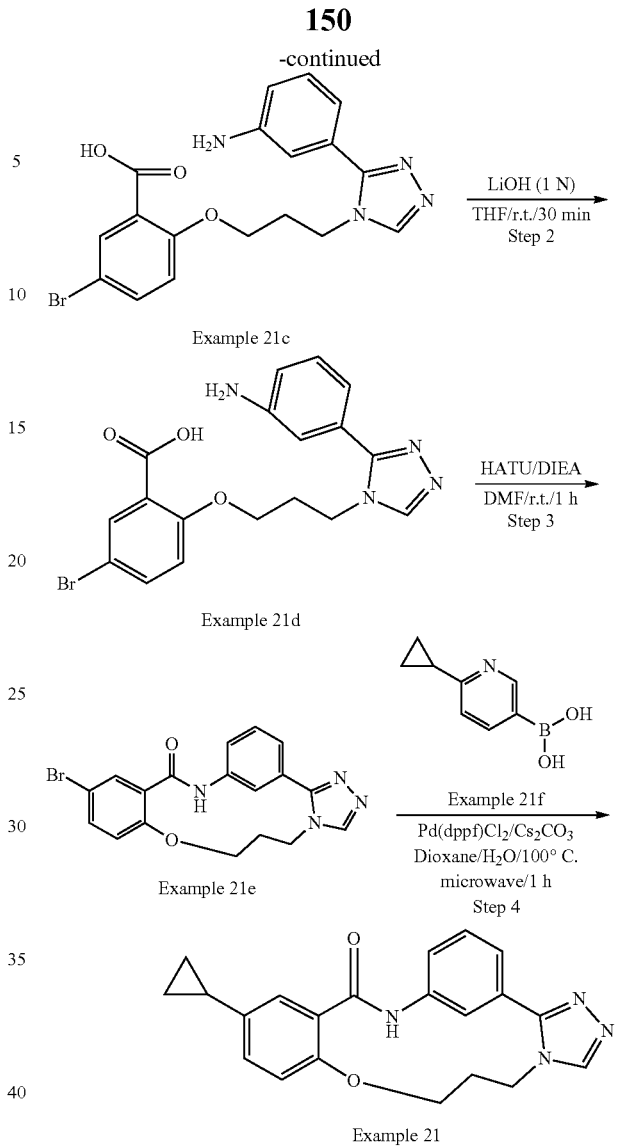

Step 1: Example 21c

A slurry of Example 21a (110 mg, 0.50 mmol), Example 21b (174 mg, 24.5 mmol), and PPh$_3$ (199 mg 0.76 mmol) in dry DMF (4 mL) was degassed by bubbling N$_2$ through the solution for 2 min using a syringe needle. Then the mixture was cooled to 0° C. Then DIAD (202 mg, 1.00 mmol) was added to the mixture dropwise, which was stirred at 0° C. for 1 h. To the mixture was added water (30 mL), which was then extracted with EtOAc (30 mL*3). The combined organic layer was dried over anhydrous magnesium sulfate and concentrated under reduced pressure. The residue was purified by Prep-TLC (DCM/MeOH=10/1) to give the desired product Example 21c (120 mg, yield 55%) as a white solid. LCMS [M+1]$^+$=430.9, 432.9

Step 2: Example 21d

To a mixture of Example 21c (120 mg, 0.28 mmol) in THF (2 mL) was added LiOH (4 mL, 1N). The mixture was stirred at r.t. for 30 min. The mixture was adjusted pH to 7.0 and lyophilized to give the desired product Example 21d (260 mg, crude) as a white solid, which was used in the next step without further purification. LCMS [M+1]⁺=416.9, 418.9

Step 3: Example 21e

To a mixture of Example 21d (130 mg, crude) and HATU (60 mg, 0.16 mmol) in DMF (4 mL) was added DIEA (36 mg, 0.28 mmol), which was stirred at r.t. for 1 h. To the mixture was added water (30 mL), which was then extracted with EtOAc (30 mL*3). The combined organic layer was dried over anhydrous magnesium sulfate and concentrated under reduced pressure. The residue was purified by Prep-TLC (DCM/MeOH=10/1) to give the desired product Example 21e (20 mg, yield 18% over two step) as a white solid. LCMS [M+1]⁺=398.9, 400.9

Step 4: Example 21

To a mixture of Example 21e (20 mg, 0.05 mmol), Example 21f (12 mg, 0.075 mmol), and Cs₂CO₃ (49 mg, 0.15 mmol) in dioxane/H₂O (3 mL, v/v=10/1) was added Pd(dppf)Cl₂ (10 mg, 0.014 mmol). Then the mixture was degassed by bubbling N₂ through the solution for 2 min using a syringe needle. After that, the mixture was heated at 100° C. for 1 h under microwave. The mixture was directly purified by Prep-HPLC to give the desired product Example 21 (7.4 mg, yield 34%) as a white solid. LCMS [M+1]⁺=438.0. As the ¹HNMR of desired product in CDCl₃ or DMSO-d₆ cannot reflect all hydrogen, respectively, the two sets of spectral graphs were complementary relationship. ¹H NMR (400 MHz, DMSO-d₆) δ 10.11 (s, 1H), 8.64 (s, 1H), 8.55 (d, J=1.8 Hz, 1H), 7.78 (dd, J=8.1, 2.3 Hz, 1H), 7.55 (d, J=8.0 Hz, 2H), 7.51 (d, J=7.1 Hz, 1H), 7.43 (s, 1H), 7.37 (t, J=7.8 Hz, 1H), 7.27 (d, J=8.1 Hz, 2H), 7.20 (d, J=8.8 Hz, 1H), 2.07 (s, 1H), 1.02-0.79 (m, 4H).

¹H NMR (400 MHz, Chloroform-d) δ 8.49 (s, 1H), 8.22 (s, 1H), 7.85 (d, J=7.7 Hz, 1H), 7.64 (s, 2H), 7.40 (dd, J=14.2, 6.5 Hz, 3H), 7.14 (s, 1H), 6.95 (d, J=8.6 Hz, 1H), 4.47 (s, 2H), 4.13 (s, 2H).

Example 22: General Procedure for Synthesis of Compound Example 22

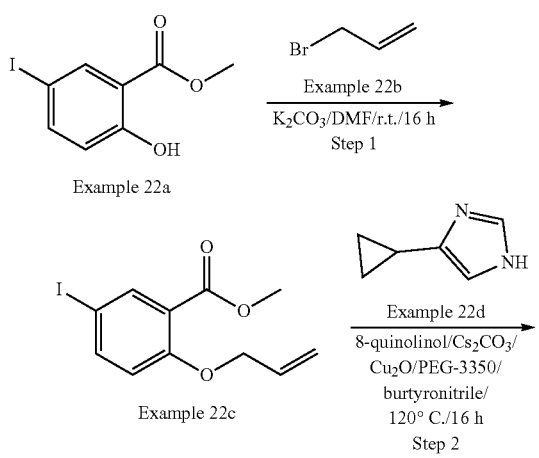

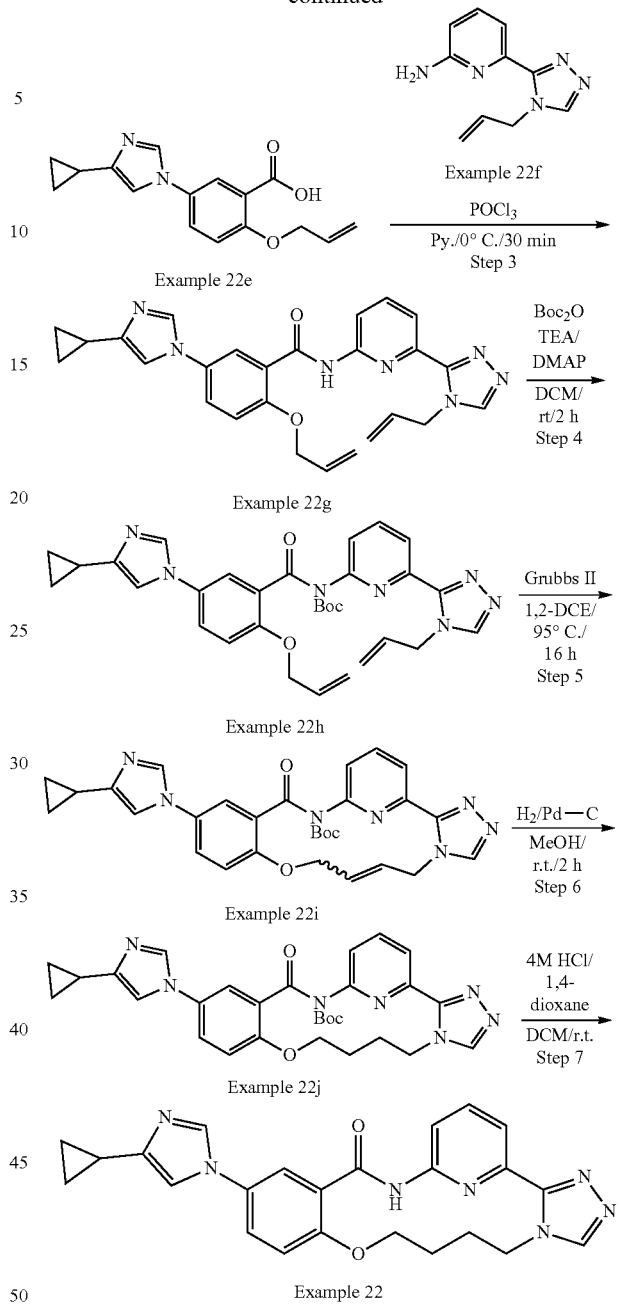

Step 1: Example 22c

A mixture of Example 22a (5.0 g, 18.0 mmol), Example 22b (3.2 g, 27.0 mmol) and K₂CO₃ (3.7 g, 27.0 mmol) in DMF (40 mL) was stirred at room temperature for 16 h. The reaction was diluted with water, and extracted with EtOAc (50 mL*3). The combined organic layer washed with brine (50 mL), dried over Na₂SO₄ and concentrated to give the desired product Example 22c (6.0 g, yield>100%) as yellow oil. LCMS [M+1]⁺=318.9

Step 2: Example 22e

To a solution of Example 22c (5.5 g, 17.3 mmol), Example 22d (2.8 g, 25.9 mmol) in butyronitrile (200 mL)

and PEG-3350 (4.3 g) were added 8-quinolinol (376 mg, 2.6 mmol), Cu$_2$O (243 mg, 1.7 mmol) and Cs$_2$CO$_3$ (11.2 g, 34.6 mmol) successively. The mixture was sealed, degassed by nitrogen for three times and heated at 120° C. for 16 h. The reaction mixture was filtered, and washed by EtOAc. The filtrates were concentrated and purified by silica gel chromatography (DCM/MeOH=50/50) to give the desired product Example 22e (3.5 g, yield 71%) as dark oil. LCMS [M+1]$^+$=285.0

Step 3: Example 22g

Example 22e (3.5 g, 123.2 mmol) and Example 22f (2.5 g, 123.2 mmol) were dissolved in pyridine (50 mL) and cooled to 0° C. POCl$_3$ (5.7 g, 36.97 mmol) was added slowly at 0° C. and the mixture was stirred at 0° C. for 0.5 h. The reaction was quenched by adding water slowly at 0° C., concentrated and purified by silica gel chromatography (DCM/MeOH=90/10) to give the desired product Example 22g (1.1 g, yield 19%) as yellow oil.
LCMS [M+1]$^+$=468.0

Step 4: Example 22h

To a solution of Example 22g (1.1 g, 2.36 mmol) in dry DCM (12 mL) were added Boc$_2$O (616 mg, 2.83 mmol), TEA (476 mg, 4.71 mmol) and DMAP (57 mg, 0.47 mmol) successively. The mixture was stirred at ambient temperature for 16 h. The reaction was diluted with DCM/MeOH (10/1, 50 mL), washed by saturated. NH$_4$Cl (aq.) twice. The organic layer was separated, concentrated and purified by silica gel chromatography (EtOAc/MeOH=80/20) to give the desired product Example 22h (650 mg, yield 49%) as a yellow solid. LCMS [M+1]$^+$=568.0

Step 5: Example 22i

Under an atmosphere of N$_2$, a mixture of Example 22h (650 mg, 1.15 mmol) and Grubbs II (146 mg, 0.17 mmol) in 1,2-DCE (60 mL) was refluxed for 16 h. The resulting mixture was concentrated under reduced pressure to obtain crude product. The residue was purified by silica gel chromatography (EtOAc/MeOH=70/30) to give the desired product Example 22i (30 mg, yield 5%) as a gray solid. LCMS [M+1-100]$^+$=440.0

Step 6: Example 22j

To a solution of Example 22i (15 mg, 0.028 mmol) in MeOH (2 mL) was added 5% Pd/C (20 mg). The mixture was degassed by hydrogen for three times and stirred under a hydrogen balloon for 2 h. The reaction was filtered, and concentrated to give the desired product Example 22j (15 mg, yield 99%) as a yellow solid. LCMS [M+1-100]$^+$=442.0

Step 7: Example 22

To a solution of Example 22i (15 mg, 0.028 mmol) in DCM (2 mL) was added 4M HCl/dioxane (0.5 mL) at room temperature. The reaction was stirred at this temperature for 15 min. The mixture was concentrated to dryness and purified by prep-TLC (EtOAc/MeOH=5/1) to give the desired product Example 22 (2 mg, yield 17%) as a gray solid. LCMS [M+1]$^+$=442.0. $^1$H NMR (400 MHz, Chloroform-d) δ 11.42 (s, 1H), 8.29 (d, J=3.0 Hz, 1H), 8.23 (s, 1H), 8.05 (s, 1H), 8.03 (s, 1H), 7.95 (d, J=7.8 Hz, 1H), 7.51 (s, 1H), 7.31 (s, 1H), 7.13 (s, 1H), 7.05 (s, 1H), 4.37 (m, 2H), 4.30 (m, 2H), 2.72 (m, 1H), 2.34 (m, 1H), 2.21 (m, 1H), 2.11 (m, 1H), 2.01 (m, 1H), 1.43 (m, 4H).

Example 23: General Procedure for Synthesis of Compound Example 23

Step 1: Example 23c

A slurry of Example 23a (400 mg, 1.72 mmol), Example 23b (596 mg, 2.58 mmol) and PPh$_3$ (676 mg, 2.58 mmol) in dry DMF (6 mL) was cooled to 0° C. Then DIAD (695 mg, 3.44 mmol) was added to the mixture dropwise, which was stirred at 0° C. for 1 h. To the mixture was added water (30 mL), which was then extracted with EtOAc (30 mL*3). The combined organic layer was dried over anhydrous magnesium sulfate and concentrated under reduced pressure. The residue was purified by silica gel chromatography (DCM/MeOH=10/1) to give the desired product Example 23c (600 mg, yield 78%) as a white solid. LCMS [M+1]⁺=445.9, 447.9

Step 2: Example 23d

A mixture of Example 23c (600 mg, 1.35 mmol) in THF (4 mL), was added LiOH (4 mL, 1N). The mixture was stirred at r.t. for 30 min. The mixture was adjusted pH to 7.0, and then lyophilized to give the desired product Example 23d (1.0 g, crude yield 100%) as a white solid. LCMS [M+1]⁺=431.9, 433.9

Step 3: Example 23e

To a mixture of Example 23d (250 mg, crude) in pyridine (60 mL) at 0° C. was added POCl₃ (105 mg, 0.69 mmol), which was stirred at 0° C. for 1 h. To the mixture was added water (30 mL), which was then extracted with EtOAc (50 mL*3). The combined organic layer was saturated with brine, dried over anhydrous magnesium sulfate and concentrated under reduced pressure. The residue was washed by MeOH (5 mL) to give the crude product Example 23e (250 mg, crude yield 100%) as a pink solid. LCMS [M+1]⁺=413.9, 415.9

Step 4: Example 23

To a mixture of Example 23e (100 mg, 0.24 mmol), Example 23f (47 mg, 0.29 mmol), and K₃PO₄ (153 mg, 0.72 mmol) in DMF (3 mL) was added Pd(dppf)Cl₂ (18 mg, 0.024 mmol). Then the mixture was degassed by bubbling N₂ through the solution for 2 min using a syringe needle. After that, the mixture was heated at 100° C. for 1 h by microwave. The mixture was directly purified by Prep-HPLC, followed by prep-TLC (DCM/MeOH=10/1) to give the desired product Example 23 (1.1 mg, yield 1%) as a white solid.

LCMS [M+1]⁺=453.0. ¹H NMR (400 MHz, Chloroform-d) δ 11.46 (s, 1H), 8.68 (d, J=2.0 Hz, 1H), 8.48 (d, J=2.4 Hz, 1H), 8.23 (s, 1H), 8.05 (dd, J=13.4, 7.8 Hz, 2H), 7.92 (t, J=7.9 Hz, 1H), 7.78 (dd, J=8.1, 2.3 Hz, 1H), 7.71 (dd, J=8.5, 2.4 Hz, 1H), 7.20 (d, J=8.1 Hz, 1H), 7.13 (d, J=8.6 Hz, 1H), 4.36 (t, J=4.8 Hz, 2H), 4.33-4.26 (m, 2H), 2.09 (q, J=7.8, 7.3 Hz, 3H), 2.04-1.96 (m, 2H), 1.07-1.01 (m, 4H)

Example 24: General Procedure for Synthesis of Compound Example 24

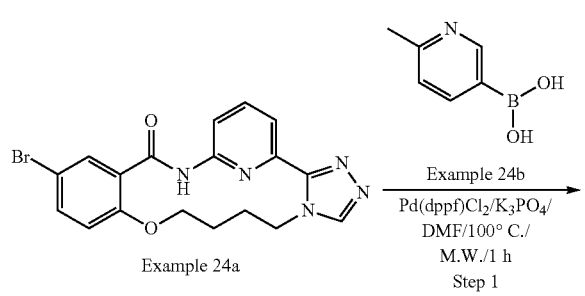

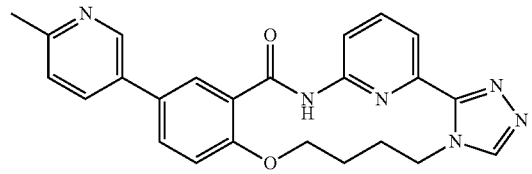

Example 24

Step 1: Example 24

To a slurry of Example 24a (60 mg, 0.24 mmol), Example 24b (20 mg, 0.24 mmol), and K₃PO₄ (92 mg, 0.72 mmol) in DMF (3 mL) was added Pd(dppf)Cl₂ (20 mg, 0.024 mmol). Then the mixture was degassed by bubbling N₂ through the solution for 2 min using a syringe needle. After that, the mixture was heated at 100° C. for 1 h by microwave. The mixture was concentrated and purified by Prep-HPLC, followed by prep-TLC (DCM/MeOH=15/1) to give the desired product Example 24 (1.5 mg, yield 3%) as a white solid. LCMS [M+1]⁺=427.0. ¹H NMR (400 MHz, Chloroform-d) δ 11.48 (s, 1H), 8.76 (d, J=2.4 Hz, 1H), 8.51 (d, J=2.5 Hz, 1H), 8.24 (s, 1H), 8.06 (dd, J=12.7, 7.8 Hz, 2H), 7.94 (t, J=7.9 Hz, 1H), 7.84 (dd, J=8.1, 2.4 Hz, 1H), 7.74 (dd, J=8.4, 2.5 Hz, 1H), 7.24 (m, 1H), 7.15 (d, J=8.6 Hz, 1H), 4.38 (t, J=5.1 Hz, 2H), 4.31 (t, J=8.6 Hz, 2H), 2.73 (m, 2H), 2.62 (m, 3H), 2.12 (m, 2H).

Example 25: General Procedure for Synthesis of Compound Example 25

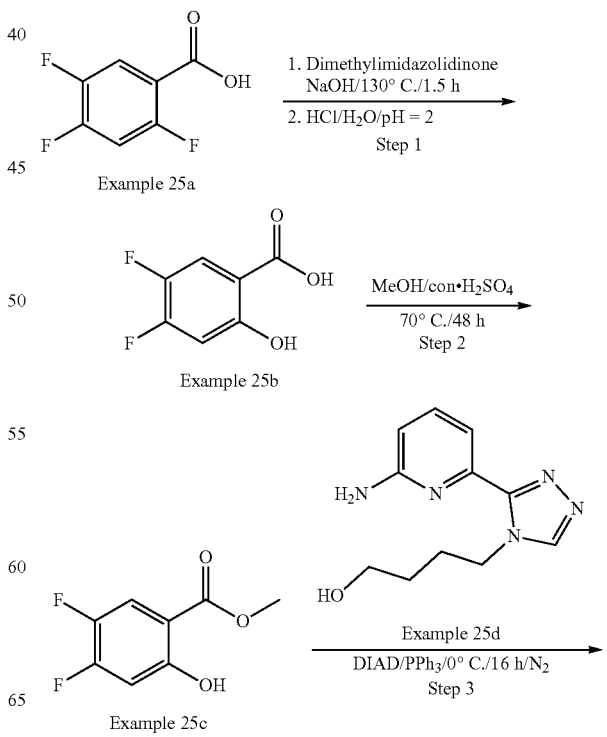

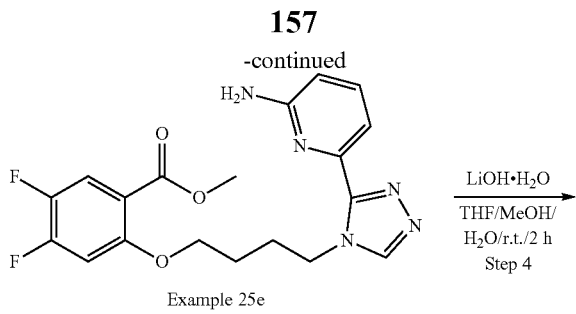

Example 25e

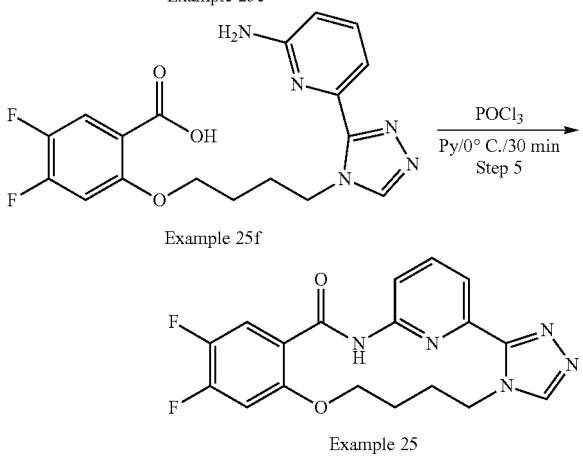

Example 25f

Example 25

Step 1: Example 25b

To a solution of Example 25a (10 g, 56.8 mmol) in dimethylimidazolidinone (120 mL) was added NaOH (9.1 g, 227.3 mmol) slowly. The mixture was heated to 130° C. and stirred for 1.5 h. After cooling to room temperature, the reaction was poured into ice water and acidified by con.HCl to pH=3~4, which was stirred for about 30 min and filtered. The cake was washed by water and dried to give the desired product Example 25b (7.5 g, yield 75%) as a white solid. LCMS [M-1]$^-$=173.0 $^1$H NMR (400 MHz, DMSO-d$_6$) δ 7.71 (dd, J=10.9, 9.3 Hz, 1H), 7.06 (dd, J=12.1, 6.8 Hz, 1H).

Step 2: Example 25c

To a solution of Example 25b (7.5 g, 43.1 mmol) in MeOH (150 mL) was added con.H$_2$SO$_4$ (5 mL). The mixture was refluxed at 70° C. for 48 h. The mixture was concentrated, diluted with EtOAc, washed by sat.NaHCO$_3$ (twice) and brine. The organic layer was separated, dried over Na$_2$SO$_4$ and filtered. The solvent was removed in vacuo to give the desired product Example 25c (4.5 g, yield 56%) as a yellow solid. LCMS [M+1]$^+$=189.0

Step 3: Example 25e

Example 25c (1.0 g, 5.3 mmol), Example 25d (1.24 g, 5.3 mmol) and PPh$_3$ (1.7 g, 6.38 mmol) were dissolved in dry DMF (25 mL) and cooled to 0° C. DIAD (1.3 g, 6.38 mmol) was added slowly under nitrogen atmosphere at this temperature. The mixture was stirred from 0° C. to r.t. for 16 h. Water was added, and the mixture was extracted with EtOAc (50 mL*3). The combined organic layers were concentrated and purified by silica gel chromatography (EtOAc/MeOH=75/25) to give the desired product Example 25e (260 mg, yield 12%) as light yellow oil. LCMS [M+1]$^+$=404.0

Step 4: Example 25f

To a solution of Example 25e (260 mg, 0.65 mmol) in THF/MeOH/H$_2$O (3 mL/2 mL/1 mL) was added LiO.H$_2$O (136 mg, 3.23 mmol). The mixture was stirred at r.t. for 2 h. The reaction was concentrated, acidified by 2N HCl (aq.) to pH=3~4. The solution was purified by Prep-HPLC to give the desired product Example 25f (75 mg, yield 30%) as a light yellow solid. LCMS [M+1]$^+$=390.0

Step 5: Example 25

To a solution of Example 25f (60 mg, 0.15 mmol) in pyridine (5 mL) at 0° C. was added POCl$_3$ (30 mg, 0.19 mmol) slowly and the mixture was stirred at 0° C. for 0.5 h. The reaction was quenched by adding water slowly at 0° C., concentrated and purified by Prep-HPLC to give the desired product Example 25 (5 mg, yield 9%) as an off-white solid. LCMS [M+1]$^+$=372.0. $^1$H NMR (400 MHz, DMSO-d$_6$) δ 10.37 (s, 1H), 8.67 (s, 1H), 8.26 (d, J=8.3 Hz, 1H), 8.03 (t, J=7.9 Hz, 1H), 7.89 (dd, J=14.7, 8.9 Hz, 2H), 7.33 (dd, J=12.6, 6.6 Hz, 1H), 4.67 (t, J=5.8 Hz, 2H), 4.17 (d, J=6.0 Hz, 2H), 3.34 (m, 2H), 1.85 (m, 2H).

Example 28: General Procedure for Synthesis of Compound Example 28

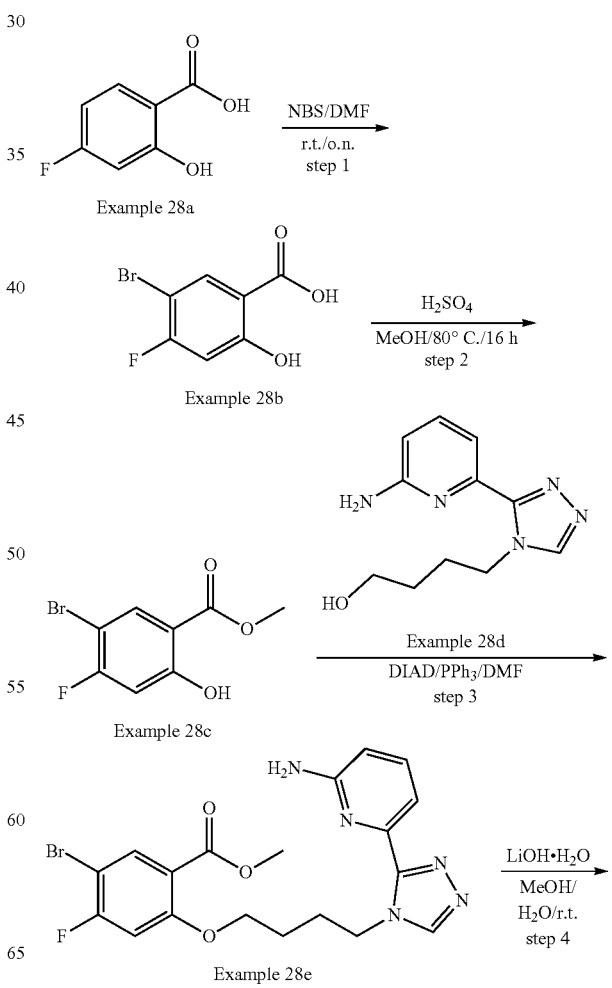

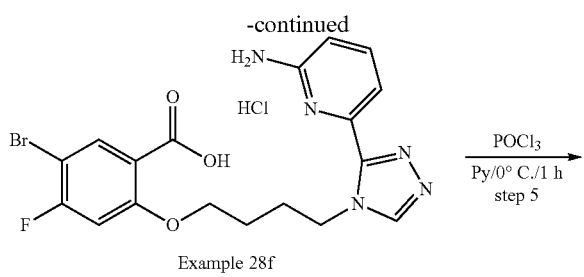

Example 28f

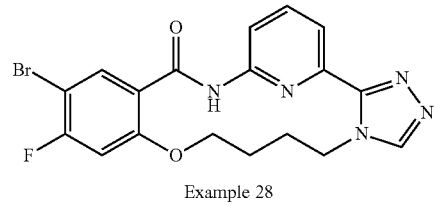

Example 28

Step 1: Example 28b

To a solution of Example 28a (5 g, 32.05 mmol) in DMF (64 mL) was added NBS (6.3 g, 35.26 mmol), which was stirred at r.t. for overnight. The mixture was extracted with EtOAc (400 mL), washed with water (4*500 mL). The organic phase was dried, concentrated to give Example 28b (7 g, yield 93%) as a white solid. LCMS [M+1]$^+$=236.9.

Step 2: Example 28c

To a solution of Example 28b (7 g, 29.3 mmol) in MeOH (50 mL) was added con.H$_2$SO$_4$ (4 mL) dropwise at r.t., which was then stirred at 80° C. for 16 h. The mixture was concentrated to remove MeOH, diluted with water, extracted with EtOAc, dried, concentrated and purified by silica gel chromatography (Petroleum Ether/EtOAc=100/5) to give Example 28c (5.5 g, yield 75%). LCMS [M+1]$^+$=250.9.

Step 3: Example 28e

To a solution of Example 28c (1.0 g, 4 mmol), Example 28d (940 mg, 4 mmol) and PPh$_3$ (2 g, 8 mmol) in anhydrous DMF (10 mL) was added DIAD (1.6 g, 8 mmol) dropwise at 0° C. under N2, which was then stirred at r.t. for 16 h. The mixture was diluted with water, extracted with EtOAc, and purified by silica gel chromatography (EtOAc/MeOH=90/10) to give Example 28e (1.1 g, yield 59%) as yellow oil. LCMS [M+1]$^+$=465.9.

Step 4: Example 28f

To a solution of Example 28e (1 g, 2.16 mmol) in MeOH (10 mL) was added LiO.H$_2$O (280 mg, 6.5 mmol) in water (5 mL) dropwise, which was stirred at r.t. for 16 h. The mixture was adjusted pH to 4 with 1 N HCl (aq.), and then concentrated to give crude Example 28f (1.9 g, crude yield 100%, with LiCl) as a white solid. LCMS [M+1]$^+$=449.9.

Step 5: Example 28

To a solution of Example 28f (1.7 g, 3.8 mmol) in pyridine (20 mL) was added POCl$_3$ (1.74 g) dropwise at 0° C., which was stirred at r.t. for 2 h. The mixture was quenched with water, extracted with DCM/MeOH (10/1), dried, concentrated and purified by silica gel chromatography (DCM/MeOH=90/10) to give the desired product Example 28 (260 mg, yield 15%) as a white solid. LCMS [M+1]+=433.9. $^1$H NMR (400 MHz, Chloroform-d) δ 11.15 (s, 1H), 8.49 (d, J=8.1 Hz, 1H), 8.22 (s, 1H), 8.04 (dd, J=12.5, 7.8 Hz, 2H), 7.93 (t, J=7.9 Hz, 1H), 6.84 (d, J=9.6 Hz, 1H), 4.32-4.28 (m, 4H), 2.70 (m, 2H), 2.10 (m, 2H).

Example 29: General Procedure for Synthesis of Compound Example 29

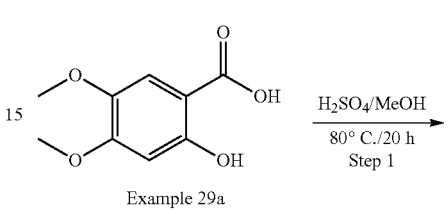

Example 29a

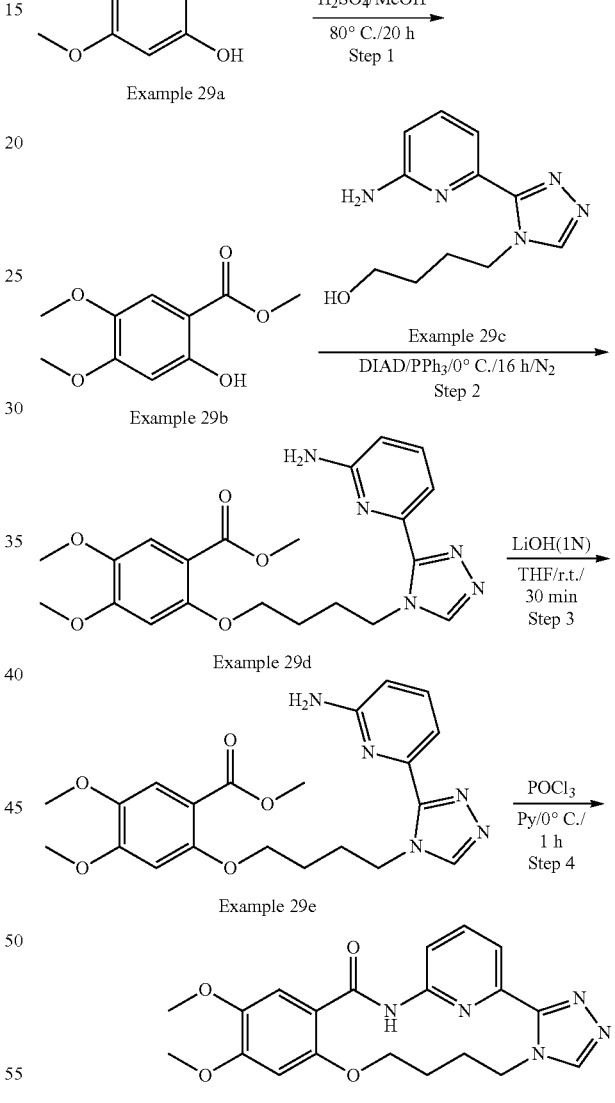

Step 1: Example 29b

To a solution of Example 29a (5 g, 25.2 mmol) in MeOH (50 mL) was added H$_2$SO$_4$ (5 mL), which was stirred at 80° C. for 20 h. The mixture was concentrated and purified by silica gel chromatography (Petroleum Ether/EtOAc=3/1) to give the desired product Example 29b (4.4 g, yield 83%) as a white solid. LCMS [M+1]$^+$=213.0

Step 2: Example 29d

To a solution of Example 29b (1 g, 5 mmol), Example 29c (1.1 g, 5 mmol), and PPh$_3$ (2.6 g, 10 mmol) was added DIAD (2 g, 10 mmol) at 0° C. The mixture was stirred from 0° C. to r.t. for 16 h. The mixture was diluted with water and extracted by EtOAc (200 mL*2). The combined organic phase was washed with brine, dried over Na$_2$SO$_4$, filtrated and concentrated under reduced pressure. The residue was purified by silica gel chromatography (Petroleum Ether/EtOAc=3/1) to give the desired product Example 29d (1.5 g, yield 71%) as yellow oil. LCMS [M+1]$^+$=428.0

Step 3: Example 29e

A solution of Example 29d (1.5 g, 3.5 mmol) and LiO.H$_2$O (441 mg, 10.5 mmol) in MeOH/H$_2$O (10 mL/10 mL) was stirred at r.t. for 16 h. The mixture was concentrated and acidified by 1N HCl to pH=5. Then concentrated and purified by Prep-HPLC to give the desired product Example 29e (400 mg, yield 27%) as a white solid. LCMS [M+1]$^+$=414.0

Step 4: Example 29

To a solution of Example 29e (207 mg, 0.5 mmol) in pyridine (10 mL) was added POCl$_3$ (230 mg, 1.5 mmol) at 0° C., which was stirred at 0° C. for 2 hours. The mixture was diluted with water and concentrated. The residue was purified by Prep-HPLC to give Example 29 (21 mg, yield 10%) as a white solid. LCMS [M+1]$^+$=396.1. $^1$H NMR (400 MHz, Chloroform-d) δ 10.27 (s, 1H), 8.46 (d, J=8.4 Hz, 2H), 8.03 (d, J=7.6 Hz, 1H), 7.86 (t, J=8.0 Hz, 1H), 7.56 (s, 1H), 6.27 (s, 1H), 4.72 (s, 2H), 4.07 (t, J=7.1 Hz, 2H), 3.87 (s, 3H), 3.82 (s, 3H), 2.15-2.09 (m, 2H), 2.05-1.98 (m, 2H).

Example 30: General Procedure for Synthesis of Compound Example 30

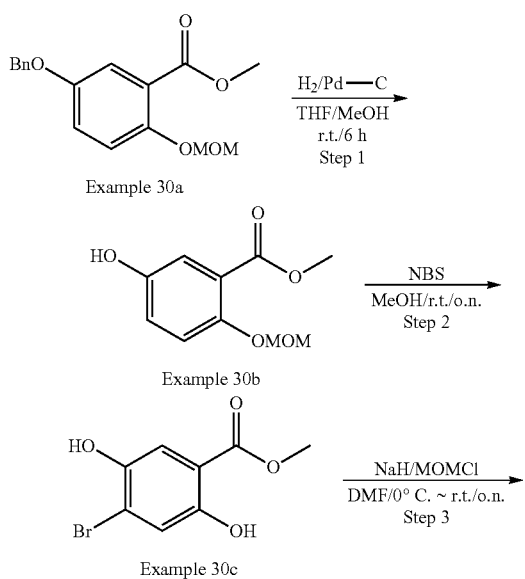

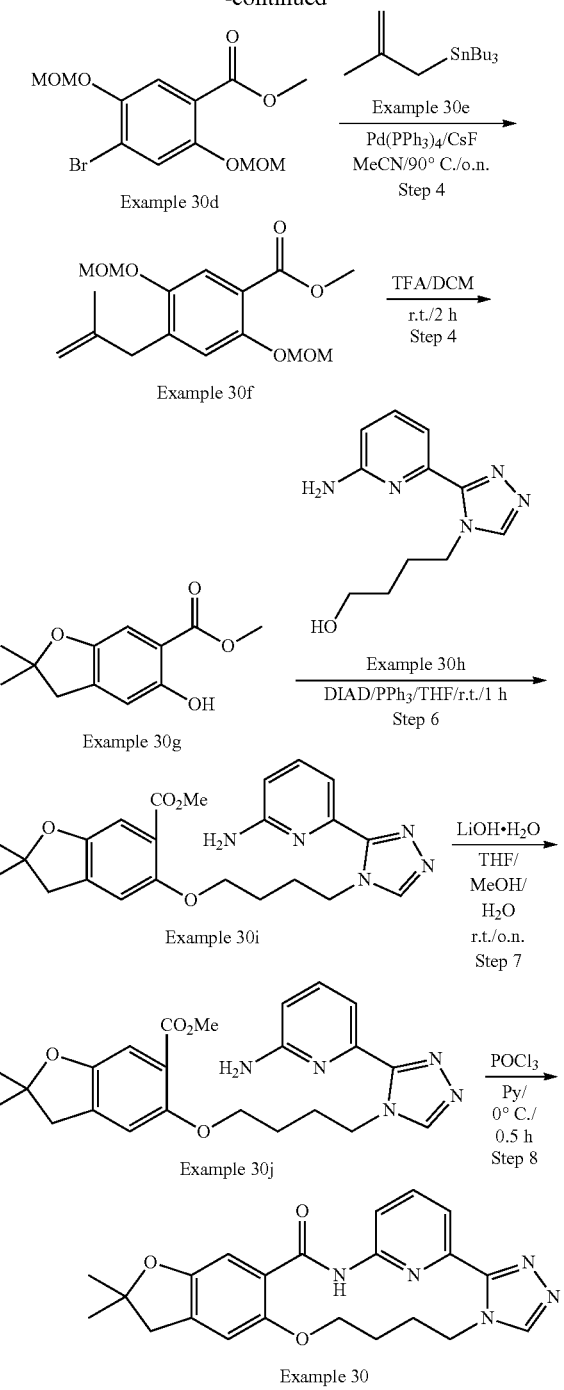

Step 1: Example 30b

To a solution of Example 30a (1 g, 3.31 mmol) in THF/MeOH (10 mL/5 mL) was added 5% Pd/C (200 mg). The mixture was stirred at r.t. for 6 h under 1 atm hydrogen atmosphere. The mixture was filtrated and the filtrate was concentrated to give the desired product Example 30b (670 mg, yield 96%) as yellow oil. LCMS [M+1]$^+$=213.0

Step 2: Example 30c

To a solution of Example 30b (100 mg, 0.47 mmol) in MeOH (2 mL) was added NBS (92 mg, 0.52 mmol). The mixture was stirred at r.t. overnight under $N_2$. The mixture was extracted with EtOAc (10 mL*2). The combined organic phase was washed with brine, dried over $Na_2SO_4$, filtrated and the filtrate was concentrated under reduced pressure. The residue was purified by Prep-HPLC to give the desired product Example 30c (8 mg, yield 7%) as a yellow solid. LCMS $[M+1]^+=246.9$ Step 3: Example 30d To a solution of Example 30c (4.2 g, 17.0 mmol) in DMF (40 mL) was added NaH (1.7 g, 42.5 mmol, 60% in mineral oil) at 0° C. under $N_2$. The mixture was stirred at this temperature for 0.5 h and warmed to r.t. for 0.5 h. Then MOMCl (3.4 g, 42.5 mmol) was added at 0° C., the resulting mixture was stirred at r.t. overnight under $N_2$. The mixture was extracted with EtOAc (100 mL*2). The combined organic phase was washed with brine, dried over $Na_2SO_4$, filtrated and the filtrate was concentrated under reduced pressure. The residue was purified by silica gel chromatography (Petroleum ether/EtOAc=10/1) to give the desired product Example 30d (910 mg, yield 16%) as yellow oil. LCMS $[M+1-32]^+=302.9$ Step 4: Example 30f To a solution of Example 30d (300 mg, 0.89 mmol) in MeCN (8 mL) were added Example 30e (463 mg, 1.34 mmol), $Pd(PPh_3)_4$ (103 mg, 0.089 mmol) and CsF (136 mg, 0.89 mmol). The mixture was stirred at 90° C. overnight under $N_2$. The mixture was concentrated under reduced pressure. The residue was purified by prep-TLC (Petroleum ether/EtOAc=5/1) to give the desired product Example 30f (210 mg, yield 76%) as colorless oil. LCMS $[M+1-32]^+=279.0$ Step 5: Example 30g To a solution of Example 30f (210 mg, 0.68 mmol) in TFA/DCM (3 mL/3 mL) was stirred at r.t. for 2 h. The mixture was extracted with DCM (20 mL*2). The combined organic phase was washed with brine, dried over $Na_2SO_4$, filtrated and the filtrate was concentrated under reduced pressure. The residue was purified by prep-TLC (Petroleum ether/EtOAc=10/1) to give the desired product Example 30g (50 mg, yield 33%) as colorless oil. LCMS $[M+1]^+=223.0$ Step 6: Example 30i To a solution of Example 30g (800 mg, 3.6 mmol) in THF (10 mL) were added Example 30h (1.26 g, 5.4 mmol) and $PPh_3$ (1.9 g, 7.2 mmol). The mixture was cooled to 0° C. and added DIAD (1.8 g, 9.0 mmol) under $N_2$. The resulting mixture was stirred at r.t. for 1 h under $N_2$. The mixture was extracted with EtOAc (30 mL*2). The combined organic phase was washed with brine, dried over $Na_2SO_4$, filtrated and the filtrate was concentrated under reduced pressure. The residue was purified by silica gel chromatography (DCM/MeOH=20/1) to give the desired product Example 30i (670 mg, yield 42%) as yellow oil. LCMS $[M+1]^+=438.1$ Step 7: Example 30j To a solution of Example 30i (670 mg, 1.53 mmol) in $THF/MeOH/H_2O$ (5 mL/5 mL/2 mL) was added $LiO.H_2O$ (193 mg, 4.6 mmol). The mixture was stirred at r.t. overnight. The reaction mixture was acidified by 1N HCl to pH=3~4. The solvent was evaporated under reduced pressure to give the crude desired product Example 30j (700 mg, crude yield 100%) as a white solid, which was used in next step. LCMS $[M+1]^+=424.0$ Step 8: Example 30

To a solution of Example 30j (700 mg, crude, 1.53 mmol) in pyridine (20 mL) was added $POCl_3$ (1.17 g, 7.65 mmol) at 0° C. The mixture was stirred at 0° C. for 0.5 h. The mixture was poured onto the $H_2O$ (50 mL) and extracted with EtOAc (50 mL*2). The combined organic phase was washed with brine, dried over $Na_2SO_4$, filtrated and the filtrate was concentrated under reduced pressure. The residue was suspended in MeCN/MeOH/DMSO (2 mL/2 mL/0.5 mL) and stirred at r.t. for 0.5 h, and then the suspension was filtrated. The solid was dried to give Example 30 (23 mg, yield 4%) as a white solid. LCMS $[M+1]^+=406.0$. $^1H$ NMR (400 MHz, DMSO-$d_6$) δ 11.43 (s, 1H), 8.67 (s, 1H), 8.03 (t, J=7.9 Hz, 1H), 7.88 (d, J=8.0 Hz, 1H), 7.82 (d, J=7.6 Hz, 1H), 7.24 (s, 1H), 7.21 (s, 1H), 4.30-4.19 (m, 4H), 3.06 (s, 2H), 2.45-2.36 (m, 2H), 1.98-1.91 (m, 2H), 1.41 (s, 6H).

Example 31: General Procedure for Synthesis of Compound Example 31

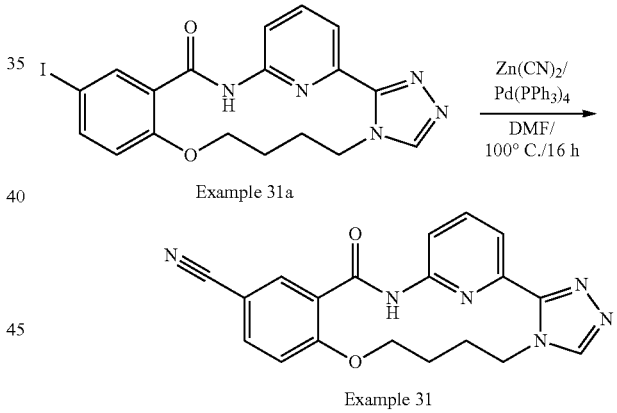

Step 1: Example 31

To a solution of Example 31a (90 mg, 0.20 mmol) in DMF (2 mL) were added $Zn(CN)_2$ (57 mg, 0.49 mmol) and $Pd(PPh_3)_4$ (33 mg, 0.03 mmol). The mixture was stirred at 100° C. under $N_2$ for 16 h. To the mixture was added $H_2O$ (30 mL), then extracted with EtOAc (10 mL*3). The combined organic phase was washed with brine, dried over $Na_2SO_4$, filtrated and the filtrate was concentrated. The residue was purified by Prep-HPLC to obtain the desired product Example 31 (6.8 mg, yield 7%) as a white solid. LCMS $[M+1]^+=361.0$. $^1H$ NMR (400 MHz, DMSO-$d_6$) δ 10.94 (s, 1H), 8.69 (d, J=1.5 Hz, 1H), 8.25 (t, J=1.8 Hz, 1H), 8.12-7.98 (m, 2H), 7.85 (dd, J=7.7, 5.6 Hz, 2H), 7.45 (d, J=8.8 Hz, 1H), 4.38 (t, J=5.0 Hz, 2H), 4.31-4.16 (m, 2H), 2.43 (d, J=10.0 Hz, 2H), 1.93 (s, 2H).

Example 32: General Procedure for Synthesis of Compound Example 32

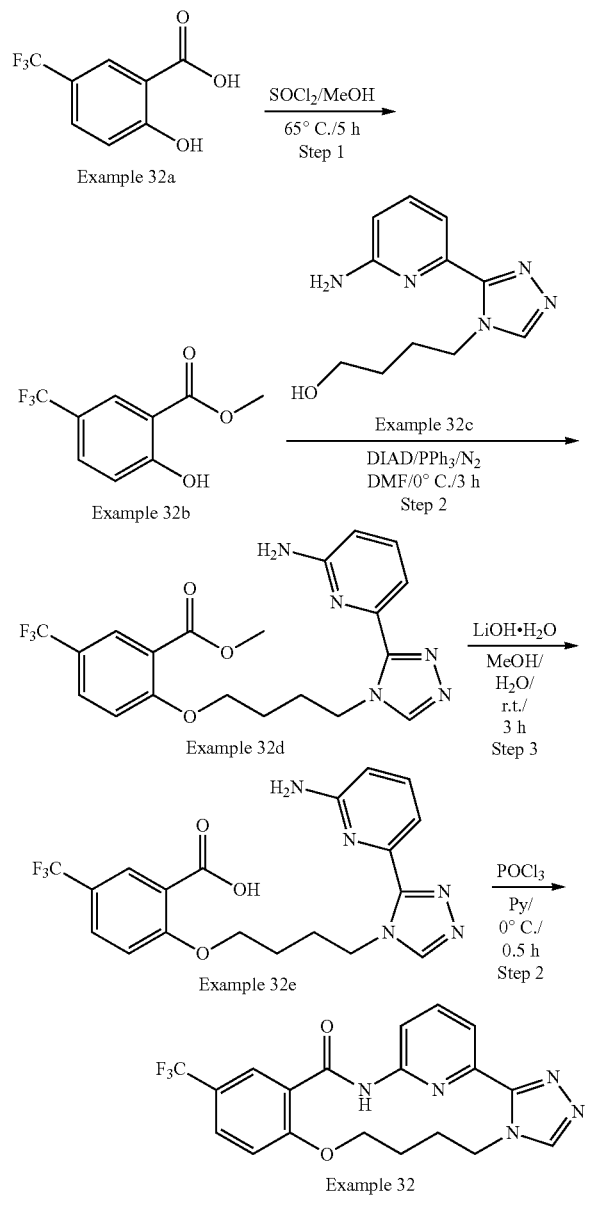

Step 1: Example 32b

To the solution of Example 32a (900 mg, 4.37 mmol) in MeOH (20 mL) at 0° C. was added SOCl₂ (1 mL), and the mixture was heated at 65° C. for 5 h. After the temperature was cooled down to r.t., it was concentrated under reduced pressure. The residue was purified by silica gel chromatography (pure petroleum ether) to give the desired product Example 32b (780 mg, yield 81%) as colorless liquid.

Step 2: Example 32d

To a mixture of Example 32b (670 mg, 3.05 mmol), Example 32c (710 mg, 3.05 mmol), PPh₃ (1.18 g, 4.5 mmol) was added dried DMF (15 mL), and the mixture was degassed for N₂ protection. Then, DIAD (1.23 g) was injected into the mixture at 0° C. dropwise, and the reaction solution was stirred for 3 h. After extraction with EtOAc (10 mL*2), the combined organic layer was dried over Na₂SO₄, filtered and concentrated under reduced pressure. The residue was purified by silica gel chromatography (DCM/MeOH=95/5) to give the desired product Example 32d (1.05 g, yield 79%) as colorless oil. LCMS [M+1]$^+$=436.0

Step 3: Example 32e

To the solution of Example 32d (260 mg, 0.6 mmol) in MeOH/H₂O (2 mL/1 mL) was added LiO.H₂O (75 mg, 1.8 mmol) at r.t., and the mixture was stirred at r.t. for 3 h. Then, the pH was adjusted to 3 by HCl (2 M), and the mixture was concentrated under reduced pressure to give the crude product Example 32e (300 mg, crude yield 100%) as colorless oil. LCMS [M+1]$^+$=422.0

Step 4: Example 32

To a solution of crude Example 32e (300 mg, 0.6 mmol) in pyridine (6 mL) at 0° C. were added POCl₃ (460 mg, 3 mmol). The reaction was stirred at 0° C. for 30 min. Then, water (20 mL) was added to quench the reaction. The resulting solution was filtrated and the filtrate was washed by water twice. Then, the solid was purified by Prep-TLC to give the desired product Example 32 (32 mg, yield 13%) as a yellow solid. LCMS [M+1]$^+$=404.0. $^1$H NMR (400 MHz, DMSO-d₆) δ 11.07 (s, 1H), 8.66 (s, 1H), 8.17 (d, J=2.4 Hz, 1H), 8.03 (t, J=7.9 Hz, 1H), 7.92 (dd, J=8.8, 2.4 Hz, 1H), 7.84 (d, J=2.6 Hz, 1H), 7.82 (d, J=3.0 Hz, 1H), 7.44 (d, J=8.8 Hz, 1H), 4.37 (t, J=5.0 Hz, 2H), 4.27-4.14 (m, 2H), 2.46-2.33 (m, 2H), 1.92 (q, J=6.5 Hz, 2H).

Example 33: General Procedure for Synthesis of Compound Example 33

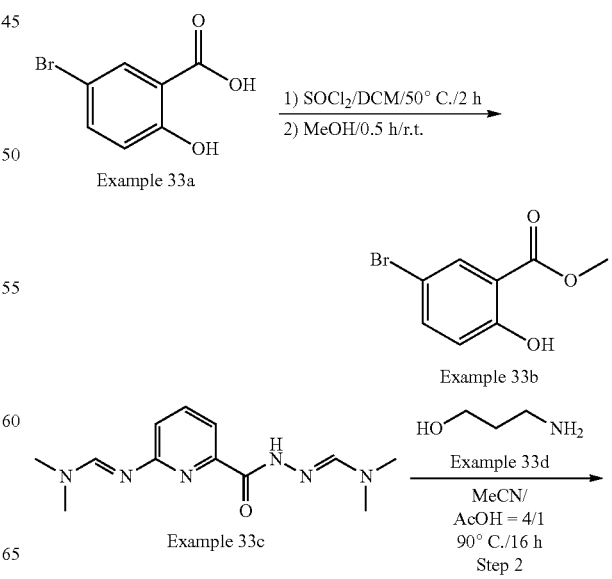

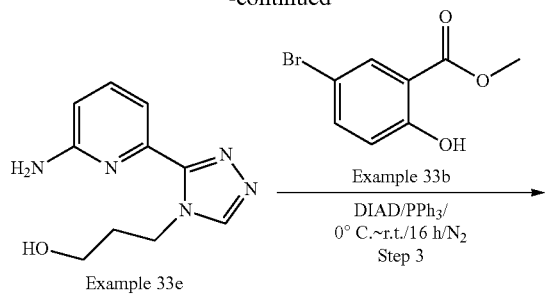

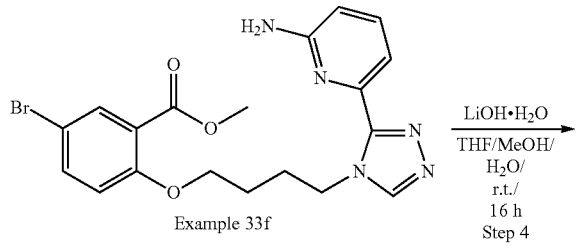

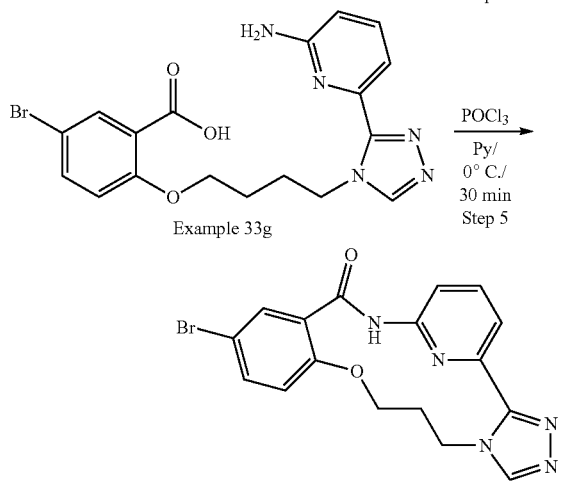

dry DMF (20 mL) and cooled to 0° C. DIAD (1.05 g, 5.2 mmol) was added slowly under nitrogen atmosphere at this temperature. The mixture was stirred from 0° C. to r.t. for 16 h. Water was added, and the mixture was extracted with EtOAc (50 mL*3). The combined organic layers were concentrated and purified by silica gel chromatography (EtOAc/MeOH=60/40) to give the desired product Example 33f (700 mg, yield 37%) as yellow oil. LCMS $[M+1]^+=432.1/434.0$ Step 4: Example 33g To a solution of Example 33f (700 mg, 1.62 mmol) in THF/MeOH/H$_2$O (15 mL/10 mL/5 mL) was added LiO.H$_2$O (340 mg, 8.12 mmol). The mixture was stirred at r.t. for 16 h (Monitored by LCMS). The reaction was concentrated, acidified to pH=3~4 with 1N HCl (aq.), filtered. The solid was collected and dried to give the desired product Example 33g (540 mg, yield: 79.8%) as a white solid. LCMS $[M+1]^+=417.9/419.9$ Step 5: Example 33

To a solution of Example 33g (100 mg, 0.24 mmol) in pyridine (24 mL) at 0° C. was added POCl$_3$ (110 mg, 0.72 mmol) slowly and the mixture was stirred at 0° C. for 0.5 h. The reaction was quenched with water slowly at 0° C., concentrated and purified by Prep-HPLC to give the desired product Example 33 (14 mg, yield 15%) as a yellow solid. LCMS $[M+1]^+=401.9$. $^1$H NMR (400 MHz, DMSO-d$_6$) δ 10.41 (s, 1H), 8.71 (s, 1H), 7.95 (t, J=7.8 Hz, 1H), 7.84 (d, J=7.6 Hz, 1H), 7.48-7.40 (m, 2H), 7.31 (d, J=7.9 Hz, 1H), 6.99 (d, J=8.8 Hz, 1H), 4.74 (s, 2H), 4.06 (s, 2H), 2.18 (s, 2H).

Example 35: General Procedure for Synthesis of Compound Example 35

Step 1: Example 33b

To a solution of Example 33a (20 g, 92.1 mmol) in DCM (150 mL) was added SOCl$_2$ (13 g, 110.6 mmol) and DMF (1 mL). The mixture was heated to 50° C. and stirred for 2 h. After cooling to room temperature, the mixture was concentrated. MeOH (100 mL) was added into the mixture, which was stirred for another 30 min. The solvent was removed to give the desired product Example 33b (21 g, yield 100%) as a white solid. LCMS $[M+1]^+=231.0/233.0$ Step 2: Example 33e To a solution of Example 33c (10 g, 38.2 mmol) in MeCN (120 mL) were added AcOH (30 mL) and Example 33d (5.7 g, 76.3 mmol). The mixture was stirred at 90° C. for 16 h. The mixture was cooled to r.t. and concentrated. The residue was basified to pH=8 with 5N NaOH (aq.), concentrated and purified by silica gel chromatography (DCM/MeOH=30/1) to give the desired product Example 33e (5.5 g, yield 66%) as a white solid. LCMS $[M+1]^+=220.1$ Step 3: Example 33f Example 33b (1.0 g, 4.3 mmol), Example 33e (952 mg, 4.6 mmol) and PPh$_3$ (1.36 g, 5.2 mmol) were dissolved in

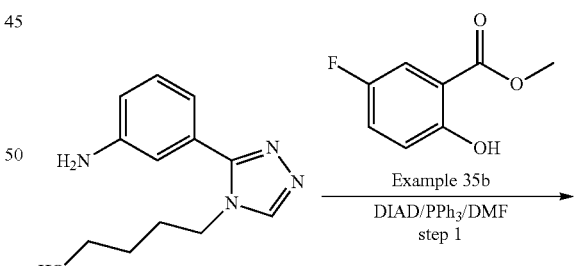

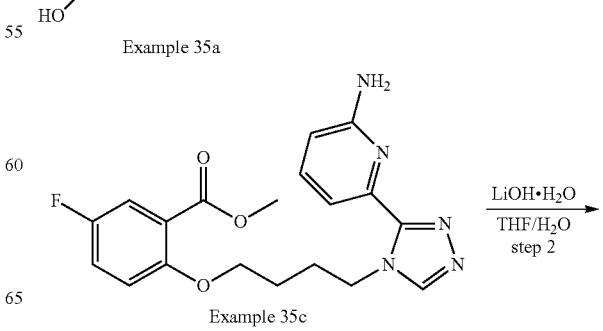

169

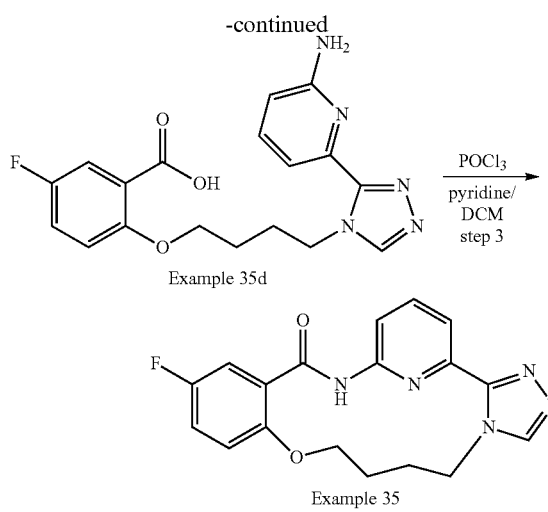

Example 35d

Example 35

Step 1: Example 35c

To a solution of Example 35a (1.1 g, 4.72 mmol), Example 35b (1.2 g, 7.08 mmol) and PPh₃ (2.47 g, 9.44 mmol) in DMF (22 mL) was added DIAD (1.43 g, 7.08 mmol) at 0° C. under N₂, which was stirred for 1 h. The reaction mixture was poured into water (30 mL) and extracted with EtOAc (20 mL*5). The combined organic layers were washed with brine (30 mL*2), dried over Na₂SO₄, filtered and concentrated under reduced pressure. The residue was purified by silica gel chromatography (Petroleum Ether/EtOAc=1/1, then DCM/MeOH=10/1) to afford the desired product Example 35c (1.58 g, yield 87%) as yellow oil.

LCMS [M+1]⁺=386.0.

Step 2: Example 35d

To a solution of Example 35c (1.48 g, 3.84 mmol) in THF (14 mL) was added a solution of LiO.H₂O (646 mg, 15.37 mmol) in H₂O (3 mL) at room temperature, which was stirred for 48 h. The reaction mixture was concentrated and extracted with EtOAc (20 mL*3). The aqueous layer was adjusted to pH 5 with 1N HCl and concentrated to afford the crude product Example 35d (2.4 g, yield 100%) as a white solid. LCMS [M+1]⁺=372.0.

Step 3: Example 35

To a solution of Example 35d (2 g, 5.39 mmol) in pyridine/DCM (1/1, 500 mL) was added POCl₃ (8.26 g, 53.9 mmol) at 0° C., which was stirred for 0.5 h. The mixture was quenched with water (10 mL) and concentrated under reduced pressure. H₂O (30 mL) was added and the mixture was stirred for another 0.5 h and then filtered. The cake was washed with H₂O (15 mL*2) and then purified by Prep-HPLC to afford the desired product Example 35 (32.9 mg, yield 2%) as a white solid. LCMS [M+1]⁺=354.0.

¹H NMR (400 MHz, DMSO-d₆) δ 11.31 (s, 1H), 8.67 (s, 1H), 8.07-8.03 (t, J=8.0 Hz, 1H), 7.86 (dd, J=12.0, 4.0 Hz, 2H), 7.71 (dd, J=12.0, 4.0 Hz, 1H), 7.47 (m, 1H), 7.34 (dd, J=16.0, 8.0 Hz, 1H), 4.33-4.22 (m, 4H), 2.42 (d, 2H), 1.95 (s, 2H).

170

Example 37: General Procedure for Synthesis of Compound Example 37

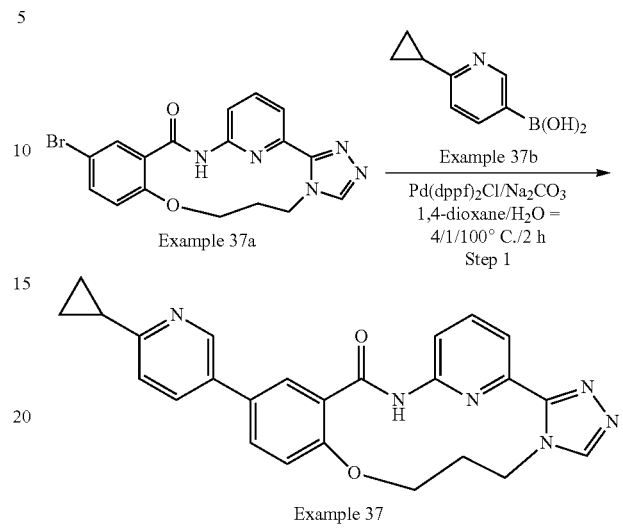

Step 1: Example 37

To a solution of Example 37a (60 mg, 0.15 mmol), Example 37b (30 mg, 0.18 mmol) in 1,4-dioxane/H₂O (2 mL/0.5 mL) were added Pd(dppf)Cl₂ (11 mg, 0.015 mmol) and Na₂CO₃ (32 mg, 0.30 mmol). The mixture was degassed by nitrogen for three times and heated at 100° C. for 2 h. The reaction mixture was filtered, washed with EtOAc and concentrated. The residue was purified by Prep-HPLC to give the desired product Example 37 (28 mg, yield 43%) as a yellow solid. LCMS [M+1]⁺=439.0 ¹H NMR (400 MHz, DMSO-d₆) δ 10.34 (s, 1H), 8.72 (s, 1H), 8.60 (s, 1H), 7.92 (t, J=7.7 Hz, 1H), 7.83 (t, J=7.3 Hz, 2H), 7.66-7.58 (m, 2H), 7.32 (dd, J=15.5, 8.0 Hz, 2H), 7.11 (d, J=8.6 Hz, 1H), 4.77 (m, 2H), 4.17-4.07 (m, 2H), 2.20 (m, 2H), 2.12-2.06 (m, 1H), 0.92 (dd, J=10.0, 6.4 Hz, 4H).

Example 38: General Procedure for Synthesis of Compound Example 38

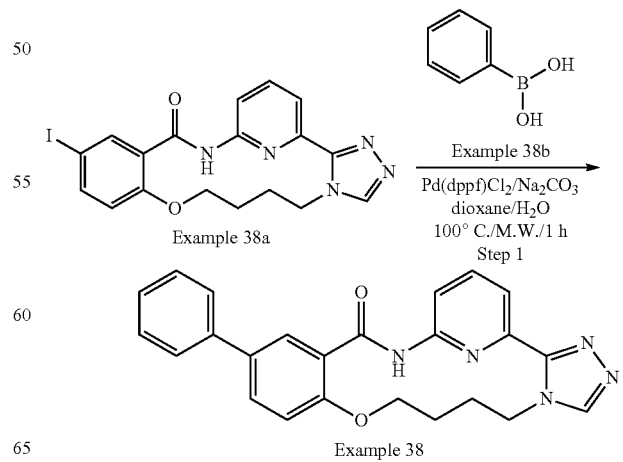

Step 1: Example 38

To a slurry of Example 38a (150 mg, 0.33 mmol), Example 38b (52 mg, 0.42 mg), and Na₂CO₃ (69 mg, 0.65 mmol) in dioxane/H₂O (3.0 mL/0.5 mL) was added Pd(dppf)Cl₂ (20 mg, 0.024 mmol). Then the mixture was degassed by bubbling N₂ through the solution for 2 min using a syringe needle. After that, the mixture was heated at 100° C. for 1 h by microwave. The mixture was directly purified by Prep-HPLC, followed by prep-TLC (DCM/MeOH=15/1) to give the desired product Example 38 (13.8 mg, yield 10%) as a white solid. LCMS [M+1]⁺=412.0. ¹H NMR (400 MHz, DMSO-d₆) δ 11.29 (s, 1H), 8.68 (s, 1H), 8.24 (d, J=2.6 Hz, 1H), 8.06 (t, J=7.9 Hz, 1H), 7.94-7.88 (m, 2H), 7.86 (d, J=7.6 Hz, 1H), 7.71-7.62 (m, 2H), 7.47 (t, J=7.6 Hz, 2H), 7.38 (dd, J=8.1, 4.3 Hz, 2H), 4.38 (d, J=5.4 Hz, 2H), 4.26 (t, J=8.6 Hz, 2H), 2.44 (m, 2H), 1.97 (m, 2H).

Example 39: General Procedure for Synthesis of Compound Example 39

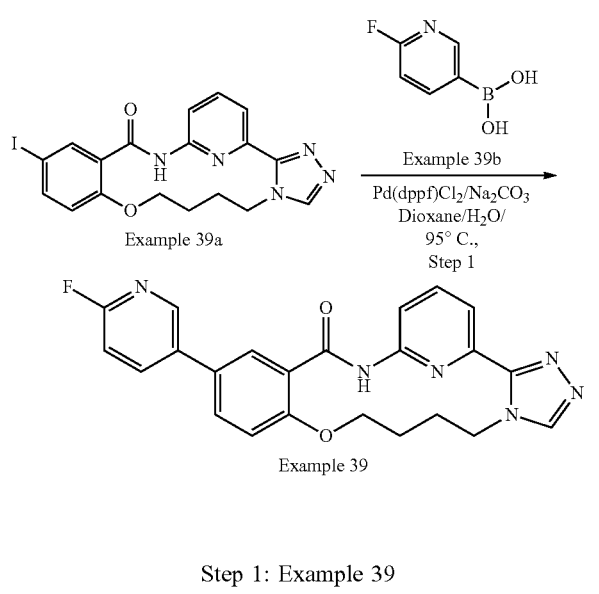

Step 1: Example 39

To a mixture of Example 39a (150 mg, 0.33 mmol), Example 39b (51 mg, 0.36 mmol), Na₂CO₃ (102 mg, 1.0 mmol) in dioxane (3 mL) and H₂O (1.5 mL) was added Pd(dppf)Cl₂ (24 mg, 0.03 mmol). Then the mixture was degassed by bubbling N₂ through the solution for 2 min using a syringe needle. After that, the mixture was heated at 95° C. for 16 h. The mixture was filtered and directly purified by silica gel chromatography (MeOH:DCM=1:20) followed by prep-TLC (MeOH:DCM=1:10) to give the desired product Example 39 (25 mg, yield 18%) as white solid. LCMS [M+1]⁺=431.0. ¹H NMR (400 MHz, DMSO-d₆) δ 11.22 (s, 1H), 8.68 (s, 1H), 8.56 (s, 1H), 8.31 (d, J=2.7 Hz, 1H), 8.24 (d, J=2.6 Hz, 1H), 8.07 (t, J=7.9 Hz, 1H), 7.95 (dd, J=8.7, 2.6 Hz, 1H), 7.88 (dd, J=14.5, 7.8 Hz, 2H), 7.42 (d, J=8.7 Hz, 1H), 7.28 (dd, J=8.5, 2.9 Hz, 1H), 4.38 (t, J=5.1 Hz, 2H), 4.33-4.21 (m, 2H), 3.15 (d, J=5.2 Hz, 2H), 1.97 (m, 2H).

Example 40: General Procedure for Synthesis of Compound Example 40

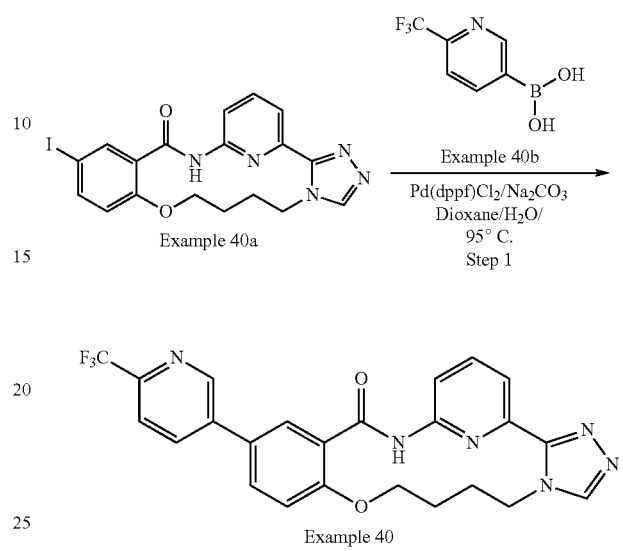

Step 1: Example 40

To a mixture of Example 40a (150 mg, 0.33 mmol), Example 40b (46 mg, 0.36 mmol), Na₂CO₃ (102 mg, 1.0 mmol) in dioxane (3 mL) and H₂O (1.5 mL) was added Pd(dppf)Cl₂ (24 mg, 0.03 mmol). Then the mixture was degassed by bubbling N₂ through the solution for 2 min using a syringe needle. After that, the mixture was heated at 95° C. for 16 h. The mixture was filtered and directly purified by silica gel chromatography (MeOH:DCM=1:20), followed by prep-TLC (MeOH:DCM=1:10) to give product Example 40 (16.9 mg, yield 11%) as white solid. LCMS [M+1]⁺=481.0. ¹H NMR (400 MHz, Chloroform-d) δ 11.43 (s, 1H), 8.98 (s, 1H), 8.58 (s, 1H), 8.24 (s, 1H), 8.14-8.00 (m, 3H), 7.95 (t, J=7.8 Hz, 1H), 7.79 (s, 2H), 7.20 (d, J=9.0 Hz, 1H), 4.41 (m, 2H), 4.36-4.26 (m, 2H), 2.74 (m, 2H), 2.13 (m, 2H).

Example 41: General Procedure for Synthesis of Compound Example 41

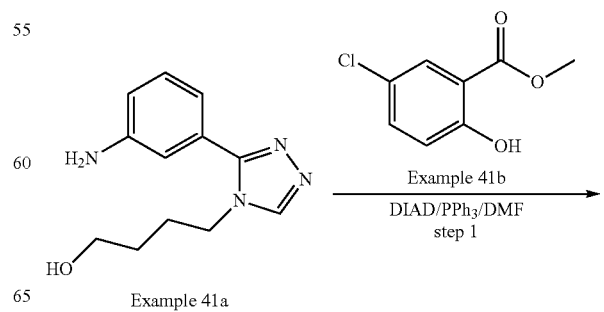

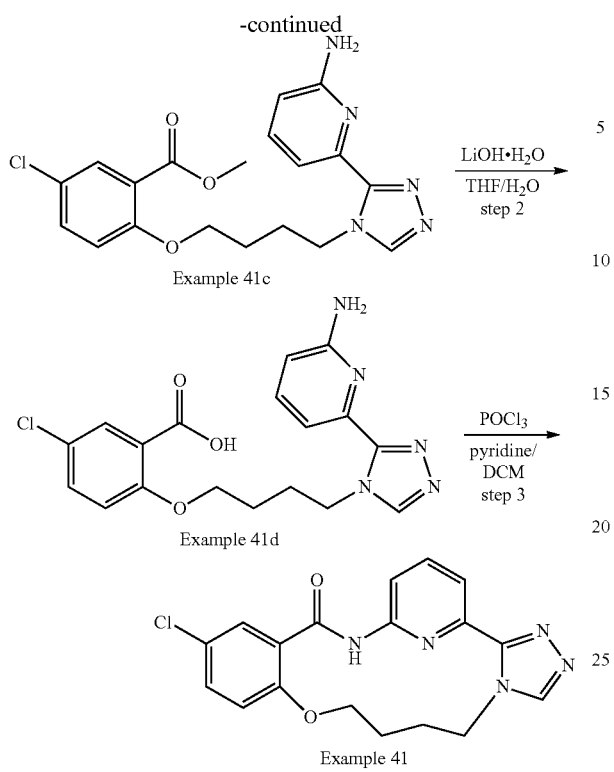

Example 41c

Example 41d

Example 41

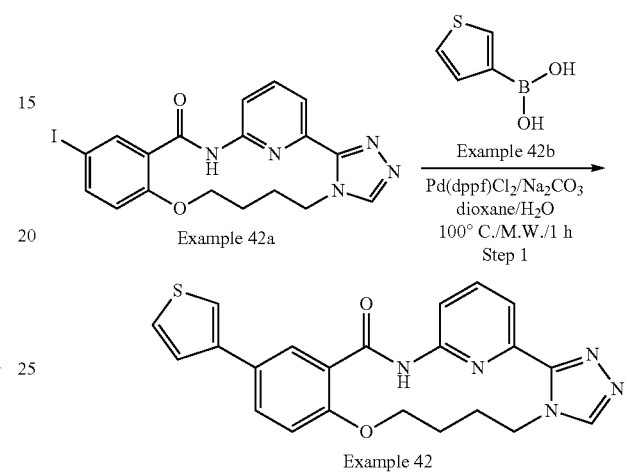

Example 42a

Example 42b

Example 42

Step 1: Example 41c

To a solution of Example 41a (1.0 g, 4.29 mmol), Example 41b (1.2 g, 6.43 mmol) and PPh₃ (2.25 g, 8.58 mmol) in DMF (20 mL) was added DIAD (1.3 g, 6.43 mmol) at 0° C. under N₂, which was stirred for 2 h. The reaction mixture was poured into water (30 mL) and extracted with EtOAc (20 mL*3). The combined organic layers were washed with brine (30 mL*2), dried over Na₂SO₄, filtered and concentrated under reduced pressure. The residue was purified by silica gel chromatography (Petroleum Ether/EtOAc=1/1, then DCM/MeOH=10/1) to afford the desired product Example 41c (1.1 g, yield 64%) as yellow oil.

LCMS [M+1]⁺=402.0.

Step 2: Example 41d

To a solution of Example 41c (1.1 g, 2.74 mmol) in THF (10 mL) was added a solution of LiO.H₂O (4.61 mg, 10.97 mmol) in H₂O (3 mL) at room temperature, which was stirred for 16 h. The reaction mixture was concentrated and extracted with EtOAc (20 mL*3). The aqueous layer was adjusted to pH 5 with 1N HCl (aq.) and$_{concentrated}$ to afford the desired product Example 41d (1.6 g, yield 100%) as a white solid including salt.

Step 3: Example 41

To a$_{solution}$ of Example 41d (800 mg, 2.06 mmol) in pyridine/DCM (1/1, 200 mL) was added POCl₃ (3.16 g, 20.6 mmol) at 0° C., which was stirred for 1 h. The mixture was quenched with water (10 mL) carefully and concentrated under reduced pressure. The residue was purified by Prep-HPLC to afford the desired product Example 41 (12.7 mg, yield 2%) as a yellow solid. LCMS [M+1]⁺=370.0, 372.0.

¹H NMR (400 MHz, DMSO-d₆) δ 11.18 (s, 1H), 8.67 (s, 1H), 8.08-8.04 (t, J=8.0 Hz, 1H), 7.87 (m, 3H), 7.64 (d, J=8.0 Hz, 1H), 7.33 (d, J=8.0 Hz, 1H), 4.32-4.22 (m, 4H), 2.43 (m, 2H), 1.94 (m, 2H).

Example 42: General Procedure for Synthesis of Compound Example 42

Step 1: Example 42

To a slurry of Example 42a (150 mg, 0.33 mmol), Example 42b (84 mg, 0.65 mmol), Na₂CO₃ (69 mg, 0.65 mmol) in dioxane/H₂O (3.0 mL/0.5 mL) was added Pd(dppf)Cl₂ (20 mg, 0.024 mmol). Then the mixture was degassed by bubbling N₂ through the solution for 2 min using a syringe needle. After that, the mixture was heated at 100° C. for 1 h by microwave. The mixture was directly purified by Prep-HPLC, followed by prep-TLC (DCM/MeOH=20/1) to give the desired product Example 42 (3.1 mg, yield 2%) as a white solid. LCMS [M+1]⁺=418.0. ¹H NMR (400 MHz, DMSO-d₆) δ 11.26 (s, 1H), 8.67 (s, 1H), 8.26 (d, J=2.5 Hz, 1H), 8.06 (t, J=7.9 Hz, 1H), 7.97-7.81 (m, 4H), 7.65 (dd, J=5.1, 2.9 Hz, 1H), 7.56 (dd, J=5.0, 1.4 Hz, 1H), 7.33 (d, J=8.7 Hz, 1H), 4.36 (t, J=5.0 Hz, 2H), 4.30-4.21 (m, 2H), 2.44 (m, 2H), 1.96 (m, 2H).

Example 43: General Procedure for Synthesis of Compound Example 43

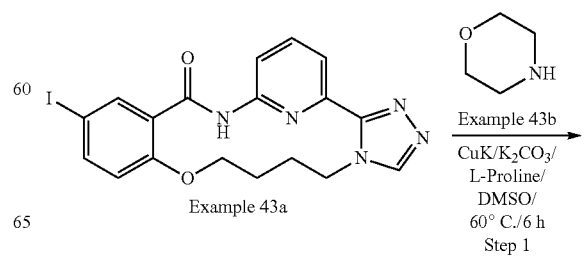

Example 43a

Example 43b

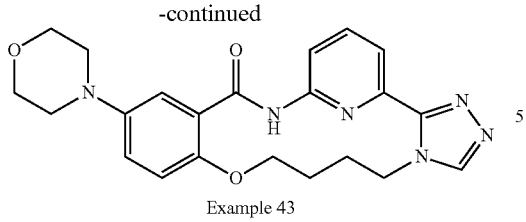

Example 43

Step 1: Example 43

To a mixture of Example 43a (30 mg, 0.065 mmol), Example 43b (47 mg, 0.195 mmol) and K₃CO₃ (36 mg, 0.260 mmol) in DMSO (3 mL) was added CuI (2.5 mg, 0.013 mmol) and L-Proline (3.0 mg, 0.026 mmol). Then the mixture was degassed by bubbling N₂ through the solution for 2 min using a syringe needle. After that, the mixture was heated at 60° C. for 6 h. The mixture was directly purified by Prep-HPLC to give the desired product Example 43 (2.8 mg, yield 10%) as an off-white solid. LCMS [M+1]⁺=421.1. ¹H NMR (400 MHz, DMSO-d₆) δ 11.45 (s, 1H), 8.67 (s, 1H), 8.05 (t, J=7.9 Hz, 1H), 7.89 (d, J=8.1 Hz, 1H), 7.84 (d, J=7.6 Hz, 1H), 7.53 (s, 1H), 7.22 (s, 2H), 4.30-4.22 (m, 4H), 3.77-3.72 (m, 4H), 3.09-3.05 (m, 4H), 2.43 (m, 2H), 1.98-1.91 (m, 2H).

Example 44: General Procedure for Synthesis of Compound Example 44

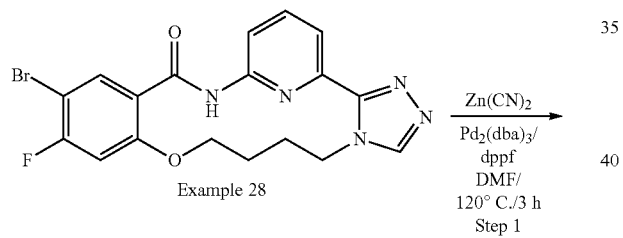

Step 1: Example 44

A mixture of Example 28 (110 mg, 0.25 mmol), Zn(CN)₂ (66 mg, 0.56 mmol), Pd₂(dba)₃ (25 mg, 0.03 mmol) and dppf (33 mg, 0.06 mmol) in DMF (3 mL) was stirred at 120° C. under N₂ for 3 h. The mixture was diluted with MeOH, filtered and the filtrate was concentrated. The residue was purified by Prep-HPLC, followed by prep-TLC (DCM/MeOH=10/1, twice) to afford the desired product Example 44 (7.2 mg, yield 8%) as a white solid. LCMS [M+1]⁺=379.0. ¹H NMR (400 MHz, DMSO-d₆) δ 10.76 (s, 1H), 8.67 (s, 1H) 8.33 (d, J=8.0 Hz, 1H), 8.06 (t, J=7.9 Hz, 1H), 7.86-7.82 (m, 2H), 7.54 (d, J=12.0, 1H), 4.38 (brs, 2H), 4.25-4.02 (m, 2H), 2.44-2.40 (m, 2H), 1.97-1.92 (m, 2H).

Example 45: General Procedure for Synthesis of Compound Example 45

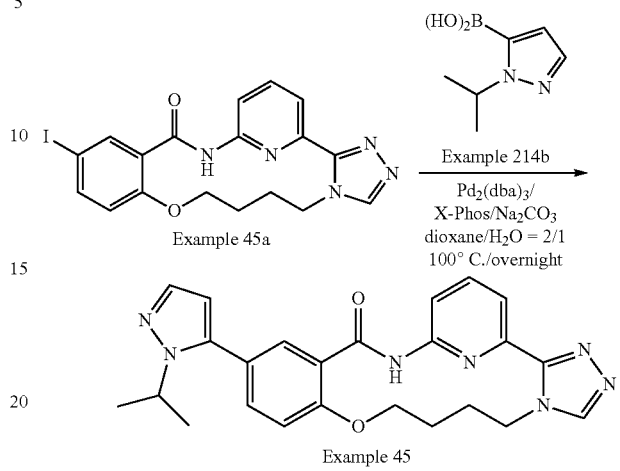

Step 1: Example 45

To a solution of Example 45a (335 mg, 0.70 mmol), Example 45b (163 mg, 1.05 mmol) in 1,4-dioxane/H₂O=2/1 (5.0 mL) were added Pd₂(dba)₃ (32 mg, 0.04 mmol), X-Phos (17 mg, 0.04 mmol) and Na₂CO₃ (150 mg, 1.40 mmol). The mixture was degassed by nitrogen for three times and heated at 100° C. overnight. The reaction mixture was concentrated under reduced pressure, and then purified by silica gel chromatography (DCM/MeOH=20/1) to provide the desired product Example 45 (5.0 mg, yield 2%) as a white solid. LCMS [M+1]⁺=444.1. ¹H NMR (400 MHz, DMSO-d₆) δ 11.24 (s, 1H), 8.68 (s, 1H), 8.06 (t, J=7.9 Hz, 1H), 7.96 (d, J=2.4 Hz, 1H), 7.88 (dd, J=10.4, 7.9 Hz, 2H), 7.68-7.61 (m, 1H), 7.53 (d, J=1.8 Hz, 1H), 7.42 (d, J=8.6 Hz, 1H), 6.32 (d, J=1.8 Hz, 1H), 4.53-4.43 (m, 1H), 4.39 (m, 2H), 4.27 (t, J=8.6 Hz, 2H), 2.44 (m, 2H), 1.98 (d, J=8.5 Hz, 2H), 1.37 (d, J=6.5 Hz, 6H).

Example 46: General Procedure for Synthesis of Compound Example 46

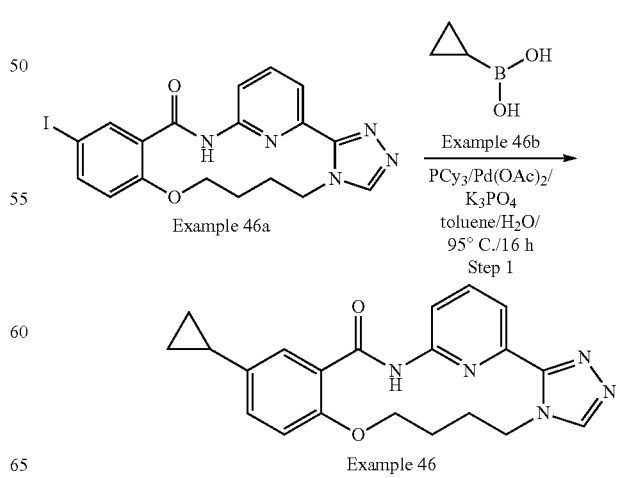

To a mixture of Example 46a (200 mg, 0.43 mmol), Example 46b (93 mg, 1.10 mmol), and K$_3$PO$_4$ (322 mg, 1.5 mmol) in toluene/H$_2$O (6 mL/2 mL) were added PCy$_3$ (12 mg, 0.04 mmol) and Pd(OAc)$_2$ (10 mg, 0.04 mmol). Then the mixture was degassed by bubbling N$_2$ through the solution for 2 min using a syringe needle. After that, the mixture was heated at 95° C. for 16 h. The mixture was concentrated and purified by silica gel chromatography (DCM/MeOH=20/1), followed by prep-TLC (DCM/MeOH=15/1) to give the desired product Example 46 (20 mg, yield 12%) as a white solid. LCMS [M+1]$^+$=376.0. $^1$H NMR (400 MHz, Chloroform-d) δ 11.49 (s, 1H), 8.22 (s, 1H), 8.05 (d, J=8.1 Hz, 1H), 8.01 (d, J=7.6 Hz, 1H), 7.98 (d, J=2.5 Hz, 1H), 7.91 (t, J=7.9 Hz, 1H), 7.24 (d, J=2.8 Hz, 1H), 6.94 (d, J=8.5 Hz, 1H), 4.31-4.25 (m, 5H), 2.69 (m, 2H), 2.11-1.90 (m, 3H), 0.98 (dd, J=8.4, 1.9 Hz, 2H), 0.72 (dd, J=4.9, 1.8 Hz, 2H).

Example 47: General Procedure for Synthesis of Compound Example 47

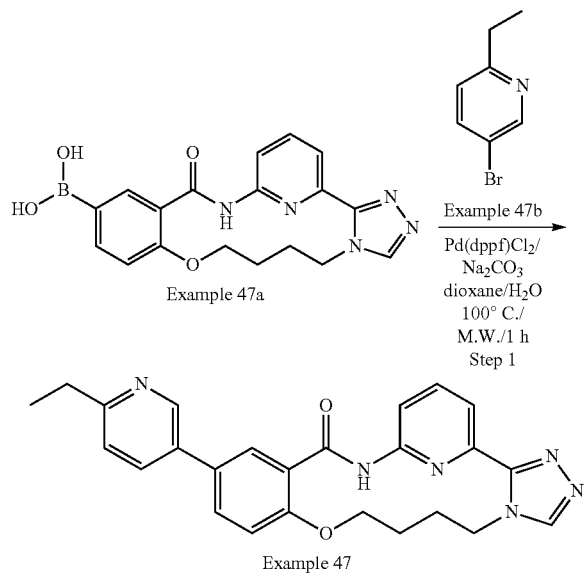

To a slurry of Example 47a (200 mg, crude), Example 47b (80 mg, 0.43 mmol), Na$_2$CO$_3$ (92 mg, 0.87 mmol) in dioxane/H$_2$O (3.0 mL/0.5 mL) was added Pd(dppf)Cl$_2$ (32 mg, 0.043 mmol). Then the mixture was degassed by bubbling N$_2$ through the solution for 2 min using a syringe needle. After that, the mixture was heated at 100° C. for 1 h by microwave. The mixture was directly purified by Prep-HPLC, followed by prep-TLC (DCM/MeOH=20/1) to give the desired product Example 47 (2.0 mg, yield 1% over two steps) as a white solid. LCMS [M+1]$^+$=441.0. $^1$H NMR (400 MHz, DMSO-d$_6$) δ 11.25 (s, 1H), 8.78 (s, 1H), 8.68 (s, 1H), 8.23 (d, J=2.6 Hz, 1H), 8.05 (d, J=7.9 Hz, 1H), 8.02-7.97 (m, 1H), 7.90 (td, J=16.8, 16.2, 8.2 Hz, 3H), 7.38 (dd, J=20.7, 8.4 Hz, 2H), 4.38 (m, 2H), 4.33-4.20 (m, 2H), 2.78 (d, J=7.6 Hz, 2H), 1.97 (m, 3H), 1.26 (d, J=7.6 Hz, 4H).

Example 48: General Procedure for Synthesis of Compound Example 48

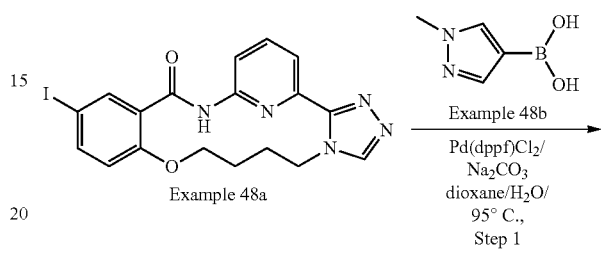

To a mixture of Example 48a (200 mg, 0.43 mmol), Example 48b (60 mg, 0.48 mmol), Na$_2$CO$_3$ (138 mg, 1.30 mmol) in dioxane (4 mL) and H$_2$O (2 mL) was added Pd(dppf)Cl$_2$ (32 mg, 0.04 mmol). Then the mixture was degassed by bubbling N$_2$ through the solution for 2 min using a syringe needle. After that, the mixture was heated at 95° C. for 16 h. The mixture was filtered and directly purified by silica gel chromatography (DCM/MeOH=20/1) and pre-TLC (DCM/MeOH=15/1) to give the desired product Example 48 (20 mg, yield 11%) as a white solid. LCMS [M+1]$^+$=416.0. $^1$H NMR (400 MHz, Chloroform-d) δ 11.49 (s, 1H), 8.37 (d, J=2.4 Hz, 1H), 8.22 (s, 1H), 8.07 (d, J=8.1 Hz, 1H), 8.03 (d, J=7.5 Hz, 1H), 7.93 (t, J=7.9 Hz, 1H), 7.78 (s, 1H), 7.67 (s, 1H), 7.61 (dd, J=8.5, 2.4 Hz, 1H), 7.04 (d, J=8.5 Hz, 1H), 4.35-4.26 (m, 4H), 3.96 (s, 3H), 2.71 (m, 2H), 2.09 (m, 2H).

Example 50: General Procedure for Synthesis of Compound Example 50

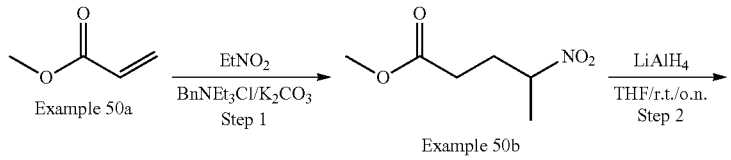

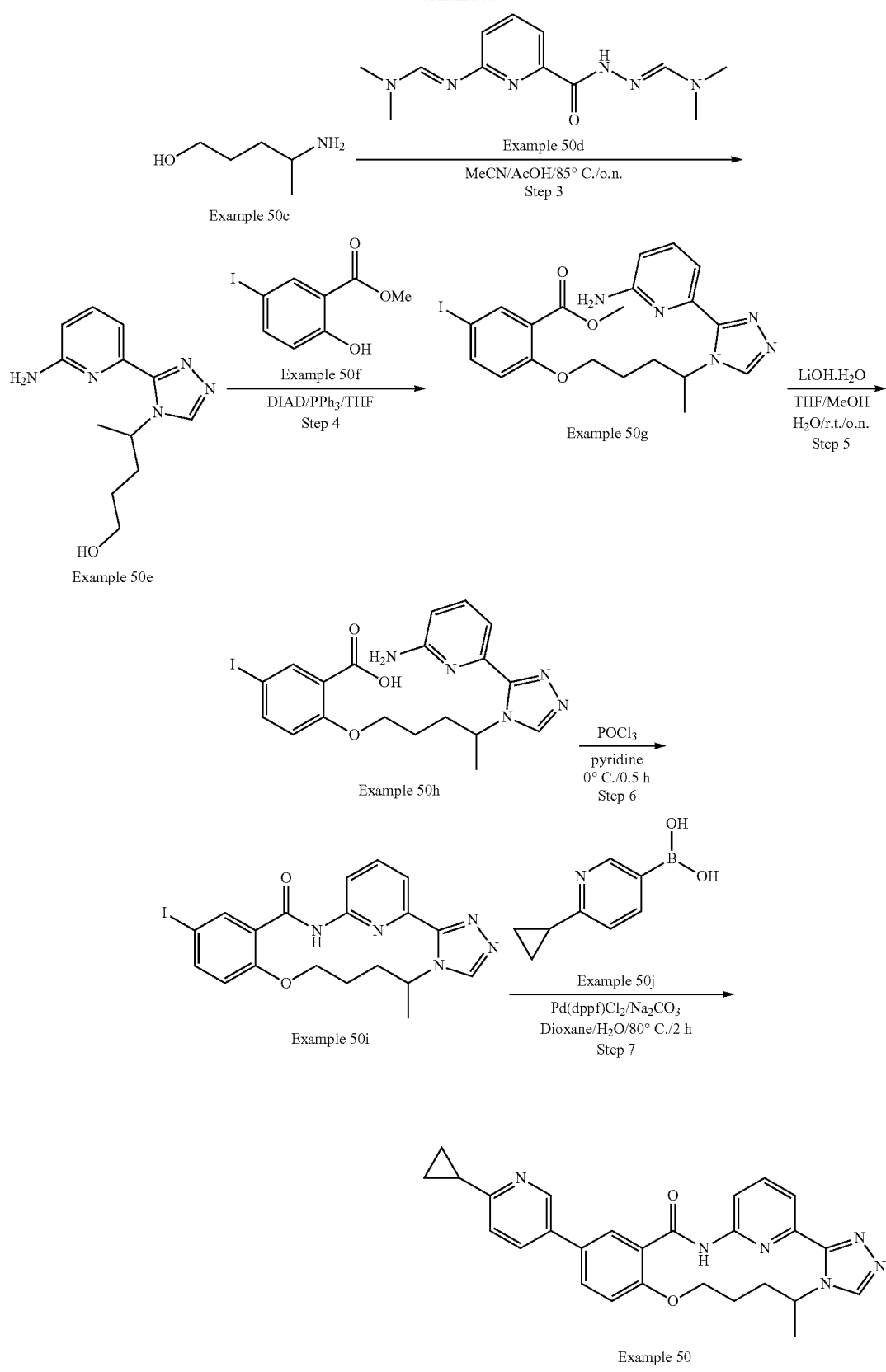

Step 1: Example 50a

To a solution of Benzyltriethyl ammonium chloride (cas: 56-37-1, 13.2 g, 58 mmol) in EtNO$_2$ (61 g, 813 mmol) was added K$_2$CO$_3$ (9.6 g, 70 mmol) at room temperature, which was stirred for 5 min. Example 50a (10.0 g, 116 mmol) was added and then the reaction mixture was stirred at room temperature for 16 h. The mixture was diluted with EtOAc and filtered. The cake was washed with EtOAc and the filtrate was concentrated under reduced pressure and purified by silica gel chromatography (Petroleum Ether/EtOAc=10/1-5/1) to afford the desired product Example 50b (11.0 g, yield 59%) as yellow oil.

Step 2: Example 50c

To a solution of Example 50b (9 g, 55.9 mmol) in THF (160 mL) cooled to 0-5° C. was slowly added LiAlH$_4$ (7.4 g, 195.6 mmol). The mixture was stirred at r.t. overnight under N$_2$. The reaction mixture was cooled to −10° C. and quenched with H$_2$O (7 mL), followed by aq. 15% NaOH (7 ml) and H$_2$O (21 ml). The resulting mixture was stirred for 1 h and filtrated. The filtrate was concentrated to give the desired product Example 50c (3.3 g, yield 58%) as yellow oil. LCMS [M+1]$^+$=104.1

Step 3: Example 50e

To a solution of Example 50c (900 mg, 8.74 mmol) in MeCN/HOAc (8 mL/2 mL) was added Example 50d (458 mg, 1.75 mmol). The mixture was stirred at 85° C. overnight under N$_2$. The solvent was evaporated. The residue was alkalized by aq. 10% NaOH to pH=10~11 and concentrated. The residue was suspended in DCM/MeOH (100 mL/10 mL) and stirred at r.t. for 0.5 h. The suspension was filtrated, and the filtrate was concentrated, purified by silica gel chromatography (DCM/MeOH=10/1) to give the desired product Example 50e (180 mg, yield 42%) as yellow oil. LCMS [M+1]$^+$=248.1

Step 4: Example 50g

To a solution of Example 50f (202 mg, 0.73 mmol) in THF (4 mL) were added Example 50e (180 mg, 0.73 mmol) and PPh$_3$ (382 mg, 1.46 mmol). Then the mixture was cooled to 0° C. and added DIAD (368 mg, 1.82 mmol) slowly under N$_2$. The resulting mixture was stirred at this temperature for 10 min and warmed to r.t. for 0.5 h. The mixture was extracted with EtOAc (20 mL*2). The combined organic phase was washed with brine, dried over Na$_2$SO$_4$, filtrated and the filtrate was concentrated under reduced pressure. The residue was purified by silica gel chromatography (DCM/MeOH=20/1) to give the desired product Example 50g (260 mg, yield 70%) as yellow oil. LCMS [M+1]$^+$=507.9

Step 5: Example 50h

To a solution of Example 50g (260 mg, 0.51 mmol) in THF/MeOH/H$_2$O (2 mL/2 mL/1 mL) was added LiO.H$_2$O (65 mg, 1.54 mmol). The mixture was stirred at r.t. overnight. The reaction mixture was acidified by 1M HCl to pH=3~4. The solvent was evaporated to give the desired product Example 50h (280 mg, crude yield 100%) as a white solid, which was used in next step without purification. LCMS [M+1]$^+$=493.9

Step 6: Example 50i

To a solution of Example 50h (280 mg, crude, 0.51 mmol) in pyridine (5 mL) was added POCl$_3$ (390 mg, 2.55 mmol) at 0° C. The mixture was stirred at 0° C. for 30 min under N$_2$. The mixture was extracted with EtOAc (20 mL*2). The combined organic phase was washed with brine, dried over Na$_2$SO$_4$, filtrated and the filtrate was concentrated under reduced pressure to give the desired product Example 50i (130 mg, yield 54%) as a yellow solid. LCMS [M+1]$^+$=475.9.

Step 7: Example 50

To a solution of Example 50i (65 mg, 0.14 mmol) in Dioxane/H$_2$O (2 mL/0.4 mL) were added Example 50j (45 mg, 0.27 mmol), Na$_2$CO$_3$ (44 mg, 0.41 mmol) and Pd(dppf)Cl$_2$ (10 mg, 0.014 mol). The mixture was stirred at 80° C. for 2 h under N$_2$. The mixture was filtrated and the filtrate was concentrated under reduced pressure. The residue was purified by Prep-HPLC to give Example 50 (17 mg, yield 26%) as a white solid. LCMS [M/2+1]$^+$=234.1. $^1$H NMR (400 MHz, DMSO-d$_6$) δ 11.28 (s, 1H), 8.86 (s, 1H), 8.69 (d, J=2.5 Hz, 1H), 8.18 (d, J=2.5 Hz, 1H), 8.06 (t, J=7.9 Hz, 1H), 7.94-7.84 (m, 3H), 7.80 (d, J=7.6 Hz, 1H), 7.35 (dd, J=12.6, 8.5 Hz, 2H), 4.63-4.54 (m, 1H), 4.49 (d, J=9.3 Hz, 1H), 4.19 (t, J=9.8 Hz, 1H), 3.19-3.11 (m, 1H), 2.18-2.09 (m, 2H), 1.85-1.72 (m, 2H), 1.53 (d, J=6.9 Hz, 3H), 0.99-0.93 (m, 4H).

Example 51: General Procedure for Synthesis of Compound Example 51

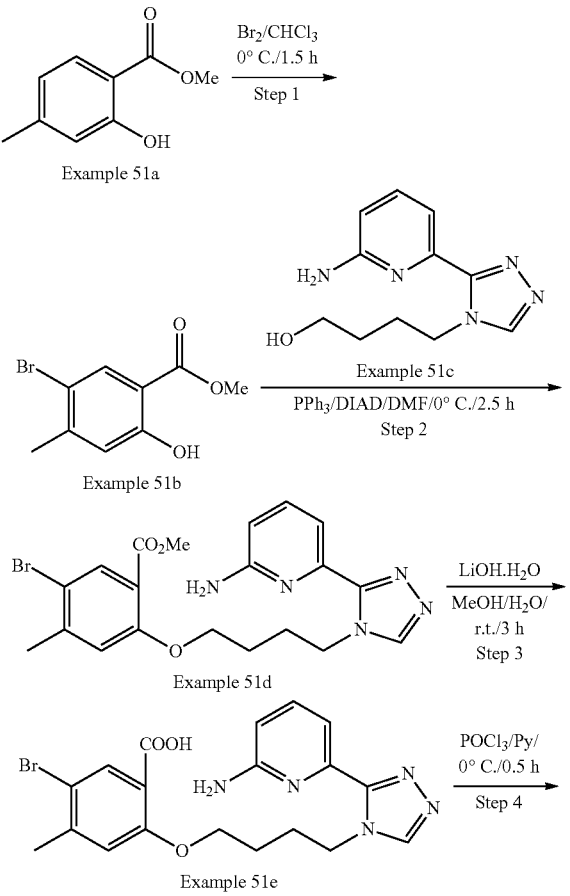

-continued

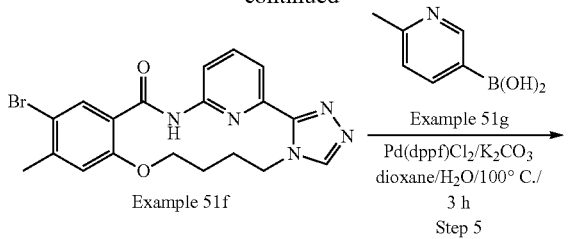

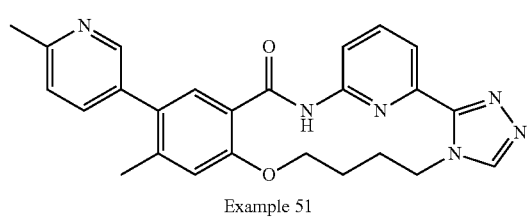

Example 51

Step 1: Example 51b

To a solution of Example 51a (500 mg, 3 mmol) in CHCl$_3$ (15 mL) was added Br$_2$ (480 mg, 3 mmol) at 0° C. After stirred for 1.5 h at 0° C., the reaction was quenched by saturated Na$_2$SO$_3$ (20 mL). After extraction with DCM (20 mL), the organic layer was dried over Na$_2$SO$_4$, and concentrated under reduced pressure. The residue was purified by silica gel chromatography (pure petroleum ether) to give the desired product Example 51b (360 mg, yield 49%) as colorless oil, which turned into a white solid after staying at room temperature. LCMS [M+1]$^+$=244.9/246.9

Step 2: Example 51d

A mixture of Example 51b (360 mg, 1.5 mmol), Example 51c (350 mg, 1.5 mmol), and PPh$_3$ (590 mg, 2.25 mmol) in dry DMF (6 mL) was stirred at 0° C. under N$_2$ atmosphere. To the mixture was injected DIAD (606 mg, 3 mmol), which was stirred for a further 2.5 h. Then, water (50 mL) was added to the reaction mixture. After extraction with EtOAc (20 mL), the organic layer was dried over Na$_2$SO$_4$, and concentrated under reduced pressure. The residue was purified by silica gel chromatography (DCM/MeOH=7/3) to give the desired product Example 51d (656 mg, yield 97%) as yellow oil, which turned into a yellow solid after staying at room temperature overnight. LCMS [M+1]$^+$=459.9/461.9

Step 3: Example 51e

To a solution of Example 51d (656 mg, 1.4 mmol) in MeOH/H$_2$O (4 mL/2 mL) was added LiO.H$_2$O (180 mg, 4.3 mmol) with stirring at r.t. After 3 h reaction, the pH of the reaction solution was adjusted to nearly 5 by HCl (aq.). The mixture was then concentrated under reduce pressure to give the crude desired product Example 51e (700 mg, yield 100%) as a yellow solid. LCMS [M+1]$^+$=445.9/447.9

Step 4: Example 51f

To a solution of Example 51e (700 mg, crude, 1.4 mmol) in pyridine (6 mL) was added POCl$_3$ (940 mg, 6.2 mmol) with stirring at 0° C. After 0.5 h reaction, water (10 mL) was added to quench the reaction, and the mixture was filtrated. The filtrate was washed by water for several times to give the crude desired product Example 51f (100 mg, 50% purity, yield 8%) as a yellow solid. LCMS [M+1]$^+$=427.9/429.9

Step 5: Example 51

A mixture of Example 51f (100 mg, 0.23 mmol), Example 51g (35 mg, 0.26 mmol), K$_2$CO$_3$ (65 mg, 0.46 mmol), and Pd(dppf)Cl$_2$ (17 mg, 0.02 mmol) in dioxane/H$_2$O (2 mL/1 mL) was stirred at 100° C. for 3 h. Then the solution was filtered and purified by Prep-HPLC, followed by Prep-TLC to give the desired product Example 51 (14 mg, yield 28%) as a white solid. LCMS [M+1]$^+$=441.0 $^1$H NMR (400 MHz, DMSO-d$_6$) δ 11.32 (s, 1H), 8.68 (s, 1H), 8.43 (s, 1H), 8.05 (t, J=7.9 Hz, 1H), 7.87 (dd, J=13.5, 7.8 Hz, 2H), 7.81 (s, 1H), 7.73-7.68 (m, 1H), 7.34 (d, J=7.9 Hz, 1H), 7.30 (s, 1H), 4.39 (m, 2H), 4.27 (t, J=8.5 Hz, 2H), 2.52 (s, 3H), 2.31 (s, 3H), 1.35-1.14 (m, 4H).

Example 52: General Procedure for Synthesis of Compound Example 52

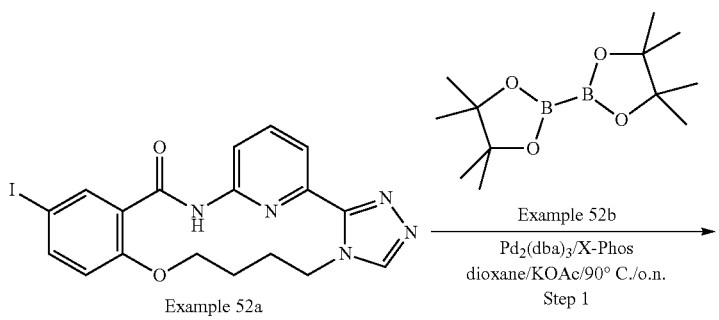

185

-continued

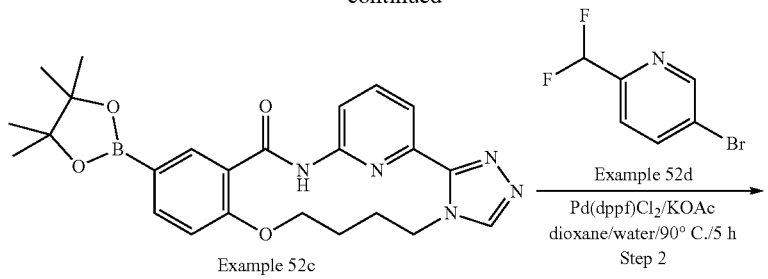

Example 52c

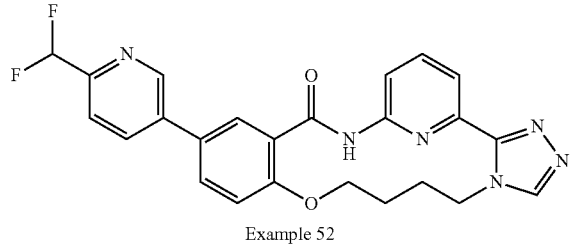

Example 52

Step 1: Example 52c

To a mixture of Example 52a (461 mg, 1.00 mmol) in dioxane (5 mL) were added Example 52b (305 mg, 1.29 mmol), Pd$_2$(dba)$_3$ (73 mg, 0.10 mmol), X-phos (45 mg, 0.10 mmol) and KOAc (294 mg, 3.00 mmol). The mixture was stirred at 100° C. for overnight under N$_2$ protection. The crude mixture was used in the next step directly without workup.

Step 2: Example 52

To the above mixture was added Example 52d (206 mg, 1.00 mmol), Pd(dppf)Cl$_2$ (36 mg, 0.05 mmol) and H$_2$O (0.5 mL). The mixture was stirred at 100° C. for 45 min under microwave. The mixture was poured into water (50 mL) and extracted with EtOAc (20 mL*3). The combined organic phase was washed with brine, dried over Na$_2$SO$_4$, filtrated and the filtrate was concentrated under reduced pressure. The residue was purified by prep-TLC to afford the desired product Example 52 (22 mg, yield 5%, over two steps) as a white solid. LCMS [M+1]$^+$=463.0. $^1$H NMR (400 MHz, DMSO-d$_6$) δ 11.21 (s, 1H), 9.03 (d, J=2.2 Hz, 1H), 8.68 (s, 1H), 8.31 (dd, J=6.8, 2.4 Hz, 2H), 8.10-8.02 (m, 2H), 7.89 (dd, J=14.9, 7.9 Hz, 2H), 7.78 (d, J=8.2 Hz, 1H), 7.45 (d, J=8.7 Hz, 1H), 7.01 (t, J=54 Hz, 1H), 4.40 (t, J=4.9 Hz, 2H), 4.33-4.21 (m, 2H), 2.49 (m, 2H), 1.98 (m, 2H).

Example 53: General Procedure for Synthesis of Compound Example 53

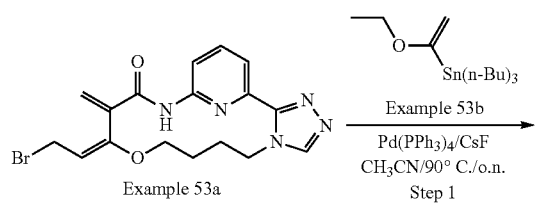

Example 53a

186

-continued

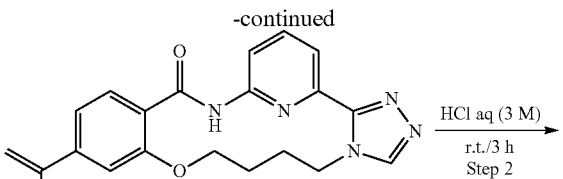

Example 53c

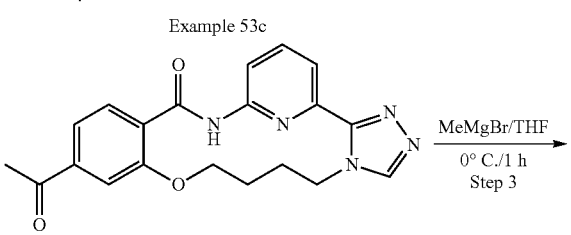

Example 53d

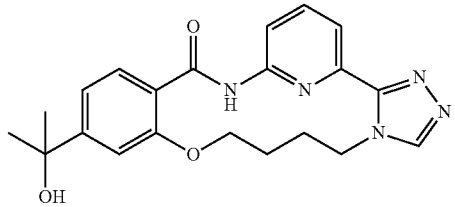

Example 53

Step 1: Example 53c

A mixture of Example 53a (100 mg, 0.23 mmol), Example 53b (106 mg, 1.2 mmol), Pd(PPh$_3$)$_4$ (27 mg, 0.024 mmol) and CsF (56 mg, 0.36 mmol) in CH$_3$CN (10 mL) was stirred at 90° C. under N$_2$ atmosphere overnight. The mixture was diluted with H$_2$O (20 mL) and then extracted with EtOAc (40 mL). The organic layer was dried over Na$_2$SO$_4$, filtered and concentrated under reduced pressure. The residue was purified by silica gel chromatography (DCM/MeOH=10/1) to give the desired product Example 53c (80 mg, yield 85%)

as yellow oil, which turned into a yellow solid after staying overnight. LCMS [M+1]$^+$=406.0

Step 2: Example 53d

A solution of Example 53c (80 mg, 0.19 mmol) in HCl (aq. 10 mL, 3 mol/L) was stirred at r.t. After 3 h, the pH of the reaction mixture was adjusted to nearly 8 with NaHCO$_3$ (aq.), and then extracted with EtOAc (40 mL). The organic layer was dried over Na$_2$SO$_4$, filtered and concentrated under reduced pressure to give the crude product Example 53d (80 mg, crude yield 113%) as a white solid, which was used in the next step without further purification. LCMS [M+1]$^+$=378.0.

Step 3: Example 53

To a solution of Example 53d (80 mg, 0.21 mmol) in THF (3 mL) was added MeMgBr (0.5 mL, 3 mol/L in THF) with stirring at 0° C. After 1 h, water (2 mL) was added to quench the reaction, and the mixture was purified by Prep-HPLC to give the desired product Example 53 (12.0 mg, yield 15%) as a white solid. LCMS [M+1]$^+$=394.0. $^1$H NMR (400 MHz, DMSO-d$_6$) δ 11.33 (s, 1H), 8.67 (s, 1H), 8.04 (t, J=7.9 Hz, 1H), 7.94 (d, J=8.2 Hz, 1H), 7.89 (d, J=8.1 Hz, 1H), 7.84 (d, J=7.6 Hz, 1H), 7.35 (d, J=1.6 Hz, 1H), 7.24 (dd, J=8.2, 1.5 Hz, 1H), 5.21 (s, 1H), 4.35 (t, J=5.0 Hz, 2H), 4.30-4.22 (m, 2H), 2.50-2.48 (m, 2H), 1.97 (s, 2H), 1.44 (s, 6H).

Example 54: General Procedure for Synthesis of Compound Example 54

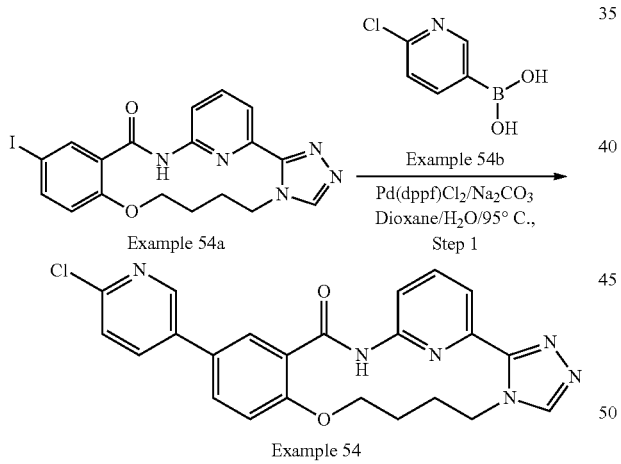

To a mixture of Example 54a (200 mg, 0.43 mmol), Example 54b (75 mg, 0.48 mmol), Na$_2$CO$_3$ (138 mg, 1.3 mmol) in dioxane (4 mL) and H$_2$O (2 mL) was added Pd(dppf)Cl$_2$ (32 mg, 0.04 mmol). Then the mixture was degassed by bubbling N$_2$ through the solution for 2 min using a syringe needle. After that, the mixture was heated at 95° C. for 16 h. The mixture was filtered and directly purified by silica gel chromatography (MeOH:DCM=1:20), followed by prep-TLC (MeOH:DCM=1:10) to give the desired product Example 54 (28.9 mg, yield 15%) as white solid. LCMS [M+1]$^+$=447.0. $^1$H NMR (400 MHz, DMSO-d$_6$) δ 11.21 (s, 1H), 8.76 (d, J=2.6 Hz, 1H), 8.68 (s, 1H), 8.27 (d, J=2.6 Hz, 1H), 8.20 (dd, J=8.3, 2.7 Hz, 1H), 8.07 (t, J=7.9 Hz, 1H), 7.99 (dd, J=8.6, 2.6 Hz, 1H), 7.88 (dd, J=13.7, 7.8 Hz, 2H), 7.60 (d, J=8.3 Hz, 1H), 7.43 (d, J=8.7 Hz, 1H), 4.40 (d, J=5.3 Hz, 2H), 4.27 (t, J=8.5 Hz, 2H), 2.54 (m, 2H), 1.98 (m, 2H).

Example 55: General Procedure for Synthesis of Compound Example 55

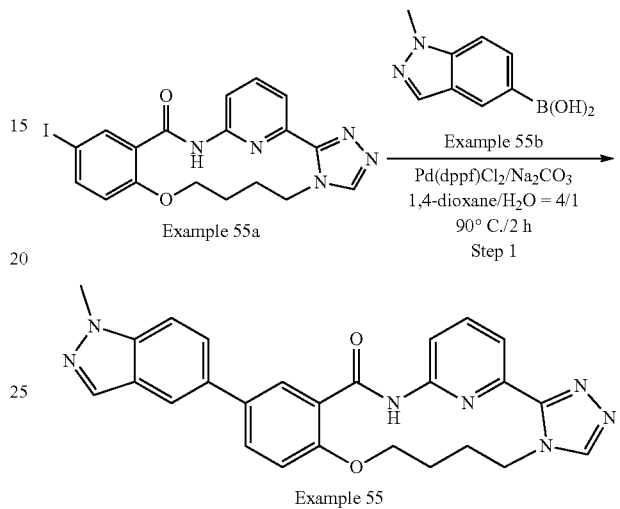

To a solution of Example 55a (100 mg, 0.22 mmol), Example 55b (46 mg, 0.26 mmol) in 1,4-dioxane/H$_2$O (2 mL/0.5 mL) were added Pd(dppf)Cl$_2$ (16 mg, 0.022 mmol) and Na$_2$CO$_3$ (46 mg, 0.43 mmol). The mixture was degassed by nitrogen for three times and heated at 90° C. for 2 h. The reaction mixture was filtered, washed with EtOAc and concentrated. The residue was purified by prep-TLC to afford the crude product which was triturated in MeOH, filtered and dried to give the desired product Example 55 (8 mg, yield 8%) as a white solid. LCMS [M+1]$^+$=466.0. $^1$H NMR (400 MHz, DMSO-d$_6$) δ 11.33 (s, 1H), 8.68 (s, 1H), 8.29 (d, J=2.5 Hz, 1H), 8.10 (s, 1H), 8.08-8.02 (m, 2H), 7.96-7.90 (m, 2H), 7.87 (d, J=7.6 Hz, 1H), 7.73 (s, 2H), 7.39 (d, J=8.7 Hz, 1H), 4.38 (m, 2H), 4.30-4.24 (m, 2H), 4.07 (s, 3H), 2.50 (m, 2H), 1.99 (m, 2H).

Example 56: General Procedure for Synthesis of Compound Example 56

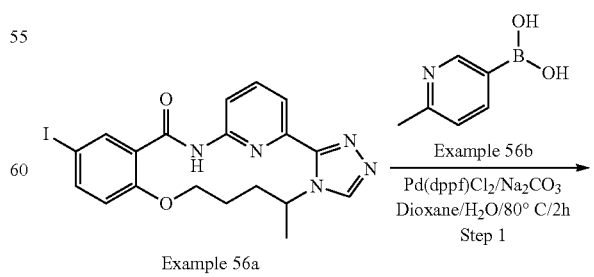

-continued

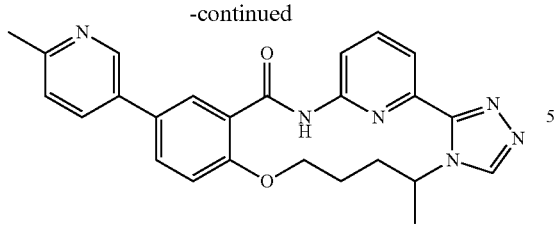

Example 56

To a solution of Example 56a (65 mg, 0.14 mmol) in Dioxane/H₂O (2 mL/0.4 mL) were added Example 56b (37 mg, 0.27 mmol), Na₂CO₃ (44 mg, 0.41 mmol) and Pd(dppf)Cl₂ (10 mg, 0.014 mol). The mixture was stirred at 80° C. for 2 h under N₂. The mixture was filtrated and the filtrate was concentrated under reduced pressure. The residue was purified by Prep-HPLC to give the desired product Example 56 (15 mg, yield 25%) as a white solid. LCMS [M+1]⁺=441.0. ¹H NMR (400 MHz, DMSO-d₆) δ 11.28 (s, 1H), 8.86 (s, 1H), 8.75 (d, J=2.5 Hz, 1H), 8.21 (d, J=2.5 Hz, 1H), 8.07 (t, J=7.9 Hz, 1H), 7.97 (dd, J=8.0, 2.5 Hz, 1H), 7.92 (dd, J=8.6, 2.5 Hz, 1H), 7.87 (d, J=8.1 Hz, 1H), 7.80 (d, J=7.6 Hz, 1H), 7.34 (dd, J=8.4, 6.5 Hz, 2H), 4.64-4.56 (m, 1H), 4.50 (d, J=9.4 Hz, 1H), 4.20 (t, J=9.8 Hz, 1H), 3.16 (t, J=10.3 Hz, 1H), 2.50 (s, 3H), 2.18-2.08 (m, 1H), 1.85-1.73 (m, 2H), 1.53 (d, J=6.8 Hz, 3H).

Example 57: General Procedure for Synthesis of Compound Example 57

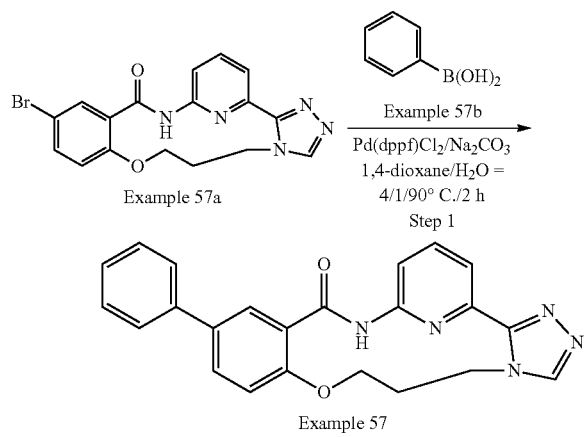

To a solution of Example 57a (100 mg, 0.25 mmol), Example 57b (37 mg, 0.30 mmol) in 1,4-dioxane/H₂O (2 mL/0.5 mL) were added Pd(dppf)Cl₂ (18 mg, 0.025 mmol) and Na₂CO₃ (53 mg, 0.50 mmol). The mixture was degassed by nitrogen for three times and heated at 90° C. for 2 h. The reaction mixture was filtered, washed with EtOAc and concentrated. The residue was purified by prep-TLC to give the crude product, which was stirred in EtOAc/MeOH (6 mL, v/v=5/1) for 15 min, filtered and dried to give the desired product Example 57 (62 mg, yield 62%) as a white solid. LCMS [M+1]⁺=398.0. ¹H NMR (400 MHz, DMSO-d₆) δ 10.34 (s, 1H), 8.72 (s, 1H), 7.92 (t, J=7.8 Hz, 1H), 7.82 (d, J=7.7 Hz, 1H), 7.62 (dd, J=8.6, 2.4 Hz, 1H), 7.58 (d, J=2.8 Hz, 2H), 7.56 (s, 1H), 7.40 (t, J=7.6 Hz, 2H), 7.35 (d, J=7.9 Hz, 1H), 7.29 (t, J=7.3 Hz, 1H), 7.11 (d, J=8.6 Hz, 1H), 4.77 (br, 2H), 4.16-4.09 (m, 2H), 2.21 (d, J=7.9 Hz, 2H).

Example 58: General Procedure for Synthesis of Compound Example 58

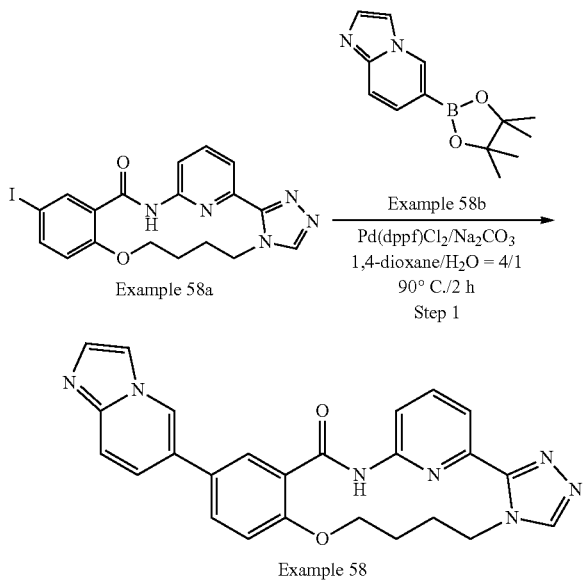

To a solution of Example 58a (113 mg, 0.27 mmol), Example 58b (80 mg, 0.33 mmol) in 1,4-dioxane/H₂O (2 mL/0.5 mL) were added Pd(dppf)Cl₂ (20 mg, 0.027 mmol) and Na₂CO₃ (58 mg, 0.55 mmol). The mixture was degassed by nitrogen for three times and heated at 90° C. for 2 h. The reaction mixture was filtered, washed with EtOAc and concentrated. The residue was purified by prep-TLC to afford the crude product which was triturated in MeOH, filtered and dried to give the desired product Example 58 (2 mg, yield 2%) as a white solid. LCMS [M+1]⁺=452.0. ¹H NMR (400 MHz, DMSO-d₆) δ 11.28 (s, 1H), 8.99 (s, 1H), 8.68 (s, 1H), 8.28 (d, J=2.6 Hz, 1H), 8.07 (d, J=7.9 Hz, 1H), 7.97 (s, 1H), 7.96 (s, 1H), 7.93 (s, 1H), 7.87 (d, J=7.6 Hz, 1H), 7.65 (d, J=9.5 Hz, 1H), 7.60 (s, 1H), 7.58 (s, 1H), 7.43 (d, J=8.7 Hz, 1H), 4.39 (m, 2H), 4.27 (m, 2H), 2.47 (m, 2H), 1.98 (m, 2H).

Example 59: General Procedure for Synthesis of Compound Example 59

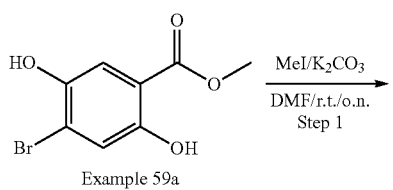

Example 59a

Step 3: Example 59e

To a solution of Example 59d (2.3 g, 4.8 mmol) in MeOH/H$_2$O (16 mL/8 mL) was added LiO.H$_2$O (609 mg, 14.5 mmol) with stirring at r.t. After 2 h, the pH of the reaction solution was adjusted to nearly 5 by HCl (aq.). The mixture was then concentrated under reduce pressure, and the residue was mixed with water. The precipitate was collected and dried to give the desired product Example 59e (860 mg, yield 39%) as a yellow solid. LCMS [M+1]$^+$=461.9, 463.9

Step 4: Example 59

To a solution of Example 59e (300 mg, 0.65 mmol) in pyridine (4 mL) was added POCl$_3$ (497 mg, 3.25 mmol) with stirring at 0° C. After 1 h, water (10 mL) was added to quench the reaction, and the mixture was purified by Prep-TLC to give the desired product Example 59 (14 mg, yield 5%) as a pink solid. LCMS [M+1]$^+$=444.0. $^1$H NMR (400 MHz, Chloroform-d) δ 10.19 (s, 1H), 8.51-8.37 (m, 2H), 8.08 (d, J=7.8 Hz, 1H), 7.92 (t, J=8.0 Hz, 1H), 7.67 (s, 1H), 6.99 (s, 1H), 4.69 (m, 2H), 4.06 (m, 2H), 3.92 (s, 3H), 2.06 (m, 4H). $^1$H NMR (400 MHz, DMSO-d$_6$) δ 10.42 (s, 1H), 8.66 (s, 1H), 8.31 (d, J=8.3 Hz, 1H), 8.03 (t, J=8.0 Hz, 1H), 7.91 (d, J=7.6 Hz, 1H), 7.53 (s, 1H), 7.34 (s, 1H), 4.65 (m, 2H), 4.13 (m, 2H), 3.84 (s, 3H), 1.86 (m, 4H).

Example 60: General Procedure for Synthesis of Compound Example 60

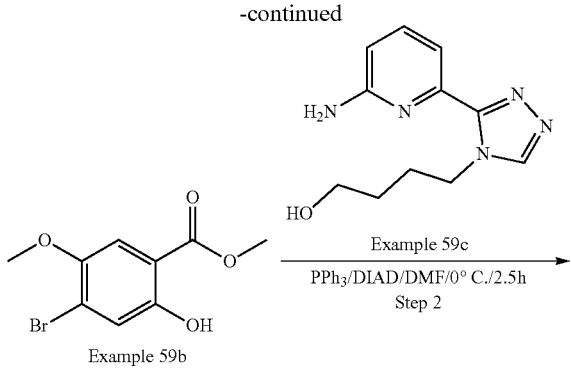
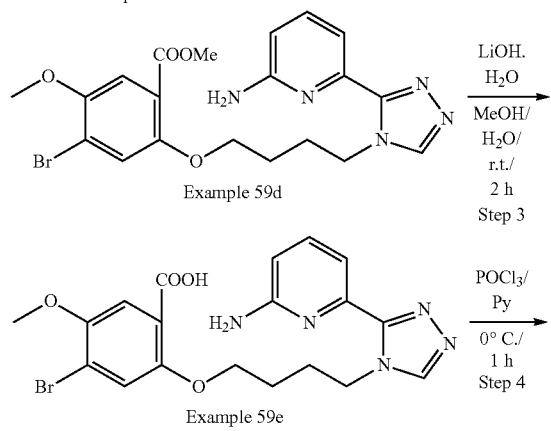
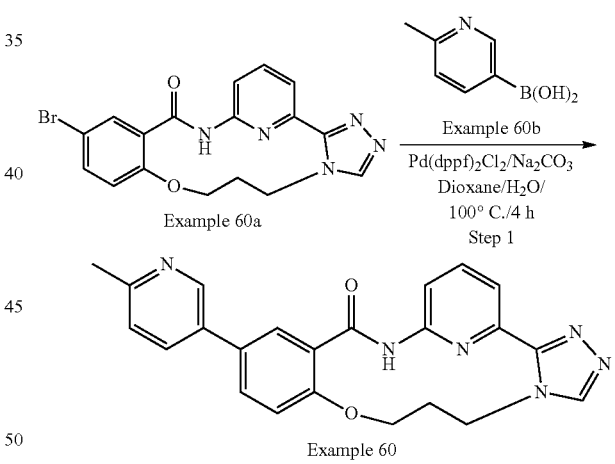

Step 1: Example 59b

To a solution of Example 59a (4.90 g crude, 19.8 mmol) in DMF (100 mL) was added K$_2$CO$_3$ (4.12 g, 29.8 mmol) at r.t. After stirred for about 10 min at 0° C., MeI (1.97 g, 13.9 mmol) was added to the mixture, which was stirred overnight. Water (200 mL) was added into the reaction solution, which was then extracted with EtOAc (100 mL). The organic layer was dried over Na$_2$SO$_4$, and concentrated under reduced pressure. The residue was purified by silica gel chromatography (Petroleum ether/EtOAc=9/1) to give the desired product Example 59b (1.21 g, yield 23%) as yellow oil. LCMS [M+1]$^+$=260.9, 262.9

Step 2: Example 59d

A mixture of Example 59b (1.21 g, 4.6 mmol), Example 59c (1.08 g, 4.6 mmol), and PPh$_3$ (1.82 g, 7.0 mmol) in dry DMF (25 mL) was stirred at 0° C. under N$_2$ atmosphere. To the mixture was injected DIAD (1.87 g, 9.3 mmol), which was stirred for a further 2.5 h. Then, water (50 mL) was added to the reaction solution. After extraction with EtOAc (20 mL), the organic layer was dried over Na$_2$SO$_4$, and concentrated under reduced pressure. The residue was purified by silica gel chromatography (DCM/MeOH=4/1) to give the desired product Example 59d (2.3 g, yield 100%) as yellow oil. LCMS [M+1]$^+$=475.9, 477.9

To a mixture of Example 60a (100 mg, 0.25 mmol), Example 60b (52 mg, 0.38 mmol), Na$_2$CO$_3$ (80 mg, 0.75 mmol) in dioxane/H$_2$O (3 mL, v/v=10/1) was added Pd(dppf)Cl$_2$ (18 mg, 0.025 mmol). Then the mixture was degassed by bubbling N$_2$ through the solution for 2 min using a syringe needle. After that, the mixture was heated at 100° C. for 4 h. The mixture was concentrated and directly purified by Prep-HPLC, followed by prep-TLC (DCM/MeOH=10/1) to give the desired product Example 60 (15.3 mg, yield 15%) as a white solid. LCMS [M+1]$^+$=413.0. $^1$H NMR (400 MHz, DMSO-d$_6$) δ 10.34 (s, 1H), 8.71 (s, 1H), 8.64 (d, J=2.0 Hz, 1H), 7.95-7.84 (m, 2H), 7.81 (d, J=7.6 Hz, 1H), 7.68-7.58 (m, 2H), 7.33 (d, J=7.9 Hz, 1H), 7.26 (d, J=8.1 Hz, 1H), 7.11 (d, J=8.6 Hz, 1H), 4.76 (m, 2H), 4.11 (m, 2H), 2.45 (s, 3H), 2.19 (m, 2H).

Example 61: General Procedure for Synthesis of Compound Example 61

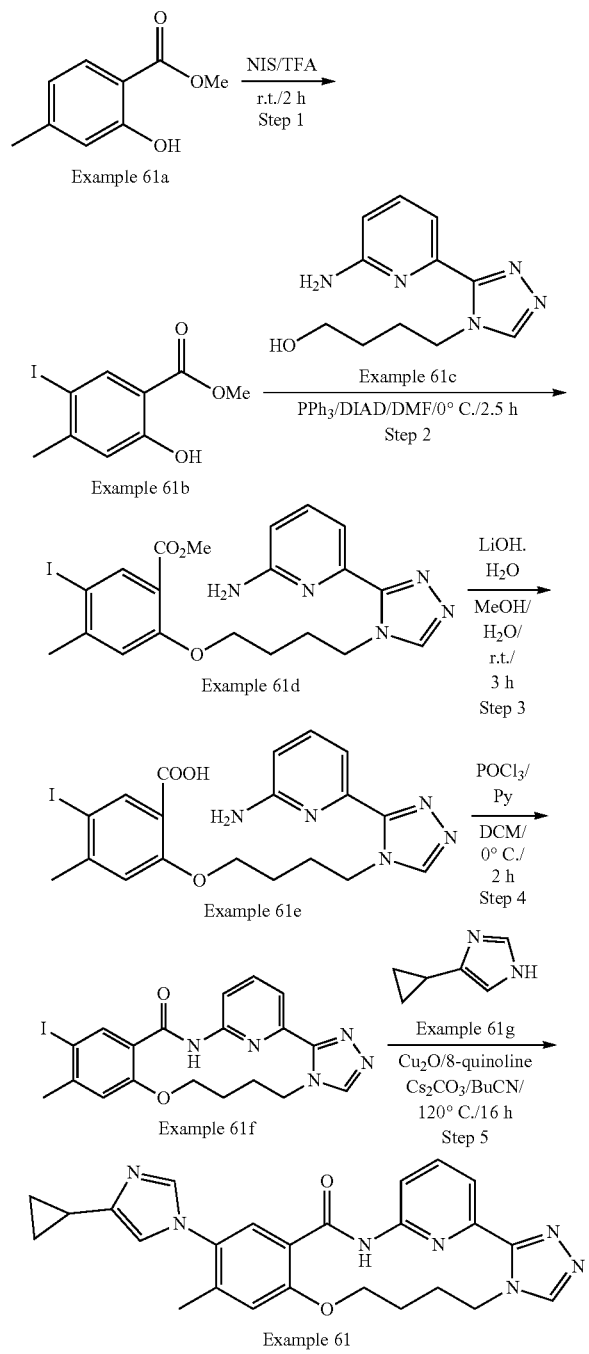

Step 1: Example 61b

To a solution of Example 61a (3.32 g, 20 mmol) in TFA (20 mL) was added NIS (4.95 g, 22 mmol). After stirred at r.t. for 2 h, the reaction was concentrated. The residue was dissolved in EtOAc (50 mL) and washed by sat. NaHCO$_3$ (10 mL*3). The organic layer was dried over Na$_2$SO$_4$, and concentrated to give the crude product Example 61b (6.1 g, yield 100%) as a yellow solid. LCMS [M+1]$^+$=292.9

Step 2: Example 61d

A mixture of Example 61b (5.50 g, 18.83 mmol), Example 61c (3.66 g, 15.69 mmol), and PPh$_3$ (8.22 g, 31.38 mmol) in dry DMF (35 mL) was stirred at 0° C. under N$_2$ atmosphere. To the mixture was injected DIAD (6.34 g, 31.38 mmol) slowly and the mixture was stirred at 0° C. for another 2.5 h. Then, water (150 mL) was added to the reaction mixture. After extraction with EtOAc (50 mL*3), the combined organic layer was dried over Na$_2$SO$_4$, and concentrated under reduced pressure. The residue was purified by silica gel chromatography (DCM/MeOH=10/1) to give the desired product Example 61d (6.60 g, yield 75%) as a yellow solid. LCMS [M+1]$^+$=507.9

Step 3: Example 61e

To a solution of Example 61d (6.60 g, 13.02 mmol) in MeOH/H$_2$O (40 mL/10 mL) was added LiO.H$_2$O (3.12 g, 78.10 mmol) at r.t. After 3 h, the pH of the reaction solution was adjusted to nearly 4 by HCl (aq.). The precipitate was filtered and dried to give desired product Example 61e (5.50 g, yield 83%) as a white solid. LCMS [M+1]$^+$=493.9

Step 4: Example 61f

To a solution of Example 61e (1.00 g, 2.03 mmol) in pyridine/DCM (10 mL/100 mL) was added POCl$_3$ (3.10 g, 20.28 mmol) with stirring at 0° C. After 2 h, water (50 mL) was added to quench the reaction, and the mixture was concentrated. The residue was triturated with MeOH (10 mL) twice to give the crude desired product Example 61f (400 mg, yield 40%) as a yellow solid. LCMS [M+1]$^+$=475.8

Step 5: Example 61

A mixture of Example 61f (300 mg, 0.63 mmol), Example 61g (204 mg, 1.89 mmol), 8-quinoline (36 mg, 0.25 mmol), Cs$_2$CO$_3$ (411 mg, 1.26 mmol) and Cu$_2$O (36 mg, 0.25 mmol) in BuCN (5 mL) was stirred at 120° C. for 16 h under N$_2$. Then the solution was filtrated and purified by Prep-HPLC, followed by Prep-TLC (DCM/MeOH=20/1) to give the desired product Example 61 (6.6 mg, yield 2%) as a white solid. LCMS [M+1]$^+$=456.0. $^1$H NMR (400 MHz, DMSO-d$_6$) δ 11.25 (s, 1H), 8.67 (s, 1H), 8.04 (t, J=7.9 Hz, 1H), 7.85 (t, J=7.0 Hz, 2H), 7.76 (s, 1H), 7.62 (s, 1H), 7.34 (s, 1H), 7.10 (s, 1H), 4.37 (m, 2H), 4.25 (t, J=8.5 Hz, 2H), 2.47 (m, 2H), 2.19 (s, 3H), 1.96 (m, 2H), 1.82 (m, 1H), 0.82-0.73 (m, 2H), 0.69 (d, J=4.4 Hz, 2H).

Example 62: General Procedure for Synthesis of Compound Example 62

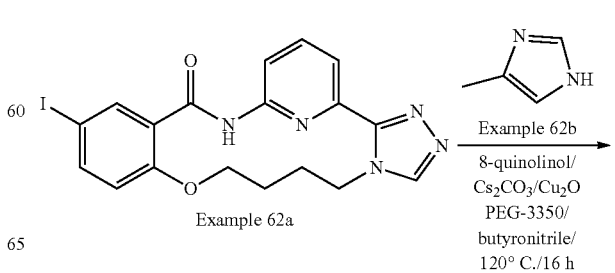

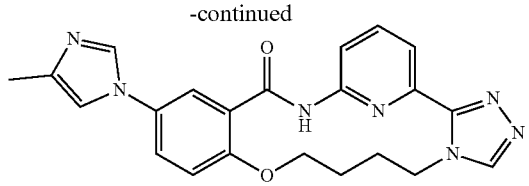

Example 62

Step 1: Example 62

To a solution of Example 62a (230 mg, 0.5 mmol), Example 62b (62 mg, 0.75 mmol), 8-quinolinol (11 mg, 0.075 mmol), $Cs_2CO_3$ (326 mg, 1 mmol) and PEG-3350 (180 mg) in butyronitrile (10 mL) was added $Cu_2O$ (12 mg, 0.0785 mmol). Then the mixture was degassed with $N_2$ three times, heated to 120° C. and stirred overnight for 16 h. The mixture was cooled to room temperature, concentrated under reduced pressure. The residue was purified by Prep-HPLC to give the desired product 33 mg (impure), which was further purified by prep-TLC (DCM/MeOH=10/1) to give the desired product Example 62 (16 mg, yield 8%) as a white solid. LCMS [M+1]$^+$=416.0. $^1$H NMR (400 MHz, DMSO-$d_6$) δ 11.22 (s, 1H), 8.68 (s, 1H), 8.12 (d, J=1.5 Hz, 1H), 8.10-8.04 (m, 2H), 7.88 (t, J=7.8 Hz, 2H), 7.81 (dd, J=8.9, 3.0 Hz, 1H), 7.49-7.37 (m, 2H), 4.37 (t, J=5.2 Hz, 2H), 4.32-4.19 (m, 2H), 2.44 (m, 2H), 2.15 (d, J=11.6 Hz, 3H), 1.96 (m, 2H).

Example 63: General Procedure for Synthesis of Compound Example 63

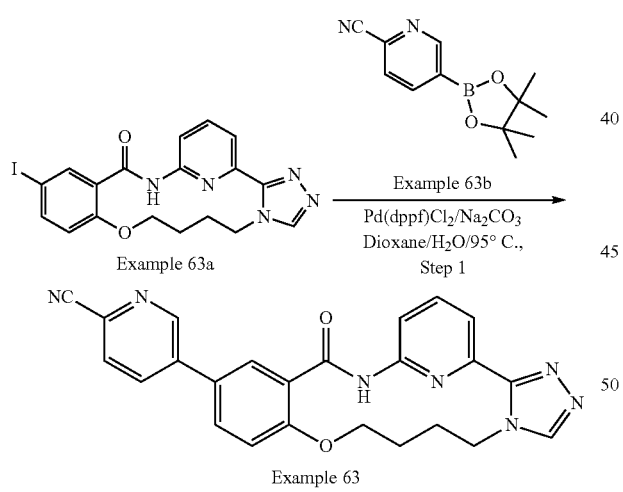

Step 1: Example 63

To a mixture of Example 63a (200 mg, 0.43 mmol), Example 63b (110 mg, 0.48 mmol), $Na_2CO_3$ (138 mg, 1.3 mmol) in dioxane (4 mL) and $H_2O$ (2 mL) was added Pd(dppf)Cl$_2$ (32 mg, 0.04 mmol). Then the mixture was degassed by bubbling $N_2$ through the solution for 2 min using a syringe needle. After that, the mixture was heated at 95° C. for 16 h. The mixture was filtered and directly purified by silica gel chromatography (MeOH:DCM=1:20), followed by prep-TLC (MeOH:DCM=1:10) to give the desired product Example 63 (7.5 mg, yield 4%) as white solid. LCMS [M+1]$^+$=438.0. $^1$H NMR (400 MHz, Chloroform-d) δ 11.40 (s, 1H), 8.98 (s, 1H), 8.57 (s, 1H), 8.24 (s, 1H), 8.06 (d, J=8.0 Hz, 2H), 7.95 (t, J=8.0 Hz, 1H), 7.79 (d, J=8.1 Hz, 2H), 7.20 (d, J=8.5 Hz, 2H), 4.48-4.21 (m, 4H), 2.35-2.07 (m, 4H).

Example 64: General Procedure for Synthesis of Compound Example 64

Step 1: Example 64c

A solution of Example 64a (1.2 g, 5.0 mmol), Example 64b (1.25 g, 5.0 mmol) and PPh$_3$ (1.3 g, 5.0 mmol) in dry DMF (40 mL) was cooled to 0° C., and DIAD (1.0 g, 5.0 mmol) was injected in portions via a syringe. Then the mixture was stirred for 4 h at 0-5° C. Water (400 mL) was added and the mixture was extracted with EtOAc (200 mL*3). The combined organic layer was concentrated under reduced pressure, and the residue was purified by silica gel chromatography (DCM/MeOH=91/9) to give the desired product Example 64c (1.4 g, yield 60%) as an orange gel. LCMS [M+1]⁺=463.9/465.9.

Step 2: Example 64d

A solution of Example 64c (1.4 g, 3.25 mmol) and LiO.H₂O (667 mg, 16.3 mmol) in MeOH/THF/H₂O (20 mL/20 mL/20 mL) was stirred at r.t. overnight. The mixture was adjusted to pH=2-3 with conc. HCl, and then concentrated under reduced pressure to give the crude product Example 64d (HCl salt, 3.5 g, yield>100%) as a white solid, which was used in the next step without further purification. LCMS [M+1]⁺=449.9/451.9.

Step 3: Example 64e

A solution of Example 64d (3.5 g, 7.8 mmol) in pyridine (60 mL) was cooled to 0° C. POCl₃ (4.8 g, 31.4 mmol) was added dropwise at 0-5° C., and the resulting mixture was stirred overnight at 0-20° C. Water (50 mL) was added to the mixture, which was stirred for 10 min. The mixture was filtrated, and the solid was washed with water (100 mL*2), and dried under reduced pressure to give the crude product Example 64e (1.1 g, yield 69%) as a brown solid, which was used in the next step without further purification. LCMS [M+1]⁺=431.9/433.9.

Step 4: Example 64

To a mixture of Example 64e (200 mg, 0.46 mmol), Example 64f (60 mg, 0.48 mmol), and Na₂CO₃ (138 mg, 1.30 mmol) in dioxane/H₂O (4 mL/2 mL) was added Pd(dppf)Cl₂ (32 mg, 0.04 mmol). The resulting mixture was degassed by bubbling N₂ through the solution for 2 min, which was then heated at 95° C. for 16 h. The mixture was directly purified by silica gel chromatography (DCM/MeOH=50/1 to 10/1) to give the desired product Example 64 (43.4 mg, yield 21%) as a white solid. LCMS [M+1]⁺=445.0. ¹H NMR (400 MHz, DMSO-d₆) δ 11.06 (s, 1H), 8.67 (s, 1H), 8.61 (s, 1H), 8.12-8.02 (m, 2H), 7.89-7.84 (m, 3H), 7.42-7.34 (m, 2H), 4.37 (t, J=5.1 Hz, 2H), 4.29-4.22 (m, 2H), 2.51 (s, 3H), 2.47-2.51 (m, 2H), 1.95 (m, 2H).

Example 65: General Procedure for Synthesis of Compound Example 65

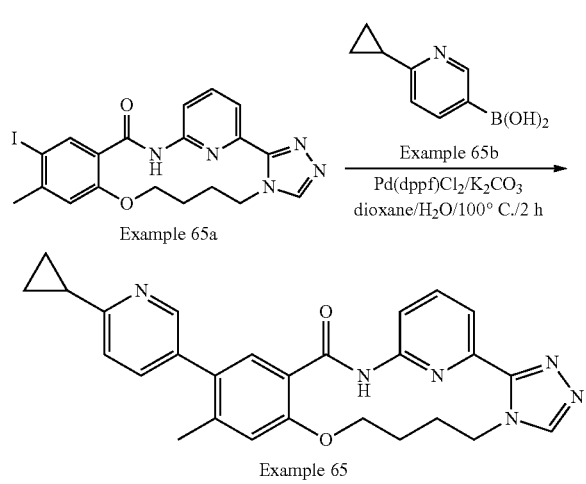

Step 1: Example 65

A mixture of Example 65a (200 mg, 0.42 mmol), Example 65b (76 mg, 0.46 mmol), K₂CO₃ (116 mg, 0.84 mmol), and Pd(dppf)Cl₂ (31 mg, 0.04 mmol) in dioxane/H₂O (4 mL/2 mL) was stirred at 100° C. for 2 h. Then the solution was filtrated and purified by Prep-HPLC to give the desired product Example 65 (8 mg, yield 4%) as a white solid. LCMS [M+1]⁺=467.1

¹H NMR (400 MHz, DMSO-d₆) δ 11.31 (s, 1H), 8.67 (s, 1H), 8.37 (d, J=2.3 Hz, 1H), 8.03 (t, J=7.9 Hz, 1H), 7.85 (dd, J=13.4, 7.9 Hz, 2H), 7.78 (s, 1H), 7.64 (dd, J=8.0, 2.4 Hz, 1H), 7.36 (d, J=8.0 Hz, 1H), 7.27 (s, 1H), 4.36 (t, J=5.0 Hz, 2H), 4.30-4.20 (m, 2H), 2.50-2.40 (m, 2H), 2.29 (s, 3H), 2.20-2.10 (m, 1H), 2.00-1.90 (m, 2H), 1.00-0.90 (m, 4H).

Example 66: General Procedure for Synthesis of Compound Example 66

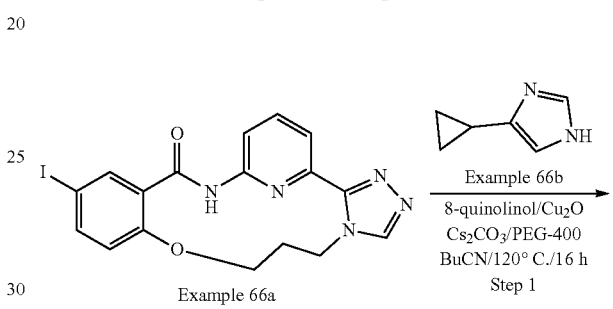

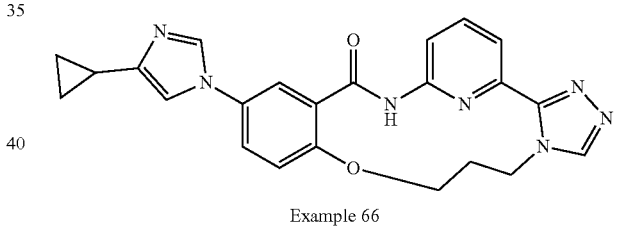

Step 1: Example 66

A slurry of Example 66a (100 mg, 0.22 mmol), Example 66b (37 mg, 0.34 mmol) and Cu₂O (6 mg, 0.04 mmol), 8-quinolinol (6 mg, 0.04 mmol), and PEG-400 (100 mg) in BuCN (5 mL) were degassed by bubbling N₂ through the solution for 2 min using a syringe needle. Then the mixture was heated to 120° C. for 16 h. After then the mixture was purified by Prep-HPLC, followed by prep-TLC (DCM/MeOH=10/1) to give the desired product Example 66 (7.0 mg, yield 7%) as a white solid. LCMS [M+1]⁺=428.0. ¹H NMR (400 MHz, DMSO-d₆) δ 10.41 (s, 1H), 8.71 (s, 1H), 7.97-7.87 (m, 2H), 7.82 (d, J=7.6 Hz, 1H), 7.55-7.45 (m, 2H), 7.37 (s, 1H), 7.30 (d, J=7.8 Hz, 1H), 7.09 (d, J=8.8 Hz, 1H), 4.75 (m, 2H), 4.08 (m, 2H), 2.18 (m, 2H), 1.77 (dt, J=8.2, 3.4 Hz, 1H), 0.74 (dt, J=8.2, 2.8 Hz, 2H), 0.63 (dt, J=4.9, 2.7 Hz, 2H).

Example 67: General Procedure for Synthesis of Compound Example 67

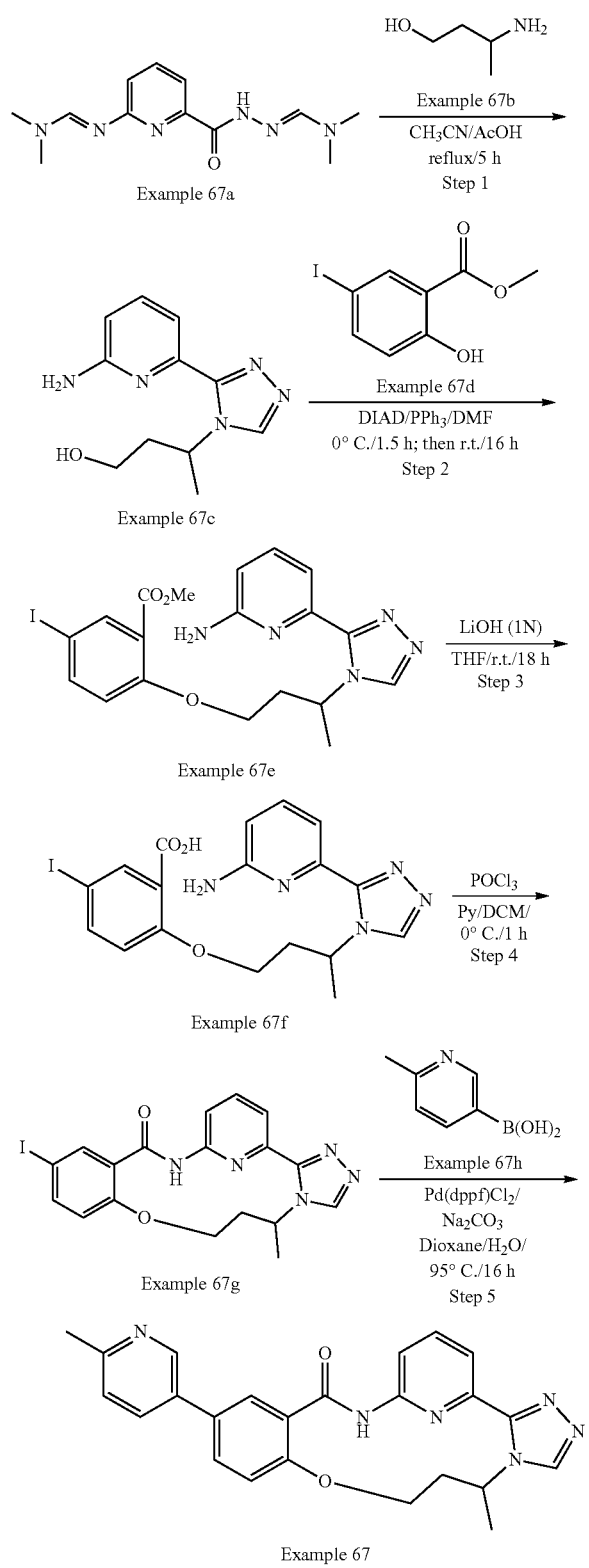

Step 1: Example 67c

To a solution of Example 67a (10 g, 38 mmol) in CH$_3$CN/AcOH (80 mL/20 mL) was added Example 67b (5.1 g, 57 mmol). The mixture was heated at reflux for 5 h. After cooling to r.t., the mixture was concentrated under reduced pressure. The residue was dissolved in water and 1N aqueous NaOH was added to adjust pH to 8. The resulting mixture was concentrated under reduced pressure and purified by silica gel chromatography (DCM/MeOH=10/1) to give the desired product (Example 67c, 5.5 g, yield 62%) as yellow oil. LCMS [M+1]$^+$=234

Step 2: Example 67e

A slurry of Example 67c (4 g, 17.2 mmol), Example 67d (6.2 g, 22.4 mg) and PPh$_3$ (9 g, 34.4 mmol) in dry DMF (40 mL) was cooled to 0° C. Then DIAD (5.2 g, 25.8 mmol) was added to the mixture dropwise, which was stirred at 0° C. for 1.5 h and r.t. for 16 h. To the mixture was added water (150 mL), which was extracted with EtOAc (50 mL*3). The combined organic layer was dried over anhydrous magnesium sulfate and concentrated under reduced pressure. The residue was purified by silica gel chromatography (DCM/MeOH=20/1) to give the desired product Example 67e (2 g, yield 24%) as a yellow solid. LCMS [M+1]$^+$=493.9

Step 3: Example 67f

To a mixture of Example 67e (2 g, 4.1 mmol) in THF (30 mL), was added LiO.H$_2$O (810 mg, 20.0 mmol) in H$_2$O (10 mL). The mixture was stirred at r.t. for 18 h. The mixture was adjusted to pH 4 and then lyophilized to give the crude product Example 67f (1.4 g, 72%) as a white solid. LCMS [M+1]$^+$=479.9

Step 4: Example 67g

To a mixture of Example 67f (500 mg, 1.04 mmol) in pyridine (100 mL) at 0° C. was added POCl$_3$ (1.6 g, 10 mmol) dropwise. The mixture was stirred at 0° C. for 1 h. To the mixture was added water (30 mL), which was then concentrated under reduced pressure. MeOH/H$_2$O (50 mL/50 mL) was added and the mixture was stirred at r.t. for 15 min, and filtered. The cake was washed with MeOH, dried in vacuo to give crude product Example 67g (220 mg, 46%) as a pink solid. LCMS [M+1]$^+$=461.9

Step 5: Example 67

To a mixture of Example 67g (220 mg, 0.48 mmol), Example 67h (72 mg, 0.52 mmol), Na$_2$CO$_3$ (152 mg, 1.4 mmol) in dioxane (4 mL) and H$_2$O (2 mL) was added Pd(dppf)Cl$_2$ (35 mg, 0.05 mmol). Then the mixture was degassed by bubbling N$_2$ through the solution for 2 min using a syringe needle. After that, the mixture was heated at 95° C. for 16 h. The mixture was directly purified by silica gel chromatography (DCM/MeOH=20/1) and prep-TLC (DCM/MeOH=15/1) to give the desired product Example 67 (25 mg, yield 12%) as a white solid. LCMS [M+1]$^+$=214.1/427.0. $^1$H NMR (400 MHz, Chloroform-d) δ 9.14 (s, 1H), 8.71 (d, J=2.4 Hz, 1H), 8.43 (s, 1H), 8.03-7.91 (m, 3H), 7.80 (dd, J=8.1, 2.4 Hz, 1H), 7.71-7.61 (m, 2H), 7.25 (s, 1H), 7.05 (d, J=8.6 Hz, 1H), 5.63 (br, 1H), 4.30 (d, J=8.1 Hz, 2H), 2.95 (br, 1H), 2.63 (s, 3H), 2.13 (t, J=12.7 Hz, 1H), 1.65 (d, J=7.0 Hz, 3H).

Example 68: General Procedure for Synthesis of Compound Example 68

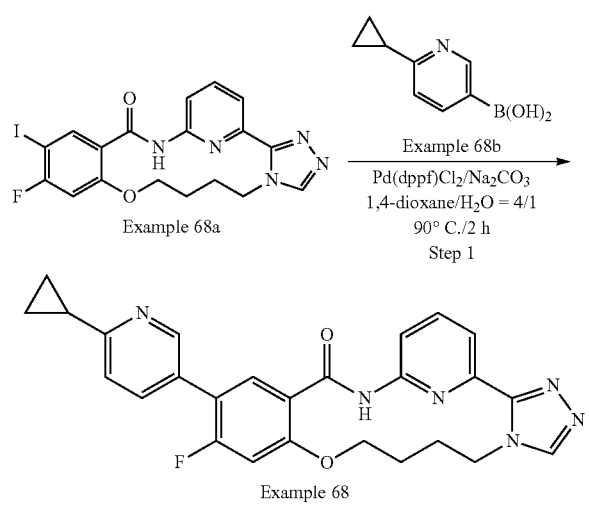

Step 1: Example 68

To a solution of Example 68a (25 mg, 0.05 mmol), Example 68b (11 mg, 0.06 mmol) in 1,4-dioxane/H₂O (4 mL/1 mL) were added Pd(dppf)Cl₂ (4 mg, 0.005 mmol) and Na₂CO₃ (11 mg, 0.1 mmol). The mixture was degassed by nitrogen for three times and heated at 90° C. for 2 hs. The reaction mixture was filtered, washed with EtOAc and concentrated. The residue was purified by prep-TLC (DCM/MeOH=15/1) to afford the crude product which was triturated in MeOH (2 mL), filtered and dried to give the desired product Example 68 (8 mg, yield 33%) as a gray solid. LCMS [M+1]⁺=471.0. ¹H NMR (400 MHz, DMSO-d₆) δ 11.06 (s, 1H), 8.69 (s, 1H), 8.55 (s, 1H), 8.05 (t, J=8.5 Hz, 2H), 7.86 (t, J=7.3 Hz, 2H), 7.81 (d, J=8.3 Hz, 1H), 7.39 (dd, J=10.2, 7.3 Hz, 2H), 4.37 (m, 2H), 4.26 (t, J=8.5 Hz, 2H), 2.44 (m, 2H), 2.14 (m, 1H), 1.95 (m, 2H), 0.99-0.93 (m, 4H).

Example 69: General Procedure for Synthesis of Compound Example 69

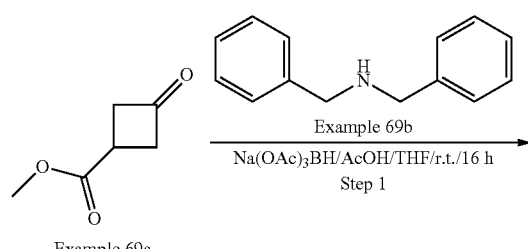

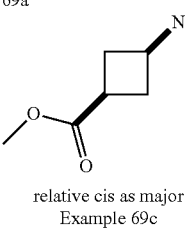

relative cis as major
Example 69c

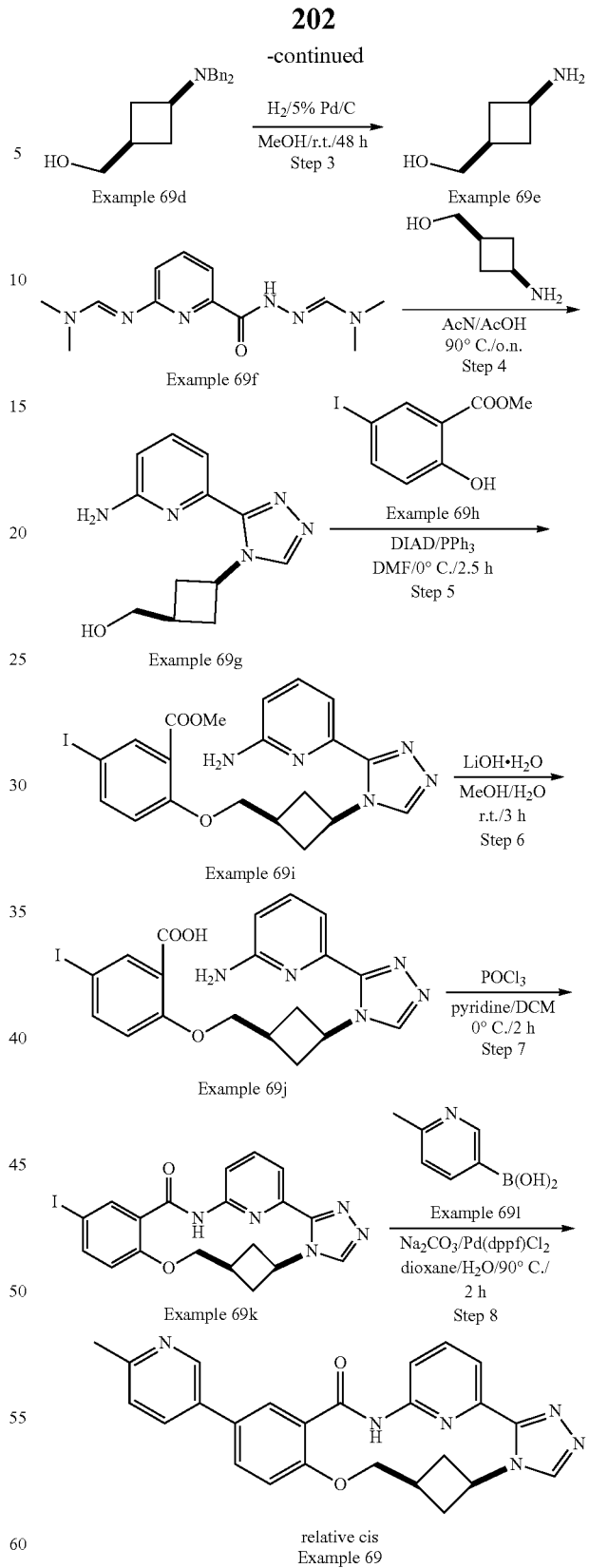

Step 1: Example 69c

To a solution of Example 69a (10 g, 78 mmol) in THF (100 mL) were added Na(OAc)₃BH (33 g, 156 mmol) and HOAc (2 mL). After stirring at r.t. for 30 min, Example 69b (23 g, 117 mmol) was added into the mixture, which was stirred at r.t. for 16 h. H$_2$O (500 mL) was added to the mixture, which was then extracted with EtOAc (100 mL*3). The organic layer was dried over Na$_2$SO$_4$ and concentrated. The residue was purified by silica gel chromatography (Petroleum Ether/EtOAc=10/1) to give the desired product Example 69c (22 g, yield 91%) as colorless oil with relative cis as major. LCMS [M+1]$^+$=310.1

Step 2: Example 69d

To a mixture of LiAlH$_4$ (418 mg, 11 mmol) in THF (30 mL) was added Example 69c (3.09 g, 10 mmol) in THF (20 mL) dropwise at 0° C. The mixture was stirred at 0° C. for 2 h. H$_2$O (1 mL), 15% NaOH (aq., 1 mL) and H$_2$O (3 mL) were added into the mixture in turn. The precipitate was filtered and the filtrate was dried to give desired product Example 69d (3.01 g, yield 100%) as yellow oil. LCMS [M+1]$^+$=282.1

Step 3: Example 69e

A mixture of Example 69d (3 g, 10.7 mmol) and 5% Pd/C (500 mg) in MeOH (40 mL) was stirred at r.t. under H$_2$ atmosphere for 48 h. The suspension was filtered and dried to give desired product Example 69e (1.1 g, yield 100%) as light yellow oil.

Step 4: Example 69g

A mixture of Example 69e (1.01 g, crude), Example 69f (1.31 g, 5.0 mmol) in MeCN/AcOH (20 mL, v/v=4/1) was heated at 90° C. for overnight. Then the mixture was concentrated under reduced pressure and to the residue was added MeOH (10 mL)/conc. HCl (5 mL, 12 N), which was stirred for 1 h. Then the mixture was adjusted pH to 7.0 and concentrated under reduced pressure. The residue was directly purified by silica gel chromatography (DCM/MeOH=1/0~10/1) to give the crude product Example 69g (1.2 g, yield 100%) as a yellow solid. LCMS [M+1]$^+$=246.0

Step 5: Example 69i

A mixture of Example 69g (1.20 g, 4.9 mmol), Example 69h (1.77 g, 6.4 mmol), and PPh$_3$ (2.57 g, 9.8 mmol) in dry DMF (20 mL) was stirred at 0° C. under N$_2$ atmosphere. To the mixture was injected DIAD (1.98 g, 9.8 mmol) slowly and the mixture was stirred at 0° C. for another 2.5 h. Then, water (150 mL) was added to the reaction mixture, which was then extracted with EtOAc (50 mL*3). The combined organic layer was dried over Na$_2$SO$_4$, and concentrated under reduced pressure. The residue was purified by silica gel chromatography (DCM/MeOH=10/1) to give the desired product Example 69i (2 g, yield 83%) as a yellow solid. LCMS [M+1]$^+$=505.9

Step 6: Example 69j

To a solution of Example 69i (2 g, 3.96 mmol) in MeOH/H$_2$O (30 mL/10 mL) was added LiO.H$_2$O (0.95 g, 23.76 mmol) at r.t. After 3 h, the pH of the reaction solution was adjusted to nearly 4 by HCl (aq.). The precipitate was filtered and dried to give desired product Example 69j (1.8 g, yield 92%) as a white solid. LCMS [M+1]$^+$=491.9

Step 7: Example 69k

To a solution of Example 69j (1.7 g, 3.462 mmol) in pyridine/DCM (15 mL/150 mL) was added POCl$_3$ (5.3 g, 34.62 mmol) dropwise with stirring at 0° C. After 2 h, water (20 mL) was added to quench the reaction, and the mixture was concentrated. The residue was triturated with MeOH (10 mL) twice to give the crude product Example 69k (1.1 g, yield 64%) as a yellow solid. LCMS [M+1]$^+$=473.9

Step 8: Example 69

To a mixture of Example 69k (500 mg, crude), Example 69i (187 mg, 1.374 mmol) and Na$_2$CO$_3$ (224 mg, 2.114 mmol) in dioxane/H$_2$O (12 mL, v/v=5/1) was added Pd(dppf)Cl$_2$ (87 mg). Then the mixture was degassed by bubbling N$_2$ through the solution for 2 min using a syringe needle. After that, the mixture was heated at 90° C. for 2 h. The mixture was concentrated under reduced pressure and the residue was purified by Prep-HPLC give the desired product Example 69 (relative cis, 2.5 mg, yield 4%) as a gray solid. LCMS [M+1]$^+$=439.0. $^1$H NMR (400 MHz, DMSO-d$_6$) δ 11.00 (s, 1H), 8.76 (d, J=2.5 Hz, 1H), 8.70 (s, 1H), 8.12 (d, J=2.5 Hz, 1H), 8.05 (t, J=7.9 Hz, 1H), 7.99 (dd, J=8.1, 2.5 Hz, 1H), 7.91 (dt, J=15.3, 8.2 Hz, 3H), 7.33 (d, J=8.3 Hz, 2H), 5.03 (t, J=7.2 Hz, 1H), 4.27 (m, 2H), 3.48 (s, 3H), 2.49 (m, 3H), 2.26 (d, J=7.6 Hz, 2H).

Example 70: General Procedure for Synthesis of Compound Example 70

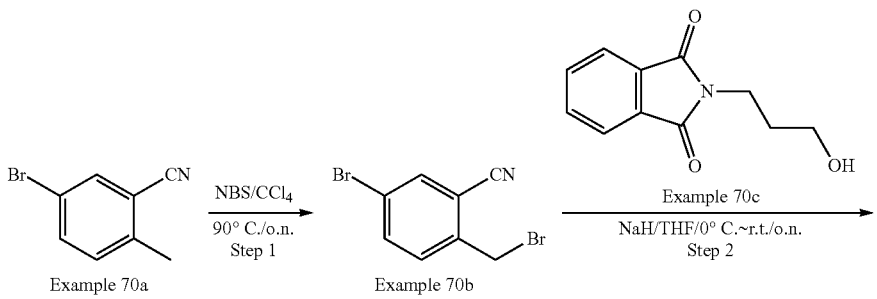

-continued

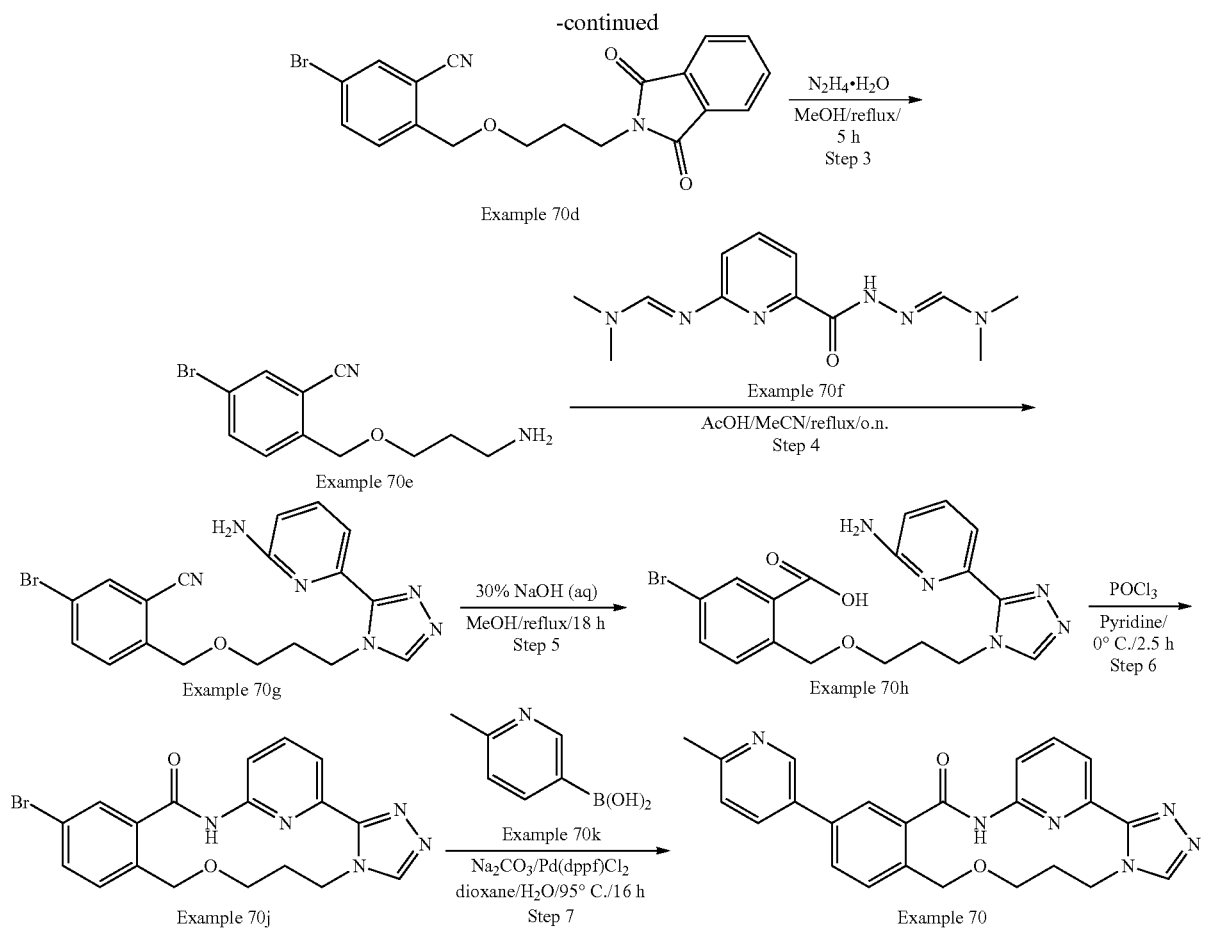

Step 1: Example 70b

To a solution of Example 70a (10.0 g, 51.5 mmol) in CCl$_4$ (200 mL) were added NBS (9.1 g, 51.5 mmol) and AIBN (836 mg, 5.1 mmol). The resulting mixture was stirred at 90° C. overnight. After cooling to r.t., the mixture was diluted with water (100 mL), and extracted with DCM (50 mL*2). The organic phase was dried over Na$_2$SO$_4$ and concentrated under reduce pressure. The residue was purified by silica gel chromatography (Petroleum Ether/EtOAc=10/1) to give the desired product Example 70b (6.0 g, yield 43%) as a white solid.

Step 2: Example 70d

To a solution of Example 70c (3.42 g, 16.65 mmol) in dry THF (20 mL) was added NaH (721 mg, 60% in mineral oil, 18.03 mmol) at 0° C. The suspension was stirred for 30 min. Example 70b (3.8 g, 13.86 mmol) was added dropwise over 5 min, and after 10 min, the ice bath was removed. The reaction mixture was stirred at r.t. overnight. To the mixture was added water (100 mL), which was then extracted with EtOAc (150 mL*2). The organic phase was dried over Na$_2$SO$_4$ and concentrated under reduce pressure to give the crude product Example 70d (5.0 g, crude yield 90%) as yellow oil. LCMS [M+1]$^+$=400.1

Step 3: Example 70e

To a stirred solution of Example 70d (5.0 g, 0.53 mmol) in MeOH (100 mL) was added hydrazine monohydrate (10 mL). The mixture was stirred at reflux for 5 h and then cooled at r.t. The white precipitate was filtered and washed with EtOH/DCM (150 mL, v/v=1/10) and the filtrate was evaporated under vacuum. The residue was suspended in EtOH/DCM (100 mL, v/v=1/10) and the remaining precipitate was filtered again and washed with EtOH/DCM (50 mL, v/v=1/10). (It was repeated until no more white solid appeared after concentration of the filtrate). After concentration, Example 70e (1.2 g, yield 36%) was obtained as a pale yellow solid and used for the next step without further purification. LCMS [M+1]$^+$=270.1

Step 4: Example 70g

To a solution of Example 70f (800 mg, 3.05 mmol) in a mixture of CH$_3$CN/AcOH (36 mL, v/v=4/1) was added Example 70e (800 mg, 3.05 mmol). The resulting mixture was heated to reflux for 18 h and then cooled to room temperature. The solvent was removed under reduced pressure. The residue was dissolved in water (50 mL) and 30% aqueous NaOH was added to adjust to pH 8~9. The residue was concentrated, slurried with DCM/MeOH (50 mL*2, v/v=10/1), and then filtered. The filtrate was concentrated to give the crude product Example 70g (2.0 g, crude yield 159%) as a yellow solid, which was used without further purification. LCMS [M+1]$^+$=412.9/414.9

Step 5: Example 70h

To a mixture of Example 70g (2.0 g, crude, 3.05 mmol) in MeOH (15 mL) was added 30% NaOH (aq. 25 mL), which was refluxed for 18 h. After cooling, the solvent was removed in vacuo. The residue was dissolved in water, and the solution was acidified to pH~3.5 with 2N HCl (aq.). The precipitate was collected by filtration and dried to give the desired product Example 70h (800 mg, yield 61% over 2 steps) as a yellow solid. LCMS [M+1]$^+$=431.9/433.9

Step 6: Example 70j

To a mixture of Example 70h (800 mg, 1.85 mmol) in pyridine (200 mL) at 0° C. was added POCl$_3$ (4 mL) slowly. The mixture was stirred at 0° C. for 2.5 h. To the mixture was added water (50 mL), which was concentrated under reduced pressure. The residue was purified by silica gel chromatography (DCM/MeOH=20/1) to give the desired product Example 70j (30 mg, yield 4%) as a white solid. LCMS [M+1]$^+$=413.9/415.9

Step 7: Example 70

To a mixture of Example 70j (21 mg, 0.05 mmol), Example 70k (30 mg, 0.22 mmol), and Na$_2$CO$_3$ (50 mg, 0.47 mmol) in dioxane/H$_2$O (1.0 mL, v/v=3/1) was added Pd(dppf)Cl$_2$ (2 mg). Then the mixture was degassed by bubbling N$_2$ through the solution for 2 min using a syringe needle. After that, the mixture was heated at 95° C. for 16 h. The mixture was concentrated and directly purified by prep-TLC (DCM/MeOH=20/1) to give the desired product Example 70 (7.0 mg, yield 33%) as a white solid. LCMS [M+1]+=427.0. $^1$H NMR (400 MHz, Chloroform-d) δ 10.49 (s, 1H), 8.80 (d, J=2.4 Hz, 1H), 8.22 (s, 1H), 8.17 (dd, J=5.1, 3.1 Hz, 2H), 8.11 (d, J=7.7 Hz, 1H), 7.97 (d, J=7.9 Hz, 1H), 7.94-7.89 (m, 1H), 7.76 (dd, J=7.8, 2.1 Hz, 1H), 7.58 (d, J=7.9 Hz, 1H), 7.32 (d, J=8.0 Hz, 1H), 4.77 (d, J=7.2 Hz, 2H), 4.68 (s, 2H), 4.01-3.93 (m, 2H), 2.66 (s, 3H), 2.36 (d, J=6.6 Hz, 2H).

Example 71: General Procedure for Synthesis of Compound Example 71

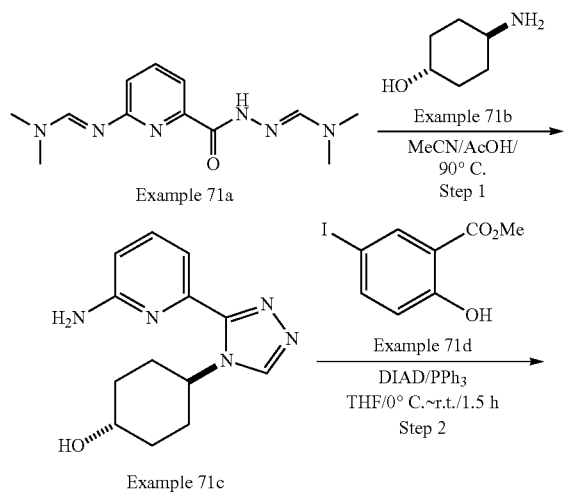

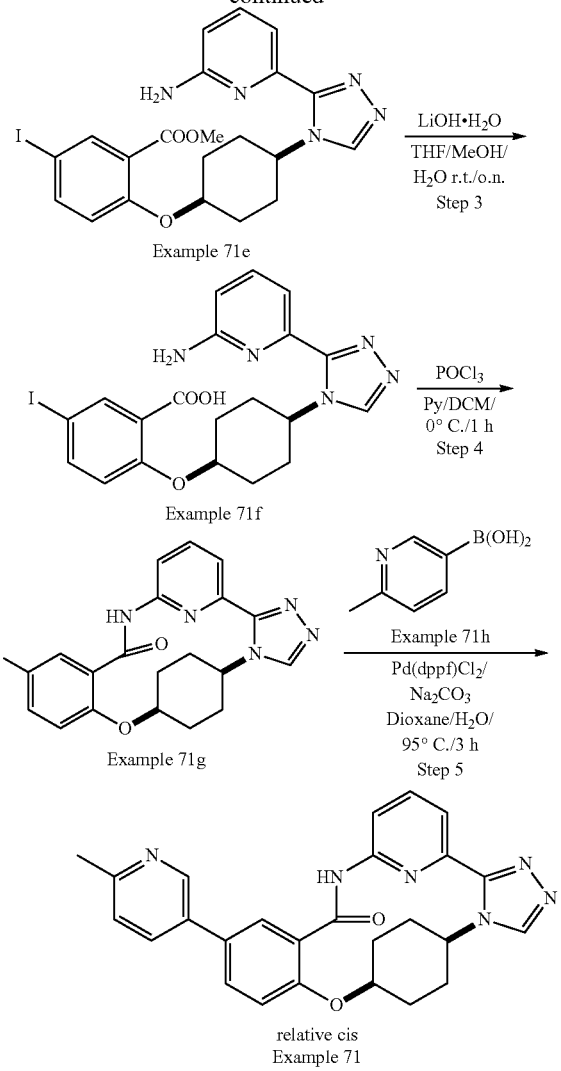

Step 1: Example 71c

A solution of Example 71a (5.0 g, 19 mmol) and Example 71b (4.4 g, 38 mmol) in MeCN (30 mL) and AcOH (7.5 mL) was stirred at 90° C. overnight. The solution was diluted with 2N NaOH (15 mL), and then extracted with EtOAc (30 mL*2). The combined organic phase was concentrated under reduced pressure. The residue was purified by silica gel chromatography (DCM/MeOH=10/1) to give the desired product Example 71c (1.8 g, yield 36%) as a white solid. LCMS [M+1]$^+$=260.0

Step 2: Example 71e

To a solution of Example 71c (1.8 g, 6.4 mmol) in DMF (20 mL) were added Example 71d (1.5 g, 5.8 mmol) and PPh$_3$ (3.0 g, 11.6 mmol). Then the mixture was cooled to 0° C. and DIAD (1.8 g, 8.7 mmol) was added dropwise under N$_2$. The resulting mixture was stirred at this temperature for 10 min and warmed to r.t. for 1 h. The mixture was extracted with EtOAc (50 mL*2). The combined organic phase was washed with brine, dried over Na$_2$SO$_4$, filtrated and the filtrate was concentrated under reduced pressure. The residue was purified by silica gel chromatography (DCM/MeOH=15/1) to give the desired product Example 71e (2.3 g, yield 75%) as yellow oil. LCMS [M+1]⁺=520.0

Step 3: Example 71f

To a solution of Example 71e (2.3 g, 4.4 mmol) in THF/MeOH/H₂O (60 mL/20 mL/20 mL) was added LiO.H₂O (279 mg, 6.6 mmol). The mixture was stirred at r.t. overnight. The solvent was evaporated and the residue was acidified to pH 2~3 with 3N HCl. The resulting solution was extracted with EtOAc, and the organic layer was concentrated to give the desired product Example 71f (1.8 g, yield 81%) as a yellow solid. LCMS [M+1]⁺=506.0

Step 4: Example 71g

To a solution of Example 71f (100 mg, 0.20 mmol) in DCM/pyridine (30 mL/3 mL) was added POCl₃ (303 mg, 2.0 mmol) dropwise at 0° C. The mixture was stirred at 0° C. for 1 h under N₂. The reaction was quenched with H₂O (0.5 mL). The solvent was evaporated and MeOH (3 mL) was added to the residue. The suspension was stirred at r.t. for 10 min and filtrated. The solid was dried to give the desired product Example 71g (100 mg, crude) as a yellow solid, which was used in next step. LCMS [M+1]⁺=488.0

Step 5: Example 71

To a solution of Example 71g (100 mg, 0.21 mmol) in Dioxane/H₂O (4 mL/2 mL) were added Example 71h (31 mg, 0.23 mmol), Na₂CO₃ (65 mg, 0.62 mmol) and Pd(dppf)Cl₂ (15 mg, 0.02 mmol). The mixture was stirred at 95° C. for 3 h under N₂. The mixture was filtrated and the filtrate was concentrated under reduced pressure. The residue was purified by Prep-HPLC to give the desired product Example 71 (11.8 mg, yield 13% over two steps) as a white solid. LCMS [M+1]⁺=453.0. ¹H NMR (400 MHz, DMSO-d₆) δ 10.29 (s, 1H), 8.75 (d, J=2.6 Hz, 1H), 8.65 (s, 1H), 8.04 (t, J=7.8 Hz, 1H), 7.97 (dd, J=8.2, 2.7 Hz, 1H), 7.89 (d, J=2.5 Hz, 1H), 7.85-7.77 (m, 1H), 7.73 (d, J=7.6 Hz, 1H), 7.63 (d, J=8.0 Hz, 1H), 7.33 (dd, J=12.4, 8.4 Hz, 2H), 5.01 (s, 1H), 4.64 (s, 1H), 2.96 (d, J=13.2 Hz, 3H), 1.98 (d, J=12.9 Hz, 3H), 1.78-1.42 (m, 5H).

Example 72: General Procedure for Synthesis of Compound Example 72

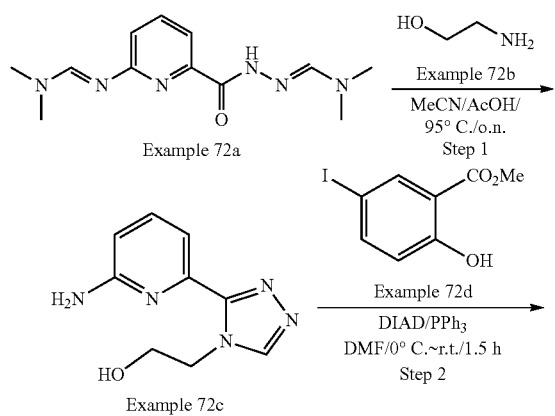

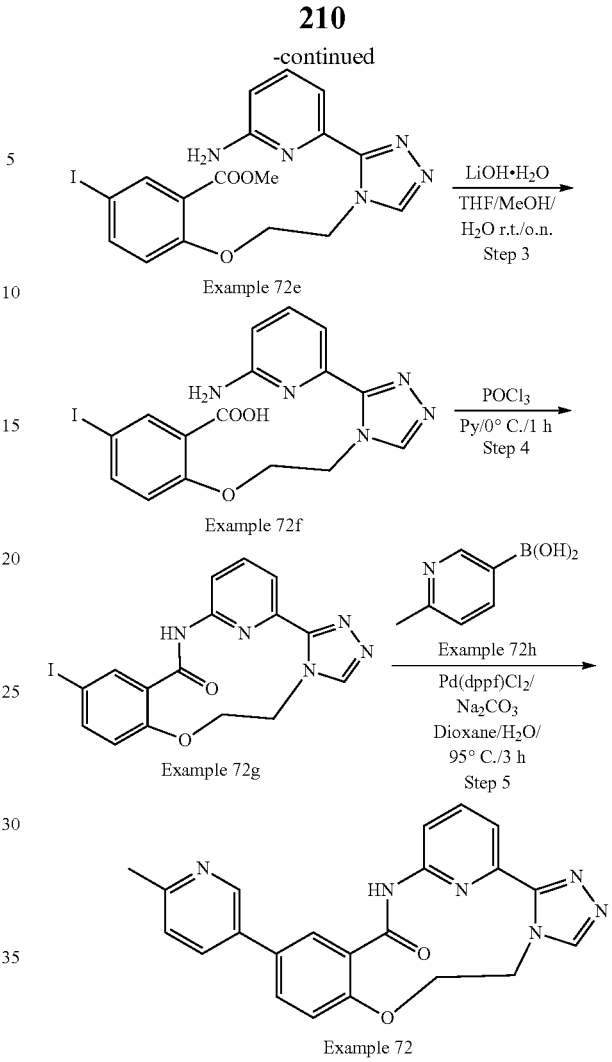

Step 1: Example 72c

A solution of Example 72a (10 g, 38 mmol) and Example 72b (12 g, 191 mmol) in MeCN (60 mL) and AcOH (15 mL) was stirred at 95° C. overnight. The solution was diluted with 2N NaOH (30 mL), and extracted with EtOAc (50 mL*2). The combined organic phase was concentrated under reduced pressure. The residue was purified by silica gel chromatography (DCM/MeOH=20/1) to give the desired product Example 72c (5 g, yield 64%) as a white solid. LCMS [M+1]⁺=206.0

Step 2: Example 72e

To a solution of Example 72c (4.5 g, 22.0 mmol) in DMF (45 mL) were added Example 72d (6.7 g, 24.1 mmol) and PPh₃ (11.5 g, 43.9 mmol). Then the mixture was cooled to 0° C. and DIAD (6.7 g, 32.9 mmol) was added dropwise under N₂. The resulting mixture was stirred at this temperature for 10 min and warmed to r.t. for 1 h. The mixture was extracted with EtOAc (800 mL*2). The combined organic phase was washed with brine, dried over Na₂SO₄, filtrated and the filtrate was concentrated under reduced pressure. The residue was purified by silica gel chromatography (DCM/MeOH=15/1) to give the desired product Example 72e (2.1 g, yield 21%) as a white solid. LCMS [M+1]⁺=466.0

Step 3: Example 72f

To a solution of Example 72e (2.1 g, 4.5 mmol) in THF/MeOH/H₂O (60 mL/20 mL/20 mL) was added LiO.H₂O (285 mg, 6.8 mmol). The mixture was stirred at r.t. overnight. The solvent was evaporated and the residue was acidified with 3N HCl to pH 2~3. The resulting solution was extracted with EtOAc, and the organic layer was concentrated to give the desired product Example 241f (2.0 g, yield 99%) as a white solid. LCMS [M+1]⁺=452.0

Step 4: Example 72g

To a solution of Example 72f (500 mg, 1.1 mmol) in pyridine (100 mL) was added POCl₃ (1.7 g, 11 mmol) dropwise at 0° C. The mixture was stirred at 0° C. for 1 h under N₂. The reaction was quenched with H₂O (15 mL). The solvent was evaporated and MeOH (20 mL) was added to the residue. The suspension was stirred at r.t. for 10 min and filtrated. The solid was dried to give the desired product Example 72g (500 mg, crude) as a pink solid, which was used in next step. LCMS [M+1]⁺=434.0

Step 5: Example 72

To a solution of Example 72g (300 mg, 0.69 mmol) in Dioxane/H₂O (6 mL/3 mL) were added Example 72h (104 mg, 0.76 mmol), Na₂CO₃ (220 mg, 2.1 mmol) and Pd(dppf)Cl₂ (51 mg, 0.07 mmol). The mixture was stirred at 95° C. for 3 h under N₂. The mixture was filtrated and the filtrate was concentrated under reduced pressure. The residue was purified by silica gel chromatography (DCM/MeOH=15/1) to obtained 20 mg brown solid, which was slurried (EtOAc/MeOH=20/1) to give the desired product Example 72 (18.6 mg, yield 7% over two steps) as a pale-brown solid. LCMS [M+1]⁺=399.0. ¹H NMR (400 MHz, DMSO-d₆) δ 10.53 (s, 1H), 8.72 (d, J=22.3 Hz, 2H), 8.15 (d, J=8.3 Hz, 1H), 8.05-7.88 (m, 3H), 7.78 (dd, J=15.8, 7.9 Hz, 2H), 7.30 (d, J=8.2 Hz, 1H), 7.16 (d, J=8.7 Hz, 1H), 5.31 (m, 2H), 4.52 (m, 2H), 2.52 (s, 3H).

Example 73: General Procedure for Synthesis of Compound Example 73

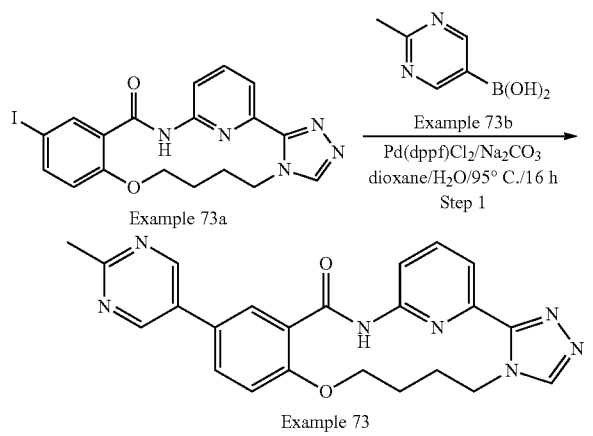

To a mixture of Example 73a (200 mg, 0.43 mmol), Example 73b (66 mg, 0.47 mmol), Na₂CO₃ (138 mg, 1.3 mmol) in dioxane (4 mL) and H₂O (2 mL) was added Pd(dppf)Cl₂ (32 mg, 0.04 mmol). Then the mixture was degassed by bubbling N₂ through the solution for 2 min using a syringe needle. After that, the mixture was heated at 95° C. for 16 h. The mixture was directly purified by silica gel chromatography (DCM/MeOH=20/1) and prep-TLC (DCM/MeOH=15/1) to give the desired product (Example 73, 8 mg, yield 4%) as a white solid. LCMS [M+1]⁺=214.6/418.0. ¹H NMR (400 MHz, Chloroform-d) δ 11.44 (s, 1H), 8.89 (s, 2H), 8.52 (d, J=2.5 Hz, 1H), 8.23 (s, 1H), 8.09-8.03 (m, 2H), 7.94 (t, J=7.9 Hz, 1H), 7.75-7.71 (m, 1H), 7.19 (d, J=8.6 Hz, 1H), 4.43-4.26 (m, 4H), 2.80 (s, 3H), 2.75 (br, 2H), 2.12 (br, 2H).

Example 74: General Procedure for Synthesis of Compound Example 74

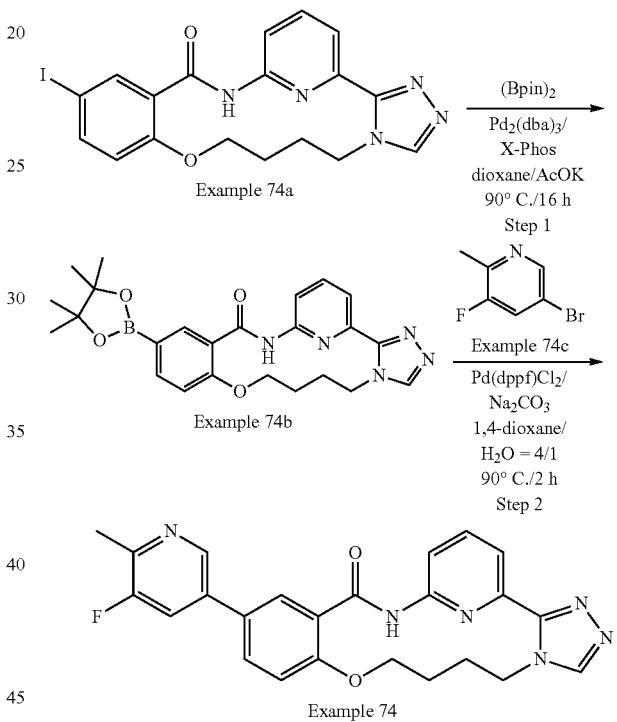

Step 1: Example 74b

To a solution of Example 74a (2.0 g, 4.3 mmol), (Bpin)₂ (3.3 g, 13.0 mmol) in 1,4-dioxane (25 mL) were added Pd₂(dba)₃ (400 mg, 0.43 mmol), x-phos (210 mg, 0.43 mmol) and KOAc (850 mg, 8.7 mmol). The mixture was degassed by nitrogen for three times and heated at 100° C. for 16 h. The reaction mixture was filtered, washed with EtOAc/MeOH (v/v=10/1) and concentrated. The residue was purified by silica gel chromatography (DCM/MeOH=96/4) to afford the desired product Example 74b (1.4 g, yield 70%) as a yellowish solid. LCMS [M+1]⁺=462.1

Step 2: Example 74

To a solution of Example 74b (150 mg, 0.33 mmol), Example 74c (68 mg, 0.36 mmol) in 1,4-dioxane/H₂O (4 mL/1 mL) were added Pd(dppf)Cl₂ (24 mg, 0.033 mmol)

and Na$_2$CO$_3$ (70 mg, 0.66 mmol). The mixture was degassed by nitrogen for three times and heated at 95° C. for 2 h. The reaction mixture was filtered, washed with EtOAc and concentrated. The residue was purified by prep-TLC (DCM/MeOH=15/1) to afford the crude product, which was triturated in MeOH (5 mL), filtered and dried to give the desired product Example 74 (30 mg, yield 21%) as a gray solid. LCMS [M/2+1]$^+$=223.1. $^1$H NMR (400 MHz, DMSO-d$_6$) δ 11.18 (s, 1H), 8.67 (s, 1H), 8.64 (d, J=1.8 Hz, 1H), 8.25 (d, J=2.5 Hz, 1H), 8.05 (t, J=7.9 Hz, 1H), 7.97 (ddd, J=8.4, 7.1, 2.2 Hz, 2H), 7.86 (dd, J=13.6, 7.8 Hz, 2H), 7.38 (d, J=8.7 Hz, 1H), 4.36 (t, J=5.1 Hz, 2H), 4.28-4.21 (m, 2H), 2.46 (d, J=3.0 Hz, 3H), 2.42 (d, J=8.6 Hz, 2H), 2.00-1.88 (m, 2H).

Example 75: General Procedure for Synthesis of Compound Example 75

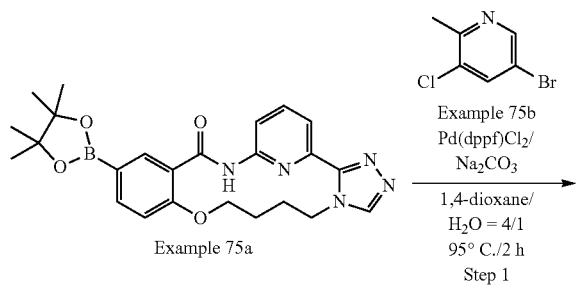

To a solution of Example 75a (150 mg, 0.33 mmol), Example 75b (75 mg, 0.36 mmol) in 1,4-dioxane/H$_2$O (4 mL/1 mL) were added Pd(dppf)Cl$_2$ (24 mg, 0.033 mmol) and Na$_2$CO$_3$ (70 mg, 0.66 mmol). The mixture was degassed by nitrogen for three times and heated at 95° C. for 2 h. The reaction mixture was filtered, washed with EtOAc and concentrated. The residue was purified by prep-TLC (DCM/MeOH=15/1) to give the desired product Example 75 (49.0 mg, yield 33%) as a gray solid. LCMS [M/2+1]$^+$=231.0. $^1$H NMR (400 MHz, DMSO-d$_6$) δ 11.18 (s, 1H), 8.73 (d, J=2.1 Hz, 1H), 8.68 (s, 1H), 8.24 (d, J=2.6 Hz, 1H), 8.18 (d, J=2.1 Hz, 1H), 8.04 (d, J=7.9 Hz, 1H), 7.98 (dd, J=8.7, 2.6 Hz, 1H), 7.86 (dd, J=13.0, 7.8 Hz, 2H), 7.39 (d, J=8.6 Hz, 1H), 4.36 (t, J=5.0 Hz, 2H), 4.30-4.20 (m, 2H), 2.56 (s, 3H), 2.43 (br, 2H), 1.96 (d, J=7.1 Hz, 2H).

Example 77: General Procedure for Synthesis of Compound Example 77

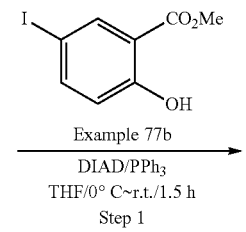

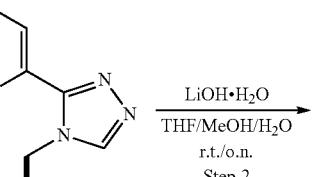

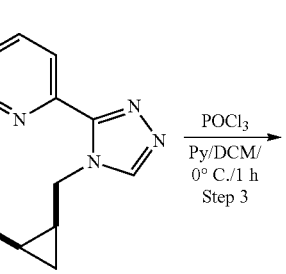

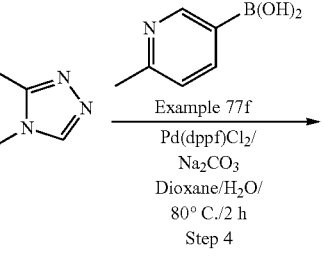

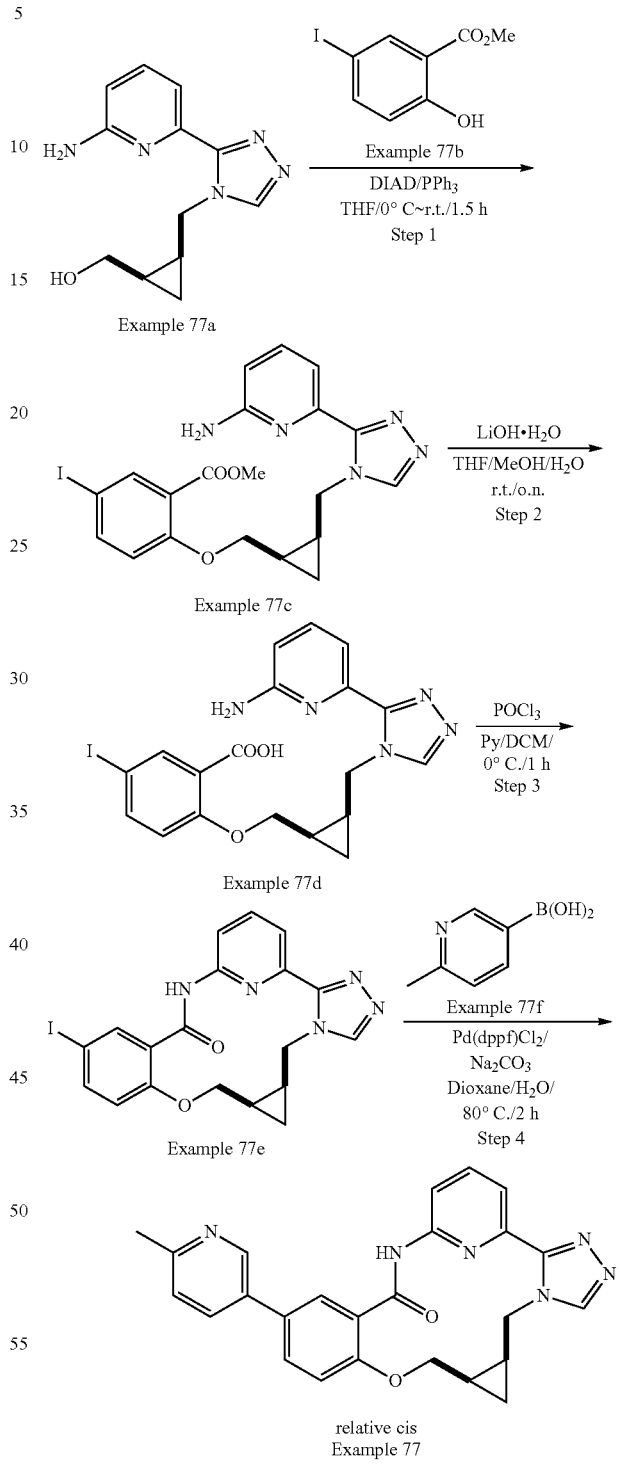

relative cis
Example 77

Step 1: Example 77c

To a solution of Example 77a (800 mg, 3.26 mmol) in THF (16 mL) was added Example 77b (908 mg, 3.26 mmol) and PPh$_3$ (3.4 g, 13.1 mmol). Then the mixture was cooled

215 to 0° C. and DIAD (3.3 g, 16.3 mmol) was added dropwise under N₂. The resulting mixture was stirred at this temperature for 10 min and warmed to r.t. for 1 h. The mixture was extracted with EtOAc (50 mL*2). The combined organic phase was washed with brine, dried over Na₂SO₄, filtrated and the filtrate was concentrated under reduced pressure. The residue was purified by silica gel chromatography (DCM/MeOH=20/1) to give the desired product Example 77c (930 mg, yield 58%) as a yellow solid. LCMS [M+1]⁺=505.9

Step 2: Example 77d

To a solution of Example 77c (730 mg, 1.44 mmol) in THF/MeOH/H₂O (7 mL/7 mL/3 mL) was added LiO.H₂O (182 mg, 4.34 mmol). The mixture was stirred at r.t. overnight. The solvent was evaporated and the residue was acidified by 2N HCl to pH=4~5. The resulting suspension was filtrated, and the solid was dried to give the desired product Example 77d (490 mg, yield 69%) as a yellow solid. LCMS [M+1]⁺=491.9

Step 3: Example 77e

To a solution of Example 77d (70 mg, 0.14 mmol) in DCM/pyridine (10 mL/1 mL) was added POCl₃ (109 mg, 0.71 mmol) dropwise at 0° C. The mixture was stirred at 0° C. for 1 h under N₂. The reaction was quenched with H₂O (0.5 mL). The solvent was evaporated and H₂O (2 mL) was added to the residue. The suspension was stirred at r.t. for 10 min and filtrated. The solid was dried to give the desired product Example 77e (45 mg, crude) as a yellow solid, which was used in next step. LCMS [M+1]⁺=473.9

Step 4: Example 77

To a solution of Example 77e (45 mg, 0.10 mmol) in Dioxane/H₂O (2 mL/0.4 mL) were added Example 77f (26 mg, 0.19 mmol), Na₂CO₃ (30 mg, 0.28 mmol) and Pd(dppf)Cl₂ (7 mg, 0.01 mmol). The mixture was stirred at 80° C. for 2 hs under N₂. The mixture was filtrated and the filtrate was concentrated under reduced pressure. The residue was purified by Prep-HPLC to give the desired product Example 77 (2 mg, yield 5% over two steps) as a white solid. LCMS [M+1]⁺=439.0. ¹H NMR (400 MHz, DMSO-d₆) δ 10.75 (s, 1H), 8.77 (s, 1H), 8.75 (d, J=2.5 Hz, 1H), 8.03 (t, J=7.9 Hz, 1H), 8.00-7.95 (m, 2H), 7.87-7.82 (m, 2H), 7.69 (d, J=8.0 Hz, 1H), 7.43 (d, J=8.7 Hz, 1H), 7.32 (d, J=8.1 Hz, 1H), 4.95 (dd, J=14.0 Hz, 3.2 Hz, 1H), 4.79 (dd, J=13.8, 8.8 Hz, 1H), 4.63 (dd, J=11.1, 4.7 Hz, 1H), 4.30 (dd, J=11.1, 9.3 Hz, 1H), 2.48 (s, 3H), 1.46-1.37 (m, 1H), 1.17-1.10 (m, 1H), 0.64-0.58 (m, 1H), 0.50-0.44 (m, 1H).

Example 78: General Procedure for Synthesis of Compound Example 78

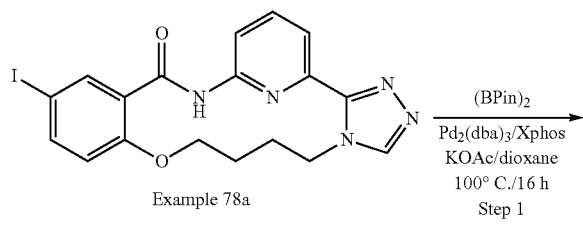

216

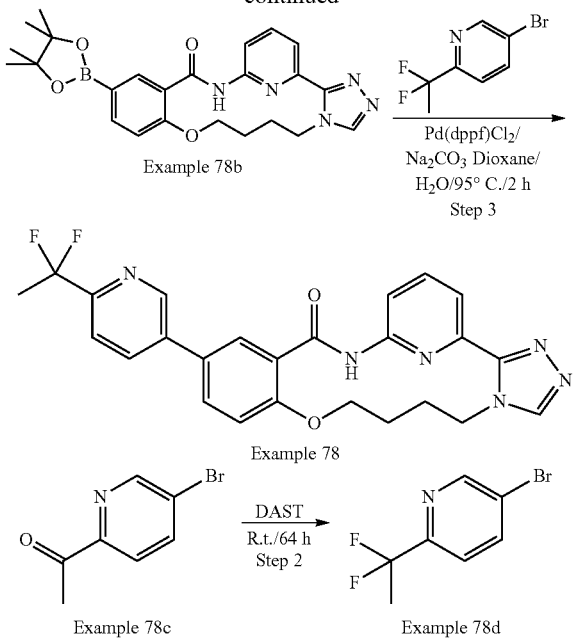

Step 1: Example 78b

To a solution of Example 78a (1.0 g, 2.2 mmol), (Bpin)₂ (1.7 g, 6.5 mmol) in 1,4-dioxane (10 mL) were added Pd₂(dba)₃ (199 mg, 0.2 mmol), x-phos (103 mg, 0.2 mmol) and KOAc (425 mg, 4.3 mmol). The mixture was degassed by nitrogen for three times and heated at 100° C. for 16 h. The reaction mixture was filtered, the filtrate was concentrated and purified by silica gel chromatography (DCM/MeOH=10/1) to afford the desired product Example 78b (400 mg, yield 40%) as a pale-yellow solid. LCMS [M+1]⁺=462.1

Step 2: Example 78d

To a solution of Example 78c (500 mg, 2.5 mmol) in DAST (5 mL) was stirred at r.t. for 64 h. The solution was quenched with ice water, extracted with EtOAc, and the organic layer was concentrated to afford the crude product Example 78d (500 mg, yield 90%) as brown oil.

Step 3: Example 78

To a solution of Example 78b (100 mg, 0.22 mmol), Example 78d (53 mg, 0.24 mmol) in 1,4-dioxane/H₂O (4 mL/1 mL) were added Pd(dppf)Cl₂ (16 mg, 0.02 mmol) and Na₂CO₃ (69 mg, 0.65 mmol). The mixture was degassed by nitrogen for three times and heated at 95° C. for 2 h. The reaction mixture was filtered, washed with EtOAc and concentrated. The residue was purified by prep-TLC (DCM/MeOH=20/1) to afford the crude product, which was further purified by Prep-HPLC to give the desired product Example 78 (4.1 mg, yield 4%) as a pink solid. LCMS [M+1]⁺=477.0. ¹H NMR (400 MHz, DMSO-d₆) δ 11.20 (s, 1H), 8.99 (s, 1H), 8.67 (s, 1H), 8.28 (d, J=10.2 Hz, 2H), 8.10-7.97 (m, 2H), 7.87 (dd, J=15.5, 7.9 Hz, 2H), 7.77 (d, J=8.2 Hz, 1H), 7.43 (d, J=8.7 Hz, 1H), 4.38 (br, 2H), 4.25 (br, 2H), 2.48 (m, 2H), 2.16-1.84 (m, 5H).

Example 79: General Procedure for Synthesis of Compound Example 79

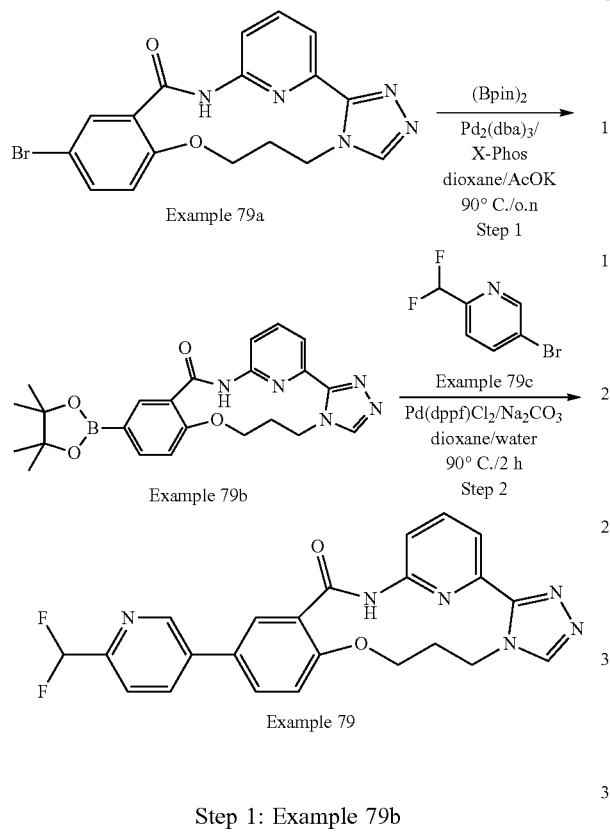

Step 1: Example 79b

To a solution of Example 79a (700 mg, 1.75 mmol), (Bpin)$_2$ (1.3 g, 5.25 mmol) in 1,4-dioxane (10 mL) were added Pd$_2$(dba)$_3$ (160 mg, 0.175 mmol), x-phos (85 mg, 0.175 mmol) and KOAc (345 mg, 3.5 mmol). The mixture was degassed by nitrogen for three times and heated at 100° C. for 16 h. The reaction mixture was filtered, washed with EtOAc/MeOH and concentrated. The residue was purified by silica gel chromatography (DCM/MeOH=87/13) to afford the desired product Example 79b (570 mg, yield 73%) as a yellow solid. LCMS [M+1]$^+$=448.1

Step 2: Example 79

To a solution of Example 79b (645 mg, 1.44 mmol), Example 79c (250 mg, 1.20 mmol) in 1,4-dioxane/H$_2$O (8 mL/2 mL) were added Pd(dppf)Cl$_2$ (88 mg, 0.12 mmol) and Na$_2$CO$_3$ (255 mg, 2.40 mmol). The mixture was degassed by nitrogen for three times and heated at 95° C. for 2 h. The reaction mixture was filtered, washed with EtOAc and concentrated. The residue was purified by silica gel chromatography (DCM/MeOH=81/19) to afford the crude product (380 mg) which was triturated by DMSO (5 mL), filtered and the DMSO solution was further purified by Prep-HPLC to give the desired product Example 79 (28 mg, yield 5%) as an off-white solid. LCMS [M/2+1]$^+$=225.0. $^1$H NMR (400 MHz, DMSO-d$_6$) δ 10.40 (s, 1H), 8.92 (s, 1H), 8.73 (s, 1H), 8.20 (d, J=8.6 Hz, 1H), 7.91 (t, J=7.8 Hz, 1H), 7.81 (d, J=7.7 Hz, 1H), 7.75 (d, J=8.6 Hz, 2H), 7.69 (d, J=8.2 Hz, 1H), 7.33 (d, J=8.0 Hz, 1H), 7.16 (d, J=8.5 Hz, 1H), 6.96 (t, J=55.0 Hz, 1H), 4.13 (m, 2H), 3.25 (m, 2H), 2.20 (m, 2H).

Example 80: General Procedure for Synthesis of Compound Example 80

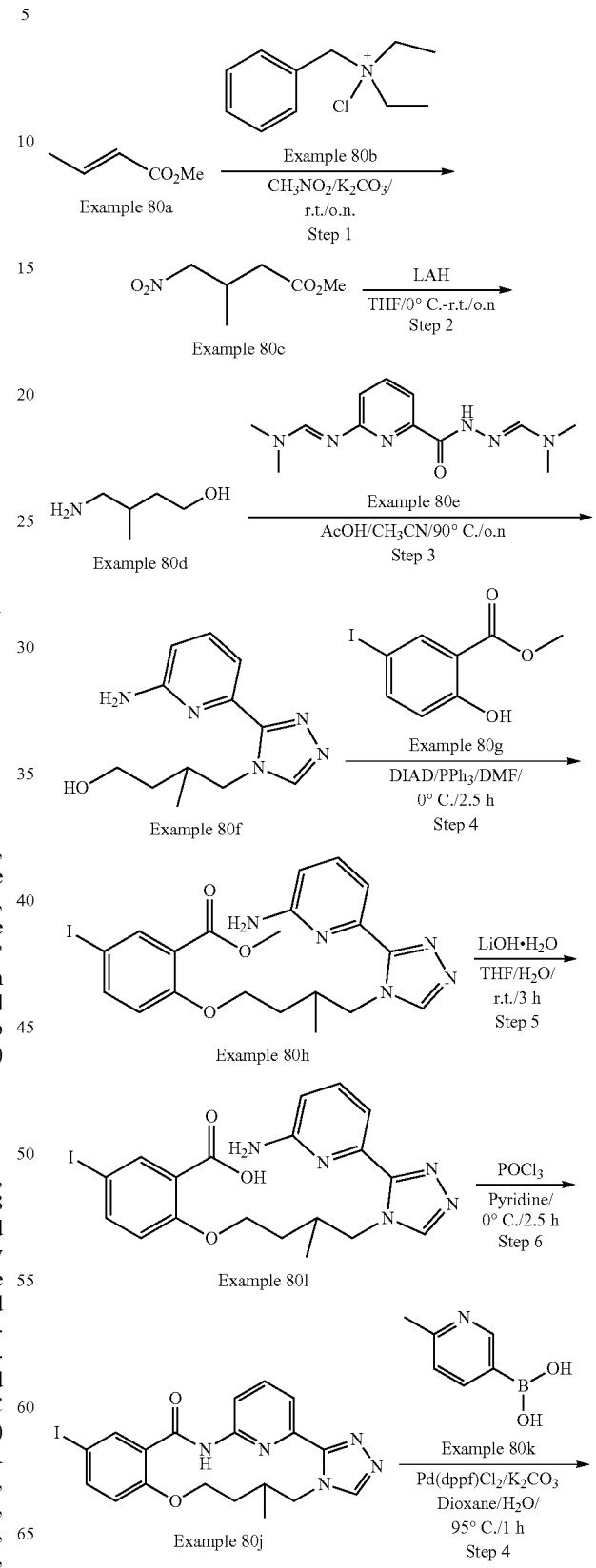

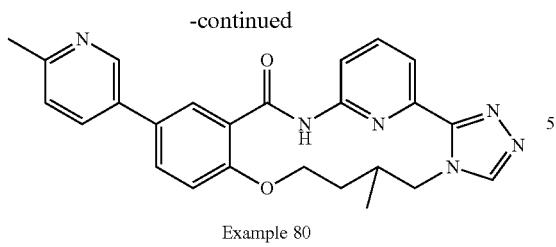

Example 80

Step 1: Example 80c

A slurry of Example 80a (20.0 g, 200 mmol), Example 80b (19.8 g, 100 mmol), CH$_3$NO$_2$ (89.0 g, 1400 mmol), and K$_2$CO$_3$ (19.3 g, 140 mmol) was stirred at r.t. for overnight. The mixture was diluted by DCM (200 mL), and filtered. The organic layer was concentrated and purified by silica gel chromatography (DCM/MeOH=50/1) to give the desired product Example 80c (30.0 g, yield 94%) as colorless oil.

Step 2: Example 80d

To a mixture of Example 80c (30.0 g, 204 mmol) in THF (500 mL) was added LAH (27.1 g, 714 mmol) at 0° C. carefully. The mixture was stirred at r.t. for overnight. The mixture was cooled to −5° C., and quenched by 15% NaOH (100 mL), which was then filtered. The filtrate was concentrated to give the desired product Example 80d (35.0 g, crude yield 166%) as colorless oil. LCMS [M+1]$^+$=104.1.

Step 3: Example 80f

A mixture of Example 80d (20.0 g, crude), Example 80e (27.0 g, 105 mmol) in MeCN/AcOH (200 mL, v/v=4/1) was heated at 90° C. for overnight. Then the mixture was concentrated under reduced pressure and to the residue was added MeOH (100 mL)/conc. HCl (50 mL, 6 N), which was stirred at r.t. for 1 h. Then the mixture was adjusted pH to 7.0 and concentrated under reduced pressure. The residue was directly purified by silica gel chromatography (DCM/MeOH=10/0-10/1) to give the desired product Example 80f (2.2 g, yield 9%) as a pale-yellow solid. LCMS [M+1]$^+$=248.1.

Step 4: Example 80h

A slurry of Example 80f (2.25 g, 8.1 mmol), Example 80g (2.0 g, 8.1 mmol) and PPh$_3$ (2.56 g, 9.7 mmol) in dry DMF (20 mL) under N$_2$ was cooled to 0° C. Then, DIAD (1.96 g, 9.7 mmol) was added to the above mixture dropwise, which was stirred at 0° C. for 2.5 h. To the mixture was added water (20 mL), which was then extracted with EtOAc (30 mL*3). The combined organic layer was dried over anhydrous magnesium sulfate and concentrated under reduced pressure. The residue was purified by silica gel chromatography (DCM/MeOH=20/1) to give the desired product Example 80h (2.9 g, yield 70%) as a yellow solid. LCMS [M+1]$^+$=507.9

Step 5: Example 80i

To a mixture of Example 80h (2.9 g, 5.72 mmol) in THF (10 mL) was added LiO.H$_2$O (2.3 g, 57.2 mmol) in H$_2$O (20 mL). The mixture was stirred at r.t. for 3 h. The pH of the mixture was adjusted to 3, which was then concentrated in vacuo to give the crude product Example 80i (6.7 g, containing LiCl salt, crude yield 236%) as a white solid. LCMS [M+1]$^+$=493.9

Step 6: Example 80j

To a mixture of Example 80i (6.5 g, 13.2 mmol) in pyridine (100 mL) at 0° C. was added POCl$_3$ (2.0 g, 13.2 mmol) slowly. The mixture was stirred at 0° C. for 2.5 h. To the mixture was added water (30 mL), which was concentrated under reduced pressure. MeOH (60 mL) and H$_2$O (60 mL) was added and the resulting mixture was stirred at r.t. for 15 min, and then filtered. The filtered cake was washed with MeOH, dried in vacuo to give the desired product Example 80j (2.4 g, yield 38%) as a pink solid. LCMS [M+1]$^+$=475.9

Step 4: Example 80

To a mixture of Example 80j (475 mg, 1.0 mmol), Example 80k (138 mg, 1.0 mmol), and K$_2$CO$_3$ (690 mg, 5.0 mmol) in dioxane/H$_2$O (15 mL/3 mL) was added Pd(dppf)Cl$_2$ (111 mg, 0.15 mmol). Then the mixture was degassed by bubbling N$_2$ through the solution for 2 min using a syringe needle. After that, the mixture was heated at 95° C. for 1 h. The mixture was concentrated and directly purified by silica gel chromatography (DCM/MeOH=20/1), followed by prep-TLC (DCM/MeOH=15/1) to give the desired product Example 80 (12.6 mg, yield 3%) as a white solid. LCMS [M+1]$^+$=441.0. $^1$H NMR (400 MHz, DMSO-d$_6$) δ 11.25 (s, 1H), 8.75 (d, J=2.4 Hz, 1H), 8.67 (s, 1H), 8.23 (d, J=2.5 Hz, 1H), 8.05 (t, J=7.9 Hz, 1H), 7.97 (dd, J=8.0, 2.5 Hz, 1H), 7.94 (dd, J=8.6, 2.4 Hz, 1H), 7.88 (dd, J=10.9, 7.8 Hz, 2H), 7.39 (d, J=8.6 Hz, 1H), 7.33 (d, J=8.1 Hz, 1H), 4.58-4.51 (m, 1H), 4.43 (dd, J=13.4, 3.1 Hz, 1H), 4.28 (t, J=10.3 Hz, 1H), 3.87 (t, J=12.5 Hz, 1H), 3.26 (d, J=10.6 Hz, 1H), 2.48 (s, 3H), 2.04 (t, J=12.9 Hz, 1H), 1.68 (t, J=12.2 Hz, 1H), 0.95 (d, J=6.5 Hz, 3H).

Example 81: General Procedure for Synthesis of Compound Example 81

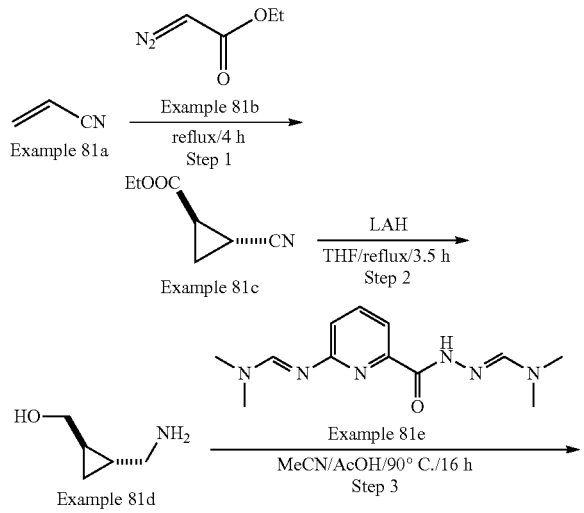

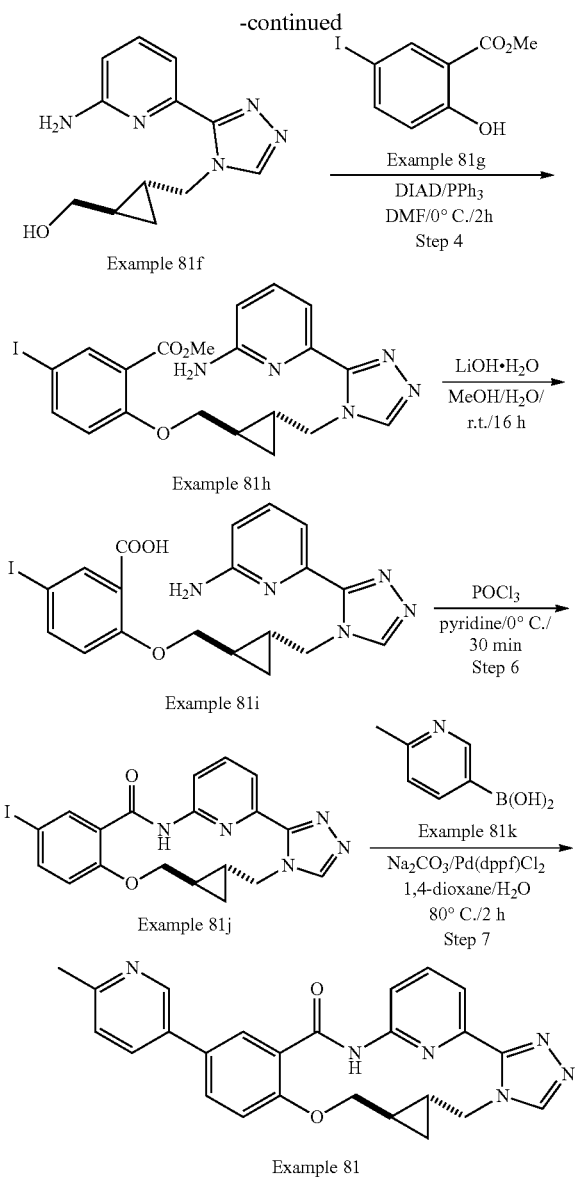

Step 3: Example 81f

A solution of Example 81d (5.6 g, 55.4 mmol) and Example 81e (7.2 g, 27.7 mmol) in MeCN/AcOH (160 mL/40 mL) was stirred at 90° C. for 16 h. The mixture was concentrated under vacuum. The residue was added 1N HCl (20 mL, aq.) and stirred at r.t. for 4 h. Then the mixture was adjusted to pH=11 with 30% NaOH solution. The mixture was concentrated under reduced pressure. The residue was purified by silica gel column (DCM/MeOH=10/1) to give the desired product Example 81f (2.8 g, yield 41%) as yellow oil. LCMS [M+1]$^+$=246

Step 4: Example 81h

To a solution of Example 81f (1.0 g, 4 mmol), Example 81g (1.1 g, 4 mmol) and PPh$_3$ (4.1 g, 16 mmol) in dry DMF was added DIAD at 0° C. and the mixture was stirred at 0° C. for 2 h. The mixture was diluted with water and extracted with EtOAc (200 mL*2). The combined organic layer was dried over anhydrous magnesium sulfate and concentrated under reduced pressure. The residue was purified by silica gel chromatography (DCM/MeOH=10/1) to give the desired product Example 81h (900 mg, yield 44%) as a white solid. LCMS [M+1]$^+$=505.9.

Step 5: Example 81i

A mixture of Example 81h (900 mg, 1.8 mmol) and LiO.H$_2$O (227 mg, 5.4 mmol) in MeOH/H$_2$O (10 mL/10 mL) was stirred at r.t. for 16 h. The solvent was concentrated and the residue was adjusted to pH about 5 with 1N HCl (aq.). The mixture was filtered to give the desired product Example 81i (700 mg, yield 79%) as a yellow solid. LCMS [M+1]$^+$=491.9.

Step 6: Example 81j

To a solution of Example 81i (350 mg, 0.7 mmol) in pyridine/DCM (12 mL/120 mL) was added POCl$_3$ (322 mg, 2.1 mmol) at 0° C. and the mixture was stirred at 0° C. for 30 min. The mixture was diluted with water and concentrated. The residue was washed by MeOH/H$_2$O (10 mL/10 mL) to give the desired product Example 81j (250 mg, yield 75%) as a red solid. LCMS [M+1]$^+$=473.9

Step 7: Example 81

A solution of Example 81j (250 mg, 0.5 mmol), Example 81k (137 mg, 1.0 mmol) Na$_2$CO$_3$ (159 mg, 1.5 mmol) and Pd(dppf)Cl$_2$ (37 mg, 0.05 mmol) in 1,4-dioxane/H$_2$O (3 mL/0.5 mL) was degassed by N$_2$ for 2 times and stirred at 80° C. for 2 h. The mixture was diluted with water and extracted with EtOAc (100 mL*2). The combined organic layer was concentrated and purified by prep-TLC (DCM/MeOH=10/1) to give the desired product Example 81 (7 mg, yield 3%) as a white solid. LCMS [M+1]$^+$=439.0. $^1$H NMR (400 MHz, DMSO-d$_6$) δ 11.64 (s, 1H), 8.74 (d, J=11.7 Hz, 2H), 8.29 (s, 1H), 8.07 (t, J=7.9 Hz, 1H), 7.99 (t, J=7.6 Hz, 2H), 7.92 (d, J=8.7 Hz, 1H), 7.85 (d, J=7.5 Hz, 1H), 7.50 (d, J=8.7 Hz, 1H), 7.34 (d, J=8.0 Hz, 1H), 5.28 (t, J=7.6 Hz, 1H), 4.87 (d, J=13.9 Hz, 1H), 3.63-3.52 (m, 1H), 3.41 (t, J=10.0 Hz, 1H), 2.50 (s, 3H), 2.13 (m, 1H), 1.38 (m, 1H), 1.09 (m, 1H), 0.78 (m, 1H).

Step 1: Example 81c

Example 81a (38 g, 700 mmol) was stirred under reflux as Example 81b (40 g, 350 mmol) was added dropwise over period of 2.5 h. After completion of addition, the mixture was stirred at reflux for addition 1.5 h. The reaction was distilled under vacuum to give the desired product Example 81c (7.9 g, yield 16%) as yellow oil. LCMS [M+1]$^+$=139.9

Step 2: Example 81d

To a solution of LAH (3.2 g, 85.2 mmol) in dry THF (120 mL) was stirred under reflux as Example 81c (7.9 g, 56.8 mmol) in THF (20 mL) was added dropwise over period of 2 h. After addition, the mixture was stirred at reflux for addition 1.5 h. The mixture was carefully quenched by water blew 20° C. Then the mixture was filtered and the filtrate was concentrated to give the crude product Example 81d (6.6 g, yield 100%) as yellow oil. LCMS [M+1]$^+$=102.

Example 82: General Procedure for Synthesis of Compound Example 82

Example 83: General Procedure for Synthesis of Compound Example 83

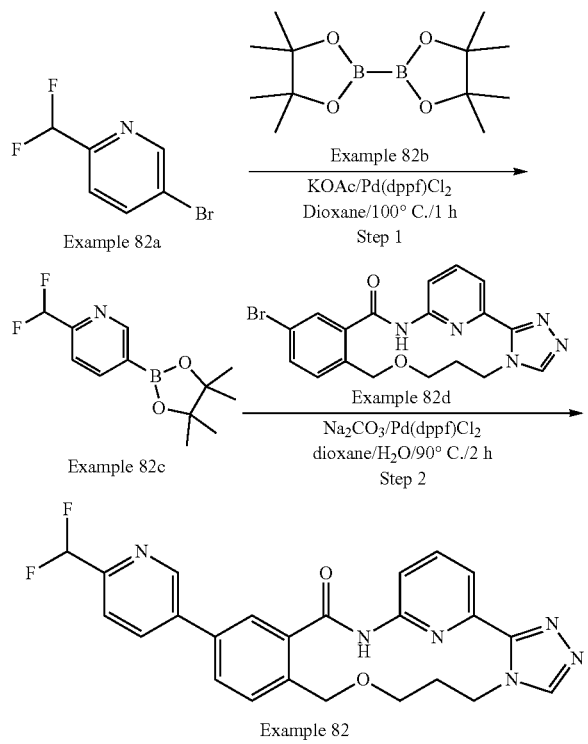

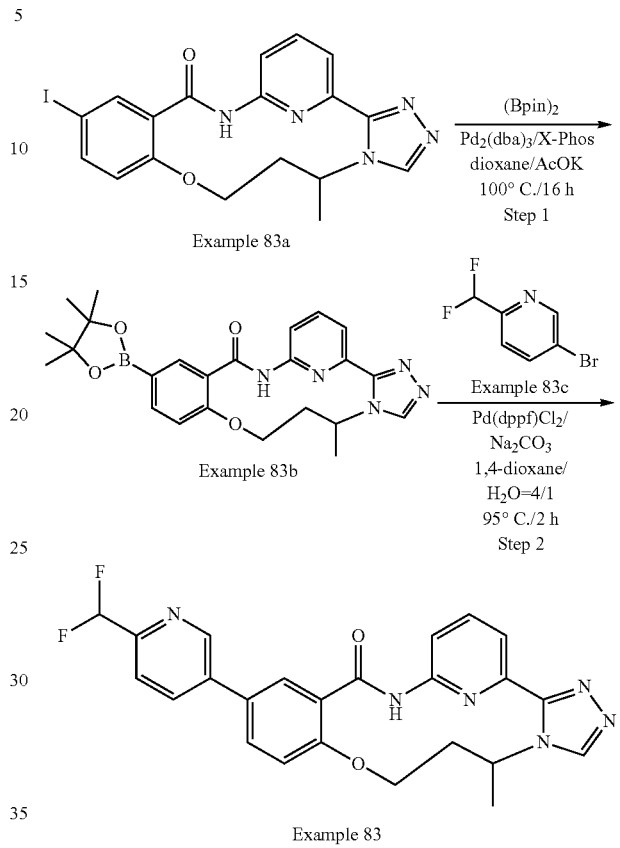

Step 1: Example 82c

To a mixture of Example 82a (50 mg, 0.24 mmol), Example 82b (66 mg, 0.26 mmol), and KOAc (47 mg, 0.48 mmol) in Dioxane (2 mL) was added Pd(dppf)Cl$_2$ (17 mg, 0.024 mmol). Then the mixture was degassed by bubbling N$_2$ through the solution for 2 min using a syringe needle. After heated at 100° C. for 1 h, the mixture was cooled to r.t. and filtered. The filtrate Example 82c (2 mL) was used for next step directly. LCMS [M+1]$^+$=256.0

Step 2: Example 82

To the Example 82c (2 mL, from Step 1) was added Example 82d (15 mg, 0.036 mmol), Na$_2$CO$_3$ (12 mg, 0.11 mmol), Pd(dppf)Cl$_2$ (5 mg) and H$_2$O (0.2 mL). Then the mixture was degassed by bubbling N$_2$ through the solution for 2 min using a syringe needle. After heating at 90° C. for 2 h, the mixture was concentrated under reduced pressure. The residue was purified by Prep-HPLC to give the desired product Example 82 (6.0 mg, yield 36%) as a white solid. LCMS [M+1]$^+$=463.0. $^1$H NMR (400 MHz, Chloroform-d) δ 10.50 (s, 1H), 8.93 (s, 1H), 8.25-8.06 (m, 5H), 7.97 (t, J=7.9 Hz, 1H), 7.83-7.73 (m, 2H), 7.63 (d, J=7.9 Hz, 1H), 6.71 (t, J=54.0 Hz, 1H), 4.78 (t, J=5.3 Hz, 2H), 4.70 (s, 2H), 4.02-3.92 (m, 2H), 2.36 (dt, J=10.8, 6.6 Hz, 2H).

Step 1: Example 83b

To a solution of Example 83a (200 mg, 0.43 mmol), (Bpin)$_2$ (330 mg, 1.3 mmol) in 1,4-dioxane (4 mL) were added Pd$_2$(dba)$_3$ (40 mg, 0.04 mmol), x-phos (21 mg, 0.04 mmol) and KOAc (85 mg, 0.87 mmol). The mixture was degassed by nitrogen for three times and heated at 100° C. for 16 h. The reaction mixture was filtered, washed with MeOH (5 mL) and concentrated. The residue was purified by silica gel chromatography (DCM/MeOH=96/4) to afford the desired product Example 83b (150 mg, yield 75%) as a yellow solid. LCMS [M+1]$^+$=462.1

Step 2: Example 83

To a solution of Example 83b (150 mg, 0.33 mmol), Example 83c (74 mg, 0.36 mmol) in 1,4-dioxane/H$_2$O (4 mL/1 mL) were added Pd(dppf)Cl$_2$ (24 mg, 0.033 mmol) and Na$_2$CO$_3$ (103 mg, 0.98 mmol). The mixture was degassed by nitrogen for three times and heated at 95° C. for 2 h. The reaction mixture was filtered, washed with MeOH and concentrated. The residue was purified by prep-TLC (DCM/MeOH=15/1) to afford the crude product, which was triturated in MeOH (5 mL), filtered and dried to give the desired product Example 83 (25 mg, yield 17%) as a white solid. LCMS [M+1]$^+$=463.0. $^1$H NMR (400 MHz, DMSO-d$_6$) δ 10.56 (s, 1H), 8.95 (s, 1H), 8.87 (s, 1H), 8.56 (m, 1H), 8.13 (m, 1H), 7.88 (m, 1H), 7.74 (m, 1H), 7.66 (d, J=8.4 Hz, 1H), 7.60 (m, 1H), 7.38-7.35 (m, 1H), 7.26-7.08 (m, 1H), 6.94 (t, J=54 Hz, 1H), 4.35 (m, 2H), 3.88 (m, 1H), 2.40 (m, 2H), 1.48 (d, J=7.2 Hz, 3H).

Example 84: General Procedure for Synthesis of Compound Example 84

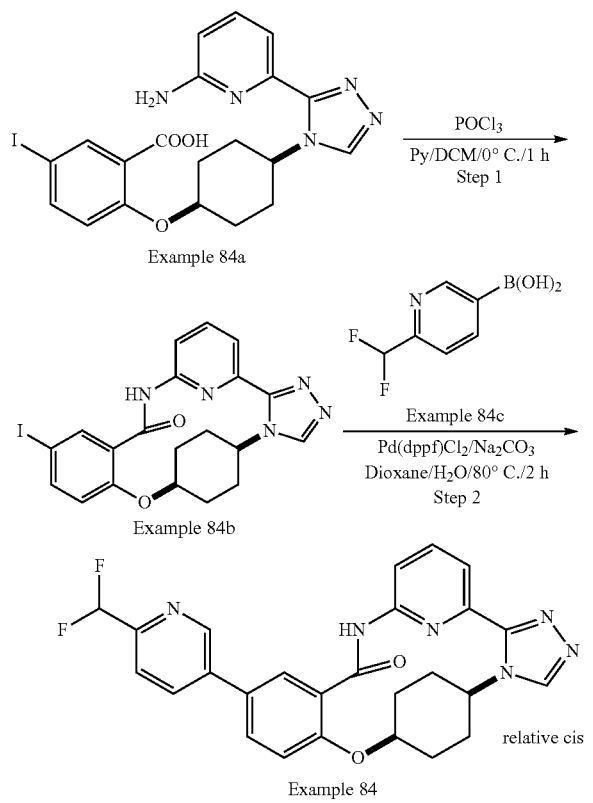

Step 1: Example 84b

To a solution of Example 84a (500 mg, 1.0 mmol) in DCM/pyridine (200 mL/20 mL) was added POCl₃ (1.5 g, 10.0 mmol) dropwise at 0° C. The mixture was stirred at 0° C. for 1 h under N₂. The reaction was quenched with H₂O (15 mL). The solvent was evaporated and MeOH (15 mL) was added to the residue. The suspension was stirred at r.t. for 10 min, filtrated, and dried to give the desired product Example 84b (80 mg, crude) as a yellow solid, which was used in next step. LCMS [M+1]⁺=487.9.

Step 5: Example 84

To a solution of Example 84b (80 mg, 0.16 mmol) in Dioxane/H₂O (3 mL/1.5 mL) were added Example 84c (31 mg, 0.18 mmol), Na₂CO₃ (52 mg, 0.49 mmol) and Pd(dppf)Cl₂ (12 mg, 0.02 mmol). The mixture was stirred at 95° C. for 3 h under N₂. The mixture was filtrated and the filtrate was concentrated under reduced pressure. The residue was purified by Prep-TLC (DCM/MeOH=20/1) and slurried (EtOAc/MeOH=20/1) to give the desired product Example 83 (15 mg, yield 19% over two steps) as a white solid. LCMS [M+1]⁺=489.0. ¹H NMR (400 MHz, DMSO-d₆) δ 10.29 (s, 1H), 9.02 (d, J=2.4 Hz, 1H), 8.68 (s, 1H), 8.36-8.23 (m, 1H), 8.09-7.97 (m, 2H), 7.92 (dd, J=8.8, 2.6 Hz, 1H), 7.74 (dd, J=10.9, 7.9 Hz, 2H), 7.63 (d, J=8.0 Hz, 1H), 7.39 (d, J=8.8 Hz, 1H), 7.00 (t, J=55.0 Hz, 1H), 5.02 (s, 1H), 4.64 (d, J=12.7 Hz, 1H), 2.94 (d, J=13.3 Hz, 2H), 1.97 (d, J=13.9 Hz, 2H), 1.67 (t, J=14.0 Hz, 2H), 1.53 (d, J=12.3 Hz, 2H).

Example 86: General Procedure for Synthesis of Compound Example 86

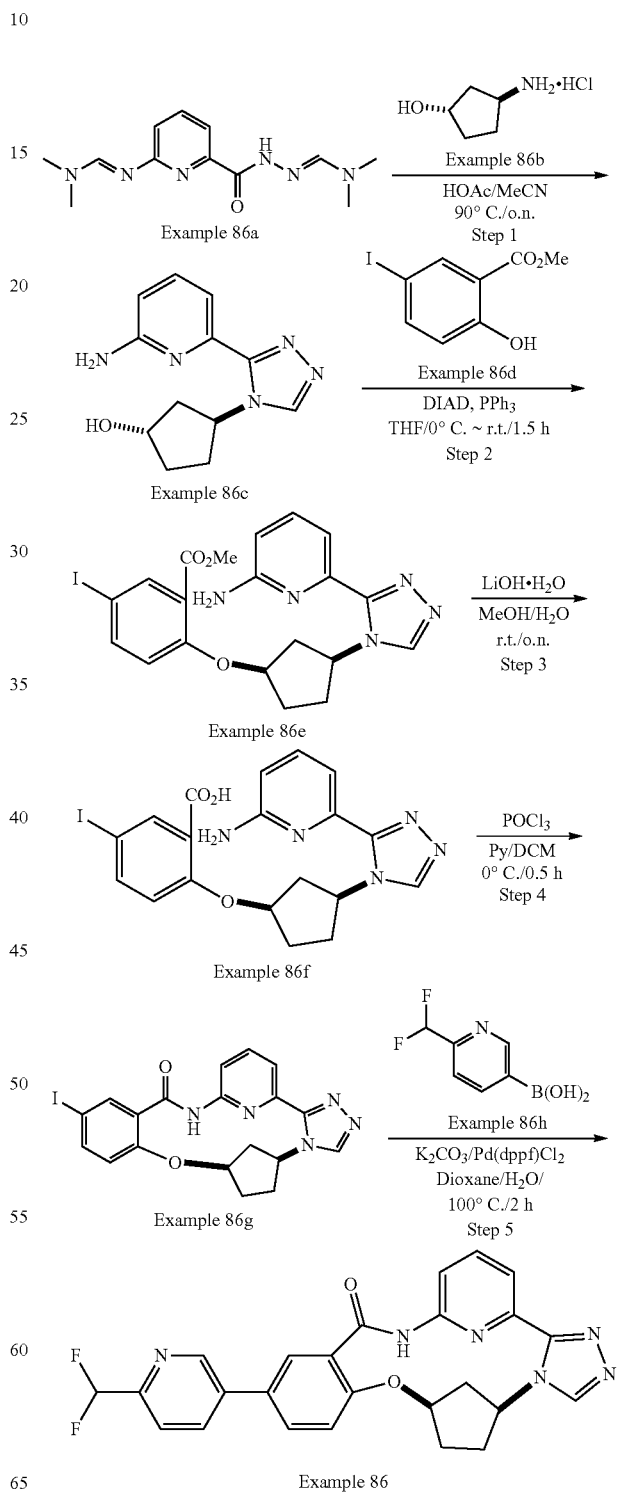

Step 1: Example 86c

To a solution of Example 86a (1.0 g, 3.82 mmol) in HOAc/MeCN (2 mL/8 mL) were added Example 86b (628 mg, 4.58 mmol). The mixture was stirred at 90° C. overnight under $N_2$. After overnight reaction, HCl (2 M, 10 mL) was added to the reaction solution, which was stirred for about 2 h. Then, the pH of the reaction solution was adjusted to about 9 by $K_2CO_3$ (aq.), and the mixture was concentrated under reduced pressure. MeOH/DCM (4 mL/20 mL) was added to the residue, which was filtered and the filtrate was purified by silica gel chromatography (DCM/MeOH=4/1) to give the desired product Example 86c (425 mg, yield 45%) as a white solid. LCMS $[M+1]^+=246.0$

Step 2: Example 86e

To the solution of Example 86c (425 mg, 1.73 mmol) in THF (10 mL) were added Example 86d (482 mg, 1.73 mmol) and $PPh_3$ (1.82 g, 6.94 mmol). The mixture was stirred at 0° C. for 10 min under $N_2$. Then, DIAD (1.75 g, 8.67 mmol) was slowly injected into the above mixture at 0° C. under $N_2$. After 1.5 h's reaction at r.t., the reaction solution was concentrated under reduced pressure, and the residue was purified by silica gel chromatography (DCM/MeOH=9/1) to give the desired product Example 86e (780 mg, yield 89%) as a pale-yellow solid. LCMS $[M+1]^+=505.9$

Step 3: Example 86f

To a solution of Example 86e (780 mg, 1.54 mmol) in MeOH/$H_2O$ (8 mL/2 mL) was added $LiOH·H_2O$ (324 mg, 7.72 mmol) with stirring at r.t. After overnight, the pH of the reaction solution was adjusted to nearly 5 by HCl (aq.). The mixture was then concentrated under reduce pressure, and the residue was mixed with water. The precipitate was collected and dried to give the desired product Example 86f (700 mg, yield 93%) as a pale-yellow solid. LCMS $[M+1]^+=491.9$

Step 4: Example 86g

To a solution of Example 86f (100 mg, 0.2 mmol) in DCM/pyridine (20 mL/2 mL) was added $POCl_3$ (153 mg, 1 mmol) solution in DCM (1 mL) with stirring at 0° C. After 0.5 h, water (5 mL) was added to quench the reaction. Then, the reaction mixture was concentrated under reduced pressure, and the residue was slurried by $H_2O$ and the solid was filtrated to give the crude product Example 86g (77 mg, yield 81%) as a pink solid. LCMS $[M+1]^+=473.9$

Step 5: Example 86

A mixture of Example 86g (77 mg, 0.16 mmol), Example 86h (28 mg, 0.16 mmol), $K_2CO_3$ (45 mg, 0.33 mmol), and Pd(dppf)$Cl_2$ (12 mg, 0.20 mmol) in dioxane/$H_2O$ (2 mL/1 mL) was stirred at 100° C. for 2 h. Then the solution was filtrated and purified by Prep-HPLC to give the crude product. The crude was purified by Prep-TLC (DCM/MeOH=10/1) to get the desired product Example 86 (6 mg, yield 8%) as a gray solid. LCMS $[M+1]^+=475.0$. $^1$H NMR (400 MHz, DMSO-$d_6$) δ 10.22 (s, 1H), 8.99 (d, J=2.3 Hz, 1H), 8.69 (s, 1H), 8.26 (dd, J=8.2, 2.3 Hz, 1H), 7.92 (d, J=2.4 Hz, 1H), 7.73 (d, J=8.2 Hz, 3H), 7.66 (s, 1H), 7.57 (s, 1H), 7.30 (s, 1H), 6.98 (t, J=55.0 Hz, 1H), 4.96 (s, 2H), 3.26 (s, 2H), 2.09 (s, 2H), 1.98 (q, J=7.2 Hz, 1H), 1.89-1.76 (m, 1H).

Example 87: General Procedure for Synthesis of Compound Example 87

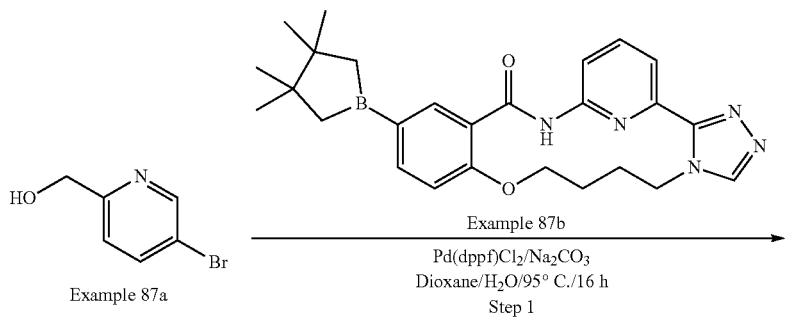

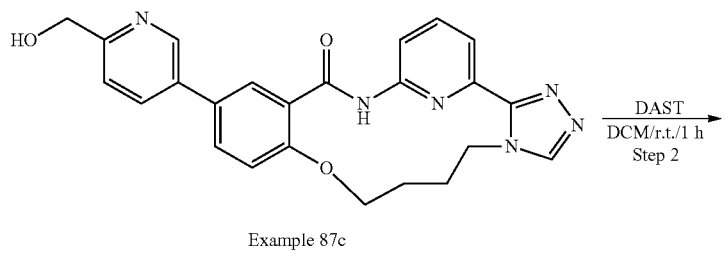

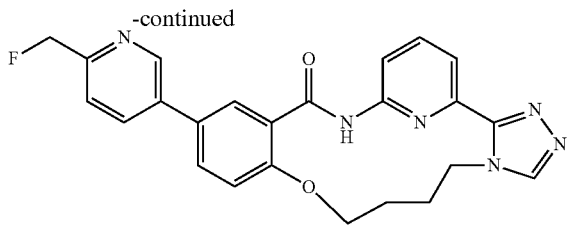

Example 87

Step 1: Example 87c

To a solution of Example 87a (147 mg, 0.78 mmol), Example 87b (400 mg, 0.87 mmol) in 1,4-dioxane/H$_2$O (6 mL/2 mL) were added Pd(dppf)Cl$_2$ (63 mg, 0.09 mmol) and Na$_2$CO$_3$ (276 mg, 2.6 mmol). The mixture was degassed by nitrogen for three times and heated at 95° C. for 16 h. The reaction mixture was filtered, washed with EtOAc and concentrated. The residue was purified by silica gel (DCM/MeOH=10/1) to give the desired product Example 87c (280 mg, yield 81%) as a yellow solid. LCMS [M/2+1]$^+$=222.

Step 2: Example 87

To a solution of Example 87c (150 mg, 0.34 mmol) in DCM (2 mL) was added DAST (1 mL) at 0° C., which was stirred at RT. for 1 h. The solution was quenched with ice water, extracted with EtOAc, and the organic layer was concentrated under reduced pressure. The residue was purified by Prep-HPLC to give the desired product Example 87 (2.5 mg, yield 2%) as a pray solid. LCMS [M+1]$^+$=445.0. $^1$H NMR (400 MHz, DMSO-d$_6$) δ 11.23 (s, 1H), 8.92 (s, 1H), 8.68 (s, 1H), 8.28 (d, J=2.5 Hz, 1H), 8.19 (d, J=8.3 Hz, 1H), 8.07 (t, J=7.9 Hz, 1H), 8.00 (dd, J=8.7, 2.5 Hz, 1H), 7.88 (dd, J=16.0, 7.8 Hz, 2H), 7.59 (d, J=8.2 Hz, 1H), 7.43 (d, J=8.7 Hz, 1H), 5.51 (d, J=47.0 Hz, 1H), 4.39 (s, 2H), 4.26 (t, J=8.6 Hz, 2H), 2.50 (br, 2H), 1.97 (br, 2H).

Example 88 & 89: General Procedure for Synthesis of Compounds Example 88 & Example 89

Step 1: Example 88 & Example 89

Example 56 (156 mg, 0.35 mmol) was purified by chiral HPLC (CHIRALCEL OD, 5.0 cm I.D.*25 cm L, 100% MeOH, 60 mL/min) to afford Example 88 (Peak 1, 47 mg, 99.61% ee, yield 60%) as a white solid, LCMS [M+1]$^+$=441.0, and Example 89 (Peak 2, 55 mg, 99.80% ee, yield 70%) as a pale-yellow solid, LCMS [M+1]$^+$=441.0. The structures were temporarily assigned.

NMR for Example 88

$^1$H NMR (400 MHz, DMSO-d$_6$) δ 11.28 (s, 1H), 8.85 (s, 1H), 8.75 (d, J=2.4 Hz, 1H), 8.20 (d, J=2.6 Hz, 1H), 8.07 (t, J=7.9 Hz, 1H), 7.97 (dd, J=8.1, 2.5 Hz, 1H), 7.92 (dd, J=8.6, 2.6 Hz, 1H), 7.86 (d, J=8.0 Hz, 1H), 7.80 (d, J=7.6 Hz, 1H), 7.34 (t, J=8.2 Hz, 2H), 4.58 (d, J=6.9 Hz, 1H), 4.50 (d, J=9.6 Hz, 1H), 4.19 (t, J=9.7 Hz, 1H), 3.16 (t, J=9.9 Hz, 1H), 2.48 (s, 3H), 2.12 (s, 1H), 1.84-1.70 (m, 2H), 1.53 (d, J=6.9 Hz, 3H).

NMR for Example 89

$^1$H NMR (400 MHz, DMSO-d$_6$) δ 11.28 (s, 1H), 8.85 (s, 1H), 8.75 (d, J=2.5 Hz, 1H), 8.20 (d, J=2.5 Hz, 1H), 8.07 (t, J=7.9 Hz, 1H), 7.97 (dd, J=8.1, 2.5 Hz, 1H), 7.92 (dd, J=8.6, 2.6 Hz, 1H), 7.86 (d, J=8.0 Hz, 1H), 7.80 (d, J=7.6 Hz, 1H), 7.34 (t, J=8.2 Hz, 2H), 4.59 (s, 1H), 4.50 (d, J=9.5 Hz, 1H), 4.19 (t, J=9.7 Hz, 1H), 3.15 (d, J=11.7 Hz, 1H), 2.48 (s, 3H), 2.12 (s, 1H), 1.82-74 (m, 2H), 1.53 (d, J=6.9 Hz, 3H).

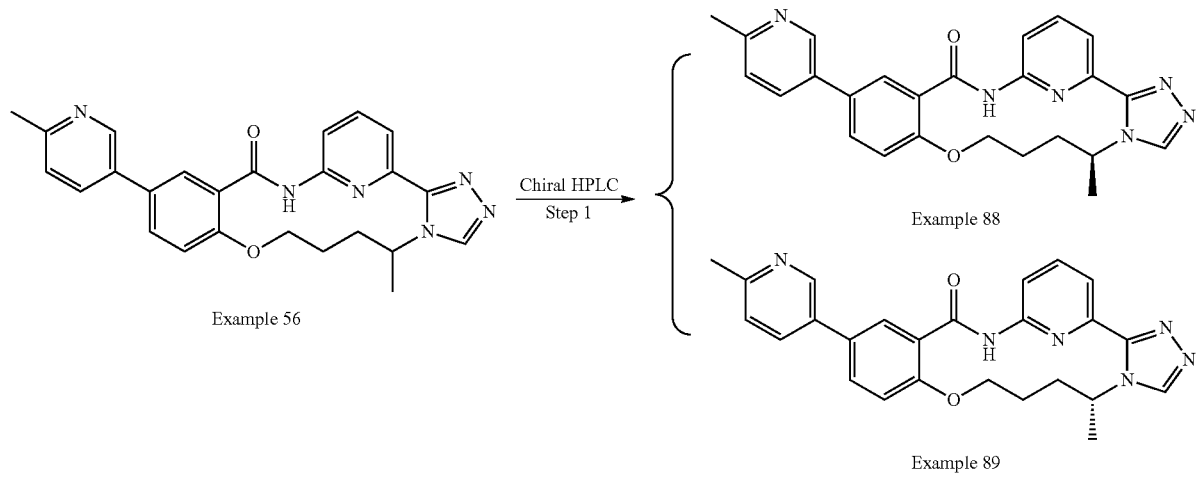 [SMILES: Cc1ccc(-c2ccc3c(c2)C(=O)Nc2cccc(n2)-c2nncn2C(C)CCCO3)cn1 ; Cc1ccc(-c2ccc3c(c2)C(=O)Nc2cccc(n2)-c2nncn2[C@@H](C)CCCO3)cn1 ; Cc1ccc(-c2ccc3c(c2)C(=O)Nc2cccc(n2)-c2nncn2[C@H](C)CCCO3)cn1]

Example 88: General Procedure for Synthesis of Compound Example 88 (Method 2)

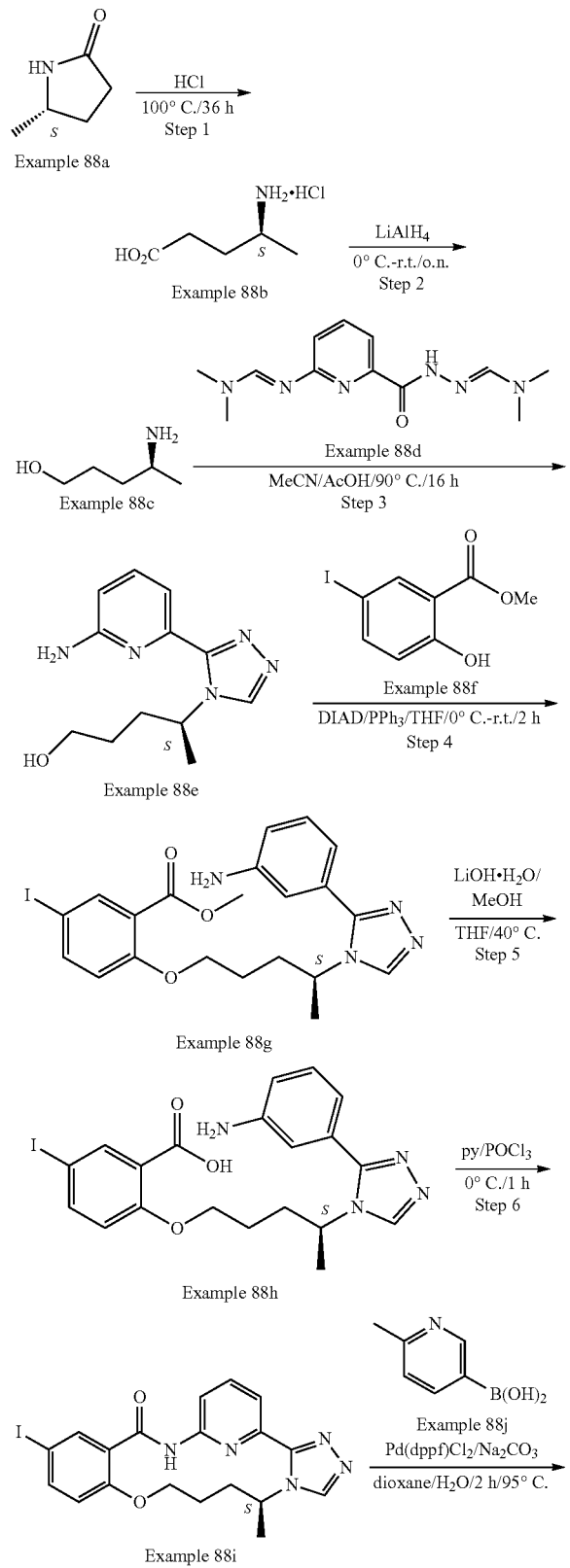

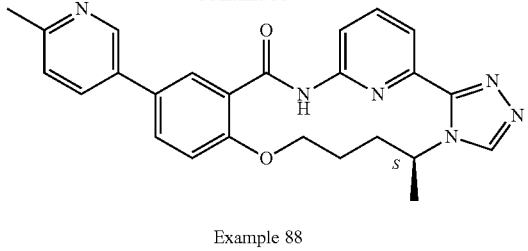

Example 88

Step 1: Example 88b

A solution of Example 88a (cas: 1558-60-7, 21 g, 0.21 mol) in 6N HCl (180 mL) was heated to 100° C. for 36 h. The mixture was cooled to r.t., and concentrated under reduced pressure to give a brown solid. Then MeCN (100 mL) was added, and the mixture was stirred for 15 min at room temperature, and then filtrated. The solid was dried under reduced pressure to give the desired product Example 88b (24 g, yield 73%) as a white solid, which was used in the next step without further purification. $^1$H NMR (400 MHz, Methanol-$d_4$) δ 3.36 (dt, J=13.5, 6.7 Hz, 1H), 2.51-2.40 (m, 2H), 2.04-1.91 (m, 1H), 1.81 (dq, J=14.5, 7.4 Hz, 1H), 1.30 (d, J=6.6 Hz, 3H).

Step 2: Example 88c

A solution of Example 88b (24 g, 0.16 mol) in THF (500 mL) was cooled to 0° C. under $N_2$ protection. Then LiAlH$_4$ (15 g, 0.39 mol) was added carefully in portions during 2 h. The mixture was stirred for 30 min at 0° C., and warmed to room temperature for overnight with stirring. Water (15 mL), 15% NaOH (aq., 15 mL) and water (45 mL) were added subsequently, and the resulting mixture was stirred for 30 min, and then filtrated. The solid was washed by THF (50 mL), and the organic layer was concentrated under reduced pressure, which was purified by reduced pressure distillation to give the desired product Example 88c (4.41 g, yield 27%) as colorless liquid.

$^1$H NMR (400 MHz, Chloroform-d) δ 6.46 (s, 1H), 3.76 (h, J=6.4 Hz, 1H), 3.68-3.51 (m, 1H), 2.92 (dddd, J=8.2, 6.3, 4.1, 2.3 Hz, 1H), 2.72 (s, 2H), 1.76-1.51 (m, 3H), 1.35 (dddd, J=14.7, 8.8, 6.7, 3.1 Hz, 1H), 1.20 (d, J=6.3 Hz, 3H).

Step 3: Example 88e

A solution of Example 88c (4.41 g, 42.88 mmol) and Example 88d (2.25 g, 8.58 mmol) in MeCN (80 mL) and AcOH (20 mL) was degassed with $N_2$ three times, and heated to 90° C. for 16 h. The mixture was cooled to room temperature, and then 6N HCl (10 mL) was added. The resulting mixture was stirred for 1 h, and concentrated under reduced pressure. The residue was cooled to 0° C. and adjusted pH=10~11 with 30% NaOH (aq.). The mixture was stirred for 30 min, and concentrated under reduced pressure, which was purified by silica gel chromatography (DCM/MeOH=91/9) to give the desired product Example 88e (542 mg, yield 26%) as a pale yellow gel. LCMS [M+1]$^+$=248.1

Step 4: Example 88g

A solution of Example 88e (480 mg, 1.94 mmol), Example 88f (540 mg, 1.94 mmol) and PPh$_3$ (1.27 g, 4.86 mmol) in dry THF (20 mL) was degassed with $N_2$ three times and cool to 0° C. DIAD (1.18 g, 5.83 mmol) was added dropwise and the mixture was stirred for 2 h at 0° C.~r.t. The mixture was concentrated under reduced pressure, which was purified by silica gel chromatography (EtOAc/MeOH=91/9) to give the desired product Example 88g (700 mg, yield 71%) as pale yellow gel. LCMS [M+1]$^+$=507.9

Step 5: Example 88h

A solution of Example 88g (700 mg, 1.38 mmol) and LiO.H$_2$O (174 mg, 4.14 mmol) in MeOH (20 mL), THF (20 mL) and water (5 mL) was heated to 40° C. overnight. The mixture was cooled to room temperature, and adjusted pH=3~4 with 1N HCl. Then the mixture was concentrated under reduced pressure to give the desired product Example 88h (860 mg, crude, yield 100%) as a white solid, which was used in the next step without further purification. LCMS [M+1]$^+$=493.9

Step 6: Example 88i

A solution of Example 88h (860 mg, crude, 1.38 mmol) in pyridine (70 mL) was cooled to 0° C. under N$_2$ protection. Then POCl$_3$ (845 mg, 5.52 mmol) was added dropwise and the mixture was stirred for 1 h at 0° C. Water (5 mL) was added to the mixture, which was concentrated under reduced pressure. Water (20 mL) was added to the residue, which was stirred for 30 min at room temperature, and filtrated. The solid was washed by water (20 mL), dried under reduced pressure to give the desired product Example 88i (280 mg, yield 42%) as a pink solid. LCMS [M+1]$^+$=475.9

Step 7: Example 88

To a solution of Example 88i (280 mg, 0.59 mmol), Example 88j (121 mg, 0.88 mmol) and Na$_2$CO$_3$ (188 mg, 1.77 mmol) in dioxane (30 mL) and water (5 mL) was added Pd(dppf)Cl$_2$ (43 mg, 0.059 mmol). The mixture was degassed with N$_2$ three times, heated to 95° C. for 2 h. The mixture was cooled to room temperature, and concentrated under reduced pressure. The residue was purified by prep-TLC (DCM/MeOH=10/1) to give 90 mg crude product. Then EtOAc (5 mL) was added, and the mixture was slurried for 30 min at room temperature, and filtrated. The solid was washed by EtOAc (2 mL), and dried under reduced pressure to give the desired product Example 88 (72 mg, yield 27%) as a pale brown solid. (>99% ee). LCMS [M+1]$^+$=441.0. $^1$H NMR (400 MHz, DMSO-d$_6$) δ 11.28 (s, 1H), 8.85 (s, 1H), 8.74 (d, J=2.4 Hz, 1H), 8.20 (d, J=2.6 Hz, 1H), 8.06 (t, J=7.9 Hz, 1H), 7.97 (dd, J=8.1, 2.5 Hz, 1H), 7.92 (dd, J=8.6, 2.6 Hz, 1H), 7.86 (d, J=8.1 Hz, 1H), 7.80 (d, J=7.6 Hz, 1H), 7.34 (t, J=8.1 Hz, 2H), 4.59 (s, 1H), 4.50 (d, J=9.8 Hz, 1H), 4.19 (t, J=9.8 Hz, 1H), 3.16 (t, J=9.9 Hz, 1H), 2.49 (s, 3H), 2.12 (s, 1H), 1.77 (q, J=14.4, 13.1 Hz, 2H), 1.53 (d, J=6.9 Hz, 3H).

Example 90: General Procedure for Synthesis of Compound Example 90

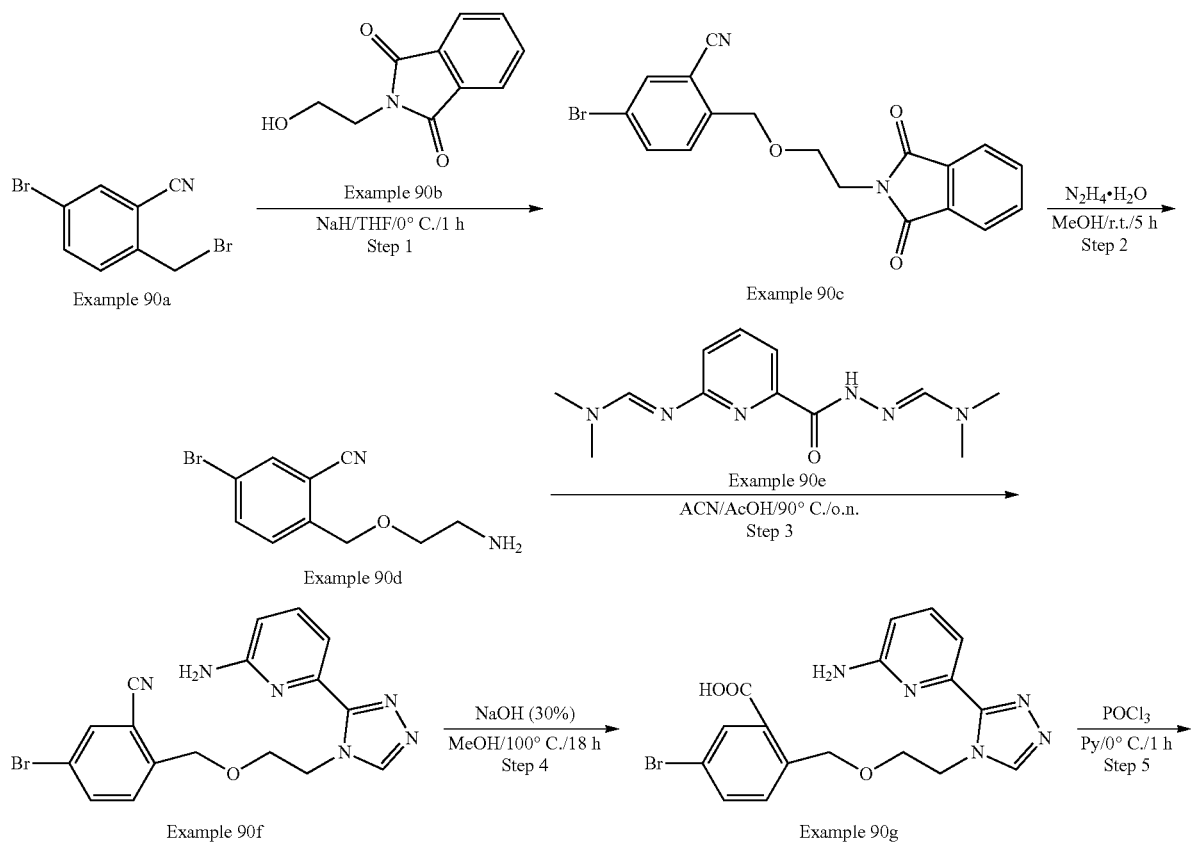

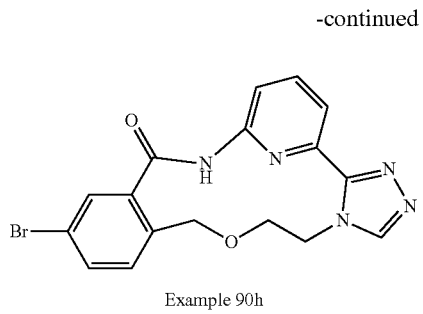

Example 90h

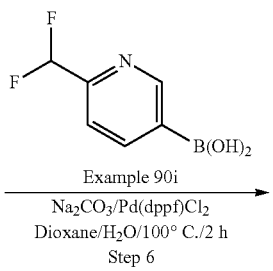

Example 90i

Na₂CO₃/Pd(dppf)Cl₂
Dioxane/H₂O/100° C./2 h
Step 6

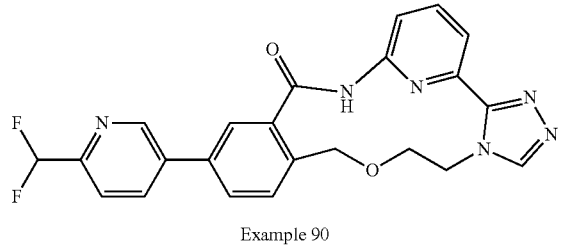

Example 90

Step 1: Example 90c

To a slurry of Example 90b (2.0 g, 7.27 mmol) in THF (30 mL) at 0° C. was added NaH (349 mg, 8.72 mmol), which was stirred for 30 min. Then Example 90a (1.39 g, 7.27 mmol) was added at 0° C. and the resulting mixture was warmed to r.t. overnight. To the mixture was added water (20 mL), which was then extracted by EtOAc (30 mL*3). The combined organic layer was saturated with brine, dried over anhydrous magnesium sulfate and concentrated under reduced pressure to give the crude product Example 90c (2.5 g, crude yield 90%) as yellow oil. LCMS [M+1]⁺=384.9/386.9

Step 2: Example 90d

To a mixture of Example 90c (2.5 g, crude) in MeOH (10 mL) was added N₂H₄.H₂O (5 mL, 80% in water), which was stirred at r.t. for 5 h. Water (20 mL) was added to the mixture, which was then extracted with DCM (30 mL*3). The combined organic layer was saturated with brine, dried over anhydrous magnesium sulfate and concentrated under reduced pressure. The residue was directly purified by silica gel chromatography (DCM/MeOH=1/0~10/1) to give the crude product Example 90d (580 mg, yield 31% over two step) as yellow oil. LCMS [M+1]⁺=253.9/255.9

Step 3: Example 90f

A mixture of Example 90d (580 mg, 2.27 mmol), Example 90e (1.19 g, 4.54 mmol) in MeCN/AcOH (10 mL, v/v=4/1) was heated at 90° C. overnight. The mixture was concentrated under reduced pressure and to the residue was added MeOH (10 mL)/conc. HCl (5 ml, 12 N), which was stirred at r.t. for 1 h. Then the mixture was adjusted to pH 7.0 and concentrated under reduced pressure. The residue was directly purified by silica gel chromatography (DCM/MeOH=1/0~30/1) to give the crude product Example 90f (600 mg, 50% purity @254 nm, yield 33%) as a yellow solid. LCMS [M+1]⁺=398.9/400.9

Step 4: Example 90g

To a mixture of Example 90f (600 mg, 50% purity, 0.75 mmol) in MeOH (10 mL) was added 30% aq. NaOH (10 mL), which was heated at 100° C. overnight. The mixture was then concentrated in vacuo and then adjusted to pH 7.0 with conc. HCl. Then the mixture was concentrated under reduced pressure and the residue was directly purified by reversed phase column (H₂O/MeCN=1/0~0/1), but desired product was absorbed on silica gel (3.0 g). The desired product Example 90g (~3.0 g, absorbed on silica gel) as a white solid was used in the next step directly without further purification. LCMS [M+1]⁺=417.9/419.9

Step 5: Example 90h

To a mixture of Example 90g (2.0 g, contain silica gel, 0.48 mmol) in pyridine (100 mL) at 0° C. was added POCl₃ (734 mg, 4.80 mmol), which was stirred at 0° C. for 1 h. To the mixture was added water (2 mL), which was then concentrated under reduced pressure. To the residue was added H₂O (100 mL), which was extracted with DCM (100 mL*3). The combined organic layer was saturated with brine, dried over anhydrous magnesium sulfate and concentrated under reduced pressure. The residue was purified by prep-TLC (DCM/MeOH=20/1), followed by Prep-HPLC to give the desired product Example 90h (25 mg, yield 8% over two step) as a white solid. LCMS [M+1]⁺=399.9/401.9

Step 6: Example 90

To a mixture of Example 90h (25 mg, 0.063 mmol), Example 90i (16 mg, 0.094 mmol), and Na₂CO₃ (20 mg, 0.19 mmol) in Dioxane/H₂O (4 mL, v/v=10/1) was added Pd(dppf)Cl₂ (5 mg). Then the mixture was degassed by bubbling N₂ through the solution for 2 min using a syringe needle. After that, the mixture was heated at 90° C. for 2 h. The mixture was concentrated under reduced pressure and the residue was purified by Prep-HPLC to give the desired product Example 90 (3.8 mg, yield 14%) as a white solid. LCMS [M+1]⁺=449.0. ¹H NMR (400 MHz, DMSO-d₆) δ 10.84 (s, 1H), 8.84-8.77 (m, 1H), 8.59 (s, 1H), 8.12 (dd, J=8.1, 1.9 Hz, 1H), 7.94 (t, J=7.8 Hz, 1H), 7.85 (d, J=7.5 Hz, 1H), 7.74 (dd, J=8.0, 1.6 Hz, 1H), 7.69 (d, J=8.2 Hz, 1H), 7.63-7.55 (m, 2H), 7.31 (d, J=7.8 Hz, 1H), 6.95 (t, J=54.9 Hz, 1H), 4.80 (s, 2H), 4.02 (br, 2H), 3.69 (br, 2H).

Example 91: General Procedure for Synthesis of Compound Example 91

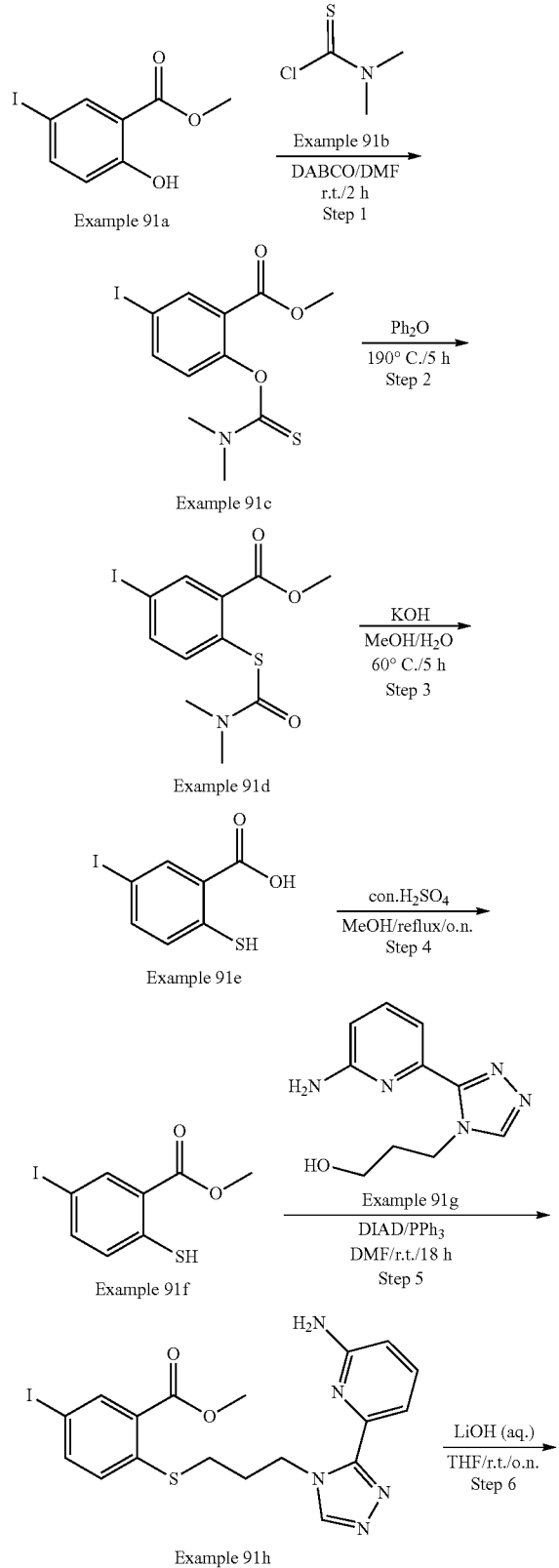
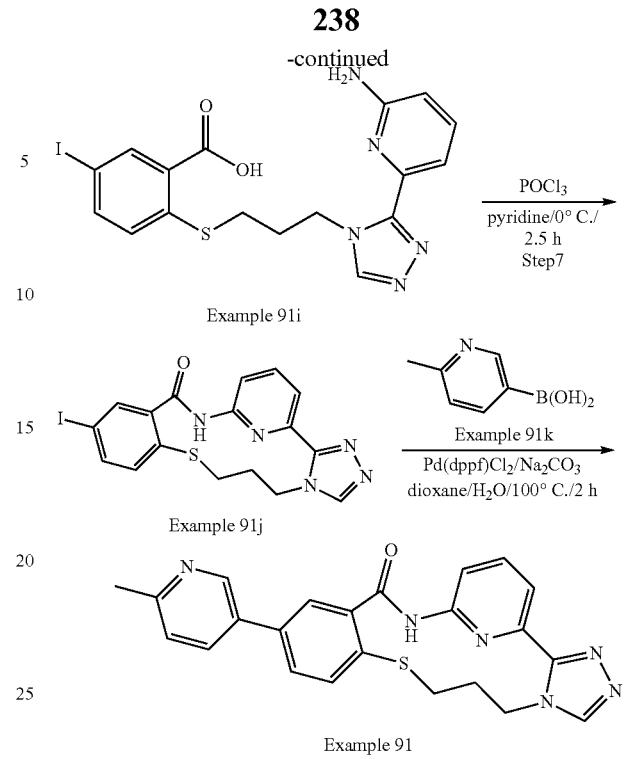

Step 1: Example 91c

To a mixture of Example 91a (20.0 g, 71.9 mmol), and DABCO (16.1 g, 143.9 mmol) in DMF (400 mL) was added Example 91b (13.3 g, 107.9 mmol). Then the mixture was stirred at room temperature for 2 h. The reaction mixture was poured into water (500 mL) with stirring. The precipitate was filtered, and the filter cake was washed with $H_2O$ (150 mL*3) and dried in vacuo to afford the desired product Example 91c (19.0 g, yield 73%) as a yellow solid. LCMS $[M+1]^+=365.9$

Step 2: Example 91d

To a hot $Ph_2O$ (300 mL) at 190° C. was added Example 91c (19 g, 52.1 mmol), which was stirred for 5 h. The reaction mixture was cooled to 25° C. and then directly purified by silica gel chromatography (Petroleum Ether/EtOAc=14/1~0/1) to afford the desired product Example 91d (14.37 g, yield 75%) as a yellow solid. LCMS $[M+1]^+=365.9$

Step 3: Example 91e

To a solution of KOH (3.07 g, 55.0 mmol) in 95% MeOH (200 mL) was added Example 91d (3.65 g, 10.0 mmol), and the reaction mixture was stirred at 60° C. for 5 h. The mixture concentrated to dryness, diluted with ice-water (50 mL), and extracted with EtOAc (50 mL). The aqueous layer was acidified with 6N HCl to pH=1~2, and stirred for 15 min. The resulting mixture was then filtered, and the solid was washed with water (10 mL) and dried to give the crude product Example 91e (2.7 g, yield 96%) as a white solid. LCMS $[M-1]^-=278.8$.

Step 4: Example 91f

A mixture of crude Example 91e (2.7 g, 1.0 mmol) and conc. $H_2SO_4$ (0.5 mL) in MeOH (100 mL) was heated to reflux overnight. The mixture concentrated in vacuo, and then diluted with ice-water (50 mL), which was then extracted with EtOAc (25 mL*2). The organic layer was washed with brine, dried over $Na_2SO_4$, and concentrated in vacuo. The residue was purified by silica gel chromatography (Petroleum ether/EtOAc=1/5) to afford the desired compound Example 91f (1.6 g, yield 88%) as a yellow solid. LCMS [M−1]⁻=292.8.

Step 5: Example 91h

A mixture of Example 91f (816 mg, 7.77 mmol), Example 91g (608 mg, 2.77 mmol) and $PPh_3$ (1.80 g. 6.93 mmol) in DMF (10 mL) was treated with DIAD (1.46 g, 7.21 mmol) in DMF (5 mL) at 10° C., which was stirred at r.t. for 18 h. The mixture was diluted with $H_2O$ (20 mL) and then extracted with EtOAc (40 mL). The organic layer was dried over $Na_2SO_4$, filtered and concentrated under reduced pressure. The residue was purified by silica gel chromatography (DCM/MeOH=10/1) to give the desired product Example 91h (1.0 g, yield 73%) as a white solid. LCMS [M+1]⁺=495.9.

Step 6: Example 91i

To a solution of Example 91h (1.0 g, 2.0 mmol) in THF (10 mL) was added 1N LiOH (aq., 4 mL, 4.0 mmol) with stirring at r.t for overnight. The pH of the reaction mixture was adjusted to nearly 1-2 by 1N HCl(aq.). The precipitate was filtered and the solid was dried under reduce pressure to give the desired product Example 91i (800 mg, yield 83%) as a white solid. LCMS [M+1]⁺=481.8.

Step 7: Example 91j

To a mixture of Example 91i (300 mg, 0.3 mmol) in pyridine (100 mL) at 0° C. was added $POCl_3$ (455 mg, 3.0 mmol) slowly. The mixture was stirred at 0° C. for 2.5 h. To the mixture was added ice-water (50 mL), which was concentrated under reduced pressure. The residue was purified by silica gel chromatography (DCM/MeOH=20/1), followed by prep-TLC (DCM/MeOH=20/1) to give the desired product Example 91j (40 mg, yield 29%) as a white solid. LCMS [M+1]⁺=463.8

Step 8: Example 91

To a mixture of Example 91j (40 mg, 0.086 mmol), Example 91k (18 mg, 0.129 mmol), and $Na_2CO_3$ (28 mg, 0.258 mmol) in dioxane/$H_2O$ (1.8 mL, v/v=3/1) was added Pd(dppf)$Cl_2$ (3 mg). Then the mixture was degassed by bubbling $N_2$ through the solution for 2 min using a syringe needle. After that, the mixture was heated at 100° C. for 2.0 h. The mixture was concentrated and directly purified by prep-TLC (DCM/MeOH=20/1) to give the desired product Example 91 (28 mg, yield 76%) as a white solid. LCMS [M+1]⁺=429.0. ¹H NMR (400 MHz, Chloroform-d) δ 8.71 (s, 1H), 8.47 (d, J=2.4 Hz, 1H), 8.21 (d, J=7.8 Hz, 1H), 8.14 (s, 1H), 7.84 (t, J=7.9 Hz, 1H), 7.60-7.55 (m, 2H), 7.44 (dd, J=8.2, 2.1 Hz, 1H), 7.35 (d, J=2.1 Hz, 1H), 7.24 (s, 1H), 7.17 (d, J=8.0 Hz, 1H), 3.17 (s, 2H), 2.57 (s, 3H), 2.09 (d, J=9.0 Hz, 2H), 1.78 (m, 2H).

Example 93: General Procedure for Synthesis of Compound Example 93

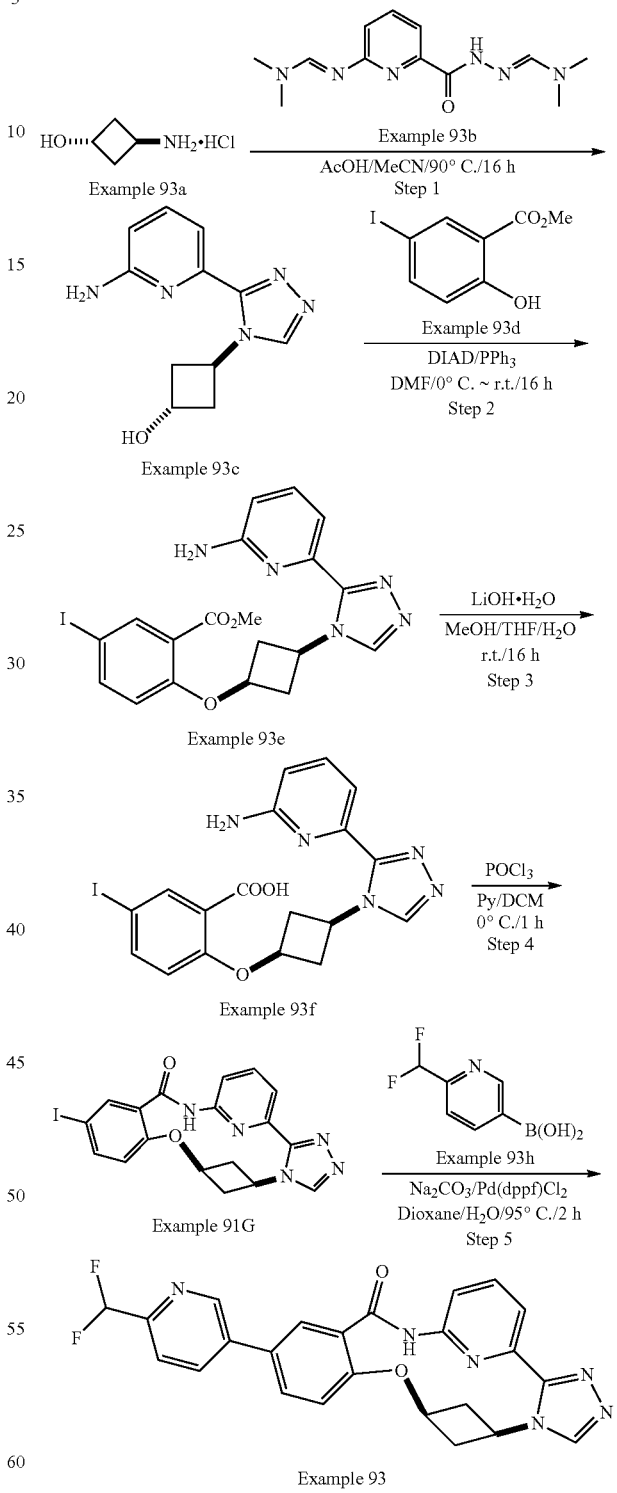

Step 1: Example 93c

To a solution of Example 93a (2.0 g, 16.18 mmol) in MeCN (32 mL) was added AcOH (8 mL) and Example 93b (2.12 g, 8.09 mmol). The mixture was stirred at 90° C. for 16 h. The mixture was cooled to r.t., followed by addition of 1N HCl (aq., 2 mL), which was stirred for another 2 hs. The mixture was basified by 30% NaOH (aq.) to pH=9 and concentrated. The residue was purified by column chromatography (DCM/MeOH=78/22) to give the desired product Example 93c (1.5 g, yield 41 %) as light yellow oil. LCMS [M+1]⁺=232.0

Step 2: Example 93e

Example 93c (1.5 g, 6.5 mmol), Example 93d (1.8 g, 6.5 mmol) and PPh₃ (3.4 g, 13.0 mmol) were dissolved in dry DMF (30 mL), which was cooled to 0° C. DIAD (2.6 g, 13.0 mmol) was added slowly under nitrogen atmosphere at this temperature. The mixture was stirred from 0° C. to r.t. for 16 h. Water was added, and the mixture was extracted with EtOAc (50 mL*3). The combined organic layers were concentrated and purified by silica gel chromatography (EtOAc/MeOH=70/30) to give the desired product Example 93e (1.7 g, yield 55%) as yellow oil. LCMS [M+1]⁺=491.9

Step 3: Example 93f

To a solution of Example 93e (1.7 g, 3.5 mmol) in THF/MeOH/H₂O (15 mL/10 mL/5 mL) was added LiO.H₂O (436 mg, 10.4 mmol). The mixture was stirred at r.t. for 16 h. The reaction was concentrated, acidified by 1N HCl (aq.) to pH=3~4, and filtered. The solid was collected and dried to give the desired product Example 93f (1.1 g, yield 67%) as a white solid. LCMS [M+1]⁺=477.9

Step 4: Example 93g

To a solution of Example 93f (550 mg, 1.15 mmol) in pyridine/DCM (5 mL/70 mL) at 0° C. was added POCl₃ (530 mg, 3.46 mmol) slowly and the mixture was stirred at 0° C. for 1 h. The reaction was quenched by adding water slowly at 0° C., concentrated and purified by silica gel chromatography (DCM/MeOH=90/10) to give the desired product Example 93g (15 mg, yield 3%) as a white solid. LCMS [M+1]⁺=459.9

Step 5: Example 93

A mixture of Example 93g (15 mg, 0.033 mmol), Example 93h (6.8 mg, 0.039 mmol), Pd(dppf)Cl₂ (2.5 mg, 0.0033 mmol) and Na₂CO₃ (7 mg, 0.065 mmol) in 1,4-dioxane (1 mL)/H₂O (0.25 mL) was heated at 95° C. under nitrogen atmosphere for 2 h. The reaction was cooled to room temperature, filtered and concentrated. The residue was purified by prep-TLC (DCM/MeOH=15/1) to give the desired product Example 93 (3 mg, yield 20%) as a white solid. LCMS [M+1]⁺=461.0. ¹H NMR (400 MHz, DMSO-d₆) δ 10.45 (s, 1H), 8.98 (s, 1H), 8.66 (s, 1H), 8.27 (d, J=8.3 Hz, 1H), 7.95 (d, J=2.4 Hz, 1H), 7.75 (t, J=8.6 Hz, 2H), 7.67-7.61 (m, 1H), 7.39 (d, J=7.5 Hz, 1H), 7.27 (d, J=8.0 Hz, 1H), 6.99 (t, J=54 Hz, 1H), 6.58 (d, J=8.6 Hz, 1H), 4.96 (t, J=8.7 Hz, 1H), 4.74 (s, 1H), 2.93 (s, 2H), 1.97 (d, J=13.1 Hz, 2H).

Example 94: General Procedure for Synthesis of Compound Example 94

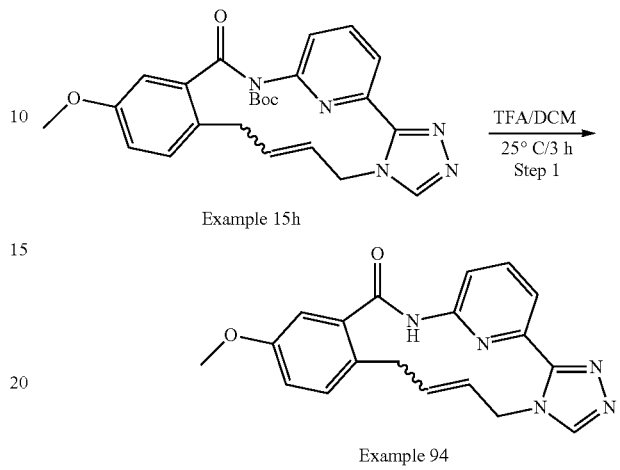

Step 1: Example 94

To a mixture of Example 15h (100 mg, crude) in DCM (4 mL) was added TFA (1 mL), which was stirred at 25° C. for 3 h. The mixture was added into sat.NaHCO₃ (30 mL) and extracted with EtOAc (20 mL*3). The combined organic layers were washed by brine, dried over NaSO₄ and concentrated under reduced pressure. The residue was purified by prep-HPLC to give the desired product Example 94 (9.7 mg, 12.5% yield) as a white solid. LCMS [M+1]⁺=348.0. ¹H NMR (400 MHz, DMSO-d₆) δ 10.59 (s, 0.69H), 10.37 (s, 0.32H), 8.63 (s, 0.62H), 8.62 (s, 0.29H), 7.97-7.82 (m, 2H), 7.24 (d, J=8.3 Hz, 1H), 7.12 (m, J=8.0, 1.8 Hz, 1H), 6.89-6.72 (m, 2H), 5.66-5.56 (m, 1H), 5.36-5.28 (m, 1H), 4.79 (s, 1H), 4.62 (s, 2H), 3.65 (s, 1H), 3.62 (s, 2H), 3.46 (s, 1H), 3.34 (s, 1H).

Example 95: General Procedure for Synthesis of Compound Example 95

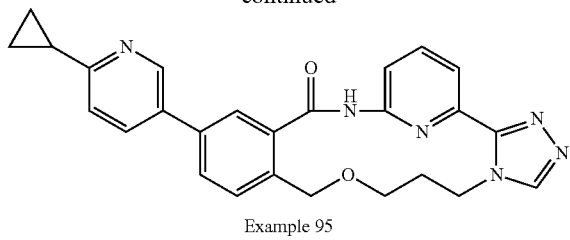

Example 95

Step 1: Example 95b

To a mixture of Example 95b (180 mg, 0.42 mmol) in pyridine (60 mL) at 0° C. was added POCl$_3$ (319 mg, 2.09 mmol), which was stirred at 0° C. for 1 h. After then, to the mixture was added water (2 mL) and concentrated under reduced pressure to give a residue. To the residue was added H$_2$O (100 mL), which was extracted with DCM (100 mL*3). The combined organic layer was saturated with brine, dried over anhydrous magnesium sulfate and concentrated under reduced pressure. The residue was purified by silica gel chromatography (DCM/MeOH=20/0-20/1) to give the desired product Example 95b (50 mg, yield 30%) as a white solid. LCMS [M+1]$^+$=413.9/415.9

Step 2: Example 95

To a mixture of Example 95b (15 mg, 0.036 mmol), Example 95c (9 mg, 0.054 mmol), and Na$_2$CO$_3$ (12 mg, 0.11 mmol) in Dioxane/H$_2$O (2 mL, v/v=10/1) was added Pd(dppf)Cl$_2$ (5 mg). Then the mixture was degassed by bubbling N$_2$ through the solution for 2 min using a syringe needle. After that, the mixture was heated at 100° C. for 2 h. The mixture was concentrated under reduced pressure and the residue was purified by prep-HPLC to give the desired product Example 95 (2.7 mg, yield 16%) as a white solid. LCMS [M+1]$^+$=453.0. $^1$H NMR (400 MHz, Chloroform-d) δ 10.47 (s, 1H), 8.72 (d, J=2.0 Hz, 1H), 8.22 (s, 1H), 8.20-8.09 (m, 3H), 7.95 (t, J=7.9 Hz, 1H), 7.81 (dd, J=8.1, 2.3 Hz, 1H), 7.73 (dd, J=7.8, 1.9 Hz, 1H), 7.56 (d, J=7.9 Hz, 1H), 7.23 (d, J=8.2 Hz, 1H), 4.78 (s, 2H), 4.67 (s, 2H), 3.99-3.93 (m, 2H), 2.40-2.31 (m, 2H), 2.14-2.05 (m, 1H), 1.09-1.03 (m, 4H).

Example 96: General Procedure for Synthesis of Compound Example 96

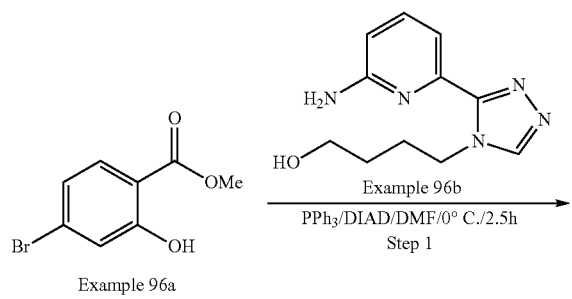

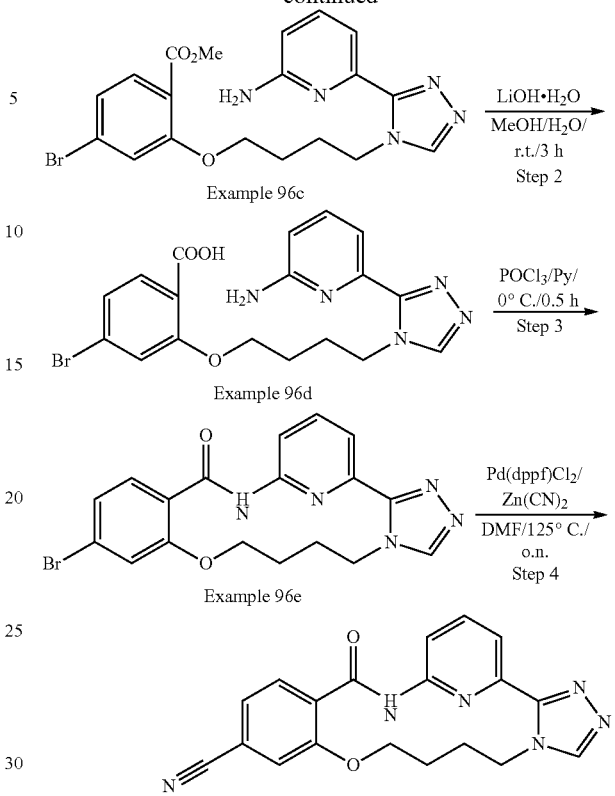

Step 1: Example 96c

A mixture of Example 96a (1.0 g, 4.3 mmol), Example 96b (1.0 g, 4.3 mmol) and PPh$_3$ (1.69 g, 6.45 mmol) in dry DMF (10 mL) was stirred at 0° C. under N$_2$ atmosphere. To the above mixture was injected DIAD (1.04 g, 5.16 mmol), which was stirred for another 2.5 h. The mixture was diluted with H$_2$O (20 mL) and then extracted with EtOAc (40 mL). The organic layer was dried over Na$_2$SO$_4$, filtered and concentrated under reduced pressure. The residue was purified by silica gel chromatography (DCM/MeOH=7/3) to give the desired product Example 96c (700 mg, yield 37%) as yellow oil, which turned into a yellow solid after staying overnight. LCMS [M+1]$^+$=445.9/447.9.

Step 2: Example 96d

To a solution of Example 96e (700 mg, 1.57 mmol) in MeOH/H$_2$O (10 mL/10 mL) was added LiO.H$_2$O (180 mg, 4.3 mmol) with stirring at r.t. After 3 h, the pH of the reaction mixture was adjusted to nearly 5 by HCl(aq.). The resulting mixture was concentrated under reduce pressure to give the crude product Example 96d (856 mg, yield 100%) as a white solid, which was used in the next step without further purification. LCMS [M+1]$^+$=431.9/433.9.

Step 3: Example 96e

To a solution of Example 96d (856 mg, crude, 1.98 mmol) in pyridine (6 mL) was added POCl$_3$ (940 mg, 6.2 mmol) with stirring at 0° C. After 0.5 h, water (10 mL) was added to quench the reaction, and the mixture was filtrated. The filtrate was washed by water for several times to give the crude product Example 96e (200 mg, yield 24%) as a white solid. LCMS [M+1]⁺=413.9/415.9.

Step 4: Example 96

A mixture of Example 96e (100 mg, 0.23 mmol), Zn(CN)₂ (35 mg, 0.26 mmol), K₂CO₃ (65 mg, 0.46 mmol), and Pd(dppf)Cl₂ (17 mg, 0.02 mmol) in DMF (3 mL) was stirred at 125° C. for overnight. Then the solution was filtrated and purified by Prep-HPLC to give the desired product Example 96 (2.2 mg, yield 27%) as a white solid. LCMS [M+1]⁺=361. $^1$H NMR (400 MHz, DMSO-d₆) δ 11.00 (s, 1H), 8.67 (s, 1H), 8.10-8.01 (m, 2H), 7.84 (dd, J=15.2, 7.4 Hz, 3H), 7.59 (dd, J=7.8, 1.4 Hz, 1H), 4.36 (d, J=5.1 Hz, 2H), 4.27-4.21 (m, 2H), 2.42 (d, J=14.4 Hz, 2H), 1.92 (s, 2H).

Example 97: General Procedure for Synthesis of Compound Example 97

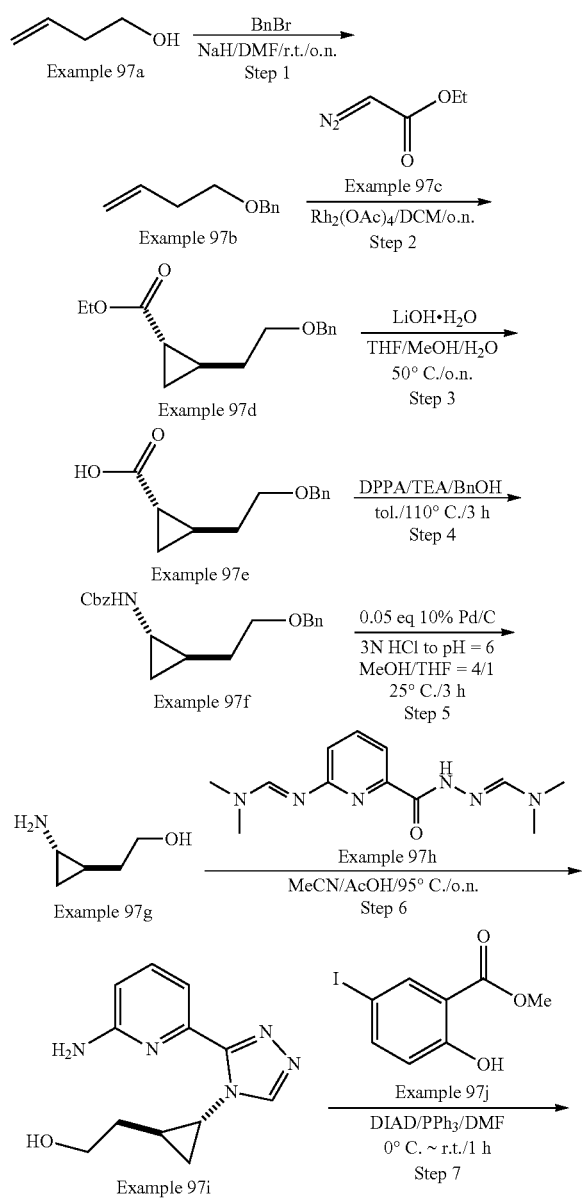

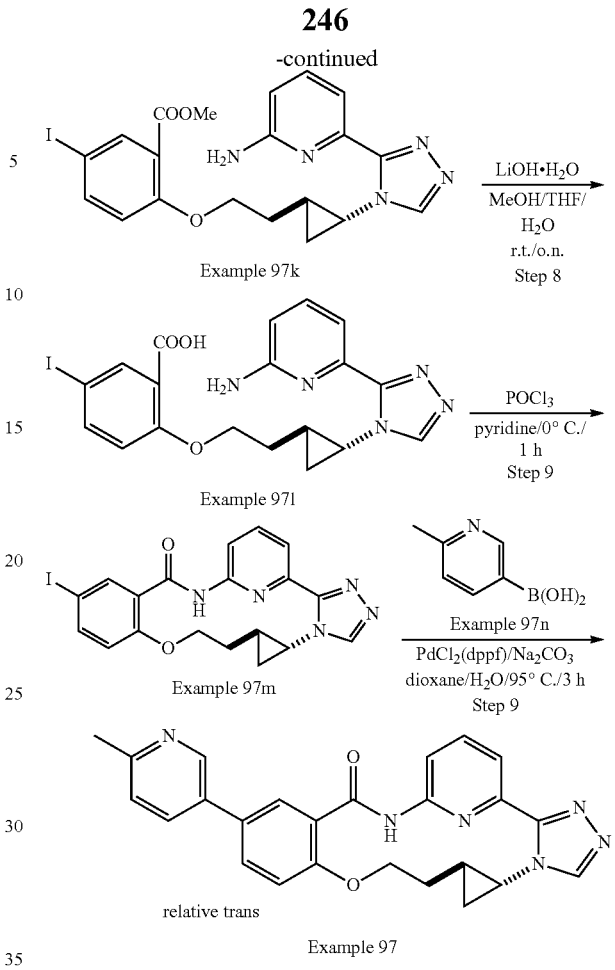

Step 1: Example 97b

To a solution of Example 97a (10 g, 139 m mol) in DMF (600 mL) in an ice bath was added NaH (6 g, 278 mmol, 60% in mineral oil) slowly. After 20 min, BnBr (26 g, 153 mmol) was added dropwise into the above mixture. The resulting solution was stirred at r.t. overnight, which was then quenched with H₂O (200 mL), concentrated under reduced pressure, and extracted with EtOAc (300 mL). The organic layer was concentrated and purified by silica gel chromatography (100% Petroleum Ether) to give the desired product Example 97b (15 g, yield 67%) as yellow oil. LCMS [M+1]⁺=163.0

Step 2: Example 97d

To a solution of Example 97b (15 g, 92.6 mmol) in DCM (300 mL) was added Rh₂(OAc)₄ (150 mg), then Example 97c (32 g, 278 mmol) was added dropwise into the reaction over 10 h. The resulting solution was stirred at r.t. overnight. The solution was concentrated and purified by silica gel chromatography (Petroleum Ether/EtOAc=20/0-20/1) to give the desired product Example 97d (crude, 4.1 g, yield 18%) as yellow oil. LCMS [M+1]⁺=249.1

Step 3: Example 97e

A solution of Example 97d (4.1 g, 16.5 mmol), LiO.H₂O (3.5 g, 82.7 mmol) in MeOH (30 mL), THF (90 mL) and H₂O (30 mL), was heated to 50° C. overnight. The solution was washed with EtOAc (30 mL), acidified by 3N HCl (20 mL), and then extracted with EtOAc (20 mL*2). The organic layer was concentrated to give the crude product Example 97e (3 g, crude yield 83%) as colorless oil. LCMS [M−1]⁻=219.1

Step 4: Example 97f

Under an atmosphere of $N_2$, Example 97e (2.5 g, 11.4 mmol), DPPA (3 mL), $Et_3N$ (3.4 g, 34.1 mmol) were dissolved in toluene (50 mL), after 2 min, BnOH (2.4 mL) was added. The resulting solution was stirred at 110° C. for 3 h. The solution was concentrated and purified by silica gel chromatography (EtOAc/Petroleum Ether=1/5) to give the desired product Example 97f (2.9 g, yield 78%) as colorless oil. LCMS [M+1]⁺=326.0

Step 5: Example 97g

Under an atmosphere of $H_2$, Example 97f (2.5 g, 7.7 mmol) was dissolved in MeOH (100 mL) and THF (25 mL), then 10% Pd/C (125 mg) was added into the reaction. The solution was adjust pH=6 by 3N HCl and heated to 25° C. for 3 h. The solution was filtered, and the filtrate was concentrated to obtain the desired product Example 97g (2.3 g, yield 100%) as colorless oil. LCMS [M+1]⁺=102.1

Step 6: Example 97i

A solution of Example 97g (2.1 g, 20.8 mmol) and Example 97h (3.6 g, 13.9 mmol) in MeCN (60 mL) and AcOH (15 mL) was stirred at 95° C. overnight. The solution was diluted with 2N NaOH (30 mL), and extracted with EtOAc (50 mL*2). The combined organic phase was concentrated under reduced pressure. The residue was purified by silica gel chromatography (DCM/MeOH=10/1) to give the desired product Example 97i (1 g, yield 30%) as yellow oil. LCMS [M+1]⁺=246.0

Step 7: Example 97k

To a solution of Example 97i (700 mg, 3 mmol) in DMF (10 mL) were added Example 97j (920 mg, 3.3 mmol) and $PPh_3$ (1.6 g, 6.0 mmol). Then the mixture was cooled to 0° C. and DIAD (915 mg, 4.5 mmol) was added dropwise under $N_2$. The resulting mixture was stirred at this temperature for 10 min and warmed to r.t. for 1 h. The mixture was extracted with EtOAc (25 mL*2). The combined organic phase was washed with brine, dried over $Na_2SO_4$, filtrated and the filtrate was concentrated under reduced pressure. The residue was purified by silica gel chromatography (DCM/MeOH=10/1) to give the desired product Example 97k (1 g, yield 71%) as pale-yellow oil. LCMS [M+1]⁺=505.9

Step 8: Example 97l

To a solution of Example 97k (1 g, 2.0 mmol) in THF/MeOH/$H_2O$ (12 mL/4 mL/4 mL) was added LiO.$H_2O$ (125 mg, 3.0 mmol). The mixture was stirred at r.t. overnight. The solvent was evaporated and the residue was acidified by 3N HCl to pH=2~3. The resulting solution was extracted by EtOAc, and the organic layer was concentrated to give the desired product Example 97l (1.5 g, yield 100%) as a white solid. LCMS [M+1]⁺=491.9

Step 9: Example 97m

To a solution of Example 97l (400 mg, 0.41 mmol) in pyridine (200 mL) was added $POCl_3$ (624 mg, 2.0 mmol) dropwise at 0° C. The mixture was stirred at 0° C. for 1 h under $N_2$. The reaction was quenched with $H_2O$ (80 mL). The solvent was concentrated and purified by silica gel chromatography (MeOH/DCM=1/10) to give the desired product Example 97m (50 mg, yield 13%) as a white solid. LCMS [M+1]⁺=474.0

Step 10: Example 97

To a solution of Example 97m (50 mg, 0.1 mmol) in Dioxane/$H_2O$ (2 mL/1 mL) were added Example 97n (16 mg, 0.12 mmol), $Na_2CO_3$ (34 mg, 0.32 mmol) and Pd(dppf)$Cl_2$ (8 mg, 0.01 mmol). The mixture was stirred at 95° C. for 3 h under $N_2$. The mixture was filtrated and the filtrate was concentrated under reduced pressure. The residue was purified by silica-gel chromatography (DCM/MeOH=20/1) to obtained a brown solid (40 mg), which was slurried by EtOAc/MeOH (v/v=10/1) to give the desired product Example 97 (14 mg, yield 30%) as a gray solid. LCMS [M+1]⁺=439.0. ¹H NMR (400 MHz, DMSO-$d_6$) δ 11.26 (s, 1H), 8.76 (d, J=2.4 Hz, 1H), 8.66 (s, 1H), 8.10 (s, 1H), 7.98 (dd, J=8.0, 2.5 Hz, 2H), 7.89 (d, J=8.6 Hz, 1H), 7.71 (d, J=7.6 Hz, 2H), 7.34 (d, J=8.1 Hz, 1H), 7.27 (d, J=8.6 Hz, 1H), 4.42 (s, 1H), 4.16 (s, 1H), 3.46 (s, 1H), 2.52 (s, 13H), 2.18 (s, 2H), 1.54 (q, J=8.6, 6.9 Hz, 2H), 1.24-1.05 (m, 1H).

Example 98: General Procedure for Synthesis of Compound Example 98

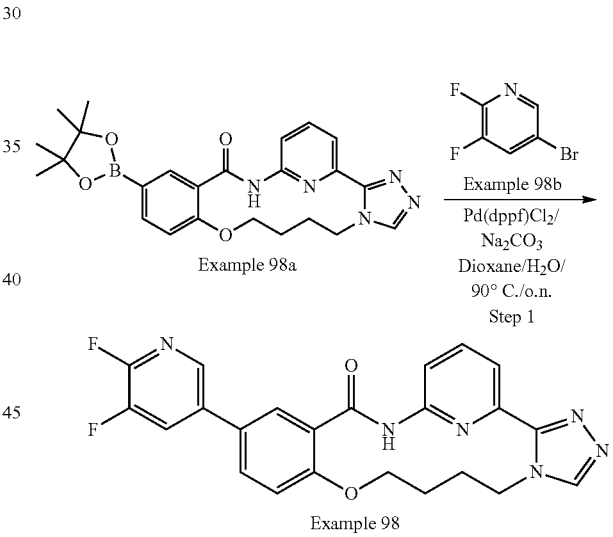

Step 1: Example 98

To a mixture of Example 98a (100 mg, 0.22 mmol), Example 98b (62 mg, 0.33 mmol), and $Na_2CO_3$ (70 mg, 0.66 mmol) in Dioxane/$H_2O$ (2 mL, v/v=10/1) was added Pd(dppf)$Cl_2$ (10 mg). Then the mixture was degassed by bubbling $N_2$ through the solution for 2 min using a syringe needle. After that, the mixture was heated at 90° C. for overnight. The mixture was concentrated under reduced pressure and the residue was purified by prep-HPLC, followed by prep-TLC (DCM/MeOH=20/1) to give the desired product Example 98 (4.2 mg, yield 4%) as a white solid. LCMS [M+1]⁺=449.0/¹H NMR (400 MHz, DMSO-$d_6$) δ 11.17 (s, 1H), 8.67 (s, 1H), 8.49-8.37 (m, 2H), 8.26 (d, J=1.9 Hz, 1H), 8.06 (t, J=7.9 Hz, 1H), 7.98 (d, J=6.7 Hz, 1H), 7.86

(dd, J=12.4, 7.9 Hz, 2H), 7.41 (d, J=8.7 Hz, 1H), 4.37 (s, 2H), 4.29-4.18 (m, 2H), 1.95 (s, 2H), 1.21 (s, 2H).

Example 99: General Procedure for Synthesis of Compound Example 99

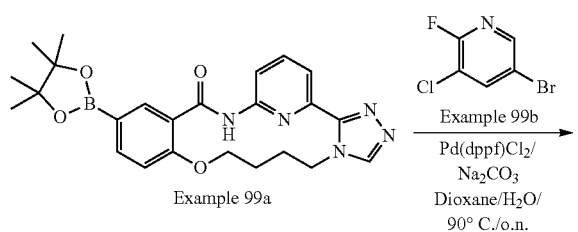

Step 1: Example 99

To a mixture of Example 99a (100 mg, 0.22 mmol), Example 99b (69 mg, 0.33 mmol), and Na$_2$CO$_3$ (70 mg, 0.66 mmol) in Dioxane/H$_2$O (2 mL, v/v=10/1) was added Pd(dppf)Cl$_2$ (10 mg). Then the mixture was degassed by bubbling N$_2$ through the solution for 2 min using a syringe needle. After that, the mixture was heated at 90° C. for overnight. The mixture was concentrated under reduced pressure and the residue was purified by prep-HPLC to give the desired product Example 99 (15.4 mg, yield 16%) as a white solid. LCMS [M+1]$^+$=465.0. $^1$H NMR (400 MHz, DMSO-d$_6$) δ 11.16 (s, 1H), 8.67 (s, 1H), 8.58-8.50 (m, 2H), 8.26 (d, J=2.4 Hz, 1H), 8.05 (t, J=7.9 Hz, 1H), 7.98 (dd, J=8.6, 2.4 Hz, 1H), 7.86 (dd, J=11.6, 7.9 Hz, 2H), 7.39 (d, J=8.7 Hz, 1H), 4.36 (t, J=4.5 Hz, 2H), 4.29-4.20 (m, 2H), 2.44 (s, 2H), 1.95 (s, 2H).

Example 100: General Procedure for Synthesis of Compound Example 100

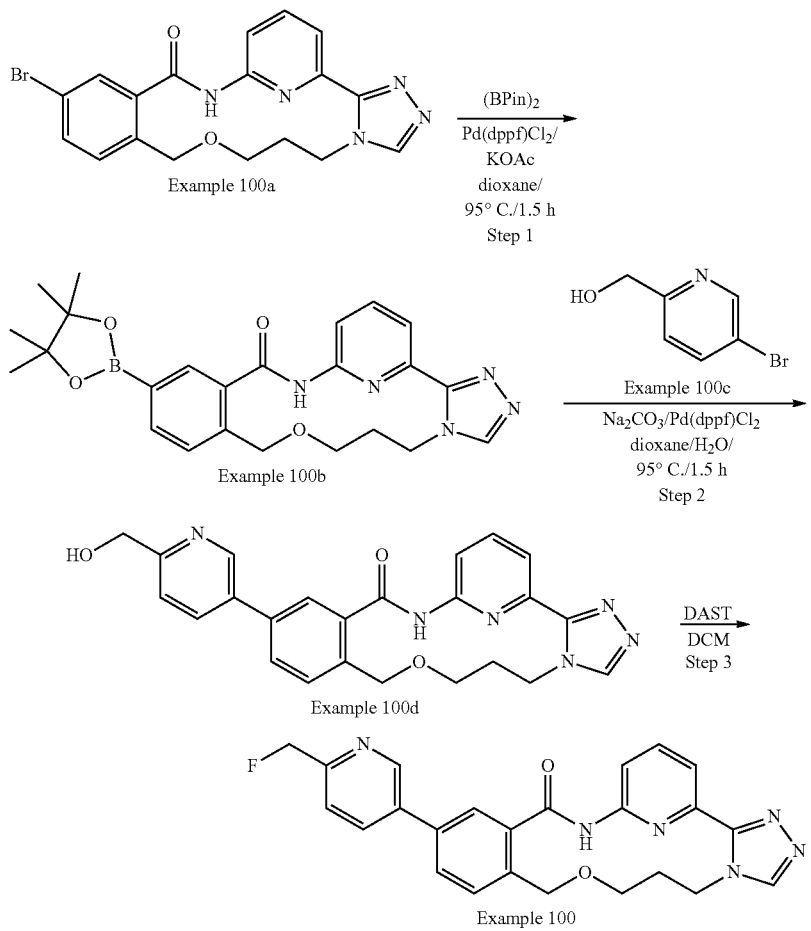

Step 1: Example 100b

To a mixture of Example 100a (53 mg, 0.128 mmol), Bis(pinacolato)diboron (34 mg, 0.134 mmol), and KOAc (32 mg, 0.32 mmol) in dioxane (1.2 mL) was added Pd(dppf)Cl$_2$ (5 mg, 0.006 mmol). Then the mixture was degassed by bubbling N$_2$ through the solution for 2 min using a syringe needle. After being heated at 95° C. for 1.5 h, the mixture Example 100b was cooled to r.t., which was used for next step without further purification. LCMS [M+1]$^+$=462.1

Step 2: Example 100d

Example 100c (49 mg, 0.256 mmol), and Na$_2$CO$_3$ (41 mg, 0.384 mmol) were added to the cooled mixture of Example 100b (crude mixture, 0.128 mmol), followed by water (0.3 mL) and Pd(dppf)Cl$_2$ (3 mg). Then the mixture was degassed by bubbling N$_2$ through the solution for 2 min using a syringe needle. After that, the mixture was heated at 95° C. for 1.5 h. The mixture was concentrated and directly purified by Prep-TLC (DCM/MeOH=20/1) to give the product Example 100d (30.0 mg, yield 53% over two steps) as a white solid. LCMS [M+1]+=443.1

Step 3: Example 100

To a solution of Example 100d (25 mg, 0.057 mmol) in dry CH$_2$Cl$_2$ (5 mL) was added DAST (0.15 mL) at 5° C. under a nitrogen atmosphere. The reaction mixture was stirred at 5-10° C. for 2 h, and then quenched by the addition of saturated aqueous sodium bicarbonate. The resulting mixture was allowed to stir for 10 min. The mixture was extracted with DCM, and the combined extracts were washed with brine, dried over Na$_2$SO$_4$, filtered, concentrated, and purified by Prep-TLC (DCM/MeOH=20/1) to give the desired product Example 100 (6.6 mg, yield 26%) as an off-white solid. LCMS [M+1]$^+$=445.1.

$^1$H NMR (400 MHz, Chloroform-d) δ 10.49 (s, 1H), 8.86 (d, J=2.3 Hz, 1H), 8.25-8.14 (m, 3H), 8.11 (d, J=7.7 Hz, 1H), 8.02 (dd, J=8.1, 2.4 Hz, 1H), 7.96 (t, J=7.9 Hz, 1H), 7.78 (dd, J=7.9, 2.2 Hz, 1H), 7.59 (t, J=7.8 Hz, 2H), 5.56 (d, J=46.8 Hz, 2H), 4.78 (t, J=7.0 Hz, 2H), 4.69 (s, 2H), 3.97 (t, J=4.8 Hz, 2H), 2.36 (p, J=6.4 Hz, 2H).

Example 101: General Procedure for Synthesis of Compound Example 101

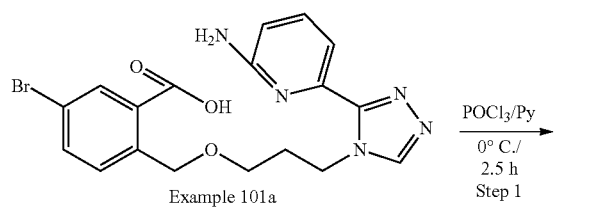

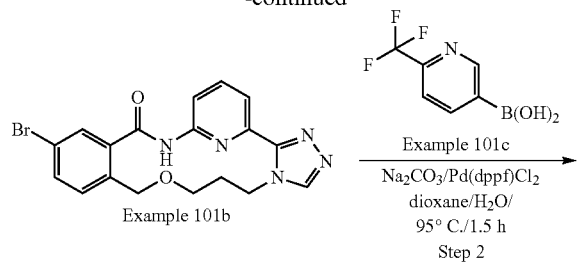

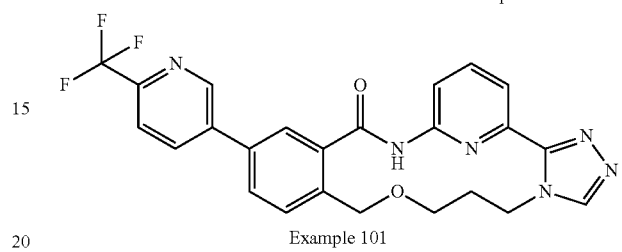

Step 1: Example 101b

To a mixture of Example 101a (300 mg, 0.69 mmol) in pyridine (100 mL) at 0° C. was added POCl$_3$ (300 mg, 1.96 mmol) slowly. The mixture was stirred at 0° C. for 2.5 h. To the mixture was added water (50 mL), which was concentrated under reduced pressure. The residue was purified by silica gel chromatography (DCM/MeOH=20/1) to give the desired product Example 101b (30 mg, yield 10%) as a white solid. LCMS [M+1]$^+$=413.9/415.9

Step 2: Example 101

To a mixture of Example 101b (30 mg, 0.073 mmol), Example 101c (14 mg, 0.073 mmol), and Na$_2$CO$_3$ (23 mg, 0.22 mmol) in dioxane/H$_2$O (1 mL, v/v=4/1) was added Pd(dppf)Cl$_2$ (3 mg). Then the mixture was degassed by bubbling N$_2$ through the solution for 2 min using a syringe needle. After that, the mixture was heated at 95° C. for 1.5 h. The mixture was concentrated and directly purified by prep-HPLC to give the desired product Example 101 (5.0 mg, yield 14%) as a white solid. LCMS [M+1]$^+$=481.0. $^1$H NMR (400 MHz, Chloroform-d) δ 10.51 (s, 1H), 9.00 (d, J=2.2 Hz, 1H), 8.28-8.09 (m, 5H), 7.97 (t, J=7.9 Hz, 1H), 7.87-7.76 (m, 2H), 7.64 (d, J=7.9 Hz, 1H), 4.79 (s, 2H), 4.71 (s, 2H), 4.04-3.90 (m, 2H), 2.37 (s, 2H).

Example 102: General Procedure for Synthesis of Compound Example 102

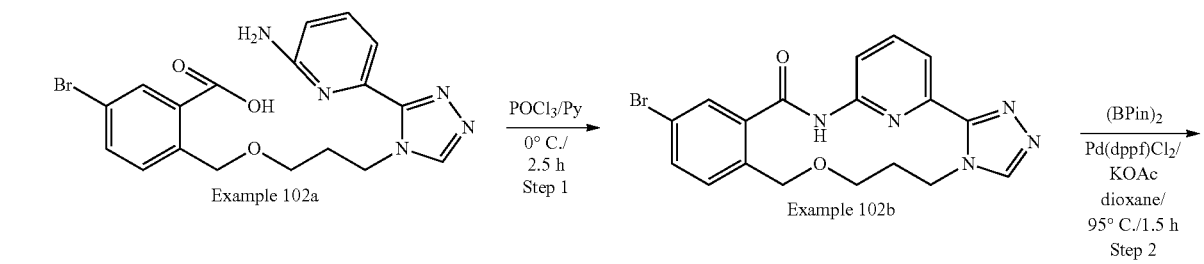

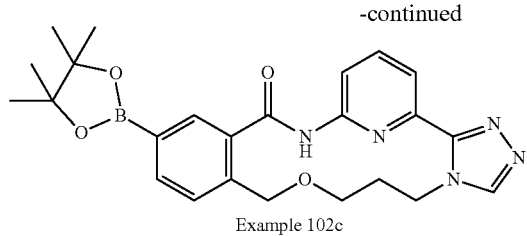 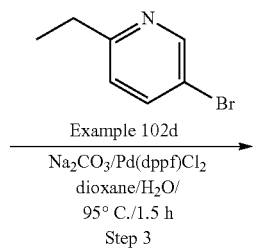

Example 102c — Example 102d

Na₂CO₃/Pd(dppf)Cl₂
dioxane/H₂O/
95° C./1.5 h
Step 3

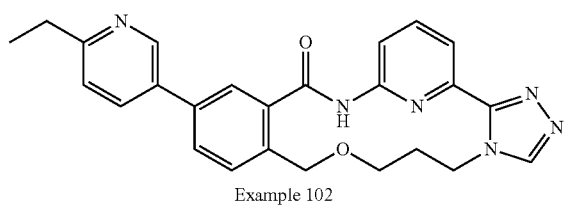

Example 102

Step 1: Example 102b

To a mixture of Example 102a (1.00 g, 2.31 mmol) in pyridine (200 mL) at 0° C. was added POCl₃ (1.42 g, 9.28 mmol) in DCM (50 mL) slowly. The mixture was stirred at 0° C. for 2.5 h. To the mixture was added water (80 mL), which was concentrated under reduced pressure. The residue was purified by silica gel chromatography (DCM/MeOH=20/1) to give the desired product Example 102b (100 mg, yield 10%) as a white solid.

LCMS [M+1]⁺=413.9/415.9

Step 2: Example 102c

To a mixture of Example 102b (42 mg, 0.10 mmol), Bis(pinacolato)diboron (26 mg, 0.11 mmol), and KOAc (25 mg, 0.25 mmol) in dioxane (1 mL) was added Pd(dppf)Cl₂ (4 mg, 0.005 mmol). Then the mixture was degassed by bubbling N₂ through the solution for 2 min using a syringe needle. After heated at 95° C. for 1.5 h. The mixture Example 102c was cooled to r.t., which was used for next step without further purification. LCMS [M+1]⁺=462.1

Step 3: Example 102

Example 102d (37 mg, 0.20 mmol), and Na₂CO₃ (32 mg, 0.30 mmol) were added to the cooled mixture of Example 102c (crude mixture, 0.10 mmol), followed by water (0.3 mL) and Pd(dppf)Cl₂ (3 mg). Then the mixture was degassed by bubbling N₂ through the solution for 2 min using a syringe needle. After that, the mixture was heated at 95° C. for 1.5 h. The mixture was concentrated and directly purified by Prep-TLC (DCM/MeOH=20/1), followed by Prep-HPLC to give the desired product Example 102 (10.0 mg, yield 23% over two steps) as a white solid. LCMS [M+1]+=441.1. ¹H NMR (400 MHz, Chloroform-d) δ 10.50 (s, 1H), 8.85 (s, 1H), 8.23-8.11 (m, 5H), 7.96 (t, J=7.9 Hz, 1H), 7.78 (d, J=7.8 Hz, 1H), 7.61 (d, J=7.6 Hz, 1H), 7.45 (d, J=5.6 Hz, 1H), 4.77 (d, J=5.6 Hz, 2H), 4.69 (s, 2H), 4.01-3.94 (m, 2H), 3.05 (d, J=8.7 Hz, 2H), 2.36 (s, 2H), 1.42 (t, J=7.5 Hz, 3H).

Example 103: General Procedure for Synthesis of Compound Example 103

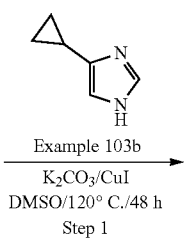

Example 103b

K₂CO₃/CuI
DMSO/120° C./48 h
Step 1

Example 103a

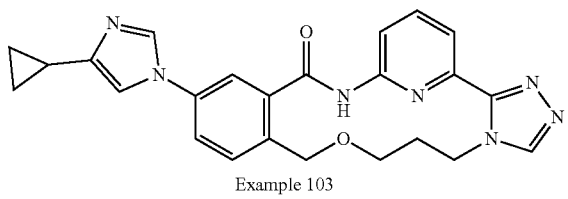

Example 103

Step 1: Example 103

A mixture of Example 103a (83 mg, 0.2 mmol), Example 103b (32 mg, 0.3 mmol), K,CO₃ (55 mg, 0.4 mmol), and CuI (8 mg, 0.04 mmol) in dry DMSO (2 mL) was heated at 120° C. for 48 h. The reaction was cooled to r.t., and then purified by prep-HPLC, followed by prep-TLC (DCM/MeOH=10/1) to give the desired product Example 103 (2.2 mg, yield 3%) as a white solid. LCMS [M+1]⁺=442.1

¹H NMR (400 MHz, Chloroform-d) δ 10.53 (s, 1H), 8.23 (s, 1H), 8.14 (t, J=7.9 Hz, 2H), 8.07 (s, 1H), 7.99-7.94 (m, 2H), 7.59 (s, 2H), 7.13 (s, 1H), 4.77 (s, 2H), 4.67 (s, 2H), 3.96 (t, J=4.8 Hz, 2H), 2.35 (s, 2H), 1.98-1.94 (m, 1H), 0.96 (d, J=7.8 Hz, 2H), 0.88 (d, J=5.1 Hz, 2H).

Example 104: General Procedure for Synthesis of Compound Example 104

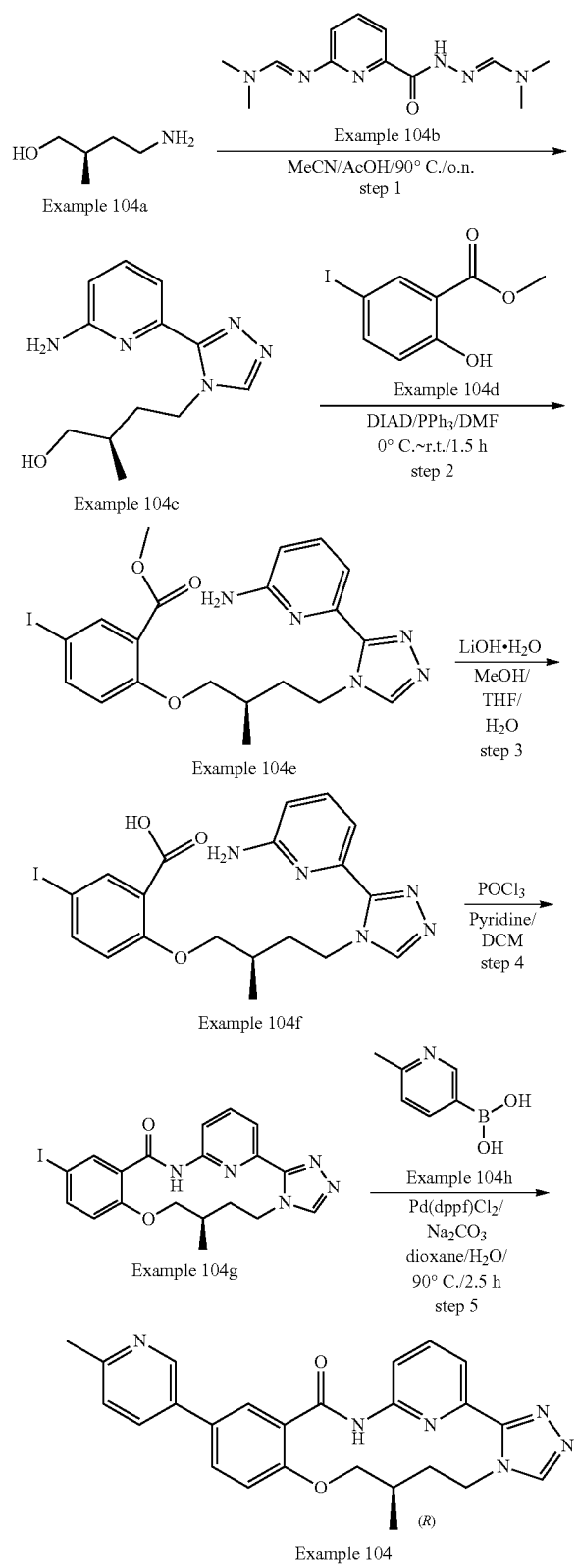

Step 1: Example 104c

A solution of Example 104a (2.0 g, 19.4 mmol) and Example 104b (3.4 g, 12.9 mmol) in MeCN/MeOH (75 mL, v/v=4/1) was stirred at 90° C. overnight. The mixture was concentrated and diluted with 2N NaOH (aq.), and the resulting mixture was extracted with DCM/i-PrOH (100 mL*6, v/v=4/1). The combined organic layer was concentrated and purified by silica gel chromatography (DCM/MeOH=30/1-10/1) to afford the desired product Example 104c (570 mg, yield 18%) as yellow oil and crude product (1 g). LCMS [M+1]$^+$=247.9

Step 2: Example 104e

To a solution of Example 104c (570 mg, 2.31 mmol), Example 104d (706 mg, 2.54 mmol) and PPh$_3$ (1.21 g, 4.62 mmol) in DMF was added DIAD (699 mg, 3.46 mmol) at 0° C. under N$_2$, which was stirred at r.t. for 1.5 h. The reaction mixture was diluted with water (20 mL) and extracted with EtOAc (20 mL*5). The organic layer was washed with brine (20 mL*3) and dried over Na$_2$SO$_4$, filtered and concentrated, which was purified by silica gel chromatography (DCM/MeOH=50/1-20/1) to afford the desired product Example 104e (1.06 g, yield 90%) as yellow oil. LCMS [M+1]$^+$=507.9

Step 3: Example 104f

To a solution of Example 104e (1.06 g, 2.09 mmol) in THF/MeOH/H$_2$O (15 mL, v/v/v=3/1/1) was added LiO.H$_2$O (176 mg, 4.18 mmol) at room temperature, which was stirred at 30° C. for 2 h. The mixture was concentrated, diluted with H$_2$O (20 mL), and then extracted with DCM (15 mL*3). The aqueous layer was adjusted pH to 4 with 3N HCl and concentrated, which was slurried with DCM/MeOH (30 mL, v/v=10/1) at room temperature for 15 min. The resulting suspension was filtered and the cake was washed with DCM/MeOH (10 mL*2, v/v=10/1). The filtrated was concentrated to afford the desired product Example 104f (1.02 g, yield 99%) as yellow oil. LCMS [M+1]$^+$=493.9

Step 4: Example 104g

To a solution of Example 104f (1.02 g, 2.07 mmol) in pyridine/DCM (300 mL, v/v=1/2) was added POCl$_3$ (1.55 g, 10.34 mmol) over a period of 15 min at 0° C. After addition, the reaction mixture was warmed to room temperature and stirred for 2.5 h. The mixture was then quenched by H$_2$O (5 mL) and concentrated to afford the crude product, which was slurried with H$_2$O (30 mL) at room temperature for 16 h. The mixture was filtered and the cake was washed with H$_2$O (5 mL*3) and dried in vacuo to afford the desired product Example 104g (283 mg, yield 29%) as an orange solid. LCMS [M+1]$^+$=475.9

Step 5: Example 104

To a solution of Example 104g (50 mg, 0.105 mmol), Example 104h (17.3 mg, 0.126 mmol) and Na$_2$CO$_3$ (33 mg, 0.316 mmol) in dioxane/H$_2$O (2.5 mL, v/v=4/1) was added Pd(dppf)Cl$_2$ (7.7 mg, 0.011 mmol) at room temperature under N$_2$. The reaction mixture was heated to 90° C. for 2.5 h under N$_2$. The reaction mixture was purified by prep-HPLC to afford the desired product Example 104 (11.5 mg, yield 25%) as a white solid. LCMS [M+1]$^+$=441.0. $^1$H NMR (400 MHz, DMSO-d$_6$) δ 8.76-8.73 (m, 2H), 8.22 (s, 1H), 8.08-8.04 (t, 1H), 8.00-7.84 (m, 5H), 7.43-7.41 (d, J=8.0 Hz, 1H), 7.35-7.33 (d, J=8.0 Hz, 1H), 4.40-4.36 (d, 2H), 4.28-4.25 (t, 1H), 4.02-3.97 (t, 1H), 2.43 (s, 3H), 2.05 (s, 1H), 1.14 (d, J=8.0 Hz, 4H).

Example 105: General Procedure for Synthesis of Compound Example 105

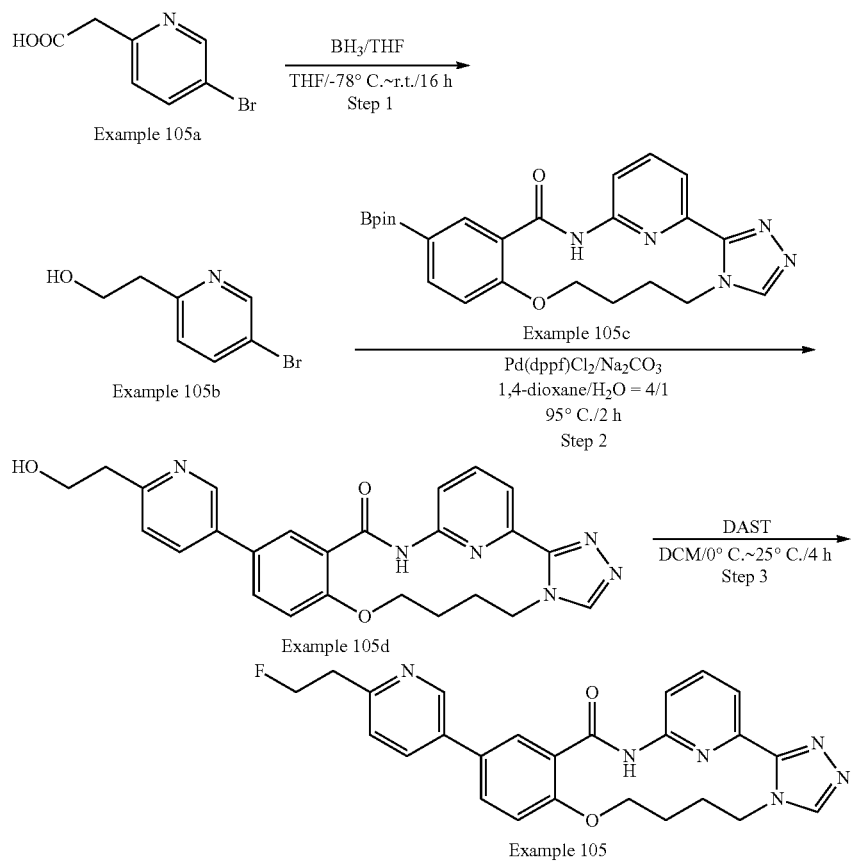

Step 1: Example 105b

To a solution of Example 105a (2.16 g, 10.0 mmol) in dry THF (80 mL) was added slowly added BH$_3$/THF (1.0 M, 30 mL) at −78° C. under nitrogen atmosphere. After addition, the mixture was allowed to stir from −78° C. to r.t. for 16 h. The reaction was quenched by saturated aqueous K$_2$CO$_3$, extracted by EtOAc (50 mL*2), dried over Na$_2$SO$_4$, filtered and concentrated. The residue was purified by silica gel chromatography (Petroleum Ether/EtOAc=30/70) to give the desired product Example 105b (1.6 g, yield 79%) as colorless oil. LCMS [M+1]$^+$=202.0/204.0

Step 2: Example 105d

To a solution of Example 105b (105 mg, 0.52 mmol), Example 105c (200 mg, 0.43 mmol) in 1,4-dioxane/H$_2$O (4 mL/1 mL) were added Pd(dppf)Cl$_2$ (32 mg, 0.043 mmol) and Na$_2$CO$_3$ (92 mg, 0.87 mmol). The mixture was degassed by nitrogen for three times and heated at 95° C. for 2 h. The reaction mixture was filtered, washed with EtOAc and concentrated. The residue was purified by silica gel chromatography (DCM/MeOH=90/10) to give the desired product Example 105d (106 mg, yield 54%) as a gray solid. LCMS [M/2+1]$^+$=229.0

Step 3: Example 105

To a solution of Example 105d (50 mg, 0.11 mmol) in dry DCM (2 mL) was added DAST (88 mg, 0.55 mmol) slowly at 0° C. After addition, the mixture was warmed to 25° C. and stirred for 4 h. The reaction was quenched by water, concentrated and purified directly by prep-HPLC to give the desired product Example 105 (2 mg, yield 4%) as a white solid. LCMS [M/2+1]$^+$=230.1. $^1$H NMR (400 MHz, DMSO-d$_6$) δ 11.23 (s, 1H), 8.83 (d, J=2.4 Hz, 1H), 8.68 (s, 1H), 8.24 (d, J=2.6 Hz, 1H), 8.09-8.02 (m, 2H), 7.95 (dd, J=8.6, 2.6 Hz, 1H), 7.90 (d, J=8.1 Hz, 1H), 7.85 (d, J=7.6 Hz, 1H), 7.42 (dd, J=8.4, 6.7 Hz, 2H), 4.89 (t, J=6.1 Hz, 1H), 4.77 (t, J=6.1 Hz, 1H), 4.40-4.34 (m, 2H), 4.29-4.22 (m, 2H), 3.20 (s, 1H), 3.13 (s, 1H), 1.96 (s, 2H).

Example 106: General Procedure for Synthesis of Compound Example 106

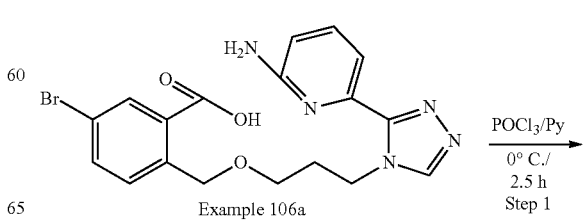

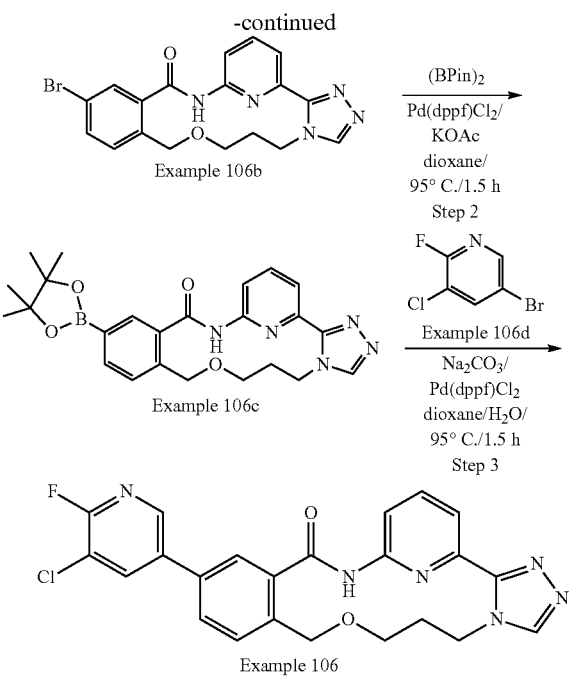

8.24 (s, 1H), 8.20-8.06 (m, 4H), 7.97 (t, J=7.9 Hz, 1H), 7.73 (dd, J=7.9, 2.1 Hz, 1H), 7.61 (d, J=7.8 Hz, 1H), 4.78 (s, 2H), 4.69 (s, 2H), 3.98 (d, J=5.1 Hz, 2H), 2.36 (s, 2H).

Example 107: General Procedure for Synthesis of Compound Example 107

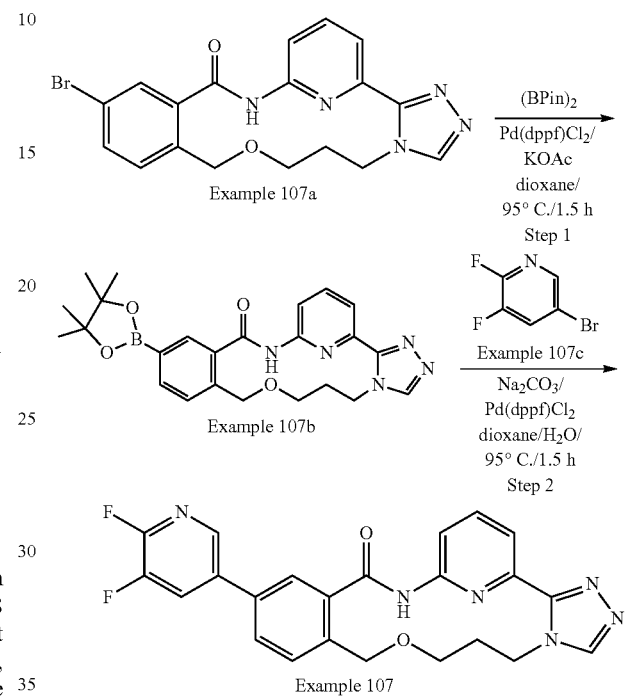

Step 1: Example 106b

To a mixture of Example 106a (1.00 g, 2.31 mmol) in pyridine (200 mL) at 0° C. was added POCl₃ (1.42 g, 9.28 mmol) in DCM (50 mL) slowly. The mixture was stirred at 0° C. for 2.5 h. To the mixture was added water (80 mL), which was concentrated under reduced pressure. The residue was added water (50 mL), and extracted with DCM/MeOH (50 mL*3, v/v=10/1). The organic lays were dried and concentrated, purified by silica gel chromatography (DCM/MeOH=20/1) to give the desired product Example 106b (220 mg, yield 23%) as a white solid. LCMS [M+1]⁺=413.9/415.9

Step 2: Example 106c

To a mixture of Example 106b (27 mg, 0.065 mmol), Bis(pinacolato)diboron (18 mg, 0.068 mmol), and KOAc (16 mg, 0.1625 mmol) in dioxane (1 mL) was added Pd(dppf)Cl₂ (3 mg, 0.0033 mmol). Then the mixture was degassed by bubbling N₂ through the solution for 2 min using a syringe needle. After being heated at 95° C. for 1.5 h, the mixture Example 106c was cooled to r.t., which was used for next step without further purification. LCMS [M+1]⁺=462.1

Step 3: Example 106

Example 106d (28 mg, 0.13 mmol), and Na₂CO₃ (20 mg, 0.20 mmol) were added to the cooled mixture of Example 106c (crude mixture, 0.065 mmol), followed by water (0.3 mL) and Pd(dppf)Cl₂ (3 mg). Then the mixture was degassed by bubbling N₂ through the solution for 2 min using a syringe needle. After that, the mixture was heated at 95° C. for 1.5 h. The mixture was concentrated and directly purified by Prep-TLC (DCM/MeOH=20/1) to give the desired product Example 106 (3.0 mg, yield 10% over two steps) as a white solid. LCMS [M+1]+=465.1. ¹H NMR (400 MHz, Chloroform-d) δ 10.50 (s, 1H), 8.36 (d, J=1.8 Hz, 1H),

Step 1: Example 107b

To a mixture of Example 107a (27 mg, 0.065 mmol), Bis(pinacolato)diboron (18 mg, 0.068 mmol), and KOAc (16 mg, 0.1625 mmol) in dioxane (1 mL) was added Pd(dppf)Cl₂ (3 mg, 0.0033 mmol). Then the mixture was degassed by bubbling N₂ through the solution for 2 min using a syringe needle. After being heated at 95° C. for 1.5 h, the mixture Example 107b was cooled to r.t., which was used for next step without further purification. LCMS [M+1]⁺=462.1

Step 3: Example 107

Example 107c (26 mg, 0.13 mmol), and Na₂CO₃ (20 mg, 0.20 mmol) were added to the cooled mixture of Example 107b (crude mixture, 0.065 mmol), followed by water (0.3 mL) and Pd(dppf)Cl₂ (3 mg). Then the mixture was degassed by bubbling N₂ through the solution for 2 min using a syringe needle. After that, the mixture was heated at 95° C. for 1.5 h. The mixture was concentrated and directly purified by Prep-TLC (DCM/MeOH=20/1) to give the desired product Example 107 (4.6 mg, yield 16% over two steps) as a white solid. LCMS [M+1]⁺=449.1. ¹H NMR (400 MHz, Chloroform-d) δ 10.49 (s, 1H), 8.26 (s, 1H), 8.15 (d, J=7.3 Hz, 4H), 7.97 (s, 1H), 7.84 (t, J=9.3 Hz, 1H), 7.72 (d, J=7.7 Hz, 1H), 7.60 (d, J=7.8 Hz, 1H), 4.75 (d, J=46.7 Hz, 4H), 3.99 (s, 2H), 2.38 (s, 2H).

Example 108: General Procedure for Synthesis of Compound Example 108

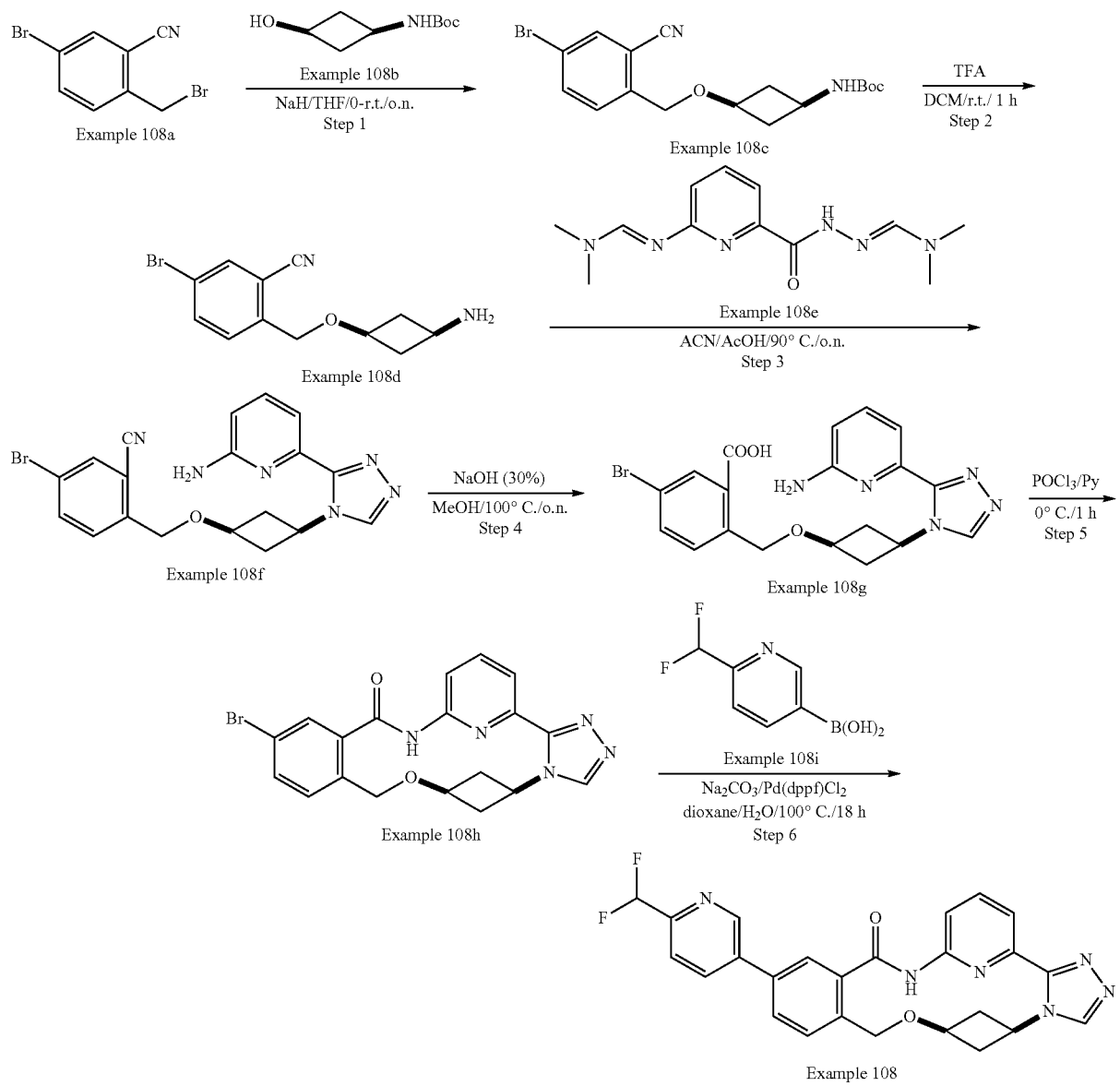

Step 1: Example 108

To a slurry of Example 108b (1.87 g, 10.0 mmol) in THF (150 mL) at 0° C. was added NaH (480 mg, 12 mmol, 60% in mineral oil), which was stirred for 30 min. Then Example 108a (2.75 g, 10.0 mmol) was added at 0° C. and the mixture was warmed to r.t. for overnight. Water (1 mL) was added to the mixture, which was then concentrated under reduced pressure. The residue was directly purified by silica gel chromatography (Petroleum Ether/EtOAc=2/1~0/1) to give the desired product Example 108c (2.80 g, yield 73%) as a white solid. LCMS [M+1]$^+$=380.9/382.9

Step 2: Example 108d

To a mixture of Example 108d (2.80 g, 7.35 mmol) in DCM (10 mL) was added TFA (10 mL), which was stirred at r.t. for 1 h. Then, the mixture was concentrated under reduced pressure to give the crude product Example 108d (2.80 g, crude yield 100%) as yellow oil. LCMS [M+1]$^+$=280.9/282.9

Step 3: Example 108f

A mixture of Example 108d (2.80 g, crude), Example 108e (1.93 g, 7.35 mmol) in MeCN/AcOH (20 mL, v/v=4/1) was heated at 90° C. for overnight. Then the mixture was concentrated under reduced pressure and to the residue was added MeOH (10 mL)/conc. HCl (5 ml, 12 N), which was stirred for 1 h. Then the mixture was adjusted pH to 7.0 and concentrated under reduced pressure. The residue was directly purified by silica gel chromatography (DCM/MeOH=1/0~10/1) to give the crude product, which was washed by MeOH (5 mL) to give the desired product Example 108f (800 mg, yield 26%) as a yellow solid. LCMS [M+1]$^+$=424.9/426.9

Step 4: Example 108g

To a mixture of Example 108f (500 mg, 1.17 mmol) in MeOH (15 mL) was added 30% aq. NaOH (3 mL), which was heated to 100° C. for overnight. Then the mixture was concentrated in vacuo and adjusted pH to 7.0 by conc. HCl. The precipitate was filtered and dried for overnight in vacuo to give the desired product Example 108g (300 mg, yield 57%) as a white solid. LCMS [M+1]$^+$=443.9/445.9

Step 5: Example 108h

To a mixture of Example 108g (200 mg, 0.45 mmol) in pyridine (60 mL) at 0° C. was added POCl$_3$ (689 mg, 4.50 mmol), which was stirred at 0° C. for 1 h. To the mixture was added water (1 mL), which was then concentrated under reduced pressure. To the residue was added H$_2$O (30 mL), which was then extracted with DCM (30 mL*3). The combined organic layer was saturated with brine, dried over anhydrous magnesium sulfate and concentrated under reduced pressure. The residue was directly purified by silica gel chromatography (DCM/MeOH=1/0~20/1) to give the desired product Example 108h (10 mg, yield 5%) as a white solid. LCMS [M+1]$^+$=425.9/427.9

Step 6: Example 108

To a mixture of Example 108h (10 mg, 0.023 mmol), Example 108i (6 mg, 0.035 mmol), and Na$_2$CO$_3$ (7 mg, 0.069 mmol) in dioxane/H$_2$O (2 mL, v/v=10/1) was added Pd(dppf)Cl$_2$ (5 mg). Then the mixture was degassed by bubbling N$_2$ through the solution for 2 min using a syringe needle. After that, the mixture was heated at 90° C. for overnight. The mixture was concentrated under reduced pressure. The residue was purified by prep-HPLC to give the desired product Example 108 (7.6 mg, yield 38%) as a white solid. LCMS [M+1]$^+$=475.0. $^1$H NMR (400 MHz, Chloroform-d) δ 11.78 (s, 1H), 8.94 (s, 1H), 8.29 (s, 1H), 8.21 (dd, J=18.4, 9.1 Hz, 3H), 8.11 (d, J=6.8 Hz, 1H), 7.96 (t, J=7.9 Hz, 1H), 7.76 (d, J=8.0 Hz, 2H), 7.55 (d, J=7.8 Hz, 1H), 6.85 (s, OH), 6.71 (s, OH), 6.57 (s, OH), 4.89-4.78 (m, 1H), 4.62 (s, 2H), 4.43 (p, J=6.7 Hz, 1H), 3.89-3.77 (m, 2H), 2.90 (td, J=13.3, 11.1, 5.6 Hz, 2H).

Example 109: General Procedure for Synthesis of Compound Example 109

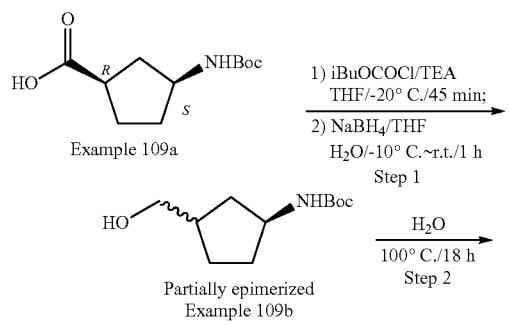

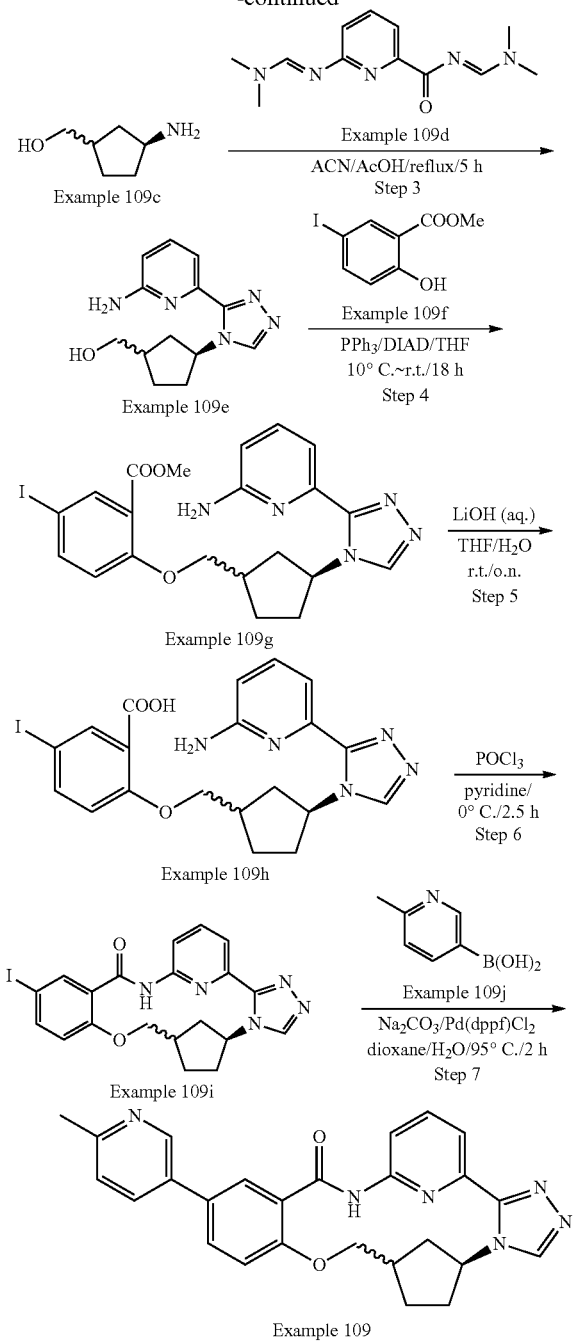

Step 1: Example 109b

To a solution of Example 109a (2.0 g, 8.7 mmol) and Et$_3$N (1.33 mL, 9.6 mmol) in anhydrous THF (50 mL) at −20° C. was added iBuOCOCl (1.2 mL, 9.2 mmol) dropwise, which was stirred for 45 min at −20° C. The insoluble material was formed, which was then filtered off. A solution of NaBH$_4$ (1.0 g, 26.2 mmol) in THF/H$_2$O (16 mL/4 mL) was added dropwise to the above filtrate at −10° C., which was stirred at r.t, for 1 h. 0.1N HCl (100 mL) was added slowly and the resulting mixture was then extracted with EtOAc (200 mL*2), dried over Na$_2$SO$_4$, filtered and concentrated under reduced pressure to give the crude product Example 109b (1.2 g, yield 64%) as a yellow solid.
LCMS [M−56+1]⁺=160.1 & [M−100+1]⁺=116.1 & [M+Na]⁺=238.1

Step 2: Example 109c

A solution of Example 109b (3.0 g, 13.94 mmol) in H₂O (100 mL) was refluxed at 100° C. for 18 h. Water was removed by azeotroping with EtOH (50 mL*). Example 109c (1.6 g, yield 100%) was obtained as colorless oil, which was used for the next step without further purification. LCMS [M+1]⁺=116.1

Step 3: Example 109e

To a solution of Example 109d (3.66 g, 13.94 mmol) in CH₃CN/AcOH (80 mL, v/v=4/1) was added Example 109c (1.6 g, 13.94 mmol). The resulting mixture was heated under reflux for 5 h and then cooled to room temperature. The solvent was removed under reduced pressure. The residue was dissolved in water (50 mL) and 30% aqueous NaOH was added to adjust pH to 8~9. The resulting mixture was concentrated, slurried with DCM/MeOH (50 mL*2, v/v=10/1), and then filtered. The filtrate was concentrated, and then purified by silica gel chromatography (DCM/MeOH=10/1) to give the desired compound Example 109e (1.2 g, yield 33%) as a yellow solid. LCMS [M+1]⁺=260.1

Step 4: Example 109g

A mixture of Example 109e (1.2 g, 4.63 mmol), Example 109f (1.93 g, 6.94 mmol) and PPh₃ (1.83 g, 6.94 mmol) in THF (50 mL) was treated with DIAD (1.5 g, 7.40 mmol) in THF (5 mL) at 10° C., which was stirred at r.t. for 18 h. The mixture was diluted with H₂O (20 mL) and then extracted with EtOAc (100 mL). The organic layer was dried over Na₂SO₄, filtered and concentrated under reduced pressure. The residue was purified by silica gel chromatography (DCM/MeOH=10/1) to give the desired product Example 109g (780 mg, yield 33%) as a white solid. LCMS [M+1]⁺=519.9.

Step 5: Example 109h

To a solution of Example 109g (780 mg, 1.5 mmol) in THF (3 mL) was added 1N LiOH (aq., 3 mL, 3.0 mmol), which was stirred at r.t for overnight. The pH of the reaction mixture was adjusted to nearly 4-5 by 1N HCl (aq.). The precipitate was filtered and dried under reduce pressure to give the desired product Example 109h (510 mg, yield 67%) as a white solid. LCMS [M+1]⁺=505.9

Step 6: Example 109i

To a mixture of Example 109h (505 mg, 1.0 mmol) in pyridine (120 mL) at 0° C. was added POCl₃ (0.5 mL) slowly. The mixture was stirred at 0° C. for 2.5 h. To the mixture was added ice-water (50 mL), which was concentrated under reduced pressure. The residue was purified by silica gel chromatography (DCM/MeOH=20/1) to afford a crude product, which was further slurried by water (20 mL) to give the desired product Example 109i (300 mg, yield 62%) as a white solid. LCMS [M+1]⁺=487.9

Step 7: Example 109

To a mixture of Example 109i (150 mg, 0.3 mmol), Example 109j (62 mg, 0.45 mmol), and Na₂CO₃ (96 mg, 0.9 mmol) in dioxane/H₂O (3 mL, v/v=3/1) was added Pd(dppf)Cl₂ (11 mg). Then the mixture was degassed by bubbling N₂ through the solution for 2 min using a syringe needle. After that, the mixture was heated at 95° C. for 2 h. The mixture was concentrated and directly purified by Prep-HPLC, followed by prep-TLC (DCM/MeOH=10/1) twice, to give the desired product Example 109 (13.5 mg, yield 10%) as a white solid. LCMS [M+1]+=453.0 and M/2+1:227.1. ¹H NMR (400 MHz, DMSO-d₆) major δ 11.25 (s, 1H), 8.76-8.75 (m, 1H), 8.68 (s, 1H), 8.19 (d, J=2.4 Hz, 1H), 8.07-7.83 (m, 5H), 7.33 (d, J=8.4 Hz, 2H), 5.14-5.06 (m, 1H), 4.38 (dd, J=33.4, 9.4 Hz, 2H), 3.81-3.72 (m, 1H), 2.65-2.58 (m, 1H), 2.48 (s, 3H), 2.14-1.65 (m, 5H). ¹H NMR (400 MHz, DMSO-d₆) minor δ 10.61 (s, 1H), 8.86 (s, 1H), 8.76-8.75 (m, 1H), 8.07-7.83 (m, 6H), 7.67 (d, J=8.0 Hz, 1H), 7.42 (d, J=8.4 Hz, 1H), 5.32-5.23 (m, 1H), 4.32-4.30 (m, 1H), 4.09-4.07 (m, 1H), 3.81-3.72 (m, 1H), 2.47 (s, 3H), 3.02-2.99 (m, 1H), 2.76-2.74 (m, 1H), 2.14-1.65 (m, 3H), 1.55-1.48 (m, 1H).

Example 110: General Procedure for Synthesis of Compound Example 110

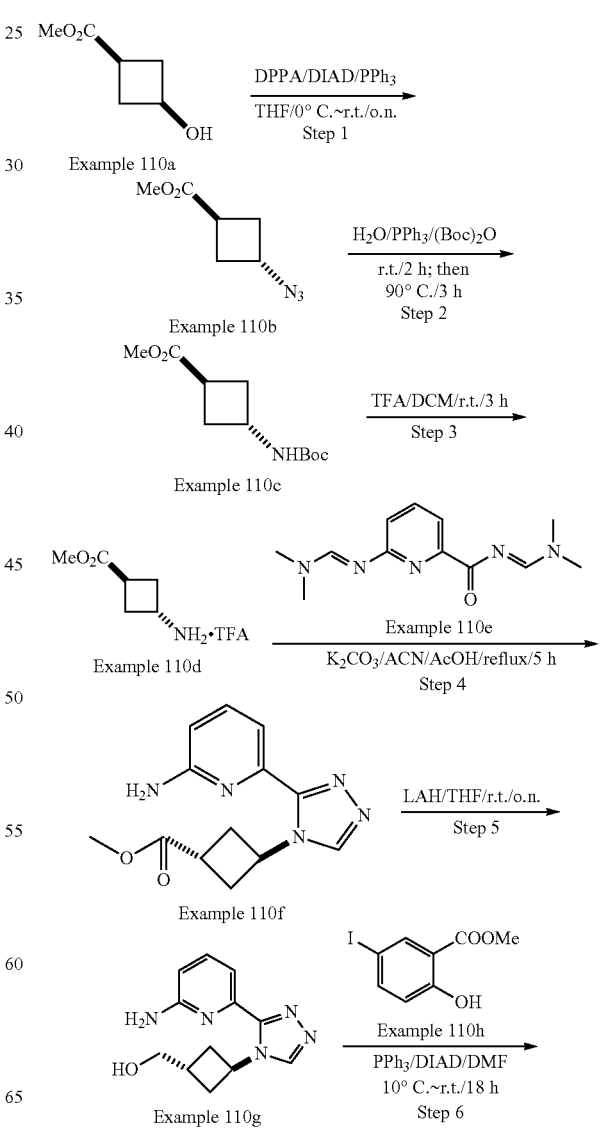

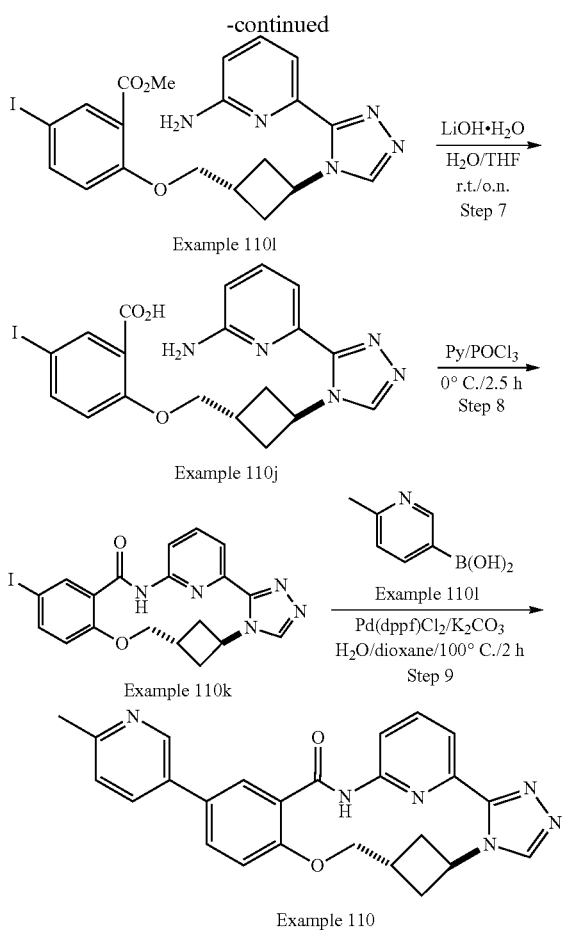

Example 110l

Example 110j

Example 110k

Example 110

Step 1: Example 110

To a mixture of Example 110a (2.00 g, 11.50 mmol) and PPh₃ (3.60 g, 13.80 mmol) in THF (20 mL) were injected DIAD (2.78 g, 13.80 mmol) and DPPA (3.79 g, 13.80 mmol) at 0° C. under N₂ protection, which was stirred at room temperature for overnight. The mixture Example 110b was used for the next step without purification.

Step 2: Example 110c

A mixture of Example 110b (crude mixture) and PPh₃ (13.5 g, 51.9 mmol), (Boc)₂O (14.9 g, 69.24 mmol) in water (10 mL) was stirred at room temperature for 2 h under N₂ protection, which was heated at 90° C. for 3 h and then cooled to r.t. The mixture was extracted by EtOAc (100 mL). The organic layer was dried over Na₂SO₄, filtered and concentrated under reduced pressure. The residue was purified by silica gel chromatography (Petroleum Ether/EtOAc=80/20) to give the desired product Example 110c (2.8 g, yield 25% over two steps) as a white solid. LCMS [M−56+1]⁺=174.1.

Step 3: Example 110d

A mixture of Example 110c (2.8 g, 12.2 mmol) and DCM (20 mL)/TFA (5 mL) was stirred at room temperature for 3 h. The resulting mixture was concentrated to give the desired compound Example 110d (1.5 g, yield 33%) as a yellow solid, which was used for the next step without purification. LCMS [M+1]⁺=130.1

Step 4: Example 110f

To a solution of Example 110d (2.26 g, 10.0 mmol) and K₂CO₃ (2.76 g, 20.0 mmol) in ACN/AcOH (80 mL, v/v=4/1) was added Example 110e (2.61 g, 10.0 mmol). The resulting mixture was heated under reflux for 5 h and then cooled to room temperature. The solvent was removed under reduced pressure. The residue was dissolved in water (50 mL) and 30% aqueous NaOH was added to adjust pH to 8~9. The resulting mixture was concentrated, slurried with DCM/MeOH (50 mL*2, v/v=10/1), and then filtered. The filtrate was concentrated, and then purified by silica gel chromatography (DCM/MeOH=10/1) to give the desired compound Example 110f (1.5 g, yield 33%) as a yellow solid. LCMS [M+1]⁺=274.0

Step 5: Example 110g

To a mixture of Example 110f (400 mg, 1.5 mmol) in THF (10 mL) was added LAH (220 mg, 7.5 mmol) at 0° C. carefully. The mixture was stirred at r.t. for overnight. The mixture was cooled to −5° C., and quenched by 15% NaOH (10 mL), which was then filtered. The filtrate was concentrated to give the desired product Example 110g (245 mg, crude yield 66%) as colorless oil. LCMS [M+1]⁺=246.0.

Step 6: Example 110i

A mixture of Example 110g (245 mg, 1.0 mmol), Example 110h (417 mg, 1.5 mmol) and PPH₃, (394 g. 1.5 mmol) in DMF (5 mL) was treated with DIAD (300 mg, 1.5 mmol) in DMF (5 mL) at 10° C., which was stirred at r.t. for 18 h. The mixture was diluted with H₂O (20 mL) and then extracted with EtOAc (100 mL). The organic layer was dried over Na₂SO₄, filtered and concentrated under reduced pressure. The residue was purified by silica gel chromatography (DCM/MeOH=10/1) to give the desired product Example 110i (160 mg, yield 32%) as a white solid. LCMS [M+1]⁺=505.9.

Step 7: Example 110j

To a solution of Example 110i (130 mg, 0.25 mmol) in THF (3 mL) was added 1N LiOH (aq., 3 mL, 3.0 mmol), which was stirred at r.t for overnight. The pH of the reaction mixture was adjusted to nearly 4-5 by 1N HCl(aq.). The precipitate was dried under reduce pressure to give the desired product Example 110j (510 mg crude, yield 100%) as a white solid. LCMS [M+1]⁺=491.9

Step 8: Example 110k

To a mixture of Example 110j (510 mg crude, 0.25 mmol) in pyridine (12 mL) at 0° C. was added POCl₃ (0.2 mL) slowly. The mixture was stirred at 0° C. for 2.5 h. To the mixture was added ice-water (5 mL), which was concentrated under reduced pressure. The residue was purified by silica gel chromatography (DCM/MeOH=20/1) to afford a crude product, which was further slurried by water (20 mL) to give the desired product Example 110k (60 mg crude, yield 94%) as a white solid. LCMS [M+1]⁺=473.9

Step 9: Example 110

To a mixture of Example 110k (60 mg, 0.12 mmol), Example 110l (31 mg, 0.24 mmol), and K₂CO₃ (49 mg, 0.36 mmol) in dioxane/H₂O (3 mL, v/v=3/1) was added Pd(dppf)Cl₂ (11 mg, 0.11 mmol). Then the mixture was degassed by bubbling N₂ through the solution for 2 min using a syringe needle. After that, the mixture was heated at 100° C. for 2 h. The mixture was concentrated and directly purified by Prep-HPLC to give the desired product Example 110 (1.2 mg, yield 2%) as a white solid.

LCMS [M+1]⁺=439.0 and [M/2+1]⁺=220.1. ¹H NMR (400 MHz, DMSO-d₆) δ 10.67 (s, 1H), 8.94 (s, 1H), 8.72 (s, 1H), 8.03-7.90 (m, 3H), 7.73 (d, J=9.0 Hz, 1H), 7.68 (s, 1H), 7.30 (dd, J=8.4, 4.1 Hz, 2H), 7.20 (d, J=7.6 Hz, 1H), 4.30 (s, 1H), 3.42 (s, 1H), 2.68-2.56 (m, 4H), 2.44 (s, 3H).

Example 111: General Procedure for Synthesis of Compound Example 111

Step 2: Example 111

A solution of Example 111c (70 mg, 0.3 mmol), Example 111d (100 mg, 0.2 mmol), Na₂CO₃ (64 mg, 0.6 mmol) and Pd(dppf)Cl₂ (15 mg, 0.02 mmol) in 1,4-dioxane/H₂O (2 mL/0.4 mL) was stirred at 85° C. for 2 h under N₂ atmosphere. The mixture was concentrated and purified by prep-HPLC to give the desired product Example 111 (2 mg, yield 1%) as a white solid. LCMS [M+1]⁺=487.0. ¹H NMR (400 MHz, DMSO-d₆) δ 11.25 (s, 1H), 8.67 (s, 1H), 8.45 (d, J=2.6 Hz, 1H), 8.18 (d, J=2.6 Hz, 1H), 8.10-7.98 (m, 2H), 7.92-7.82 (m, 3H), 7.37 (d, J=8.7 Hz, 1H), 6.91 (d, J=8.6 Hz, 1H), 4.38 (dt, J=18.1, 5.0 Hz, 4H), 4.26 (t, J=8.6 Hz, 2H), 3.66 (t, J=4.6 Hz, 2H), 2.48 (s, 2H), 1.96 (s, 2H).

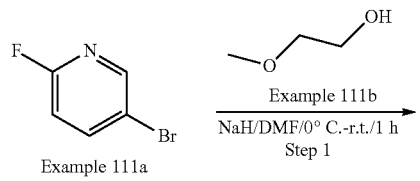

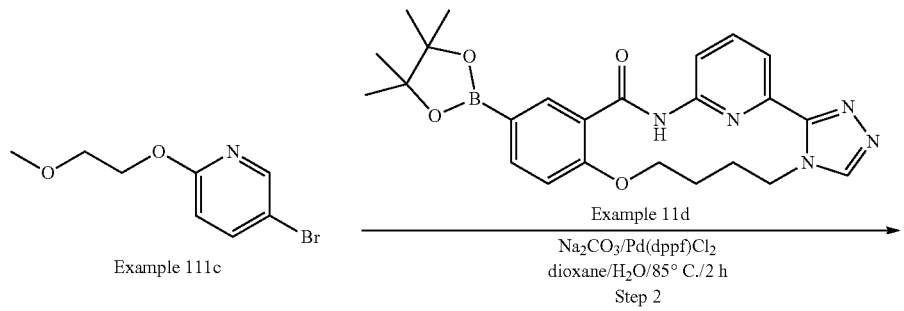

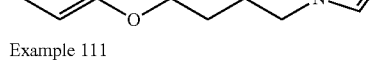

Example 111

Step 1: Example 111c

To a solution of Example 111a (1.0 g, 5.7 mmol) in DMF (30 mL) was added NaH (568 mg, 14.2 mmol) at 0° C., which was stirred at 0° C. for 15 min. Example 111b (432 mg, 5.7 mmol) was added to the reaction mixture, which was stirred for another 30 min. The mixture was diluted with sat. NaHCO₃ solution, and then extracted with EtOAc (200 mL*2). The combined organic layer was concentrated and purified by silica gel chromatography (Petroleum Ether/EtOAc=10/1) to give the desired product Example 111c (900 mg, yield 69%) as colorless oil.

Example 112: General Procedure for Synthesis of Compound Example 112

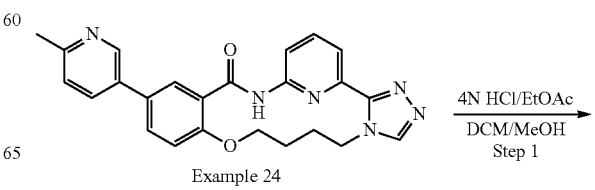

-continued

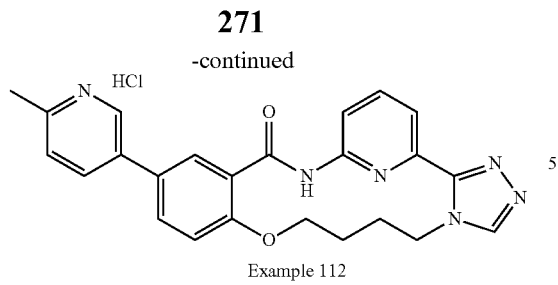

Example 112

Example 113

Step 1: Example 112

To a solution of Example 24 (120 mg 0.28 mmol) in DCM (2 mL) and MeOH (0.2 mL) was treated with HCl (4M in EtOAc, 0.4 mL), which was then stirred at r.t. for 0.5 h. The precipitate was filtered and dried at high vacuum to give the desired product Example 112 (140 mg, yield 93%) as a white solid. LCMS [M+1]$^+$=427.2. $^1$H NMR (400 MHz, DMSO-d$_6$) δ 11.17 (s, 1H), 9.13 (s, 1H), 8.78 (s, 1H), 8.75 (d, J=8.6 Hz, 1H), 8.38 (d, J=2.2 Hz, 1H), 8.09 (t, J=8.0 Hz, 2H), 7.91 (t, J=7.9 Hz, 2H), 7.87 (d, J=7.8 Hz, 1H), 7.47 (d, J=8.8 Hz, 1H), 4.40 (m, 2H), 4.32-4.24 (m, 2H), 2.73 (m, 3H), 1.97 (m, 2H).

Example 113: General Procedure for Synthesis of Compound Example 113

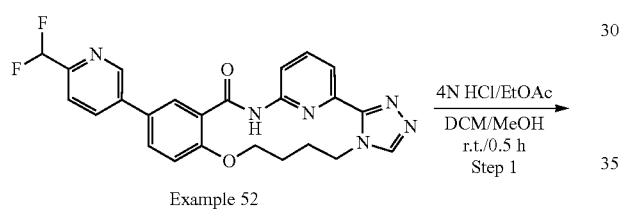

Step 1: Example 113

To a solution of Example 52 (110 mg 0.24 mmol) in DCM (2 mL) and MeOH (0.2 mL) was treated with HCl (4M in EtOAc, 0.4 mL), which was then stirred at r.t. for 0.5 h. The precipitate was filtered and dried at high vacuum to give the desired product Example 113 (99 mg, yield 83%) as a white solid. LCMS [M+1]$^+$=463.2. $^1$H NMR (400 MHz, DMSO-d$_6$) δ 11.21 (s, 1H), 9.02 (d, J=1.7 Hz, 1H), 8.87 (s, 1H), 8.32 (dd, J=5.0, 2.4 Hz, 2H), 8.12-8.01 (m, 2H), 7.89 (dd, J=16.7, 7.8 Hz, 2H), 7.78 (d, J=8.2 Hz, 1H), 7.45 (d, J=8.8 Hz, 1H), 7.01 (t, J=56.0 Hz, 1H), 4.39 (t, J=4.8 Hz, 2H), 4.33-4.26 (m, 2H), 2.46-2.41 (m, 2H), 1.97 (s, 2H).

Example 114: General Procedure for Synthesis of Compound Example 114

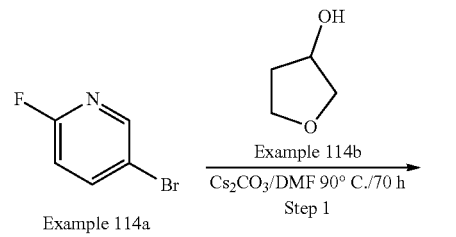

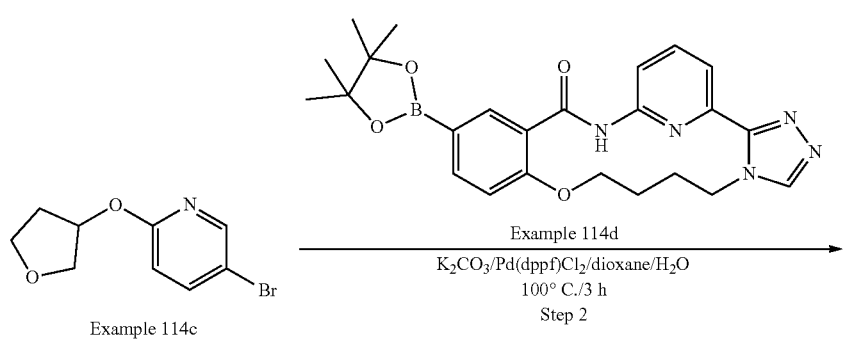

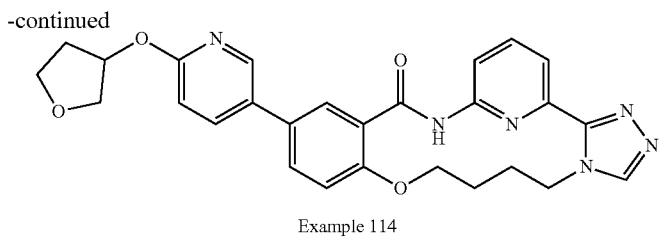

Example 114

Step 1: Example 114c

To a solution of Example 114a (290 mg, 1.65 mmol) in DMF (5 mL) were added Cs$_2$CO$_3$ (1.07 g, 3.29 mmol) and Example 114b (218 mg, 2.47 mmol). Then, the mixture was degassed by bubbling N$_2$ through the solution for 2 min, sealed and heated at 90° C. for 70 h. After the reaction solution was cooled to r.t., water (10 mL) was added and the mixture was stirred for 10 min. The solid was collected by filtration, washed with water and dried to get the desired Example 114c (374 mg, yield 93%) as a white solid. LCMS [M+1]$^+$=243.9/245.9

Step 2: Example 114

A mixture of Example 114c (100 mg, 0.41 mmol), Example 114d (189 mg, 0.41 mmol), K$_2$CO$_3$ (113 mg, 0.82 mmol), and Pd(dppf)Cl$_2$ (15 mg, 0.02 mmol) in dioxane/H$_2$O (4 mL/1 mL) was degassed by bubbling N$_2$ through the solution, and heated at 100° C. for 3 h. After the mixture was cooled to r.t., the mixture was filtrated, and the filtrate was concentrated and purified directly by Prep-HPLC to get a crude product, which was further slurried by MeOH and filtrated. The remaining white solid was collected and dried to afford the desired product Example 14 (4 mg, yield 2%) as a white solid. LCMS [M+1]$^+$=499.0. $^1$H NMR (400 MHz, DMSO-d$_6$) δ 11.24 (s, 1H), 8.66 (s, 1H), 8.49-8.38 (m, 1H), 8.20-8.13 (m, 1H), 8.07-7.95 (m, 2H), 7.85 (q, J=7.7 Hz, 3H), 7.33 (d, J=8.7 Hz, 1H), 6.88 (d, J=8.6 Hz, 1H), 5.52 (d, J=6.2 Hz, 1H), 4.33 (t, J=5.0 Hz, 2H), 4.23 (t, J=8.5 Hz, 2H), 3.98-3.70 (m, 4H), 2.43 (s, 2H), 2.23 (dd, J=14.1, 7.0 Hz, 1H), 2.02 (t, J=6.4 Hz, 1H), 1.94 (s, 2H).

Example 115: General Procedure for Synthesis of Compound Example 115

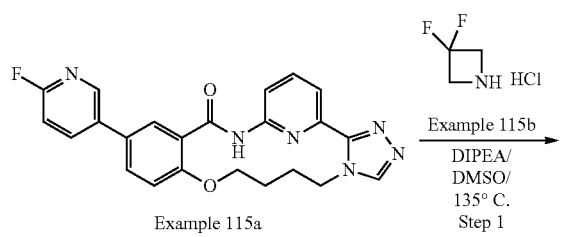

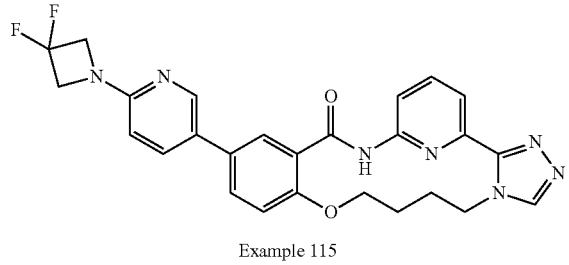

Example 115

Step 1: Example 115

To a solution of Example 115a (150 mg, 0.35 mmol) and Example 115b (113 mg, 0.87 mmol) in DMSO (2.0 mL) was added N,N-diisopropylethylamine (0.5 mL). The mixture was heated at 135° C. for 4 h. The reaction mixture was cooled to r.t., diluted with H$_2$O (20 mL), and then extracted with DCM (100 mL). The organic layer was dried over Na$_2$SO$_4$, filtered and concentrated under reduced pressure. The residue was purified by Prep-HPLC, followed by prep-TLC (DCM/MeOH=20/1) to give the desired product Example 115 (2.0 mg, yield 1%) as a white solid. LCMS [M+1]$^+$=504.1. $^1$H NMR (400 MHz, DMSO-d$_6$) δ 11.27 (s, 1H), 8.67 (s, 1H), 8.46 (d, J=2.5 Hz, 1H), 8.16 (d, J=2.6 Hz, 1H), 8.06 (t, J=7.9 Hz, 1H), 7.95 (dd, J=8.6, 2.5 Hz, 1H), 7.90 (d, J=8.0 Hz, 1H), 7.87-7.84 (m, 2H), 7.36 (d, J=8.7 Hz, 1H), 6.68 (d, J=8.6 Hz, 1H), 4.41 (t, J=12.5 Hz, 4H), 4.36 (t, J=5.0 Hz, 2H), 4.26 (t, J=8.6 Hz, 2H), 2.44 (m, 2H), 1.97-1.93 (m, 2H).

Example 116: General Procedure for Synthesis of Compound Example 116

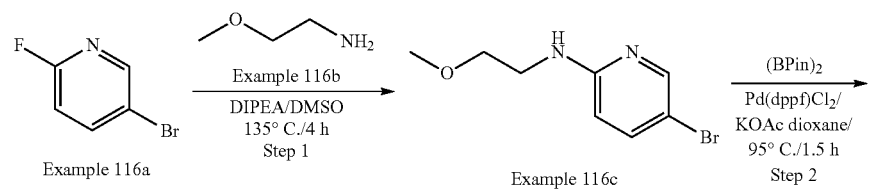

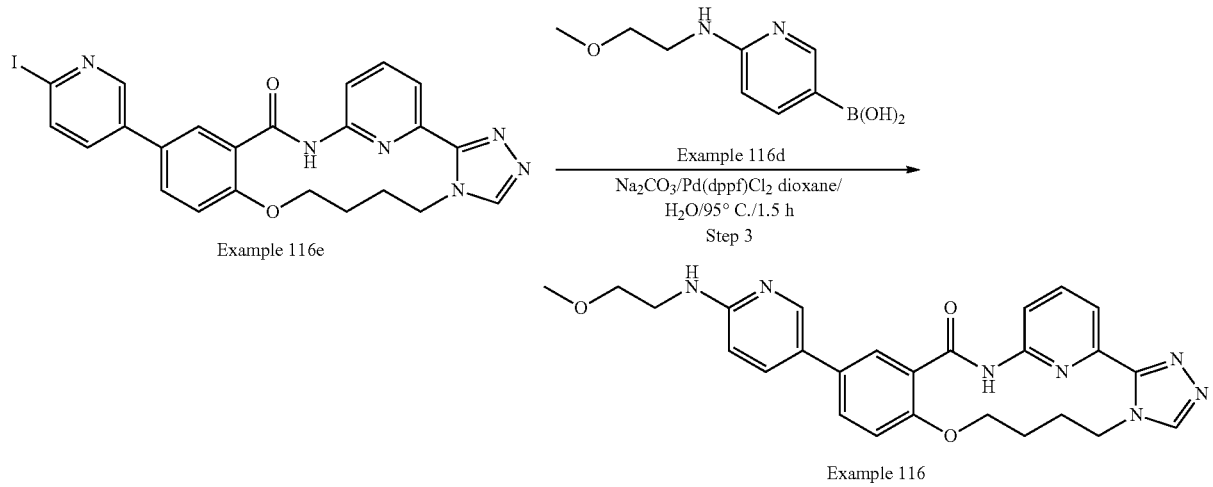

Example 116d

Example 116e

Example 116

Step 1: Example 116b

To a solution of Example 116a (528 mg, 3.0 mmol) and Example 116b (450 mg, 6.0 mmol) in DMSO (4 mL) was added N,N-diisopropylethylamine (780 mg, 6.0 mmol). The mixture was heated at 135° C. for 4 h. The reaction mixture was cooled to r.t., diluted with $H_2O$ (20 mL), and then extracted with EtOAc (100 mL). The organic layer was dried over $Na_2SO_4$, filtered and concentrated under reduced pressure to give the desired product Example 116c (620 mg, yield 90%) as a white solid. LCMS $[M+1]^+$=230.9/232.9.

Step 2: Example 116d

To a mixture of Example 116c (140 mg, 0.605 mmol), bis(pinacolato)diboron (162 mg, 0.636 mmol), and KOAc (149 mg, 1.52 mmol) in dioxane (2 mL) was added Pd(dppf)$Cl_2$ (22 mg, 0.03 mmol). Then the mixture was degassed by bubbling $N_2$ through the solution for 2 min using a syringe needle. After being heated at 95° C. for 1.5 h, the mixture Example 116d was cooled to r.t., which was used for next step without further purification.
LCMS $[M+1]^+$=197.0

Step 3: Example 116

Example 116e (279 mg, 0.605 mmol), and $Na_2CO_3$ (193 mg, 1.815 mmol) were added to the cooled mixture of Example 116d (crude mixture, 0.605 mmol), followed by water (0.3 mL) and Pd(dppf)$Cl_2$ (22 mg). Then the mixture was degassed by bubbling $N_2$ through the solution for 2 min using a syringe needle. After that, the mixture was heated at 95° C. for 1.5 h. The mixture was concentrated and directly purified by Prep-HPLC, followed by Prep-TLC (DCM/MeOH=20/1, twice) to give the desired product Example 116 (6.3 mg, yield 21% over two steps) as a white solid. LCMS $[M+1]^+$=486.1. $^1$H NMR (400 MHz, DMSO-$d_6$) δ 11.30 (s, 1H), 8.69 (s, 1H), 8.28 (d, J=2.5 Hz, 1H), 8.11 (d, J=2.6 Hz, 1H), 8.06 (t, J=7.9 Hz, 1H), 7.90 (d, J=8.1 Hz, 1H), 7.85 (d, J=7.6 Hz, 1H), 7.79 (dd, J=8.6, 2.6 Hz, 1H), 7.69 (dd, J=8.7, 2.6 Hz, 1H), 7.33 (d, J=8.7 Hz, 1H), 6.76 (s, 1H), 6.60 (d, J=8.6 Hz, 1H), 4.35 (d, J=5.3 Hz, 2H), 4.26 (t, J=8.6 Hz, 2H), 3.45 (d, J=3.6 Hz, 5H), 3.26 (s, 4H), 1.96 (s, 2H).

Example 117: General Procedure for Synthesis of Compound Example 117

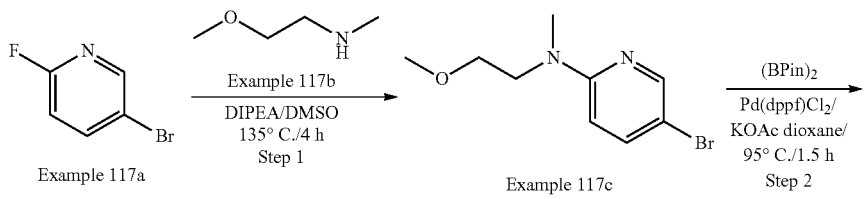

-continued

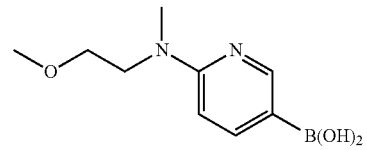

Example 117d

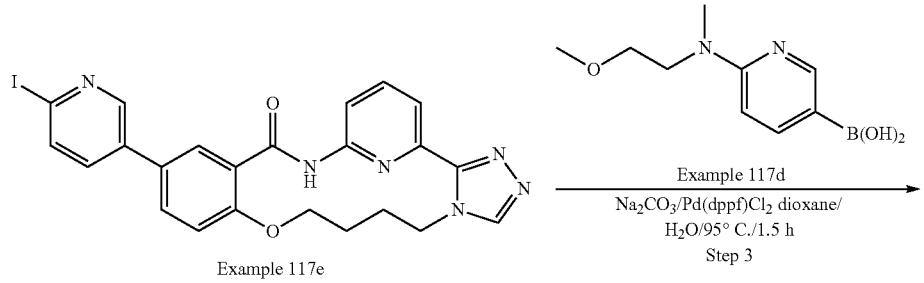

Step 1: Example 117b

To a solution of Example 117a (450 mg, 2.55 mmol) and Example 117b (342 mg, 3.84 mmol) in DMSO (3.0 mL) was added N,N-diisopropylethylamine (660 mg, 5.10 mmol). The mixture was heated at 135° C. for 4 h. The reaction mixture was cooled to r.t., diluted with $H_2O$ (20 mL), and then extracted with EtOAc (100 mL). The organic layer was dried over $Na_2SO_4$, filtered and concentrated under reduced pressure to give the desired product Example 117c (300 mg, yield 48%) as a white solid. LCMS [M+1]$^+$=244.9/246.9.

Step 2: Example 117d

To a mixture of Example 117c (294 mg, 1.2 mmol), bis(pinacolato)diboron (324 mg, 1.28 mmol), and KOAc (298 mg, 3.04 mmol) in dioxane (4 mL) was added Pd(dppf)Cl$_2$ (44 mg, 0.06 mmol). Then the mixture was degassed by bubbling $N_2$ through the solution for 2 min using a syringe needle. After being heated at 95° C. for 1.5 h, the mixture Example 117d was cooled to r.t., which was used for next step without further purification. LCMS [M+1]$^+$=211.1

Step 3: Example 117

Example 117e (442 mg, 0.958 mmol), and $Na_2CO_3$ (382 mg, 3.6 mmol) were added to the cooled mixture of Example 117d (crude mixture, 1.2 mmol), followed by water (0.5 mL) and Pd(dppf)Cl$_2$ (40 mg). Then the mixture was degassed by bubbling $N_2$ through the solution for 2 min using a syringe needle. After that, the mixture was heated at 95° C. for 1.5 h. The mixture was concentrated and directly purified by Prep-HPLC, followed Prep-TLC (DCM/MeOH=20/1, twice) to give the desired product Example 117 (32 mg, yield 7% over two steps) as a white solid. LCMS [M+1]$^+$=500.1. $^1$H NMR (400 MHz, DMSO-d$_6$) δ 11.29 (s, 1H), 8.67 (s, 1H), 8.39 (d, J=2.6 Hz, 1H), 8.13 (d, J=2.6 Hz, 1H), 8.05 (t, J=7.9 Hz, 1H), 7.89 (d, J=8.1 Hz, 1H), 7.84 (d, J=7.6 Hz, 1H), 7.80 (dt, J=8.9, 3.1 Hz, 2H), 7.32 (d, J=8.7 Hz, 1H), 6.70 (d, J=8.9 Hz, 1H), 4.34 (t, J=5.1 Hz, 2H), 4.30-4.22 (m, 2H), 3.71 (t, J=5.8 Hz, 2H), 3.50 (t, J=5.7 Hz, 2H), 3.24 (s, 3H), 3.04 (s, 3H), 2.45 (s, 2H), 1.95 (s, 2H).

Example 118: General Procedure for Synthesis of Compound Example 118

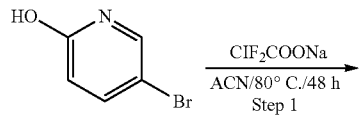

Example 118a

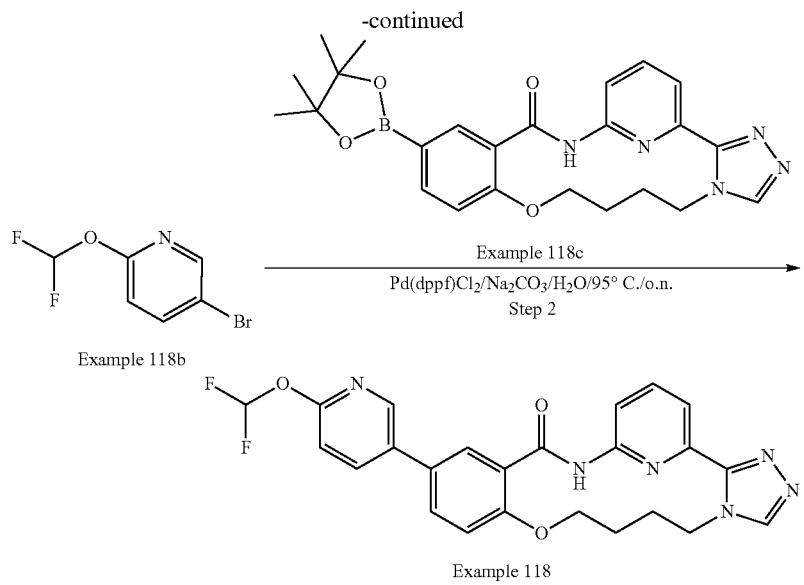

Step 1: Example 118b

To a solution of Example 118a (2 g, 11.5 mmol) in MeCN (50 mL) was added ClF₂CO₂Na (1.94 g, 13.8 mmol) at room temperature. Then the mixture was heated to 80° C. and stirred for 48 h. The mixture was cooled to room temperature, and sat. NH₄Cl (20 mL) was added, which was stirred for 20 min, followed by extraction with EtOAc (100 mL*2). The combined organic layer was dried over Na₂SO₄, and concentrated under reduced pressure. The residue was purified by silica gel chromatography (EtOAc/Petroleum Ether=9/91) to give the desired product Example 118b (160 mg, yield 6%) as a pale yellow solid.

Step 2: Example 118

To a solution of Example 118b (77 mg, 0.345 mmol), Example 118c (160 mg, 0.597 mmol), Pd(dppf)Cl₂ (24 mg, 0.0328 mmol) and Na₂CO₃ (70 mg, 0.66 mmol) in dioxane (10 mL), was added water (1 mL). Then the mixture was degassed with N₂ three times, heated to 95° C. and stirred overnight. The mixture was concentrated under reduced pressure, and purified by silica gel chromatography (DCM/MeOH=88/12) to give 10 mg of pale brown solid, which was washed with MeOH (1 mL*3) to give the desired product Example 118 (5 mg, yield 3%) as a white solid. LCMS [M+1]⁺=479.0. ¹H NMR (400 MHz, DMSO-d₆) δ 11.21 (s, 1H), 8.66 (s, 1H), 8.12 (d, J=2.6 Hz, 1H), 8.09-8.01 (m, 2H), 7.97 (dd, J=9.7, 2.6 Hz, 1H), 7.91-7.71 (m, 4H), 7.33 (d, J=8.7 Hz, 1H), 6.63 (d, J=9.7 Hz, 1H), 4.34 (t, J=5.0 Hz, 2H), 4.30-4.17 (m, 2H), 2.44 (d, J=8.5 Hz, 2H), 2.00-1.88 (m, 2H).

Example 119: General Procedure for Synthesis of Compound Example 119

Step 1: Example 119

To a solution of Example 119a (50 mg, 0.105 mmol), Example 119b (22 mg, 0.126 mmol) and Na₂CO₃ (33 mg, 0.316 mmol) in dioxane/H₂O (2.5 mL, v/v=4/1) was added Pd(dppf)Cl₂ (7.7 mg, 0.011 mmol) at room temperature under N₂. The reaction mixture was heated to 90° C. and stirred for 3 h under N₂. The reaction mixture was purified by prep-HPLC and prep-TLC (DCM/MeOH=10/1) to afford the desired product Example 119 (5.2 mg, yield 10%) as a gray solid. LCMS [M+1]⁺=477.0. ¹H NMR (400 MHz, DMSO-d₆) δ 11.16 (s, 1H), 9.03 (s, 1H), 8.73 (s, 1H), 8.31

(s, 2H), 8.09-8.02 (m, 2H), 7.89-7.85 (t, J=8.0 Hz, 2H), 7.78-7.76 (d, J=8.0 Hz, 1H), 7.48-7.46 (d, J=8.0 Hz, 1H), 7.15-6.87 (t, 1H), 4.47-4.36 (t, 2H), 4.29-4.20 (m, 1H), 4.04-4.00 (t, 1H), 3.16-3.15 (d, J=8.0 Hz, 1H), 2.06 (s, 1H), 1.58 (s, 1H), 1.15-1.13 (d, J=8.0 Hz, 3H).

Example 120: General Procedure for Synthesis of Compound Example 120

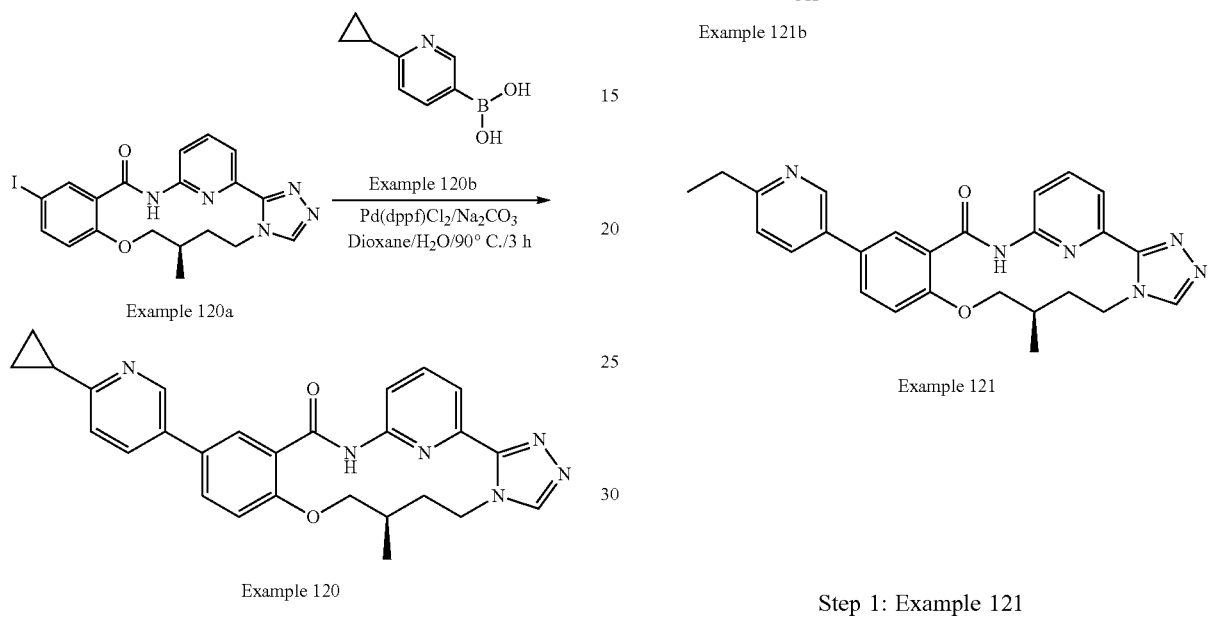

Step 1: Example 120

To a solution of Example 120a (50 mg, 0.105 mmol), Example 120b (21 mg, 0.126 mmol) and Na$_2$CO$_3$ (33 mg, 0.316 mmol) in dioxane/H$_2$O (2.5 mL, v/v=4/1) was added Pd(dppf)Cl$_2$ (7.7 mg, 0.011 mmol) at room temperature under N$_2$. The reaction mixture was heated to 90° C. and stirred for 3 h under N$_2$. The reaction mixture was purified by prep-HPLC and prep-TLC (DCM/MeOH=10/1) to afford the desired product Example 120 (15.0 mg, yield 10%) as a white solid. LCMS [M+1]$^+$=467.0. $^1$H NMR (400 MHz, DMSO-d$_6$) δ 11.21 (s, 1H), 8.73-8.70 (d, J=8.0 Hz, 2H), 8.20-8.19 (d, J=8.0 Hz, 1H), 8.08-8.04 (t, 1H), 7.95-7.84 (m, 4H), 7.42-7.36 (dd, J=8.0 Hz, 2H), 4.40-4.38 (dd, J=8.0 Hz, 2H), 4.26-4.25 (d, J=4.0 Hz, 1H), 3.99-3.97 (t, 1H), 3.16 (t, 1H), 2.15-2.12 (m, 2H), 1.58 (s, 1H), 1.14-1.13 (d, J=4.0 Hz, 3H), 0.98-0.93 (m, 4H).

Example 121: General Procedure for Synthesis of Compound Example 121

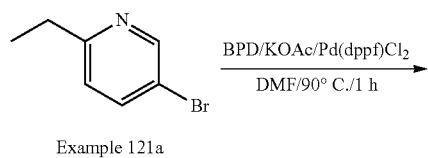

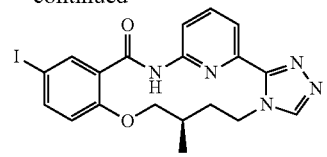

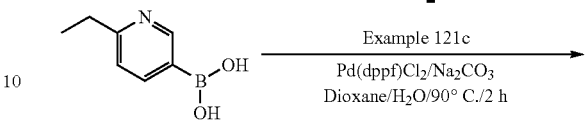

Step 1: Example 121

To a solution of Example 121a (100 mg, 0.54 mmol), BPD (CAS: 73183-34-3, 409 mg, 1.61 mmol) and KOAc (105 mg, 1.07 mmol) in DMF (3 mL) was added Pd(dppf)Cl$_2$ (39 mg, 0.054 mmol) at room temperature under N$_2$. The reaction mixture was heated to 80° C. and stirred for 1 h under N$_2$. The reaction mixture was concentrated under reduced pressure and purified by silica gel chromatography (DCM/MeOH=1/0~10/1) to afford the desired product Example 121b (21.0 mg, yield 26%) as a black solid. LCMS [M+1]$^+$=152.0

Step 2: Example 121

To a solution of Example 121c (50 mg, 0.105 mmol), Example 121b (19 mg, 0.126 mmol) and Na$_2$CO$_3$ (33 mg, 0.316 mmol) in dioxane/H$_2$O (2.5 mL, v/v=4/1) was added Pd(dppf)Cl$_2$ (7.7 mg, 0.011 mmol) at room temperature under N$_2$. The reaction mixture was heated to 90° C. and stirred for 2 h under N$_2$. The reaction mixture was concentrated under reduced pressure and purified by prep-TLC (DCM/MeOH=10/1) to afford the desired product Example 121 (14.8 mg, yield 31%) as a white solid. LCMS [M+1]$^+$=455.1. $^1$H NMR (400 MHz, DMSO-d$_6$) δ 11.21 (s, 1H), 8.79-8.78 (d, J=4.0 Hz, 1H), 8.73 (s, 1H), 8.22 (s, 1H), 8.08-8.04 (m, 1H), 8.01-7.99 (dd, J=8.0 Hz, 1H), 7.95-7.92 (dd, J=8.0 Hz, 1H), 7.89-7.84 (dd, J=8.0 Hz, 2H), 7.43-7.41 (d, J=8.0 Hz, 1H), 7.36-7.34 (d, J=8.0 Hz, 1H), 4.41-4.40 (m, 2H), 4.38-4.36 (m, 1H), 4.03-3.98 (t, 1H), 3.25 (m, 1H), 2.81-2.75 (m, 2H), 2.05 (s, 1H), 1.59 (d, 1H), 1.26-1.23 (t, 3H), 1.15-1.13 (d, J=8.0 Hz, 3H).

Example 122: General Procedure for Synthesis of Compound Example 122

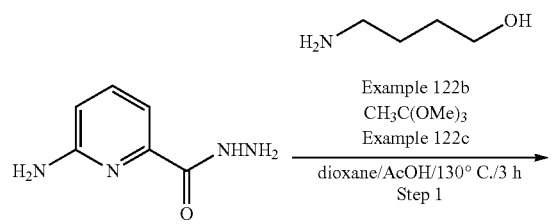

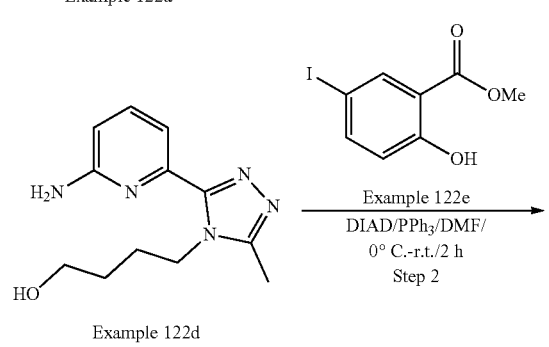

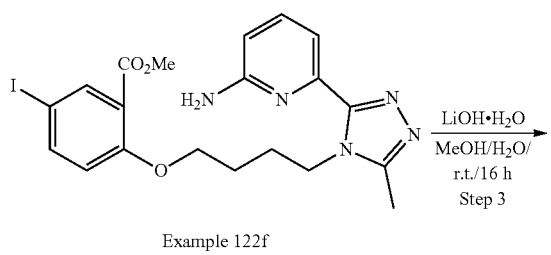

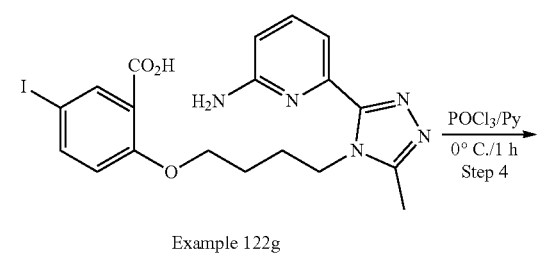

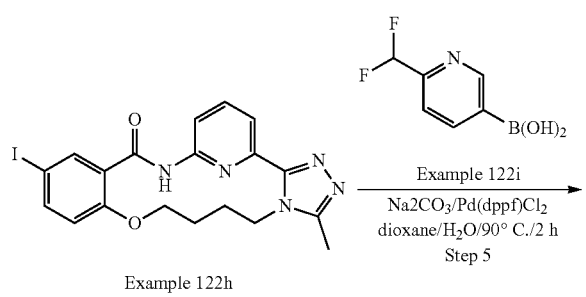

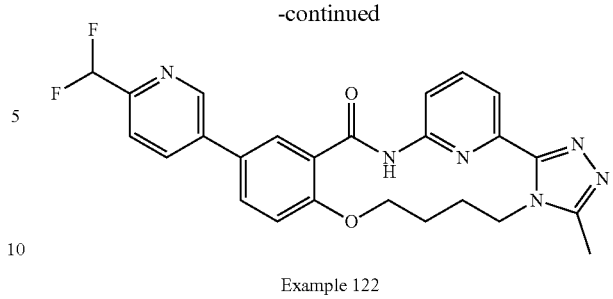

Example 122

Step 1: Example 122d

To a solution of Example 122a (1.5 g, 10 mmol), Example 122b (4.4 g, 50 mmol) and Example 122c (1.8 g, 15 mmol) in dioxane/H$_2$O (50 mL/15 mL) was sealed and stirred at 130° C. for 3 h. The mixture was concentrated and purified by silica gel column (DCM/MeOH=10/1) to give the desired product Example 122d (400 mg, yield 16%) as a red solid. LCMS [M+1]$^+$=248.1

Step 2: Example 122f

To a solution of Example 122d (400 mg, 1.6 mmol), Example 122e (450 mg, 1.6 mmol) and PPh$_3$ (1 g, 4 mmol) in dry DMF (10 mL) was added DIAD (969 mg, 4.8 mmol) at 0° C. The mixture was stirred from 0° C. to r.t. for 2 h. The mixture was diluted with water and extracted by EtOAc (100 mL*2). The combined organic layer was concentrated and purified by silica gel column (DCM/MeOH=10/1) to give the desired product Example 122f (900 mg, yield 100%) as yellow oil. LCMS [M+1]$^+$=507.9

Step 3: Example 122g

To a solution of Example 122f (900 mg, 1.8 mmol) and LiO.H$_2$O (227 mg, 5.4 mmol) in MeOH/H$_2$O (10 mL/10 mL) was stirred at r.t. for 16 h. The mixture was concentrated and adjusted pH to 5 by 1N HCl. The mixture was filtered to give the desired product Example 122g (500 mg, yield 56%) as a white solid. LCMS [M+1]$^+$=493.9

Step 4: Example 122h

To a solution of Example 122g (500 mg, 1 mmol) in pyridine (100 mL) was added POCl$_3$ (459 mg, 3 mmol) at 0° C. The mixture was stirred at 0° C. for 1 h. The mixture was concentrated in vacuum. The residue was washed with water and filtered to give the desired product Example 122h (400 mg, yield 84%) as a pink solid. LCMS [M+1]$^+$=475.9

Step 5: Example 122

A solution of Example 122h (50 mg, 0.1 mmol), Example 122i (20 mg, 0.12 mmol), Na$_2$CO$_3$ (31 mg, 0.3 mmol) and Pd(dppf)Cl$_2$ (8 mg, 0.01 mmol) in dioxane/H$_2$O (2 mL/0.4 mL) was stirred at 90° C. for 2 h under N$_2$. The mixture was concentrated and purified by prep-TLC (DCM/MeOH=10/1) to give the desired product Example 122 (3 mg, yield 6%) as a gray solid. LCMS [M+1]$^+$=477.0. $^1$H NMR (400 MHz, DMSO-d$_6$) δ 11.24 (s, 1H), 9.02 (s, 1H), 8.30 (dd, J=7.3, 2.4 Hz, 2H), 8.03 (d, J=8.2 Hz, 2H), 7.87 (d, J=8.1 Hz, 1H), 7.78 (t, J=6.9 Hz, 2H), 7.43 (d, J=8.7 Hz, 1H), 7.01 (t, J=56.0 Hz, 1H), 4.37 (d, J=5.7 Hz, 2H), 4.08 (t, J=8.6 Hz, 2H), 2.48 (s, 2H), 1.98 (s, 2H).

Example 123: General Procedure for Synthesis of Compound Example 123
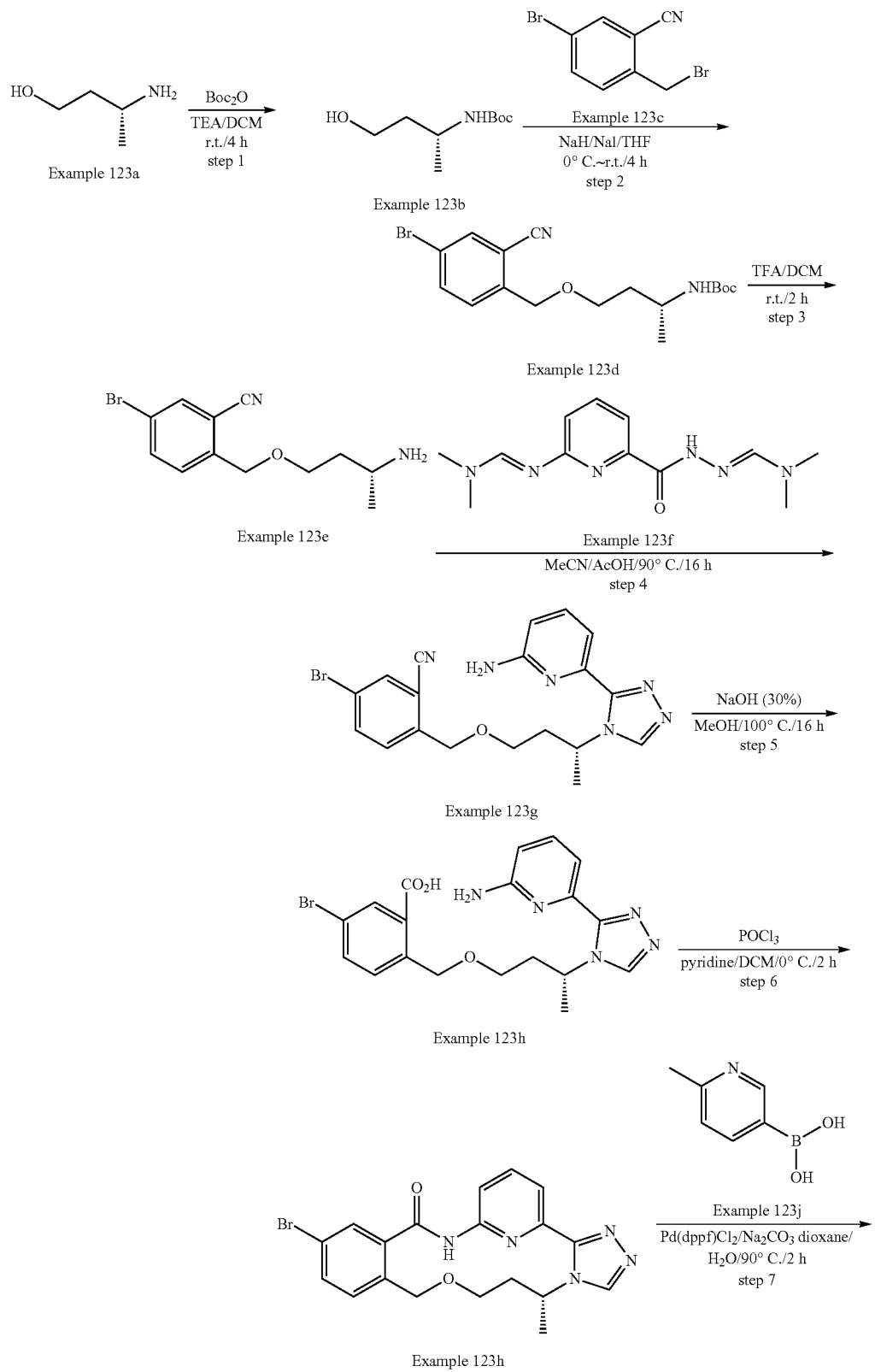

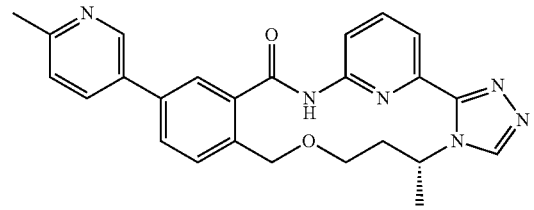

Example 123

Step 1: Example 123b

To a solution of Example 123a (1.0 g, 11.22 mmol) and TEA (1.7 g, 16.83 mmol) in DCM (10 mL) was added Boc$_2$O (2.6 g, 12.34 mmol), which was stirred for 4 h at room temperature. The reaction mixture was concentrated under reduced pressure, diluted with H$_2$O (20 mL), and then extracted with EtOAc (20 mL*3). The organic layer was washed with brine (20 mL*2), dried over Na$_2$SO$_4$, filtered and concentrated to afford the crude product Example 123b (1.83 g, crude yield 86%) as a white solid.

$^1$H NMR (400 MHz, chloroform-d) δ 4.42 (s, 1H), 3.90-3.88 (d, J=8.0 Hz, 1H), 3.64-3.60 (m, 2H), 3.42 (s, 1H), 1.85-1.76 (m, 1H), 1.44 (s, 9H), 1.34-1.25 (m, 1H), 1.19-1.17 (d, J=8.0 Hz, 3H).

Step 2: Example 123d

To a solution of Example 123b (263 mg, 1.4 mmol) in THF (10 mL) was added NaH (123 mg, 3.08 mmol, 60% in mineral oil) slowly at 0° C. under N$_2$. After addition, the suspension was stirred for 30 min. NaI (252 mg, 1.68 mmol) and Example 123c (460 mg, 1.68 mmol) were added and the reaction mixture was stirred at room temperature for 16 h. The mixture was quenched by 0.1N HCl (aq.) and the pH was adjusted to 8 with sat. NaHCO$_3$ (aq.). The resulting mixture was extracted with EtOAc (15 mL*3) and the organic layer was washed with brine (15 mL*2), dried over Na$_2$SO$_4$, filtered and concentrated, which was purified by silica gel chromatography (Petroleum ether/EtOAc=6/1), to afford the desired product Example 123d (444 mg, yield 83%) as a deep yellow solid. LC-MS [M+1-100]$^+$=282.9/284.9

Step 3: Example 123e

To a solution of Example 123d (444 mg, 1.15 mmol) in DCM (5 mL) was added TFA (2 mL) at room temperature, which was stirred for 2 h. The reaction mixture was concentrated under reduced pressure. The residue was dissolved in H$_2$O (10 mL) and the pH was adjusted to 8 with sat. NaHCO$_3$ (aq.), and then extracted with EtOAc (5 mL*5). The organic layer was dried over Na$_2$SO$_4$, filtered and concentrated to afford the crude product Example 123e (300 mg, yield 92%) as a yellow solid. LC-MS [M+1]$^+$=282.9/284.9

Step 4: Example 123g

A solution of Example 123e (300 mg, 1.06 mmol) and Example 123f (304 mg, 1.17 mmol) in MeCN/AcOH (v/v=4/1, 5 mL) was heated to 90° C. and stirred for 16 h. The reaction mixture was concentrated under reduced pressure and purified by silica gel chromatography (DCM/MeOH=10/1) to afford the desired product Example 123g (300 mg, yield 66%) as a white solid. LC-MS [M+1]$^+$=426.9/428.9

Step 5: Example 123h

To a solution of Example 123g (300 mg, 0.7 mmol) in MeOH (5 mL) was added 30% NaOH solution (7 mL) at room temperature, which was heated at 100° C. for 16 h. The reaction mixture was cooled to room temperature and concentrated. The pH was adjusted to 2 with 2N HCl and the mixture was concentrated. The residue was slurried in DCM/MeOH (v/v=10/1, 10 mL) at room temperature for 15 min, filtered and concentrated to afford the crude product Example 123h (165 mg, yield 53%) as a yellow solid. LC-MS [M+1]$^+$=445.9/447.9

Step 6: Example 123i

To a solution of Example 123h (165 mg, 0.37 mmol) in pyridine/DCM (v/v=2/1, 48 mL) was added POCl$_3$ (283 mg, 1.85 mmol) dropwise at 0° C. under N$_2$. The colorless solution turned orange. The reaction mixture was stirred at 0° C. for 2 h. The reaction mixture was quenched by H$_2$O (3 mL) and concentrated, which was slurried in H$_2$O (20 mL) at room temperature for 20 min, and then filtered. The filter cake was washed with H$_2$O (10 mL*5), dried in vacuo to afford the desired product Example 123i (48 mg, yield 30%) as an orange solid. LC-MS [M+1]$^+$=427.9/429.9

Step 7: Example 123

To a solution of Example 123i (48 mg, 0.112 mmol), Example 123j (18.4 mg, 0.134 mmol) and Na$_2$CO$_3$ (35.6 mg, 0.336 mmol) in dioxane/H$_2$O (v/v=4/1, 2.5 mL) was added Pd(dppf)Cl$_2$ at room temperature under N$_2$, which was heated at 90° C. for 2 h. The reaction mixture was concentrated and purified by prep-TLC (DCM/MeOH=10/1), followed by prep-HPLC to afford the desired product Example 123 (16 mg, yield 33%) as a white solid. LC-MS [M+1]$^+$=441.0. $^1$H NMR (400 MHz, DMSO-d$_6$) δ 10.8 (s, 1H), 8.88 (s, 1H), 8.74 (s, 2H), 8.07-8.03 (t, J=8.0 Hz, 1H), 7.99-7.97 (d, J=8.0 Hz, 1H), 7.89-7.81 (m, 3H), 7.71-7.69 (d, J=8.0 Hz, 1H), 7.59-7.57 (d, J=8.0 Hz, 1H), 7.36-7.34 (d, J=8.0 Hz, 1H), 5.66 (s, 1H), 4.71-4.61 (d, 1H), 3.69-3.63 (d, 1.6H), 2.5 (s, 3H), 2.35-2.31 (m, 2H), 1.94-1.90 (m, 1H), 1.44-1.42 (d, J=8.0 Hz, 3H).

Example 124: General Procedure for Synthesis of Compound Example 124

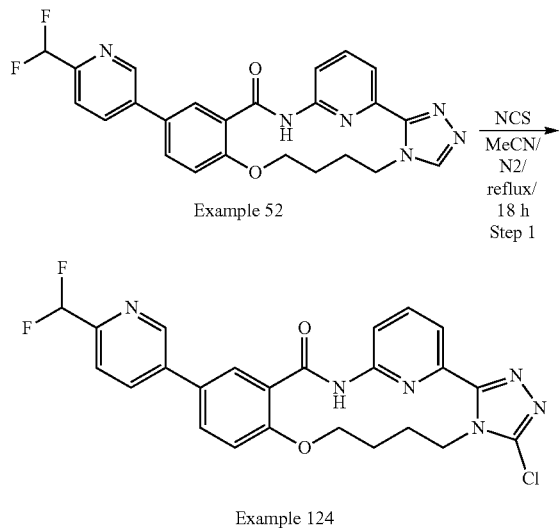

A solution of Example 52 (26 mg, 0.05 mmol) and NCS (9 mg, 0.07 mmol) in MeCN (20 mL) was heated to 80° C. at N₂ protection for 18 h, which was then concentrated and purified by prep-TLC (DCM/MeOH=10/1) to give the desired product Example 124 (14 mg, yield 56%) as a white solid. LCMS [M+1]$^+$=497.3

$^1$H NMR (400 MHz, DMSO-d₆) δ 11.02 (s, 1H), 9.02 (s, 1H), 8.77 (s, 1H), 8.33-8.29 (m, 1H), 8.20 (d, J=6.4 Hz, 1H), 8.19 (s, 1H), 8.03-7.95 (m, 2H), 7.77 (d, J=8.2 Hz, 1H), 7.36 (d, J=8.7 Hz, 1H), 7.01 (t, J=54.0 Hz, 1H), 4.26 (s, 2H), 4.04-3.97 (m, 2H), 2.46-2.42 (m, 2H), 1.84 (s, 2H).

Example 125: General Procedure for Synthesis of Compound Example 125

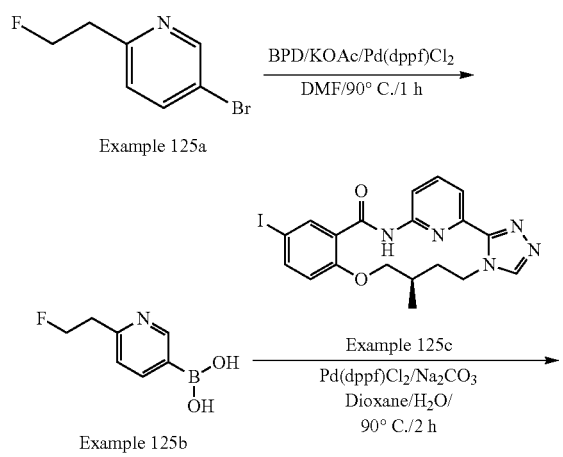

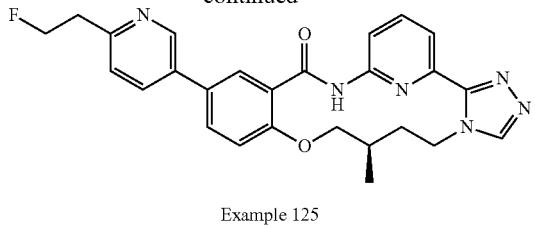

Step 1: Example 125b

To a solution of Example 125a (100 mg, 0.49 mmol), BPD (CAS: 73183-34-3, 373 mg, 1.47 mmol) and KOAc (96 mg, 0.98 mmol) in DMF (3 mL) was added Pd(dppf)Cl₂ (35.8 mg, 0.049 mmol) at room temperature under N₂. The reaction mixture was heated to 90° C. and stirred for 1 h under N₂. The reaction mixture was concentrated under reduced pressure to afford the crude product Example 125b (605 mg, crude yield>100%) as a black solid, which was used for the next step without further purification. LCMS [M+1]$^+$=170.0

Step 2: Example 125

To a solution of Example 125c (82 mg, 0.174 mmol), Example 125b (crude 605 mg, theoretically 79 mg, 0.47 mmol) and Na₂CO₃ (148 mg, 1.4 mmol) in dioxane/H₂O (5 mL, v/v=4/1) was added Pd(dppf)Cl₂ (34 mg, 0.0467 mmol) at room temperature under N₂. The reaction mixture was heated to 90° C. and stirred for 2 h under N₂. The reaction mixture was concentrated under reduced pressure and purified by prep-TLC (DCM/MeOH=10/1) and prep-HPLC to afford the desired product Example 125 (13.2 mg, yield 16%) as a yellow solid. LCMS [M/2+1]$^+$=237.1. $^1$H NMR (400 MHz, DMSO-d₆) δ 11.20 (s, 1H), 8.83 (s, 1H), 8.74 (s, 1H), 8.24-8.23 (m, 1H), 8.08-8.03 (m, 2H), 7.97-7.94 (dd, J=8.0 Hz, 1H), 7.89-7.84 (dd, J=8.0 Hz, 2H), 7.44-7.42 (m, 1H), 6.51 (s, 1H), 4.91-4.88 (t, 1H), 4.79-4.76 (t, 1H), 4.41-4.39 (d, J=8.0 Hz, 2H), 4.28 (m, 1H), 4.03-4.01 (d, J=8.0 Hz, 1H), 3.14 (t, 2H), 2.06 (s, 1H), 1.60 (s, 1H), 1.15-1.13 (d, J=8.0 Hz, 3H).

Example 126: General Procedure for Synthesis of Compound Example 126

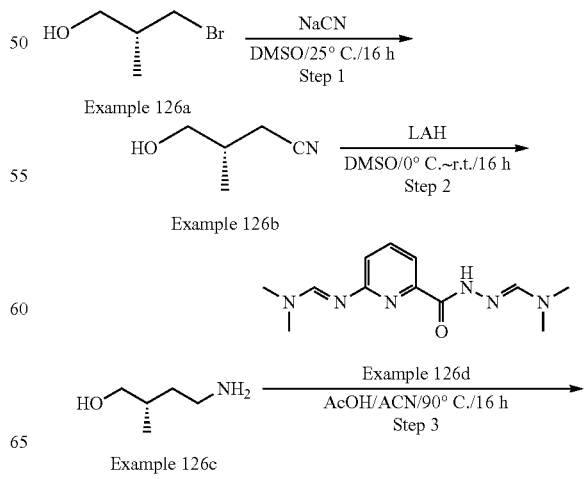

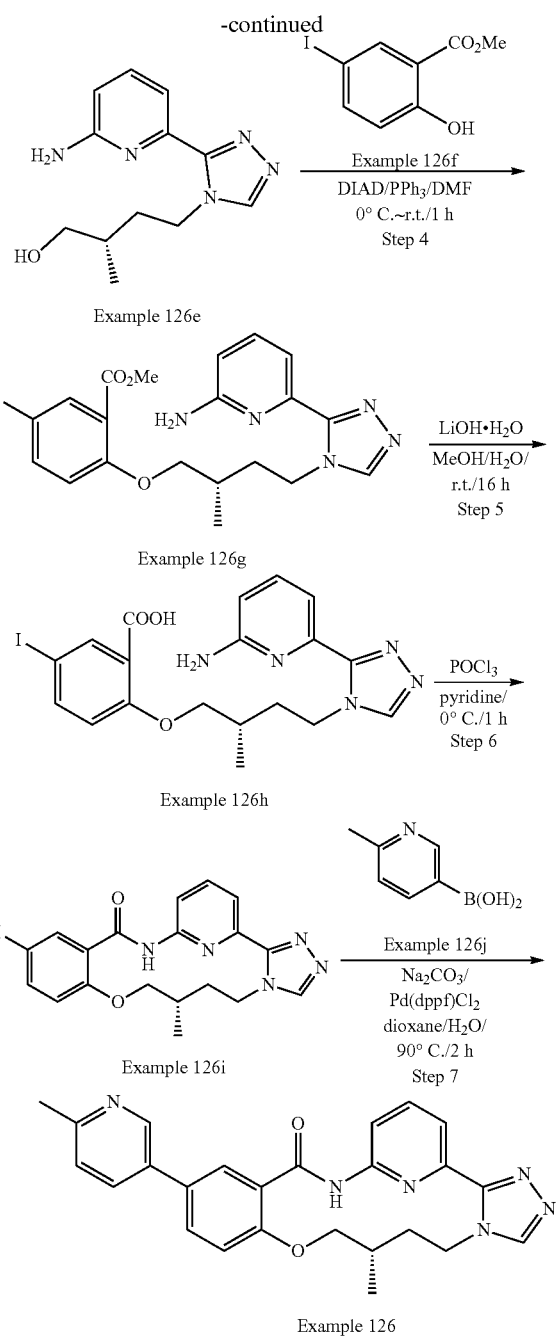

Step 1: Example 126b

A solution of Example 126a (5 g, 32.6 mmol) and NaCN (1.9 g, 39.1 mmol) in DMSO (55 mL) was stirred at 25° C. for 16 h. The mixture was diluted with water and extracted with EtOAc (200 mL*2). The combined organic layer was concentrated to give the crude product Example 126b (2.6 g, crude yield 81%) as colorless oil.

Step 2: Example 126c

To a solution of Example 126b (2.6 g, 26.3 mmol) in dry THF (150 mL) was added LAH (5 g, 131.5 mmol) at 0° C. The mixture was stirred from 0° C. to r.t. for 16 h. The mixture was quenched by H$_2$O (5 mL) under 20° C., then diluted with 15% NaOH (5 mL) and water (15 mL). The mixture was filtered and concentrated to give the crude product Example 126c (2 g, yield 74%) as colorless oil. LC-MS [M+1]$^+$=104.1

Step 3: Example 126e

A solution of Example 126c (1.9 g, 18.4 mmol) and Example 126d (1.6 g, 6.1 mmol) in MeCN/AcOH (50 mL/10 mL) was stirred at 90° C. for 16 h. To the mixture was added 5N HCl (20 mL), which was stirred at r.t. for 2 h. The reaction's pH was adjusted to 11 by 30% NaOH (aq.), concentrated, and purified by silica gel chromatography (DCM/MeOH=10/1) to give the desired product Example 126e (530 mg, 35%) as yellow oil. LC-MS [M+1]$^+$=248.1

Step 4: Example 126g

To a solution of Example 126e (530 mg, 2.1 mmol), Example 126f (584 mg, 2.1 mmol) and PPh$_3$ (1.37 g, 5.25 mmol) in dry DMF was added DIAD (1.27 g, 6.3 mmol) at 0° C. The mixture was stirred from 0° C. to r.t. for 1 h. The mixture was diluted with water and extracted by EtOAc (200 mL*2). The combined organic layer was concentrated and purified by silica gel chromatography (DCM/MeOH=10/1) to give the desired product Example 126g (900 mg, yield 84%) as yellow oil. LC-MS [M+1]$^+$=507.9

Step 5: Example 126h

A solution of Example 126g (900 mg, 1.8 mmol) and LiO.H$_2$O (227 mg, 5.4 mmol) in MeOH/H$_2$O (20 mL/10 mL) was stirred at r.t. for 16 h. The mixture was concentrated and the pH was adjusted to 5 by 1N HCl (aq.). The mixture was then extracted by DCM (100 mL*2), and concentrated to give the crude product Example 126h (650 mg, crude yield 73%) as a yellow solid. LC-MS [M+1]$^+$=493.9

Step 6: Example 126i

To a solution of Example 126h (650 mg, 1.3 mmol) in pyridine (100 mL) was added POCl$_3$ (597 mg, 3.9 mmol) at 0° C. The mixture was stirred at 0° C. for 1 h. The reaction was quenched by water and concentrated. The residue was washed by water, filtered and dried to give the desired product Example 126i (450 mg, yield 73%) as a pink solid. LC-MS [M+1]$^+$=475.9

Step 7: Example 126

A solution of Example 126i (150 mg, 0.3 mmol), Example 126j (63 mg, 0.45 mmol), Na$_2$CO$_3$ (95 mg, 0.9 mmol) and Pd(dppf)Cl$_2$ (22 mg, 0.03 mmol) in dioxane/H$_2$O (2 mL/0.4 mL) was stirred at 90° C. for 2 h under N$_2$. The mixture was concentrated and purified by prep-TLC (DCM/MeOH=10/1) to give the desired product Example 126 (27 mg, yield 20%) as a gray solid. LC-MS [M+1]$^+$=441.0. $^1$H NMR (400 MHz, DMSO-d$_6$) δ 11.21 (s, 1H), 8.75 (s, 2H), 8.22 (s, 1H), 8.05 (d, J=7.7 Hz, 1H), 7.98 (d, J=7.3 Hz, 1H), 7.93 (d, J=8.3 Hz, 1H), 7.87 (d, J=10.9 Hz, 2H), 7.42 (d, J=8.7 Hz, 1H), 7.34 (d, J=8.1 Hz, 1H), 4.39 (s, 2H), 4.26 (s, 1H), 4.00 (s, 1H), 3.15 (s, 2H), 2.48 (s, 3H), 2.06 (s, 1H), 1.14 (d, J=6.9 Hz, 3H).

Example 127: General Procedure for Synthesis of Compound Example 127
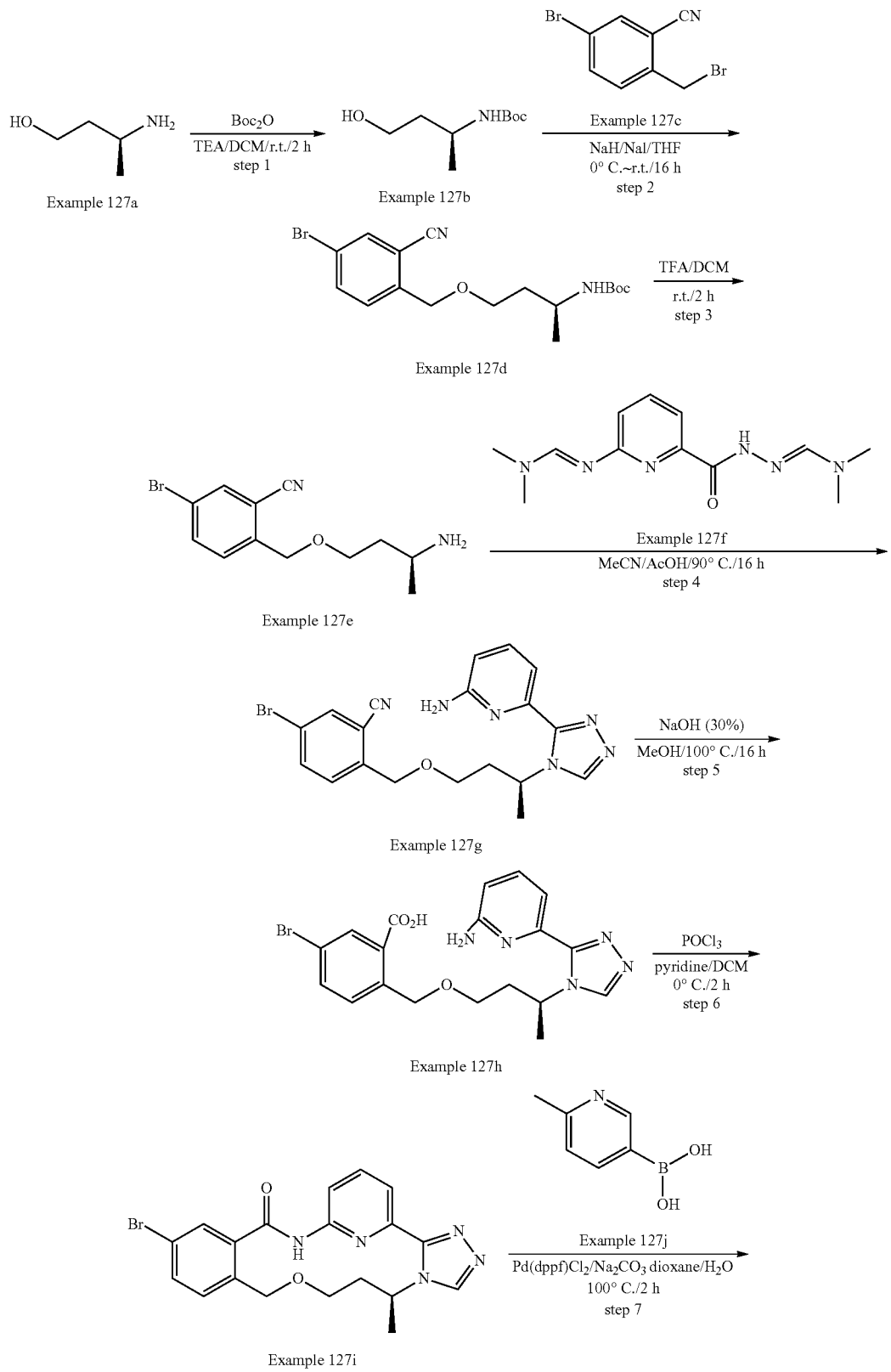

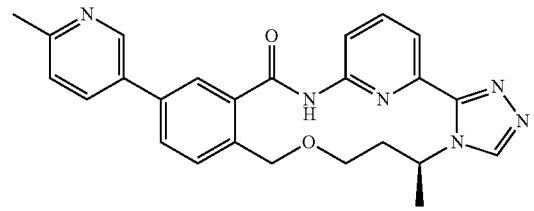

Example 127

Step 1: Example 127b

To a solution of Example 127a (10 g, 0.11 mol) and TEA (17 g, 0.17 mol) in DCM (100 mL) was added $Boc_2O$ (29.4 g, 0.13 mol), which was stirred for 2 h at room temperature. The reaction mixture was concentrated under reduced pressure and which was purified by silica gel chromatography (Petroleum ether/EtOAc=1/1) to give the desired product Example 127b (11.5 g, yield 55%) as a white solid.

Step 2: Example 127d

To a solution of Example 127b (3 g, 0.016 mol) in THF (100 mL) was added NaH (1.4 g, 0.035 mol, 60% in mineral oil) slowly at 0° C. under $N_2$ protection. After addition, the suspension was stirred for 0.5 h, followed by addition of NaI (2.9 g, 0.019 mol) and Example 127c (5.2 g, 0.019 mol). The reaction mixture was stirred at room temperature for 16 h. which was then quenched by water (2 mL) and concentrated. The residue was purified by silica gel chromatography (Petroleum ether/EtOAc=5/1) to afford the desired product Example 127d (2.9 g, yield 47%) as a yellow solid. LC-MS $[M+1-100]^+=282.9/284.9$

Step 3: Example 127e

To a solution of Example 127d (2.9 g, 7.6 mmol) in DCM (30 mL) was added TFA (10 mL) at room temperature and stirred for 2 h. The reaction mixture was concentrated under reduced pressure to afford the crude product Example 127e (3.2 g, yield 100%) as a white solid, which was used in next step without any purification. LC-MS $[M+1]^+=282.9/284.9$

Step 4: Example 127g

A solution of Example 127e (3.2 g, 7.6 mmol) and Example 127f (2.4 g, 9.12 mmol) in MeCN/AcOH (v/v=4/1, 25 mL) was heated to 90° C. for 16 h. The reaction mixture was concentrated and purified by silica gel chromatography (DCM/MeOH=10/1) to afford the desired product Example 127g (2.2 g, yield 64%) as a white solid. LC-MS $[M+1]^+=426.9/428.9$

Step 5: Example 127h

To a solution of Example 127g (2.2 g, 4.8 mmol) in MeOH (10 mL) was added 30% NaOH solution (40 mL) at room temperature, which was heated at 100° C. for 16 h. The reaction mixture was cooled to room temperature and the pH was adjusted to 5 with 2N HCl, which was extracted with DCM (50 mL*3), concentrated and purified by silica gel chromatography (DCM/MeOH=10/1) to give the desired product Example 127h (1.2 g, yield 56%) as a yellow solid. LC-MS $[M+1]^+=445.9/447.9$

Step 6: Example 127i

To a solution of Example 127h (1 g, 2.2 mmol) in pyridine/DCM (v/v=2/1, 66 mL) was added $POCl_3$ (1 g, 6.7 mmol) at 0° C. under $N_2$ protection. The reaction mixture was stirred at 0° C. for 2 h. The reaction mixture was quenched by $H_2O$ (10 mL) and concentrated, which was purified by silica gel chromatography (DCM/MeOH=10/1) to give the desired product Example 127i (200 mg, yield 21%) as white solid. LC-MS $[M+1]^+=427.9/429.9$

Step 7: Example 127

To a solution of Example 127i (50 mg, 0.12 mmol), Example 127j (20 mg, 0.14 mmol) and $Na_2CO_3$ (38 mg, 0.36 mmol) in dioxane/$H_2O$ (v/v=4/1, 2.5 mL) was added Pd(dppf)$Cl_2$ (5 mg) at room temperature under $N_2$, which was heated at 100° C. for 2 h. The reaction mixture was concentrated and purified by prep-TLC (DCM/MeOH=10/1) to afford the desired product Example 127 (15 mg, yield 29%) as a white solid. LC-MS $[M+1]^+=441.0$ $^1H$ NMR (400 MHz, DMSO-$d_6$) δ 10.80 (s, 1H), 8.88 (s, 1H), 8.74 (s, 1H), 8.05 (t, J=7.9 Hz, 1H), 7.98 (d, J=7.5 Hz, 1H), 7.93-7.79 (m, 3H), 7.70 (d, J=8.1 Hz, 1H), 7.58 (d, J=7.9 Hz, 1H), 7.35 (d, J=8.1 Hz, 1H), 5.66 (d, J=6.2 Hz, 1H), 4.71 (s, 1H), 4.60 (d, J=9.2 Hz, 1H), 3.63 (s, 2H), 2.50 (s, 3H), 2.35-2.28 (m, 1H), 1.93 (dd, J=14.5, 6.4 Hz, 1H), 1.43 (d, J=6.8 Hz, 3H).

Example 128: General Procedure for Synthesis of Compound Example 128

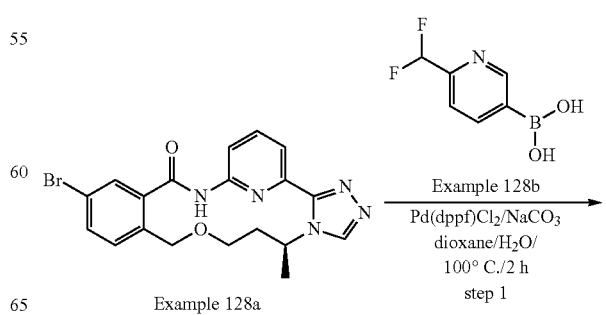

-continued

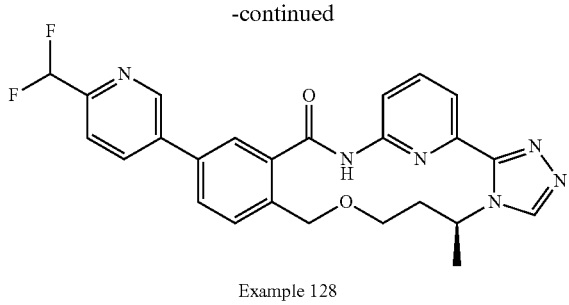

Example 128

To a solution of Example 128a (50 mg, 0.12 mmol), Example 128b (25 mg, 0.14 mmol) and Na$_2$CO$_3$ (38 mg, 0.36 mmol) in dioxane/H$_2$O (v/v=5/1, 2.5 mL) was added Pd(dppf)Cl$_2$ (5 mg) at N$_2$ protection, which was heated to 100° C. for 2 h. The reaction mixture was concentrated and purified by prep-TLC (DCM/MeOH=10/1) to afford the desired product Example 128 (15 mg, yield 26%) as a white solid.

LC-MS [M+1]$^+$=477.0. $^1$H NMR (400 MHz, DMSO-d$_6$) δ 10.81 (s, 1H), 9.00 (s, 1H), 8.89 (s, 1H), 8.31 (d, J=7.6 Hz, 1H), 8.05 (t, J=7.9 Hz, 1H), 7.99 (s, 1H), 7.91 (d, J=7.6 Hz, 1H), 7.86 (d, J=7.6 Hz, 1H), 7.79 (d, J=8.2 Hz, 1H), 7.66 (dd, J=17.1, 7.9 Hz, 2H), 7.01 (t, J=54.0 Hz, 1H), 5.66 (s, 1H), 4.73 (s, 1H), 4.62 (d, J=9.4 Hz, 1H), 3.64 (s, 2H), 2.37-2.25 (m, 1H), 1.99-1.84 (m, 1H), 1.43 (d, J=6.7 Hz, 3H).

Example 129: General Procedure for Synthesis of Compound Example 129

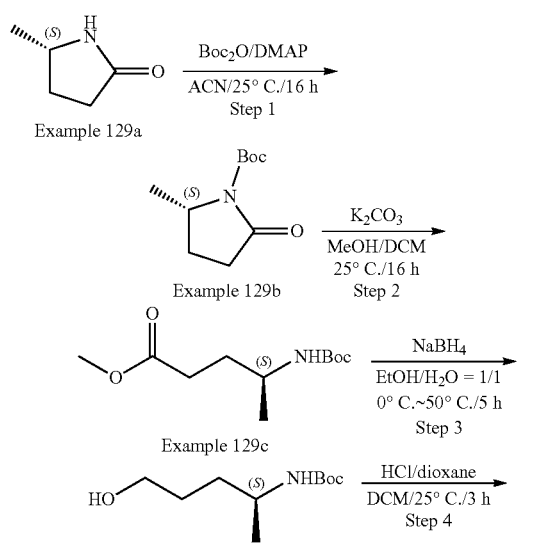

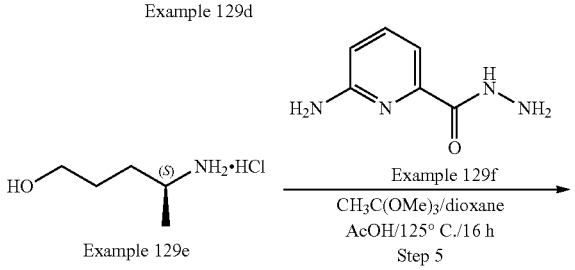

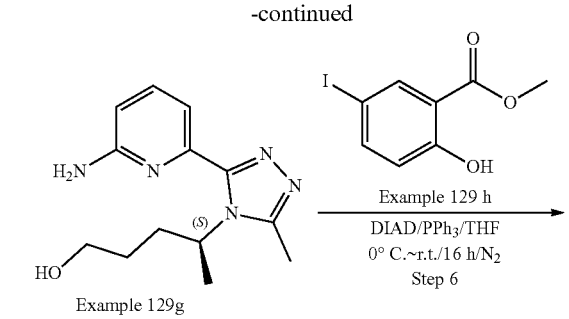

Example 129g

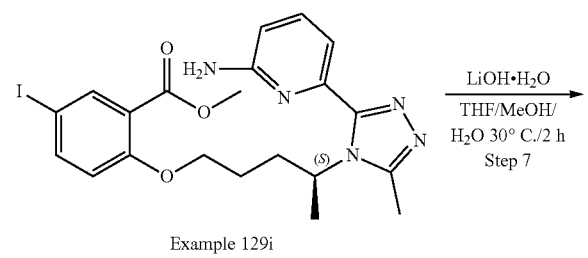

Example 129i

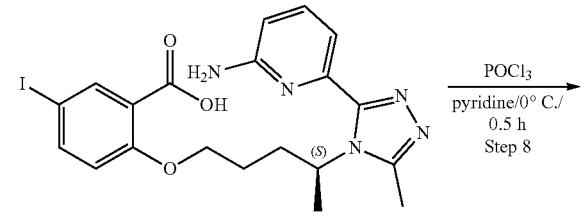

Example 129j

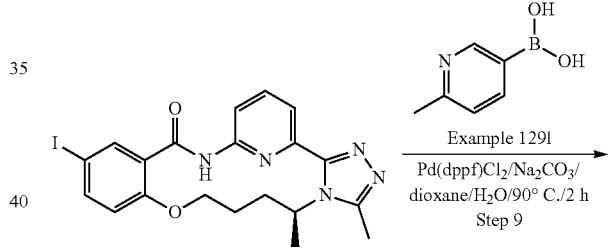

Example 129k

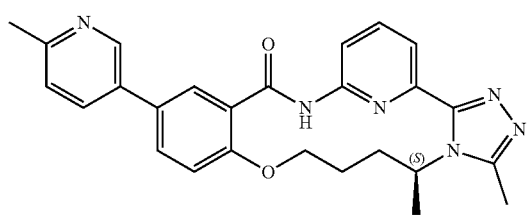

Example 129

Step 1: Example 129b

To a solution of Example 129a (2.0 g, 20.2 mmol) and (Boc)$_2$O (4.8 g, 22.2 mmol) in ACN (50 mL) was added DMAP (500 mg, 4.0 mmol). The mixture was stirred at 25° C. for 16 hours. The solvent was removed in vacuo, and the residue was diluted with EtOAc (50 mL), washed by water (30 mL) and brine (30 mL). The organic layer was dried over Na$_2$SO$_4$, filtered and concentrated to give the desired product Example 129b (2.4 g, yield 60%) as a pale yellow gel. LC-MS [M+1-56]$^+$=144.1

Step 2: Example 129c

A mixture of Example 129b (2.4 g, 12.1 mmol) and K$_2$CO$_3$ (1.7 g, 12.1 mmol) in DCM/MeOH (40 mL/8 mL) was stirred at 25° C. for 16 hours. Water was added, and the mixture was extracted with DCM (30 mL*3). The combined organic layers were concentrated and purified by silica gel chromatography (Petroleum ether/EtOAc=70/30) to give the desired product Example 129c (2.2 g, yield 79%) as a white solid. LC-MS [M+1-56]$^+$=176.0

Step 3: Example 129d

To a solution of Example 129c (2.2 g, 9.5 mmol) in EtOH/H$_2$O (25 mL, v/v=1/1) was added a suspension of NaBH$_4$ in EtOH/H$_2$O (3 mL, v/v=1/1) dropwise at 0° C. After 15 min, the solution was heated at 50° C. for 5 hours. The reaction was diluted with water (20 mL), and then extracted by DCM (100 mL*3). The combined organic layers were concentrated and purified by silica gel chromatography (Petroleum ether/EtOAc=65/35) to give the desired product Example 129d (1.6 g, yield 83%) as colorless oil. LC-MS [M+1-100]$^+$=104.1

Step 4: Example 129e

To a solution of Example 129d (1.6 g, 7.9 mmol) in DCM (30 mL) was added a solution of HCl/dioxane (30 mL). The mixture was stirred at 25° C. for 3 hours. The solvent was removed in vacuo, and the residue was treated with DCM and concentrated for three times to give the desired product Example 129e (1.0 g, yield 83%) as brown oil.

Step 5: Example 129g

A solution of Example 129f (200 mg, 1.3 mmol), Example 129e (1.0 g, 7.1 mmol) and CH$_3$C(OMe)$_3$ (187 mg, 1.6 mmol) in dioxane (3 mL) and AcOH (1 mL) was degassed with N$_2$ for three times, and heated to 125° C. for 16 hours. The mixture was cooled to room temperature, and then 6N HCl (10 mL) was added. The resulting mixture was stirred for 1 h, and concentrated under reduced pressure. The residue was cooled to 0° C. and the pH was adjusted to 9-10 with 30% NaOH (aq.). The mixture was stirred for 30 min, and concentrated under reduced pressure, which was purified by silica gel chromatography (DCM/MeOH=92/8) to give the desired product Example 129g (100 mg, yield 29%) as yellow oil.
LC-MS [M+1]$^+$=262.1

Step 6: Example 129i

A solution of Example 129g (100 mg, 0.38 mmol), Example 129h (107 mg, 0.38 mmol) and PPh$_3$ (251 mg, 0.96 mmol) in dry THF (4 mL) was degassed with N$_2$ three times and cool to 0° C. DIAD (193 mg, 0.96 mmol) was added dropwise and the mixture was stirred for 16 h at 0° C.~r.t. The mixture was concentrated under reduced pressure, which was purified by silica gel chromatography (EtOAc/MeOH=90/10) to give the desired product Example 129i (150 mg, yield 75%) as colorless oil.
LC-MS [M+1]$^+$=521.9

Step 7: Example 129j

A solution of Example 129i (150 mg, 0.29 mmol) and LiO.H$_2$O (24 mg, 0.58 mmol) in THF (3 mL), MeOH (2 mL) and water (1 mL) was stirred at 30° C. for 3 h. The mixture was adjusted pH=3~4 with 1N HCl. Then the mixture was concentrated under reduced pressure to give the crude product Example 129j (146 mg, crude yield 100%) as a white solid, which was used in the next step without further purification. LC-MS [M+1]$^+$=507.9

Step 8: Example 129k

A solution of Example 129j (146 mg, 0.29 mmol) in pyridine (20 mL) was cooled to 0° C. under N$_2$ protection. Then POCl$_3$ (176 mg, 1.15 mmol) was added dropwise and the mixture was stirred for 0.5 h at 0° C. Water (5 mL) was added to the mixture, which was concentrated under reduced pressure. Water (20 mL) was added to the residue, which was stirred for 30 min at room temperature, and filtrated. The solid was washed by water (10 mL), dried under reduced pressure to give the desired product Example 129k (88 mg, yield 62%) as a pink solid. LC-MS [M+1]$^+$=489.9

Step 9: Example 129

To a solution of Example 129k (50 mg, 0.10 mmol), Example 129l (17 mg, 0.12 mmol) and Na$_2$CO$_3$ (22 mg, 0.20 mmol) in dioxane (4 mL) and water (1 mL) was added Pd(dppf)Cl$_2$ (7.5 mg, 0.01 mmol). The mixture was degassed with N$_2$ three times, heated to 90° C. for 2 h. The mixture was cooled to room temperature, and concentrated under reduced pressure. The residue was purified by prep-TLC (DCM/MeOH=12/1) to give 30 mg crude product which was re-purified by prep-HPLC to give the desired product Example 129 (2.0 mg, yield 4%) as a white solid. LCMS [M+1]$^+$=455.0

$^1$H NMR (400 MHz, DMSO-d$_6$) δ 11.05 (s, 1H), 8.74 (s, 1H), 8.12 (s, 1H), 8.05 (t, J=7.9 Hz, 1H), 7.97 (d, J=8.2 Hz, 1H), 7.90 (d, J=8.4 Hz, 1H), 7.85 (s, 1H), 7.66 (d, J=7.6 Hz, 1H), 7.33 (d, J=8.1 Hz, 2H), 4.59 (s, 1H), 4.36 (s, 1H), 4.24 (s, 1H), 2.52 (s, 3H), 2.48 (s, 3H), 2.08-1.92 (m, 2H), 1.77 (s, 2H), 1.35 (s, 3H).

Example 130: General Procedure for Synthesis of Compound Example 130

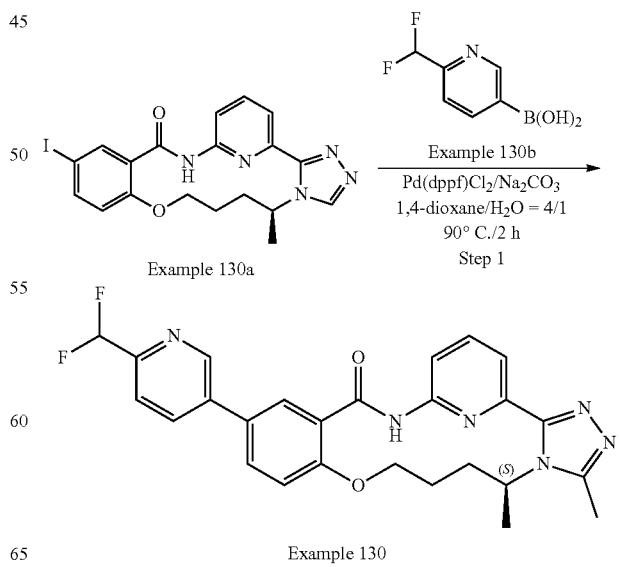

Step 1: Example 130

To a solution of Example 130a (30 mg, 0.06 mmol), Example 130b (13 mg, 0.07 mmol) in 1,4-dioxane/H₂O (4 mL/1 mL) were added Pd(dppf)Cl₂ (5 mg, 0.006 mmol) and Na₂CO₃ (13 mg, 0.12 mmol). The mixture was degassed by nitrogen for three times and heated at 90° C. for 2 hours. The reaction mixture was filtered, washed with EtOAc and concentrated. The residue was purified by prep-TLC (DCM/MeOH=15/1) to give the crude product which was re-purified by prep-HPLC to give the desired product Example 130 (2.5 mg, yield 8%) as a white solid. LC-MS [M+1]$^+$=491.0. $^1$H NMR (400 MHz, DMSO-d₆) δ 11.01 (s, 1H), 9.01 (s, 1H), 8.29 (d, J=8.2 Hz, 1H), 8.21 (s, 1H), 8.03 (dt, J=18.2, 8.2 Hz, 2H), 7.84 (s, 1H), 7.76 (d, J=8.2 Hz, 1H), 7.66 (d, J=7.5 Hz, 1H), 7.36 (d, J=8.7 Hz, 1H), 7.07 (d, J=55.1 Hz, 1H), 4.57 (s, 1H), 4.36 (s, 1H), 4.25 (s, 1H), 2.52 (s, 3H), 2.01 (s, 2H), 1.77 (s, 2H), 1.34 (s, 3H).

Example 131: General Procedure for Synthesis of Compound Example 131

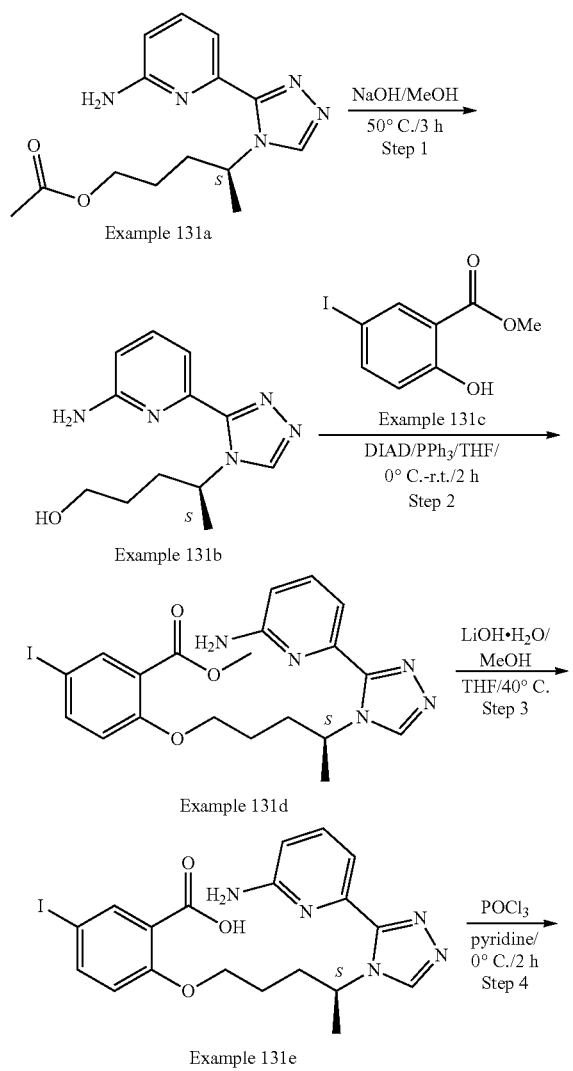

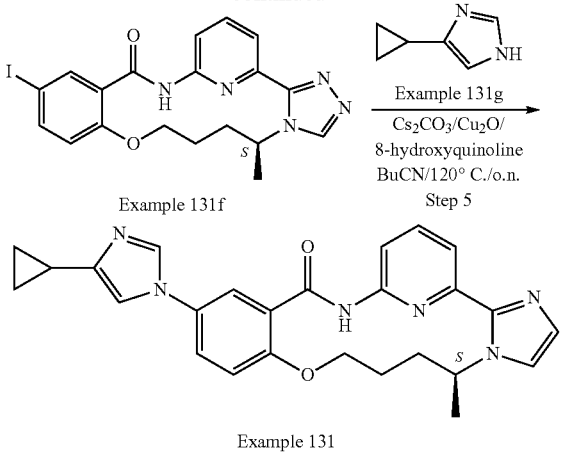

Example 131

Step 1: Example 131b

A solution of Example 131a (900 mg, 3.11 mmol) and NaOH (374 mg, 9.34 mmol) in MeOH (30 mL) and water (10 mL) was heated to 50° C. for 3 h. The mixture was cooled to room temperature, and concentrated under reduced pressure, which was purified by silica gel chromatography (DCM/MeOH=91/9) to give the desired product Example 131b (252 mg, yield 33%) as a colorless gel. LCMS [M+1]$^+$=248.1

Step 2: Example 131d

A solution of Example 131b (252 mg, 1.02 mmol), Example 131c (284 mg, 1.02 mmol) and PPh₃ (668 mg, 2.55 mmol) in dry THF (20 mL) was degassed with N₂ three times and cool to 0° C. DIAD (619 mg, 3.06 mmol) was added dropwise and the mixture was stirred for 2 h at 0-5° C. The mixture was concentrated under reduced pressure, which was purified by silica gel chromatography (EtOAc/MeOH=91/9) to give the desired product Example 131d (378 mg, yield 55%) as a pale yellow gel. LCMS [M+1]$^+$=507.9

Step 3: Example 131e

A solution of Example 131d (378 mg, 0.75 mmol) and LiO.H₂O (125 mg, 2.98 mmol) in MeOH (10 mL), THF (10 mL) and water (1 mL) was heated to 40° C. for 3 h. The mixture was cooled to room temperature, and pH was adjusted to 3-4 with 6N HCl (aq.). Then the mixture was concentrated under reduced pressure to give the desired product Example 131e (500 mg, crude yield 100%) as a yellow gel, which was used in the next step without further purification. LCMS [M+1]$^+$=493.9

Step 4: Example 131f

A solution of Example 131e (500 mg, crude, 0.75 mmol) in pyridine (10 mL) was cooled to 0° C. under N₂ protection. Then POCl₃ (570 mg, 3.73 mmol) was added dropwise and the mixture was stirred for 2 h at 0-5° C. Water (5 mL) was added to the mixture, which was concentrated under reduced pressure. Additional water (20 mL) was added to the residue, which was stirred for 30 min at room temperature, and filtrated. The solid was washed by water (5 mL), dried under reduced pressure to give the desired product Example 131f (210 mg, yield 59%) as a pink solid. LCMS [M+1]$^+$=475.9

Step 5: Example 131

To a solution of Example 131f (140 mg, 0.3 mmol), Example 131g (50 mg, 0.45 mmol), Cu$_2$O (7 mg, 0.045 mmol) and Cs$_2$CO$_3$ (293 mg, 0.9 mmol) in BuCN (2 mL), was added 8-hydroxyquinoline (13 mg, 0.09 mmol). The mixture was degassed with N$_2$ three times, heated to 120° C. overnight. The mixture was cooled to room temperature, and concentrated under reduced pressure, which was purified by pre-HPLC to give crude product (15 mg), followed by prep-TLC purification (DCM/MeOH=10/1) to give the desired product Example 131 (11 mg, yield 8%) as a white solid. LCMS [M+1]$^+$=456.0. $^1$H NMR (400 MHz, DMSO-d$_6$) δ 11.25 (s, 1H), 8.86 (s, 1H), 8.12-7.98 (m, 3H), 7.88-7.71 (m, 3H), 7.47 (d, J=1.5 Hz, 1H), 7.36 (d, J=8.9 Hz, 1H), 4.58 (s, 1H), 4.47 (d, J=9.6 Hz, 1H), 4.18 (t, J=9.7 Hz, 1H), 3.13 (d, J=12.2 Hz, 1H), 2.10 (s, 1H), 1.86-1.69 (m, 3H), 1.52 (d, J=6.9 Hz, 3H), 0.78 (m, 2H), 0.72-0.64 (m, 2H).

Example 132: General Procedure for Synthesis of Compound Example 132

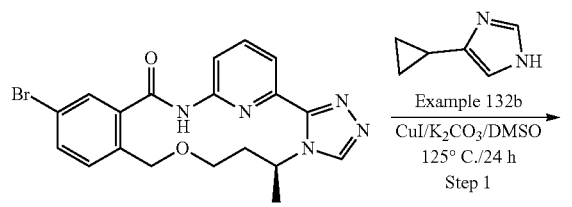

A mixture of Example 132a (38 mg, 0.088 mmol), Example 132b (36 mg, 0.34 mmol), K$_2$CO$_3$ (61 mg, 0.44 mmol), CuI (5 mg) in dry DMSO (1.0 mL) was heated at 125° C. for 20 h. The reaction was cooled to r.t., and water (5 mL) was added. The resulting mixture was stirred for 5 min, and filtered to give the crude product, which was purified by Prep-TLC (DCM/MeOH=15/1), followed by prep-HPLC purification (by Ultimate XB-C18, 50×250 mm, 10 μm, speed: 80 mL/min, eluent: A/B=H$_2$O/CH$_3$CN=from 80/20 to 50/50 for 10 min, then to 10/90 for 45 min, Ret. Time=35.5 min) to give the desired product Example 132 (2 mg, yield 5%) as a white solid. LC-MS [M+1]$^+$=456.1. $^1$H NMR (400 MHz, Chloroform-d) δ 10.69 (s, 1H), 8.37 (s, 1H), 8.09 (t, J=7.9 Hz, 2H), 8.00-7.93 (m, 2H), 7.82 (d, J=1.5 Hz, 1H), 7.59-7.49 (m, 2H), 7.11 (d, J=1.5 Hz, 1H), 5.94 (q, J=7.0 Hz, 1H), 4.75 (d, J=9.7 Hz, 1H), 4.46 (d, J=9.7 Hz, 1H), 4.02 (t, J=9.6 Hz, 1H), 3.85-3.73 (m, 1H), 2.46 (dt, J=14.7, 7.1 Hz, 1H), 2.16 (dd, J=14.7, 7.0 Hz, 1H), 1.91 (ddd, J=13.3, 8.5, 5.1 Hz, 1H), 1.57 (s, 3H), 1.31 (d, J=8.8 Hz, 1H), 0.90 (m, 2H), 0.86-0.80 (m, 2H).

Example 133: General Procedure for Synthesis of Compound Example 133

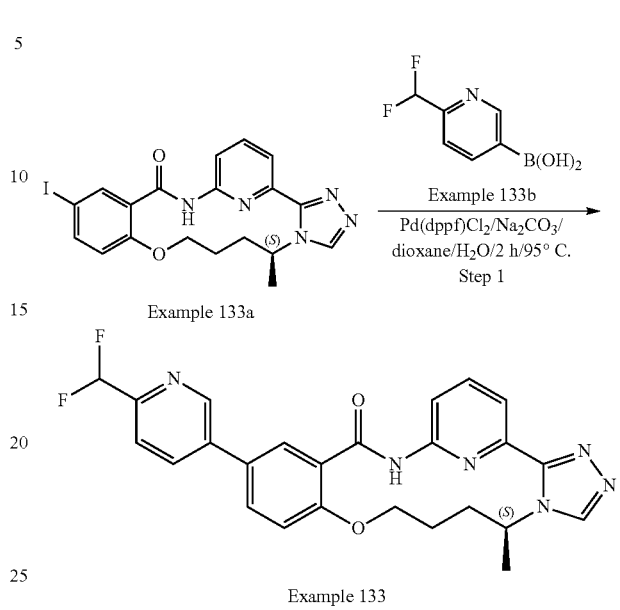

To a solution of Example 133a (70 mg, 0.15 mmol), Example 133b (38 mg, 0.22 mmol) and Na$_2$CO$_3$ (32 mg, 25.13 mmol) in dioxane (5 mL) and water (1 mL) was added Pd(dppf)Cl$_2$ (11 mg, 0.015 mmol). The mixture was degassed with N$_2$ three times, and heated to 95° C. for 2 h. The mixture was cooled to room temperature, and concentrated under reduced pressure. The residue was purified by prep-HPLC to give 15 mg crude product, then purified by prep-TLC (DCM/MeOH=10/1) to give the desired product Example 133 (10 mg, yield 14%) as a white solid. LC-MS [M+1]$^+$=477.0. $^1$H NMR (400 MHz, DMSO-d$_6$) δ 11.24 (s, 1H), 9.02 (d, J=2.3 Hz, 1H), 8.86 (s, 1H), 8.30 (dd, J=10.5, 2.4 Hz, 2H), 8.11-7.99 (m, 2H), 7.87 (d, J=8.1 Hz, 1H), 7.79 (dd, J=11.9, 7.9 Hz, 2H), 7.41 (d, J=8.7 Hz, 1H), 7.01 (t, J=53.6 Hz, 1H), 4.59 (s, 1H), 4.52 (d, J=9.9 Hz, 1H), 4.21 (t, J=9.8 Hz, 1H), 3.16 (d, J=11.5 Hz, 1H), 2.13 (s, 1H), 1.86-1.70 (m, 2H), 1.53 (d, J=7.0 Hz, 3H).

Example 134: General Procedure for Synthesis of Compound Example 134

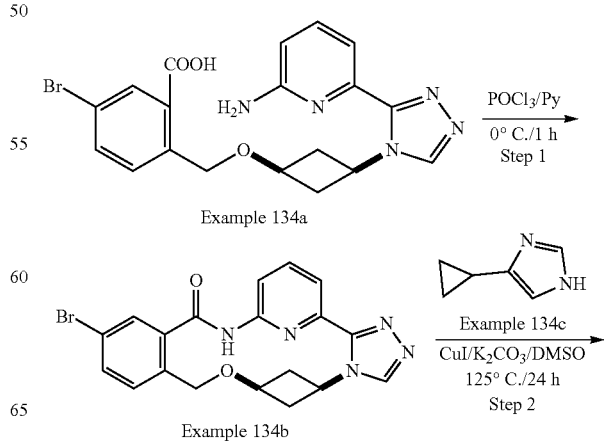

-continued

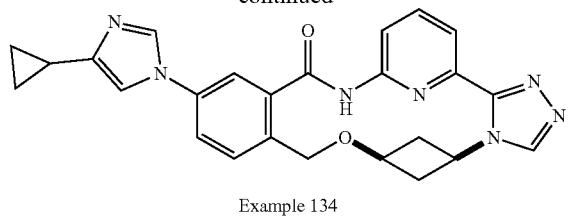

Example 134

Step 1: Example 134b

To a mixture of Example 134a (290 mg, 2.31 mmol) in pyridine (70 mL) at 0° C. was added POCl₃ (0.3 mL) slowly. The mixture was stirred at 0° C. for 1 h. To the mixture was added water (80 mL), which was concentrated under reduced pressure. To the residue was added water (50 nit), which was stirred at r.t. for 15 min, filtered and dried at 45° C. to give the desired product Example 134b (150 mg, yield 54%) as a white solid.
LC-MS [M+1]⁺=425.9/427.9

Step 2: Example 134

A mixture of Example 134b (100 mg, 0.235 mmol), Example 134c (108 mg, 1.0 mmol), K₂CO₃ (162 ma, 1.175 mmol), CuI (11 mg, 0.058 mmol) in dry DMSO (2 mL) was heated at 125° C. for 24 h. The reaction was cooled to r.t. and water (25 mL) was added. The resulting mixture was stirred for 5 min, and filtered to give the crude product, which was purified by prep-HPLC (by Ultimate XB-C18, 50×250 mm, 10 μm, speed: 80 mL/min, eluent: A/B=H₂O/CH₃CN=from 75/25 to 45/55 over 30 min, Ret. Time 24.94 min), followed by prep-TLC (DCM/MeOH=10/1) to give the desired product Example 134 (1.2 mg, yield 1%) as a white solid. LC-MS [M+1]⁺=454.0. ¹H NMR (400 MHz, Chloroform-d) δ 11.80 (s, 1H), 8.23-8.15 (m, 3H), 8.04 (s, 1H), 7.97 (t, J=7.9 Hz, 1H), 7.83 (s, 1H), 7.50 (s, 2H), 7.12 (s, 1H), 4.83 (t, J=8.9 Hz, 1H), 4.58 (s, 2H), 4.41 (t, J=6.9 Hz, 1H), 3.81 (s, 2H), 2.88 (s, 2H), 1.96 (d, J=38.7 Hz, 1H), 0.89 (d, J=7.0 Hz, 2H), 0.83 (s, 2H).

Example 135: General Procedure for Synthesis of Compound Example 135

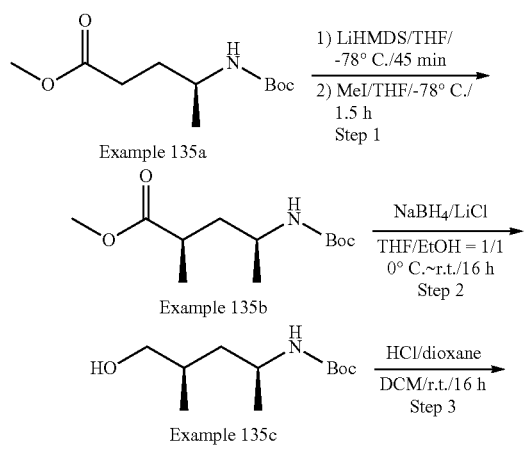

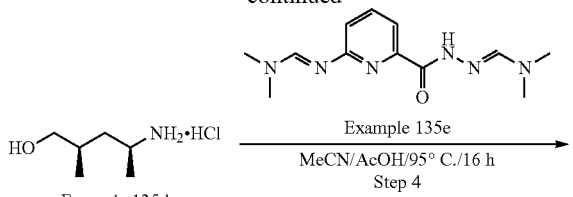

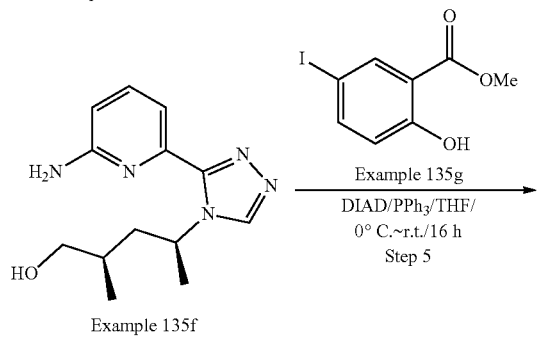

Example 135f

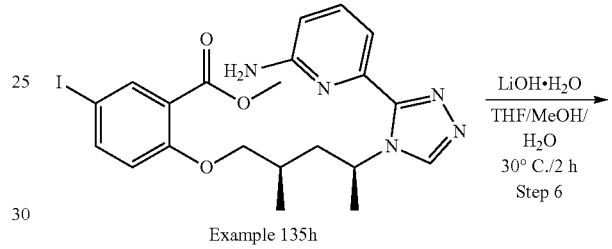

Example 135h

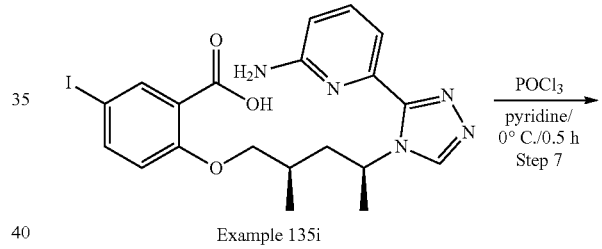

Example 135i

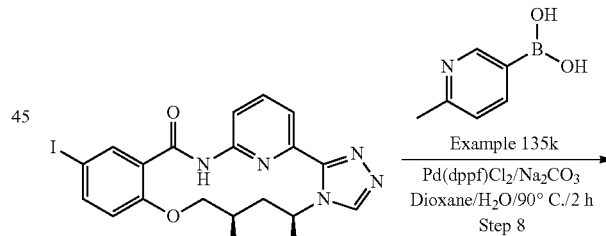

Example 135j

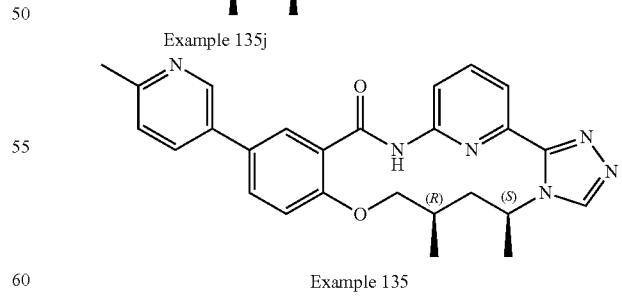

Example 135

Step 1: Example 135b

Example 135a (50.0 g, 216.5 mmol) was dissolved in dry THF (1 L) followed by addition of LiHMDS (1.08 L, 1.0 M in THF) in two portions at −78° C. After stirring for 45 min at −78° C., MeI (154 g, 1082.3 mmol) was added in one portion. The resulting mixture was stirred at −78° C. for another 1.5 h. The reaction was quenched by 1N HCl (aq.) at 0° C. The mixture was extracted with EtOAc (500 mL*3). The combined organic layers were dried over $Na_2SO_4$, filtered and concentrated to afford a residue which was purified by silica gel chromatography (Petroleum Ether/EtOAc=40/1) to give the desired product Example 135b (19 g, yield 36%) as yellowish oil. LCMS $[M+1-100]^+$=146.1
$^1$H NMR (400 MHz, Chloroform-d) δ 4.29 (s, 1H), 3.71 (s, 1H), 3.66 (s, 3H), 2.50 (d, J=7.0 Hz, 1H), 1.80-1.74 (m, 1H), 1.47 (d, J=5.2 Hz, 1H), 1.42 (s, 9H), 1.17 (d, J=7.0 Hz, 3H), 1.12 (d, J=6.5 Hz, 3H).

Step 2: Example 135c $NaBH_4$ (11.8 g, 310.2 mmol) and LiCl (13.0 g, 310.2 mmol) were combined in a 1 L three necked flask in THF/EtOH (v/v=1/1, 400 mL) and stirred at 0° C. for 15 min. A solution of Example 135b (19.0 g, 77.6 mmol) in THF/EtOH (v/v=1/1, 100 mL) was added into the mixture dropwise at 0° C. After addition, the reaction was stirred from 0° C. to r.t. for 16 h. The reaction was quenched by adding water at 0° C., and extracted with DCM/MeOH (v/v=10/1, 300 mL*3). The combined organic layers were dried over $Na_2SO_4$, filtered and concentrated to give the crude product which was purified by silica gel chromatography (Petroleum Ether/EtOAc=67/33) to give the desired product Example 135c (14.5 g, yield 86%) as colorless oil. LCMS $[M+1-100]^+$=118.1. $^1$H NMR (400 MHz, Chloroform-d) δ 4.47 (d, J=8.3 Hz, 1H), 3.72 (dd, J=15.2, 8.0 Hz, 1H), 3.50 (d, J=6.2 Hz, 1H), 3.40 (dd, J=10.7, 6.2 Hz, 1H), 2.50 (s, 1H), 1.67 (dt, J=12.8, 6.5 Hz, 1H), 1.56 (dd, J=13.3, 7.8 Hz, 1H), 1.45 (d, J=11.2 Hz, 1H), 1.41 (s, 9H), 1.11 (d, J=6.4 Hz, 3H), 0.92 (d, J=6.7 Hz, 3H).

Step 3: Example 135d

To a solution of Example 135c (14.5 g, 66.8 mmol) in DCM (25 mL) was added a solution of 4M HCl/dioxane (150 mL). The mixture was stirred at 25° C. for 4 h. The solvent was removed in vacuo, and the residue was treated with DCM and concentrated for three times to give the desired product Example 135d (10.3 g, yield 100%) as brown oil (HCl salt).

Step 4: Example 135f

A solution of Example 135e (7.0 g, 26.7 mmol) and Example 135d (10.3 g, 66.8 mmol) in MeCN (90 mL) and AcOH (22 mL) was degassed with $N_2$ for three times, and heated to 95° C. for 16 h. The mixture was cooled to room temperature, and then 6N HCl (10 mL) was added. The resulting mixture was stirred for 1 h, and concentrated under reduced pressure. The residue was cooled to 0° C. and adjusted pH to 9~10 with 30% NaOH (aq.). The mixture was stirred for 30 min, and concentrated under reduced pressure, which was purified by silica gel chromatography (DCM/MeOH=90/10) to give the desired product Example 135f (2.4 g, yield 34%) as a pale yellow gel. LCMS $[M+1]^+$=262.1

Step 5: Example 135h

A solution of Example 135f (2.4 g, 9.20 mmol), Example 135g (2.56 g, 9.20 mmol) and $PPh_3$ (6.0 g, 23.04 mmol) in dry THF (60 mL) was degassed with $N_2$ three times and cool to 0° C. DIAD (4.6 g, 23.04 mmol) was added dropwise and the mixture was stirred for 16 h at 0-5° C. The mixture was concentrated under reduced pressure, which was purified by silica gel chromatography (EtOAc/MeOH=80/20) to give the desired product Example 135h (1.9 g, yield 40%) as a pale yellow gel. LCMS $[M+1]^+$=521.9

Step 6: Example 135i

A solution of Example 135h (1.9 g, 3.60 mmol) and $LiO.H_2O$ (770 mg, 18.2 mmol) in THF (15 mL), MeOH (10 mL) and water (5 mL) was stirred at 30° C. for 2 h. The pH was adjusted to 3-4 with 1N HCl (aq.). Then the mixture was concentrated under reduced pressure to give the desired product Example 135i (1.46 g, crude yield 100%) as a white solid, which was used in the next step without further purification. LCMS $[M+1]^+$=507.9

Step 7: Example 135j

A solution of Example 135i (1.46 g, 2.88 mmol) in pyridine (140 mL) was cooled to 0° C. under $N_2$ protection. Then $POCl_3$ (2.2 g, 14.40 mmol) was added dropwise and the mixture was stirred for 0.5 h at 0-5° C. Water (5 mL) was added to the mixture, which was concentrated under reduced pressure. Additional water (20 mL) was added to the residue, which was stirred for 30 min at room temperature, and filtrated. The solid was washed by water (20 mL), dried under reduced pressure to give the desired product Example 135j (1.0 g, yield 71%) as a pink solid. LCMS $[M+1]^+$=489.9

Step 8: Example 135

To a solution of Example 135j (208 mg, 0.43 mmol), Example 135k (70 mg, 1.02 mmol) in 1,4-dioxane/$H_2O$ (4 mL/1 mL) was added $Pd(dppf)Cl_2$ (31 mg, 0.043 mmol) and $Na_2CO_3$ (90 mg, 0.85 mmol). The mixture was degassed by nitrogen for three times and heated at 95° C. for 2 h. The reaction mixture was filtered, washed with EtOAc and concentrated. The residue was purified by silica gel chromatography (DCM/MeOH=92/8) to give the crude product (75 mg), which was re-purified by prep-TLC (DCM/MeOH=15/1) to give the desired product Example 135 (21.0 mg, yield 11%) as a white solid. LCMS $[M+1]^+$=455.1. $^1$H NMR (400 MHz, DMSO-$d_6$) δ 11.13 (s, 1H), 8.89 (s, 1H), 8.75 (s, 1H), 8.14 (s, 1H), 8.06 (t, J=7.9 Hz, 1H), 8.00-7.96 (m, 1H), 7.91 (d, J=7.2 Hz, 1H), 7.80 (d, J=8.1 Hz, 1H), 7.77 (d, J=7.5 Hz, 1H), 7.44 (d, J=8.8 Hz, 1H), 7.33 (d, J=8.1 Hz, 1H), 4.97 (s, 1H), 4.38 (d, J=9.6 Hz, 1H), 4.04 (t, J=8.8 Hz, 1H), 3.02 (d, J=12.8 Hz, 1H), 2.53 (s, 3H), 2.08 (s, 1H), 1.55 (d, J=6.9 Hz, 3H), 1.46 (s, 1H), 1.15 (d, J=6.8 Hz, 3H).

Example 136: General Procedure for Synthesis of Compound Example 136

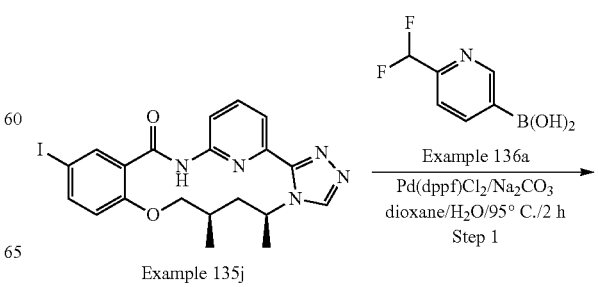

Example 135j

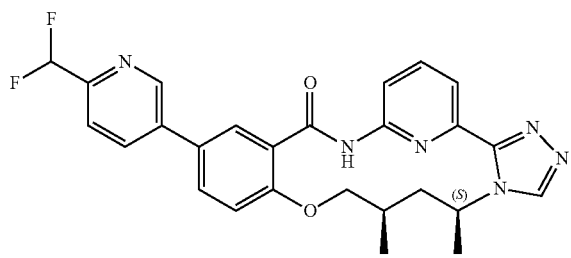

Example 136

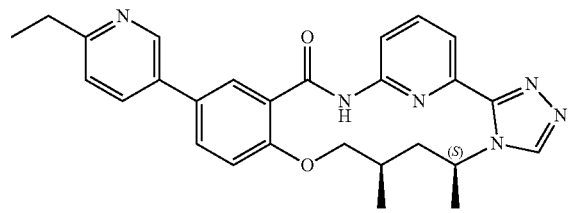

Example 137

To a solution of Example 135j (200 mg, 0.41 mmol), Example 136a (85 mg, 0.49 mmol) in 1,4-dioxane/H₂O (4 mL/1 mL) were added Pd(dppf)Cl₂ (30 mg, 0.041 mmol) and Na₂CO₃ (87 mg, 0.82 mmol). The mixture was degassed by nitrogen for three times and heated at 95° C. for 2 hours. The reaction mixture was filtered, washed with EtOAc and concentrated. The residue was purified by prep-TLC (DCM/MeOH=15/1) to give the crude product, which was re-purified by prep-HPLC to give the desired product Example 136 (17.2 mg, yield 9%) as a pink solid. LC-MS [M+1]⁺ =491.0. ¹H NMR (400 MHz, DMSO-d₆) δ 11.07 (s, 1H), 9.02 (d, J=2.3 Hz, 1H), 8.88 (s, 1H), 8.30 (dd, J=8.2, 2.3 Hz, 1H), 8.23 (d, J=2.5 Hz, 1H), 8.05 (t, J=7.9 Hz, 1H), 8.00 (dd, J=8.8, 2.6 Hz, 1H), 7.78 (dd, J=10.7, 8.0 Hz, 3H), 7.47 (d, J=8.7 Hz, 1H), 7.00 (t, J=55.1 Hz, 1H), 4.95 (s, 1H), 4.37 (dd, J=9.8, 2.6 Hz, 1H), 4.05 (t, J=8.9 Hz, 1H), 3.06-3.00 (m, 1H), 2.06 (d, J=7.0 Hz, 1H), 1.55 (d, J=6.9 Hz, 3H), 1.44 (td, J=12.2, 6.5 Hz, 1H), 1.15 (d, J=6.8 Hz, 3H).

Example 137: General Procedure for Synthesis of Compound Example 137

Step 1: Example 137c

To a solution of Example 137a (100 mg, 0.54 mmol), Example 137b (205 mg, 0.81 mmol) in 1,4-dioxane (3 mL) were added Pd(dppf)Cl₂ (40 mg, 0.054 mmol) and KOAc (105 mg, 1.08 mmol). The mixture was degassed by nitrogen for three times and heated at 100° C. for 16 hours. The reaction mixture was filtered, washed with EtOAc and concentrated to give the crude desired product Example 137c (81 mg, crude yield 100%) as a black solid, which was used for the next step directly. LCMS [M+1]⁺=152.0

Step 2: Example 137

To a solution of Example 137c (81 mg, 0.54 mmol), Example 135j (240 mg, 0.49 mmol) in 1,4-dioxane/H₂O (4 mL/1 mL) were added Pd(dppf)Cl₂ (36 mg, 0.049 mmol) and Na₂CO₃ (104 mg, 0.98 mmol). The mixture was degassed by nitrogen for three times and heated at 95° C. for 2 hours. The reaction mixture was filtered, washed with EtOAc and concentrated. The residue was purified by prep-TLC (DCM/MeOH=15/1) to give the desired product Example 137 (42.5 mg, yield 19%) as a white solid. LCMS [M+1]⁺=469.0

¹H NMR (400 MHz, DMSO-d6) δ 11.12 (s, 1H), 8.88 (s, 1H), 8.76 (d, J=2.4 Hz, 1H), 8.14 (d, J=2.5 Hz, 1H), 8.04 (t, J=7.9 Hz, 1H), 7.97 (dd, J=8.1, 2.5 Hz, 1H), 7.89 (dd, J=8.6, 2.6 Hz, 1H), 7.77 (dd, J=12.2, 7.8 Hz, 2H), 7.41 (d, J=8.7 Hz, 1H), 7.32 (d, J=8.1 Hz, 1H), 4.94 (s, 1H), 4.35 (dd, J=9.7, 2.6 Hz, 1H), 4.01 (t, J=8.9 Hz, 1H), 3.05-2.97 (m, 1H), 2.77 (q, J=7.6 Hz, 2H), 2.05 (s, 1H), 1.54 (d, J=6.9 Hz, 3H), 1.44 (dt, J=12.4, 6.0 Hz, 1H), 1.23 (t, J=7.6 Hz, 3H), 1.14 (d, J=6.8 Hz, 3H).

Example 138: General Procedure for Synthesis of Compound Example 138

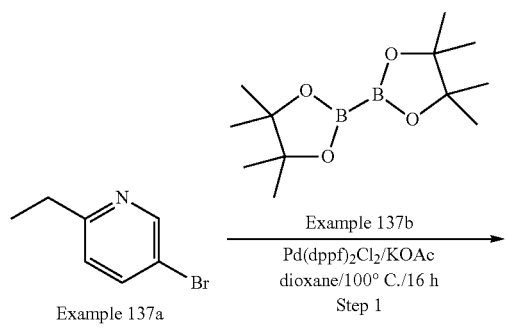

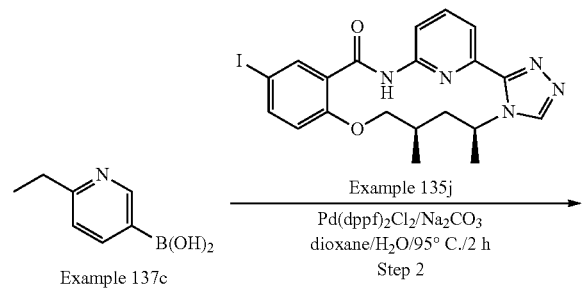

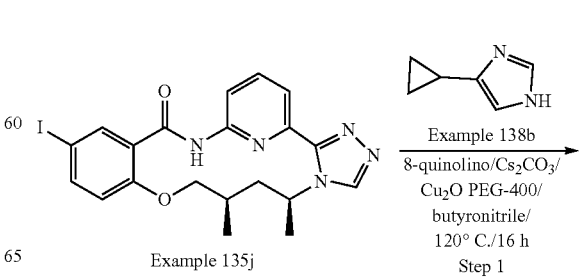

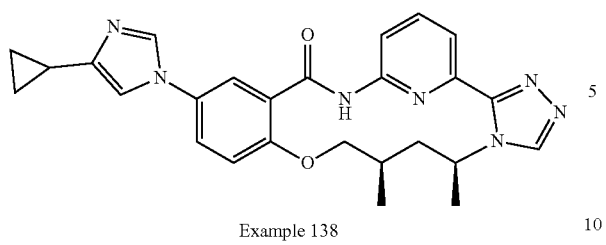

Example 138

To a solution of Example 135j (245 mg, 0.50 mmol), Example 138a (81 mg, 0.75 mmol) in butyronitrile (3 mL) and PEG-400 (190 mg) were added 8-quinolinol (11 mg, 0.075 mmol), Cu$_2$O (8 mg, 0.050 mmol) and Cs$_2$CO$_3$ (326 mg, 1.0 mmol) successively. The mixture was sealed, degassed by nitrogen for three times and heated at 120° C. for 16 hours. The reaction mixture was filtered, and washed by EtOAc. The filtrates were concentrated and purified by silica gel chromatography (DCM/MeOH=85/15) to give the crude product (105 mg), which was re-purified by prep-HPLC to afford the desired product Example 138 (4.0 mg, yield 2%) as a yellow solid. LCMS [M+1]$^+$=470.0. $^1$H NMR (400 MHz, DMSO-d$_6$) δ 11.09 (s, 1H), 8.87 (s, 1H), 8.16-8.00 (m, 2H), 7.97 (s, 1H), 7.76 (d, J=8.0 Hz, 3H), 7.52-7.35 (m, 2H), 4.95 (s, 1H), 4.34 (d, J=9.3 Hz, 1H), 4.00 (t, J=8.8 Hz, 1H), 2.99 (d, J=14.7 Hz, 1H), 2.05 (s, 1H), 1.82 (s, 1H), 1.53 (d, J=6.8 Hz, 3H), 1.43 (q, J=10.8, 10.2 Hz, 1H), 1.13 (d, J=6.5 Hz, 3H), 0.78 (m, 2H), 0.68 (m, 2H).

Example 139: General Procedure for Synthesis of Compound Example 139

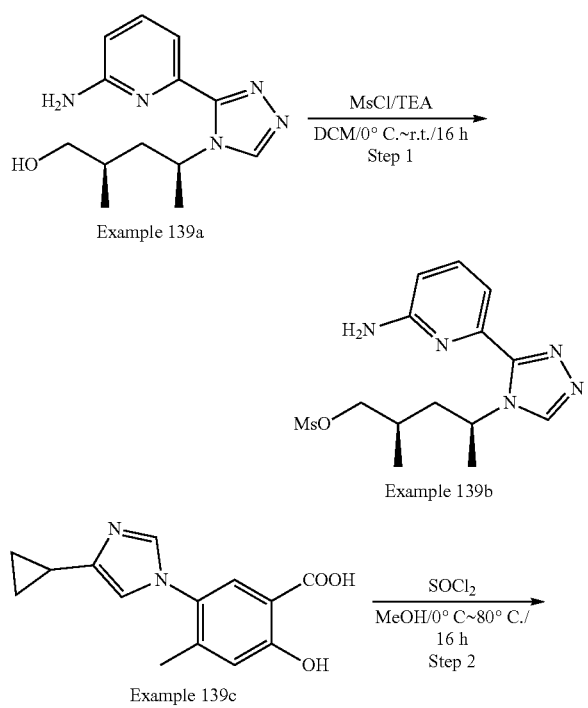

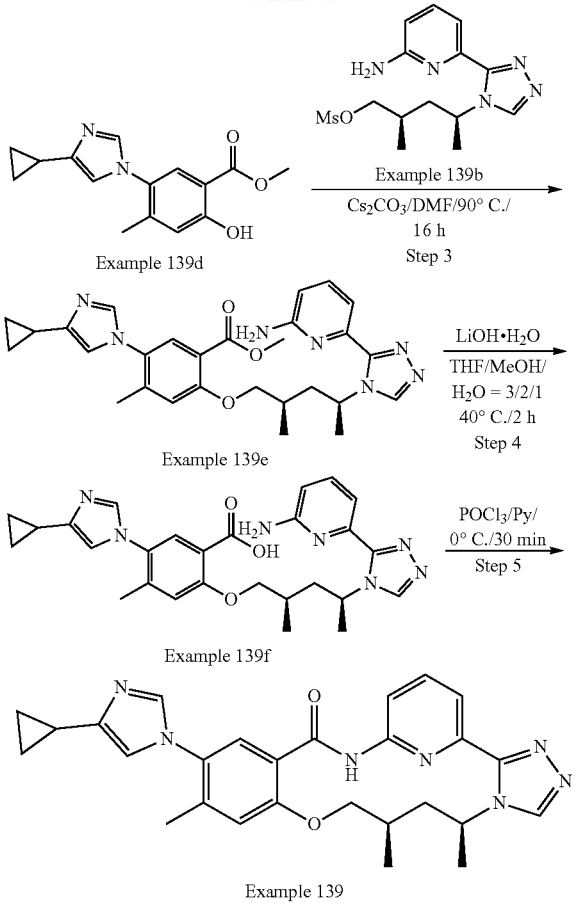

Step 1: Example 139b

To a solution of Example 139a (950 mg, 3.64 mmol) and TEA (551 mg, 5.46 mmol) in dry DCM (10 mL) was slowly added MsCl (498 mg, 4.37 mmol) at 0° C. under nitrogen atmosphere. The reaction was stirred from 0° C. to r.t. for 16 h. The reaction was concentrated directly and purified by silica gel chromatography (DCM/MeOH=93/7) to give the desired product Example 139b (294 mg, yield 24%) as yellowish oil. LCMS [M+1]$^+$=340.1.

Step 2: Example 139d

To a solution of Example 139c (1.6 g, 6.24 mmol) in MeOH (40 mL) was added SOCl$_2$ (2.2 g, 18.56 mmol) dropwise at 0° C. After addition, the mixture was allowed to stir at 80° C. for 16 h. The mixture was concentrated, purified by silica gel chromatography (DCM/MeOH=97/3) to give the desired product Example 139d (1.6 g, yield 95%) as a brown solid.
LCMS [M+1]$^+$=273.0

Step 3: Example 139e

To a solution of Example 139d (143 mg, 0.52 mmol) in DMF (5 mL) were added Example 139b (213 mg, 0.62 mmol) and Cs$_2$CO$_3$ (343 mg, 1.04 mmol). The mixture was stirred at 90° C. for 16 h. The solvent was removed in vacuo, and the residue was purified by silica gel chromatography (DCM/MeOH=80/20) to give the desired product Example 139e (280 mg, yield 100%) as colorless oil. LCMS [M+1]$^+$=516.1

Step 4: Example 139f

A solution of Example 139e (280 mg, 0.54 mmol) and LiO.H$_2$O (57 mg, 1.36 mmol) in THF (6 mL), MeOH (4 mL) and water (2 mL) was stirred at 40° C. for 2 h. The pH of the mixture was adjusted to 3-4 with 1N HCl (aq.). Then the mixture was concentrated under reduced pressure to give the desired product Example 139f (272 mg, crude yield 100%) as a white solid, which was used in the next step without further purification.
LCMS [M+1]$^+$=502.0

Step 5: Example 139

A solution of Example 139f (272 mg, 0.54 mmol) in pyridine (27 mL) was cooled to 0° C. under N$_2$ protection. Then POCl$_3$ (416 mg, 2.72 mmol) was added dropwise and the mixture was stirred for 0.5 h at 0-5° C. Water (5 mL) was added to the mixture, which was concentrated under reduced pressure. MeOH (20 mL) was added to the residue, which was concentrated for three times, purified firstly by prep-TLC (DCM/MeOH=15/1) to obtain the crude product, which was re-purified by prep-HPLC to give the desired product Example 139 (7.1 mg, yield 3%) as a white solid. LCMS [M+1]$^+$=484.0
$^1$H NMR (400 MHz, DMSO-d$_6$) δ 11.16 (s, 1H), 8.88 (s, 1H), 8.04 (t, J=7.9 Hz, 1H), 7.77 (t, J=7.0 Hz, 2H), 7.66 (d, J=30.3 Hz, 2H), 7.39 (s, 1H), 7.10 (s, 1H), 4.96 (s, 1H), 4.39 (d, J=9.5 Hz, 1H), 4.03 (t, J=9.0 Hz, 1H), 3.04 (d, J=12.5 Hz, 1H), 2.20 (s, 3H), 2.07 (d, J=14.7 Hz, 1H), 1.82 (s, 1H), 1.55 (d, J=6.8 Hz, 3H), 1.46 (s, 1H), 1.16 (d, J=6.8 Hz, 3H), 0.78 (m, 2H), 0.69 (m, 2H).

Example 140: General Procedure for Synthesis of Compound Example 140

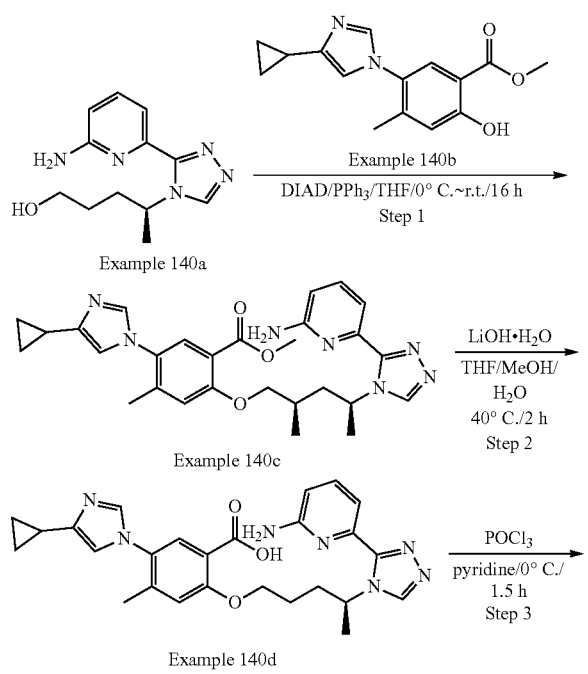

Example 140a

Example 140b

Example 140c

Example 140d

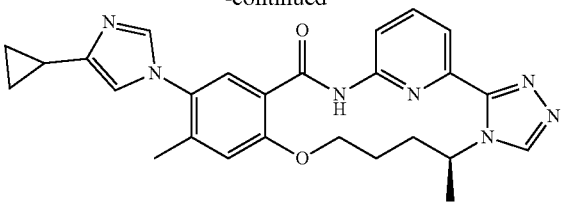

Example 140

Step 1: Example 140c

A solution of Example 140a (450 mg, 1.82 mmol), Example 140b (500 mg, 1.82 mmol) and PPh$_3$ (955 mg, 3.64 mmol) in dry THF (10 mL) was degassed with N$_2$ three times and cooled to 0° C. DIAD (736 mg, 3.64 mmol) was added dropwise and the mixture was stirred for 16 h at 0° C.~r.t. The mixture was concentrated under reduced pressure, which was purified by silica gel chromatography (EtOAc/MeOH=83/17) to give the desired product Example 140c (400 mg, yield 44%) as a yellowish gum. LCMS [M+1]$^+$=502.1

Step 2: Example 140d

A solution of Example 140c (400 mg, 0.80 mmol) and LiO.H$_2$O (168 mg, 4.00 mmol) in THF (6 mL), MeOH (4 mL) and water (2 mL) was stirred at 40° C. for 2 h. The mixture was adjusted pH=3~4 with 1N HCl. Then the mixture was concentrated under reduced pressure to give the desired product Example 140d (388 mg, crude yield 100%) as a white solid, which was used in the next step without further purification. LCMS [M+1]$^+$=488.0

Step 3: Example 140

A solution of Example 140d (388 mg, 0.80 mmol) in pyridine (40 mL) was cooled to 0° C. under N$_2$ protection. Then POCl$_3$ (609 mg, 4.00 mmol) was added dropwise and the mixture was stirred for 1.5 h at 0° C. Water (5 mL) was added to the mixture, which was concentrated under reduced pressure. The residue was treated with MeOH for three times and the crude material was purified by silica gel chromatography (DCM/MeOH=90/10) to afford the crude product (145 mg), which was re-purified by prep-TLC (DCM/MeOH=15/1) to give the pure product Example 140 (34.0 mg, yield 9%) as a white solid. LCMS [M+1]$^+$=470.1. $^1$H NMR (400 MHz, DMSO-d$_6$) δ 11.28 (s, 1H), 8.87 (s, 1H), 8.05 (t, J=7.9 Hz, 1H), 7.81 (dd, J=12.3, 7.8 Hz, 2H), 7.75 (s, 2H), 7.32 (s, 1H), 7.14 (s, 1H), 4.59 (d, J=6.7 Hz, 1H), 4.52 (d, J=9.7 Hz, 1H), 4.19 (t, J=9.8 Hz, 1H), 3.13 (t, J=9.3 Hz, 1H), 2.19 (s, 4H), 1.88-1.72 (m, 3H), 1.53 (d, J=6.9 Hz, 3H), 0.85-0.64 (m, 4H).

Example 141: General Procedure for Synthesis of Compound Example 141

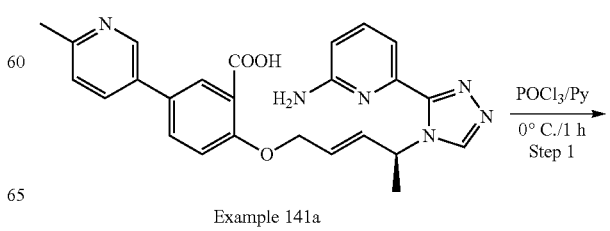

Example 141a

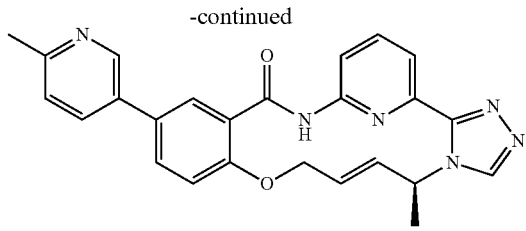

Example 141

A solution of Example 141a (60 mg, 0.13 mmol) in pyridine (13 mL) was cooled to 0° C. under $N_2$ protection. Then $POCl_3$ (100 mg, 0.66 mmol) was added dropwise and the mixture was stirred for 1 h at 0° C. Water (5 mL) was added to the mixture, which was concentrated under reduced pressure. The residue was purified firstly by silica chromatography (DCM/MeOH=91/9) to give the crude product, which was re-purified by prep-TLC (DCM/MeOH=10/1) for three times to give the desired product Example 141 (7.8 mg, yield 14%) as a white solid. LCMS $[M+1]^+$=439.0. $^1H$ NMR (400 MHz, DMSO-$d_6$) δ 10.55 (s, 1H), 8.72 (d, J=2.5 Hz, 1H), 8.71 (s, 1H), 8.10 (d, J=2.6 Hz, 1H), 8.04 (d, J=8.2 Hz, 1H), 7.95 (dd, J=8.0, 2.5 Hz, 1H), 7.80-7.76 (m, 1H), 7.69 (t, J=7.9 Hz, 1H), 7.60 (dd, J=8.7, 2.6 Hz, 1H), 7.37 (d, J=8.2 Hz, 1H), 7.10 (d, J=8.8 Hz, 1H), 6.21 (d, J=13.5 Hz, 2H), 5.96 (d, J=13.7 Hz, 1H), 5.06-4.90 (m, 2H), 2.52 (s, 3H), 1.61 (dd, J=32.2, 6.5 Hz, 3H).

Example A: ASK1 KINOMEscan™ Assay (Biochemical Kd)

The binding of compounds to ASK1 were determined using DiscoverX's proprietary technology. KINOMEscan™ is based on a competition binding assay that quantitatively measures the ability of a compound to compete with an immobilized, active-site directed ligand. The assay is performed by combining three components: DNA-tagged ASK1 kinase; immobilized ligand; and a test compound. The ability of the test compound to compete with the immobilized ligand is measured via quantitative PCR of the DNA tag. Streptavidin-coated magnetic beads were treated with biotinylated small molecule ligands for 30 minutes at room temperature to generate affinity resins for ASK1 kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining DNA-tagged ASK1 kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions were performed in polypropylene 384-well plate. Each fraction had a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.504 non-biotinylated affinity ligand) and incubated at room temperature with shaking for 30 minutes. The kinase concentration in the eluates was measured by qPCR. Most Kds were determined using a compound top concentration=30,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM. Binding constants (Kds) were calculated with a standard dose-response curve using the Hill equation: Response=Background+{(Signal−Background)/[1+($Kd^{Hill\ Slope}$/$Dose^{Hill\ Slope}$)]}, the Hill Slope was set to −1, and curves were fitted using a non-linear least square fit with the Levenberg-Marquardt algorithm.

The ASK1 binding data is shown in the table below:

| Ex. | ASK1, Kd (nM) |
| --- | --- |
| 1 | A |
| 2 | A |
| 3 | B |
| 4 | D |
| 5 | C |
| 6 | B |
| 7 | A |
| 8 | B |
| 9 | C |
| 10 | A |
| 11 | A |
| 12 | B |
| 13 | D |
| 14 | B |
| 15 | D |
| 16 | B |
| 17 | B |
| 18 | A |
| 19 | B |
| 20 | B |
| 21 | D |
| 22 | A |
| 23 | A |
| 24 | A |
| 25 | C |
| 26 | C |
| 28 | C |
| 29 | C |
| 30 | A |
| 31 | A |
| 32 | B |
| 33 | C |
| 35 | B |
| 37 | A |
| 38 | A |
| 39 | A |
| 40 | A |
| 41 | B |
| 42 | A |
| 43 | A |
| 44 | B |
| 45 | C |
| 46 | A |
| 47 | A |
| 48 | A |
| 50 | A |
| 51 | A |
| 52 | A |
| 53 | A |
| 54 | A |
| 55 | A |
| 56 | A |
| 57 | B |
| 58 | A |
| 59 | C |
| 60 | A |
| 61 | A |
| 63 | A |
| 64 | C |
| 65 | A |
| 66 | A |

-continued

| Ex. | ASK1, Kd (nM) |
|---|---|
| 67 | A |
| 68 | A |
| 69 | A |
| 70 | A |
| 71 | A |
| 72 | D |
| 73 | A |
| 74 | A |
| 75 | B |
| 77 | A |
| 78 | A |
| 79 | B |
| 80 | A |
| 81 | A |
| 82 | A |
| 83 | D |
| 84 | A |
| 86 | A |
| 87 | A |
| 88 | A |
| 89 | A |
| 90 | D |
| 91 | D |
| 92 | A |
| 93 | C |
| 94 | D |
| 95 | A |
| 96 | B |
| 97 | A |
| 98 | A |
| 99 | A |
| 100 | A |
| 101 | B |
| 102 | A |
| 103 | A |
| 104 | A |
| 105 | A |
| 106 | B |
| 107 | B |

A: <10 nM
10 nM ≤ B < 100 nM
100 nM ≤ C < 1 μM
D ≥1 μM

Example B. HK-2 Phospho-p38 HTRF Assay (Cellular IC$_{50}$)

Human kidney-2 (HK-2) proximal tubular cells were obtained from the American Type Culture Collection (CRL-2190). These cells have endougenous expression of ASK1 kinase and the kinase can be activated through phosphorylation by H2O2 treatment. Monolayers of HK-2 cells were grown on 384-well plates at 8000 cells/well and incubated at 37° C. with 5% CO$_2$/95% air in keratinocyte serum-free medium (Thermofisher, Carlsbad, Calif.) supplemented with recombinant human EGF (5 ng/mL) and bovine pituitary extract (50 μg/mL). 24 hours after seeding, cells were treated with test compounds for various concentrations for 2 hours and followed by 30 min treatment of H$_2$O$_2$ with final concentration of 1 mM. At the end of cell treatment, the cell medium was removed, and the cells were washed once with ice-cold PBS and subjected to measure the level of phosphor-p38 (downstream target of ASK1 activation) using Cisbio's P38 phospho-T180/Y182 HTRF kit from Cisbio (Cat. 64P38PEG). IC$_{50}$ were determined using an 11-point 4-fold compound dilution series with one DMSO control point. All compounds for IC$_{50}$ measurements were distributed by Tecan d300e digital dispenser (non-contact dispensing) in 100% DMSO. The compounds were then diluted directly into the assays such that the final concentration of DMSO was 0.4%. Most IC$_{50}$s were determined using a compound top concentration=1,000 nM. An IC$_{50}$ value reported as >1,000 nM indicates the inhibition is less than 50% at the top dose. IC50 were calculated with a log (dose)-response curve using four parameter variable nonlinear fitting, with log(dose) in X-axis and (Em665/Em620× 10000) ratio as Y-axis.

The p38 MAPK IC$_{50}$ are shown in the table below:

| Ex. | IC$_{50}$ (nM) |
|---|---|
| 2 | C |
| 19 | B |
| 22 | A |
| 23 | B |
| 24 | A |
| 30 | A |
| 37 | A |
| 38 | A |
| 39 | A |
| 40 | A |
| 42 | B |
| 43 | A |
| 46 | B |
| 47 | A |
| 48 | A |
| 50 | A |
| 52 | A |
| 53 | C |
| 54 | A |
| 55 | C |
| 56 | A |
| 61 | A |
| 63 | B |
| 66 | B |
| 67 | A |
| 69 | A |
| 70 | A |
| 71 | A |

A: <100 nM
100 nM ≤ B < 1 μM
D ≥1 μM

Example C: Phase 1 Study to Evaluate Safety of a Compound Described Herein in Subjects with Non-Alcoholic Steatohepatitis (NASH)

The primary objective of this study is to characterize the safety, tolerability and dose-limiting toxicities (DLTs) for a compound described herein when administered orally to subjects with NASH.

The safety and tolerability of multiple doses of a compound described herein;

The effects of 2 dose levels (25 mg and 50 mg) of a compound described herein on insulin resistance and glucose homeostasis; and Effects of a compound described herein on hepatocellular function as measured by assessment of liver enzymes and biochemical markers of hepatic and metabolic function and inflammation.

Patients: Eligible subjects will be men and women 18 years to 75 years of age.

Criteria:

Inclusion Criteria:

Institutional Review Board (IRB approved written Informed Consent and privacy language as per national regulation (eg, Health Insurance Portability and Accountability Act [HIPAA] Authorization for US sites) must be obtained from the subject or legally authorized representative prior to any study related procedures, including screening evaluations and tests Subject is ≥18 years of age and <76 years old at the time of consent Subject has had a percutaneous liver biopsy within 12 months from Screening that shows a definitive diagnosis of NASH with advanced (Brunt stage 3) hepatic fibrosis Exclusion Criteria:

Subject is a pregnant or lactating female

Subject with current, significant alcohol consumption or a history of significant alcohol consumption for a period of more than 3 consecutive months any time within 1 year prior to screening. Significant alcohol consumption is defined as more than 20 gram per day in females and more than 30 grams per day in males, on average (a standard drink in the US is considered to be 14 grams of alcohol).

Subject is unable to reliably quantify alcohol consumption based upon local study physician judgment.

Subject uses drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to Screening.

Subject requires use of drugs with a narrow therapeutic window metabolized by CYP3A4 such as fast acting opioids (alfentanil and fentanyl), immunosuppressive drugs (cyclosporine, sirolimus, and tacrolimus), some cardiovascular agents (ergotamine, quinidine and dihydroergotamine), and select psychotropic agents (pimozide).

Subject has prior or has planned (during the study period) bariatric surgery (eg, gastroplasty, Roux-en-Y gastric bypass).

Subject has concurrent infection including diagnoses of fever of unknown origin and evidence of possible central line sepsis (subjects must be afebrile at the start of therapy).

Subject with a platelet count below 100,000/mm3 at Screening.

Subject with clinical evidence of hepatic decompensation as defined by the presence of any of the following abnormalities at Screening:

Serum albumin less than 3.5 grams/deciliter (g/dL).

An INR greater than 1.1.

Direct bilirubin greater than 1.3 milligrams per deciliter (mg/dL).

Subject has a history of bleeding esophageal varices, ascites, or hepatic encephalopathy Subject has a history of hepatitis C. Patients found on screening to have hepatitis C antibody, even if PCR negative for HCV RNA, are excluded from this study.

Subject has evidence of other forms of chronic liver disease:

Hepatitis B as defined by presence of hepatitis B surface antigen.

Evidence of ongoing autoimmune liver disease as defined by compatible liver histology.

Primary biliary cirrhosis as defined by the presence of at least 2 of these criteria (i) Biochemical evidence of cholestasis based mainly on alkaline phosphatase elevation (ii) Presence of anti-mitochondrial antibody (iii) Histologic evidence of nonsuppurative destructive cholangitis and destruction of interlobular bile ducts.

Primary sclerosing cholangitis.

Wilson's disease as defined by ceruloplasmin below the limits of normal and compatible liver histology.

Alpha-1-antitrypsin deficiency as defined by diagnostic features in liver histology (confirmed by alpha-1 antitrypsin level less than normal; exclusion at the discretion of the study physician).

History of hemochromatosis or iron overload as defined by presence of 3+ or 4+ stainable iron on liver biopsy.

Drug-induced liver disease as defined on the basis of typical exposure and history.

Known bile duct obstruction.

Suspected or proven liver cancer.

Any other type of liver disease other than NASH.

Subject with serum ALT greater than 300 units per liter (U/L) at Screening.

Subject with serum creatinine of 1.5 mg/dL or greater at Screening.

Subject using of any prescription or over-the-counter medication or herbal remedy that are believed to improve or treat NASH or liver disease or obesity during the period beginning 30 days prior to randomization. Subjects who are using Vitamin E or omega-3 fatty acids may continue their use.

Subject with a history of biliary diversion.

Subject with known positivity for Human Immunodeficiency Virus infection.

Subject with an active, serious medical disease with likely life expectancy of less than 5 years.

Subject with active substance abuse, including inhaled or injection drugs, in the year prior to Screening.

Subject with known allergies to the study drug or any of its excipients.

Subject with malignant disease (other than basal and squamous cell carcinoma of the skin and in situ.

Study Design:

Allocation: Randomized

Endpoint Classification: Safety/Efficacy Study

Intervention Model: Parallel Assignment

Masking: Double Blind (Subject, Investigator)

Primary Purpose: Treatment

Primary Outcome Measures:

The primary objective of this study is to characterize the safety, which includes the tolerability and dose-limiting toxicity (DLT), for a compound described herein when administered intravenously to subjects with biopsy-proven NASH. Specifically, this measure will be assessed by number of subjects experiencing treatment emergent adverse events indicative of DLT.

Secondary Outcome Measures:

A secondary objective is to characterize the first-dose PK profile of compound described herein. The PK profile is assessed by the AUC (area under the plasma concentration versus time curve) and Cmax (peak plasma concentration) of a compound described herein.

A secondary objective for the study is to characterize the PK profile and serum level accumulation of a compound described herein following administration of daily oral doses beginning 3 days after the first dose.

A secondary objective is to evaluate change in serum alanine aminotransferase (ALT), aspartate aminotransferase (AST), ratio of AST:ALT, alkaline phosphatase, and gamma glutamyl transpeptidase (GGTP); change in AST/platelet ratio index. [Time Frame: Baseline; Week 7 (End of Study)] [Designated as safety issue: No]

A secondary objective for this study is to evaluate change in serum alanine aminotransferase (ALT), aspartate aminotransferase (AST), ratio of AST:ALT, alkaline phosphatase, and gamma glutamyl transpeptidase (GGTP) levels; and change in AST/platelet ratio index.

Hepatocellular function as measured by assessment of liver enzymes and biochemical markers of hepatic and metabolic function.

| Arms | Assigned Interventions |
| --- | --- |
| Active Comparator: Cohort 1 Patient receives dose of compound described herein or placebo | Drug: Compound described herein Drug: Placebo |
| Active Comparator: Cohort 2 Patient receives dose of described herein or Placebo | Drug: Compound described herein Drug: Placebo |
| Active Comparator: Cohort 3 Patient receives dose of compound described herein or placebo | Drug: Compound described herein Drug: Placebo |

This study is a dose ranging study to assess in sequential fashion, the safety, tolerability, and dose limiting toxicities (DLTs) of a compound described herein, in subjects with biopsy-proven NASH with advanced fibrosis. This is a dose escalation design comprised of 3 sequential cohorts to evaluate the safety of a compound described herein when administered orally once a day for 7 weeks. Each cohort will consist of 8 subjects, 6 randomized to receive a compound described herein and 2 randomized to receive placebo. Based on data safety monitoring board (DSMB) and FDA review, 2 additional cohorts may be implemented, consisting of 8 subjects.

Example D: Pharmaceutical Compositions

Example D1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example D2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example D: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (Ia), or a pharmaceutically acceptable salt, solvate, tautomer, or stereoisomer thereof:

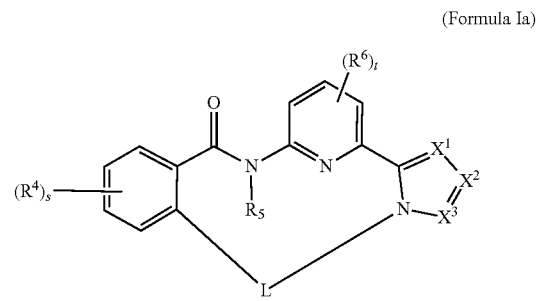

(Formula Ia)

wherein:
L is

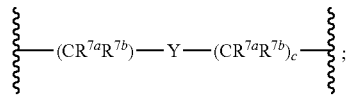

each $R^{7a}$ and $R^{7b}$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^{7a}$ and $R^{7b}$ on the same carbon atom are taken together to form an oxo;

or two $R^{7a}$ are taken together to form an optionally substituted cycloalkyl;

each Y is independently —$NR^{7c}$—, —O—, —S—, —S(=O)—, or —S(=O)$_2$—;

each $R^{7c}$ is independently hydrogen, —S(=O)$R^b$, —S(=O)$_2R^d$, —S(=O)$_2NR^cR^d$, —C(=O)$R^b$, —$CO_2R^a$—C(=O)$NR^cR^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

c is 2-8;
$X^1$ is N or $CR^1$;
$X^2$ is N or $CR^2$;
$X^3$ is N or $CR^3$;

each $R^1$, $R^2$, and $R^3$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^4$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or two $R^4$ are taken together to form an optionally substituted cycloalkyl, optionally substituted heterocycloalkyl, optionally substituted aryl, or optionally substituted heteroaryl;

$R^5$ is hydrogen, —S(=O)$R^b$, —S(=O)$_2R^d$, —S(=O)$_2NR^cR^d$, —C(=O)$R^b$, —$OCO_2R^a$, —C(=O)$NR^cR^d$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^6$ is independently hydrogen, halogen, —CN, —$OR^a$, —$SR^a$, —S(=O)$R^b$, —$NO_2$, —$NR^cR^d$, —S(=O)$_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^aC(=O)NR^cR^d$, —$NR^aC(=O)R^b$, —$NR^aC(=O)OR^a$, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^a$ is hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

$R^b$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each $R^c$ and $R^d$ is independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

or $R^c$ and $R^d$, together with the nitrogen atom to which they are attached, form an optionally substituted heterocycloalkyl or optionally substituted heteroaryl;

s is 1-3; and t is 1-3.

2. The compound of claim 1, wherein the compound of Formula (Ia) is of Formula (Ib), or a pharmaceutically acceptable salt, solvate, tautomer, or stereoisomer thereof:

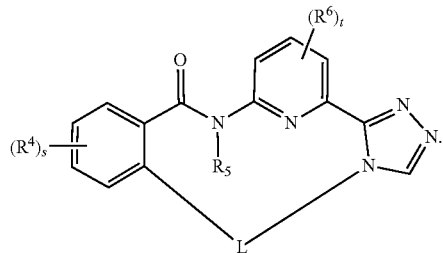

Formula (Ib)

3. The compound of claim 1, or a pharmaceutically acceptable salt, solvate, tautomer, or stereoisomer thereof, wherein:

each $R^4$ is independently hydrogen, halogen, —CN, —$OR^a$, —$NR^cR^d$, —$CO_2R^a$, —C(=O)$NR^cR^d$, optionally substituted $C_1$-$C_6$ alkyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl, or two $R^4$ are taken together to form an optionally substituted heterocycloalkyl.

4. The compound of claim 1, or a pharmaceutically acceptable salt, solvate, tautomer, or stereoisomer thereof, wherein:

each $R^4$ is independently hydrogen, halogen, —CN, —$OR^a$, optionally substituted $C_1$-$C_6$ alkyl, optionally substituted cycloalkyl, optionally substituted heterocycloalkyl, optionally substituted aryl, or optionally substituted heteroaryl.

5. The compound of claim 1, or a pharmaceutically acceptable salt, solvate, tautomer, or stereoisomer thereof, wherein:

s is 1 or 2.

6. The compound of claim 1, or a pharmaceutically acceptable salt, solvate, tautomer, or stereoisomer thereof, wherein:

each $R^6$ is hydrogen.

7. The compound of claim 1, or a pharmaceutically acceptable salt, solvate, tautomer, or stereoisomer thereof, wherein:

$R^5$ is hydrogen or optionally substituted $C_1$-$C_6$ alkyl.

8. The compound of claim 1, or a pharmaceutically acceptable salt, solvate, tautomer, or stereoisomer thereof, wherein:

each $R^{7a}$ and $R^{7a}$ is independently hydrogen, halogen, or optionally substituted $C_1$-$C_6$ alkyl;

or $R^{7a}$ and $R^{7b}$ on the same carbon atom are taken together to form an oxo;

or two $R^{7a}$ are taken together to form an optionally substituted cycloalkyl;

Y is —$NR^{7c}$—, —O—, —S—, —S(=O)—, or —S(=O)$_2$—;

$R^{7c}$ is hydrogen or optionally substituted $C_1$-$C_6$ alkyl, c is 2-4.

9. The compound of claim 8, or a pharmaceutically acceptable salt, solvate, tautomer, or stereoisomer thereof, wherein:

Y is —O—.

10. The compound of claim 8, or a pharmaceutically acceptable salt, solvate, tautomer, or stereoisomer thereof, wherein:

each $R^{7a}$ and $R^{7b}$ is independently hydrogen, halogen, or optionally substituted $C_1$-$C_6$ alkyl or two $R^{7a}$ are taken together to form an optionally substituted cycloalkyl.

11. The compound of claim 8, or a pharmaceutically acceptable salt, solvate, tautomer, or stereoisomer thereof, wherein:

each $R^{7a}$ and $R^{7b}$ is hydrogen.

12. The compound of claim 1, or a pharmaceutically acceptable salt, solvate, tautomer, or stereoisomer thereof, wherein:

L is

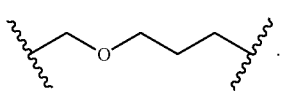

13. The compound of claim 1 selected from the group consisting of:

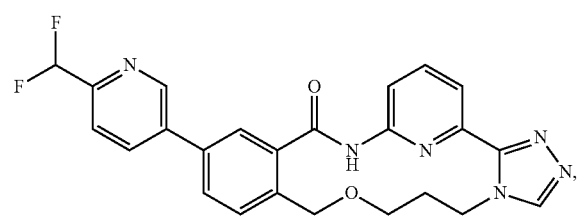

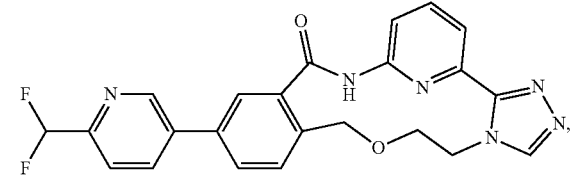

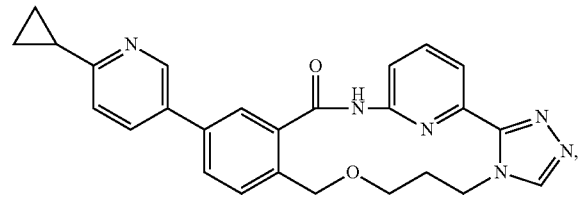

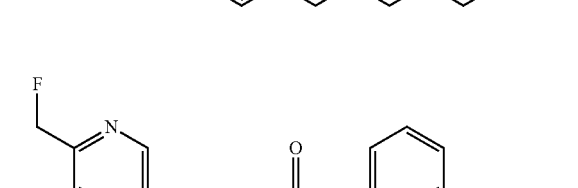

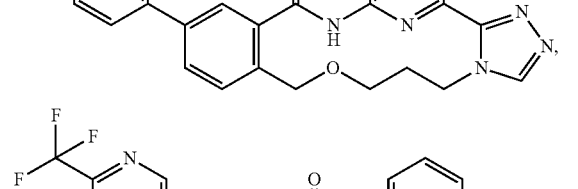

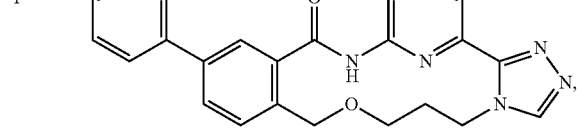

-continued

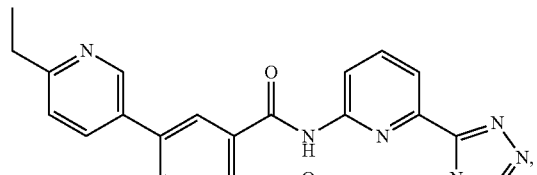

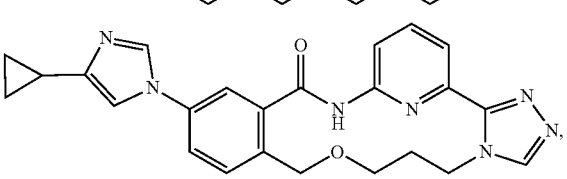

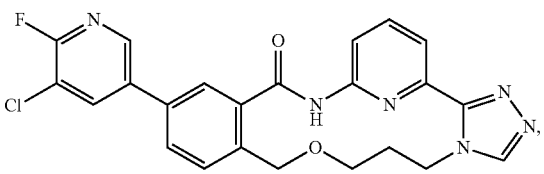

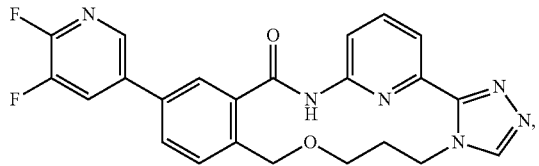

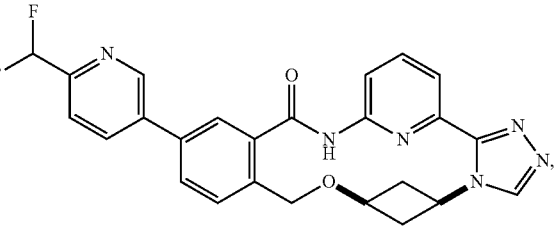

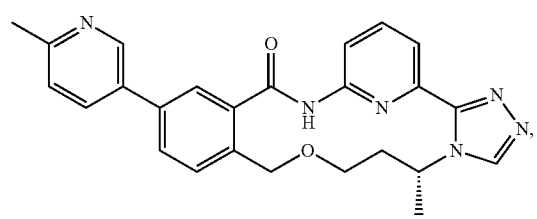

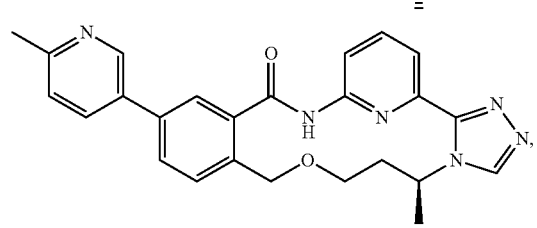

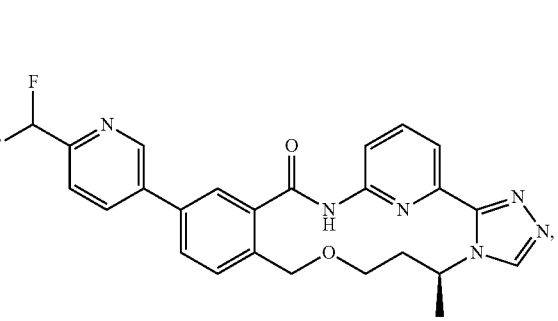

-continued

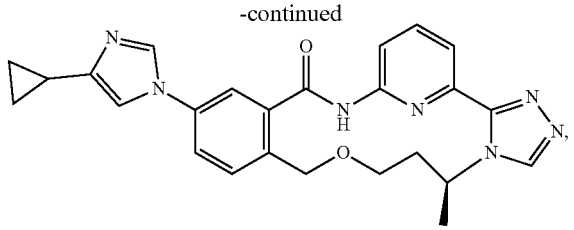

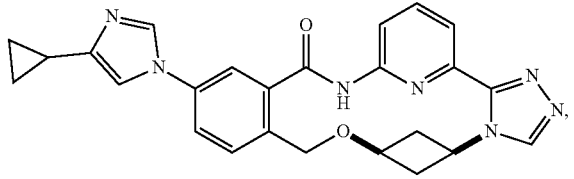

and

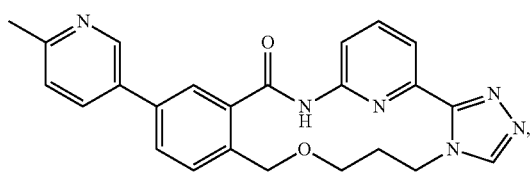 [SMILES: Cc1ccc(-c2ccc3c(c2)C(=O)Nc2cccc(n2)-c2nncn2CCCOC3)cn1]

or a pharmaceutically acceptable salt, solvate, tautomer, or stereoisomer thereof.

14. A pharmaceutical composition comprising a therapeutically effective amount of a compound of claim 1, or a pharmaceutically acceptable salt, solvate, tautomer, or stereoisomer thereof, and a pharmaceutically acceptable excipient.

15. A method for treating a disease in a mammal comprising administering to the mammal a therapeutically effective amount of the compound of claim 1, or a pharmaceutically acceptable salt, solvate, tautomer, or stereoisomer thereof.

16. The method of claim 15, wherein the disease is selected from the group consisting of a blood disease, an autoimmune disorder, a pulmonary disorder, hypertension, an inflammatory disease, a fibrotic disease, diabetes, diabetic nephropathy, a renal disease, a respiratory disease, a cardiovascular disease, acute lung injury, acute or chronic liver disease, and a neurodegenerative disease.

* * * * *